United States Patent
Hamberger et al.

(10) Patent No.: US 11,827,915 B2
(45) Date of Patent: Nov. 28, 2023

(54) METHOD FOR PRODUCTION OF NOVEL DITERPENE SCAFFOLDS

(71) Applicant: Board of Trustees of Michigan State University, East Lansing, MI (US)

(72) Inventors: Björn Hamberger, Okemos, MI (US); Sean Johnson, Bedford, MA (US); Wajid Waheed Bhat, Haslett, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 99 days.

(21) Appl. No.: 17/265,482

(22) PCT Filed: Aug. 2, 2019

(86) PCT No.: PCT/US2019/044887
§ 371 (c)(1),
(2) Date: Feb. 2, 2021

(87) PCT Pub. No.: WO2020/028795
PCT Pub. Date: Feb. 6, 2020

(65) Prior Publication Data
US 2022/0372526 A1    Nov. 24, 2022

Related U.S. Application Data

(60) Provisional application No. 62/714,216, filed on Aug. 3, 2018.

(51) Int. Cl.
| | |
|---|---|
| *C12N 9/10* | (2006.01) |
| *C12P 5/00* | (2006.01) |
| *C12N 15/82* | (2006.01) |
| *C12P 17/02* | (2006.01) |
| *C12P 17/06* | (2006.01) |

(52) U.S. Cl.
CPC ............ *C12P 5/002* (2013.01); *C12N 9/1022* (2013.01); *C12N 9/1085* (2013.01); *C12N 15/8243* (2013.01); *C12P 17/02* (2013.01); *C12P 17/06* (2013.01); *C12Y 202/01007* (2013.01); *C12Y 205/01029* (2013.01)

(58) Field of Classification Search
None
See application file for complete search history.

(56) References Cited

U.S. PATENT DOCUMENTS

| | | |
|---|---|---|
| 2003/0175678 A1 | 9/2003 | Bowen et al. |
| 2012/0064629 A1 | 3/2012 | Mendez et al. |
| 2016/0318893 A1 | 11/2016 | Hamberger et al. |
| 2018/0037912 A1 | 2/2018 | Hamberger et al. |

FOREIGN PATENT DOCUMENTS

| | | |
|---|---|---|
| CN | 105456245 | 4/2016 |
| WO | 2015113570 | 8/2015 |
| WO | WO-2020028795 A1 | 2/2020 |

OTHER PUBLICATIONS

Caniard, et al., BMC Plant Biol. 12 (1), 119 (Year: 2012).*
Ngo et al. in The Protein Folding Problem and Tertiary Structure Prediction, 1994.*
Chen et al. Archives of Biochemistry and Biophysics, vol. 324, No. 2, pp. 255-266, Dec. 20, 1995.*
Toll, Current Opinion in Plant Biology, vol. 9, pp. 297-304, Apr. 2006.*
"U.S. Appl. No. 62/714,216, Preliminary Amendment Filed Aug. 8, 2018", 3 pgs.
"International Application Serial No. PCT/US2019/044887, International Search Report dated Dec. 11, 2019", 5 pgs.
"International Application Serial No. PCT/US2019/044887, Invitation to Pay Additional Fees dated Oct. 18, 2019", 3 pgs.
"International Application Serial No. PCT/US2019/044887, Written Opinion dated Dec. 11, 2019", 5 pgs.
"International Application Serial No. PCT/US2019/044887, International Preliminary Report on Patentability dated Feb. 18, 2021", 7 pgs.
Hong, L.-L., et al., "Unusual Anti-allergic Diterpenoids from the Marine Sponge *Hippospongia lachne*", *Scientific Reports 7. Article No. 43138*, (2017), 7 pgs.
Hong, L.-L., et al., "Unusual Anti-allergic Diterpenoids from the Marine Sponge *Hippospongia lachne*", Supplementary Information, *Scientific Reports 7, Article No. 43138*, (2017), 34 pgs.
Johnson, S. R., "Systematic diterpene synthase discovery across Lamiaceae", (Abstract), *57th Annual Meeting of the Phytochemical Society of North America*, Aug. 4-8, 2018, University of San Luis Potosi, San Luis Potosi, Mexico, (2018), p. 26 (2 pgs.).
Lou, H., et al., "Vulgarisin A, a New Diterpenoid with a Rare 5/6/4/5 Ring Skeleton from the Chinese Medicinal Plant *Prunella vulgaris*", *Org. Lett.* 16(10), (2014), 2696-2699.
Lou, H., et al., "Vulgarisin A, a New Diterpenoid with a Rare 5/6/4/5 Ring Skeleton from the Chinese Medicinal Plant *Prunella vulgaris*", Supporting Information, *Org. Lett.* 16(10), (2014), 1-19.
Lou, H.-Y., et al., "Vulgarisins B-D, three novel diterpenoids with a rare skeleton isolated from *Prunella vulgaris* Linn", *Tetrahedron Letters* 58(5), (2017), 401-404.
"European Application Serial No. 19843571.1, Supplementary Partial European Search Report dated Sep. 22, 2021", 12 pgs.
"RecName: Full=Miltiradiene synthase KSL1, chloroplastic {ECO:0000303|PubMed:28445526}; EC=4.2.3.131 {ECO:0000269|PubMed:28381502}, ECO:0000269|PubMed:28445526}; AltName:Full=Kaurene synthase 1 ECO:0000303|PubMed:28381502};Short=IrKSL1 {ECO:0000303|PubMed:2}", (Jul. 5, 2017), 1 pg.
"European Application Serial No. 19843571.1, Extended European Search Report dated Jan. 26, 2022", 16 pgs.
"RecName: Full=Kolavenyl diphosphate synthase TPS5, chloroplastic {ECO : 0000303 !PubMed:29315936}; EC=5.5.1.29 {ECO : 00002-69 !PubMed:29315936}; AltName: Full=Terpene synthase 5 {ECO:0000303! PubMed:29315936}; Short=VacTPS5 {ECO:0000303!PubMed:29315936}; F", (Jun. 20, 2018), 1 pg.

(Continued)

*Primary Examiner* — Richard G Hutson
(74) *Attorney, Agent, or Firm* — Schwegman Lundberg & Woessner, P.A.

(57) ABSTRACT

Enzymes and methods are described herein for manufacturing terpenes, including terpenes.

8 Claims, 22 Drawing Sheets

Specification includes a Sequence Listing.

(56) References Cited

OTHER PUBLICATIONS

Bremner, Paul D., et al., "Neo-Clerodane Diterpenoid Insect Antifeedants from Ajuga reptans cv Catlins Giant", Phytochemistry, 47(7), (1998), 1227-1232.
Crocoll, Christoph, et al., "Terpene synthases of oregano (*Origanum vulgare* L.) and their roles in the pathway and regulation of terpene biosynthesis", Plant Molecular Biology, 73(6), (2010), 587-603.
Johnson, Sean R., et al., "A Database-Driven Approach Identifies Additional Diterpene Synthase Activities in the Mint Family (*Lamiaceae*)", J. Biol. Chem. 294(4), (2019), 1349-1362.
"Dictionary of Natural Products 26.2", [online]. [Archived on Feb. 20, 2018]. Retrieved from the Internet: <URL: https://web.archive.org/web/20180220224845/http://dnp.chemnetbase.com/faces/chemical/ChemicalSearch.xhtml;jsessionid=7993CED448E4ED19650860B9148462FE>, (2018), 1 pg.
"European Application Serial No. 19843571.1, Communication Pursuant to Article 94(3) EPC dated Dec. 2, 2022", 1 pg.
Alvarenga, S. A., et al., "A computer-assisted approach for chemotaxonomic studies—Diterpenes in Lamiaceae", Phytochemistry 56(6), (Mar. 2001), 583-595.
Andersen-Ranberg, J., et al., "Expanding the Landscape of Diterpene Structural Diversity through Stereochemically Controlled Combinatorial Biosynthesis", Angew Chem Int Ed 55(6), (2016), 2142-2146.
Arima, Y., et al., "Natural product synthesis from (8aR)- and (8aS)-bicyclofarnesols: synthesis of (+)-wiedendiol A, (+)-norsesterterpene diene ester and (−)-subersic acid", Tetrahedron: Asymmetry 18(14), (2007), 1701-1711.
Banerjee, A., et al., "P450s controlling metabolic bifurcations in plant terpene specialized metabolism.", Phytochem Rev 17(1), (2018), 81-111.
Barton, D. H. R., et al., "Diterpenoid bitter principles. Part III. The constitution of clerodin", J Chem Soc (Resumed), (1961), 5061-5073.
Belles, X., et al., "Insect antifeedant activity of clerodane diterpenoids against larvae of Spodoptera Littoralis (Boisd.) (Lepidoptera)", J Chem Ecol 11(10), (1985), 1439-1445.
Benson, D. A., et al., "GenBank", Nucleic Acids Res 41(D1), (2013), D36-D42.
Boachon, B., et al., "Phylogenomic Mining of the Mints Reveals Multiple Mechanisms Contributing to the Evolution of Chemical Diversity in Lamiaceae", Molecular Plant. 11, (Aug. 2018), 1084-1096.
Boalino, D. M., et al., "Labdane Diterpenes of Leonurus sibiricus", J Nat Prod 67(4), (2004), 714-717.
Bohlmann, F., et al., "Neue labdan- und pimaren-derivate aus Palafoxia rosea", Phytochemistry 18(1), (1979), 115-118.
Busta, L., et al., "Moving beyond the ubiquitous: the diversity and biosynthesis of specialty compounds in plant cuticular waxes", Phytochem Rev:1-30, (2017), 1-30.
Camacho, C., et al., "BLAST+: architecture and applications", BMC Bioinformatics 10:421, (2009), 9 pgs.
Challis, G. L., et al., "Genome Mining for Novel Natural Product Discovery", J Med Chem 51(9), (2008), 2618-2628.
Chau, M., et al., "Regioselectivity of taxoid-O-acetyltransferases: heterologous expression and characterization of a new taxadien—5a-ol-O-acetyltransferase", Archives of Biochemistry and Biophysics 430(2), (Oct. 15, 2004), 237-246.
Chen, F., et al., "The Family of terpene synthases in plants: a mid-size family of genes for specialized metabolism that is highly diversified throughout the kingdom", The Plant Journal 66(1), (Apr. 2011), 212-229.
Chen, X., et al., "A (−)-kolavenyl diphosphate synthase catalyzes the first step of salvinorin A biosynthesis in Salvia divinorum", J Exp Bot 68(5), (2017), 1109-1122.
Chen, Y.-L., et al., "Bioactive Cembrane Diterpenoids of Anisomeles indica", J Nat Prod 71(7), (2008), 1207-1212.
Coll, J., et al., "neo-Clerodane diterpenoids from Ajuga: structural elucidation and biological activity", Phytochem Rev 7(1), (2008), 25-49.
Cui, G., et al., "Functional divergence of diterpene syntheses in the medicinal plant Salvia miltiorrhiza Bunge", Plant Physiol 169(3), (2015), 1607-1618.
Dairi, T., et al., "Eubacterial Diterpene Cyclase Genes Essential for Production of the Isoprenoid Antibiotic Terpentecin", J Bacteriol 183(20), (2001), 6085-6094.
Ennajdaoui, H., et al., "Trichome specific expression of the tobacco (*Nicotiana sylvestris*) cembratrien-ol synthase genes is controlled by both activating and repressing cis-regions", Plant Mol Biol 73(6), (2010), 673-685.
Federhen, S., et al., "The NCBI Taxonomy database", Nucleic Acids Res 40(D1), (2012), D136-D143.
Fischedick, J. T., et al., "NMR spectroscopic search module for Spektraris, an online resource for plant natural product identification—Taxane diterpenoids from Taxus × media cell suspension cultures as a case study", Phytochemistry 113, (2015), 87-95.
Gao, W., et al., "A Functional Genomics Approach to Tanshinone Biosynthesis Provides Stereochemical Insights", Org Lett 11(22), (2009), 5170-5173.
Geuskens, R. B. M., et al., "Antifeedant activity of some ajugarin derivatives in three lepidopterous species", Experientia 39(4), (1983), 403-404.
Gonzalez, A. G., et al., "Diterpenes from Salvia mellifera", Phytochemistry 30(12), (1991), 4067-4070.
Gray, C. A., et al., "The absolute stereochemistry of a diterpene from Ballota aucheri", Phytochemistry 63(4), (2003), 409-413.
Gunnewich, N., et al., "A diterpene synthase from the clary sage Salvia sclarea catalyzes the cyclization of geranylgeranyl diphosphate to (8R)-hydroxy-copalyl diphosphate", Phytochemistry 91, (2013), 93-99.
Guo, J., et al., "CYP76AH1 catalyzes turnover of miltiradiene in tanshinones biosynthesis and enables heterologous production of ferruginol in yeasts", Proc. Natl. Acad. Sci. USA, 110(29), (2013), 12108-12113.
Hamano, Y., et al., "Functional Analysis of Eubacterial Diterpene Cyclases Responsible for Biosynthesis of a Diterpene Antibiotic, Terpentecin", J Biol Chem 277(40), (2002), 37098-37104.
Hamberger, B., et al., "Plant P450s as versatile drivers for evolution of species-specific chemical diversity", Philosophical transactions of the Royal Society of London B: Biological Sciences 368(1612), (Feb. 19, 2013).
Han, Q.-B., et al., "Maoecrystal Z, a Cytotoxic Diterpene from Isodon eriocalyx with a Unique Skeleton", Org Lett 8(21), (2006), 4727-4730.
Harris, L. J., et al., "The Maize An2 Gene is Induced by Fusarium Attack and Encodes and ent-Copalyl Diphosphate Synthase", Plant Mol Biol 59(6), (2005), 881-894.
Heller, S. R., et al., "InChI, the IUPAC International Chemical Identifier", J Cheminform 7. doi:10.1186/s13321-015-0068-4., (2015).
Helliwell, C. A., et al., "The CYP88A cytochrome P450, ent-kaurenoic acid oxidase, catalyzes three steps of the gibberellin biosynthesis pathway", Proc. Natl. Acad. Sci. USA 98(4), (2001), 2065-2070.
Heskes, A.M., et al., "Biosynthesis of bioactive diterpenoids in the medicinal plant Vitex agnus-castus", Plant J 93(5): 943-958, 2018., (Mar. 2018), 16 pgs.
Hillwig, M. L., et al., "Domain loss has independently occurred multiple times in plant terpene synthase evolution", The Plant Journal 68(6), (2011), 1051-1060.
Huang, A. C., et al., "Unearthing a sesterterpene biosynthetic repertoire in the Brassicaceae through genome mining reveals convergent evolution", Proc. Natl. Acad. Sci. USA 114(29), (2017), E6005-E6014.
Huerta-Cepas, J., et al., "ETE 3: Reconstruction, Analysis, and Visualization of Phylogenomic Data", Mol Biol Evol 33(6), (2016), 1635-1638.
Ikeda, H., et al., "Biosynthesis of mercapturic acid derivative of the labdane-type diterpene, cyslabdan that potentiates imipenem activity against methicillin-resistant *Staphylococcus aureus*: cyslabdan is generated by mycothiol-mediated xenobiotic detoxification", J. Ind Microbiol Biotechnol 43(2-3), (2016), 325-342.

(56) References Cited

OTHER PUBLICATIONS

Jia, M., et al., "Extreme promiscuity of a bacterial and a plant diterpene synthase enables combinatorial biosynthesis", Metabolic Engineering 37, (2016), 24-34.
Jin, B., et al., "Functional diversification of kaurene synthase-like genes", Plant Physiol 174, (2017), 955-973.
Keeling, C. I., et al., "The Primary Diterpene Synthase Products of Picea abies Levopimaradiene/Abietadiene Synthase (PaLAS) are Epimers of a Thermally Unstable Diterpenol", J Biol Chem 286(24), (2011), 21145-21153.
King, A. J., et al., "Production of Bioactive Diterpenoids in the Euphorbiaceae Depends on Evolutionarily Conserved Gene Clusters", The Plant Cell Online 26(8), (2014), 3286-3298.
Kirby, J., et al., "Cloning of casbene and neocembrene synthases from Euphorbiaceae plants and expression in *Saccharomyces cerevisiae*", Phytochemistry 71(13), (2010), 1466-1473.
Klein Gebbinck, E. A., et al., "Insect antifeedant activity of clerodane diterpenes and related model compounds", Phytochemistry 61(7), (2002), 737-770.
Kodama, Y., et al., "The sequence read archive: explosive growth of sequencing data", Nucleic Acids Res 40(D1), (2012), D54-D56.
Kuhn, S., et al., "From chemical shift data through prediction to assignment and NMR LIMS—multiple functionalities of nmrshiftdb2", Journal of Cheminformatics 4(Suppl 1):P52, (2012), 1 pg.
Li, B., "A large-scale chloroplast phylogeny of the Lamiaceae sheds new light on its subfamilial classification", Scientific Reports 6:34343, (2016), 34343.
Li, J.-L., et al., "IeCPS2 is potentially involved in the biosynthesis of pharmacologically active Isodon diterpenoids rather than gibberellin", Phytochemistry 76, (2012), 32-39.
Li, R., et al., "Clerodane diterpenes: sources, structures, and biological activities", Nat Prod Rep 33(10), (2016), 1166-1226.
Li, X.-N., et al., "Structure and Cytotoxicity of Diterpenoids from Isodon eriocalyx", J Nat Proc 73(11), (2010), 1803-1809.
Li-Mei, L., et al., "ent-Kaurane and Cembrane Diterpenoids from Isodon sculponeatus and Their Cytotoxicity", J Nat Prod 72(10), (2009), 1851-1856.
Lopez-Perez, J. L., et al., "NAPROC-13: a database for the dereplication of natural product mixtures in bioassay-guided protocols", Bioinformatics 23(23), (2007), 3256-3257.
Loub, W. D., et al., "NAPRALERT: computer handling of natural product research data", J Chem Inf Comput Sci 25(2), (1985), 99-103.
Monaco, P., et al., "Terpenes from the bled resin of Araucaria hunsteinii", Rendiconto della Academia delle scienze fisiche e matematiche 48, (1982), pp. 465-470.
Ohaski, A., et al., "The isolation and in vivo Potent Antitumor activity of clerodane diterpenoid from the olepresin of the brazilian medicinal plant, copaifera langsdorfi desfon", Bioorganic and Medicinal Chemistry Letters 4(24), (Dec. 1994), 2889-2892.
Ondari, M.E., et al., "The Taxol Pathway 10-O-Acetyltransferase shows Regioselective Promiscuity with the Oxetane Hydroxyl of 4-deacetyltaxanes", J Am Chem Soc 130(50), (Nov. 14, 2008), 17187-17194.
Pateraki, Irini, et al., "Manoyl Oxide (13R), the Biosynthetic Precursor of Forskolin, is Synthesized in Specialized Root Cork Cells in Coleus forskohlii", Plant Physiology, vol. 164, (Mar. 2014), 1222-1236.

Pelot, K. A., et al., "Biosynthesis of the oxygenated diterpene nezukol in the medicinal plant Isodon rubescens is catalyzed by a pair of diterpene synthases", PLOS ONE 12(4):e0176507, (2017), 17 pgs.
Pelot, K.A., et al., "Biosynthesis of the psychotropic plant diterpene salvinorin A: Discovery and characterization of the Salvia divinorum clerodienyl diphosphate synthase", Plant J 89(5): 885-897, 2017., (Mar. 2017), 13 pgs.
Peters, R.J., "Two Rings in them All: The labdane-related diterpenoids", Natural Product Reports 27(11): 1521-1530., (Oct. 1, 2010), 29 pgs.
Roengsumran, S., et al., "Labdane diterpenoids from Croton oblongifolius", Phytochemistry 50(3), (Feb. 10, 1999), 449-453.
Rudi, A., et al., "Chelodane, Barekoxide, and Zaatirin—Three New Diterpenoids from the Marine Sponge Chelonaplysilla erecta", J Nat Prod 55(10), (Oct. 1, 1992), 1408-1414.
Schalk, M., et al., "Toward a Biosynthetic Route to Sclareol and Amber Odorants", J Am Chem Soc 134(46), (2012), 18900-18903.
Scotti, M. T., et al., "SistematX, an Online Web-Based Cheminformatics Tool for Data Management of Secondary Metabolites", Molecules 23(1):103, (2018).
Sievers, et al., "Fast, Scalable Generation of High-Quality Protein Multiple Sequence Alignments Using Clustal Omega", Mol. Syst. Biol., vol. 7 (5539), (2011), 1-6.
Stamatakis, A., "RAxML version 8: a tool for phylogenetic analysis and post-analysis of large phylogenies", Bioinformatics 30(9), (2014), 1312-1313.
Suzuki, H., et al., "Two labdane diterpenoids from Nicotiana setchellii", Phytochemistry 22(5), (1983), 1294-1295.
Urones, J. G., et al., "Compounds with the labdane skeleton from Halimium viscosum", Phytochemistry 35(3), (Feb. 1994), 713-719.
Vogel, B. S., et al., "Abietadiene synthase from grand fir (*Abies grandis*) cDNA isolation, characterization, and bacterial expression of a bifunctional diterpene cyclase involved in resin acid biosynthesis", J Biol Chem 271(38), (1996), 23262-23268.
Wu, C.L., et al., "Labdanoids and bis(bibenzyls) from *Jungermannia* species", Phytochemistry 44(1), (1997), 101-105.
Xiang, W., et al., "ent-Clerodanoids from Isodon scoparius", Helvetica Chimica Acta 87(11), (Nov. 24, 2004), 2860-2865.
Xu, H., et al., "Analysis of the Genome Sequence of the Medicinal Plant Salvia miltiorrhiza", Molecular Plant 9(6), (2016), 949-952.
Yamada, Y., et al., "Chemical diversity of labdane-type bicyclic diterpene biosynthesis in Actinomycetales microorganisms", The Journal of Antibiotics 69(7), (Jan. 27, 2016), 515-523.
Zerbe, P., et al., "Diterpene synthases of the biosynthetic system of medicinally active diterpenoids in Marrubium vulgare", Plant J. 79(6), (2014), 914-927.
Zerbe, P., et al., "Exploring diterpene metabolism in non-model species:transcriptome-enabled discovery and functionalcharacterization of labda-7,13E-dienyl diphosphate synthasefromGrindelia robusta", The Plant Journal, 83(5), (Jun. 28, 2015), 783-793.
Zerbe, P., et al., "Plant diterpene synthases: exploring modularity and metabolic diversity for bioengineering", Trends in Biotechnology 33(7)., (May 20, 2015), 419-428.
Zhan, X., et al., "Additional diterpenes from Physcomitrella patens synthesized by copalyl diphosphate/kaurene synthase (PpCPS/KS)", Plant Physiology and Biochemistry 96, (2015), 110-114.

* cited by examiner

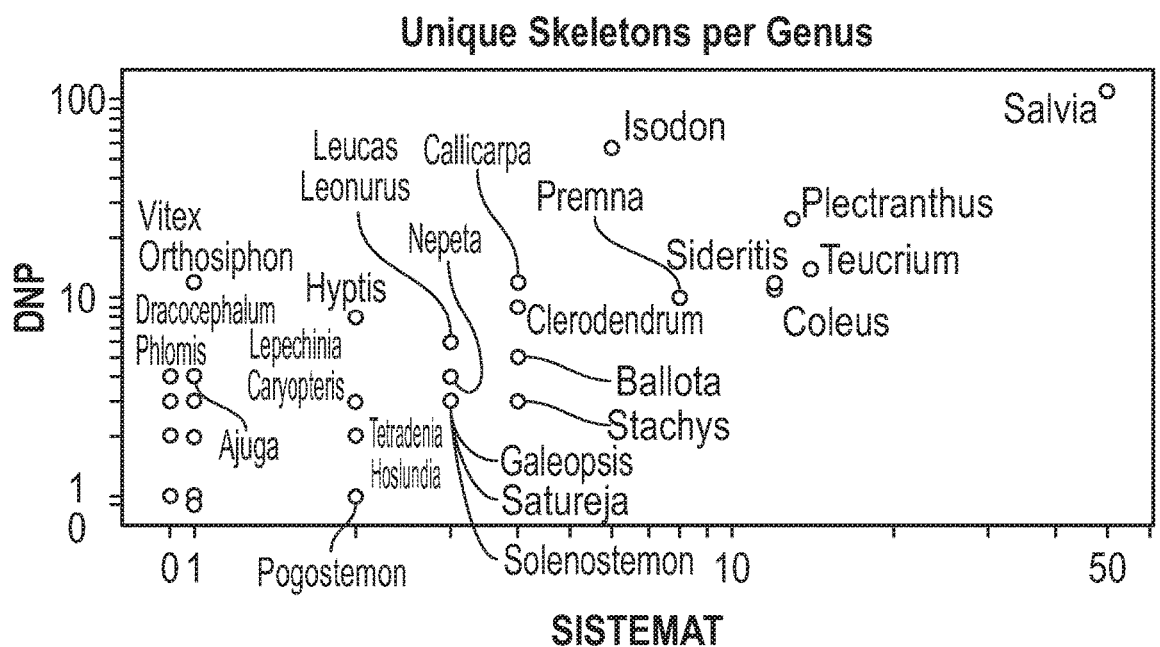
FIG. 1A
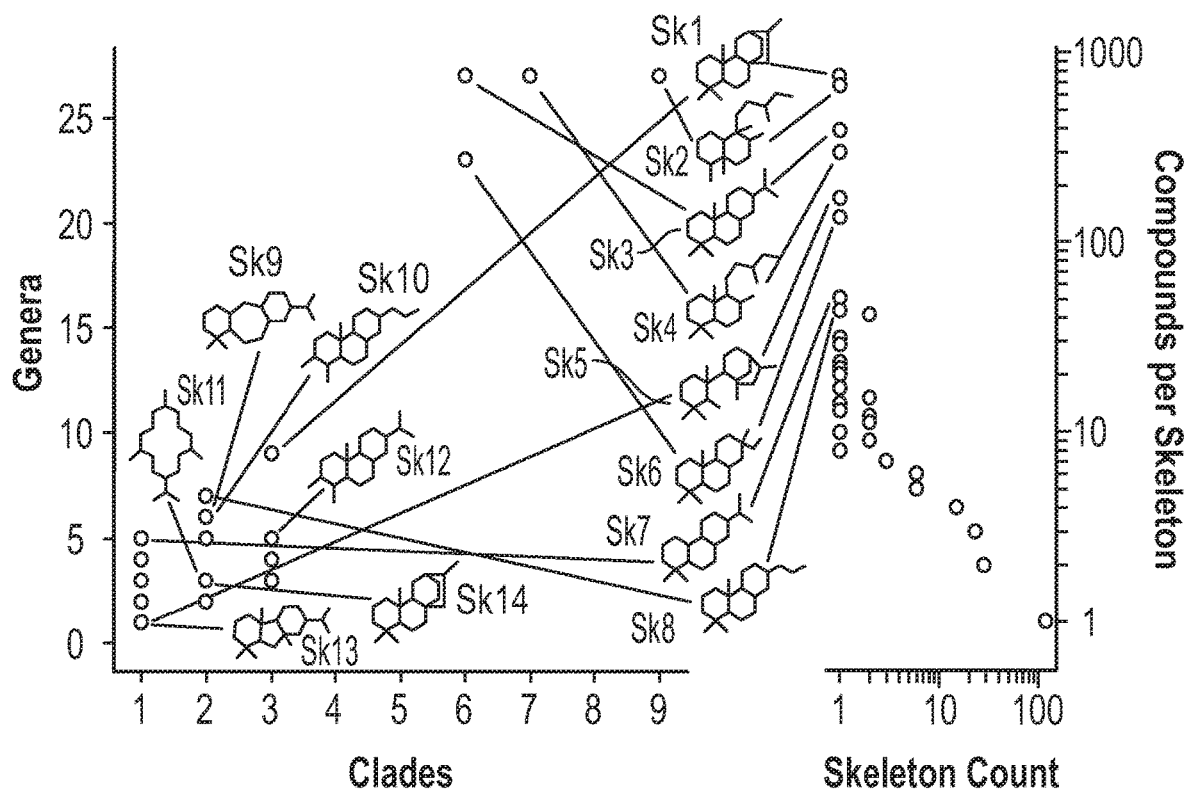
FIG. 1B
FIG. 1C

METHOD FOR PRODUCTION OF NOVEL DITERPENE SCAFFOLDS

GOVERNMENT FUNDING

This application is a U.S. national stage filing under 35 U.S.C. 371 from International Application No. PCT/US2019/044887, filed on 2 Aug. 2019, and published as WO 2020/028795 A1 on 6 Feb. 2020, which claims the benefit of U.S. Provisional Application Ser. No. 62/714,216, filed Aug. 3, 2018, which application is incorporated by reference herein its entirety.

BACKGROUND

Plant-derived terpenoids have a wide range of commercial and industrial uses. Examples of uses for terpenoids include specialty fuels, agrochemicals, fragrances, nutraceuticals and pharmaceuticals. However, currently available methods for petrochemical synthesis, extraction, and purification of terpenoids from the native plant sources have limited economic sustainability.

SUMMARY

Described herein are enzymes useful for production of a variety of terpenes, diterpenes and terpenoids. In some cases, the enzymes synthesize diterpenes. The enzymes were isolated from the mint family (Lamiaceae). Members of the mint family accumulate a wide variety of industrially and medicinally relevant diterpenes. While there are more than 7000 plant species in Lamiaceae, diterpene synthase (diTPS) genes have been characterized from just eleven. The Mint Evolutionary Genomics Consortium, (see website at mints-.planthiology.msu.edu) has now sequenced leaf transcriptomes from at least 48 phylogenetically diverse Lamiaceae species, more than doubling the number of mint species for which transcriptomes are available. The available chemotaxonomic and enzyme activity data are described herein for diterpene synthases (diTPSs) in Lamiaceae. The diTPS sequences and terpenes produced are also described herein. One of the new enzymes produces neo-cleroda-4(18),13E-dienyl diphosphate, a molecule with promising applications in agricultural biotechnology as a precursor to potent insect anti-feedants.

Described herein are expression systems that include at least one expression cassette having at least one heterologous promoter operably linked to at least one nucleic acid segment encoding an enzyme with at least 90% sequence identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 57, 59, or 176. In some cases, the expression systems can have more than one expression cassettes or expression vectors, each expression cassette or expression vector can have at least one nucleic acid segment encoding an enzyme with at least 90% sequence identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 57, 59, or 176. Host cells that include such expression systems are also described herein.

Methods are also described herein that include incubating a host cell comprising a heterologous expression system that includes at least one expression cassette having a heterologous promoter operably linked to a nucleic acid segment encoding an enzyme with at least 90% sequence identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 57, 59, or 176. The expression system within host cell can include more than one expression cassettes or expression vectors.

In addition, methods are described herein for synthesizing a diterpene comprising incubating a terpene precursor with at least one enzyme having at least 90% sequence identity to SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 57, 59, or 176. Such methods can include incubating more than one terpene precursor and/or incubating more than one enzyme in a mixture to produce one or more terpenes or terpenoid compounds.

A variety of diterpenes are also described herein.

DESCRIPTION OF THE FIGURES

FIG. 1A-1D illustrate the distribution of diterpenes in Lamiaceae. Note that Table 4 provides a comparison of different sources for data about Lamiaceae diterpene chemotaxonomy. FIG. 1A illustrates diterpene skeletons per genus according to both the Dictionary of Natural Products (DNP) and SISTEMAT. FIG. 1B illustrates the distribution of skeletons among Lamiaceae clades and genera, based on the DNP. Structures are shown for selected skeletons, where black structures are chose where a biosynthetic route is known from Lamiaceae, and gray structures are those for which the pathway remains unknown. FIG. 1C illustrates the distribution of compounds among skeletons, based on the DNP. FIG. 1D illustrates diterpene structures per genus according to both the DNP and the NAPRALERT database. Darker spots indicate overlapping data points, some labels omitted due to space constraints.

FIG. 2A shows a maximum likelihood tree of newly characterized (blue) class II diTPS enzymes. FIG. 2B shows a maximum likelihood tree of newly characterized (blue) class I diTPS enzymes. The maximum likelihood tree of newly characterized (blue) class II and class I diTPS enzymes are shown in the context of previously reported (black) diTPSs from Lamiaceae. The bifunctional ent-kaurene synthase from *Physcomitrella patens* was used as an outgroup. After each enzyme type are listed the experimentally verified substrates (green) and their products, where the numbers correspond to compound numbers in FIG. 3. Units for scale bars are substitutions per site. Abbreviations for species are listed in Table 5 and those not listed in Table 5 are as follows: Ie, *Isodon eriocalyx*; Ir, *Isodon rubescens*; Mv, *Marrubium vulgare*; Sd, *Salvia divinorum*; Sm, *Salvia miltiorrhiza*; Sp, *Salvia pomifera*; Ss, *Salvia sclarea*; Vac, *Vitex agnus-castus*.

FIG. 3A shows products of diterpene synthases from Lamiaceae. Blue numbers indicate compounds experimentally verified to be products of new enzymes identified using the methods described herein. At the center is geranylgeranyl diphosphate (GGPP), a precursor to ail of these diterpenes. The inner ring fire class II products, the product show in the outer ring are class I products derived from the compound in the connected segment of the inner ring. FIG. 3B(A) to 3B(H) show overlapping portions of a phylogenetic tree generated from the peptide sequences from the reference set, alongside those from the new transcriptome data, including established substrates and products for each enzyme.

FIG. 4A shows products detected by gas chromatography from activity assays of *Ajuga replans* cleroda-4

(18),13E-dienyl diphosphate synthase (ArTPS2) and *Salvia sclarea* sclareol synthase (SsSS) in-vitro with purified protein contacted with GGPP, and in-vivo of *N. benthamiana* cells that transiently expressed the gene combinations, FIG. 4B shows products detected by gas chromatography from activity assays of PcTPS1+SsSS, in-vitro with purified protein contacted with GGPP, and in-vivo of *N. benthamiana* cells that transiently expressed the gene combinations. FIG. 4C shows mass spectra for the products of ArTPS2 and PcTPS1, and their combinations with SsSS.

FIG. 5A shows structures that can be generated by the activities of new class 1 diTPSs. Filled in blue boxes indicate which enzymes are capable of each conversion. FIG. 5B illustrates structures that can be produced by the newly characterized enzyme activities including some of the new class II enzymes. Blue genes are newly characterized. Blue square: TPS-e from that position on the key catalyzes the shown transformation. White square: corresponding TPS-e does not catalyze the shown activity. Grey square: corresponding TPS-e was not tested on the substrate.

FIG. 6A shows GC total ion chromatograms of extracts from *N. benthamiana* expressing OmTPS1 and OmTPS5, compared to extracts of various tissues of *O. majorana*. FIG. 6B shows a mass spectrum of peak B, from *O. majorana* leaf (where peak B is shown in FIG. 6A). FIG. 6C show's a mass spectrum of peak C from *O. majorana* leaf compared to reference spectrum for palustrinol from the NIST17 library (where peak C is shown in FIG. 6A).

FIG. 7A shows GC-MS-total ion and extracted ion chromatograms illustrating production of ent-kaurene (identified from peak 1) from in vivo assays in *N. benthamiana* transiently expressing the gene combinations shown. The mass spectrum of peak 1 is shown below the chromatograms, demonstrating that peak 1 is ent-kaurene as identified through direct comparison with biosynthesized authentic standards with reference enzymes. FIG. 7B show's GC-MS-total ion and extracted ion chromatograms illustrating production of ent-dolabradiene (identified from peak 2) from in vivo assays in *N. benthamiana* transiently expressing the gene combinations shown. The mass spectrum of peak 2 is shown below the chromatograms, demonstrating that peak 2 is ent-dolabradiene as identified through direct comparison with biosynthesized authentic standards with reference enzymes. FIG. 7C shows GC-MS-total ion and extracted ion chromatograms illustrating production of (13R)-ent-manoyl oxide (identified from peak 3) from in vivo assays in *N. benthamiana transiently expressing the gene combinations shown. The mass spectrum of peak 3 is shown below the chromatograms, demonstrating that peak 3 is* (13R)-ent-manoyl oxide as identified through direct comparison with biosynthesized authentic standards with reference enzymes.

DETAILED DESCRIPTION

Figure 1D:
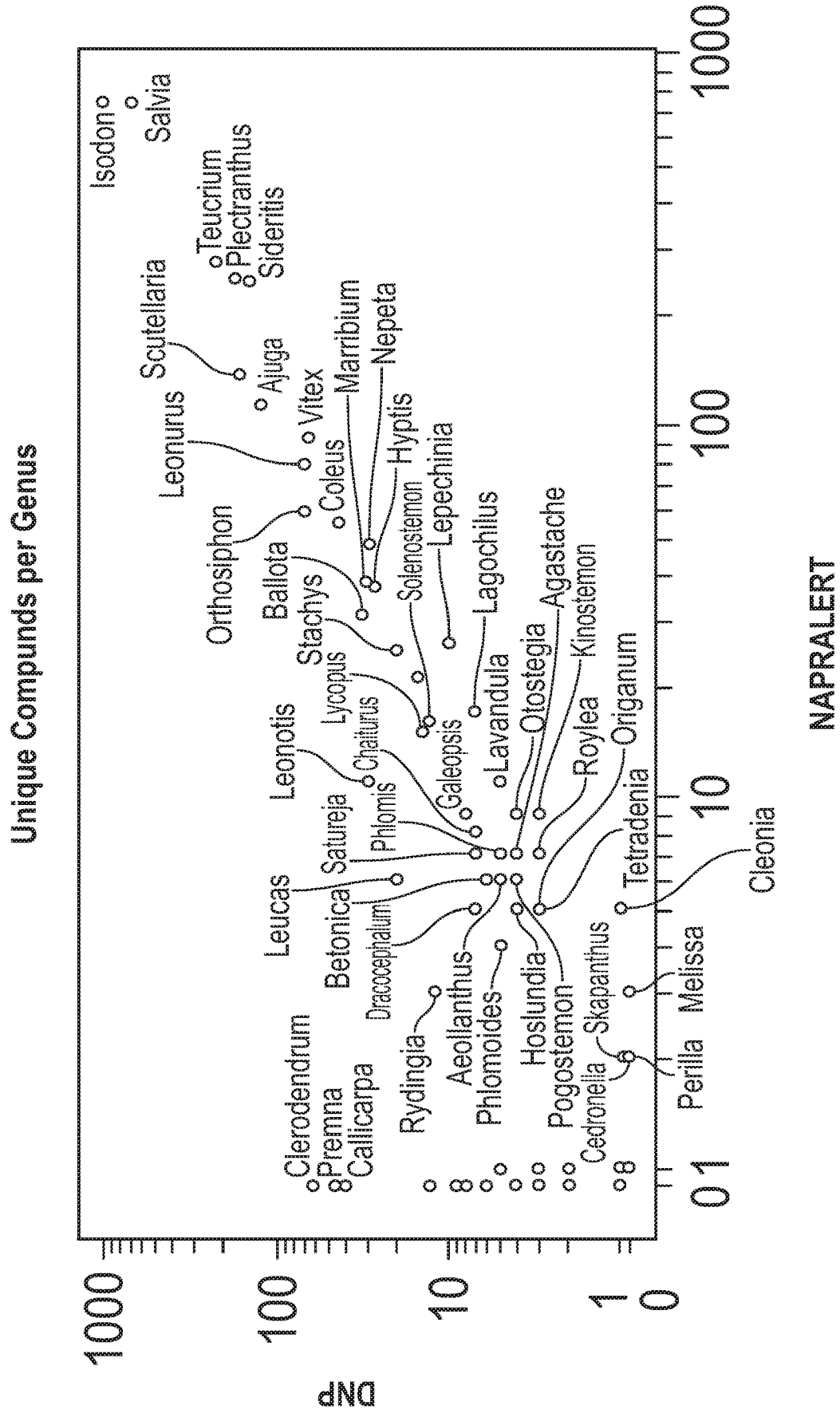

Described herein are new enzymes and compounds, as well as methods that fire useful for manufacturing such compounds. The compounds that can be made by the enzymes and methods are new compounds and compounds that were previously difficult to make.

The enzymes described herein are from a variety of mint plant species and can synthesize a variety of terpene skeletons and terpenes.

Terpenes

The enzymes described herein can facilitate synthesis of a variety of terpenes, diterpenes, and terpenoids. For example, the enzymes described herein can facilitate synthesis of terpenes, diterpenes, and terpenoids can generally have the structure of Formula I:

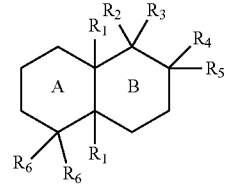

I

In some cases, the terpenes, diterpenes, and terpenoids can generally have the structure of Formula II:

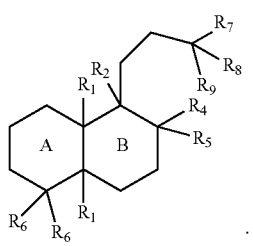

III

In some cases, the terpenes, diterpenes, and terpenoids can generally have the structure of Formula III:

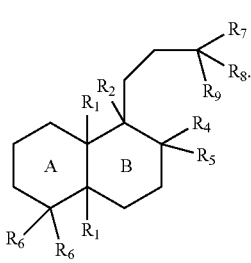

III

The substituents of Formulae I, II, and III can be as follows:
each $R_1$ can separately be hydrogen or lower alkyl;
$R_2$ can be hydrogen, lower alkyl, hydroxy, a bond to an adjacent ring carbon, or form a $C_4$-$C_6$ cycloheteroalkyl with $R_3$;
$R_3$ can be a branched $C_5$-$C_6$ alkyl with 0-2 double bonds, can form a $C_4$-$C_6$ cycloheteroalkyl with $R_2$; can form a cycloalkyl with $R_4$, or can form a cycloheteroalkyl ring with $R_4$, wherein the $C_5$-$C_6$ alkyl can optionally have one hydroxy, phosphate or diphosphate substituent, and wherein each cycloalkyl or cycloheteroalkyl ring can have 0-2 double bonds, and each cycloalkyl or cycloheteroalkyl ring can have 0-2 alkyl or 0-2 alkene substituents;
$R_4$ can be hydrogen, lower alkyl, lower alkene, hydroxy, a carbon bonded to $R_9$, an oxygen bonded to $R_9$, form a cycloalkyl ring with $R_3$, or form a cycloheteroalkyl ring with $R_3$, wherein each cycloalkyl ring or cycloheteroalkyl ring can have 0-2 double bonds, and each cycloalkyl ring or cycloheteroalkyl ring can have 0-2 alkyl or 0-2 alkene substituents;

$R_5$ can be hydrogen, hydroxy, lower alkyl, a lower alkene, a bond with an adjacent carbon, form a cycloalkyl ring with a ring atom of a ring formed by $R_3$ and $R_4$, wherein the cycloalkyl ring can have 0-2 double bonds, and the cycloalkyl ring can have 0-2 alkyl or 0-2 alkene substituents;

each $R_6$ can separately be hydrogen, lower alkyl, lower alkene, or form a bond with an adjacent carbon;

$R_7$ can be lower alkyl, lower alkene, or form a cycloalkyl ring with a $R_5$, $R_8$ can be lower alkyl, hydroxy, phosphate, diphosphate, or form a bond with an adjacent carbon; or $R_9$ can be hydrogen, lower alkyl, lower alkene, =$CH_2$, hydroxy, phosphate, diphosphate, form a bond with an adjacent carbon, form a cycloalkyl ring with $R_4$, or form a cycloheteroalkyl ring with $R_4$, wherein each cycloalkyl ring or cycloheteroalkyl ring can have 0-2 double bonds, and each cycloalkyl ring or cycloheteroalkyl ring can have 0-2 alkyl or 0-2 alkene substituents.

The alkyl group(s) can have one to ten carbon atoms. In some cases, the alkyl groups can be lower alkyl group(s) (e.g., C1-C6 alkyl groups). In some cases, where substituents such as $R_1$, $R_2$, $R_5$, and $R_6$ are lower alkyl groups, they can be a $C_1$-$C_3$ lower alkyl. In some cases, where substituents such as $R_1$, $R_2$, $R_5$, and $R_6$ are lower alkyl groups, they are an ethyl or methyl group.

Cycloalkyl groups are cyclic alkyl groups such as, but not limited to, cyclopropyl, cyclobutyl, cyclopentyl, cyclohexyl, cycloheptyl, and cyclooctyl groups. In some cases, the cycloalkyl group can have 3 to about 8-12 ring members, whereas in other cases the number of ring carbon atoms range from 4, 5, 6, or 7. Cycloalkyl groups can include cycloalkyl rings having at least one double bond between 2 carbons (i.e., cycloalkenyl rings). Thus, for example, the A, B and/or C rings can also be a cycloalkenyl group such as a cyclohexenyl, cyclopentenyl, or cyclohexadienyl group. Cycloalkenyl groups can have from 4 to about 8-12 ring members.

Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups. The term "cycloalkenyl" alone or in combination denotes a cyclic alkenyl group.

Heterocycloalkyl groups include ring groups containing 3 or more ring members, of which, one or more is a heteroatom such as, but not limited to, N, O, and S. The compounds described herein that have heteroatoms typically have an oxygen heteroatom. In some embodiments, heterocyclyl groups include 3 to about 15 ring members, whereas other such groups have 3 to about 10 ring members. A heterocyclyl group designated as a $C_2$-heterocyclyl can be a 5-ring with two carbon atoms and three heteroatoms, 6-ring with two carbon atoms and four heteroatoms and so forth. A $C_3$-heterocyclyl can be a 5-ring with three carbons and two heteroatoms, a 6-ring with three carbons and three heteroatoms, and so forth. A $C_4$-heterocyclyl can be a 5-ring four carbons and one heteroatom, a 6-ring with four carbons and two heteroatoms, and so forth. The number of carbon atoms plus the number of heteroatoms sums up to equal the total number of ring atoms. A heterocyclyl ring can also include one or more double bonds. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or they can be substituted. Heterocyclyl groups include, but Eire not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups In some cases, only one of the $R_6$ groups is a lower alkyl, while the other is hydrogen.

In some cases, $R_2$ is hydrogen when $R_3$ forms a ring with $R_4$.

Although in many diterpenes, each $R_6$ is a lower alkyl, in some cases one $R_6$ is a lower alkene white the other is bond that contributes to lower alkene. For example, in some cases the two $R_6$ groups form a lower alkene together, for example, a =$CH_2$ group.

The compounds produced by the enzymes described herein are typically terpenes or diterpenes. Diterpenes are a class of chemical compounds composed of two terpene units, often with the molecular formula. $C_{20}H_{32}$, though some can include 1-2 heteroatoms or other substituents. Diterpenes generally consist of four isoprene subunits. The positions of various atoms in a diterpene can, for example, be numbered as shown below.

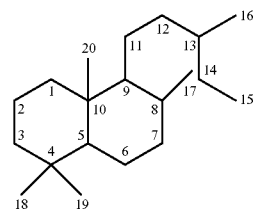

The enzymes described herein can produce compounds with the following skeletons (Sk1-Sk14), where 1-2 of the ring atoms can in some cases be heteroatoms (e.g., oxygen or nitrogen). If a heteroatom is present in it is usually an oxygen atom.

Sk1 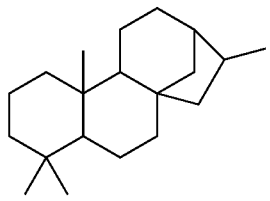
Sk2 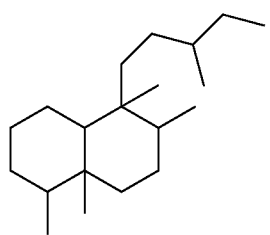
Sk3 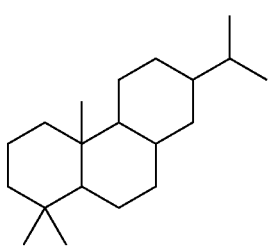
Sk4 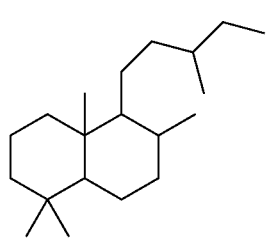
Sk5 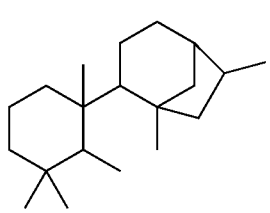
Sk6 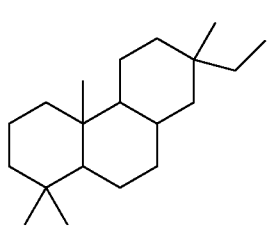
Sk7 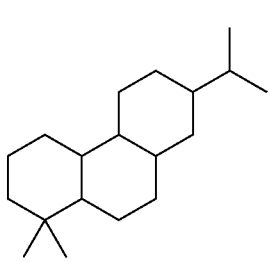
Sk8 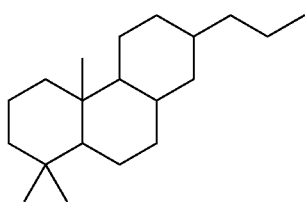
Sk9 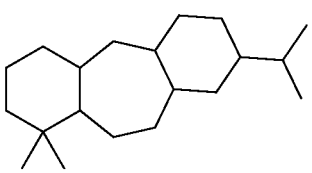
Sk10 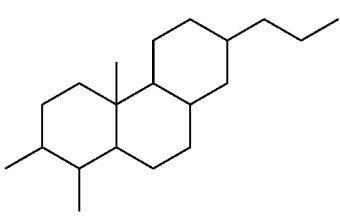
Sk11 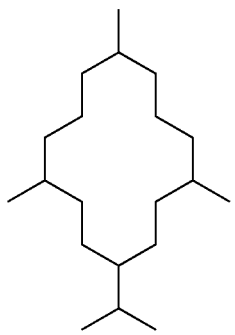
Sk12 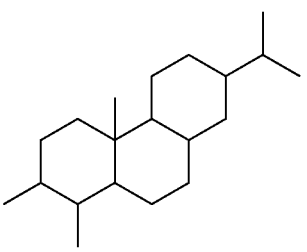
Sk13 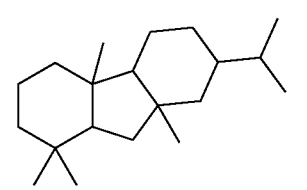
Sk14 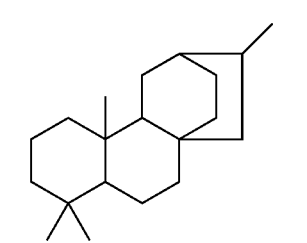

-continued

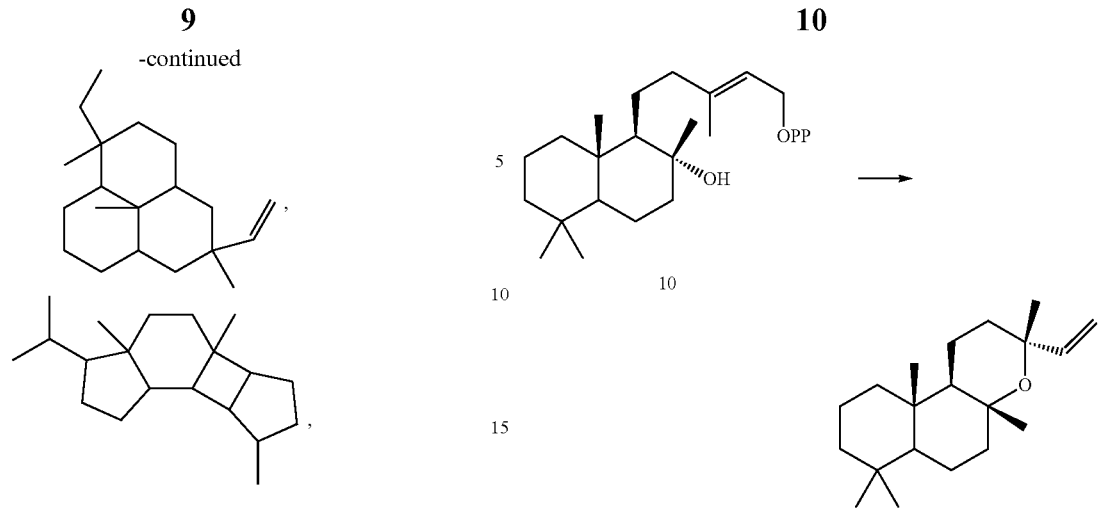

a combination thereof.

Enzymes

The enzymes described herein are from a variety of mint plant species and can synthesize a variety of terpenes, diterpene skeletons, and terpenoid compounds.

The ArTPS3, LlTPS4, OmTPS4, OmTPS5, PaTPS3, PvTPS1, and SoYPS1 enzymes can also convert peregrinol diphosphate (PgPP) [5] to a combination of compounds 1, 2, and 3, as illustrated below.

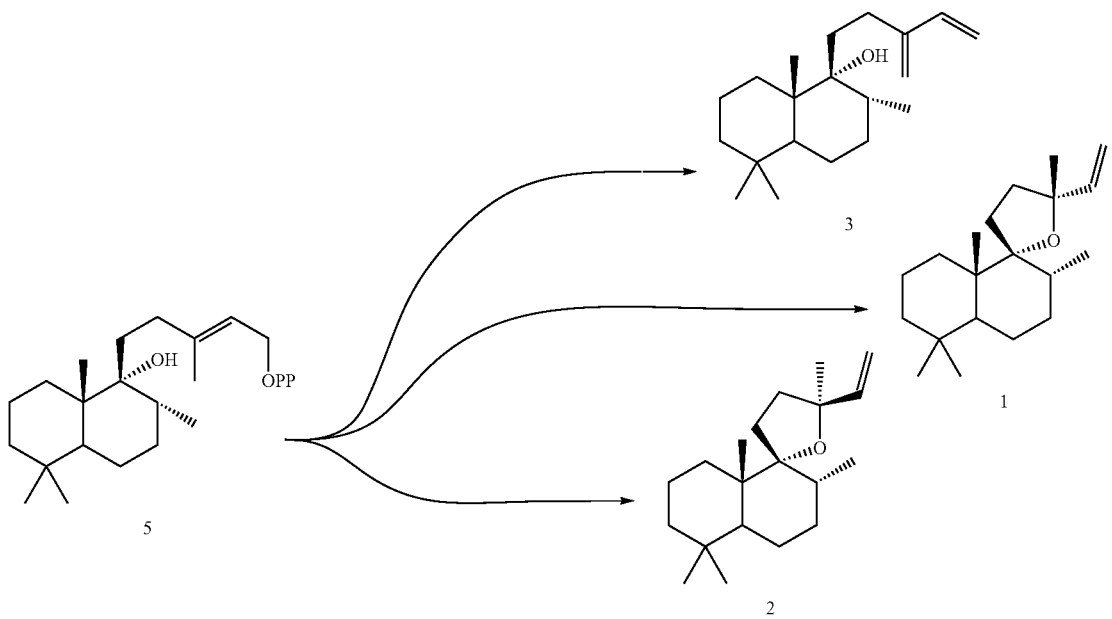

For example, an *Ajuga reptans* miltiradiene synthase (ArTPS3), a *Leonotis leonurus* sandaracopimaradiene synthase (LlTPS4), a *Mentha spicata* class I diterpene synthase (MsTPS1), an *Origanum majorana* trans-abienol synthase (OmTPS3), an *Origanum majorana* manool synthase (OmTPS4), an *Origanum majorana* palustradiene synthase (OmTPS5), *Perovskia atriplicifolia* miitiradiene synthase (PaTPS3), *Prunella vulgaris* miltiradiene synthase (PvTPS1), *Salvia officinalis* miitiradiene synthase (SoTPS1) were identified and isolated as described herein.

Eight of these enzymes, ArTPS3, LlTPS4, MsTPS1, OmTPS4, OmTPS5, PaTPS3, PvTPS1, and SoTPS1 can convert a labda-13-en-8-ol diphosphate ((+)-8-LPP) [compound 10]) to 13R-(+)-manoyl oxide [8].

However, MsTPS1 produced only compound 3 from compound 5, white the OmTPS3 enzyme produced only 1, and 2. The OmTPS4 enzyme produced compound 4 (shown below) in addition to compounds 1, 2, and 3.

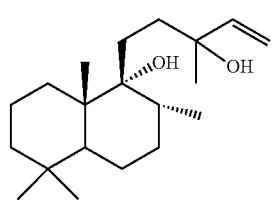

The ArTPS3, PaTPS3, PvTPS1, and SoTPS1 enzymes can also convert (+)-copalyl diphosphate ((+)-CPP) [31]) to miltiradiene [32],

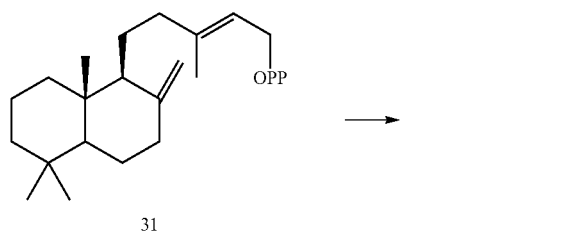

However, LlTPS4 and MsTPS1 converted (+)-copalyl diphosphate ((+)-CPP) [31]) to sadaracopimaradiene [27], white OmTPS3 converted (+)-copalyl diphosphate ((+)-CPP) [31]) to trans-biformene [34],

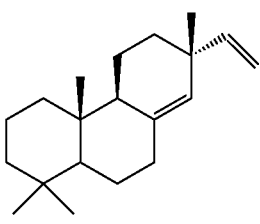

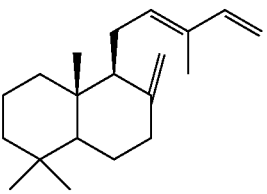

The *Ajuga reptans* miltiradiene synthase (ArTPS3) has the amino acid sequence shown below (SEQ ID NOT).

```
  1 MSLSFTIKVT PFSGQRVHSS TESFPIQQFP TITTKSAMAV
 41 KCSSLSTATV SFQDFVGKIR DTINGKVDNS PAATTIHPAD
 81 IPSNLCVVDT LQRLGVDRYF QSEIDSVLND TYRFWQQKGE
121 DIFTDVACRA MAFRLLRVKG YEVSSDELAS YAEQEHVNLQ
161 PSDITTVIEL YRASQTRLYE DEGNLEKLHT WTSNFLKQQL
201 QSETISDEKL HKQVEYYLKN YHGILDRACV RQSLDLYDIN
241 QYQNLKSTDR FPTLSNEDLL EFAKQDFNFC QAQHQKELQQ
281 LQRWYADCKL DTLTYGRDVV RVASFLTAAI FCEPEFSDAR
321 LAFAKHIILV TRIDDFFDHG GSIEESYKIL DLVKEWEDKP
361 AEEYPSKEVE ILFTAVYNTV NDLAEMAYIE QGRSIKPLLI
401 KLWVEILTSF KKELDSWTED TELTLEEYLA SSWVSIGCRI
441 CSLNSLQFLG ITLSEEMLSS EECMELCRHV SSVDRLLNDV
481 QTFEKERLEN TINSVSLQLA EAQREGRTIT EEEAMSKIKD
521 LADYHRRQLM QMVYKDGTIF PRQCKDVFLR VCRIGYYLYA
561 SGDEFTTPQQ MMGDMKSLVY EPLNTSSS
```

A nucleic acid encoding the *Ajuga reptans* miltiradiene synthase (ArTPS3) with SEQ ID NOT is shown below as SEQ ID NO:2.

```
   1 ATGTCACTCT CGTTCACCAT CAAAGTCACC CCCTTTTCGG
  41 GCCAGAGAGT TCACAGCAGC ACAGAAAGCT TTCCAATCCA
  81 ACAATTTCCA ACGATCACCA CCAAATCCGC CATGGCTGTC
 121 AAATGCAGCA GCCTCAGTAC CGCAACAGTA AGCTTCCAGG
 161 ATTTCGTCGG AAAAATCAGA GATACGATCA ACGGGAAAGT
 201 TGACAATTCT CCAGCAGCGA CCACTATTCA TCCTGCAGAT
 241 ATACCCTCCA ATCTCTGCGT GGTGGATACC CTCCAAAGAT
 281 TGGGAGTTGA CCGTTACTTC CAATCTGAAA TCGACAGCGT
 321 TCTTAACGAC ACATACAGGT TCTGGCAGCA GAAAGGAGAA
 361 GATATCTTCA CTGATGTTGC TTGTCGTGCA ATGGCATTTC
 401 GACTTTTGCG AGTTAAAGGA TATGAAGTTT CATCAGATGA
 521 ACTCGCTTCG TATGCTGAAC AAGAGCATGT TAACCTGCAA
 561 CCAAGTGACA TAACTACGGT TATCGAGCTT TACAGAGCAT
 601 CACAGACAAG ATTATATGAA GACGAGGGCA ATCTTGAGAA
 641 GTTACATACT TGGACTAGCA ATTTTCTGAA GCAACAATTG
 681 CAGAGTGAAA CTATTTCTGA CGAGAAATTG CACAAACAGG
 721 TGGAGTATTA CTTGAAGAAC TACCACGGCA TACTAGACCG
 761 TGCTGGAGTT AGACAAAGTC TCGATTTATA TGACATAAAC
 801 CAATACCAGA ATCTAAAATC TACAGATAGA TTCCCTACTT
 841 TAAGTAACGA AGATTTACTT GAATTCGCGA AGCAAGATTT
 881 TAACTTTTGC CAAGCTCAAC ACCAGAAAGA GCTTCAGCAA
 921 CTGCAAAGGT GGTATGCGGA TTGTAAATTG GATACATTGA
 961 CTTACGGAAG AGATGTGGTA CGTGTTGCAA GTTTCCTGAC
1001 AGCTGCAATT TTTGGTGAGC CTGAATTCTC TGATGCTCGT
1041 CTAGCCTTCG CCAAACACAT CATCCTCGTG ACACGTATTG
1081 ATGATTTCTT CGATCATGGT GGGTCTATAG AAGAGTCATA
1121 CAAGATCCTG GATTTAGTAA AGAATGGGA AGATAAGCCA
1161 GCTGAGGAAT ATCCTTCCAA GGAAGTTGAA ATCCTCTTTA
1201 CAGCAGTATA TAATACAGTA AATGACTTGG CAGAAATGGC
1241 TTATATTGAG CAAGGCCGTT CCATTAAACC TCTTCTAATT
1281 AAACTGTGGG TTGAAATACT GACAAGTTTC AAGAAAGAAC
```

-continued

```
1321 TGGATTCATG GACAGAAGAC ACAGAACTAA CCTTGGAGGA

1361 GTACTTGGCT TCCTCCTGGG TGTCGATCGG TTGCAGAATC

1401 TGCAGTCTCA ATTCGCTGCA GTTCCTTGGT ATAACATTAT

1441 CCGAAGAAAT GCTTTCAAGC GAAGAGTGCA TGGAGTTGTG

1481 TAGGCATGTT TCTTCAGTCG ACAGGCTACT CAATGACGTG

1521 CAAACTTTCG AGAAGGAACG CCTAGAAAAT ACGATAAACA

1561 GTGTGAGCCT ACAGCTAGCA GAAGCTCAGA GAGAAGGAAG

1601 AACCATTACA GAAGAGGAGG CTATGTCAAA GATTAAAGAC

1641 CTGGCTGATT ATCACAGGAG ACAACTGATG CAGATGGTTT

1681 ATAAGGATGG GACCATATTT CCGAGACAAT GCAAAGATGT

1721 CTTTTTGAGG GTATGCAGGA TTGGCTACTA CTTATACGCG

1761 AGCGGCGATG AATTCACTAC TCCACAACAA ATGATGGGGG

1801 ATATGAAATC ATTGGTTTAT GAACCCCTAA ACACTTCATC

1841 CTCTTGA
```

The *Leonotis leonurus* sandaracopimaradiene synthase (LITPS4) has the amino acid sequence shown below (SEQ ID NO:3).

```
  1 MSVAFNLIVV RFPGHGIQSS RETFPAKIIT RTKSSMRFQS

41 SLNTSTDFVG KIREMIRGKT DNSINPLDIP STLCVIDTLH

81 SFGIDRYFQS EINSVLHHTY RLWNDRNNII FKDVICCAIA

121 FRLLRVKGYQ VSSDELAPFA QQQVTGLQTS DIATILELYR

161 ASQERLHEDD DTLDKLHDWS SNLLKLHLLN ENIPDHKLHK

201 RVGYFLKNYH GMLDRVAVRR NIDLHNINHY QIPEVADRFP

241 TEAFLEFSRQ DFNICQAQHQ KELQQLHRWY ADCRLDTLNH

281 GTDVVHFANF LTSAIFGEPE FSEARLAFAK QVILITRMDD

321 FFDHDGSREE SHKILHLVQQ WKEKPAEEYG SKEVEILFTA

361 VYTTVNSLAE KACMEQGRSV KQLLIKLWVE LLTSFKKELD

401 SWTEKMALTL DEYLSFSWVS IGCRLCILNS LQFLGIKLSE

441 EMLWSQECLD LCRHVSSVVR LLNDLQTFKK ERIENTINGV

481 DVQLAARKGE RAITEEEAMS KIKEMADHHR RKLMQIVYKE

521 GTIFPRECKD VFLRVCRIGY YLYSGDELTS PQQMKEDMKA

561 LVHESSS
```

A nucleic acid encoding the *Leonotis leonurus* sandaracopimaradiene synthase (LITPS4) with SEQ ID NO:3 is shown below as SEQ ID NO:4.

```
   1 ATGTCGGTGG CGTTCAACCT CATAGTCGTC CGTTTTCCGG

41 GCCATGGAAT TCAGAGCAGT AGAGAAACTT TTCCAGCCAA

81 AATTATTACC AGAACTAAAT CAAGCATGAG ATTCCAAAGC

121 AGCCTCAACA CTTCAACAGA TTTCGTGGGA AAAATAAGAG

161 AGATGATCAG AGGGAAAACT GATAATTCTA TTAATCCCCT

201 GGATATTCCC TCCACTCTAT GCGTAATCGA CACCCTACAC

241 AGCTTCGGAA TTGATCGCTA CTTTCAATCC GAAATCAACT

281 CTGTTCTTCA CCACACATAC AGATTATGGA ACGACAGAAA

321 TAATATCATC TTCAAAGATG TCATTTGCTG CGCAATTGCC

361 TTTAGACTTT TGCGAGTGAA AGGATATCAA GTCTCATCAG

401 ATGAACTGGC GCCATTTGCC CAACAACAGG TGACTGGACT

441 ACAAACAAGC GACATTGCCA CGATTCTAGA GCTCTACAGA

481 GCATCACAGG AGAGATTACA CGAAGACGAC GACACTCTTG

521 ACAAACTACA TGATTGGAGC AGCAACCTTC TGAAGCTGCA

561 TCTGCTGAAT GAGAACATTC CTGATCATAA ACTGCACAAA

601 CGGGTGGGGT ATTTCTTGAA GAACTACCAT GGCATGCTAG

641 ATCGCGTTGC GGTTAGACGA AACATCGACC TTCACAACAT

681 AAACCATTAC CAAATCCCAG AAGTTGCAGA TAGGTTCCCT

721 ACTGAAGCTT TTCTTGAATT TTCAAGGCAA GATTTTAATA

761 TTTGCCAAGC TCAACACCAG AAAGAACTTC AGCAACTGCA

801 TAGGTGGTAT GCAGATTGTA GATTGGACAC ACTGAATCAC

841 GGAACAGACG TAGTACATTT TGCTAATTTT CTAACTTCAG

881 CAATTTTCGG AGAGCCTGAA TTCTCCGAGG CTCGTCTAGC

921 CTTTGCTAAA CAGGTTATCC TAATAACACG TATGGATGAT

961 TTCTTCGATC ACGATGGGTC TAGAGAAGAA TCACACAAGA

1001 TCCTCCATCT AGTTCAACAA TGGAAAGAGA AGCCCGCCGA

1041 AGAATATGGT TCAAAGGAAG TTGAGATCCT CTTTACAGCA

1081 GTGTACACTA CAGTAAATAG CTTGGCAGAA AAGGCTTGTA

1121 TGGAGCAAGG CCGTAGTGTC AAACAACTTC TAATTAAGCT

1161 GTGGGTCGAG CTGCTAACAA GTTTCAAGAA AGAATTGGAT

1201 TCATGGACGG AGAAGATGGC GCTAACCTTG GATGAGTACT

1241 TGTCTTTCTC CTGGGTGTCA ATTGGCTGCA GACTCTGCAT

1281 TCTCAATTCC CTGCAATTTC TTGGGATAAA ATTATCTGAA

1321 GAAATGCTGT GGAGTCAAGA GTGTCTGGAT TTATGCCGGC

1361 ATGTTTCATC AGTGGTTCGC CTGCTCAACG ATTTACAAAC

1401 TTTCAAGAAG GAGCGCATAG AAAATACGAT AAACGGTGTG

1441 GACGTTCAGC TAGCTGCTCG TAAAGGCGAA AGAGCCATTA

1481 CAGAAGAGGA GGCCATGTCC AAGATTAAGG AAATGGCTGA

1521 CCATCACAGG AGAAAACTGA TGCAAATTGT GTATAAAGAA

1561 GGAACCATTT TTCCAAGAGA ATGCAAAGAT GTGTTTTTGA

1601 GAGTGTGCAG GATTGGCTAC TATCTCTACT CGGGCGATGA

1641 GTTAACTTCT CCACAACAAA TGAAGGAGGA TATGAAAGCG

1681 TTGGTACATG AATCATCCTC TTGA
```

The *Mentha spicata* class I diterpene synthase (MsTPS1) has the amino acid sequence shown below (SEQ ID NO:5).

```
  1 MSSIRNLSLH IDLPKAEKKL VEKIRERIRN GRVEMSPSAY
 41 DTAWVAMVPS RGYSGRPGFP ECVDWIIENQ NPDGSWGLDS
 81 DQPLLVKDSL SSTLACLLAL RKWKTHNQLV QRGMEFIDSR
121 GWAATDDDNQ ISPIGFNIAF PAMINYAKEL NLTLPLHPPS
161 IHSLLHIRDS EIRKRNWEYV AEGVVDDTSN WKQIIGTHQR
201 NNGSLFNSPA TTAAVIHSH DDKCFRYLIS TLENSNGGWV
241 PTIYPYDIYA PLCMIDTLER LGIHTYFEVE LSGIFDDIYR
281 NWQEREEEIF CNVMCRALAF RLLRMRGYHV SSDELAEFVD
321 KEEFFNSVSM QESGEGTVLE LYRASLTKIN EEERILDKIH
361 AWTKPFLKHQ LLNRSIRDKR LEKQVEYDLK NFYGALVRFQ
401 NRRTIDSYDA KSIQTSKTAY RCSTVYNEDF IHLSVEDFKI
441 SRAQYLKELE EMNKWYSDCR LDLLTKGRNA CRESYILTAA
481 IIVDPHESMA RISYAQSILL ITVFDDFFDH YGSKEEALNI
521 IDLVKEWKPA GSYCSKEVEI LFTALHDTIN EIAAKADAEQ
561 GFSSKQQLIN MWVELLESAV REKDSLSXNK VSTLEEYLSF
601 APITIGCKLC VLTSVHFLGI KLSEEIWTSE ELSSLCRHGN
641 VVCRLLNDLK TYEREREENT LNSVSVQTVG GGVSEEEAVT
681 KVEEVLEFHR RKVMQLACRR GGSSVPRECK ELVWKTCTIG
721 YCLYGHDGGD ELSSPKDILK DINAMMFEPL K
```

A nucleic acid encoding the *Mentha spicata* class I diterpene synthase (MsTPS1) with SEQ ID NO:5 is shown below as SEQ ID NO:6.

```
   1 ATGAGTTCCA TTCGAAATTT AAGTTTGCAT ATTGATCTGC
  41 CAAAGGCCGA GAAGAAGTTG GTTGAGAAAA TCAGAGAGAG
  81 GATAAGAAAT GGGAGGGTGG AGATGTCGCC GTCGGCTTAC
 121 GACACCGCGT GGGTGGCCAT GGTGCCGTCT CGAGGATATT
 161 CCGGCAGGCC GGGTTTCCCG GAGTGCGTGG ATTGGATAAT
 201 CGAGAACCAG AATCCCGACG CGTCGTGGGG TTTGGATTCG
 241 GATCAACCAC TTCTGGTCAA AGACTCCCTC TCGTCCACCT
 281 TGGCATGCCT ACTTGCCCTG CGTAAATGAA AAACACACAA
 321 CCAACTAGTG CAAAGGGGCA TGGAGTTCAT CGACTCCCGT
 361 GGTTGGGCTG CAACTGATGA TGACAATCAG ATTTCTCCTA
 401 TTGGATTCAA TATTGCCTTT CCTGCAATGA TTAATTACGC
 441 CAAAGAGCTT AATTTAACTC TGCCTCTACA TCCACCTTCG
 481 ATTCATTCAT TGTTACACAT TAGAGATTCA GAAATAAGAA
 521 AGCGAAACTG GGAATACGTA GCTGAAGGAG TAGTCGACGA
 561 TACAAGCAAT TGGAAGCAAA TAATCGGCAC GCATCAAAGA
 601 AATAATGGAT CCTTGTTCAA CTCACCTGCT ACCACTGCAG
 641 CTGCTGTTAT TCACTCTCAC GACGATAAAT GTTTCCGATA
 681 TTTGATCTCC ACTCTTGAGA ATTCTAACGG TGGATGGGTA
 721 CCAACTATCT ATCCATACGA TATATACGCT CCTCTCTGCA
 761 TGATCGATAC GCTAGAAAGA TTAGGAATAC ACACATATTT
 801 TGAAGTTGAA CTCACCGGCA TTTTTGATGA CATATACAGG
 841 AATTGGCAAG AGAGAGAAGA AGAGATCTTT TGTAATGTTA
 881 TGTGTCGACC TCTGGCATTT CGGCTTCTAC GAATGAGGGG
 921 ATATCATGTT TCATCTGATG AACTAGCAGA ATTTGTGGAC
 961 AAGGAGGAGT TTTTTAATAG CGTGAGCATG CAAGAGAGCG
1001 GCGAAGGCAC AGTGCTTGAG CTTTACAGAG CTTCACTCAC
1041 AAAAATCAAC GAAGAAGAAA GGATTCTCGA CAAAATTCAT
1081 GCATGGACCA AACCATTTCT CAAGCACCAG CTTCTCAACC
1121 GCAGCATTCG CGACAAACGA TTAGAGAAGC AGGTGGAATA
1161 CGACTTGAAG AACTTCTACG GCGCACTAGT CCGATTCCAG
1201 AACAGAAGAA CCATCGACTC TACGATGCT AAATCAATCC
1241 AAATTTCGAA AACAGCATAT AGGTGCTCTA CAGTTTACAA
1281 TGAAGACTTC ATCCATTTAT CCGTTGAGGA CTTCAAAATC
1321 TCCCGAGCAC AATACCTAAA AGAACTTGAA GAAATGAACA
1361 AGTGGTACTC TGATTGTAGG TTGGACCTCT TAACTAAAGG
1401 AAGAAATGCA TGTCGAGAAT CTTACATTTT AACAGCTGCA
1441 ATCATTGTCG ATCCTCACGA ATCCATGGCT CGLATCTCTT
1481 ACGCTCAATC TATTCTTCTT ATAACTGTTT TCGACGACTT
1521 TTTCGATCAT TATGGGTCTA AAGAAGAGGC TCTCAATATT
1561 ATTGATCTAG TCAAGGAATG GAAGCCAGCT GGCAGTTACT
1601 GCTCCAAAGA AGTGGAGATT TTGTTTACTG CATTACACGA
1641 CACGATAAAT GAGATTGCAG CCAAGGCTGA TGCAGAGCAA
1681 GGCTTTTCTT CCAAACAACA GCTTATCAAC ATGTGGGTGG
1721 AGCTACTTGA GAGCGCCGTG AGAGAAAAGG ACTCGCTGAG
1761 TGGNAACAAA GTGTCGACTC TAGAAGAGTA CTTATCTTTC
1801 GCACCAATCA CCATCGGCTG CAAACTTTGC GTCCTGACGT
1841 CTGTCCATTT CCTCGGAATC AAACTGTCCG AGGAAATCTG
1881 GACTTCCGAG GAGTTGAGCA GTCTGTGCAG GCACGGCAAT
1921 GTTGTCTGCA GACTGCTCAA CGACCTCAAG ACTTACGAGA
1961 GAGAGCGCGA AGAGAACACG CTCAACAGCG TGAGCGTGCA
2001 GACAGTGGGA GGAGGCGTTT CGGAGGAAGA GGCGGTGACG
2041 AAGGTGGAGG AGGTGTTGGA ATTTCATAGA AGAAAAGTGA
2081 TGCAGCTCGC GTGTCGAAGA GGAGGAAGCA GTGTTCCGAG
2121 AGAATGTAAG GAGCTGGTGT GGAAGACGTG CACGATAGGT
2161 TACTGCTTGT ACGGTCACGA CGGAGGCGAT GAGTTATCGT
2201 CTCCGAAGGA TATTCTAAAG GACATTAATG CAATGATGTT
2241 TGAGCCTCTC AAGTGA
```

A *Nepeta mussinii* ent-kaurene synthase (NmTPS2) was identified and isolated as described herein. This NmTPS2 enzyme was identified as an ent-kaurene synthase, which converts ent-CPP [16] into ent-kaurene [19].

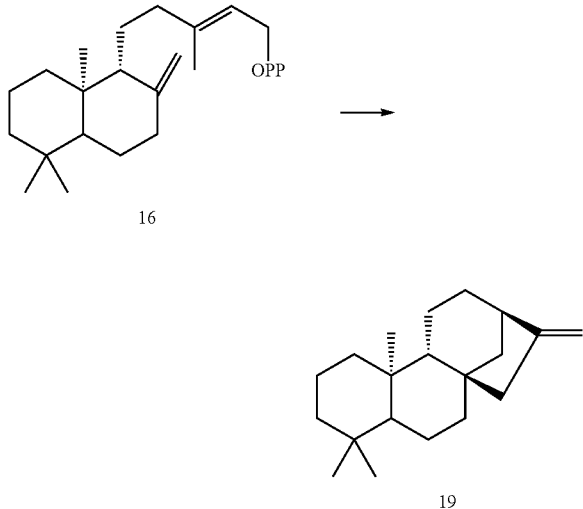

16

19

The *Nepeta mussinii* ent-kaurene synthase (NmTPS2) has the amino acid sequence shown below (SEQ ID NO:7).

```
  1 MSLPLSSCVL FPPNDSRFPV SRFSRASASL EVGLQGATSA
 41 KVSSQSSCFE ETKRRITKLF HKDELSVSTY DTAWVAMVPS
 81 PTSSEEPCFP GCLTWLLENQ CRDGSWARPH HHSLLKKDVL
121 SSTLACILAL KKWGVCEEQI NKGLHFIELN CASATEKCQI
161 TPVGFDIIFP AMLDYARDFS LNLRLEPTTF NDLMDKRDLE
201 LKRCYQNYTP EREAYLAYIV EGMGRLQDWE LVMKYQRKNG
241 SLFNCPSTTA AAFIALRDSA CLNYLNLSLK KFGNAVPAVY
281 PLDIYSQLCT VDNLERLGIN QYFIAEIQSV LDETYRCWIQ
321 GNEDIFLDTS TCALAFRILR MNGYDVTSDS TTKILEECFS
361 SSFRGNMTDI NTTLDLYRAS ELMLYPDEKD LEKHNLRLKL
401 LLKQKLSTVL IQSFQLGRNI NEEVKQTLEH PFYASLDRIA
441 KRKNIEHYNF DNTRILKTSY CSPNFGNKDF FFLSIEDFNW
481 CQVIHRQELA ELERWLIENR LDELKFARSK SAYCYFSAAA
521 TFFAPELSDA RMSWAKSGVL TTVVDDFFDV GGSMEELKNL
561 IQLVELWDVD ASTKCSSHNV HIIFSALRRT IYEIGNKGFK
601 LQGRNITNHI IDIWLDLLNS MMKETEWARD NFVPTIDEYM
641 SNAYTSFALG PIVLPTLYLV GPKLSEEMIN HSEYHNLFKL
681 MSTCGRLLND IRGYERELKD GKLNALSLYI INNGGKVSKE
721 AGISEMKSWI EAQRRELLRL VLESNKSVLP KSCKELFWHM
761 CSVVHLFYCK DDGFTSQDLI QVVNAVIHEP IALKDFKVHE
```

A nucleic acid encoding the *Nepeta mussinii* ent-kaurene synthase (NmTPS2) with SEQ ID NO:7 is shown below as SEQ ID NO:8.

```
   1 ATGTCTCTTC CGCTCTCCTC TTGTGTCTTA TTTCCCCCCA
  41 ATGACTCACG TTTTCCGCTC TCCCGCTTTT CTCGCGCTTC
  81 AGCTTCTTTG GAAGTCGGGC TTCAAGGAGC TACTTCAGCA
 121 AAAGTCTCCT CACAATCATC GTGTTTTGAG GAGACAAAGA
 161 GAAGGATAAC AAAGTTGTTT CATAAGGACG AACTTTCGGT
 201 TTCGACATAT GACACAGCAT GGGTTGCTAT GGTCCCTTCT
 241 CCAACTTCTT CAGAGGAACC TTGCTTCCCA GGTTGTTTGA
 281 CTTGGTTGCT TGAAAACCAG TGTCGAGATG GTTCATGGGC
 321 TCGTCCCCAC CATCACTCTT TGTTAAAAAA AGATGTCCTT
 361 TCTTCTACCT TGGCATGCAT TCTCGCACTT AAAAAATGGG
 401 GGGTTGGTGA AGAACAAATC AACAAGGGTT TGCATTTTAT
 441 AGAGCTAAAT TGTGCTTCAG CTACCGAGAA GTGTCAAATT
 481 ACTCCCGTGG GGTTTGACAT TATATTTCCT GCCATGCTTG
 521 ATTATGCAAG AGACTTCTCT TTGAACTTGC GTTTAGAGCC
 561 AACTACGTTT AATGATTTGA TGGATAAAAG GGATTTAGAG
 601 CTCAAAAGGT GTTACCAAAA TTACACACCG GAGAGGGAAG
 641 CATACTTGGC ATATATAGTT GAAGGAATGG GAAGATTGCA
 681 AGATTGGGAA TTGGTGATGA AATATCAAAG AAAGAATGGA
 721 TCTCTTTTCA ATTGTCCATC TACAACTGCA GCAGCTTTTA
 761 TTGCCCTTCG GGATTCTGCG TGCCTCAACT ATCTGAATTT
 801 GTCTTTGAAA AAGTTCGGGA ATGCAGTTCC TGCAGTTTAT
 841 CCTCTAGATA TATATTCTCA ACTTTGCACG GTTGATAATC
 881 TTGAAAGGCT GGGGATCAAC AATATTTTA TAGCAGAAAT
 921 TCAGAGTGTG TTGGATGAAA CGTACAGATG TTGGATACAG
 961 CGAAACGAAG ACATATTTTT GGACACCTCA ACTTGTCCTT
1001 TAGCATTCCG AATATTGAGA ATGAATGGCT ATGATGTGAC
1041 TTCAGATTCA CTTACAAAAA TCCTAGAAGA GTGCTTTTCA
1081 AGTTCCTTTC GTGGAAATAT GACAGACATT AACACAACTC
1121 TTGACTTATA TAGGGCATCA GAACTTATGT TATATCCAGA
1161 TGAAAAGGAT CTGGAGAAAC ATAATTTAAG GCTTAAACTC
1201 TTACTTAAGC AAAAACTATC CACTGTTTTA ATCCAATCAT
1241 TTCAACTTGG AAGAAATATC AATGAAGAGG TGAAACAGAC
1281 TCTCGAGCAT CCCTTTTATG CAAGTTTGGA TAGGATTGCA
1321 AAGCGGAAAA ATATAGAGCA TTACAACTTT GATAACACAA
1361 GAATTCTTAA AACTTCATAT TGTTCGCCAA ATTTTGGCAA
1401 CAAGGATTTC TTTTTTCTTT CCATAGAAGA CTTCAATTGG
1441 TGTCAAGTCA TACATCGACA AGAACTCGGA GAACTTGAAA
1481 GATGGTTAAT TGAAAATAGA TTGGATGAGC TGAAGTTTGC
```

-continued

```
1521 AAGGAGTAAG TCTGCATACT GTTATTTTTC TGCGGCAGCA

1561 ACTTTTTTIG CTCCAGAATT GTCGGATGCC CGCATGTCAT

1601 GGGCTAAAAG TGGTGTTCTA ACCACAGTGG TAGATGACTT

1641 TTTTGATGTT GGAGGTTCTA TGGAGGAATT GAAGAACTTA

1681 ATTCAATTGG TTGAACTATG GGATGTGGAT GCTAGCACAA

1721 AATGCTCTTC TCATAATGTC CATATAATAT TTTCAGCACT

1761 TAGGCGCACC ATCTATGAGA TAGGGAACAA AGGATTTAAG

1801 CTACAAGGAC GTAACATTAC CAATCATATA ATTGACATTT

1841 GGCTAGATTT ACTAAACTCT ATGATGAAAG AAACCGAATG

1881 GGCCAGAGAC AACTTTGTCC CAACAATTGA TGAATACATG

1921 AGCAATGCAT ATACATCGTT TGCTCTGGGG CCAATTGTCC

1961 TTCCAACTCT CTATCTTGTC GGGCCCAAGC TCTCAGAAGA

2001 GATGATTAAC CACTCCGAAT ACCATAACCT ATTCAAATTG

2041 ATGAGTACGT GCGGACGTCT TCTAAATGAC ATCCGTGGTT

2081 ATGAGAGAGA ACTGAAAGAT GGTAAATTGA ACGCGTTATC

2121 ATTGTACATA ATTAATAATG GTGGTAAAGT AAGTAAAGAA

2161 GCTGGCATCT CGGAGATGAA AAGTTGGATC GAGGCACAAC

2201 GAAGAGAGTT ACTGAGATTA GTTTTGGAGA GCAACAAAAG

2241 CGTCCTTCCG AAGTCGTGCA AGGAATTGTT TTGGCATATG

2281 TGCTCAGTGG TGCATCTATT CTACTGCAAA GATGATGGAT

2321 TCACCTCGCA GGATTTGATT CAAGTTGTAA ATGCAGTTAT

2361 TCATGAACCT ATTGCTCTCA AGGATTTTAA GGTGCATGAA

2401 TAA
```

An *Origanum majorana* trans-abienol synthase (OmTPS3) was identified and isolated. When this OmTPS3 enzyme was expressed in *N. benthamiana* with *Hyptis suaveolens* labda-7,13E-dienyl diphosphate synthase (HsTPS1) a new compound, labda-7,12E,14-triene [24], was produced. The HsTPS1 enzyme produced labda-7,13(16),14-triene [22] when HsTPS1 was expressed in *N. benthamiana*.

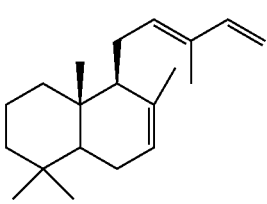

24

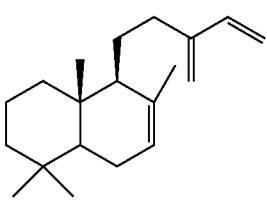

22

OmTPS3 also produced trans-abienol [11] from labda-13-en-8-ol diphosphate ((+)-8-LPP) [10]).

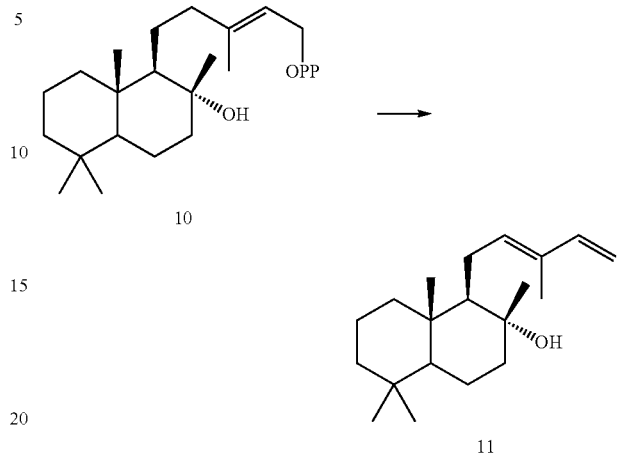

The *Origanum majorana* trans-abienol synthase (OmTPS3) has the amino acid sequence shown below (SEQ ID NO:9).

```
MASLAFTPGA ATFSGNVVRR RKDNFPVHGF PTTIRSSVSV

TVKCYVSTTN LMVNIKEKFK GKNVNSLTVE AADDDMPSNL

CIIDTLQRLG IDRYFQPQVD SVLDHAYKLW QGKEKDTVYS

DISIHAMAFR LLRVKGYQVS SEELDPYIDV ERMKKLKTVD

VPTVIELYRA AQERMYEEEG SLERLHVWST NFLMHQLQAN

SIPDEKLHKL VEYYLKNYHG ILDRVGVRRN LDLFDISHYP

TLRARVPNLC TEDFLSFAKE DFNTCQAQHQ KEHEQLQRWF

EDCRFDTLKF GRETAVGAAH FLSSAILGES ELCNVRLALA

KHMVLVVFID DFFDHYGSRE DSFKILHLLK EWKEKPAGEY

GSEEVEILFT AVYNTVNELA EMAHVEQGRN IKGFLIELWV

EIVSIFKIEL DTWSNDTTLT LDEYLSSSWV SVGCRICILV

SMQLLGVQLT DEMLLSDECI NLCKHVSMVD RLLNDVGTFE

KERKENTGNS VSLLLAAAVK EGRPITEEEA IIKIKKMAEN

ERRKLMQIVY KRESVFPRKC KDMFLKVCRI GCYLYASGDR

FTSPQKMKED VKSLIYESL
```

A nucleic acid encoding the *Origanum majorana* trans-abienol synthase (OmTPS3) with SEQ ID NO:9 is shown below as SEQ ID NO: 10.

```
ATGGCGTCGC TCGCGTTCAC ACCCGGAGCC GCCACTTTCT

CCCCCAACCT AGTTCGGAGG AGGAAAGATA ACTTTCCGGT

CCACGGATTT CCGACGACGA TCAGGTCATC GGTCTCCGTC

ACCGTCAAAT GCTACGTCAG TACAACGAAT TTGATGGTGA

AAATCAAAGA GAAGTTCAAG GGTAAAAACG TCAATTCGCT

GACAGTTGAA GCTGCTGATG ACGATATGCC CTCTAATCTG
```

```
                     -continued
TGCATAATTG ACACCCTCCA ACGATTGGGA ATCGACCGTT

ACTTCCAACC CCAACTCGAC TCTGTTCTCG ACCACGCCTA

CAAACTATGG CAAGGGAAAG AGAAAGATAC GGTGTATTCG

GACATTAGTA TTCATGCGAT GGCATTTAGA CTTTTACGAG

TCAAAGGCTA TCAAGTCTCT TCGGAGGAAC TGGATCCATA

CATCGATGTG GAGCGAATGA AGAAACTGAA AACAGTTGAT

GTTCCGACGG TTATCGAACT GTACAGAGCG GCACAGGAGA

GAATGTATGA AGAAGAAGGT AGCCTTGAGA GACTCCATGT

TTGGAGCACC AACTTCCTCA TGCACCAGCT GCAGGCTAAC

TCAATTCCTG ATGAAAAGCT ACACAAACTG GTGGAATACT

ACTTGAAGAA CTACCATGGC ATACTGGATA GAGTTGGAGT

TCGACGAAAC CTCGACCTAT TCGACATAAG CCATTATCCA

ACACTCAGAG CTAGGGTTCC GAACCTATGT ACCGAAGATT

TTCTATCGTT CGCGAAGGAA GATTTCAATA CTTGCCAAGC

CCAACACCAG AAAGAACATG AGCAACTACA AAGGTGGTTC

GAAGATTGTA GGTTCGATAC GTTGAAGTTC GCAAGGGAGA

CAGCCGTAGG CGCTGCTCAT TTTCTATCTT CAGCAATACT

TGGTGAATCT GAACTATGTA ATGTTCGTCT TGCCCTTGCT

AAGCATATGG TGCTTGTGGT ATTCATCGAT GACTTCTTCG

ACCATTATGG CTCTAGAGAA GACTCCTTCA AGATCCTCCA

CCTCTTAAAA GAATGGAAAG AGAAGCCGGC CGGAGAATAC

GGTTCCGAGG AAGTCGAAAT CCTCTTCACA GCCGTATACA

ATACAGTAAA CGAGTTGGCG GAGATGGCTC ATGTCGAACA

AGGACGTAAT ATCAAAGGAT TTCTAATTGA ATTGTGGGTT

GAAATAGTGT CAATTTTCAA GATAGAACTG GATACATGGA

GCAATGACAC AACACTAACC TTGGATGAGT ACTTGTCCTC

CTCATGGGTG TCGGTCGGTT GCAGAATCTG CATCCTCGTC

TCAATGCACC TCCTCGGTGT ACAACTAACC GACGAAATGC

TTCTGAGCGA CGAGTGCATA AACCTGTGTA AGCATGTCTC

GATGGTCGAT CGCCTCCTCA ACGACGTCGG AACATTCGAG

AAGGAACGGA AGGAGAATAC AGGAAACAGT GTGAGCCTTC

TGCTAGCAGC AGCTGTGAAA GAAGGAAGGC CTATTACCGA

AGAGGAAGCT ATTATTAAAA TTAAAAAAAT GGCGGAAAAC

GAGAGGAGGA AACTAATGCA GATTGTGTAT AAAAGAGAGA

GTGTTTTCCC CAGAAAATGC AAGGATATGT TCTTGAAGGT

GTGTAGAATT GGGTGCTATC TATACGCGAG CGGCGACGAA

TTTACGTCTC CTCAGAAAAT GAAGGAAGAT GTGAAATCCT

TAATTTATGA ATCCTTGTAG
```

The *Origanum majorana* manool synthase (OmTPS4) can also convert ent-copalyl diphosphate (ent-CPP) [16] to ent-manool [20].

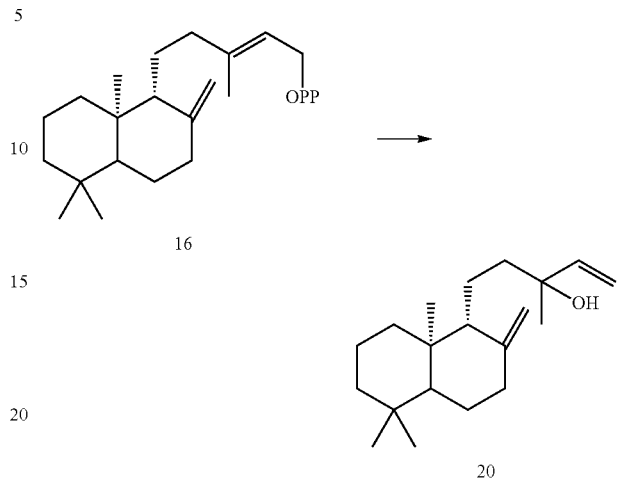

In addition, *Origanum majorana* manool synthase (OmTPS4) can also convert (+)-copalyl diphosphate ((+)-CPP) [31]) to manool [33].

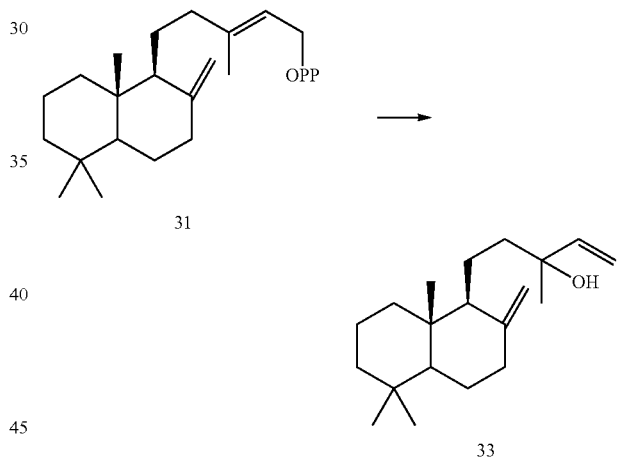

The *Origanum majorana* manool synthase (OmTPS4) can have the amino acid sequence shown below (SEQ ID NO:11).

```
MSLAFSHVST FFSGQRVVGS RREIIPVNGV PTTANKPSFA

VKCNLTTKDL MVKMKEKLKG QDGNLTVGVA DMPSSLCVID

TLERLGVDRY FRSEIHVILH DTYRLWQQKD KDICSNVTTH

AMAFRLLRVN GYEVSSEELA PYANLEHFSQ QKVDTAMAIE

LYRAAQERIH EDESGLDKIL AWTTTFLEQQ LLTNSILDNK

LHKLVEYYLN NYHGQTNRVG ARRHLDLYEM SHYQNLKPSH

SLCNEDLLAF AKQGFRDFQI QQQKEFEQLQ RWYEDCRLDK

LSYGRDVVKI SSFMASILMD DPELADVRLS IAKQMVLVTR

IDDFFDHGGS REDSYKIIEL VKEWKEKAEY DSEEVKILFT
```

```
AVYTTVNELA EACVQQGRNS TTVKEFLVQL WIEILSAFKV

ELDTWSDGTE VSLDEYLSWS WISNGCRVSI VTTMHLLPTK

LCSDEMLRSE ECKDLCRHVS MVCRLLNDIH SFEKEHEENT

GNSVSILVAG EDTEEEAIGK IKEIVEYERR KLMQIVYKRG

TILPRECKDI FLKACRATFY VYSSTDEFTS PRQVMEDMKT

LSS
```

A nucleic acid encoding *Origanum majorana* manool synthase (OmTPS4) with SEQ ID NO:11 is shown below as SEQ ID NO: 12.

```
ATGTCACTCG CCTTCAGCCA TGTTAGTACC TTTTTCTCCC

GCCAAAGAGT CGTCGGAAGC AGGAGAGAGA TTATTCCAGT

TAACCGAGTT CCGACGACGG CCAATAAGCC GTCGTTCGCC

GTTAAGTGCA ACCTTACTAC AAAGGATTTG ATGGTGAAAA

TGAAGGAGAA GTTGAAGGGG CAAGACCGTA ATTTGACTGT

CGGAGTAGCC GATATGCCCT CTAGCCTGTG CGTGATCGAC

ACTCTTGAAA GGTTGGGAGT TGACCGATAC TTCCGATCTG

AAATCCACGT TATTCTACAC GACACTTACC GGTTATGGCA

ACAAAAGGAC AAAGATATAT GTTCCAACGT TACTACTCAT

GCAATGGCGT TTAGACTTCT GAGAGTGAAT GGATACGAGG

TTTCATCAGA GGAACTGGCT CCATATGCTA ACCTAGAGCA

CTTTAGCCAG CAAAAAGTTG ATACTGCAAT GGCTATAGAG

CTCTACAGAG CAGCACAGGA GAGAATACAC GAAGACGAGA

GCGGTCTCGA CAAAATACTT GCTTGGACCA CCACTTTTCT

CGAGCAACAG CTGCTCACTA ACTCCATTCT TGACAATAAA

TTGCATAAAC TGGTGGAGTA CTACTTGAAC AACTACCACG

CCCAAACGAA TAGGGTCGGA GCTAGACGAC ACCTCGACCT

ATATGAGATG AGCCATTACC AAAATCTAAA ACCTTCACAT

AGTCTATGCA ATGAAGACCT TCTAGCATTT GCAAAGCAAG

GTTTTCGAGA TTTTCAAATC CAGCAGCAGA AAGAATTCGA

GCAACTGCAA AGGTGGTATG AAGATTGCAG GTTGGACAAG

TTGAGTTATG GGAGAGATGT AGTAAAAATT TCTAGTTTCA

TGGCTTCAAT ATTGATGGAT GATCCAGAAT TAGCCGATGT

TCGTCTCTCC ATCGCCAAAC AGATGGTGCT CGTGACACGT

ATCGATGATT tCTTCGACCA CGGTGGCTCT ACAgAaGACT

CCTACAAGAT CATTGAACTA GTAAAAGAAT GGAAGGAGAA

GGCaGAATAC GATTCCGAGG AAGTAAAAAT CCTTTTTACA

GCAGTATACA CCACAGTAAA TGAGCTAGCA GAGGCTTGTG

TTCAACAAGG AAGGAATAGT ACTACTGTCA AAGAATTCCT

AGTTCAGTTG TGGATTGAAA TACTATCAGC TTTCAAGGTC

GAGCTAGATA CGTGGAGCGA TGGCACGGAA GTAAGCCTGG

ACGAGTACTT GTCGTGGTCG TGGATTTCGA ATGGCTGCAG

AGTGTCTATA GTAACGACGA TGCATTTGCT CCCTACGAAA

TTATGCAGTG ATGAAATGCT TAGGAGTGAA GAGTGCAAGG

ATTTGTGTAG GCATGTTTCT ATGGTTGGCC GCTTGCTCAA

CGACATCCAC TCTTTTGAGA AGGAGCATGA GGAGAATACG

GGAAACAGTG TGAGCATTCT AGTAGCAGGT GAGGATACCG

AAGAGGAAGC TATTGGAAAG ATCAAAGAGA TAGTTGAGTA

TGAGAGGAGA AAATTGATGC AAATTGTGTA CAAGAGAGGA

ACCATTCTCC CAAGAGAATG CAAAGACATA TTCTTGAAGG

CGTGTAGGGC TACATTTTAC GTGTACTCGA GCACGGATGA

GTTTACGTCT CCTCGACAAG TGATGGAAGA TATGAAAACC

CTAAGCTCCT AG
```

*Origanum majorana* palustradiene synthase (OmTPS5) can also convert (+)-copalyl diphosphate ((+)-CPP) [31]) to palustradiene [29].

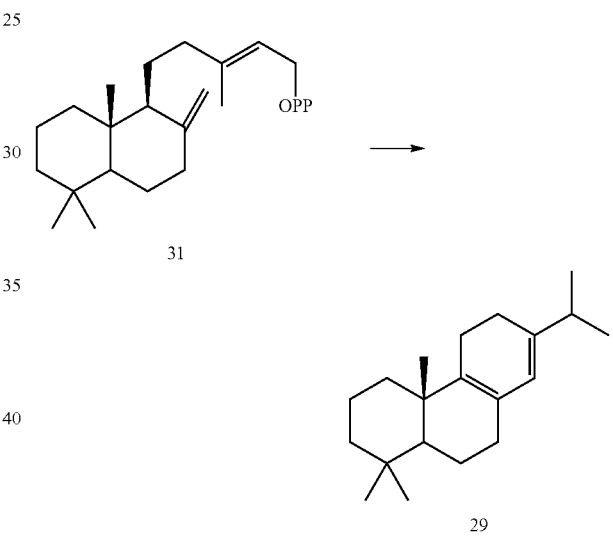

The *Origanum majorana* palustradiene synthase (OmTPS5) can have the amino acid sequence shown below (SEQ ID NO: 13).

```
MVSACLKLKN NPFLDHRFRK SSNGFSVNFP ATMLTTVKCS

RDNSEDLIAK IKERMNEKFV TVPAREYSVI EHRNPKPAWC

GGLQSKTVIE EEVCSRLFLV EHLQDLGVDR FFQSEIQHIL

HHTFRLWQQK DEQVFKDVTC RAMAFRLLRL EGYHVSSGEL

GEYVDEEKFF RTVRLEWRST DTILELYKAS QVRLPEDDND

NSNILKNLHE WTFIFLKEQL RRKTILDKGL ERKVEFYLKN

YHGILDAVKH RRSLDHTRFW KTTAYNPAVY DEDLERLSAQ

DFMARQAQSQ KELEMLLKWY DECRLDKMEY GRNVIHVSHF

LNANNFPDPR LSETRLSFAK TMTLVTRLDD FFDHHGSRED

SVLIIELIRQ WNEPSTITTI FPSEEVEILY SALHSTVTDI
```

```
AEKAYPIQGR CIKSLIIHLW VEILSSFMSE MDSCTAETQP

DFHEYLGFAW ISIGCRICIL IAIHFLGEKV SQQMVMGAEC

TELCRHVSTI ARLLNDLQTF KKEREERKVN SVIIQLKGDK

ISEEVAVSNI ERMVEYHRKE LLKMVVRREG SLVPKRCKDV

FWKSCNIAYY LYAFTDEFTS PQQMKEDMKL LFRDPINCVP

SIPS
```

A nucleic acid encoding the *Origanum majorana* palustradiene synthase (OmTPS5) with SEQ ID NO:13 is shown below as SEQ ID NO:14.

```
ATGGTATCTG CATGTCTAAA ACTCAAAAAT AATCCTTTCT

TGGACCATCG ATTCAGGAAA AGCAGCAATG GATTTTCAGT

TAATTTTCCG GCGACCATGC TCACCACTGT CAAGTGCAGC

CGCGATAATT CAGAAGACTT GATAGCAAAG ATAAAGAAA

GGATGAATGA AAAATTTGTT ACGGTGCCGG CGAGGGAATA

TTCCGTCATT GAGCATCGGA ATCCGAAGCC GGCGTGGTGC

GGTCGTITGC AATCCAAAAC AGTAATAGAA GAAGAAGTGT

GCAGCCGTCT GTTTCTGGTC GAACACCTTC AAGATTTAGG

AGTAGACCGC TTCTTTCAAT CAGAAATCCA ACATATTCTA

CATCACACAT TCAGATTATG GCAGCAAAAA GATGAACAAG

TTTTTAAAGA CGTGACATGT CGCGCCATGG CATTCAGACT

CCTGCGTCTC GAAGGTTATC ATGTCTCGTC AGGAGAATTG

GGGGAGTATG TTGATGAGGA AAAATTCTTT AGAACGGTAA

GGTTAGAATG GAGAAGTACG GATACAATTC TTGAGCTGTA

CAAAGCATCA CAGGTAAGAC TACCTGAAGA CGACAACGAC

AATTCCAATA TCCTCAAAAA CTTGCACGAA TGGACCTTCA

TATTTTTGAA GGAGCAGTTG CGGCGTAAAA CTATTCTTGA

TAAAGGTTTA GAGAGAAAGG TAGAATTTTA CTTGAAGAAT

TACCACGGCA TATTAGACGC GGTTAAGCAT AGACGAAGCC

TCGATCACAC ACGATTCTGG AAAACTACTG CGTATAACCC

TGCAGTGTAT GATGAGGATC TTTTCCGATT GTCGGCCCAA

GATTTCATGG CTCGCCAAGC TCAGAGCCAA AAGGAACTTG

AGATGTTGCT CAAGTGGTAC GATGAATGTA GACTGGACAA

GATGGAGTAT GGGCGAAACG TGATACACGT TTCCCATTTC

TTAAACGCAA ACAACTTCCC CGATCCTCGC CTGTCCGAAA

CTCGTCTATC CTTTGCGAAA ACCATGACTC TCGTCACGCG

TTTGGATGAT TTCTTCGATC ACCATGGCTC TAGAGAAGAT

TCGGTCCTCA TCATCGAATT AATAAGGCAG TGGAATGAGC

CTTCAACTAT TACAACAATA TTCCCCTCCG AAGAAGTGGA

GATTCTCTAC TCTGCACTCC ACTCCACCGT AACAGATATA

GCAGAGAAGG CTTATCCCAT CCAGGGTCGC TGCATCAAAT

CGCTCATAAT TCATCTGTGG GTCGAGATAC TGTCGAGCTT

CATGAGCGAA ATGGACTCGT GCACCGCGGA AACTCAGCCG

GACTTTCACG AGTACTTAGG GTTTGCATGG ATCTCGATCG

GCTGCAGAAT CTGCATTCTC ATAGCTATAC ATTTCTTGGG

GGAGAAGGTA TCTCAACAAA TGGTTATGGG TGCTGAGTGC

ACCGAGTTAT GTAGGCACGT TTCTACGATC GCACGCCTTC

TCAACGATCT CCAAACCTTT AAGAAGGAGA GAGAAGAGAG

GAAGGTAAAC AGCGTGATAA TCCAGCTCAA AGGGGATAAG

ATATCGGAGG AGGTGGCCGT GTCAATATA GAGAGAATGG

TTGAATATCA CAGGAAAGAG CTGCTGAAGA TGGTGGTTCG

GAGAGAAGGA AGCTTGGTTC CTAAGAGGTG TAAGGACGTG

TTCTGGAAAT CCTGCAACAT TGCTTACTAT CTGTACGCTT

TTACAGATGA ATTCACTTCG CCTCAACAAA TGAAGGAAGA

TATGAAACTA CTCTTTCGTC ATCCAATCAA CTGCGTTCCT

TCAATTCCTT CATGA
```

The *Perovskia atriplicifolia* miltiradiene synthase (PaTPS3) can have the amino acid sequence shown below (SEQ ID NO: 15).

```
MLLAFNISDV PLSQHRVILS RREHFPRHAF QEFPMIAATK

SSVNAICSLA TPIDLMGKIK EKFKAKDGDP LAAAAIQLAA

DIPSSLCITD TLQRLGVDRY FQSEIDSILE ETHKLWKVKD

RDIYSEVTTH AMAFRLLRVK GYEVSSEELA PYAEQERFDL

QTIDLATVIE LYRAAQERTC EENDNSLEKL LAWTTTFLKH

QLLTNSIPDT KLHKQVEYYL KNYHGILDRM GVRRSLDLYD

ISHYRPLRAR FPNLCNEDFL SFARQDFSMC QAQHQKELEQ

LQRWYSDCRL DALLKFGRNV VRVSSFLTSA IIGEPELSEV

RLVFAKHIIL VTLIDDLFDH GGTREESYKI LELVTEWKEK

TAAEYGSEEV EILETAVYNT VNELVERAHV EQGRSVKEFL

IKLWVQILSI FKIELDTWSD ETALTLDEYL SSSWVSIGCR

ICILMSMQFI GIKLTDEMLL SEECTDLCRH VSMVDRLLND

VQTFEKERKE NTGNSVSLLL AANKDVTEEE AIRRAKEMAE

CNRRQLMQIV YKTGTIFPRK CKDMFLKVCR IGCYLYASGD

EFTSPQQMME DMKSLVYEPL YLPN
```

A nucleic acid encoding the *Perovskia atriplicifolia* miltiradiene synthase (PaTPS3) with SEQ ID NO: 13 is shown below as SEQ ID NO: 16.

```
ATGTTACTTG CGTTCAACAT AAGCGATGTC CCTCTCTCGC

AGGATAGAGT AATTCTGAGC AGGAGGGAAC ATTTTCCACC

TCATGCATTC CAGGAATTTC CGATGATCGC CGCTACTAAG

TCATCTGTTA ATGCCATTTG CAGCCTCGCT ACTCCAACTG

ATTTGATGGG AAAAATAAAA GAGAAGTTCA AGGCCAAGGA
```

-continued

```
CGGCGATCCT CTTGCCGCCG CGGCTATTCA ACTCGCGGCG

GATATACCCT CGAGTCTGTG TATAATCGAC ACCCTCCAGA

GGTTGGGAGT CGACCGATAC TTCCAATCCG AAATCGACTC

TATTCTAGAG GAAACACACA AGTTATGGAA AGTGAAAGAT

AGAGATATAT ACTCTGAGGT TACTACTCAT GCAATGGCGT

TTAGACTTCT GCGAGTGAAG GGATATGAAG TTTCATCAGA

CGAACTACCT CCGTATGCTC ACCAAGAGCG CTTTGACCTG

CAAACGATTG ATCTGGCGAC GGTTATCGAG CTTTACAGAG

CAGCACAGGA GAGAACATGC GAAGAAAACG ACAACAGTCT

TGAGAAACTA CTTGCTTGGA CCACCACCTT TCTCAAGCAC

CAATTGCTCA CCAACTCCAT ACCTGACACC AAATTGCACA

AACAGGTGGA ATACTACTTG AAGAACTACC ACGGGATATT

AGATAGAATG GGAGTTAGAC GAAGCCTCGA CCTATACGAC

ATAAGCCATT ATCGACCTCT GAGAGCAAGA TTCCCTAATC

TGTGTAATGA AGATTTCCTA TCATTTGCGA GGCAAGATTT

CAGTATGTGC AACCCCAAC ACCAGAAGGA ACTTGAGCAA

CTGCAAAGGT GGTATTCTGA TTGTAGGTTG GACGCGTTGT

TGAAGTTTGG AAGAAATGTA GTGCGCGTTT CTAGCTTTCT

GACTTCAGCA ATTATTGGTG AACCCGAATT GTCTGAAGTT

CGACTAGTCT TTGCCAAACA TATTATTCTC GTTACACTTA

TTCATGATTT ATTCGATCAT GGTGGAACTA GAGLAGAGTC

ATACAAGATC CTTGAATTAG TAACAGAATG GAAAGAGAAG

ACCGCAGCAG AATATGGTTC CGAGGAAGTT GAAATCCTTT

TTACAGCGGT CTACAACACA GTAAATGAGT TGGTAGAGAG

GGCTCATGTC GAACAAGGGC GCAGTGTCAA AGAATTTCTT

ATTAAACTGT GGGTTCAAAT ACTATCAATT TTCAAGATAG

AATTAGATAC ATGGAGCGAT GAGACTGCGC TAACCTTGGA

TGAATACTTG TCTTCGTCGT GGGTGTCAAT TGGTTGCAGA

ATCTGCATTC TCATGTCGAT GCAATTCATC GGTATAAAAT

TAACTGATGA AATGCTTCTG AGTGAAGAGT GCACTGATTT

GTGTAGGCAT GTTTCGATGG TTGACCGGCT GCTCAACGAT

GTGCAAACCT TCGAGAAGGA ACGCAAAGAA AATACAGGAA

ACAGTGTAAG CCTTCTGCTA GCAGCTAACA AAGATGTTAC

TGAAGAGGAA GCAATTAGAA GAGCAAAAGA AATGGCGGAA

TGCAACAGGA GACAACTGAT GCAGATTGTG TATAAAACAG

GAACCATTTT CCCAAGAAAA TGCAAAGATA TGTTTCTCAA

GGTATGCAGG ATTGGCTGTT ATTTGTATGC AAGCGGCGAC

GAATTCACAT CTCCACAACA AATGATGGAA GATATGAAAT

CCTTCGTTTA TGAACCCCTC TACCTACCTA ATTAA
```

A *Perovskia atriplicifolia* miltiradiene synthase (PaTPS1) can have the amino acid sequence shown below (SEQ ID NO:17).

```
MSLTFNAGVV RFSSHRVRST KDCFTVYGFP MIANKAAFAV

KCSLTPTDLM GRVEEKFKGK NGNSLAASTT VESADIPSNL

CIIDTLQRLG VDRYFQTEIN AILEDTYRLW ERKDKDIYSD

ATTHAMAFRL LRVKGYEVSS EELAPYADQE CVNVQTADVA

TVIELYRAAQ VRISEEESSL KKLHAWTTTF LKYQLQSNSI

PEKKLHKLVE YYLKNYHGIL DRMGVRMDLD LFDISHYRTL

QASDRFSSLR NEDFLEFARQ DFNICQAKHQ KELQQLQRWY

ADCRLDTLKF GRDVVRVANF LTSAIFGEPE LSDARLIFAK

HIVLVTCIDE FFDHGGSKEE SYKILELVEE WKEKPTGEYG

CEEVEILFTA VYSTVNELAE MAHVEQGRSV KEFLVKLWVQ

ILSIFKIELD TWSDDTELTL DSYLNNSWVS IGCRICILMS

MQFAGVKLSD EMLLSEECVD LCRHVSMVDR LLNDVQTFEK

ERKENTGNSV SLLQAAAERE GRAITEEEAI TQIKELAEYH

RRKLMQIVYK TDTIFPRKCK DMFLKVCRIG CYLYASGDEF

TTPQQMMEDM KSLVYQPLTV DDMSAKELTS VRN
```

A nucleic acid encoding the *Perovskia atriplicifolia* miitiradiene synthase (PaTPS1) with SEQ ID NO: 13 is shown below as SEQ ID NO: 18.

```
ATGTCACTCA CTTTCAACGC TGGAGTCGTC CGTTTCTCCA

GCCACCGCGT TCGGAGCACG AAAGATTGCT TTACAGTTTA

CCGATTTCCG ATGATTGCAA ATAAGGCAGC TTTCGCAGTT

AAATGCAGCC TTACTCCAAC CGATTTGATG GGGAGAGTAG

AGGAGAAGTT CAAGGGCAAA ATGGTAATT CACTAGCAGC

CTCGACGACG GTTGAATCCG CGGATATACC CTCGAACCTG

TGTATAATCG ACACCCTCCA AAGATTGGGA GTCGACCGAT

ACTTTCAAAC TGAAATCAAT GCCATTCTAG AGGACACTTA

CAGATTATGG GAACGAAAAG ACAAAGACAT ATATTCCGAT

GCCACAACTC ACGCGATGGC GTTTAGGTTA CTACGAGTGA

AAGGATACGA AGTTTCATCA GAGGAACTGG CTCCTTACGC

TGATCAAGAG TGCGTGAACG TGCAAACGGC TGATGTGGCA

ACAGTTATCG AGCTTTACAG AGCAGCGCAG GTGAGAATAA

GCGAAGAAGA GAGCAGTCTT AAGAAGCTTC ATGCTTGGAC

CACCACCTTT CTCAAATATC AGTTGCAGAG TAACTCCATA

CCTGAAAAGA AACTGCACAA ACTGGTGGAA TATTACTTGA

AGAACTACCA TGGCATATTG GATAGAATGG GAGTTCGAAT

GGACCTCGAC TTATTCGACA TCAGCCATTA TCGAACTCTA

CAAGCTTCCG ATAGGTTCTC TAGTCTGCGT AACGAAGATT

TTCTAGAGTT TGCAAGGCAA GATTTCAATA TCTGCCAAGC
```

```
CAAGCACCAG AAAGAACTCC AACAACTGCA AAGGTGGTAT
GCAGATTGCA GGCTCGACAC CTTGAAGTTC GGGAGAGACG
TCGTACGCGT TGCTAATTTT CTGACTTCAG CAATCTTTGG
CGAACCCGAG CTATCCGATG CTCGTCTGAT CTTTGCCAAG
CATATCGTGC TCGTAACATG TATCGATGAA TTCTTCGATC
ATGGTGGGTC TAAAGAAGAG TCCTACAAGA TCCTTGAATT
AGTAGAAGAA TGGAAAGAGA AGCCAACTGG AGAATATGGG
TGTGAGGAGG TTGAGATCCT TTTCACAGCA GTGTACAGTA
CAGTGAATGA GTTGGCAGAG ATGGCTCATG TCGAACAAGG
ACGTAGTGTG AAAGAGTTTC TAGTTAAACT GTGGGTGCAG
ATACTGTCGA TTTTCAAGAT AGAACTGGAT ACATGGAGTG
ATGACACGGA ACTGACGTTG ACAGCTACT TGAACAACTC
GTGGGTGTCG ATCGCATGCA GAATCTGCAT TCTCATGTCG
ATGCAGTTCG CCGGTGTAAA ACTGTCCGAC GAAATGCTTC
TGAGTGAAGA GTGTGTTGAC TTGTGCAGGC ACGTCTCCAT
GGTCGATCGC CTCCTGAACG ATGTGCAAAC TTTCGAGAAG
GAACGCAAGG AAAATACAGG AAACAGTGTG AGCCTTCTGC
AAGCAGCAGC TGAGAGAGAA GGAAGACCCA TTACAGAAGA
GGAAGCTATT ACACAGATCA AAGAATTGG TGAATACCAC
AGGAGAAAAC TGATGCAGAT TGTGTACAAA ACAGACACCA
TTTTCCCAAG AAAATGCAAA GATATGTTCT TGAAGGTGTG
CAGGATTGGG TGCTATCTGT ACGCAAGTGG AGACGAATTC
ACAACTCCAC AACAAATGAT GGAAGACATG AAATCATTGG
TTTATCAACC CCTAACAGTT GATGACATGA GTGCCAAAGA
ATTGACTTCT GTGAGAAACT AG
```

The *Salvia officinalis* miltiradiene synthase (SoTPS1) can have the amino acid sequence shown below (SEQ ID NO: 19).

```
MSLAFNAAVA TFSGHRIRSR REILPGQGFP MITNKSSFAV
KCNLTTIDLM GKITEKFKGR DSNFSAATAV QPAADIPSNL
CIIDTLQRLG VDRYFQSEID TILEDTYRLW QRKEREIFSD
ITIHAMAFRL LRVKGYVVSS EELAPYADQE RINLQRIDVA
TVIELYRAAQ ERISEDESSL EKLHAWTATY LKQQLLTNSI
PDKKLNKLVE CYLKNYHGIL DRMGVRQNLD LYDISHYQTL
KAADRFSNLR NEDFLAFARQ DFNICQEQHQ KELQQLQRWY
ADCRLDTLKY GRDVVRVANF LTSAIIGDPE LSEVRLVFAK
HIVLVTRIDD FFDHGGSREE SYKILELLKE WKEKPAAEYG
SKEVEILFIA VYNTVNELAE MAHIEQGRSV KEFLIKLWVQ
IISIFKIELD TWSDETALTL DEYLSSSWVS IGCRICILMS
MQFIGIKLSD EMLLSEECID LCREVSMVDR LLNDVQTFEK
ERKENTGNSV SLLLAANKDD SAFTEEEAIT KAKEMAECNR
RQLMKIVYKT GTIFPRKCKD MFLKVCRIGC YLYASGDEFT
SPQQMMEDMK SLVYEPLTVD PLEAKNVSGK
```

A nucleic acid encoding the *Salvia officinalis* miltiradiene synthase (SoTPS1) with SEQ ID NO: 19 is shown below as SEQ ID NO:20.

```
ATGTCCCTCG CCTTCAACGC AGCAGTTGCC ACTTTCTCCG
GCCACAGAAT TCGGAGCAGG AGAGAAATTC TTCCGGGGCA
AGGATTTCCG ATGATCACCA ACAAGTCGTC TTTCGCCGTG
AAATGTAACC TTACTACAAC AGATTTGATG GGCAAGATAA
CAGAGAAATT CAAGGGAAGA GACAGTAATT TTTCAGCAGC
AACCGCTGTT CAACCTGCGG CGGATATACC CTCTAACCTG
TGCATAATCG ACACCCTCCA AAGGTTGGGA GTCGACCGAT
ACTTCCAATC TGAAATCGAC ACTATTCTAG AGGACACATA
CAGGTTATGG CAAAGGAAAG AGAGAGAGAT ATTTTCGCAT
ATAACTATTC ATGCAATGGC ATTTAGACTT TTGCGAGTTA
AAGGATATGT AGTTTCATCA GAGGAACTGG CTCCGTATGC
TGACCAAGAG CGCATTAACC TGCAAAGGAT TGATGTAGCG
ACAGTTATCG AGCTTTACAG AGCAGCACAG GAGAGAATAA
GTGAAGACGA GAGCAGTCTT GAGAAACTAC ATGCTTGGAC
CGCCACCTAT CTCAAGCAGC AGCTGCTCAC TAACTCCATT
CCTGAGAAGA AATTGAACAA ACTGGTGGAA TGCTACTTGA
AGAACTATCA CGGGATATTA GATAGAATGG GAGTTAGACA
AAACCTCGAC CTCTACGACA TAAGCCACTA TCAAACTCTA
AAAGCTGCAG ATAGGTTCTC TAATCTACGT AATGAAGATT
TTCTAGCATT TGCGAGGCAA GATTTTAATA TTTGCCAAGA
ACAACACCAA AAAGAACTTC AGCAACTGCA AAGGTGGTAT
GCAGATTGTA GGTTGGACAC ATTGAAGTAT GGAAGAGATG
TCGTGCGGGT TGCTAATTTT CTAACATCAG CAATTATTGG
TGATCCTGAA TTGTCTGAAG TCCGTCTAGT CTTCGCCAAA
CATATTGTGC TTGTAACACG TATTGATGAT TTTTTCGATC
ATGGTGGATC TAGAGAAGAG TCCTACAAGA TCCTTGAATT
ACTAAAAGAA TGGAAAGAGA AGCCAGCTGC AGAATATGGT
TCCAAAGAAG TTGAAATTCT TTTCACAGCA GTATACAATA
CAGTAAACGA GTTGGCAGAG ATGGCTCACA TCGAACAAGG
ACGTAGTGTT AAAGAATTTC TAATAAAGCT GTGGGTTCAA
ATCATATCGA TTTTCAAGAT AGAATTAGAT ACATGGAGCG
ATGAGACAGC GCTGACCTTG GATGAGTACT TGTCTTCGTC
GTGGGTGTCA ATTGGGTGCA GAATCTGCAT TCTCATGTCG
ATGCAATTCA TTGGTATAAA ATTATCTGAT GAAATGCTTC
TGAGTGAAGA GTGTATTGAT TTGTGTCGGC ATGTCTCCAT
```

```
GGTTGACCGG CTGCTCAACG ACGTGCAGAC TTTCGAGAAG

GAACGCAAGG AAAATACAGG AAATAGCGTG AGCCTTCTGC

TAGCAGCTAA CAAAGACGAC AGCGCCTTTA CTGAAGAGGA

AGCTATTACA AAAGCAAAAG AAATGGCGGA ATGTAACAGG

AGACAACTGA TGAAGATTGT GTATAAAACA GGAACCATTT

TCCCAAGAAA ATGCAAAGAT ATGTTTCTGA AGGTATGCAG

GATTGGCTGT TACTTGTATG CAAGCGGCGA TGAATTCACA

TCTCCACAAC AAATGATGGA AGATATGAAA TCCTTGGTCT

ATGAACCCCT AACAGTTGAT CCTCTCGAGG CCAAAAATGT

GAGTGGCAAA TGA
```

*Ajuga reptans* (+)-copalyl diphosphate synthase (ArTPS1) is a (+)-copalyl diphosphate ((+)-CPP) [31] synthase, and compound 31 is shown below.

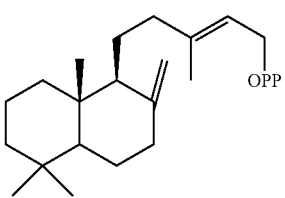

31

The *Ajuga reptans* (+)-copalyl diphosphate synthase (ArTPS1) can have the amino acid sequence shown below (SEQ ID NO:21).

```
MASLSTFHLY SSSLLHRKTL QSSPKLNLSS ECFSTRTWMN

SSKNLSLNYQ VNQKIGKLTG TRVATVDAPQ QLEHDDSTAK

GHDIVDIETQ DPIEYIRMLL NTTGDGRISV SPYDTAWIAL

IKDVEGRDFP QFPSSLEWIA NHQLADGSWG DEGFFCVYDR

LVNTIACVVA LRSWNVHHDK SQRGIQYIKE NVHQLKDGNA

EHMMCGFEVV FPALLQKAKN MGIDDLPYEA PVIQDIYHTR

EQKLKRIPLE MMHKVPTSLL FSLEGLENLD WDKLLKLQSA

DGSFLTSPSS TAFAFMQTKD EKCFQFIKNT VETFNGGAPH

TYPVDVFGRL WAVDRLQRLG ISRFFEAEIA DCLSHIHRYW

NDKGLFSGRE SDFVDIDDTS MGFRLLRMQG YDVSPNVLRN

FKNGDKFSCY GGQTIESSTP IYNLYRASQF RFPGEEILEE

ADKFAHEFLS EQLGNNQLLD KWVISDRLQE EISIGLGMPF

YATLPRVEAS YYIQHYAGAD DVWIGKTLYR MPEISNDTYL

ELARNDFKRC QAQHQFEWIY MQEWYESCNI EEFGISRKEL

LRVYFLACSS IFEVERTKER MAWAKSQIIS RMITSFENKQ

TTSSEEKETL LTEFRNINGL HKSNNTRDGD MNIVLATLHQ

FFAGFDRYTS HQLKNAWGVW LSKLQRGAVD GGADAELITT

TINVCAGHIA LKEDILSHDE YKTLTDLTSK ICQQLSHIQN

EKVVEIDGGI TAKSRLKNEE LQRDMQSLVK LVLEKSVGLN

RNIKQTFLTV AKTYYYRAYN AEETMDAHIF KVLFEPVA
```

A nucleic acid encoding the *Ajuga reptans* (+)-copalyl diphosphate synthase (ArTPS1) with SEQ ID NO:21 is shown below as SEQ ID NO:22.

```
ATCGCCTCTT TGTCCACTTT CCACCTCTAC TCTTCCTCAC

TCCTTCACCG CAAAACACTG CAATCTTCAC CAAAGCTTAA

CCTGTCTTCA GAATGCTTCT CCACCAGAAC TTGGATGAAC

AGCAGCAAAA ACTTGTCGTT AAATTACCAA GTTAATCAGA

AAATAGGAAA GCTGACAGGG ACTCGAGTTG CCACTGTGGA

TGCGCCACAA CAACTTGAAC ACGATGATTC AACTGCTAAA

GGCCATGATA TAGTCGATAT TGAAACTCAG GATCCAATTG

AATATATTAG AATGCTGTTG AACACAACAG GCGATGGCAG

AATCAGCGTT TCGCCTTACG ACACAGCATG GATTGCTCTT

ATTAAGGACG TGGAAGGACG TGATTTTCCT CAATTTCCAT

CCAGCCTTGA GTGGATCGCG AACCATCAAC TCGCTGATGG

TTCATGGGGA GACGAAGGAT TTTTCTGTGT GTATGATCGG

CTCGTAAATA CTATAGCATG TGTCGTAGCA TTGAGATCAT

CGAATGTCCA TCACGACAAG AGCCAAAGAG GAATACAATA

TATCAAGGAA AATGTGCATC AACTTAAGGA TGGAAATGCT

GAGCACATGA TGTGTGGTTT CGAAGTAGTG TTTCCTGCAC

TTCTTCAAAA AGCCAAAAAT ATGGGCATTG ATGATCTTCC

ATATGAGGCT CCTGTCATCC AGGATATTTA CCATACAAGG

GAGCAGAAAT TGAAAAGGAT ACCATTGGAG ATGATGCACA

AAGTGCCTAC TTCTCTGCTG TTTAGTTTGG AAGGACTGGA

GAATTTAGAT TGGGATAAAC TCCTTAAGTT GCAGTCAGCT

GATGGCTCTT TCCTCACTTC TCCCTCCTCT ACTGCTTTCG

CATTCATGCA AACAAAAGAC GAAAAATGCT TCCAGTTCAT

CAAGAACACT GTTGAAACCT TTAATGGAGG AGCACCACAT

ACTTATCCGG TCGATGTTTT TGGAAGACTT TGGGCGGTTG

ATAGGCTGCA GCGCCTCGGA ATTTCTCGAT TCTTTGAGGC

TGAGATTGCT GATTGCTTAA GTCACATTCA TAGATATTGG

AATGATAAGG GGCTTTTCAG TGGACGTGAA TCGGACTTTG

TCGATATTGA CGACACATCC ATGGGTTTCA GACTTCTAAG

AATGCAAGGC TATGATGTTA GTCCAAATGT ACTGAGGAAT

TTCAAGAATG GTGACAAGTT TTCATGTTAC GGAGGTCAAA

CGATCGAGTC ATCAACTCCA ATATACAATC TGTACAGACC

TTCTCAATTC CGGTTTCCAG GAGAAGAAAT TCTTGAAGAA

GCCGACAAGT TCGCCCATGA GTTCTTGTCC GAACAGCTTG

GCAACAACCA ATTGCTTGAT AAATGGGTTA TATCCGACCG
```

```
CTTGCAGGAA GAGATAAGTA TTGGATTGGG GATGCCATTT

TATGCCACCC TTCCCAGAGT TGAAGCAAGC TACTATATAC

AACATTACGC TGGTGCCGAC GACGTGTGGA TCGGCAAGAC

ACTCTACAGG ATGCCGGAAA TAAGTAATGA TACATACCTG

GAGCTAGCAA GAAATGATTT CAAGAGATGC CAAGCACAAC

ATCAGTTCGA GTGGATCTAC ATGCAAGAAT GGTATGAGAG

TTGCAACATT GAAGAATTCG GGATAAGCCG AAAGGAGCTC

CTTCGCGTTT ACTTTTTGGC TTGCTCTAGC ATCTTTGAGG

TCGAGAGGAC TAAAGAGAGA ATGGCATGGG CAAAATCTCA

AATTATTTCT AGAATGATCA CTTCTTTCTT TAATAAACAA

ACTACTTCAT CTGAGGAAAA AGAAACACTT TTAACCGAAT

TCAGAAACAT CAACGGTCTG CACAAATCAA ACAATACAAG

AGATGGAGAT ATGAACATTG TGCTTGCAAC CCTCCATCAA

TTCTTCGCTG GATTTGACAG ATATACTAGC CATCAACTGA

AAAATGCTTG GGGAGTATGG TTGACCAAGC TGCAACGAGG

AGCAGTAGAC GGTGGAGCAG ACGCAGAGCT GATAACAACC

ACCATAAACG TATGCGCCGG TCATATAGCT CTTAAGGAAG

ACATATTGTC CCACGATGAG TACAAGACTC TCACCGACCT

CACCAGCAAG ATTTGTCAGC AGCTTTCTCA TATTCAAAAC

GAAAAGGTTG TGGAAATTGA CGGTGGGATT ACAGCAAAAT

CTAGGTTGAA GAATGAGGAA CTGCAACGTG ACATGCAATC

ATTGGTGAAA TTAGTACTTG AGAAATCAGT TGGGCTCAAC

CGGAATATAA AGCAAACATT TCTAACGGTT GCAAAAACAT

ACTACTACAG AGCCTACAAT GCTGAGGAAA CTATGGATGC

CCATATATTC AAAGTTCTTT TCGAACCAGT TGCGTGA
```

*Ajuga reptans* cleroda-4(18),13E-dienyl diphosphate synthase (ArTPS2) was identified and isolated as described herein. ArTPS2 was identified as a (5R,8R,9S,10R) neo-cleroda-4(18),13E-dienyl diphosphate [38] synthase. In addition, the combination of ArTPS2 and SsSS enzymes generated neo-cleroda-4(18),14-dien-13-ol [37]. These compounds are shown below.

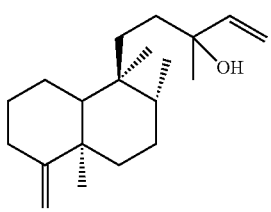

37

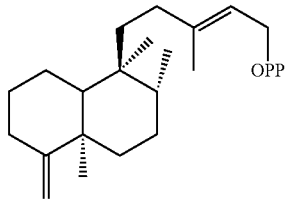

38

ArTPS2 is of particular interest for applications in agricultural biotechnology, for example, because it is useful for production of neo-clerodane diterpenoids. Neo-clerodane diterpenoids, particularly those with an epoxide moiety at the 4(18) position, have garnered significant attention for their ability to deter insect herbivores (Coll et al., Phytochem Rev 7(1):25 (2008); Klein Gebbinck et al. Phytochemistry 61(7):737-770 (2002); Li et al. Nat Prod Rep 33(10):1166-1226 (2016)). The 4(18)-desaturated products produced by ArTPS2 (e.g., compounds 37 and 38 with the =CH$_2$ 4(18) desaturation projecting from the A ring) the can be used in biosynthetic or semisynthetic routes to yield potent insect antifeedants.

The *Ajuga reptans* cleroda-4(18),13E-dienyl diphosphate synthase (ArTPS2) can have the amino acid sequence shown below (SEQ ID NO:23).

```
MSFASQATSL LSSPNRLGHV PTPSSPARFA AGGAPFWKIL

FTARSNGQYK AISRARNQGN VEYIDEIQKG PQVVLEAENS

LEDDTQKDTD QIRELVENVR VKLQNIGGGG ISISAYDTAW

VALVEDINGS GQPQFPTSLD WISNHQFPDG SWGSSKFLYY

DRILCTLACI VALKTWNVHP DKYHKGLDFI RENIHKLADE

EEVHMPIGFE VAFPSIIETA KKVGIEIPED FPGEKEIYAK

RDLKLKKIPM DILHKMPTPL LFSIEGMEGL DWQKLFKFRD

DGSFLTSPSS TAYALQQTKD ELCLKYLTDL VKKDNGGVPN

AFPVDLFDRN YTVDRLRRLG ISRYFQPEIE ECMKYVYRFW

DKRGISWARN TNVQDLDDTA QGFRNLRMHG YEVTLDVFKQ

FEKCGEFFSF HGQSSDAVLG MFNLYRASQV LFPGEHMLAD

ARKYAANYLH KRRLNNRVVD KWIINKDLEG EVAYGLDVPF

YASLPRLEAR FYIEQYGGSD DVWIGKALYR MVNVSCDTYL

ELAKLDYNKC QSVHQNEWKS FQKWYKSCSL GEFGFSEGSL

LQAYYIAAST IFEPEKSGER LAWAKTAALM ETIQQLSSQQ

KREFVDEFKH KNILKNENGE RYRSSTSLVE TLISTVNQLS

SDILLEQGRD VHQELCHVWL KWLSTWEERG NLVEAEAELL

LRTLHLNSGL DESSFSHPKY QQLLEVSTKV CHLLRLFQKR

KVYDPEGCTT DIATGTTFQI EACMQELVKL VFSRSSEDLD

SLTKLRFLDV ARSFYYTABC DPQVVESHID KVLFEKVV
```

A nucleic acid encoding the *Ajuga reptans* cleroda-4(18), 13E-dienyl diphosphate synthase (ArTPS2) with SEQ ID NO:23 is shown below as SEQ ID NO:24.

```
ATGTCATTTG CTTCCCAAGC CACCTCCCTC CTATCATCCC
CCAACCGTCT CGGCCATGTT CCGACGCCAA GCTCGCCGGC
TCGTTTCGCT GCCGGTGGTG CCCCATTTTG GAAGATATTA
TTTACAGCTA GGTCTAATGG GCAGTATAAA GCTATTTCAA
GAGCTCGTAA CCAAGGAAAT GTAGAGTACA TTGATGAGAT
TCAGAAAGGC CCGCAAGTCG TATTGGAGGC AGAAAACAGC
TTGGAAGATG ACACACAAAA AGATACTGAT CAGATAAGGG
AACTAGTGGA AAATGTCCGA GTAAAGCTGC AGAATATCCG
TGGTGGAGGG ATAAGCATAT CGGCGTACGA CACCGCATGG
GTGGCGCTGG TGGAGGACAT CAACGGCAGT GGCCAGCCAC
AGTTTCCGAC GAGCCTCGAT TGGATATCGA ACCATCAGTT
CCCTGATGGG TCATGGGCA GCAGCAAGTT TTTGTATTAT
GATCGGATTC TATGCACATT AGCATGTATA GTTGCATTGA
AAACCTGGAA TGTGCATCCT GATAAGTACC ACAAAGGGTT
GGATTTCATC AGAGAGAACA TTCACAAGCT TGCGGACGAA
GAAGAAGTGC ACATGCCAAT TGGGTTCGAA GTGGCATTCC
CATCAATTAT TGAAACAGCT AAAAAAGTAG GAATCGAAAT
CCCTGAGGAT TTTCCTGGCA AGAAAGAAAT TTATGCAAAA
AGAGATTTAA AGCTAAAAAA AATACCAATG GATATACTGC
ATAAAATGCC CACACCATTG CTCTTCAGCA TAGAAGGAAT
GGAAGGCCTT GACTGGCAAA AGCTATTCAA ATTCCGCGAT
GATGGCTCGT TTCTTACGTC TCCGTCCTCA ACAGCCTATG
CACTCCAGCA AACAAAGGAT GAGCTATGCC TCAAGTATCT
AACAGATCTT GTCAAGAAAG ACAACGGAGG AGTTCCGAAT
GCATTTCCAG TAGACCTGTT TGATCGTAAC TATACAGTAG
ACCGCTTGCG AAGGCTAGGA ATTTCACGGT ACTTTCAACC
TGAAATTGAA GAATGCATGA ATATGTTTA CAGATTTTGG
GATAAAAGAG GAATTAGCTG GGCAAGAAAT ACCAATGTTC
AGGACCTTGA TGACACTGCA CAGGGATTCA GGAATTTAAG
GATGCATGGT TATGAAGTCA CTCTAGATGT TTTCAAACAA
TTTGAGAAAT GTGGAGAGTT TTTCAGTTTT CATGGGCAAT
CCAGCGATGC TGTTTTAGGA ATGTTCAACT TGTACCGGGC
TTCTCAGGTT TTATTTCCGG GAGAACACAT GCTTGCAGAT
GCGAGGAAGT ATGCAGCCAA CTATTTGCAT AAACGAAGAC
TTAATAATAG GGTGGTCGAC AAATGGATTA TCAACAAAGA
CCTTGAAGGC GAGGTGGCAT ATGGGCTAGA TGTTCCGTTC
TACGGCAGCC TACCTCGACT CGAAGCAAGG TTCTACATAG
AACAATATGG GGGTAGTGAT GATGTGTGGA TTGGAAAAGC
TTTATACAGA ATGGTAAATG TAAGCTGCGA CACTTACCTT
GAGCTAGCAA AATTAGACTA CAACAAATGC CAATCCGTGC
ATCAGAATGA GTGGAAAAGC TTTCAAAAAT GGTACAAAAG
TTGCAGTCTT GGGGAGTTTG GGTTCAGTGA AGGAAGCCTA
CTCCAAGCTT ACTACATAGC AGCCTCAACT ATATTCGAGC
CAGAGAAATC AGGAGAACGC CTAGCTTGGG CTAAAACAGC
AGCTCTAATG GAGACAATTC AACAACTTTC CAGCCAGCAA
AAACGTGAAT TTGTTGATGA ATTCAAACAT AAAAACATAC
TGAAGAATGA AAATGGAGAA AGGTATAGAT CAAGTACCAG
TTTGGTAGAG ACTCTGATAA GCACTGTAAA TCAGCTCTCA
TCAGACATAC TATTGGAGCA AGGCAGAGAC GTTCATCAAG
AATTATGTCA CGTGTGGCTA AAATGGCTGA GTACATGGGA
GGAAAGAGGA AACCTGGTGG AAGCGGAAGC CGAGCTTCTT
CTGCGAACCT TACATCTCAA CAGCGGATTG GATGAATCAT
CATTTTCCCA CCCTAAATAT CAACAGCTCT TGGAGGTGTC
TACCAAAGTT TGCCACCTCC TTCGCCTATT TCAGAAACGA
AAGGTGTATG ATCCCGAAGG GTGTACAACC GACATAGCAA
CAGGAACAAC GTTCCAGATA GAAGCATGCA TGCAAGAACT
AGTGAAATTA GTGTTCAGCA GATCCTCAGA AGATTTAGAT
TCTCTTACTA AGTTGAGATT TTTGGATGTT GCTAGAAGTT
TCTATTACAC TGCCCATTGT GATCCACAGG TGGTCGAGTC
CCACATCGAT AAAGTATTGT TTGAGAAGGT AGTCTAG
```

The *Plectranthus barbatus* (+)-Copalyl diphosphate synthase (CfTPS16) was identified and isolated using the methods described herein, and this CfTPS116 protein can have the amino acid sequence shown below (SEQ ID NO:25).

```
MQASMSSLNL NNAPAVCSSR SQLSAKLHPP EYSTVGAWLN
RGNKNQRLGY RIRPKQLSKL TECRVASADV SGEIGKVCQS
VRTPEEVNKK IEESIKYVKE LLMTSGDGRI SVAPYDTAIV
ALIKDLEGRD APEFPSCLEW IANNQKDDGS WGDDFFCIYD
RIVNTIASVV ALKSWNVHPD KIERGVSYIK ENAHKLKGGN
LEHMTSGFEF VVPGCFDRAK ALGIEGLPYD DPIIKEIYAT
KERRLSKVPK DMIYKVPTTL LFSLEGLGME DLDWQKILKL
QSGDGSFLTS PSSTAYAFMQ TGDEKCYKFL QNAVRNCNGG
APHTYPVDVF ARLWAVDRLQ RLGISRFFQP EIKFCLDHIK
NVWTKNGVFS GRDSEFVDID DTSMGIRLLK MHGYDVDPNA
LKHFKQEDGR FSCYGGQMIE SASPIYNLYR AAQLRFPGEE
ILEEATKFAY NFLQQKLANN QIQEKWVISE HLIDEIKMGL
KMPWYATLPR VEASYYLQYY AASGDVWIGK TFYRMPEISN
DTYKELALLD FNRCQAQHQF EWIYMQEWYQ SNNIKEFGIS
KKELLLAYFL AAATIFEPER SQERIVWAKT QVVSKMITSF
```

```
LSQENALSSX QKTALFIDFG HSINGLNQIT SVEKENGLAQ

TVLATFGQLL EEYDRYTRHQ LKNAWSQWFM KLQQGDDNGG

ADAELLANTL NICAGHIAFN EDILSHNEYT SLSSLTNKIC

QRLSQIRDNK ILEIEDGSIK DKELEQEMQA LVKLVLEETG

GIDRNIKQTF LSVFKMFYYR AYHDAEAIDX HIFKVMFEPV

V
```

A nucleic acid encoding the *Plectranthus barbatus* (+)-Copalyl diphosphate synthase (CfTPS16) with SEQ ID NO:25 is shown below as SEQ ID NO:26.

```
ATGCAGGCTT CTATCTCATC TCTGAACTTG AACAATGCAC

CGGCCGTCTG CAGCAGCAGG TCACAGCTAT CCGCTAAACT

TCACCCGCCG GAATATTCCA CCGTGGGTGC ATGGCTGAAT

CGTGGCAACA AAAACCAGCG GTTGGGCTAC CGGATTCGTC

CAAAGCAACT ATCAAAACTA ACTGAGTGTC GAGTAGCAAG

TGCAGATGTG TCACAAGAGA TTGGAAAAGT CGGCCAATCT

GTTCGGACTC CTGAAGAGGT AAATAAAAAG ATAGAGGAAT

CCATCAAGTA CGTGAAGGAG CTGCTGATGA CGTCGGGCGA

CGGGCGAATC AGTGTGGCGC CCTACGACAC GGCCATAGTT

GCCCTTATCA AGGACTTGGA AGGGCGCGAT GCCCCGGAGT

TTCCATCTTG CTTGGAGTGG ATTGCAAACA ATCAAAAGA

CGATGGTTCT TGGGGGGATG ACTTCTTCTG CATCTATGAT

CGGATCGTTA ATACCATAGC ATCCGTCGTC GCCTTAAAAT

CATGGAATGT GCACCCAGAC AAGATTGAGA GAGGAGTATC

CTACATCAAG GAAAACGCGC ATAAACTAAA AGGTGGGAAT

CTCGAACACA TGACATCAGG GTTCGAGTTC GTGGTTCCCG

CGTGTTTTGA CAGAGCCAAA GCCTTGGGCA TCGAAGGCCT

TCCCTATGAT GATCCCATCA TCAAGGAGAT TTATGCTACA

AAAGAAAGGA CATTGAGCAA GGTACCGAAG GACATGATCT

ACAAAGTTCC GACAACTCTA TTGTTTAGTT TAGAGGGACT

GGGCATGGAG GATTTGGACT GGCAAAAGAT ACTGAAACTG

CAGTCGGGCG ACGGCTCATT CCTCACCTCT CCGTCGTCCA

CCGCCTACGC ATTCATGCAG ACCGGAGACG AAAAATGCTA

CAAATTCCTC CAGAACGCCG TCAGAAATTG CAACGGCGGA

GCGCCGCACA CTTATCCAGT CGACGTCTTT GCACGGCTCT

GGGCGGTCGA CCGACTTCAG CGACTCGGAA TTTCTCGCTT

CTTTCAGCCC GAGATCAAGT TTTGCCTAGA CCACATCAAA

AATGTGTGGA CTAAGAACGG AGTTTTCAGT GGACGGGATT

CAGAGTTTGT GGATATCGAC GACACATCCA TGGGCATCAG

GCTTCTGAAA ATGCACGGAT ACGATGTCGA CCCAAATGCA

CTGAAACATT TCAAGCAGGA GGATGGGAGG TTTTCATGCT

ACGGTGGTCA AATGATCGAG TCTGCATCTC CGATTTACAA
```

```
TCTCTACAGG GCTGCTCAGC TTCGTTTTCC AGGAGAAGAA

ATTCTTGAAG AAGCCACTAA ATTTGCCTAC AACTTCCTGC

AACAGAAGCT GGCCAACAAT CAAATTCAAG AAAAGTGGGT

CATATCCGAG CACCTAATTG ATGAGATAAA AATGGGATTG

AAGATGCCAT GGTACGCCAC CCTACCTAGA GTTGAGGCTT

CATACTATCT CCAATATTAT GCAGCTTCTG GCGACGTATG

GATTGGCAAG ACTTTTTACA GGATGCCAGA AATAAGTAAT

GACACGTACA AAGAGCTTGC ACTATTGGAT TTCAACCGAT

GCCAAGCACA ACATCAGTTC GAATGGATTT ACATGCAAGA

GTGGTATCAA AGCAACAACA TTAAAGAATT TGGGATAAGC

AAGAAAGAGC TTCTTCTTGC TTACTTCTTG GCTGCTGCAA

CCATTTTTGA ACCCGAACGA TCGCAAGAGC GGATCGTGTG

GGCTAAAACC CAAGTTGTTT CTAAGATGAT CACATCGTTT

CTGTCTCAAG AAAACGCTTT GTCATCGGAN CAAAAGACTG

CACTTTTCAT CGATTTTGGG CATAGTATCA ATGGCCTCAA

TCAAATAACT AGTGTTGAGA AAGAGAATGG GCTTGCTCAG

ACTGTCCTGG CAACCTTCGG ACAACTACTC GAGGAATTCG

ACAGATACAC AAGGCATCAA CTGAAAAATG CTTGGAGCCA

ATGGTTCATG AAACTGCAGC AAGGAGATGA CAATGGCGGG

GCAGACGCAG AGCTCCTAGC AAACACATTG AACATCTGCG

CTGGTCATAT TGCTTTTAAC GAAGACATAT TATCTCACAA

CGAATACACC TCTCTCTCCT CCCTCACAAA CAAAATCTGT

CAGCGGCTAA GTCAAATTCG AGATAATAAG ATACTGGAAA

TTGAGGATGG GAGCATAAAA GATAAGGAAC TAGAACAGGA

AATGCAGGCG CTGGTGAAGT TAGTCCTGGA AGAAACCGGT

GGCATCGACA GGAACATCAA GCAAACATTT TTGTCAGTTT

TCAAAATGTT TTACTACAGA GCCTACCACG ATGCTGAGGC

TATCGATGNC CATATTTTCA AAGTAATGTT TGAACCAGTC

GTATGA
```

*Hyptis suaveolens* labda-7,13E-dienyl diphosphate synthase (HsTPS1) was identified and isolated as described herein, and is a (5S, 9S, 10S) labda-7,13E-dienyl diphosphate [21] synthase. When HsTPS1 was expressed in *N. benthamiana*, labda-7,13(16), 14-triene [22] was formed. The combination of HsTPS1 with OmTPS3 produced labda-7,12E,14-triene [24].

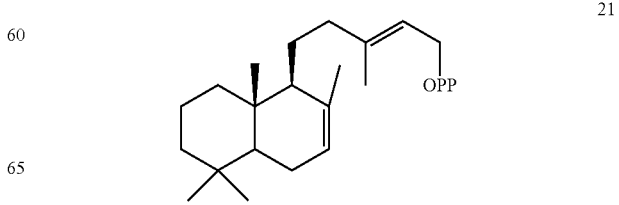

21

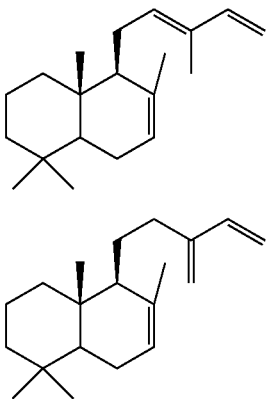

The *Hyptis suaveolens* labda-7,13E-dienyl diphosphate synthase (HsTPS1) can have the amino acid sequence shown below (SEQ ID NO:27).

```
MAYMISISNL NCSSLINTNL SAKIQLHQGL KGTWLKTSKR
MCMDQQVHGK QIAKVIESRV TDKDVSTAQD FEVLKVNRVE
DLISSIKSSL KTMEDGRISV SPYSTSWIAL IPSIDGRQTP
QFPSSLEWIV KHQLSDGSWG DALFFCVYDR LVNTIACIIA
LHTWKVHADK VKKGVSFVKE NIWKLEDANE VHMTSGFEVI
FPILLRRARD MGIDGLPSDD TPVVRMISAA RDHKLKKIPR
EVMHQVTTIL LYSLEGLEDL DWSRLFKLQS ADGSFLTSPS
STAFAFMQTN NHNCLRFITS VVQTFNGGAP DNYPIDIFAR
LWAVDRLQRL GISRFFEQEI NDCLSYVYRF WNANGVFSAG
ATNFCDLDDT SMAFRLLRLH GYDVDPNVLR KFKEGDRFCC
HSGEVAMSTS PTYALYRASQ IQFPGEEILD EAFSFTRDYL
QDWLARDQVL DKWIVSKDLP DEIKVGLEVP WYASLPRVEA
AYYMQRHYGG STDAWVAKTC YRMPDVSNDD YLELARLDFK
RCQAQHQSEL SYMQRWYDSC NVEEFGISRK ELLVAYFVAA
ATIFEPERAT ERIVWAKTEI VSKMIKAFFG EDSLDQKTML
LKEFRNSINN GSHRFMKSEH RIVNILLQAL QELLHGSDDC
RIGQLKNAWY EWLMKFEGGD EASLWGEGEL LVTTLNICTA
HFLQHHDLLL NHDYITLSEL TNRICLKLSQ IQVGEMNEMR
EDMQALTKLV IGESCIVNKN IKQTFLAVAK TFYYRAYFDA
DTVDLHIFKV LFEPIV
```

A nucleic acid encoding the *Hyptis suaveolens* labda-7,13E-dienyl diphosphate synthase (HsTPS1) with SEQ ID NO:27 is shown below as SEQ ID NO:28.

```
ATGGCGTATA TGATATCTAT TTCAAATCTC AACTGTTCCT
CGCTACTAAA CACCAATCTT TCAGCAAAGA TTCAGCTGCA
CCAAGGTCTC AAAGGAACAT GGCTAAAAAC CAGCAAACGC
ATGTGCATGG ATCAACAGGT TCATGGCAAG CAGATAGCAA
AAGTGATCGA GAGCCGAGTT ACTGATAAGG ATGTTTCCAC
TGCTCAGGAC TTTGAAGTGT TAAAGGTCAA TAGAGTGGAG
GATCTGATAT CAAGCATTAA GAGTTCATTG AAGACAATGG
AAGATGGAAG AATAAGCGTG TCGCCCTACA GCACATCATG
GATCGCACTC ATTCCAAGTA TTGATGGGCG CCAGACGCCC
CAGTTTCCAT CTTCACTGGA GTCGATCGTG AAGCATCAGC
TATCAGATGG TTCATGGGGT GATGCCCTTT TTTTCTGCGT
TTATGATCGT CTCGTAAATA CGATTGCATG CATCATTGCC
CTGCACACCT GGAAGGTTCA TGCAGACAAG GTTAAAAAG
GAGTAAGTTT TGTGAAGGAA AATATATGGA AACTTGAAGA
CGCCAACGAG GTCCACATGA CTAGTGGTTT CGAAGTTATA
TTTCCCATCC TTCTTCGAAG AGCACGAGAC ATGGGAATTG
ATGGTCTTCC TTCTGATGAT ACTCCAGTTG TTAGGATGAT
TTCTGCTGCT AGGGATCACA AATTGAAAAA GATTCCGAGG
GAGGTGATGC ACCAAGTGAC AACAACTCTA TTATATAGTT
TGGAAGGGTT GGAAGATTTA GACTGGTCAA GGCTTTTCAA
ACTTCAGTCA GCTGATGGTT CATTCTTAAC TTCTCCATCT
TCAACTGCCT TCGCATTCAT GCAAACTAAT AACCACAATT
GCTTGAGATT CATCACTAGC GTTGTCCAAA CATTCAATGG
AGGAGCTCCA GATAACTATC CAATCGACAT CTTTGCAGAA
CTGTGGGCAG TTGACAGGTT ACAGCGGTTA GGGATTTCTC
GTTTCTTCGA GCAGGAGATA AATGATTGCC TAAGCTATGT
ATATAGATTT TGGAATGCAA ATGGAGTTTT CAGTGCAGGA
GCCACTAATT TTTGTGATCT TGACGACACA TCCATGGCTT
TCCGGCTACT ACGTTTGCAT GGATATGATG TCGACCCAAA
TGTTCTGAGG AAATTCAAAG AGGGAGACAG ATTCTGTTGC
CACAGTGGTG AAGTGGCGAT GTCGACATCG CCAACGTACG
CTCTCTACAG AGCTTCCCAA ATTCAGTTTC CAGGAGAAGA
AATTCTGGAT GAAGCCTTCA GCTTCACTCG CGACTATCTA
CAGGACTGGT TAGCAAGAGA TCAAGTTCTT GATAAGTGGA
TTGTATCCAA GGACCTTCCA GATGAGATTA AGGTAGGACT
AGAGGTGCCA TGGTATGCCA GCCTGCCACG GGTAGAGGCT
GCTTATTACA TGCAACGACA TTACGGCGGG TCTACTGATG
CGTGGGTGGC CAAGACTTGT TACAGGATGC CTGATGTGAG
CAACGATGAT TACCTGGAGC TTGCAAGATT GGATTTCAAG
AGATGTCAAG CCCAACATCA GACTGAATTG AGTTACATGC
AACGATGGTA TGACAGTTGC AATGTCGAAG AATTCGGAAT
AAGCAGAAAA GAGTTGCTTG TAGCTTATTT TGTGGCTGCT
GCAACTATTT TTGAACCTGA GAGAGCAACT GAGAGAATTG
TGTGGGCAAA AACTGAAATA GTTTCTAAGA TGATCAAAGC
```

```
ATTTTTTGGT GAAGACTCAT TAGACCAAAA AACTATGTTG

TTAAAAGAAT TCAGAAACAG CATCAATAAT GGCTCCCACA

GATTCATGAA GAGTGAGCAT AGAATCGTCA ACATTCTACT

ACAAGCCTTG CAGGAGCTAT TACATGGATC TGATGATTGT

CGTATTGGTC AACTCAAAAA TGCTTGGTAT GAGTGGCTGA

TGAAATTCGA GGGAGGAGAT GAAGCAAGTT TGTGGGGAGA

AGGAGAGCTT CTTGTCACCA CCTTAAACAT TTGCACAGCT

CATTTCCTTC AACACCATGA TTTACTGTTG AATCATGACT

ACATAACTCT TTCTGAGCTC ACAAACAAGA TCTGCCTCAA

GCTTTCTCAG ATTCAGGTAG GAGAAATGAA TGAAATGAGA

GAAGATATGC AGGCGTTGAC GAAATTAGTG ATTGGGGAAT

CATGCATCGT CAACAAAAAC ATTAAGCAAA CATTTCTTGC

AGTTGCAAAG ACTTTCTATT ACAGAGCCTA CTTCGATGCC

GACACCGTTG ATCTCCATAT ATTTAAAGTT CTATTTGAGC

CCATTGTCTG A
```

*Leonotis leonurus* peregrinol diphosphate synthase (LITPS1) was identified and isolated using the methods described herein. The LITPS1 enzyme was identified as a peregrinol diphosphate (PgPP) [5] synthase, where the peregrinol diphosphate (PgPP) [5] compound is shown below.

[5]

The *Leonotis leonurus* peregrinol diphosphate synthase (LITPS1) can have the amino acid sequence shown below (SEQ ID NO:29).

```
MASTASTLNL TINSTPFVST KTQAKVSLTA CLWMQDRSSS

RHVSLKHKFC RNQQLKCRAS LDVQQVRDEV FSTAQSPESV

DKKIEERKKW VKNLLSTMDD GRINWSAYDT AWISLIKEFE

GRDATQFPST LMRIAENQLA DGSWGDPDYD CSYDRIINTL

ACVVALTTWN AHPEHNKKGI KYIKENMYKL EETPVVLMTS

AFEVVFPALL NRAKNLGIQD LPYDMPIVKE ICKIGDEKLA

RIPKKMMEKE PTSLMYAAEG VENLDWEKLL KQRTPENGSF

LSSPAATAVA FMHTKDENCL RYIMYLLDKF NGGAPNVYPI

DLWSRLWATD RIQRLGISRF FKEEIKEILS YVYSYWTDIG

VYCTRDSKYA DIDDTSMGFR LLRMHGFKMD PNVFKYFQKD

DRFVCLGGQM NDSPTATYNL YRAAQYQFPG EKILEDARKF

SQEFLQHCID TNNLLDKWVI SPRFPEELKF GMEMTWYSCL

PRIEARYYVQ HYGATEDVWL GYTFFFRMEEI SNENYKELAK

LDFSKCQAQH QTEWIHMQEW YESSNAKEFG ISRKDLLFAY

FLAAASIFET ERAKERILWA KSQIICKMVK SYLENQTASL

EHKIAFLTGF GDNNNGLHTI NKGSGPVNNV MRTLQQLLGE

FDGYISSQLE NAWAAWLTKL EQGEANDGEL LATTLNICSG

RIVYNEDTLS NKEYKAFADL TNKICQNLAQ IQNKKGDEIK

DPNEGEKDKE VEQGMQALAK LVFEESGLER SIKETFLAVV

RTYHYGAYVA DEKIDVHMFK VLFEPVE
```

A nucleic acid encoding the *Leonotis leonurus* peregrinol diphosphate synthase (LITPS1) with SEQ ID NO:29 is shown below as SEQ ID NO:30.

```
ATGGCCTCCA CTGCATCCAC TCTAAATTTG ACCATCAATA

GTACACCATT TGTAAGCACC AAAACGCAAG CAAAGGTTTC

CTTGCCCGCA TGTTTATGGA TGCAGGATAG AAGCAGCAGT

AGACACGTGT CGTTAAAACA CAAATTCTGT CGAAATCAAC

AACTTAAGTG TCGAGCAAGT CTGGATGTTC AGCAAGTACG

TGATGAAGTT TTTTCCACTG CTCAATCCCC TGAATCGGTG

GATAAAAAAA TAGAGGAACG TAAAAAATGG GTGAAGAATT

TGTTGAGTAC AATGGACGAT GGACGAATAA ATTGGTCAGC

CTATGACACG GCATGGATTT CACTTATTAA AGAATTTGAA

GGACGAGATG CTCCCCAGTT TCCGTCGACT CTCATGCGCA

TCGCGGAGAA CCAATTGGCC GACGGGTCAT GGGGCGATCC

AGATTACGAC TGCTCCTATG ATCGGATAAT AAACACACTA

GCGTGTGTTG TAGCCTTGAC AACATGGAAT GCTCATCCTG

AACACAATAA AAAGGAATA AATACATCA AGGAAAATAT

GTATAAACTA GAAGAGACGC CTGTTGTACT CATGACTAGT

GCATTTGAAG TTGTGTTTCC GGCGCTTCTT AACAGAGCTA

AAAACTTGGG CATTCAAGAT CTTCCCTATG ATATGCCCAT

CGTGAAGGAG ATTTGTAAAA TAGGGGATGA GAAGTTGGCA

AGGATACCAA AGAAAATGAT GGAGAAAGAG CCAACATCGC

TGATGTATGC CGCGGAAGGA GTCGAAAACT TGGACTGGGA

AAAGCTTCTG AAACAGCGGA CACCCGAGAA TGGCTCGTTC

CTCTCTTCCC CGGCCGCAAC TGCCGTTCCA TTTATGCACA

CAAAAGATGA AAATTGCTTA AGATACATCA TGTACCTTTT

GGACAAATTT AATGGAGGAG CACCAAATGT TTATCCGATC

GACCTCTGGT CAAGACTTTG GCAACGGAC AGGATACAAC

GTCTGGGAAT TCCCGCTTC TTTAAGGAAG AGATTAAGGA

AATCTTAAGT TATGTCTATA GCTATTGGAC AGACATTGGA

GTCTATTGTA CACGAGATTC CAAATATGCT GACATTGACG

ACACATCCAT GGGATTCAGG CTTCTGAGGA TGCACGGATT

TAAAATGGAC CCAAATGTAT TTAAATACTT CCAGAAAGAC
```

```
GACAGATTTG TTTGTCTAGG TGGTCAAATG AATGATTCTC
CAACTGCAAC ATACAATCTT TACAGGGCTG CTCAATACCA
ATTTCCAGGT GAAAAAATTC TAGAAGATGC TAGAAAGTTC
TCTCAAGAGT TTCTACAACA TTGTATAGAC ACCAATAACC
TTCTAGATAA ATGGGTGATA TCCCCGCGCT TTCCGGAAGA
GTTGAAATTT GGAATGGAGA TGACATGGTA TTCCTGCCTA
CCACGAATTG AGGCTAGATA CTACGTACAA CATTATGGTG
CTACAGAGGA CGTCTGGCTT GGAAAGACTT TTTTCAGGAT
GGAAGAAATC AGTAATGAGA ACTATAAGGA GCTTGCAAAA
CTTGATTTCA GTAAATGCCA AGCACAACAT CAGACAGAGT
GGATTCATAT GCAAGAGTGG TATGAAAGTA GCAATGCTAA
GGAATTTGGG ATAAGCAGAA AAGACCTACT TTTTGCTTAC
TTTTTGGCTG CAGCTTCCAT ATTTGAAACC GAAAGGGCAA
AAGAGAGAAT TCTGTGGGCA AAATCTCAAA TTATTTGCAA
GATGGTTAAG TCATATCTGG AAAACCAAAC GGCGTCGTTG
GAGCACAAAA TCGCCTTTTT AACTGGATTC GGAGATAACA
ACAATGGCCT GCACACAATT AATAAGGGGT CTGGACCTGT
TAACAATGTC ATGAGAACCC TCCAACAGCT CCTTGGAGAA
TTCGACGGAT ATATTAGTAG TCAATTGGAA AATGCTTGGG
CAGCATGGTT GACGAAACTC GAGCAAGGCG AGGCCAACGA
TGGCGAGCTC CTCGCAACCA CACTAAACAT TTGTTCTGGG
CGTATTGTGT ATAACGAGGA TACATTATCG AACAAGGAGT
ACAAGGCTTT CGCAGACCTC ACAAATAAAA TTTGTCAAAA
TCTTGCTCAA ATCCAAAATA AAAGGGTGA CGAAATTAAG
GATCCGAATG AAGGCGAAAA GGACAAGGAA GTCGAGCAAG
GCATGCAGGC ATTGGCTAAG TTAGTTTTTG AGGAATCTGG
GCTTGAGAGG AGTATCAAAG AAACATTCTT AGCAGTGGTG
AGAACTTATC ACTATGGGGC CTATGTTGCT GATGAGAAGA
TTGATGTCCA CATGTTCAAG GTTTTGTTCG AACCAGTTGA
ATGA
```

Nepeta mussinii (+)-copalyl diphosphate synthase (NmTPS1) was identified and isolated. The NmTPS1 enzyme can synthesize compound 31, 10 shown below.

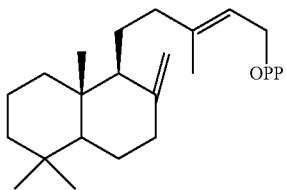

31

The Nepeta mussinii (+)-copalyl diphosphate synthase (NmTPS1) can have the amino acid sequence shown below (SEQ ID NO:31).

```
MTSISSLNLS NAAAARRRLQ LPANVHLPEF HSVCAWLNSS
SKHDPFSCRI HRKQKSKVTE CRVASVDASP VSDHKMSSPV
QTQEEANKNM EESIEYIKNL LMTSGDGRIS VSAYDTSIVA
LIKDIEGRDA PQFPSCLEWI GQNQKADGSW GDDFFCIYDR
FVNTLACIVA LKSWNLHPHK IQKGVTYIKK NVHKLKDGRP
ELMTSGFEIC VPAILQRAKD LGIQDLPYDD PMIKQITDTK
ERRLKKIPKD FIYQLPTTLL FSLEGQENLD WEKILKLQSA
DGSFLTSPSS TAAVFMHTKD EKCLKFIENA VKNCDGGVPH
TYPVDVFARL WAVDRLQRLG ISRFFQPEIK YFLDHIQSVW
TENGVFSGRD SQFCDIDDTS MGIRLLKMHG YKIDPNALEH
FKQEDGKFSC YGGQMIESAS PIYNLYRAAQ LRFPGEEILE
EAIKFSYNFL QEKLAKDEIQ EKWVISEHLI DEIKTGLKMP
WYATLPRVEA AYYLDYYAGS GDVWIGKTFY RMPEISNDTY
KEMAILDFNR CQAQHQFEWI YMQEWYESSN VKEFGISKKE
LLVAYFLAAS TIFEPERAQE RIMWAKTKIV SKMIASSLNK
QTTLSLDQKT ALFTQLEHSL NGLDSDEKDN GVAETKNLVA
TFQQLLDGFD KYTRHQLKNA WSQWLKQVQQ GEATGGADAE
LEANTLNICA GHIAFNEQVL SHNEYTTLST LTNKICHRLT
QIQDKKTLEI IDGGIRYKEL EQEMQALVKL VVEENDGGGI
DRNIKQTFLS VFKNYYYSAY HDAHTTDVHI FKVLFGPVV
```

A nucleic acid encoding the Nepeta mussinii (+)-copalyl diphosphate synthase (NmTPS1) with SEQ ID NO:31 is shown below as SEQ ID NO:32.

```
ATGACTTCAA TATCCTCTCT AAATTTGAGC AATGCAGCAG
CTGCTCGCCG CAGGTTACAA CTACCAGCAA ACGTTCACCT
GCCGGAATTT CACTCCGTCT GTGCATGGCT GAATAGCAGC
AGCAAACACG ATCCCTTTAG TTGCCGAATT CATCGAAAGC
AAAAATCGAA AGTAACCGAG TGTCGAGTAG CAAGCGTGGA
TGCATCACCA GTGAGTGATC ATAAAATGAG TTCTCCTGTT
CAAACTCAAG AAGAGGCAAA TAAAAATATG GAGGAGTCAA
TCGAGTACAT AAAGAATTTG TTGATGACAT CTGGAGACGG
GCGAATAAGC GTGTCGGCAT ACGACACGTC AATAGTCGCC
CTAATTAAGG ACATAGAAGG ACGCCACGCC CCGCAATTTC
CATCATGCCT GGAGTGGATC GGGCAAAACC AAAAGGCCGA
TGGCTCGTGG GGGGACGACT TCTTCTGTAT TTACGACCGC
TTCGTAAATA CACTAGCATG TATCGTGGCC TTGAAATCAT
GGAACCTTCA CCCTCACAAG ATTCAAAAAG GAGTGACATA
CATCAAGAAA AACGTGCATA AGCTTAAAGA TGGGAGGCCT
GAGCTGATGA CGTCAGGGTT CGAAATTTGT GTTCCCGCCA
TTCTTCAAAG AGCCAAAGAC TTGGGCATCC AAGATCTTCC
CTATGATGAT CCCATGATTA AACAGATCAC TGATACGAAA
```

```
GAGCGACGAC TCAAAAAGAT ACCGAAGGAT TTTATATACC

AATTGCCGAC GACTTTACTC TTCAGTTTGG AAGGGCAGGA

GAATTTGGAC TGGGAAAAGA TACTCAAACT GCAGTCAGCT

CACGGCTCCT TCCTTACTTC GCCGTCCTCC ACCGCCGCCG

TCTTCATGCA TACCAAAGAT GAAAAATGCT TGAAGTTCAT

AGAGAACGCC GTCAAAAATT GCGACGGCGG AGTGCCCCAT

ACCTACCCAG TAGACGTGTT TGCAAGACTT TGGGCAGTTG

ACAGACTACA ACGCCTAGGG ATTTCTCGCT TTTTTCAGCC

TGAGATTAAA TATTTCTTAG ATCACATACA AAGCGTTTGG

ACTGAGAACG GAGTTTTCAG TGGACGAGAT TCACAATTTT

GCGACATTGA TGATACGTCC ATGGGGATAA GGCTTCTGAA

AATGCATGGA TACAAATCG ACCCAAATGC ACTTGAGCAT

TTCAAGCAGG AGGATGGTAA ATTTTCGTGC TACGGTGGTC

AAATGATCGA GTCTGCATCA CCGATATACA ATCTGTACCG

AGCTGCTCAA CTCCGATTTC AGGAGAAGA AATTCTTGAA

GAGGCCATTA AATTTTCCTA TAACTTTTTG CAAGAAAAGC

TAGCCAAGGA TGAAATTCAA GAAAAATGGG TCATATCGGA

GCACTTAATT GATGAGATTA AGATCGGGCT AAAGATGCCA

TGGTACGCCA CTCTACCCCG AGTTGAAGCT GCATATTACC

TGGACTATTA TGCAGGATCC GGCGATGTGT GGATTGGCAA

GACTTTCTAC AGGATGCCAG AAATCAGTAA TGATACATAC

AAAGAAATGG CCATTTTGGA TTTCAACCGA TGCCAAGCAC

AACATCAGTT TGAATGGATT TACATGCAAG AGTGGTATGA

AAGTAGCAAC GTAAAGGAAT TTGGGATAAG CAAAAAGAG

CTACTTGTTG CTTATTTCTT GGCTGCATCA ACCATATTTG

AACCGGAAAG AGCACAAGAG AGGATTATGT GGGCAAAAAC

AAAATTGTT TCCAAAATGA TCGCATCATC TCTTAACAAA

CAAACCACTC TATCGTTAGA CCAAAAGACT GCACTTTTTA

CCCAACTCGA ACATAGTCTC AATGGCCTCG ACAGTGATGA

GAAAGATAAT GGAGTAGCTG AGACGAAAAA TCTAGTGGCA

ACCTTCCAGC AGCTGCTAGA TGGATTCGAC AAATACACTC

GCCATCAATT GAAAAATGCT TGGAGCCAGT GGTTGAAGCA

AGTGCAGCAA GGAGAGGCGA CCGGGGCGC AGACGCGGAG

CTGGAAGCAA ACACGTTGAA CATCTGTGCC GGTCATATCG

CATTCAACGA ACAAGTATTA TCGCACAACG AATACACAAC

TCTCTCCACA CTCACAAACA AGATCTGCCA CCGGCTTACC

CAAATTCAAG ACAAAAGAC GCTTGAGATA ATCGACGGCG

GCATAAGATA TAAGGAGCTG GAGCAGGAGA TGCAGGCGTT

GGTGAAATTA GTTGTTGAAG AAAACGACGG CGGCGGCATA

GACAGGAATA TTAAACAAAC ATTTTTATCA GTTTTCAAGA

ATTATTACTA CAGTGCCTAC CACGATGCTC ACACAACCGA

TGTTCATATT TTCAAAGTAT TATTTGGACC GGTCGTCTGA
```

Origanum majorana (+)-copalyl diphosphate synthase (OmTPS1) was 10 identified and isolated as describe herein. The OmTPS1 enzyme can synthesize compound 31. OmTPS1 can also synthesize palustradiene [29] (shown below), when combined with OmTPS5.

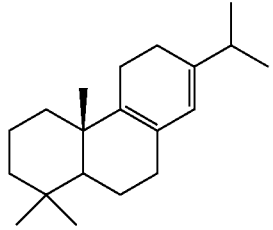

29

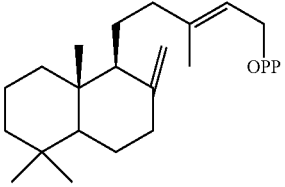

31

The Origanum majorana (+)-copalyl diphosphate synthase (OmTPS1) can have the amino acid sequence shown below (SEQ ID NO:33).

```
MTDVSSLRLS NAPAAGGRLP LPGKVHLPEF RTVCAWLNNG

CKYEPLTCRI SRRKISECRV ASLNSSQLIE KVGSPAQSLE

EANKKIEDSI EYIKNLLMTS GDGRISVSAY DTSLVALIKD

VKGRDAPQFP SCLEWIAQNQ MADGSWGDEF FCIYDRIVNT

LACLVALKSW NLHPDKIEKG VTYINENVHK LKDGSTEHMT

SGFEIVVPAT LERAKVLGIQ GLPYDHPFIK EIINTKERRL

SKIPKDLIYK LPTTLLFSLE GQGELDWEKI LKLQSSDGSF

LTSPSSTASV FMRTKDEKCL KFIENAVKNC GGGAPHTYPV

DVFARLWAVD RLQRLGISRF FQHEIKYFLD HINSVWTENG

VFSGRDSQFC DIDDTSMGVR LLKMHGYNVD PNALKHFKQE

DGNFSCYPGQ MIESASPIYN LYRAAQLRFP GEEILEEASR

FAFNFLQEKI ANHEIQEKWV ISEHLIDEIK LGLKMPWYAT

LPRVEAAYYL EYYAGSGDVW IGKTFYRMPE ISNDTYKEVA

ILDFNTCQAQ HQFEWIYMQE WYESSKVKDF GISKKDLLVA

YFLAASTIFE PERTQERIIW AKTLILSRMI TSFMNKQATL

SSQQKNAILT QLGESVDGLD KIYSGEKDSG LAETLLATFQ

QLLDGFDRYT RHQLKNAWGQ WLMKVQQGEA NGGADAELIA

NTLNICAGLI AFNEDVLLHS EYTTLSSLTN KICQRLSQIE

DEKTLEVIEG GIKDKELEED IQALVKLALE ENGGCGVDRR

IKQSFLSVFK TFYYRAYHDA ETTDLHIFKV LFGPVM
```

A nucleic acid encoding the *Origanum majorana* (+)-copalyl diphosphate synthase (OmTPS1) with SEQ ID NO:33 is shown below as SEQ ID NG:34.

```
ATGACCGATG TATCCTCTCT TCGTITGAGC AATGCACCAG
CTGCCGGCGG CAGGTTGCCG CTGCCGGGAA AGGTTCACCT
GCCTGAATTT CGCACCGTTT GTGCATGGTT GAACAATGGC
TGCAAATACG AGCCCTTGAC TTGTCGAATT AGTCGACGGA
AGATATCTGA ATGTCGAGTA GCAAGTCTGA ATTCGTCGCA
AGTAATTGAA AAGGTCGGTT CTCCTGCTCA ATCTCTAGAA
GAGGCAAACA AAAAGATCGA GGACTCCATC GAGTACATTA
AGAATCTATT GATGACATCT GGCGACGGGG GGATAAGTGT
GTCGGCTTAC GACACGTCGC TAGTCGCCCT AATAAAGGAC
GTGAAAGGAC GAGATGCCCC TCAGTTCCCG TCGTGCCTGG
AGTGGATAGC GCAAACCAA ATGGCCGACG GGTCGTGGGG
GGATGAGTTC TTCTGTATTT ACGACCGGAT CGTGAATACA
TTAGCATGCC TCGTTGCCTT GAAATCATGG AACCTTCACC
CCGACAAGAT CGAAAAGGA GTGACGTACA TCAACGAAAA
TGTGCACAAA CTGAAAGACG GGAGCACCGA GCACATGACG
TCAGGGTTCG AAATCGTGGT CCCCGCCACT CTAGAAAGAG
CCAAAGTCTT GGGCATCCAA GGCCTCCCTT ATGATCATCC
CTTCATTAAG GAGATTATTA ATACTAAGGA GCGAAGATTA
AGCAAAATAC CCAAGGATTT GATATACAAA CTGCCAACGA
CGCTGCTGTT CAGTTTAGAA GGGCAGGGAG AATTAGATTG
GGAAAAGATA CTGAAACTGC AGTCAAGCGA TGGCTCCTTC
CTTACTTCGC CCTCGTCGAC CGCCTCCGTC TTCATGCGGA
CGAAAGACGA GAAATGCCTC AAGTTCATTG AGAACGCCGT
TAAGAATTGC GGCGGGGGAG CGCCGCATAC TTACCCAGTG
GATGTGTTTG CAAGACTTTG GCAGTTGAC AGACTACAGC
GATTAGGGAT TTCTCGATTC TTCCAACACG AGATTAAATA
CTTCTTAGAT CACATTAAGA GTGTATGGAC CGAGAATGGA
GTTTTCAGTG GACGAGATTC ACAATTTTGT GATATCGACG
ACACTTCTAT GGGAGTTAGG CTTCAAAAA TGCATGGATA
CAATGTTGAT CCAAATGCGC TCAAGCATTT CAAGCAGGAG
GATGGCAAAT TCTCTTGCTA CCCTGGCCAA ATGATCGAGT
CTGCATCTCC GATATACAAT CTCTACCGAG CCGCTCAACT
CCGGTTCCCC GGAGAAGAAA TTCTCGAAGA AGCAAGTCGA
TTCGCCTTCA ACTTTCTGCA GGAAAAGATA GCCAACCATG
AAATTCAAGA AAATGGGTC ATATCTGAGC ACTTAATTGA
TGAGATAAAG TTGGGACTGA AGATGCCATG GTACGCGACT
CTGCCCCGAG TTGAGGCCGC TTATTATCTA GAGTATTATG
CTGGCTCAGG CGACGTATGG ATTGGAAAGA CTTTCTACCG
```

```
GATGCCGGAA ATCAGTAACG ATACGTATAA AGAGGTGGCC
ATTTTGGATT TCAACACATG CCAAGCTCAA CACCAGTTTG
AATGGATTTA CATGCAAGAG TGGTACGAAA GTAGCAAGGT
TAAAGATTTC GGGATAAGCA AAAAGGACCT ACTTGTTGCT
TACTTTCTGG CGGCATCGAC TATATTTGAA CCCGAAAGAA
CACAAGAGAG GATTATTTGG GCAAAAACCC TAATTCTTTC
TAGGATGATC ACATCATTTC TCAACAAACA AGCTACACTT
TCATCCCAAC AAAAGAATGC CATCTTAACA CAACTTGGAG
AGAGTGTCGA TGGCCTCGAT AAAATATATA GTGGTGAGAA
AGATTCTGGG CTGGCTGAGA CTCTGCTGGC TACCTTCCAG
CAACTGCTCG ACGGATTCGA TAGATACACT CGCCATCAAC
TGAGAAATGC TTGGGGGCAA TGGTTGATGA AAGTGCAGCA
AGGAGAGGCC AACGGTGGCG CCGACGCTGA GCTCATAGCA
AACACACTCA ATATCTGCGC CGGCCTTATC GCCTTCAACG
AAGACGTATT GTTGCACAGC GAATACACGA CTCTCTCCTC
CCTCACCAAC AAAATATGCC ACCGCCTTAG CCAGATTGAA
GATGAAAAGA CGCTTGAAGT GATTGAAGGG GGCATAAAAG
ATAAGGAACT GGAGGAGGAT ATTCAGGCGT TGGTGAAGCT
AGCCCTCGAA GAAAACGGCG GCTGCGGCGT CGACAGAAGA
ATCAAGCAGT CATTCTTATC AGTATTCAAG ACTTTTTACT
ACAGAGCCTA CCATGATGCT GAGACCACCG ATCTTCATAT
TTTCAAAGTA CTGTTGGGGC CGGGTATGTG A
```

A *Perovskia atriplicifolia* (+)-Copalyl diphosphate synthase (PaTPS1) enzyme was identified and isolated as described herein. This *Perovskia atriplicifolia* (+)-Copalyl diphosphate synthase (PaTPS1) enzyme was identified to be a (+)-copalyl diphosphate ((+)-CPP) synthase that can synthesize compound 31. The *Perovskia atriplicifolia* (+)-Copalyl diphosphate synthase (PaTPS1) can have the amino acid sequence shown below (SEQ ID NO:35).

```
MTSMSSLNLS RAPATTHRLQ LQAKVHVPEF YAVCAWLNSS
SKQAPLSCQI RCKQLSRVTE CRVASLDASQ VSEKDTSHVQ
TPDEVNKKIE DYIEYVKNLL MTSGDGRISV SPYDTSIVAL
IKDSKGRNIP QFPSCLEWIA QHQMADGSWG DQFFCIYDRI
LNTLACVVAL KSWNVHGDMI EKGVTYVKEN VHKLKDGNIE
HMTSGFEIVV PALVQRAKDL GIQGLPYDDP LIKEIADTKE
RRLKKIPKDM IYQTPTTLLF SLEGQGDLEW EKILKLQSGD
GSFLTSPSST AHVFVQTKDE KCLKFIENAV KNCSGGAPHT
YPVDVFARLW AIDRLQRLGI SRFFQPEIKY FIDHINSVWT
ENGVFSGRDS EFCDIDDTSM GIRLLKMHGY KVDPNALNHF
KQQDGKFSCY GGQMIESASP IYNLYRAAQL RFPGEEILEE
ASKFAFNFLQ EKIANDQFQE KWVISDHLID EVKLGLKMPW
YATLPRVEAA YYLQYYAGSG DVWIGKVFYR MPEISNDTYK
```

ELAILDFNRC QAQHQFEWIY MQEWYHRSSV SEFG1SKKEL

LRTYFLAAAT IFEPERTQER LVWAKTQIVS RMITSFVNNG

TTLSLDQMTA LATQIGHNFD GLDQIISAMK DHGLAGTLLT

TFQQLLDGFD RYTRHQLKNA WSQWFMKLQQ GEANGGEDAE

LLANTLNICA GFIAFNEDVL SHDEYTTLST LTNKICKRLS

QIQDKKALEV VDGSIKDKEL EQDMQALVKL VLEENGGGVD

RNIKQTFLSV FKTFYYTAYH DDETTDVHIF KVLFGPVV

A nucleic acid encoding the *Perovskia atriplicifolia* (+)-Copalyl diphosphate synthase (PaTPS1) enzyme with SEQ ID NO:35 is shown below as SEQ ID NO:36.

ATGACCTCTA TGTCCTCTCT AAATTTGAGC AGAGCACCAG

CTACCACCCA CCGGTTACAG CTACAGGCAA AGGTTCACGT

GCCGGAATTT TATGCCGTGT GTGCATGGCT GAATAGCAGC

AGCAAACAGG CACCCTTGAG TTGCCAAATT CGCTGCAAGC

AACTATCAAG AGTAACTGAA TGTCGGGTAG CAAGTCTGGA

TGCGTCGCAA GTGAGTGAAA AGCACTTC TCATGTCCAA

ACTCCCGATG AGGTGAACAA AAAGATCGAG GACTATATCG

AGTACGTCAA GAATCTGTTG ATGACGTCGG GCGACGGGCG

AATAAGCGTG TCGCCCTACG ACACGTCAAT AGTCGCCCTT

ATTAAGGACT CGAAAGGGCG CAACATCCCG CAGTTTCCGT

CGTGCCTCGA GTGGATAGCG CAGCACCAAA TGGCGGATGG

CTCATGGGGG GATCAATTCT TCTGCATTTA CGACCGGATT

CTAAATACAT TAGCATGTGT CGTAGCTTTG AAATCCTGGA

ACGTTCACGG TGACATGATC GAAAAGGAG TGACGTACGT

CAAGGAAAAT GTGCATAAGC TTAAAGATGG GAATATTGAG

CACATGACGT CGGGGTTCGA AATTGTGGTT CCCGCCCTTG

TTCAAAGAGC CAAAGACTTG GGCATCCAAG GCCTGCCCTA

TGATGATCCC CTCATCAAGG AGATTGCTGA TACAAAAGAA

AGAAGATTGA AAAAGATACC CAAGGATATG ATTTACCAAA

CGCCAACGAC ATTACTATTC AGTTTAGAAG GGCAGGGAGA

TTTGGAGTGG GAAAAGATAC TGAAACTGCA GTCAGGCGAT

GGCTCCTTCC TCACTTCGCC GTCATCCACC GCCCACGTGT

TCGTGCAGAC CAAAGATGAA AAATGCTTGA AATTCATCGA

GAACGCCGTC AAGAATTGCA GTGGAGGAGC GCCGCATACT

TATCCAGTCG ATGTCTTCGC AAGACTTTGG GCAATTGACA

GACTACAACG CCTAGGAATT TCTCGTTTCT TCCAGCCGGA

AATTAAGTAT TTCATAGACC ACATCAACAG CGTTTGGACA

GAGAACGGAG TTTTCAGTGG GCGAGATTCG GAATTTTGCG

ATATTGATGA CACGTCCATG GGCATCAGGC TTCTCAAAAT

GCACGGATAC AAAGTCGACC CAAATGCACT CAATCATTTC

AAGCAGCAAG ATGGTAAATT TTCTTGCTAC GGTGGTCAAA

TGATCGAGTC TGCATCTCCA ATATACAATC TCTACAGGGC

TGCTCAGCTA CGATTTCCAG GAGAAGAAAT TCTTGAAGAA

GCCAGTAAAT TTGCCTTTAA CTTTTTGCAA GAAAAAATAG

CCAACGATCA ATTTCAAGAA AAATGGGTGA TATCCGACCA

CTTAATCGAT GAGGTGAAGC TCGGGCTGAA GATGCCATGG

TACGCCACTC TACCCCGGGT TGAGGCTGCA TATTATCTAC

AATACTATGC TGGTTCTGGC GACGTATGGA TTGGCAAGGT

TTTCTACAGG ATGCCGGAAA TCAGCAATGA TACATACAAA

GAGCTGGCCA TATTGCATTT CAACAGATGC CAAGCACAGC

ATCAGTTCGA ATGGATTTAT ATGCAAGAGT GGTATCACAG

AAGCAGCGTT AGTGAATTCG GGATAAGCAA AAAAGAGCTG

CTTCGTACTT ACTTTCTGGC TGCAGCAACC ATATTCGAAC

CCGAGAGAAC ACAAGAGAGG CTTGTGTGGG CAAAAACCCA

AATTGTCTCT AGGATGATCA CATCATTTGT TAACAATGGA

ACTACACTAT CTTTGGACCA AATGACTGCA CTTGCAACAC

AAATCGGCCA TAATTTCGAT GGCCTCGATC AAATAATTAG

TGGTATGAAA GATCATGGAC TGGCTGGGAC TCTGCTGACA

ACCTTCCAGC AACTTCTAGA TGGATTCGAC AGATACACTC

GCCATCAACT CAAAAATGCT TGGAGCCAAT GGTTCATGAA

ACTCCACCAA GGGGAGGCGA ACGGCGGGGA AGACGCGGAG

CTCCTAGCAA ACACGCTCAA CATCTGCGCG GTTTCATTG

CTTTCAACGA AGACGTATTG TCGCACGATG AATACACGAC

TCTCTCCACC CTTACAAACA AAATCTGCAA GCGCCTTAGC

CAAATTCAAG ATAAAAAGGC GCTGGAAGTT GTCGACGGGA

GCATAAAGGA TAAGGAGCTC GAACAGGATA TGCAGGCGTT

GGTGAAGTTG GTCCTTGAAG AAAATGGCGG CGGCGTCGAC

AGGAACATCA AACAGACATT TTTGTCCGTT TTCAAGACTT

TTTACTACAC CGCCTACCAC GATGATGAGA CCACTGATGT

TCATATTTTC AAAGTACTGT TTGGACCGGT CGTATGA

*Pogostemon cablin* (10R)-labda-8,13E-dienyl diphosphate synthase (PcTPS1) was identified and isolated as described herein. This *Pogostemon cablin* (10R)-labda-8,13E-dienyl diphosphate synthase (PcTPS1) enzyme was identified to be a (10R)-labda-8,13E-dienyl diphosphate synthase, which can synthesize compound 25.

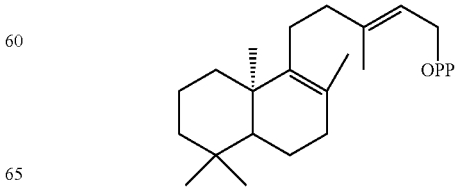

25

The combination of PcTPS1 and SsSS, both in-vitro, and in *N. benthamiana* expression produced (10R)-labda-8,14-en-13-ol [26], shown below.

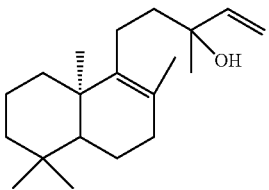

This *Pogostemon cablin* (10R)-labda-8,13E-dienyl diphosphate synthase (PcTPS1) can have the amino acid sequence shown below (SEQ ID NO:37).

```
MSFASQSHVA FVLRRPSAVA PPPPTRIPTT AALSPLKPGD
FSHGRSSFMP TSIKCNAIST SRVEEYKYTD DHNQSGLLEH
DGLISDKINE LVTKIQLMLQ NMDDGEISIS PYDTAWVSLV
EDVGGNDRPQ FPTSLEWISN NQLPDGSWGD PNAFLVHDRI
LNTLACVVAL KSWKMHPHKC NRGVSFVREN IYRMDDEKEE
HMPNGFEVVF PALLQKAKTL NIDIPYEFPG IQKFYAKRDL
KFARIPMDIL HSVPTTLLFS LEGVRCGLDL DWGKLLELQA
ADGSFLYSPS STAFALEQTK DQNCLKYLSK LVRKFDGGVP
NVYPVDLFEH NWAVDRLQRL GISRYFTPEI NQCLDYSYRY
WSNSKGMYSA SNSQIQDVDD TAMGFRLLRL NGYDVSTQGF
RQFEAGGDFF CFAGQSSQAV TGMYNLYRAS QVMFPGEKLL
EDAKKFSTNF LQQKRANNQL TDKWVIAKDV PAEVGYALDI
PWYASLPRLE ARFFIQQYGG DDDVWIGKTL YRMGYVNNNT
YLELAKLDYN TCQRLHQHEW ITIQRWYEIN LKITSVGLSK
RGVLLSYYLA AANLFEPQNS THRIAWAKTS ILVSAIQLSP
LQKRDFINQF HRSTANNGYE TSNVLVKSVI KGVHETSMDA
MLTHNKDIHR QLFNAWRKWM SVWEEGGDGE AELLLSTLNT
CDGVDESTFS DPKYEHLLEI TVRVTHQLHL IQNAETKRVG
DREEIDLSMQ QLVKLVFTKS SSDLDSCIKQ RFFAIARSFY
YVAHCDPEMV DSHIAKVLFE RVM
```

A nucleic acid encoding the *Pogostemon cablin* (10R)-labda-8,13E-dienyl diphosphate synthase (PcTPS1) enzyme with SEQ ID NO:35 is shown below as SEQ ID NO:38.

```
ATGTCATTTG CTTCTCAATC ACATGTCGCC TTTGTACTCC
GACGGCCATC TGCCGTTGCT CCGCCACCAC CGACTAGAAT
TCCGACAACA GCCGCTCTTT CTCCTCTCAA ACCAGGTGAT
TTTTCCCATG GCAGATCATC ATTTATGCCC ACTTCCATTA
AATGTAATGC AATTTCCACA TCTCGCGTCG AAGAATACAA
GTACACGGAT GATCATAATC AGAGTGGTTT ATTGGAGCAT
```

-continued
```
GATGGTTTGA TATCAGACAA GATAAATGAA TTGGTGACCA
AGATACAATT GATGCTACAA AACATGGATG ACGGAGAGAT
AAGCATCTCC CCATATGACA CCGCATGGGT GTCGTTGGTG
GAGGATGTGG GCGGCAACGA CCGCCCACAG TTTCCTACGA
GCCTGGAGTG GATATCGAAT AACCAGCTCC CCGACGGCTC
GTGGGGCGAC CCGAATGCCT TTTTGGTGCA CGACCGTATC
CTCAACACAT TGGCATGCGT CGTTGCACTC AAATCCTGGA
AAATGGACCC CCACAAATGC AATAGAGGAG TTAGTTTCGT
CACAGAAAAT ATATACAGAA TGGATGATGA AAAAGAGGAA
CACATGCCAA ATGGATTCGA AGTGGTATTT CCAGCACTCC
TTCAAAAAGC GAAAACCCTA AACATTGATA TCCCGTACGA
GTTTCCAGGA ATACAAAAAT TTTATGCCAA AAGAGATTTA
AAATTCGCCA GGATTCCAAT GGATATATTG CATAGCGTTC
CGACAACATT ACTGTTCAGC TTAGAAGGTG TAAGATGTGG
TCTTGATCTG GATTGGGGGA AGCTTCTAGA ATTGCAAGCT
GCTGATGGCT CATTTCTCTA CTCTCCATCC TCTACTGCCT
TTGCACTAGA ACAAACCAAG GATCAAAACT GCCTCAAATA
TCTATCTAAA CTTGTTCGAA AATTCGATGG CGGAGTACCC
AACGTGTACC CGGTGGACTT GTTCGAACAT AATTGGGCAG
TTGATCGTCT CCAAAGGCTC GGAATTTCTC GTTATTTTAC
GCCTGAAATC AACCAATGTC TTGATTATTC TTACAGATAT
TGGTCAAATA GTAAAGGGAT GTACTCGGCA AGCAATTCCC
AGATTCAGCA CGTTGATGAC ACCGCCATGG GATTCAGGCT
TTTGAGACTC AACGGCTACG ATGTCTCTAC ACAAGGGTTT
AGGCAATTCG AGGCAGGGGG GGACTTCTTC TGCTTCGCGG
GGCAGTCGAG CCAAGGTGTA ACCGGAATGT ACAACCTCTA
CAGAGCTTCC CAAGTGATGT TCCCTGGAGA GAAGCTACTG
GAAGATGCCA AGAAATTCTC CACCAACTTC TTGCAACAAA
AACGAGCCAA TAACCAGCTC ACTGACAAGT GGGTTATTGC
CAAAGATGTT CCAGCTGAGG TGGGATATGC CTTGGATATT
CCCTGGTATG CCAGTCTGCC CCGACTGGAA GCAAGATTTT
TCATACAACA ATACGGTGGA GACGACGACG TTTGGATCGG
CAAAACCTTG TATAGAATGG GATATGTGAA CAACAACACT
TATCTGGAAC TCGCAAAGCT AGACTACAAC ACCTGCCAAA
GGTTGCATCA GCATGAGTGG ATAACCATTC AACGATGGTA
CGAAATTAAT TTAAAAATTA CTAGTGTTGG GTTGAGCAAA
AGAGGGGTCC TGTTGAGTTA TTACTTAGCC GCAGCCAATC
TGTTTGAGCC TCAAAACTCA ACACACCGCA TCGCTTGGGC
CAAAACTTCG ATTTTAGTAA GCGCTATTCA ACTTTCTCCC
CTCCAAAAGC GCGACTTTAT TAACCAATTC CACCGCTCCA
CCGCAAATAA TGGGTATGAA ACAAGTAATG TGTTGGTGAA
```

```
GAGTGTAATC AAGGGTGTGC ATGAGCTCTC CATGGACGCT

ATGTTGACGC ACAATAAAGA CATACATCGC CAACTTTTTA

ATGCTTGGCG AAAGTGGATG TCAGTGTGGG AAGAGGGAGG

TGATGGAGAA GCGGAGCTGT TATTGTCGAC GCTTAAGACG

TGCGACGGAG TAGATGAATC CACATTCAGC GATCCCAAAT

ACGAGCACCT CTTAGAGATC ACCGTCAGAG TCACCCACCA

GCTTCATCTC ATTCAGAATG CAGAGACGAA GCGTGTGGGT

GACCGTGAGG AAATAGATTT GAGCATGCAA CAACTTGTTA

AGTTGGTGTT CACTAAATCA TCATCGGATC TGGATTCTTG

TATCAAGCAA AGATTTTTTG CGATTGCCAG AAGTTTCTAT

TACGTGGCTC ATTGTGATCC GGAGATGGTG GACTCCCACA

TAGCCAAAGT ATTGTTTGAG AGGGTGATGT AG
```

*Prunella vulgaris* 11-hydroxy vulgarisane synthase (PvHVS) was identified and isolated as described herein. The *Prunella vulgaris* 11-hydroxy vulgarisane synthase (PvHVS) enzyme catalyzes the first committed step and forms the scaffold found in all Vulgarisms, a class of diterpenes with pharmaceutical applications (e.g., gout, cancer). For example, PvHVS can synthesize 11-hydroxy vulgarisane (shown below).

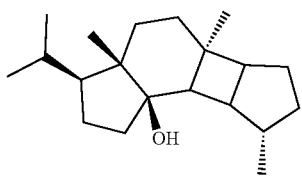

11-hydroxy vulgarisane

An example of a formula for several Vulgarism diterpenes is shown below.

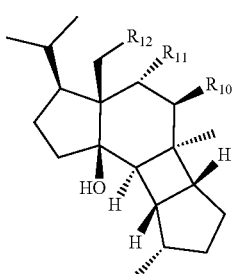

Vulgarisin B (1)

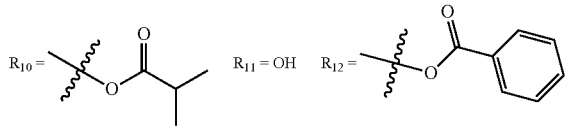

Vulgarisin C (2)

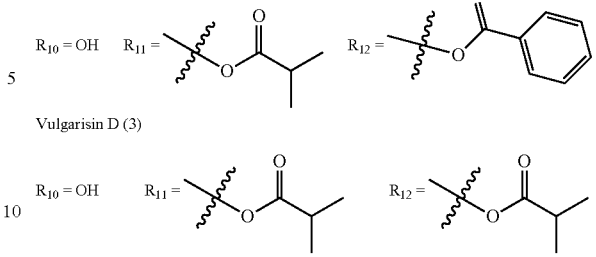

Vulgarisin D (3)

Vulgarisms B (1) and C (2) exhibit modest cytotoxicity activity against human lung carcinoma A549 cell line (Lou et al. Tetrahedron Letters 58: 401-404 (2017)).

The *Prunella vulgaris* 11-hydroxy vulgarisane synthase (PvHVS) can have the amino acid sequence shown below (SEQ ID NO:39).

```
MSSLSIPFSS AICTSSIPKI STGHHRRTAR MPAHDTSRLV

FRPSAVMVEG SPMTTSSNGK EVQRLITTEK PSMWKDIFST

FSFDNQVQEK YLKEIEELKK EVRSTLMSAT HRKLFDLIDN

LERMGIAYHF ETEIEDKLKQ AHASLEEEDD YDLFTTALRF

RLLRQHRYHV SCDPFAKFVD QDNKLKESLS SDVEGLLSLF

EASHLRIHNE DVLDEA1VFT THHLNRMKPQ LESPLKEEVK

HALRYPLHKC LGILSLRFHI DRYENDKSRD EVVLRLGQVN

FNYMQNIYMN ELYEITTWWN KLQMTSKVPY FRDRLVECYM

WGLAYHFEPE YAPVRVLITK YYMTATTVDD TYDNYATLEE

IELFTQAIDR WSEDEIDQLP DEYLKIVYKG LMNFTEEFRR

DAEERGKGYV IPYFIEETKR ATQGYANEQR WIMKREMPSF

EEYMVNSRVT SLMYVTYVAV VAVIESATKE TVDWALSDSD

IFVYTNDIGR LIDDLATHRR ERKDGTMLTS MDYYMKEYGG

TMEEGEAAFR KLMEEKWKLL NAAWVDTING KESKEIVVQV

LDLARICGTL YGDEEDGFTY PEKNFAPLVA ALLMNPIHI
```

A nucleic acid encoding the *Prunella vulgaris* 11-hydroxy vulgarisane synthase (PvHVS) enzyme with SEQ ID NO:39 is shown below as SEQ ID NO:40.

```
ATGAGCTCTC TCTCAATTCC CTTTTCTTCC GCCATTTGCA

CTTCATCAAT CCCAAAGATC AGTACTGGGC ATCATCGCCG

CACCGCGAGG ATGCCCGCGC ACGACACATC GCGTCTCGTC

TTTCGCCCTT CAGCTGTGAT GGTGGAAGGA AGTCCGATGA

CTACTTCAAG CAACGGGAAG GAAGTCCAAC GACTTATAAC

CACTTTCAAG CCTAGCATGT GGAAAGATAT TTTTTCTACC

TTCTCTTTCG ATAATCAGGT GCAAGAAAAG TATTTGAAAG

AAATTGAGGA ATTGAAGAAA GAAGTAAGAA GCACACTAAT

GAGTGCTACG CATAGGAAAT TGTTTGACTT GATCGACAAT

CTCGAGCGTA TGGGAATCGC CTATCATTTC GAGACAGAAA
```

```
TCGAAGACAA GCTCAAACAA GCTCATGCTT CTCTAGAGGA

GGAAGATGAC TACGACTTGT TCACTACTGC ACTTCGCTTT

CGTCTGCTCA GACAACATCG CTATCATGTT TCTTGCGATC

CCTTTGCGAA ATTTGTTGAC CAAGACAACA AATTGAAAGA

GAGTCTTAGT AGCGACGTCG AGGGGCTATT AAGCTTGTTC

GAGGCATCCC ATCTTCGGAT CCACAACGAG GATGTTCTAG

ATGAAGCTAT AGTGTTCACA ACCCATCACT TGAATCGAAT

GATGCCACAA TTGGAATCGC CCCTTAAAGA AGAAGTGAAG

CATGCTCTTC GATACCCCCT TCACAAGTGT CTTGGAATCC

TTAGCCTTCG TTTTCATATC GACAGATATG AGAATGATAA

GTCGAGGGAT GAAGTTGTTC TCAGACTAGG CCAAGTTAAT

TTCAATTACA TGCAGAACAT TTACATGAAC GAGCTCTATG

AAATCACCAC GTGGTGGAAC AAGTTCAGA TGACTTCAAA

AGTACCTTAC TTTAGAGATA GATTGGTAGA GTGCTATATG

TGGGGTTTGG CATATCATTT CGAACCAGAA TACGCTCCCG

TTCGAGTCCT CATTACCAAG TACTATATGA CCGCCACAAC

TGTCGACGAT ACCTATGATA ATTATGCTAC ACTCGAAGAA

ATCGAACTCT TCACTCAGGC CATTGACAGG TGGAGCGAGG

ATGAGATTGA TCAGCTACCT GATGAATACC TAAAAATAGT

GTACAAAGGT CTAATGAACT TCACTGAAGA GTTTAGACGT

GACGCAGAAG AGCGAGCGAA AGGCTATGTG ATTCCTTACT

TTATTGAAGA AACGAAGAGA GCAACACAGG GTTATGCAAA

CGAGCAGAGG TGGATAATGA AGAGAGAAAT GCCGAGTTTT

GAAGAGTATA TGGTGAACTC AAGGGTAACA TCACTTATGT

ATGTGACCTA CGTTGCTGTT GTGGCAGTCA TAGAATCAGC

TACCAAAGAA ACCGTAGATT GGGCGCTAAG TGACTCCGAT

ATCTTTGTCT ACACTAACGA TATCGGCCGA CTTATCGACG

ACCTTGCCAC TCATCGACGC GAGAGGAAAG ACGGGACAAT

GCTTACATCG ATGGATTATT ACATGAAGGA ATATGGCGGT

ACGATGAAG AGGGGAAGC TGCATTTAGG AAATTGATGG

AGGAGAAATG GAAACTTTTG AATGCAGCAT GGGTAGATAC

TATTAATGGA AAAGAGTCGA AGGAAATAGT TGTGCAAGTT

CTCGACCTCG CCAGGATATG CGGAACGCTC TATCGGGACG

AAGAAGATGG CTTCACCTAC CCAGAGAAGA ATTTTGCACC

ACTCGTTGCT GCTCTATTGA TGAATCCTAT ACATATTTGA
```

A *Chiococca alba* ent-CPP synthase (CaTPS1) was identified and isolated. This CaTPS1 enzyme was identified that converts GGPP to ent-CPP [16].

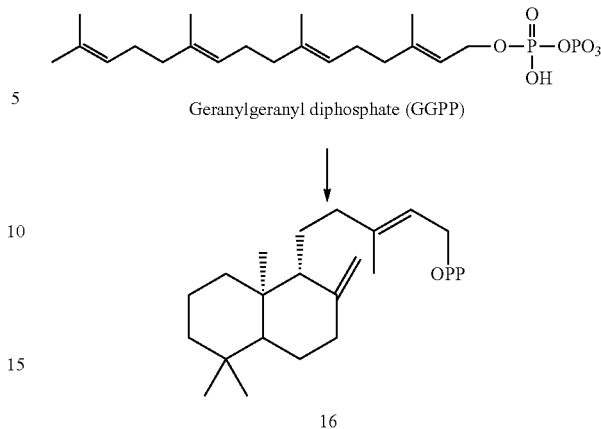

Geranylgeranyl diphosphate (GGPP)

16

The *Chiococca alba* ent-CPP synthase (CaTPS1) has the amino acid sequence shown below (SEQ ID NO:41).

```
  1 MSSSTSAAAT LLGLSPASRR FVSFPPANGP IETITGIWSP
 41 GKALHHFNFR LRCSTVSSPR TQELGQVSQN GMSGIKWHDI
 81 VEEGVTEKGT LEANTSSWIK ESIEAIRWML RTMDDGDISI
121 SAYDTAWVAL VEDINGSGGP QFPSSLEWIA NNQLPDGSWG
161 DSDIFSAHDR ILNTLGCVVA LKSWNMHPEK SEKGLLYLRD
201 NIHKLEDENV EHMPIGFEVA FPSLIEIAKK LSIDIPDDSA
241 ILQEIYARRN LKLTRIPKDI MHTVPTTLLH SLEGMPELDW
281 KRLISLKCED GSFLFSPSST AFALTQTKDA DCLRYLIKTV
321 QKENGGVPNV YPVDLFEHIW AVDRLQRLGI SRYFQSEIRE
361 CIDYVHRYWT DKGICWARNT HVYDIDDTAM GFRLLRLHGY
401 DVSADVFRYY EKDGEFVCFA GQSNQAVTGM YNLYRASQVM
441 FPGENILSDA ERFSSEFLHD KRANNELLDK WIITKDLPGE
481 VAYALDVPWY ASLPRLETRL YLEQYGGEDD VWIGKTLYRM
521 QKVNNNIYLE LGKLDYNNCQ ALHQLEWRSI QKWYNECGLG
561 EYGLSERSLL LSYYLAAASI FEPERSKERL AWAKTTMLIR
601 TIESYLSSEQ MVEDHNGAFV SEFQYYCSNL DYVNGGRHKP
641 TQRLVRTLLG TLNQISLDAV LVHGRDIHQY LRQAWEKWLI
681 ALQEGDDSDM GQEEAELLVR TLNLCAGRYA SEELLLSHPK
721 YQQLLHITTR VCNQIRHFQH KKVQDGENGR ANMGDGITSI
761 SSIESDMQEL TKLVVGNTQN DLDADTKQTF LTVAKSFYYT
801 AHCNPGTINC HIAKVLFERV L
```

A nucleic acid encoding the *Chiococca alba* ent-CPP synthase (CaTPS1) with SEQ ID NO:41 is shown below as SEQ ID NO:42.

```
  1 ATGTCTTCTT CTACCTCAGC AGCAGCAACC CTTCTCGGAT
 41 TATCGCCGGC AAGCCGCCGG TTTGTATCAT TTCCTCCGGC
 81 AAATGGACCT ATAGAAACTA TTACCGGTAT TTGGTCGCCC
```

```
121 GGCAAAGCTC TTCATCACTT TAATTTCCGT CTGCGTTGTA
161 GCACGGTGTC CAGTCCTCGC ACCCAAGAAT TGGGCCAGGT
201 GTCACAAAAT GGCATGTCTG GTATAAAGTG GCATGACATA
241 GTGGAAGAAG GAGTCACAGA AAAAGGAACT CTTGAGGCGA
281 ACACATCAAG CTGGATAAAA GAAAGCATAG AAGCCATTCG
321 TTGGATGCTG CGTACCATGG ATGACGGGGA TATCAGCATA
361 TCTGCTTATG ATACTGCATG GGTTGCCCTT GTGGAAGATA
401 TCAACGGAAG TGGCGGTCCT CAATTTCCTT CAAGCCTCGA
441 GTGGATTGCC AACAATCAGC TTCCTGATGG TTCATGGGGC
481 GACAGCGACA TCTTTTCAGC TCACGATCCG ATTCTCAACA
521 CTTTGGGATG CGTTGTTGCA TTAAAATCTT GGAACATGCA
561 CCCTGAAAAG AGTGAAAAAG GATTATTATA TTTAAGGGAT
601 AACATTCACA AGCTTGAGGA TGAAAATGTC GAGCACATGC
641 CTATCGGTTT TGAAGTGGCA TTTCCTTCAC TAATTGAGAT
681 AGCCAAAAAG TTGAGCATTG ATATTCCGGA TGATTCTGCA
721 ATCTTGCAGG AGATATATGC CAGAAGAAAT CTAAAGCTAA
761 CAAGGATACC GAAGGACATT ATGCACACAG TGCCCACAAC
801 ATTGCTCCAC AGCTTGGAAG GCATGCCAGA ACTAGACTGG
841 AAAAGGCTAA TATCTCTAAA GTGTCAGGAT GGTTCCTTTC
881 TGTTTTCTCC ATCCTCCACT GCTTTTGCCC TCACGCAAAC
921 TAAAGATGCT GATTGCCTCA GATATTTAAC TAAAACCGTA
961 CAAAAATTCA ATGGAGGAGT TCCCAATGTT TACCCCGTGG
1001 ACTTATTCGA ACACATCTGG GCTGTTGATC GACTTCAAAG
1041 ACTAGGAATT TCTCGATACT TCCAGTCAGA AATCCGCGAG
1081 TGCATCGATT ATGTTCACCG ATATTGGACG GATAAAGGTA
1121 TCTGTTGGGC TAGAAATACC CACGTTTATG ACATTGATGA
1161 TACAGCTATG GGTTTTAGAC TTCTAAGGTT GCATGGCTAC
1201 GATGTTTCTG CAGATGTTTT CAGATACTAT GAGAAGGATG
1241 GCGAATTCGT TTGCTTTGCC GGACAGTCAA ACCAGGCGGT
1281 GACCGGAATG TATAACCTGT ATAGAGCTTC TCAAGTGATG
1321 TTTCCAGGGG AGAATATACT TTCGGATGCT AGGAAATTCT
1361 CGTCCGAATT CTTGCATGAT AAGCGAGCCA ACAATGAGCT
1401 CCTAGATAAA TGGATCATAA CCAAAGATTT GCCTGGGGAG
1441 GTAGCATATG CTTTAGATGT TCCATGGTAT GCCAGTTTAC
1481 CTCGTTTAGA AACCAGATTG TATTTGGAAC AATATGGCGG
1521 CGAAGATGAT GTCTGGATTG GCAAGACATT GTACAGGATG
1561 CAAAAAGTTA ACAACAACAT CTATCTTGAA CTTGGCAAAT
1601 TAGATTACAA CAACTGTCAG GCATTGCATC AGCTTGAGTG
1641 GAGAAGCATC CAAAAATGGT ACAATGAATG CGGTCTTGGA
1681 GAGTACGGAT TAAGCGAGAG AAGCCTCCTT CTTTCGTATT
1721 ATTTGGCCGC AGCCAGTATA TTTGAAGCGG AGAGGTCAAA
1761 GGAACGGCTT GCCTGGGCCA AAACTACTAT GCTAATCCGC
1801 ACAATTGAAT CTTATTTGAG TAGTGAACAA ATGGTTGAGG
1841 ATCACAATGG AGCCTTTGTT AGCGAGTTCC AATACTATTG
1881 CAGTAACCTT GACTACGTAA ATGGTGGAAG GCATAAGCCA
1921 ACACAAAGGC TAGTGAGGAC TCTACTCGGA ACTTTAAATC
1961 AGATTCTTTT GGACGCAGTG TTAGTCCACG GCAGAGATAT
2001 CCATCAATAT TTGCGTCAAG CCTGGGAAAA GTGGTTGATA
2041 GCTTTGCAAG AGGGAGATGA TAGTGACATG GGTCAAGAGG
2081 AAGCAGAACT TTTAGTGCGC ACACTAAACC TATGCGCCGG
2121 TCGCTACGCA TCGGAGGAGC TATTGTTGTC CCATCCCAAG
2161 TATCAACAAC TTTTGCACAT CACTACTAGA GTCTGTAACC
2201 AAATTCGTCA TTTCCAACAC AAAAAGGTGC AAGATGGGGA
2241 AAATGGAAGA GCAAACATGG GTGATGGCAT CACAAGCATC
2281 AGCTCAATAG AGTCGGACAT GCAAGAACTA AGGAAATTAG
2321 TTGTCGGCAA TACCCAAAAC GATCTAGATG CTGATACGAA
2361 GCAAACATTT CTCACGGTGG CAAAAAGCTT CTACTACACC
2401 GCCCACTGCA ATCCCGGAAC AATCAATTGC CATATTGCTA
2441 AAGTATTATT TGAGAGAGTA CTTTGA
```

A *Chiococca alba* (5R,8S,9S,10S)-labda-13-en-8-ol diphosphate (ent-8-LPP) synthase (CaTPS2) was identified and isolated as described herein. This CaTPS2 enzyme was identified as an 5R,8S,9S,10S-labda-13-en-8-ol diphosphate (ent-8-LPP) synthase, which converts GGPP to 5R,8S,9S,10S)-labda-8-en-8-oi diphosphate (ent-8-LPP, [7]).

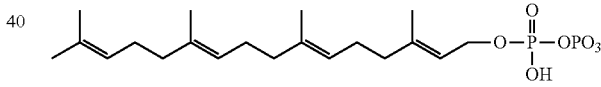

Geranylgeranyl diphosphate (GGPP)

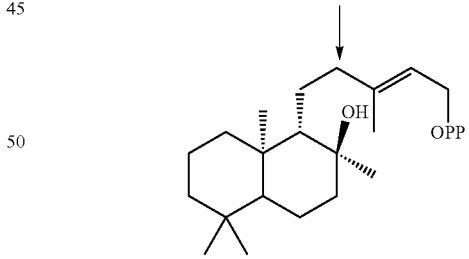

7

The *Chiococca alba* (5R,8S,9S,10S)-labda-13-en-8-ol diphosphate (ent-8-LPP) synthase (CaTPS2) has the amino acid sequence shown below (SEQ ID NO:43).

```
  1 MPVIKSHEFI EEVGPEKGTL KLSRSSRINE LVESIQTMLQ
 41 SMDDGEISMS AYDTAWVALV EDINGSSYPQ FPMSLEWIAN
 81 NQLPDGSWGD GSIFSVHDRI ISTLCCVLAL KSWNMHPDKS
```

```
121 EKGLLFIRDN IHKVGDESAE HMPIGFEVVF PSLIERAKNL

161 DIDIPDISAI LQEIYARRNL KLARIPKDIL YTVPTTLLHS

201 LEGMPELDWQ KLLPLKCEDG SFLFSPSCTA FALMQTKDGD

241 CLRYLTNTIE KFNGGVPGVY PVDLFEHIWA VDRLQRLGIS

281 RYFQTEIEEC MSYVYRYWTD KGICWARNSK VEDIDDTAMG

321 FRLLRLHGYM VSADVFAQFE KGGEFVCFAG QSNQALTGMF

361 NLYRASQVMF PGEKILADAK KFSSNFLHEK RANNELLDKW

401 IITKDLPGEV TYALDVPWYA SLPRVETRLY LEQYGGEDDV

441 WIAKTLYRMR KVNNKIYLEL GILDYNNCQA LHQLEWRSIQ

481 KWYKDSGLEE YGLSERNLLL AYYLATACIF EPERLVERLS

521 WAKTTALIYT TKSYFRTECN SGEQRKAFLH EFQQYCNDLD

561 YVSGARHKPT IRLIEALLGT LEQVSLDAIL DHGRYIHQDL

601 RNAWEKWLIA LQEGVDMDQE EAELTVLTLH LCAGSYTSEE

641 LLLSHPKYQQ LLNITSRVCH QIRQFQREKA QDTDNGRENL

681 VAITSIKAIE SDMQELAKLV LTKSTGDLAA KIKQTFLIVA

721 KSFYYTAHCL PGIISTHIAK VLFEKVF
```

A nucleic acid encoding the *Chiococca alba* (5R,8S,9S,10S)-labda-13-en-8-ol diphosphate (ent-8-LPP) synthase (CaTPS2) with SEQ ID NO:43 is shown below as SEQ ID NO:44.

```
   1 ATGCCAGTAA TAAAGTCGCA TGAGTTTATT GAAGAGGTCG

41 GCCCGGAAAA AGGAACTCTG AAGCTGAGCA GATCAAGTAG

81 GATAAACGAA CTTGTAGAAT CAATTCAAAC GATGCTTCAA

121 TCGATGGATG ATGGGAAAT AAGCATGTCT GCTTATGACA

161 CCGCGTGGGT TGCCCTTGTG GAAGATATTA ATGGAAGCAG

201 CTACCCTCAA TTCCCTATGA GCCTCGAGTG GATTGCCAAC

241 AATCAGCTTC CTGATGGTTC ATGGGGTGAC GGCAGTATCT

281 TTTCGGTTCA TGATCGGATA ATCAGCACAT TAGGATGTGT

321 TCTTGCATTA AAATCATGGA ACATGCACCC GGACAAAAGC

361 GAAAAAGGAC TGTTATTTAT AAGGGACAAT ATTCACAAGG

401 TTGGAGATGA CAGCGCTGAG CACATGCCTA TTGGTTTTGA

441 GGTGGTATTT CCTTCGCTTA TTGAGAGAGC CAAAAACTTG

481 GACATTGATA TTCCAGATAT TTCTGCTATC TTGCAAGAGA

521 TTTATGCACG AAGAAATCTA AAGCTCGCAA GGATTCCAAA

561 GGATATACTG TATACCGTGC CCACGACATT ACTTCATAGC

601 TTAGAAGGAA TGCCAGAACT GGACTGGCAA AAGCTACTGC

641 CATTAAAATG TGAGGATGGT TCATTTCTAT TTTCTCCATC

681 GTGCACTGCT TTTGCCCTCA TGCAGACTAA GGATGGTGAT

721 TGCCTCAGAT ATCTAACTAA TACCATAGAA AAATTCAATG

761 GGGGAGTTCC CGGTGTATAC CCTGTGGACT TGTTCGAACA

801 CATTTGGGCT GTTGATCGCT TGCAAAGACT AGGAATTTCC

841 CGGTATTTTC AGACAGAAAT TGAAGAATGT ATGAGTTATG

881 TTTACCGATA TTGGACGGAT AAAGGTATCT GTTGGGCTAG

921 AAACTCCAAA GTTGAAGACA TCGATGACAC AGCCATGGGT

961 TTTAGACTTC TAAGGTTGCA TGGTTACATG GTTTCTGCAG

1001 ATGTGTTTGC ACAGTTTGAG AAAGGGGGTG AATTCGTTTG

1041 CTTTGCTGGA CAGTCGAACC AGGCGCTGAC TGGAATGTTT

1081 AACCTGTATA GAGCTTCTCA AGTAATGTTT CCAGGGGAGA

1121 AGATACTTGC TGATGCCAAG AAATTCTCAT CGAACTTCTT

1161 ACATGAAAAG CGTGCAAACA ACGAGCTTCT AGATAAATGG

1201 ATCATAACTA AAGATTTGCC TGGAGAGGTG ACGTATGCGC

1241 TAGATGTTCC ATGGTACGCC AGTTTACCTC GTGTAGAAAC

1281 GAGATTATAT CTGGAACAAT ATGGAGGAGA GGATGATGTC

1321 TGGATTGCCA AGACATTGTA CAGGATGAGA AAAGTTAACA

1361 ACAAAATTTA CCTTGAACTT GGCATATTAG ATTACAATAA

1401 CTGTCAAGCA TTGCATCAGC TGGAGTGGAG AAGCATCCAA

1441 AAATGGTATA AGGATTCTGG CCTTGAAGAG TACGGGTTGA

1481 GCGAGAGGAA CCTTCTCCTG GCATATTATC TGGCCACAGC

1521 TTGTATATTT GAACCCGAAA GGTTGGTGGA GCGCCTTTCC

1561 TGGGCGAAAA CAACCGCCTT AATCTACACA ACAAAATCTT

1601 ATTTCAGAAC TGAATGCAAC TCTGGGGAAC AGAGAAAAGC

1641 TTTTCTTCAT GAGTTCCAAC AGTACTGCAA TGACCTGGAC

1681 TACGTTAGTG GCGCAAGGCA CAAGCCAACA ATAAGATTGA

1721 TCGAAGCTCT ACTTGGAACC CTAGAGCAGG TCTCTTTGGA

1761 TGCAATATTA GATCATGGCC GATATATCCA TCAAGATTTG

1801 CGTAATGCTT GGGAGAAATG GTTGATAGCT TTGCAAGAGG

1841 GAGTTGACAT GGACCAAGAA GAAGCAGAAC TTACAGTGCT

1881 CACACTACAC CTGTGTGCCG GCAGCTACAC ATCGGAGGAG

1921 TTACTGTTAT CTCATCCCAA GTATCAACAA CTTTTAAATA

1961 TCACTAGTAG AGTCTGCCAC CAAATTCGTC AATTCCAGCG

2001 CGAAAAGGCA CAGGATACGG ATAATGGAAG AGAAACTTG

2041 CTTGCCATCA CAAGCATCAA GGCGATAGAA TCAGACATGC

2081 AAGAACTTGC GAAATTAGTT CTGACCAAAT CCACTGGCGA

2121 TTTAGCTGCT AAAATCAAGC AAACATTTCT TATAGTGGCA

2161 AAGAGCTTCT ACTACACCGC ACATTGCCTT CCTGGAATTA

2201 TCAGTACCCA CATTGCCAAA GTACTATTTG AGAAAGTTTT

2241 CTGA
```

A *Chiococca alba* CaTPS3 and CaTPS4 were identified and isolated. CaTPS3 and CaTPS4 were identified as an ent-kaurene synthase, converting ent-CPP [16] into ent-kaurene [19].

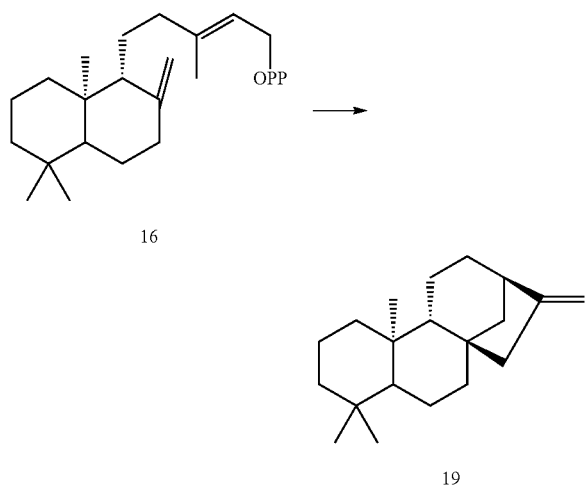

The *Chiococca alba* ent-kaurene synthase (CaTPS3) has the amino acid sequence shown below (SEQ ID NO:45).

```
  1  MMMMMVVMNT APAHSYHPFP FAGPKSSATL FSNYYCSSRK
 41  KSSPPRISAS VSLLTGVEST TAINSSDPEI KERIRKLFHD
 81  VDISLSSYDT AWVAMVPAPH SSQSPLFPQC INWLLDNQLP
121  DGSWSLPPPH HHPLLLKDAL SSTLACVLAL RRWGIGQEQV
161  DKGIRFVELN FASASDQNQH LPVGFDIIFP GMLEYARDLN
201  LNLQLESATV NALLLKRDQE LTRFFKSYSD ESKAYLAYVS
241  EGIVKLQNWD TVMKFQRKNG SLFNSPSATA AAVMHVHNPG
281  CLDYLHSVLE KHGNAVPTVY PLDIYPRLCL VDNLERLGIC
321  GHFRKEILSV LDDTYRCWMQ GDEEIFAEKS TCAIAFTLLR
361  KHGYNISADP LTPFLKEECF SNSLGGCLKD TSAVLELYRA
401  LEMIISQNES ALVKKSLWSR SFLKEHISGG CDLKGFSNQI
441  SILVDDILNF PSHATLQRVA NRRSIEQYNL DSTKILKTSY
481  CSSNFSNKDL LILAVKDFNH CQLIHREELK ELERWVTDNR
521  LDKLKFARQK SAYCYFSAAA TIFSPELSDA RMSWAKNGVL
561  ATLVDDFFDV GGSLEELKKL IELVEKWDIN VSDGCCSEPV
601  QILFSALHST IQEIGDkAFK WQARSVTNHI FKIWLDLLNS
641  MLREAEWARN ATVPTVEEYM TNGYVSFALG PIILPALYLV
681  GPKLSEEVVK DSEFHSLFKL VSTCGRLLND VHSFERESKS
721  GQLNALSLRL IHGGVGITEA AAVAEMKSSI ENLRRELLRL
761  VLRKEGSVVP RACKDLFWNM SKVLHQFYNK DDGFTSEEMI
801  QLVKSIIYEP IAVNEFLNSC HT
```

A nucleic acid encoding the *Chiococca alba* ent-kaurene synthase (CaTPS3) with SEQ ID NO:45 is shown below as SEQ ID NO:46.

```
   1 ATGATGATCA TGATCGTGGT GATGAACACA GCTCCCGCCC
  41 ACTCTTACCA TCCTTTCCCC TTTGCCGGCC CAAANTCCTC
  81 AGCCACACTT TTTTCCAATT ATTATTGTTC CAGTAGGAAG
 121 AAATCATCGC CACCTCGCAT CTCTGCCTCA GTTTCTTTGC
 241 TAACTGGAGT TGAAAGCACA ACTGCAATTA ATTCTTCAGA
 281 CCCGGAGATC AAAGAAAGAA TAAGGAAACT ATTTCATGAT
 321 GTTGATATCT CGCTTTCTTC ATATGACACT GCATGGGTGG
 361 CAATGGTCCC TGCTCCACAT TCTTCCCAGT CTCCCCTTTT
 401 TCCCCAGTGC ATTAATTGGT TATTGGACAA TCAGCTTCCT
 441 GATGGCTCAT GGAGTCTTCC TCCTCCTCAT CATCATCCTC
 481 TATTACTTAA AGATGCATTA TCCTCTACCC TTGCATGTGT
 521 TCTTGCGCTC AGGAGATGGG GAATTGGTCA AGAACAAGTT
 561 GACAAGGGTA TTCGTTTTGT TGAGTTAAAT TTTGCTTCAG
 601 CATCTGACCA GAACCAGCAT TTGCCACTTG GATTTGACAT
 641 TATATTCCCT GGCATGCTCG AATATGCTAG AGATTTAAAT
 681 TTAAATCTTC AACTAGAATC TGCAACAGTA AATGCCTTAC
 721 TTCTTAAAAG AGATCAGGAG CTTACAAGAT TCTTTAAAAG
 761 CTACTCAGAC GAGAGTAAAG CATACCTTGC ATATGTATCA
 801 GAAGGTATAG TAAAGTTACA GAACTGGGAT ACAGTTATGA
 841 AGTTCCAAAG AAAGAACGGG TCACTATTCA ATTCACTTC
 881 AGCTACAGCA GCTGCTGTTA TGCATGTCCA CAATCCTGGT
 921 TGCCTCGATT ACCTTCACTC AGTGTTGGAG AAGCATGGAA
 961 ATGCTGTTCC AACAGTTTAC CCTTTGGATA TATATCCACG
1001 CCTCTGCTTG GTTGACAACC TTGAGAGACT GGGTATTTGT
1041 GGTCATTTTA GGAAGGAAAT TCTGAGTGTA TTGGATGATA
1081 CATACAGATG CTGGATGCAG GGGGATGAAG AGATATTTGC
1121 AGAAAAATCA ACTTGTGCCA TAGCATTTAC ATTATTGCGA
1161 AAGCATGGGT ACAACATCTC TGCAGATCCA TTGACCCCAT
1201 TCTTAAAGGA AGAGTGTTTT TCCAATTCTT TGGGTGGATG
1241 TTTGAAAGAT ACTAGTGCTG TACTTGAATT ATACCGGGCA
1281 TTAGAGATGA TTATTAGCCA GAATGAATCA GCTCTGGTGA
1321 AAAAAAGCTT GTGGTCCAGA AGCTTCCTGA AAGAGCATAT
1361 TTCTGGTGGT TGTGATTTAA AGGGATTCAG CAATCAAATT
1401 TCCATACTGG TGGATGATAT CCTCAACTTT CCATCGCATG
1481 CTACTTTGCA ACGGGTTGCT AACAGGAGAA GCATAGAGCA
1521 ATACAACTTA GACAGTACAA AAATTTTAAA AACTTCATAT
1561 TGCTCGTCGA ATTTTAGCAA CAAAGATTTA TTGATCCTGG
1601 CAGTCAAAGA TTTTAATCAT TGCCAACTCA TACACCGTGA
1641 AGAACTGAAA GAACTAGAAA GGTGGGTCAC AGACAATAGA
1681 TTGGACAAGT TAAAGTTTGC TAGGCAGAAG TCTGCATACT
1721 GTTACTTTTC TGCTGCAGCA ACCATATTCT CACCTGAACT
1761 TTCTGATGCC CGCATGTCAT GGGCCAAGAA TGGTGTACTT
```

```
1801 GCTACTTTGG TTGATGACTT CTTTGACGTG GGAGGTTCTC
1841 TAGAGGAATT AAAGAAACTG ATTGACTTGG TTGAAAAGTG
1881 GGATATAAAT GTCAGTGATG GTTGTTGCTC TGAACCAGTG
1921 CAAATCCTCT TCTCAGCACT ACATAGTACA ATCCAGGAGA
1961 TTGGAGATAA AGCATTCAAA TGGCAAGCAC GCAGTGTAAC
2001 AAACCACATA TTTAAGATAT GGTTAGATTT GCTTAATTCT
2041 ATGTTGAGGG AAGCTGAGTG GGCTAGAAAT GCAACAGTGC
2081 CTACAGTTGA AGAATATATG ACAAATGGTT ATGTATCATT
2121 THCTTTGGGG CCAATTATCC TCCCTGCTCT TTATCTTGTT
2161 GGACCTAAGC TGTCAGAGGA AGTAGTTAAG GATTCTGAAT
2201 TCCACTCCCT TTTTAAGCTA GTGAGTACCT GTGGGCGGCT
2241 TCTGAATGAT GTCCACAGCT TCGAGAGGGA ATCAAAGTCC
2281 GGCCAACTAA ATGCTCTGTC TCTGCGCCTG ATTCATGGTG
2321 GTGTTGGCAT TACTGAAGCA GCTGCTGTTG CAGAGATGAA
2361 GAGTTCAATT GAGAATCTAA GGAGAGAACT GCTGAGACTA
2401 GTCTTGCGCA AGAGGGTAG TGTAGTTCCA AGAGCTTGCA
2441 AGGATTTGTT TTGGAATATG AGTAAAGTGC TACATCAATT
2481 TTACAACAAA GATGATGGAT TTACTTCAGA GGAGATGATT
2521 CAGCTTGTGA AGTCGATCAT TTATGAGCCA ATTGCGGTCA
2561 ATGAATTTTT GAATAGTTGC CATACATGA
```

The *Chiococca alba* ent-kaurene synthase (CaTPS4) has the amino acid sequence shown below (SEQ ID NO:47).

```
  1 MMIMVMNTAP VHAYHALPIP TQKSSTTLFP NYNCSSRKKS
 41 SPPRISAASV SLQTGVERTT AIHSSDLEIK ERIRKLFHDV
 81 DISLSSYDTA WVAKVPAPHS SQSPLFPQCI NWLLDNQLPD
121 GSWSLPPHHH HHHPLLLKDA LSSTLACVLA LRRWGIGQEQ
161 VDKGIRFVEL NFASASDQNQ HLPVGFDIIF PGMLEYARDL
201 NLNLQLESAT VDALLLKRDQ ELIRFFKSYS DESKAYLAYV
241 SEGIIKLQNW DTVMKFQRKN GSLFNSPSAT AAAVMHVHNP
281 GCLDYLHSVL EKHGNAVPTV YPLDIYPRLC LVDNLERLGI
321 CGHFRKEILS VLDDTYRCWM QGDEEIFAEK STCAIAFTLL
361 RKHGYNISAD PLTPFLKEEC FSNSLGGCLK DTSAVLELYR
401 ALEMIISQNE SALVKKSLWS RSFLKEHISG GCDLKGFSNQ
441 ISKQVDDILN FPSHATLQRV ANRRSIEQYN LDSTKILKTS
481 YCSSNFSNKD LLILAVKDFN HCQLIHREEL KELERWVADN
521 RLDKLKFARQ KSAYCYFSAA ATIFSPELSD ARISWAKNGV
561 LTTLVDDFFD VGGSLEELKK LIELVEKWDI NVSDGCCSEP
601 VQILFSALHS TIQEIGDKAF KWQARSVINH IIKIWLDLLN
641 SMLREAEWAR NATVPTVEEY MINGYVSFAL GPIILPALYL
681 VGPKLSEELV KDSEFHSLFK LVSTCGRLLN DVHSFERESK
721 AGQLNALSLR LIHGGVGITE AAAVAEMKSS IEKQRRELLR
761 LVLRKEGSVV PRACKDLFWN MSRVLHQFYV KDDGFTSEEM
801 IELVKSIIYE PIAVNEF
```

A nucleic acid encoding the *Chiococca alba* ent-kaurene synthase (CaTPS4) with SEQ ID NO:47 is shown below as SEQ ID NO:48.

```
   1 ATGATGATAA TGGTGATGAA CACAGCTCCC GTCCACGCTT
  41 ACCACGCTTT ACCCATTCCC ACCCAAAAAT CCTCAACCAC
  81 ACTTTTTCCC AATTATAACT GTTCCAGTAG GAAGAAATCA
 121 TCGCCACCTC GCATCTCTGC CGCCTCAGTT TCTTTGCAAA
 161 CTGGAGTTGA AGAACGACG GCAATTCATT CTTCAGACCT
 201 AGAGATCAAA GAAAGAATAA GGAAACTATT TCATGATGTT
 241 GATATCTCGC TTTCTTCATA TGACACTGCA TGGGTGGCAA
 281 TGGTCCCTGC TCCACATTCT TCCCAGTCTC CCCTTTTTCC
 321 CCAGTGCATT AATTGGTTAT TGGACAATCA GCTTCCTGAT
 361 GGCTCATGGA GTCTTCCTCC TCATCATCAT CATCATCATC
 401 CCCTATTACT TAAAGATGCA TTATCCTCTA CGCTTGCATG
 441 TGTTCTTGCG CTCAGGAGAT GGGGAATTGG TCAAGAACAA
 481 GTTGACAAGG GTATTCGTTT TGTTGAGTTA AATTTTGCTT
 521 CTGCATCTGA CCAGAACCAG CATTTGCCAG TTGGATTTGA
 561 CATTATATTC CCTGGCATGC TCGAATATGC TAGAGATTTA
 601 AATTTAAATC TTCAACTAGA ATCCGCAACT GTAGATGCCT
 641 TACTTCTCAA AAGAGATCAG GAGCTTATAA GATTCTTTAA
 681 AAGCTACTCA GACGAGAGTA AAGCATACCT TGCATATGTA
 721 TCAGAAGGTA TCATAAAGTT ACAGAACTGG GATACAGTTA
 761 TGAAGTTCCA AAGAAAGAAC GGGTCACTGT TCAATTCACC
 801 TTCAGCTACA GCAGCTGCTG TTATGCATGT CCACAATCCT
 841 GGCTGCCTCG ATTACCTTCA CTCAGTGTTG GAGAAGCATG
 881 GCAATGCTGT TCCAACAGTT TACCCTTTGG ATATATATCC
 921 ACGCCTCTGC TTGGTTGACA ACCTTGAGAG ACTGGGTATT
 961 TGTGGTCATT TTAGGAAGGA AATTCTGAGT GTATTGGATG
1001 ATACATACAG ATGCTGGATG CAGGGGGATG AAGAGATATT
1041 TGCAGAAAAA TCAACTTGTG CCATAGCATT TACATTATTG
1081 CGAAAGCATG GGTACAACAT CTCTGCAGAT CCATTGACCC
1121 CATTCTTAAA GGAAGAGTGT TTTTCCAATT CTTTGGGTGG
1161 ATGTTTGAAA GATACTAGTG CTGTACTTGA ATTATACCGG
1201 GCATTAGAGA TGATTATTAG CCAGAATGAA TCAGCTCTGG
1241 TGAAAAAAAG CTTGTGGTCC AGAAGCTTCC TGAAAGAGCA
1281 TATTTCTGGT GGTTGTGATT TAAAGGGATT CAGCAATCAA
1321 ATTTCCAAAC AGGTGGATGA TATCCTCAAC TTTCCATCGC
1361 ATGCTACTTT GCAACGGGTT GCTAACAGGA GAAGCATAGA
```

-continued

```
1401 GCAATACAAC TTAGACAGTA CAAAAATTTT AAAAACTTCA
1441 TATTGCTCGT CGAATTTTAG TAACAAAGAT TTATTGATCC
1481 TGGCAGTCAA AGATTTTAAT CATTGCCAAC TCATACACCG
1521 TGAAGAACTG AAAGAACTAG AAAGGTGGGT CGCAGACAAT
1561 AGATTGGACA AGTTAAAGTT TGCTAGGCAG AAGTCTGCAT
1601 ACTGTTACTT TTCTGCTGCA GCAACCATAT TCTCACCTGA
1641 ACTTTCTGAT GCCCGCATCT CATGGGCCAA AAATGGTGTA
1681 CTTACTACTT TGGTTGATGA CTTCTTTGAC GTGGGAGGTT
1721 CTCTAGAGGA ATTAAAGAAA CTGATTGAGT TGGTTGAAAA
1761 GTGGGATATA AATGTCAGTG ATGGTTGTTG CTCTGAACCA
1801 GTGCAAATCC TCTTCTCAGC ACTACATAGT ACAATCCAGG
1841 AGATTGGAGA TAAAGCATTC AAATGGCAAG CACGCAGTGT
1881 AACAAACCAC ATAATTAAGA TATGGTTAGA TTTGCTTAAT
1921 TCTATGTTGA GGGAAGCTGA GTGGGCTAGA AATGCAACAG
1961 TGCCTACAGT TGAAGAATAT ATGACAAATG GTTATGTATC
2001 ATTTGCCTTG GGGCCAATTA TCCTCCCTGC TCTTTATCTT
2041 GTTGGACCTA AGCTCTCAGA GGAATTAGTT AAGGATTCTG
2081 AATTCCACTC CCTTTTTAAG CTAGTGAGTA CCTGTGGGCG
2121 GCTTCTGAAT GATGTCCACA GCTTCGAGAG GGAATCAAAG
2161 GCCGGCCAAC TAAATGCTCT TTCTCTGCGC CTGATTCATG
2201 GTGGAGTTGG CATTACTGAA GCAGCTGCTG TTGCAGAGAT
2241 GAAGAGTTCA ATTGAGAAGC AAAGGAGAGA ACTGCTGAGA
2281 CTAGTCTTGC GCAAAGAGGG TAGTGTAGTT CCAAGAGCTT
2321 GCAAGGATTT GTTTTGGAAT ATGAGTAGGG TGCTACATCA
2361 ATTTTACCTC AAAGATGATG GATTTACTTC AGAGGAGATG
2401 ATTGAGCTTG TGAACTCGAT CATTTATGAG CCAATTGCCG
2441 TCAATGAATT TTGA
```

A *Chiococca alba* 13(R)-epi-dolabradiene synthase (CaTPS5) was identified and isolated. This CaTPS5 enzyme was identified as an 13(R)-epi-dolabradiene synthase, which converts ent-CPP [16] to 13(R)-epi-dolabradiene.

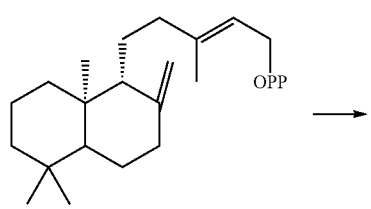

16

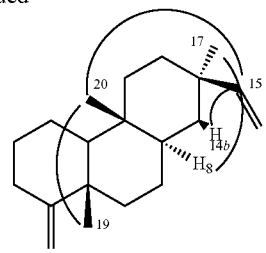

The *Chiococca alba* 13(R)-epi-dolabradiene synthase (CaTPS5) has the amino acid sequence shown below (SEQ ID NO:49).

```
  1 MIHTLPHGGQ AHFISHKTQP YYSSRPRFSS AASLDTRVRR
 41 TSPSNSSVLD FNETKERITK LFHNVDYSIS SYDTAWVAMV
 81 PDPHSSQAPL FPECINWLLD NQFHDGSWSL PHHNSLLLKD
121 VLSSTLACVL ALKRWGIGGR QIDKGVRFIE MNFGSASDNC
161 QHTPIGFDII FPGMLENARD LDLNLRLEPR IVIDMQRKRD
201 MQLTRLHESD LKGDQAYLAY VSEGMQKLQN WDLAMKFQRK
241 NGSLFNSPSA TAAAVMHVQN PASLNYLHSV VDKFGHAVPA
281 VYPLDLYARL CLVDNLERLG ICRHFTNEIE IVMEDTYRCW
321 LQDDEDIFAE ISTCALAFRL LRKHGYVVSP DPLTKIIEEE
401 DVSNSSGNGY WNDIHAVMEV HRASEVVIHE NESDLKNQNT
441 ISKHLLRHHL FNGSDVKPFP NPIYKQVDYA LKFPTPLILQ
481 RVENKTLIQN YDVDSTRLLK TSYRSSNFCN EDLLRLAVKD
521 FNDCQLLHRK ELKELERWSA DNRLHELKFA RQKAIYCSFS
561 AAATIFIPEW YEARMSLAKN SVLATVVDDF FDVGGSMEEL
601 KKLIEFVEKW DIDITKESCS EPLKIIFSAL HSTISEIGEQ
641 AVKWQGRNVT SHIIEIWLDL LNSMLRESEW TTDVHMPTLD
681 EYMEAAYVSF AMGPIIIPAL YFVGPKLSDE IVRDPEIRSL
721 HKLVSICGRL LNDMQGFERE KKAGKPNAVS IRISQNGDGI
761 TESAAFEEVK MELEDARREL LRLVVQKDGS VVPRACKDAF
801 WSVSRMLHHF YFNNDGYTSE VEMVELVNSI IHEPLK
```

A nucleic acid encoding the *Chiococca alba* 13(R)-epi-dolabradiene synthase (CaTPS5) with SEQ ID NO:49 is shown below as SEQ ID NO:50.

```
   1 ATGATTCATA CTCTCCCTCA TGGCGGCCAG GCTCACTTCA
  41 TTTCCCACAA AACACACCCT TATTATTCCA GTAGACCTCG
  81 CTTTTCTTCA GCAGCTTCTT TGGACACACG AGTCCGGAGA
 121 ACATCGCCCT CTAATTCCTC TGTCCTAGAC TTCAAGGAGA
 161 CCAAAGAAAG AATCACAAAA TTATTTCATA ATGTTGATTA
 201 TTCAATTTCT TCATATGATA CAGCATGGGT TGCTATGGTC
 241 CCGGACCCAC ATTCTTCTCA GGCTCCCCTT TTCCCAGAGT
 281 GCATAAATTG GTTGCTAGAT AATCAATTTC ATGATGGCTC
 321 CTGGAGTCTT CCTCATCACA ATTCTCTATT GCTTAAGGAT
 361 GTTTTATCCT CTACGCTTGC GTGTGTTCTT GCTCTTAAGA
 401 GATGGGGAAT AGGAGGAAGG CAGATTGACA AAGGTGTTCG
 441 CTTTATTGAG ATGAATTTTG GCTCAGCATC TGACAATTGC
 481 CAGCATACTC CAATAGGATT TGACATAATA TTTCCAGGAA
 521 TGCTTGAAAA TGCCAGAGAT TTGGATCTAA ATCTTAGACT
 561 ACAACCCAGA ATTGTAACTG ACATGCAACG TAAAAGAGAC
 601 ATGCAGCTTA CAAGACTCCA TGAAAGCGAT CTAAAGGGGG
 641 ACCAAGCATA CTTGGCATAT GTATCCGAAG GGATGCAAAA
 681 GTTACAGAAT TGGGATTTGG CGATGAAGTT TCAAAGGAAG
 721 AATGGATCGC TCTTCAACTC ACCATCAGCT ACAGCAGCCG
 801 CTGTTATGCA TGTCCAAAAT CCTGCTTCCC TCAATTATCT
 841 TCATTCAGTC GTCGACAAAT TCGGCCATGC AGTTCCGGCT
 881 GTTTACCCTT TGGATCTCTA TGCCGCGCTT TGCTTGGTTG
 921 ACAATCTTGA GAGGCTGGGT ATCTGTCGAC ATTTTACTAA
 961 TGAAATTGAA ATTGTAATGG AGGACACGTA CAGGTGCTGG
1001 CTGCAGGATG ATGAAGATAT ATTTGCCGAA ATATCAACTT
1041 GTGCCTTAGC TTTTCGGTTA TTGAGAAAAC ATGGCTATGT
1081 TGTCTCCCCA GATCCACTGA CAAAAATCAT AGAAGAAGAA
1121 GATGTTTCCA ATTCTTCTGG TAATGGATAT TGGAATGATA
1161 TACATGCTGT AATGGAAGTG CATCGGGCAT CAGAGGTGGT
1201 TATACATGAA AATGAATCGA ATTTAAAGAA TCAAAATACC
1241 ATATCAAAAC ACCTTCTCAG ACACCATCTT TTCAATGGTT
1281 CTGATGTGAA GCCCTTTCCT AATCCAATAT ACAAGCAGGT
1321 GGACTATGCT CTCAAGTTTC CAACCCCCTT AATTCTACAA
1361 CGTGTTGAAA ACAAGACCCT CATACAGAAC TACGACGTAG
```

```
1401 ACAGTACAAG ACTTCTTAAA ACTTCATATC GATCATCAAA
1441 TTTCTGCAAT GAAGATTTAC TGAGGTTAGC AGTGAAAGAT
1481 TTTAATGACT GTCAACTCCT GCACCGGAAA GAACTAAAAG
1521 AACTAGAAAG ATGGTCCGCA GATAACAGAC TGCACGAACT
1601 AAAAITTGCT CGGCAGAAAG CTATATACTG CTCCTTTTCT
1641 GCTGCAGCAA CGATTTTCAT ACCTGAATGG TACGAAGCCC
1681 GCATGTCATT GGCCAAAAAT AGTGTACTTG CTACTGTGGT
1721 TGATGACTTC TTTGATGTGG GTGGTTCGAT GGAGGAATTA
1761 AAGAAGCTAA TTGAATTTGT TGAAAAGTGG GATATTGACA
1801 TCACCAAGGA ATCCTGCTCT GAGCCACTCA AAATCATATT
1841 TTCAGCACTG CACAGTACAA TCTCTGAGAT TGGAGAGCAA
1881 GCAGTTAAAT GGCAAGGACG CAATGTAACA AGCACATAAA
1921 TTGAGATCTG GTTGGATTTG CTCAATTCGA TGTTGAGGGA
1961 GTCTCAATGG ACTACAGATG TGCACATGCC AACATTGGAT
2001 GAATATATGG AAGCTGCTTA TGTATCATTC GCCATGGGGC
2041 CAATTATCAT CCCTGCTCTG TATTTTGTTG GGCCTAAGCT
2081 ATCTGATGAA ATTGTTCGGG ATCCTGAAAT ACGATCCCTC
2121 CATAAGCTTG TGAGCATTTG TGGGCGGCTT CTAAATGATA
2161 TGCAAGGGTT CGAGAGGGAA AAGAAGGCTG GTAAACCAAA
2201 TGCCGTGTCT ATACGCATTA GTCAAAATGG TGATGGCATT
2241 ACCGAATCAG CAGCTTTCGA AGAAGTGAAG ATGGAATTAG
2281 AGGATGCAAG GAGAGAATTG CTAAGATTAG TTGTGCAAAA
2321 AGATGGTAGT GTAGTTCCAA GAGCTTGCAA GGATGCGTTT
2361 TGGAGCGTAA GCAGAATGTT GCATCATTTC TACTTCAATA
2401 ATGATGGATA CACGTCAGAG GTGGAGATGG TTGAGCTCGT
2441 GAATTCAATT ATTCATGAAC CACTAAAATA A
```

A *Salvia hispanica* (−)-kolavenyl diphosphate synthase (ShTPS1) was identified and isolated. This ShTPS1 enzyme was identified as an (−)-kolavenyl diphosphate synthase, which converts GGPP to (−)-kolavenyl diphosphate [36].

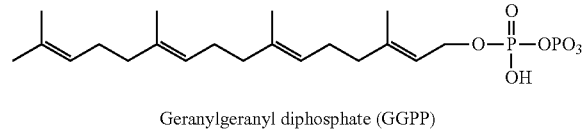

Geranylgeranyl diphosphate (GGPP)

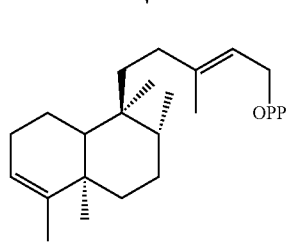

36

The *Salvia hispanica* (−)-kolavenyl diphosphate synthase (ShTPS1) has, for example, an amino acid sequence shown below (SEQ ID NO:51).

```
  1 MSIQANMSFA TSLHRSTTPG VGLPLKPCIS PSPSLSFSPN
 41 FGTFNNTSLR LKPEAGSKSY EGIRRSHQLA ASTILEGQTP
 81 ITPEVESEKT RLIERIRSML QDMDNDGQIS VSPYDTAWVA
121 LVEDIGGSGG PQFPTSLEWI SNHQYDDGSW GDRKFVLYDR
161 ILNTLACVVA LTNWKMHPNK CEKGLRFIHE NIKKLADEDE
201 ELMPVGFEIA LPSVIDLAKR LGIEIPENSA SIKRIYELRD
241 SKLKKIPMDL VHKRPTSLLF SLEGMEGLNW DKLMNFLAEG
281 SFLSSPSSTA YALQHTKNEL CLEYLLKAVK RFNGGVPNAY
321 PVDMFEHLWS VDRLQRLGIS RYFQAEIEEN MAYAYRYWTN
361 KGITWARNMV VQDSDDSAQG FRLLRLYGYD IPIDVFKHFE
401 QGGQFCSIPG QMTHAITGMY NLYRASELLF PGEHILSDAR
441 KYTGNFLHQR RITNTVVDKW IITKDLHGEV AYALDVPFYA
481 SLPRLEARFF IEQYGGDEDV WIGKTLYRMF KVNSDTYLEM
521 AKLDYKQCQS VHQLEWNSMQ RLYRDCNLGE FGLSERSLLL
561 AYYIAASTTF EPEKSSERLA WAITTILVEI IASQKLSDEQ
```

```
601 KREFVDEFVK GSIVNNQNGG RHKPGNRLVE VLINNITLMA
641 EGRGTYQQLS NAWKKWLKTW EEGGDLGEAE ARLLLHTIHL
681 SSGLDDSSFS HPKYQQLLEA TSKVCHQLRV FQSVKVYDDQ
721 ESTSQLVTRT TFQIEAGMQE LVKLVFTKTL EDLPSTTKQS
761 FFSVARSFYY TACIHADTID SHINKVLFEK IV
```

A nucleic acid encoding the *Salvia hispanica* (−)-kolavenyl diphosphate synthase (ShTPS1) with SEQ ID NO:51 is shown below as SEQ ID NO:52.

```
   1 ATGAGTATTC AAGCAAACAT GTCATTTGCC ACCTCCCTCC
  41 ACCGATCAAC CACCCCCGGA GTTGGCCTTC CGCTAAAACC
  81 ATGTATCTCT CCCTCTCCCT CTCTTTCCTT TTCCCCAAAC
 121 TTTGGCACTT TTAACAACAC AAGTTTGAGA CTCAAACCAG
 161 AGGCTGGGAG CAAAAGTTAT GAGGGGATTC GAAGAAGTCA
 201 TCAATTAGCA GCATCAACAA TTTTGGAGGG TCAAACTCCG
 241 ATTACTCCGG AGGTTGAATC GGAGAAAACA CGCCTGATTG
 281 AAAGGATTCG TTCGATGTTA CAAGACATGG ACAACGATGG
 321 CCAGATAAGT GTGTCACCAT ACGACACAGC ATGGGTGGCG
 361 CTCGTGGAAG ATATTGGTGG CAGCGGAGGG CCACAGTTTC
 401 CAACGAGCCT AGAGTGGATT TCTAACCACC AGTACGACGA
 441 TGGATCGTGG GGGGATCGCA AATTTGTTCT CTATGACCGG
 481 ATACTCAATA CATTAGCATG TGTTGTCGCA CTCACGAATT
 521 GGAAAATGCA TCCTAACAAA TGCGAAAAAG GGTTGAGGTT
 561 TATTCATGAG AATATTAAGA AACTCGCGGA TGAAGATGAA
 601 GAGCTCATGC CCGTAGGATT CGAAATCGCA CTGCCATCAG
 641 TCATTGATTT AGCTAAAAGA CTGGGTATAG AAATCCCAGA
 681 AAATTCTGCA AGCATAAAAA GAATTTATGA ATTGAGAGAT
 721 TCAAAACTTA AAAAAATACC AATGGATTTA GTGCACAAAA
 761 GGCCCACATC ACTACTCTTC AGCTTGGAAG GCATGGAAGG
 301 CCTTAACTGG GACAAACTAA TGAATTTTCT AGCCGAGGGT
 841 TCGTTTCTTT CATCGCCATC GTCCACTGCC TACGCTCTCA
 881 AACACACCAA GAATGAGTTA TGCCTAGAGT ATTTACTCAA
 921 GGCAGTCAAG AGATTCAATG GTGGAGTTCC AAATGCATAC
 961 CCTGTCGACA TGTTTGAGCA TCTGTGGTCC GTGGATCGCT
1001 TACAGAGATT AGGAATTTCT CGGTATTTTC AAGCTGAAAT
1041 TGAAGAAAAC ATGGCCTATG CTTACAGATA CTGGACAAAT
1081 AAAGGAATCA CCTGGGCAAG AAATATGGTT GTCCAAGACA
1121 GTGACGACAG CGCACAGGGA TTCAGGCTCT TAAGGTTGTA
1161 CGGATACGAT ATTCCTATAG ATGTTTTCAA ACATTTCGAG
1201 CAAGGTGGAC AATTCTGCAG CATACCAGGA CAGATGACAC
1241 ACGCTATTAC AGGAATGTAC AACTTGTATA GAGCTTCTGA
1281 ACTTCTGTTC CCTGGAGAAC ACATACTTTC TGATGCTAGA
1321 AAATACACAG GTAACTTCTT GCATCAAAGA AGAATTACTA
1361 ACACGGTAGT AGACAAGTGG ATCATTACCA AAGACCTTCA
1401 CGGCGAGGTG GCTTATGCAT TGGATGTGCC ATTCTACGCC
1441 AGTCTGCCAC GACTGGAAGC ACGATTCTTC ATAGAACAAT
1481 ATGGGGGTGA TGAAGATGTT TGGATTGGGA AAACATTGTA
1521 CAGGATGTTT AAAGTAAACT CCGACACATA CCTTGAGATG
1561 GCAAAATTAG ATTACAAACA ATGCCAGTCT GTGCATCAGT
1601 TAGAGTGGAA TAGCATGCAA AGATTGTATA GAGATTGCAA
1641 TCTAGGAGAG TTTGGGTTGA GCGAAAGAAG CCTTCTCCTA
1681 GCTTACTACA TAGCAGCCTC AACTACATTT GAGCCGGAAA
1721 AATCAAGTGA AAGACTGGCT TGGGCTATAA CAACAATTTT
1761 AGTCGAAATA ATCGCATCCC AAAAACTCTC TGATGAGCAA
1801 AAGAGAGAGT TTGTTGATGA ATTTGTAAAA GGAAGCATCG
1841 TCAATAACCA AAATGGAGGA AGACATAACC CGGGAAACAG
1881 ATTGGTTGAA GTTTTGATCA ACAATATAAC ACTGATGGCA
1921 GAAGGCAGAG GCACATATCA GCAGTTGTCT AATGCGTGGA
1961 AAAAATGGCT AAAGACATGG GAAGAGGGAG GTGACCTGGG
2001 GGAAGCACAA GCACGGCTTC TCCTGCACAC GATACATTTG
2041 AGCTCCGGAT TGGATGATTC ATCATTTTCC CATCCAAAAT
2081 ATCAGCAGCT CTTGGAGGCA ACCAGCAAAG TCTGCCACCA
2121 ACTTCGCGTA TTCCAGAGTG TAAAGGTGTA TGATGACCAA
2161 GAGTCTACAA GCCAACTGGT AACTAGGACA ACTTTCCAAA
2201 TAGAAGCAGG CATGCAAGAA CTAGTGAAAT TAGTTTTCAC
2241 AAAAACCTTG GAAGATTTGC CTTCTACTAC CAAGCAAAGC
2281 TTTTTTAGTG TTGCTAGAAG TTTCTATTAC ACTGCCTGTA
2321 TTCATGCAGA CACTATAGAC TCCCACATAA ACAAAGTATT
2361 GTTTGAAAAA ATTGTCTAG
```

A *Teucrium canadense* cleroda-4(18),13E-dienyl diphosphate synthase (TcTPS1) was identified and isolated as described herein. This TcTPS1 enzyme was identified as a cleroda-4(18), 13E-dienyl diphosphate synthase, which converts GGPP to cleroda-4(18),13E-dienyl diphosphate [38]. In addition, the combination of TcTPS1 and SsSS enzymes generated neo-cleroda-4(18),14-dien-13-ol [37]. These compounds are shown below.

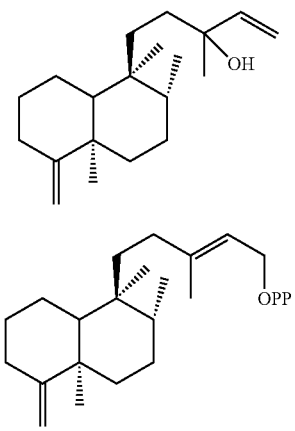

37

38

The *Teucrium canadense* cleroda-4(18), 13E-dienyl diphosphate synthase (TcTPS1) amino acid sequence is shown below as SEQ ID NO:53.

```
  1 MSFASQATSL LLSSHNATAL PPLSAARLPP LTAGAAPFGR
 41 ISFTTTSLRQ YKLVSRAQSQ EVDEIEKVTQ VVLEAEKDID
 81 QEAKVRELVE NVRVKLQNIG EGGISISPYD TAWVALVEDV
121 GGSGRPQFPE SLDWISNHQF PDGSWGSHKF LYYDRVLCTL
161 ACIVALKTWN LHPHKFDKGL KFVRENIGKL ADEEDVHMPI
201 GFEVAFPSLI ETAKRKGIDI PEDFPGKKEI YAKRDLKLKK
241 IPMDILHKIP TPLLFSIEGI EGLDWQKLFK FRDHGSFLTS
281 PSSTAHALQQ TKDELCLKYL TNLVKKNNGG VPNAFPVDLF
321 DRNYTVDRLR RLGILRYFQP EIEECMKYVY REWDKRCISW
361 ARNTHVQDLD DTVQGFRNLR MHGYDVTLDV FKQFERCGEF
401 FSFHGQSSDA VLCMFNLYRA SQVLFPGEDM LADARKYAAN
441 YLHKRRVSNR VVDKWIINKD LPGEVAYGLD VPFYASLPRL
481 EARFYVEQYG GNDDVWIGKA LYRMLNVSCD TYLELAKLDY
521 NICQAVHQKE WKSFQKWHRD GEFGLDEKSL LLAYYIAAST
561 VFEPEKSLER LAWAKTAVLM EAILSQQLPS TKKHELVDEF
601 KHASILNNQN GGSYKTRTPL VETLVNAISE LSTTILLEQD
641 RDIHLQLSNA WLKWLSRWEA RGNLVEAEAE LLLQTLHLSN
681 GLEESSFSHP KYQQLLQVIS KVCHLLRLFQ KRKVHDPEGC
721 TTDIATGTTF QIEACMQQVV KLVFTKSSHD LDSVVKQRFL
761 DVARSFYYTA HCDPQVIQSH INKVLFEKVV
```

A nucleic acid encoding the *Teucrium canadense* Cleroda-4(18),13E-dienyl diphosphate synthase (TcTPS1) has with SEQ ID NO:53 is shown below as SEQ ID NO:54.

```
   1 ATGTCATTTG CTTCCCAAGC CACCTCCCTC CTCCTTTCTT
  41 CCCACAACGC CACCGCTCTT CCGCCTCTCT CTGCCGCCCG
  81 CCTTCCGCCT CTCACTGCCG GTGCTGCTCC ATTCGGAAGA
 121 ATATCATTTA CTACTACCTC TCTTCGGCAG TATAAACTGG
 161 TGTCAAGAGC TCAAAGCCAA GAGGTGGATG AGATTGAAAA
 201 AGTGACACAA GTGGTATTGG AGGCAGAAAA AGACATCGAT
 241 CAAGAGGCGA AGGTAAGGGA GCTGGTGGAA AATGTCCGAG
 281 TGAAGCTGCA AAATATCGGG GAAGGAGGGA TAAGCATATC
 321 GCCGTACGAC ACCGCATGGG TGGCGCTGGT GGAGGATGTC
 361 GGCGGCAGCG GCAGACCGCA GTTCCCGGAG AGCCTGGATT
 401 GGATATCAAA CCACCAGTTC CCGGACGGGT CGTGGGGCAG
 441 CCACAAATTC TTGTACTATG ACCGGGTTTT GTGCACGTTA
 481 GCATGTATAG TTGCATTGAA AACTTGGAAT CTGCATCCTC
 521 ACAAATTCGA CAAAGGGTTG AAATTCGTCA GAGAGAACAT
 561 TGGAAAGCTC GCGGATGAAG AAGACGTGCA CATGCCGATT
 601 GGGTTCGAAG TGGCATTCCC ATCACTTATA GAGACTGCAA
 641 AGAGAAAAGG AATTGACATC CCGGAAGATT TCCCTGGCAA
 681 GAAAGAAATC TATGCAAAAA GAGACCTAAA GCTGAAAAAG
 721 ATACCTATGG ATATACTGCA CAAAATCCCC ACACCATTAC
 761 TGTTCAGCAT AGAAGGGATA GAAGGCCTTG ATTGGCAGAA
 801 GCTATTCAAA TTCCGCGATC ACGGCTCCTT CCTCACGTCC
 841 CCGTCCTCAA CGGCCCACGC TCTCCAGCAA ACAAAGGACG
 881 AGTTATGCCT CAAATATCTG ACCAATCTTG TCAAAAAGAA
 921 CAATGGGGGA GTTCCAAATG CATTTCCGGT GGACCTATTT
 961 GATCGTAACT ATACAGTAGA GCGCCTGAGG AGGCTGGGAA
1001 TTTTGCGCTA TTTTCAACCT GAAATCGAGG AATGCATGAA
1041 ATATGTATAC AGATICTGGG ATAAAAGAGG AATCAGCTGG
1081 GCAAGAAATA CCCATGTTCA GGACCTTGAT GATACCGTAC
1121 AGGGATTCAG GAACTTAAGG ATGCATGGTT ATGATGTCAC
1161 CTTAGATGTT TTCAAACAGT TCGAGAGATG TGGAGAATTC
1201 TTTAGCTTCC ACGGGCAATC AAGTGATGCT GTCTTAGGAA
1241 TGTTCAACTT GTACCGAGCT TCTCAGGTTC TGTTTCCAGG
1281 AGAAGACATG CTTGCAGATG CAAGGAAGTA CGCGGCCAAC
1321 TATTTGCATA AAAGAAGAGT TAGTAATAGG GTCGTGGACA
1361 AATGGATTAT TAACAAAGAT CTTCCAGGCG AGGTGGCGTA
1401 TGGGCTAGAT GTTCCGTTCT ACGCCAGTCT ACCTCGACTG
1441 GAAGCAAGAT TCTACGTCGA ACAATATGGG GGTAACGATG
1481 ATGTCTGGAT TGGAAAAGCT TTATATAGAA TGTTGAATGT
1521 GAGCTGTGAT ACTTACCTTG AGCTAGCAAA ATTAGACTAC
1561 AATATTTGCC AGGCTGTGCA TCAGAAAGAG TGGAAAAGCT
1601 TTCAAAAATG GCACAGGGAT GGGGAGTTTG GATTGGATGA
1641 AAAAAGCTTA CTTTTAGCTT ACTACATAGC AGCCTCGACT
1681 GTTTTCGAGC CTGAAAAATC TCTAGAGCGA CTGGCTTGGG
1721 CTAAACCGC AGTTCTAATG GAGGCAATTT TGTCCCAACA
1761 ACTTCCTAGC ACAAAAAAAC ATGAGCTTGT TGACGAATTT
1801 AAACATGCAA GCATCCTCAA CAACCAAAAT GGAGGAAGCT
1841 ATAAAACAAG AACTCCTTTG GTAGAGACTC TAGTAAACGC
1881 CATAAGTGAG CTCTCAACTA CCATACTATT GGAGCAAGAC
1921 AGAGACATTC ATCTGCAATT ATCTAATGCG TGGCTGAAGT
1961 GGCTAAGTAG ATGGGAGGCA AGAGGCAACC TAGTGGAAGC
2001 AGAAGCAGAG CTTCTTCTGC AAACCTTACA TCTGAGCAAT
2041 GGATTAGAAG AATCATCATT TTCTCATCCA AAATATCAAC
2081 AACTCTTACA GGTTACCAGC AAAGTCTGTC ACCTACTTCG
2121 GCTATTCCAG AAACGAAAGG TGCATGATCC GGAAGGGTGT
2161 ACAACAGACA TTGCAACAGG GACAACTTTC CAAATAGAAG
2201 CATGCATGCA ACAAGTAGTG AAATTAGTGT TCACCAAATC
2241 CTCACATGAT TTAGATTCTG TTGTTAAGCA GAGATTTTTG
2281 GATGTTGCCA GAAGTTTCTA TTACACAGCC CACTGTGATC
2321 CACAAGTGAT CCAGTCCCAC ATTAATAAAG TGTTGTTTGA
2361 AAAAGTAGTC TAG
```

*Salvia officinalis* (SoTPS2), *Scutellaria baicalensis* SbTPS1, and SbTPS2 enzymes were identified and isolated. These SoTPS2, SbTPS1, SbTPS2, CfTPS18a and CfTPS18b enzymes were all identified as ent-CPP synthases, which convert GGPP to ent-CPP.

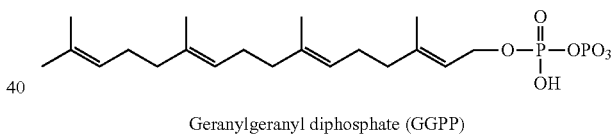

Geranylgeranyl diphosphate (GGPP)

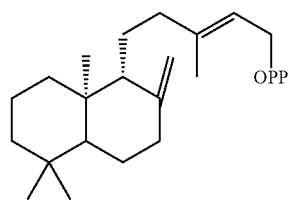

16

The *Salvia officinalis* (SoTPS2) enzyme can have the amino acid sequence shown below (SEQ ID NO:55).

```
  1 MSFASTTSLL RPSVTGFGVS PRVTSTSILS RSYGQILKGK
 41 TKYITDNRRN RQLAVKFEGQ IALDLEDGVA KQTNQEAESE
 81 KIRQLKGKIR WILQNMEDGE MSVSPYDTAW VALVEDISGG
121 GGPQFPTSLE WISKNQLADG SWGDPNYFLL YDRILNTLAC
161 VVALTTWNMH PHKCDQGLRF IRDNIEKLED EDEELILVGF
201 EIALPSLIDY AQNLGIQIQY DSPFIKKICA KRDLKLRKIP
```

-continued

```
241 MDLMHRKPTS LLYSLEGMEG LEWEKLMNLR SEGSFLSSPS
281 STAYALQHTK DELCLDYLVK AVNKFNGGVP NVYPVDMYEH
321 LWCVDRLQRL GISRYFQLEI QQCLDYVYRY WTNEGISWAR
361 YTNIRDSDDT AMGFRLLRLY GYDVSIDAFK PFEESGEFYS
401 MAGQMNHAVT GMYNLYRASQ LMFPQEHILS DARNFSAKFL
441 HQKRRTNALV DKWIITKDLP GEVGYALDVP FYASLPRLEA
481 RFFLEQYGGD DDVWIGYTLY RMPYVNSNTY LELAKVDYKN
521 CQSVHQLEWK SMQKWYRECN IGEFGLSERS LLLAYYIAAS
561 TTFEPEKSGE RLAWATTAIL IETIASQQLS DEQKREFVDE
601 FENSIIIKNQ NGGRYKARNR LVKVLINTVT LVAEGRGINQ
641 QLFNAWQKWL KTWEEGGDMG EAEAQLLLRT LHLSSGFDQS
681 SFSHPKYEQL LEATSKVCHQ LRLFQNRKVD DGQGCISRLV
721 IGTTSQIEAG MQEVVKLVFT KTSQDLTSAT KQSFFNIARS
761 FYYTAYFHAD TIDSHIYKVL FQTIV
```

A nucleic acid encoding the *Salvia officinalis* (SoTPS2) has with SEQ ID NO:55 is shown below as SEQ ID NO:56.

```
   1 ATGTCATTTG CTTCCACCAC CTCCCTCCTC CGACCAAGCG
  41 TCACTGGGTT CGGTGTTTCT CCAAGGGTTA CTTCCACCTC
  81 CATTCTTAGC CGAAGTTATG GTCAAATATT AAAAGGAAAA
 121 ACAAAATACA TAACTGATAA CCGTAGAAAT CGACAATTGG
 161 CGGTAAAATT TGAGGGCCAA ATTGCTTTGG ATTTGGAGGA
 201 TGGCGTAGCA AAGCAGACGA ATCAAGAGGC GGAATCTGAG
 241 AAGATAAGGC AACTGAAGGG AAAGATCCGA TGGATTCTGC
 281 AAAACATGGA GGACGGCGAG ATGAGCGTGT CGCCGTACGA
 321 CACCGCATGG GTGGCGCTGG TGGAAGATAT CAGCGGCGGC
 361 GGCGGGCCGC AGTTCCCGAC GAGCCTGAGG TGGATTTCCA
 401 AGAATCAGTT GGCGGATGGG TCATGGGGGG ATCCTAATTA
 441 TTTCCTTCTC TACGACAGAA TACTCAATAC TTTAGCATGT
 481 GTAGTCGCAC TCACGACTTG GAATATGCAT CCTCACAAAT
 521 GCGATCAAGG GTTGAGGTTT ATAAGAGACA ACATTGAGAA
 561 ACTTGAGGAT GAAGATGAGG AGCTAATTCT CGTAGGATTC
 601 GAGATCGCAC TGCCTTCACT CATTGATTAT GCTCAAAACC
 641 TTGGGATACA AATCGATAT GATTCTCCAT TCATTAAAAA
 681 AATTTGTGCA AAGAGAGATC TAAAACTCAG AAAAATACCA
 721 ATGGATTTAA TGCACAGAAA GCCAACATCA TTGCTCTACA
 761 GCTTGGAAGG CATGGAAGGC CTTGAGTGGG AAAAGCTAAT
 801 GAATTTGCGA TCGGAGGGTT CGTTTCTGTC ATGGCCGTCG
 841 TCCACGGCCT ACGCTCTCCA ACACACCAGG ATGAGTTAT
 881 GCCTTGACTA TCTGGTCAAG GCGGTCAACA AATTCAATGG
 921 TGGAGTTCCC AACGTGTACC CTGTCGACAT GTATGAGCAT
 961 CTATGGTGCG TAGACCGCTT GCAGAGGTTG GGAATTTCTC
1001 GCTATTTTCA ACTTGAAATT CAACAATGCC TCGACTATGT
1041 TTACAGATAC TGGACAAATG AAGGAATTTC GTGGGCAAGA
1081 TATACTAATA TCCGGGATAG TGACGACACC GCAATGGGAT
1121 TCAGGCTTCT AAGGTTGTAC GGCTATGATG TCTCTATAGA
1161 TGCTTTTAAA CCATTCGAGG AAAGCGGAGA ATTCTATAGC
1201 ATGGCAGGGC AGATGAACCA CGCTGTTACA GGAATGTACA
1241 ACTTGTACAG AGCTTCTCAA CTTATGTTCC CTCAAGAACA
1281 CATACTTTCC GATGCCAGAA ACTTCTCTGC CAAATTCTTG
1321 CATCAAAAGA GGCGTACTAA TGCACTAGTA GACAAGTGGA
1361 TCATTACCAA AGACCTTCCC GGCGAGGTTG GATATGCATT
1401 GGATGTGCCG TTCTACGCCA GTCTGCCTCG ACTGGAAGCA
1441 CGATTCTTCT TAGAACAATA TGGGGGTGAT GATGATGTTT
1481 GGATTGGAAA AACTTTGTAC AGGATGCCAT ATGTGAACTC
1521 CAACACATAC CTTGAGCTTG CAAAAGTAGA CTACAAAAAC
1561 TGCCAGTCCG TGCATCAGTT GGAGTGGAAG AGCATGCAAA
1601 AATGGTACAG AGAATGCAAT ATAGGTGAGT TTGGGTTGAG
1641 CGAAAGAAGC CTTCTCCTAG CTTACTACAT AGCAGCCTCA
1681 ACTACATTCG AGCCAGAAAA ATCAGGTGAG CGGCTCGCTT
1721 GGGCTACAAC AGCAATTTTA ATCGAGACAA TCGCGTCCCA
1761 ACAACTCTCC GATGAACAAA AGAGAGAGTT CGTTGATGAA
1801 TTTGAAAACA GCATCATTAT CAAGAATCAA AATGGAGGGA
1841 GATATAAAGC AAGAAACAGA TTGGTCAAGG TTTTGATCAA
1381 CACTGTAACA CTGGTAGCAG AAGGCAGAGG CATAAATCAG
1921 CAGTTGTTTA ATGCGTGGCA AAAATGGCTA AAGACATGGG
1961 AAGAAGGAGG TGACATGGGG GAAGCAGAGC AACTTCTTCT
2001 TCTGCGCACG CTACATTTGA GCTCCGGATT CGATCAATCA
2041 TCATTTTCCC ATCCAAAATA TGAGCAGCTC TTGGAGGCGA
2081 CCAGCAAAGT TTGCCACCAA CTTCGCCTAT TCCAGAATCG
2121 AAAGGTGGAT GATGGCCAAG GGTGTATAAG TCGATTGGTA
2161 ATTGGGACAA CTTCCCAAAT AGAAGCAGGC ATGCAAGAAG
2201 TAGTGAAATT AGTTTTCACC AAAACCTCAC AAGACTTGAC
2241 TTCTGCTACC AAGCAAAGCT TTTTCAATAT TGCTAGAAGT
2281 TTCTATTATA CTGCCTACTT TCATGCAGAC ACTATAGACT
2321 CCCACATATA CAAAGTATTG TTTCAAACAA TAGTATAG
```

A *Scutellaria baicalensis* SbTPS1 amino acid sequence shown below (SEQ ID NO: 57).

```
   1 MPFLLPSSAT SSPAFYTPAA PLAGHHVFPS FKPLIISRSS
  41 LQCNAISRPR TQEYIDVIQN GLPVIKWHEA VEEDETDKDS
  81 LNKEATSDKI RELVNLIRSM LQSMGDGEIS SSPYDAAWVA
 121 LVPDVGGSGG PQFPSSLEWI SKNQLPDGSW GDTCTFSIYD
 161 RIINTLACVV ALKSWNIHPH KTYQGISFIK ANMDKLEDEN
 201 EEHMPIGFEV ALPSLIEIAK RLDIDISSDS RGLQEIYTRR
 241 EVKLKRIPKE IMHQVPTTLL HSLEGMAELT WHKLLKLQCQ
 281 DGSFLFSPSS TAFALHQTKD HNCLHYLTKY VHKFHGGVPN
 321 VYPVDLFEHL WAVDRIQRLG ISRHFKPQVD ECIAYVYRYW
 361 TDKGICWARN SVVQDLDDTA MGFRLLRLHG YDVSADVFKH
 401 FENGGEFFCF KGQSTQAVTG MYNLYRASQL MFPGESILED
 441 AKTESSKFLQ RKRANNELLD KWIITKDLPG EVGYALDVPW
 481 YASLPRVETR FYLEQYGGED DVWIGKTLYR MPYVNNNKYL
 521 ELAKLDYSNC QSLHQQEWKN IQKWYESCNL GEFGLSERRV
 561 LLAYYVAAAC IYEPEKSNQR LAWAKTVILM ETITSYFEHQ
 601 QLSAEQRRAF VNEFEHGSIL KYANGGRYKR RSVLGTLLKT
 641 LNQLSLDILL THGRNVHQPF KNAWHKWLKT WEEGGDIEEG
 681 EAEVLVRTLN LSGEGRHDSY VLEQSLLSQP IYEQLLKATM
 721 SVCKKLRLFQ HRKDENGCMT KMRGITTLEI ESEMQELVKL
 761 VFTKSSDDLD CEIKQNFFTI ARSFYYVAYC NQGTINYHIA
 801 KVLFERVL
```

A nucleic acid encoding the *Scutellaria baicalensis* SbTPS1 with SEQ ID NO:57 is shown below as SEQ ID NO:58.

```
   1 ATGCCTTTCC TCCTCCCTTC CTCCGCCACC AGCTCCCCCG
  41 CGTTCTATAC TCCGGCCGCG CCTCTCGCCG GTCATCATGT
  31 TTTTCCATCT TTCAAGCCAC TCATTATTTC CCGTTCTTCA
 121 CTCCAATGCA ATGCAATCTC TCGACCTCGT ACCCAAGAAT
 161 ACATAGATGT GATTCAGAAT GGATTGCCAG TAATAAAGTG
 201 GCACGAAGCT GTGGAAGAAG ATGAGACAGA TAAAGATTCT
 241 CTTAATAAGG AGGCCACGTC AGACAAGATA AGAGAGTTGG
 281 TAAATCTGAT CCGTTCGATG CTCCAATCAA TGGGCGACGG
 521 AGAGATAAGC TCGTCGCCGT ACGACGCCGC ATGGGTGGCG
 561 CTGGTGCCGG ACGTCGGCGG CTCCGGCGGG CCCCAGTTCC
 601 CCTCCAGCCT CGAATGGATA TCCAAAAACC AACTCCCCGA
 641 CGGCTCCTGG GGCGACACGT GTACCTTTTC CATTTATGAT
 681 CGAATCATCA ACACACTGGC TTGCGTTGTT GCTTTGAAAT
 721 CTTGGAACAT ACATCCCCAC AAAACTTATC AAGGGATTTC
 761 ATTCATAAAG GCAAATATGG ACAAACTTGA AGACGAGAAC
 801 GAGGAGCACA TGCCGATCGG ATTTGAAGTG GCACTCCCGT
 841 CGCTAATCGA GATAGCGAAA AGGCTCGATA TCGATATTTC
 881 CAGCGATTCG AGAGGGCTGC AAGAGATATA CACGAGGAGG
 921 GAGGTAAAGC TGAAAAGGAT ACCGAAAGAG ATAATGCACC
 961 AAGTGCCCAC AACACTGCTT CATAGCTTGG AGGGTATGGC
1041 CGAGCTGACG TGGCACAAGA TTTTGAAATT ACAGTGCCAA
1081 GATGGCTCCT TTCTTTTCTC TCCATCTTCA ACTGCCTTTG
1121 CTCTTCACCA AACTAAGGAC CATAATTGTC TCCATTATTT
1161 GACCAAATAT GTTCACAAAT TTCATGGTGG AGTGCCAAAT
1201 GTTTATCCGG TGGACTTGTT CGAGCATCTA TGGGCAGTTG
1241 ATCGGATCCA ACGGCTGGGG ATTTCCCGGC ATTTCAAGCC
1281 CCAAGTTGAT GAATGTATTG CCTATGTTTA TAGATATTGG
1321 ACAGATAAAG GAATATGCTG GGCAAGAAAT TCAGTAGTTC
1361 AAGATCTTGA TGACACAGCC ATGGGATTCA GGCTTCTTAG
1401 GTTGCATGGC TACGATGTTT CAGCAGATGT TTTCAAACAT
1441 TTTGAAAATG GTGGAGAGTT CTTCTGCTTC AAAGGGCAAA
1481 GCACGCAGGC AGTGACTGGA ATGTACAATC TGTACAGAGC
1521 TTCTCAGTTG ATGTTTCCTG GAGAAAGCAT ACTGGAAGAT
1601 GCTAAGACCT TCTCATCTAA GTTTTTGCAA CGAAAACGAG
1641 CCAATAACGA GTTGTTAGAT AAGTGGATTA TTACCAAGGA
1681 TCTTCCTGGA GAGGTGGGAT ATGCTCTAGA TGTACCATGG
1721 TATGCTAGCT TACCTAGAGT TGAAACTAGA TTCTACTTGG
1801 AACAATATGG TGGTGAAGAT GATGTTTGGA TTGGCAAAAC
1841 TTTATACAGG ATGCCATATG TTAACAATAA TAAATATCTA
1881 GAACTGGCAA AATTAGACTA TAGTAACTGC CAGTCATTAC
1921 ATCAACAAGA GTGGAAAAAC ATTCAAAAAT GGTATGAGAG
1961 TTGCAATCTG GGAGAATTTG GTITGAGTGA AAGAAGGGTT
2001 CTACTAGCCT ACTACGTAGC TGCTGCCTGT ATATATGAGC
2041 CCGAAAAGTC AAACCAGCGC TTGGCTTGGG CCAAAACCGT
2081 AATTTTAATG GAGACTATTA CTTCCTATTT TGAGCACCAA
2121 CAACTCTCCG CAGAACAGAG ACGCGCCTTT GTTAATGAAT
2161 TTGAACATGG GAGTATCCTC AAATATGCAA ATGGAGGAAG
2201 ATACAAAAGG AGGAGTGTTT TGGGGACTTT GCTCAAAACA
2241 CTAAATCAGC TTTCATTGGA TATATTATTG ACACACGGTC
2281 GAAACGTTCA TCAGCCTTTC AAAAATGCGT GGCACAAGTG
```

-continued

```
2321 GCTAAAAACG TGGGAAGAAG GAGGTGACAT TGAAGAAGGC
2361 GAAGCAGAGG TATTGGTCCG AACCCTAAAC CTAAGCGGCG
2401 AAGGGAGGCA CGACTCCTAT GTATTGGAGC AATCATTATT
2441 GTCAGAACCT ATATATGAAC AACTTTTGAA AGCCACCATG
2481 AGTGTTTGCA AGAAGCTTCG ATTGTTCCAA CATCGAAAGG
2521 ATGAGAATGG ATGTATGACG AAGATGAGAG GCATTACAAC
2561 GTTAGAGATA GAATCGGAGA TGCAAGAATT AGTGAAATTA
2601 GTATTTACTA AATCCTCAGA TGATTTAGAT TGTGAAATTA
2641 AACAAAACTT TTTTACAATT CGTAGGAGTT TCTATTATGT
2681 GGCTTATTGT AACCAAGGAA CTATCAACTT TCACATTGCT
2721 AAGGTGCTCT TTGAAAGAGT TCTTTAG
```

A *Scutellaria baicalensis* SbTPS2 amino acid sequence is shown below (SEQ ID NO:59).

```
  1 MASLSTLSLN FSPAIHRKIQ QSSAKLQFQG HCFTISSCMN
 41 NSKRLSLNHQ SNHKRTSNVS ELQVATLDAP QIREKEDYST
 81 AQGYEKVDEV EDPIEYIRML LNTTGDGRIS VSPYDTAWIA
121 LIKDVEGRDA PQFPSSLEWI ANNQLSDGSW GDEKFFCVYD
161 RLVNTLACVV ALRSWNIDAE KSEKGIRYIK ENVDKLKDGN
201 PEHMTCGFEV VEPSLLQRAQ SMGIHDLPYD APVIQDIYNT
241 RESKLKRIPM EVMHKVPTSL LFSLEGLENL EWDKLLKLQS
281 SDGSFLTSPS STAYAFMHTK DPKCFEFIKN TVETFNGGAP
321 HTYPVDVFGR LWAIDRLQRL GISRFFESEI ADCLDHIYKY
361 WTDKGVFSGR ESDFVDVDDT SMGVRLLRMH GYQVDPNVLR
401 NFKQGDKFSC YGGQMIESSS PIYNLYRASQ LRFPGEDILE
441 DANKFAYEFL QEQLSNNQLL DKWVISKHLP DEIKLGLQMP
481 WYATLPRVEA KYYLQYYAGA DDVWIGKTLY RMPEISNDTY
521 LELARMDFKR CQAQHQFEWI SMQEWYESCN IEEFGISRKE
561 LLQAYFLACS SVFELERTTE RIGWAKSQII SRMIASFFNN
601 ETTTADEKDA LLTRFRNING PNRTKSGQRE SEAVNMLVAT
641 LQQYLAGFDR YTRHQLKDAW SVWFRKVQEE EAIYGAEAEL
681 LTTTLNICAG HIAFDENIMA NYDYTTLSSL TSKICQKLSE
721 IRNEKVEEME SGIKAKSSIK DKEVEHDMQS LVKLVLERCE
761 GINNRKLKQT FLSVAKTYYY RAYNADETMD IHMFKVLFEP
801 VM
```

A nucleic acid encoding the *Scutellaria baicalensis* SbTPS2 with SEQ ID NO:59 is shown below as SEQ ID NO:60.

```
   1 ATGGCCTCTC TATCAACTCT GAGCCTCAAC TTTTCCCCAG
  41 CAATTCACCG CAAAATACAG CAATCATCTG CAAAACTTCA
  81 GTTCCAGGGA CATTGTTTCA CCATAAGTTC ATGCATGAAC
 121 AACAGTAAAA GACTGTCTTT GAACCACCAA TCTAATCACA
 161 AAAGAACGTC AAACGTATCT GAGCTGCAAG TTGCCACTTT
 201 GGATGCGCCC CAAATACGTG AAAAAGAAGA CTACTCCACT
 241 GCTCAAGGCT ATGAGAAGGT GGATGAAGTA GAGGATCCTA
 281 TCGAATATAT TAGAATGCTG TTGAACACAA CAGGTGATGG
 321 GCGAATAAGT GTGTCGCCAT ACGACACAGC CTGGATCGCT
 361 CTTATTAAAG ACGTGGAAGG ACGTGATGCT CCCCAGTTCC
 401 CATCTAGTCT CGAATGGATT GCCAATAATC AACTGAGTGA
 441 TGGGTCGTGG GGCGATGAGA AGTTTTTCTG TGTGTATGAT
 481 CGCCTTGTTA ATACACTTGC ATGTGTCGTG GCATTAGAGT
 521 CATGGAATAT TGATGCTGAA AAGAGCGAGA AAGGAATAAG
 561 ATACATAAAA GAAAACGTGG ATAAACTGAA AGATGGGAAT
 601 CCAGAGCACA TGACCTGTGG TTTTGAGGTG GTGTTTCCTT
 641 CCCTTATGAT GCTCCTGTCA TCCAAGCAT TTACAATACC
 681 TCCCTATGAT GCTCCTGTCA TCCAAGACAT TTACAATACC
 721 AGGGAGAGTA AATTGAAAAG CATTCCAATG GAGGTTATCC
 761 ACAAGGTGCC AACATCTCTA TTGTTCAGCT TGGAAGGATT
 801 GGAGAATTTG GAGTGGGATA AGCTCCTCAA ACTTCAGTCT
 841 TCTGATGGTT CATTCCTCAC TTCTCCATCC TCAACTGCCT
 881 ATGCTTTCAT GCACACTAAG GACCCTAAAT GCTTCGAATT
 921 CATCAAAAAC ACCGTCGAAA CATTTAATGG AGGAGCCCCA
 961 CATACTTATC CGGTGGATGT TTTTGGAAGA CTGTGGGCCA
1001 TTGACAGGCT GCAGCGCCTC GGAATCTCTC GCTTCTTTGA
1041 GTCCGAGATT GCTGATTGCT TAGATCACAT CTATAAATAT
1081 TGGACAGACA AAGGAGTGTT CAGTGGAAGA GATCCAGATT
1121 TTGTGGATGT GGATGACACA TCCATGGGTG TTAGGCTTCT
1161 AAGGATGCAC GGATATCAAG TTGATCCAAA TGTATTGAGG
1201 AACTTCAAGC AGGGTGACAA ATTTTCATGC TATGGTGGTC
1241 AAATGATAGA GTCATCATCT CCGATATACA ATCTCTATAG
1281 GGCTTCTCAA CTCCGATTTC CAGGAGAAGA CATTCTTCAA
1321 GATGCCAACA AATTCGCATA CGAGTTCTTG CAAGAACAGC
1361 TATCCAACAA TCAACTTTTG GACAAATGGG TTATATCCAA
1401 GCACTTGCCT GATGAGATAA AGCTTGGATT GCAGATGCCA
1441 TGGTATGCCA CCCTACCCCG AGTGGAGGCT AAATACTACC
```

-continued

```
1481 TACAGTATTA TGCTGGTGCT GATGATGTCT GGATCGGCAA
1521 GACTCTCTAC AGAATGCCAG AAATCAGTAA TGATACATAT
1561 CTGGAGTTAG CAAGAATGGA TTTCAAGAGA TGCCAAGCAC
1601 AGCATCAATT TGAGTGGATT TCCATGCAAG AATGGTATGA
1641 AAGTTGCAAC ATTGAAGAAT TTGGGATAAG CAGLAAAGAG
1681 CTTCTTCAGG CTTACTTTTT GGCCTGCTCA AGTGTATTTG
1721 AACTCGAGAG GACAACAGAG AGAATAGGAT GGGCCAAATC
1761 CCAAATTATT TCAAGGATGA TAGCTTCTTT CTTCAACAAT
1801 AACAACTACA CAGCCGATGA AAAAGATGCA CTTTTAACCA
1841 GATTCAGAAA CATCAATGGC CCAAACAAAA CAAAAAGTGG
1881 TCAGAGAGAG AGTGAAGCTG TGAACATGTT GGTAGCAACG
1921 CTCCAACAAT ACCTGGCAGG ATTTGATAGA TATACCAGAC
1961 ATCAATTGAA AGATGCTTGG AGTGTGTGGT TCAGAAAAGT
2001 GCAAGAAGAA GAGGCCATCT ACGGGGCAGA AGCGGAGCTT
2041 CTAACAACCA CCTTAAACAT CTGTGCTGGT CATATTGCTT
2081 TCGACGAAAA CATAATGGCC AACAAAGATT ACACCACTCT
2121 TTCCAGCCTT ACAAGCAAAA TTTGCCAGAA GCTTTCTGAA
2161 ATTCGAAATG AAAAGGTTGA GGAAATGGAG AGTGGAATTA
2201 AAGCAAAATC AAGCATCAAA GACAAGGAAG TGGAACATGA
2241 TATGCAGTCA CTGGTGAAAT TAGTCCTGGA GAGATGTGAA
2281 GGCATAAACA ACAGAAAACT GAAGCAAACA TTTCTATCGG
2321 TTGCAAAAAC ATATTACTAC AGAGCCTATA ATGCTGATGA
2361 AACCATGGAC ATCCATATGT TCAAAGTACT TTTCGAACCA
2401 GTCATGTGA
```

An example of a *Salvia sclarea* sclareol synthase amino acid sequence is shown below (SEQ ID NO:176; NCBI accession no. AET21246.1).

```
  1 MSLAFNVGVT PFSGQRVGSR KEKFPVQGFP VTTPNRSRLI
 41 VNCSLTTIDF MAKMKENFKR EDDKFPTTTT LRSEDIPSNL
 81 CIIDTLQRLG VDQFFQYEIN TILDNTFRLW QEKHKVIYGN
121 VTTHAMAFRL LRVKGYEVSS EELAPYGNQE AVSQQTNDLP
161 MIIELYRAAN ERIYEEERSL EKILAWTTIF LNKQVQDNSI
201 PDKKLHKLVE FYLRNYKGIT IRLGARRNLE LYDMTYYQAL
241 KSTNRESNLC NEDFLVFARQ DFDIHEAQNQ KGLQQLQRWY
281 ADCRLDTLNF GRDVVIIANY LASLIIGDHA FDYVRLAFAK
321 TSVLVTIMDD FFDCHGSSQE CDKIIELVKE WKENPDAEYG
361 SEELEILFMA LYNTVNELAE RARVEQGRSV KEFLVKLWVE
401 ILSAFKIELD TWSNGTQQSF DEYISSSWLS NGSRLTGLLT
441 MQFVGVKLSD EMLMSEECTD LARHVCMVGR LLNDVCSSER
481 EREENIAGKS YSILLATEKD GRKVSEDEAI AEINEMVEYH
521 WRKVLQIVYK KESILPRRCK DVFLEMAKGT FYAYGINDEL
561 TSPQQSKEDM KSFVF
```

A nucleic acid encoding the *Salvia: sclarea* sclareol synthase with SEQ ID NO:176 is shown below as SEQ ID NO: 177.

```
   1 ATGTCGCTCG CCTTCAACGT CGGAGTTACG CCTTTCTCCG
  41 GCCAAAGAGT TGGGAGCAGG AAAGAAAAAT TTCCAGTCCA
  81 AGGATTTCCT GTGACCACCC CCAATAGGTC ACGTCTCATC
 121 GTTAACTGCA GCCTTACTAC AATAGATTTC ATGGCGAAAA
 161 TGAAAGAGAA TTTCAAGAGG GAAGACGATA AATTTCCAAC
 201 GACAACGACT CTTCGATCCG AAGATATACC CTCTAATTTG
 241 TGTATAATCG ACACCCTTCA AAGGTTGGGG GTCGATCAAT
 281 TCTTCCAATA TGAAATCAAC ACTATTCTAG ATAACACATT
 321 CAGGTTGTGG CAAGAAAAAC ACAAAGTTAT ATATGGCAAT
 361 GTTACTACTC ATGCAATGGC ATTTAGGCTT TTGCGAGTGA
 401 AAGGATACGA AGTTTCATCA GAGGAGTTGG CTCCATATGG
 441 TAACCAAGAG GCTGTTAGCC AGCAAACAAA TGACCTGCCG
 481 ATGATTATTG AGCTTTATAG AGCAGCAAAT GAGAGAATAT
 521 ATGAAGAAGA GAGGAGTCTT GAAAAAATTC TTGCTTGGAC
 561 TACCATCTTT CTCAATAAGC AAGTGCAAGA TAACTCAATT
 601 CCCGACAAAA AACTGCACAA ACTGGTGGAA TTCTACTTGA
 641 GGAATTACAA AGGCATAACC ATAAGATTGG GAGCTAGACG
 681 AAACCTCGAG CTATATGACA TGACCTACTA TCAAGCTCTG
 721 AAATCTACAA ACAGGTTCTC TAATTTATGC AACGAAGATT
 761 TTCTAGTTTT CGCAAAGGAA GATTTCGATA TACATGAAGC
 801 CCAGAACCAG AAAGGACTTC AACAACTGCA AAGGTGGTAT
 841 GCAGATTGTA GGTTGGACAC CTTAAACTTT GGAAGAGATG
 881 TAGTTATTAT TGCTAATTAT TTGGCTTCAT TAATTATTGG
 921 TGATCATGCG TTTGACTATG TTCGTCTCGC ATTTGCCAAA
 961 ACATCTGTGC TTGTAACAAT TATGGATGAT TTTTTCGACT
1001 GTCATGGCTC TAGTCAAGAG TGTGAGAGA TCATTGAATT
1041 AGTAAAAGAA TGGAAGGAGA ATCCGGATGC AGAGTACGGA
1081 TCTGAGGAGC TTGAGATCCT TTTTATGGCG TTGTACAATA
1121 CAGTAAATGA GTTGGCGGAG AGGGCTCGTG TTGAACAGGG
```

```
-continued
1161 GCGTAGTGTC AAAGAGTTTC TAGTCAAACT GTGGGTTGAA
1201 ATACTCTCAG CTTTCAAGAT AGAATTAGAT ACATGGAGCA
1241 ATGGCACGCA GCAAAGCTTC GATGAATACA TTTCTTCGTC
1281 GTGGTTGTCG AACGGTTCCC GGCTGACAGG TCTCCTGACG
1321 ATGCAATTCG TCGGAGTAAA ATTGTCCGAT GAAATGCTTA
1361 TGAGTGAAGA GTGCACTGAT TTGGCTAGGC ATGTCTGTAT
1401 GGTCGGCCGG CTGCTCAACG ACGTGTGCAG TTCTGAGAGG
1441 GAGCGCGAGG AAAATATTGC AGGAAAAAGT TATAGCATTC
1481 TACTAGCAAC TGAGAAAGAT GGAAGAAAAG TTAGTGAAGA
1521 TGAAGCCATT GCAGAGATCA ATGAAATGGT TGAATATCAC
1561 TGGAGAAAAG TGTTGCAGAT TGTGTATAAA AAAGAAAGCA
1601 TTTTGCCAAG AAGATGCAAA GATGTATTTT TGGAGATGGC
1641 TAAGGGTACG TTTTATGCTT ATGGGATCAA CGATGAATTG
1681 ACTTCTCCTC AGCAATCCAA GGAAGATATG AAATCCTTTG
1721 TCTTTTGA
```

Enzymes described herein can have one or more deletions, insertions, replacements, or substitutions in a part of the enzyme. The enzyme(s) described herein can have, for example, at least 60%, or at least 70%, or at least 80%, or at least 90%, or at least 93%, or at least 95%, or at least 96%, or at least 97%, or at least 98%, or at least 99% sequence identity to a sequence described herein.

In some cases, enzymes can have conservative changes such as one or more deletions, insertions, replacements, or substitutions that have no significant effect on the activities of the enzymes. Examples of conservative substitutions are provided below in Table 1A.

TABLE 1A

Conservative Substitutions

| Type of Amino Acid | Substitutable Amino Acids |
|---|---|
| Hydrophilic | Ala, Pro, Gly, Glu, Asp, Gln, Asn, Ser, Thr |
| Sulfhydryl | Cys |
| Aliphatic | Val, Ile, Leu, Met |
| Basic | Lys, Arg, His |
| Aromatic | Phe, Tyr, Trp |

Figure 2A:
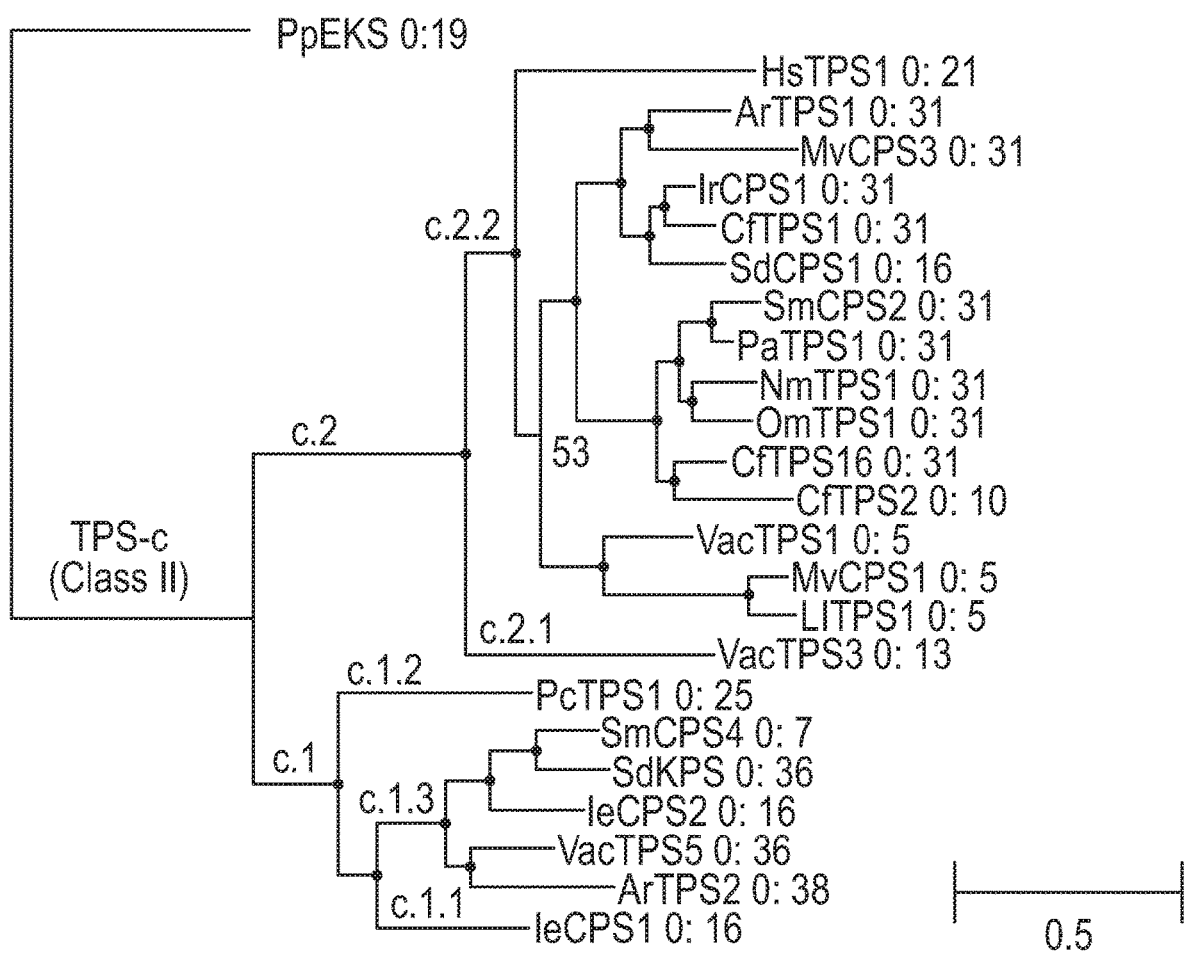
FIG. 2A-2B illustrate maximum likelihood trees of diterpene synthase (diTPS) enzymes.

Due to an increase in resolution at the taxonomic level and consistent clustering of enzymes with identical, or related function, the inventors propose a hierarchical scheme for classifying TPS genes in Lamiaceae from the TPS-e and TPS-c subfamilies. TPS-c genes (class II diTPSs) from Lamiaceae fall broadly into two clades (FIG. 2A), which tire referred to herein as c.1 and c.2. These c.1 and c.2 clades are further divided into three, and two subclades, respectively. The characterized genes from c.1.1 are all ent-CPP [16] synthases, presumably involved in primary metabolism. The taxonomic organization among c.1.1 sequences closely resembles the consensus phylogeny generated from 520 genes from each species (19), together with the short branch lengths compared to other TPS-c clades suggests that diTPSs in c.1.1 are more conserved and evolve more slowly.

The remaining TPS-c clades contain genes involved in specialized metabolism. The only characterized gene from clade c.1.2 is PcTPS1, which makes an ent-labda-8-ene diphosphate product [25]. Enzymes from clade c.1.3 catalyze the production of a variety of products, including ent-CPP [16], ent-8-LPP [7], kolavenyl-PP [36], and 38. 36 and 38 fire the only products without the labdane (Sk4) skeleton produced by Lamiaceae class II diTPSs. Compounds apparently derived from 36 are widespread among Lamiaceae (Table 6), so the inventors hypothesize that the progenitor of c.1.3 was a kolavenyl-PP synthase present in an early common ancestor. The labdane compounds produced by enzymes in c.1 are all in toe ent-configuration. With two exceptions, the known enzymes from clade c.2 all make products with the labdane skeleton in the normal configuration, suggesting that the founder of that clade may have been a normal configuration labdadiene diphosphate synthase. The exceptions are VacTPS3, the only characterized member of c.2.1, which produces syn-CPP [13], and the curious case of SdCPS1, which produces ent-CPP.

Among TPS-e (class I) genes, all but one of the characterized enzymes from e.1 are ent-kaurene [19] synthases, presumably involved in gibberellin biosynthesis. As with the c.1.1 clade, e.1 reflects the taxonomic distribution among the species. Notable in this clade are IrKSL4, which is an ent-atiserene synthase, and SmKSL2, which, in addition to ent-kaurene synthase activity, can convert ent-8-LPP 7 into ent-13-epi-manoyl oxide [6]. Andersen-Ranberg et al, (Angew Chem Int Ed 55(6):2142-2146 (2016)) have tested four of four ent-kaurene synthases and have data indicating that one was from Lamiaceae, which had toe ability to convert 7 to 6, so it is likely that this is a general characteristic of enzymes in the e.1 group.

Most of the specialized class I diTPSs in Lamiaceae fall into clade e.2. Enzymes in e.2 have lost the γ domain, present in many diTPSs, and located on the opposite end of the peptide from the class 1 active site. Characteristic of enzymes in e.2 is their ability to act on multiple substrates. The extreme example is SsSS (Caniard et al. M C Plant Biology 12:119 (2012)) which so far has been able to catalyze the dephosphorylation and minor rearrangement of all class II enzyme products that it has been tested. The range of substrates accepted by other enzymes in this group has not been tested systematically, but among the e.2 enzymes characterized in this study, only one (OmTPS4) accepted ent-CPP, and all accepted (+)-CPP [31], (+)-8-LPP [10], and PgPP [5], There is great diversity toe products of e.2 enzymes, with over 20 distinct compounds represented. Most of toe enzymes in e.2 convert (+)-CPP to miltiradiene [32], and (+)-8-LPP to 13/?-(+)-manoyl oxide [8], with other activities arising sporadically across the clade. Both characterized enzymes in the Nepetoideae specific e.2.2 have unusual activities: IrKSL6 converts (+)-CPP to isopimara-7,15-diene [28], and OmTPS5 converts (+)-CPP to palustradiene [29]. Most of the enzymes in e.2 fall into toe e.2.1 clade which also accounts for most of the known products. Enzymes that we characterized from e.2.1 lent support to emerging functionally consistent subclades. OmTPS4 activity, for three out of four substrates tested, mimics that of its nearest homolog (SsSS), notably accepting ent-CPP as a substrate to produce ent-manool [20]. LlTPS4 likewise has activities most similar to its closest homolog, MvELS, converting PgPP into 9,13(S)-epoxy-labd-14-ene [2] with greater specificity than other enzymes tested, although the products from (+)-CPP are different. From the remaining clade, e.2.3, the three characterized enzymes all come from Nepetoideae, and convert (+)-CPP into different products: IrKSL3 produces miltiradiene, IrTPS2 produces nezukol [30], and MsTPS1 produces sandaracopimaradiene [27].

The existence of two strongly supported subclades of specialized diTPSs within c.1, together with the presence of an ent-atiserene synthase in e.1, indicate that the emergence of specialized diTPSs from ent-CPP and ent-kaurene synthases is an ongoing process that has occurred multiple times in the Lamiaceae lineage. While it is evident that candidates selected from anywhere in the phylogenetic tree may have novel activities, clades that seem particularly promising and underexplored are e.2.1, c.1.2, and e.2.3. So far, including this work and previous work, diTPSs have been characterized from only four of the twelve major Lamiaceae clades: Ajugoideae, Lamioideae, Nepetoideae, and Viticoideae. Further expanding to the remaining eight Lamiaceae clades may also be a promising strategy for finding new enzyme activities.

Expression of Enzymes

Also described herein are expression systems that include at least one expression cassette (e.g., expression vectors or transgenes) that encode one or more of the enzyme(s) described herein. The expression systems can also include one or more expression cassettes encoding an enzyme that can synthesize terpene building blocks. For example, the expression systems can include one or more expression cassettes encoding terpene synthases that facilitate production of terpene precursors or building blocks such as those involved in the synthesis of isopentenyl diphosphate (IPP) or dimethylallyl diphosphate (DMAPP).

Cells containing such expression systems are further described herein. The cells containing such expression systems can be used to manufacture the enzymes (e.g., for in vitro use) and/or one or more terpenes, diterpenes, or terpenoids produced by the enzymes. Methods of using the enzymes or cells containing expression cassettes encoding such enzymes to make products such as terpenes, diterpenes, terpenoids, and combinations thereof are also described herein.

Nucleic acids encoding the enzymes can have sequence modifications. For example, nucleic acid sequences described herein can be modified to express enzymes that have modifications. Most amino acids can be encoded by more than one codon. When an amino acid is encoded by more than one codon, the codons are referred to as degenerate codons. A listing of degenerate codons is provided in Table 1B below.

TABLE 1B

Degenerate Amino Acid Codons

| Amino Acid | Three Nucleotide Codon |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

Different organisms may translate different codons more or less efficiently (e.g., because they have different ratios of tRNAs) than other organisms. Hence, when some amino acids can be encoded by several codons, a nucleic acid segment can be designed to optimize the efficiency of expression of an enzyme by using codons that are preferred by an organism, of interest. For example, the nucleotide coding regions of the enzymes described herein can be codon optimized for expression in various plant species. For example, many of the enzymes described herein were originally isolated from the mint family (Lamiaceae), however such enzymes can be expressed in a variety of host cells, including for example, as *Nicotiana benthamiana, Nicotiana tabacum, Nicotiana rustica, Nicotiana excelsior,* and *Nicotiana excelsiana.*

An optimized nucleic acid can have less than 98%, less than 97%, less than 95%, or less than 94%, or less than 93%, or less than 92%, or less than 91%, or less than 90%, or less than 89%, or less than 88%, or less than 85%, or less than 83%, or less than 80%, or less than 75% nucleic acid sequence identity to a corresponding non-optimized (e.g., a non-optimized parental or wild type enzyme nucleic acid) sequence.

The enzymes described herein can be expressed from an expression cassette and/or an expression vector. Such an expression cassette can include a nucleic acid segment that encodes an enzyme operably linked to a promoter to drive expression of the enzyme. Convenient vectors, or expression systems can be used to express such enzymes, in some instances, the nucleic acid segment encoding an enzyme is operably linked to a promoter and/or a transcription termination sequence. The promoter and/or the termination sequence can be heterologous to the nucleic acid segment that encodes an enzyme. Expression cassettes can have a promoter operably linked to a heterologous open reading frame encoding an enzyme. The invention therefore provides expression cassettes or vectors useful for expressing one or more enzyme(s).

Constructs, e.g., expression cassettes, and vectors comprising the isolated nucleic acid molecule, e.g., with optimized nucleic acid sequence, as well as kits comprising the isolated nucleic acid molecule, construct or vector are also provided.

The nucleic acids described herein can also be modified to improve or alter toe functional properties of the encoded enzymes. Deletions, insertions, or substitutions can be generated by a variety of methods such as, but not limited to, random mutagenesis and/or site-specific recombination-mediated methods. The mutations can range in size from one or two nucleotides to hundreds of nucleotides (or any value there between). Deletions, insertions, and/or substitutions are created at a desired location in a nucleic acid encoding the enzyme(s).

Nucleic acids encoding one or more enzyme(s) can have one or more nucleotide deletions, insertions, replacements, or substitutions. For example, the nucleic acids encoding one or more enzyme(s) can, for example, have less than 95%, or less than 94.8%, or less than 94.5%, or less than 94%, or less than 93.8%, or less than 94.50% nucleic acid sequence identity to a corresponding parental or wild-type sequence. In some cases, the nucleic acids encoding one or more enzyme(s) can have, for example, at least 50%, or at least 55%, or at least 60%, or at least 65%, or at least 70%, or at least 75%, or at least 80%, or at least 85%, or at 90% sequence identity to a corresponding parental or wild-type sequence. Examples of parental or wild type nucleic acid sequences for unmodified enzyme(s) with amino acid sequences SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 57, 59, or 176 include nucleic acid sequences SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, or 177 respectively. Any of these nuclei acid or amino acid sequences can, for example, encode or have enzyme sequences with less than 99%, less than 98%, less than 97%, less than 96%, less than 95%, less than 94.8%, less than 94.5%, less than 94%, less than 93.8%, less than 93.5%, less than 93%, less than 92%, less than 91%, or less than 90% sequence identity to a corresponding parental or wild-type sequence.

Also provided are nucleic acid molecules (polynucleotide molecules) that can include a nucleic acid segment encoding an enzyme with a sequence that is optimized for expression in at least one selected host organism or host cell. Optimized sequences include sequences which are codon optimized, i.e., codons which are employed more frequently in one organism relative to another organism. In some cases, the balance of codon usage is such that the most frequently used codon is not used to exhaustion. Other modifications can include addition or modification of Kozak sequences and/or moons, and/or to remove undesirable sequences, for instance, potential transcription factor binding sites.

An enzyme useful tor synthesis of terpenes, diterpenes, and terpenoids may be expressed on the surface of, or within, a prokaryotic or eukaryotic cell. In some cases, expressed enzyme(s) can be secreted by that ceil.

Techniques of molecular biology, microbiology, and recombinant DNA technology which are within the skill of the art can be employed to make and use the enzymes, expression systems, and terpene products described herein. Such techniques available in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practiced Guide to Molecular Cloning* (1984); the series *Methods In Enzymology* (S. Colowick and N, Kaplan eds., Academic Press, Inc.); *Current Protocols In Molecular Biology* (John Wiley & Sons, Inc), *Current Protocols In Protein Science* (John Wiley & Sons, Inc), *Current Protocols In Microbiology* (John Wiley & Sons, Inc), *Current Protocols In Nucleic Acid Chemistry* (John Wiley & Sons, Inc), and *Handbook of Experimental Immunology*, Vols. I-IV (D. M. Weir and C. C. Blackwell eds., 1986, Blackwell Scientific Publications).

Modified plants that contain nucleic acids encoding enzymes within their somatic and/or germ cells are described herein. Such genetic modification can be accomplished by available procedures. For example, one of skill in the art can prepare an expression cassette or expression vector that can express one or more encoded enzymes. Plant cells can be transformed by the expression cassette or expression vector, and whole plants (and their seeds) can be generated from the plant cells that were successfully transformed with the enzyme nucleic acids. Some procedures for making such genetically modified plants and their seeds are described below.

Promoters: The nucleic acids encoding enzymes can be operably linked to a promoter, which provides for expression of mRNA from the nucleic acids encoding the enzymes. The promoter is typically a promoter functional in plants and can be a promoter functional during plant growth and development. A nucleic acid segment encoding an enzyme is operably linked to the promoter when it is located downstream from the promoter. The combination of a coding region for an enzyme operably linked to a promoter forms an expression cassette, which can optionally include other elements as well.

Promoter regions are typically found in the flanking DNA upstream from the coding sequence in both the prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning gene expression on and off in response to an exogenously added agent, or to an environmental or developmental stimulus. For example, a bacterial promoter such as the $P_{tac}$ promoter can be induced to varying levels of gene expression depending on the level of isopropyl-beta-D-thiogalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired.

Expression cassettes generally include, but tire not limited to, examples of plant promoters such as the CaMV 35S promoter (Odell et al., *Nature*. 313:810-812 (1985)), or others such as CaMV 19S (Lawton et al., *Plant Molecular Biology*. 9:315-324 (1987)), nos (Ebert et al., *Proc. Natl. Acad. Sci. USA*. 84:5745-5749 (1987)), AdhI (Walker et al., *Proc. Natl. Acad. Sci. USA*. 84:6624-6628 (1987)), sucrose synthase (Yang et al., *Proc. Natl. Acad. Sci. USA*. 87:4144-4148 (1990)), α-tubulin, ubiquitin, actin (Wang et al., *Mol. Cell. Biol.* 12:3399 (1992)), cab (Sullivan et al, *Mol Gen. Genet.* 215:431 (1989)), PEPCase (Hudspeth et al., *Plant Molecular Biology*. 12:579-589 (1989)) or those associated with the R gene complex (Chandler et al., *The Plant Cell*. 1:1175-1183 (1989)). Further suitable promoters include a CYP71D16 trichome-specific promoter and the CBTS (cembratrienol synthase) promotor, cauliflower mosaic virus promoter, the Z10 promoter from a gene encoding a 10 kD zein protein, a Z27 promoter from a gene encoding a 27 kD zein protein, the plastid rRNA-operon (rrn) promoter, inducible promoters, such as the light inducible promoter derived from the pea rbcS gene (Coruzzi et al., *EMBO J.* 3:1671 (1971)), RUBISCO-SSU light inducible promoter (SSU) from tobacco and the actin promoter from rice (McElroy et al., *The Plant Cell.* 2:163-171 (1990)). Other promoters that are useful can also be employed.

Alternatively, novel tissue specific promoter sequences may be employed. cDNA clones from a particular tissue can be isolated and those clones which are expressed specifically in that tissue can be identified, for example, using Northern blotting. Preferably, the gene isolated is not present in a high copy number but is relatively abundant in specific tissues. The promoter and control elements of corresponding genomic clones can then be localized using techniques well known to those of skill in the art.

A nucleic acid encoding an enzyme can be combined with the promoter by standard methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter or the CYP71D16 trichome-specific promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter.

The nucleic acid sequence encoding for the enzyme(s) can be subcloned downstream from the promoter using restriction enzymes and positioned to ensure that the DNA is inserted in proper orientation with respect to the promoter so that the DNA can be expressed as sense RNA. Once the nucleic acid segment encoding the enzyme is operably linked to a promoter, the expression cassette so formed can be subcloned into a plasmid or other vector (e.g., an expression vector).

In some embodiments, a cDNA clone encoding an enzyme is isolated from a mint species, for example, from leaf, trichome, or root tissue. In other embodiments, cDNA clones from other species (that encode an enzyme) are isolated from, selected plant tissues, or a nucleic acid encoding a wild type, mutant or modified enzyme is prepared by available methods or as described herein. For example, the nucleic acid encoding the enzyme can be any nucleic acid with a coding region that hybridizes to SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, or 177, and that has enzyme activity. Using restriction endonucleases, the entire coding sequence for the enzyme is subcloned downstream of the promoter in a 5' to 3' sense orientation.

Targeting Sequences: Additionally, expression cassettes can be constructed and employed to target the nucleic acids encoding an enzyme to an intracellular compartment within plant cells or to direct an encoded protein to the extracellular environment. This can generally be achieved by joining a DNA sequence encoding a transit or signal peptide sequence to the coding sequence of the nucleic acid encoding the enzyme. The resultant transit, or signal, peptide can transport the protein to a particular intracellular, or extracellular, destination and can then be co-translationally or post-translationally removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product within a particular location. For example, see U.S. Pat. No. 5,258,300.

For example, in some cases it may be desirable to localize the enzymes to the plastidic compartment and/or within plant cell trichomes. The best compliment of transit peptides/secretion peptide/signal peptides can be empirically ascertained. The choices can range from using the native secretion signals akin to the enzyme candidates to be transgenically expressed, to transit peptides from proteins known to be localized into plant organelles such as trichome plastid s in general. For example, transit peptides can be selected from proteins that have a relative high titer in the trichomes. Examples include, but not limited to, transit peptides form a terpenoid cyclase (e.g. cembratrienol cyclase), the LTP1 protein, the Chlorophyll a-b binding protein 40, Phylloplanin, Glycine-rich Protein (GRP), Cytochrome P450 (CYP71D16); all from *Nicotiana* sp. alongside RUBISCO (Ribulose bisphosphate carboxylase) small unit protein from both *Arabidopsis* and *Nicotiana* sp.

3' Sequences: When the expression cassette is to be introduced into a plant ceil, the expression cassette can also optionally include 3' untranslated plant regulatory DNA sequences that act as a signal to terminate transcription and allow for the polyadenylation of the resultant mRNA. The 3' untranslated regulatory DNA sequence can include from about 300 to 1,000 nucleotide base pairs and can contain plant transcriptional and translational termination sequences. For example, 3' elements that can be used include those derived from the nopaline synthase gene of *Agrobacterium tumefaciens* (Bevan et al., *Nucleic Acid Research*. 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' untranslated regulatory sequences can be obtained as described in An (*Methods in Enzymology*. 153:292 (1987)). Many such 3' untranslated regulatory sequences are already present in plasmids available from commercial sources such as Clontech, Palo Alto, Calif. The 3' untranslated regulatory sequences can be operably linked to the 3' terminus of the nucleic acids encoding the enzyme.

Selectable and Screenable Marker Sequences: To improve identification of transformants, a selectable or screenable marker gene can be employed with the expressible nucleic acids encoding the enzyme(s). "Marker genes" are genes that impart a distinct phenotype to cells expressing the marker gene and thus allow such transformed cells to be distinguished from cells that do not have the marker. Such genes may encode either a selectable or a screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., foe R-locus trait). Of course, many examples of suitable marker genes are available can be employed in the practice of the invention.

Included within the terms 'selectable or screenable marker genes' are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extension or tobacco PR-S).

With regard to selectable secretable markers, the use of an expression system that encodes a polypeptide that becomes sequestered in the cell wall, where the polypeptide includes a unique epitope may be advantageous. Such a cell wall antigen can employ an epitope sequence that would provide low background in plant tissue, a promoter-leader sequence that imparts efficient expression and targeting across the plasma membrane, and that can produce protein that is bound in the cell wall and yet is accessible to antibodies. A normally secreted ceil wall protein modified to include a unique epitope would satisfy such requirements.

Example of protein markers suitable for modification in this manner include extension or hydroxyproline rich glycoprotein (HPRG), For example, the maize HPRG (Stiefel et al., *The Plant Cell*. 2:785-793 (1990)) is well characterized in terms of molecular biology, expression, and protein structure and therefore can readily be employed. However, any one of a variety of extensions and/or glycine-rich ceil wall proteins (Keller et al, *EMBO J.* 8:1309-1314 (1989)) could be modified by the addition of an antigenic site to create a screenable marker.

Selectable markers for use in connection with the present invention can include, but are not limited to, a neo gene (Potrykus et al., *Mol. Gen. Genet.* 199:183-188 (1985)) which codes for kanamycin resistance and can be selected for using kanamycin, G418; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or oilier ALS-inhibiting chemicals (European Patent Application 154, 204 (1985)); a methotrexate-resistant DHFK gene (Thiliet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. Screenable markers that may be employed include, hut are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* 18$^{th}$ Stabler Genetics Symposium, J. P. Gustafson and R. Appels, eds. (New York: Plenum Press) pp. 263-282 (1988); a β-lactamase gene (Sutcliffe, *Proc. Natl Acad. Sci. USA.* 75:3737-3741 (1978)), which encodes an enzyme for which various chromogenic substrates are known (e.g., PADAC, a chromogenic cephalosporin); a xy/E gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et ah, *Plant Cell Reports.* 14:403 (1995)).

Another screenable marker contemplated for use is firefly luciferase, encoded by the lux gene. The presence of the lux gene in transformed cells may be detected using, for example, X-ray film, scintillation counting, fluorescence spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences: An expression cassette of the invention can also include plasmid DMA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences can include origins of replication to provide for autonomous replication of the vector, additional selectable marker genes, for example, encoding antibiotic or herbicide resistance, unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology.* 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors can include the nopaline T DNA right and left borders to provide for efficient plant cell transformation, a selectable marker gene, unique multiple cloning sites in the T border regions, the cold replication of origin and a wide host range replicon. The binary Ti vectors carrying an expression cassette of the invention can be used to transform both prokaryotic and eukaryotic cells but is usually used to transform dicot plant cells.

DNA Delivery of the DNA Molecules into Host Cells: Methods described herein can include introducing nucleic acids encoding enzymes, such as a preselected cDNA encoding the selected enzyme, into a recipient cell to create a transformed cell. In some instances, the frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some recipient cells may show only initial and transient gene expression. However, certain cells from virtually any dicot or monocot species may be stably transformed, and these cells regenerated into transgenic plants, through tire application of the techniques disclosed herein.

Another aspect of the invention is a plant that can produce terpenes, diterpenes and terpenoids, wherein the plant has introduced nucleic acid sequence(s) encoding one or more enzymes. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons, hi some embodiments, the plant or cell is a monocotyledon plant or cell. In some embodiments, the plant or cell is a dicotyledon plant or cell. For example, the plant or cell can be a tobacco plant or cell. The cell(s) may be in a suspension cell culture or may be in an intact plant part, such as an immature embryo, or in a specialized plant tissue, such as callus, such as Type I or Type II callus.

Transformation of plant cells can be conducted by any one of a number of methods available in the art. Examples are: Transformation by direct DNA transfer into plant cells by electroporation (U.S. Pat. Nos. 5,384,253 and 5,472,869, Dekeyser et al., *The Plant Cell.* 2:591-602 (1990)); direct DNA transfer to plant cells by PEG precipitation (Hayashimoto et al., *Plant Physiol.* 93:857-863 (1990)); direct DNA transfer to plant cells by microprojectile bombardment (McCabe et al., *Bio/Technology.* 6:923-926 (1988); Gordon-Kamm et al, *The Plant Cell.* 2:603-618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack the functions tor disease induction.

One method for dicot transformation, for example, involves infection of plant ceils with *Agrobacterium tumefaciens* using the leaf-disk protocol (Horsch et al., *Science* 227:1229-1231 (1985). Methods for transformation of monocotyledonous plants utilizing *Agrobacterium tumefaciens* have been described by Hiei et al. (European Patent 0 604 662, 1994) and Saito et al. (European Patent 0 672 752, 1995).

Monocot cells such as various grasses or dicot cells such as tobacco can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature embryos can be transformed by accelerated particle treatment as described by Gordon-Kamm et al. (*The Plant Cell.* 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128.

The choice of plant tissue source for transformation may depend on the nature of the host plant and the transformation protocol. Useful tissue sources include callus, suspensions culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent ceils.

The transformation is carried out under conditions directed to the plant tissue of choice. The plant cells or tissue are exposed to the DNA or RNA encoding enzymes for an effective period of time. This may range from a less than one second pulse of electricity for electroporation to a 2-day to 3-day co-cultivation in the presence of plasmid-bearing *Agrobacterium* cells. Buffers and media used will also vary with the plant tissue source and transformation protocol. Many transformation protocols employ a feeder layer of suspended culture cells (tobacco, for example) on the surface of solid media plates, separated by a sterile filter paper disk from the plant cells or tissues being transformed.

Electroporation: Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at tins stage, and transformed cells then identified by a suitable selection or screening protocol dependent on the nature of the newly incorporated DNA.

Microprojectile Bombardment: A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium, tumefaciens* containing plasmids with either the β-glucoronidase or bar gene engineered for expression in selected plant cells. Bacteria were inactivated by ethanol dehydration prior to bombardment. A low level of transient expression of the β-glucoronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to being an effective means of reproducibly stably transforming monocots, microprojectile bombardment does not require the isolation of protoplasts (Christou et al., *PNAS* 84:3962-3966 (1987)), the formation of partially degraded cells, and no susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al, *The Plant Cell.* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing the damage inflicted on recipient cells by an aggregated projectile.

For bombardment, cells in suspension are preferably concentrated on filters or solid culture medium. Alternatively, immature embryos or other target cells may be arranged on solid culture medium. The ceils to be bombarded are positioned at an appropriate distance below the microprojectile stopping plate. If desired, one or more screens are also positioned between the acceleration device and the cells to be bombarded. Through the use of techniques set forth herein, one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with the bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore, influence transformation and integration efficiencies. For example, tire osmotic state, tissue hydration and the subculture stage or cell cycle of the recipient cells may be adjusted for optimum transformation. Execution of such routine adjustments will be known to those of skill in the art.

Selection: An exemplary embodiment of methods for identifying transformed cells involves exposing the bombarded cultures to a selective agent, such as a metabolic inhibitor, an antibiotic, or the like. Cells which have been transformed and have stably integrated a marker gene conferring resistance to the selective agent used, will grow and divide in culture. Sensitive ceils will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

The enzyme luciferase is also useful as a screenable marker in the context of the present invention. In the presence of the substrate luciferin, ceils expressing luciferase emit light which can be detected on photographic or X-ray film, in a luminometer for liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations that provide 100% inhibition followed by screening of growing tissue for expression of a screenable marker gene such as luciferase would allow one to recover transformants from, cell or tissue types that are not amenable to selection alone.

Regeneration and Seed Production: Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·m$^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits fire to be commercially useful.

Regenerated plants can be repeatedly crossed to inbred plants to introgress the nucleic acids encoding an enzyme into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced nucleic acids, the plant is self-pollinated at least once in order to produce a homozygous backcross converted inbred containing the nucleic acids encoding the enzyme(s). Progeny of these plants are true breeding.

Alternatively, seed from transformed plants regenerated from transformed tissue cultures is grown in the field and self-pollinated to generate hue breeding plants.

Seed from the fertile transgenic plants can then be evaluated for the presence and/or expression of the enzyme(s). Transgenic plant and/or seed tissue can be analyzed for enzyme expression using methods such as SDS polyacrylamide gel electrophoresis, Western blot, liquid chromatography (e.g., HPLC) or other means of detecting an enzyme product (e.g., a terpene, diterpene, terpenoid, or a combination thereof).

Once a transgenic seed expressing the enzyme(s) and producing one or more terpenes, diterpenes, and/or terpenoids in the plant is identified, the seed can be used to develop true breeding plants. The true breeding plants are used to develop a line of plants expressing terpenes, diterpenes, and/or terpenoids in various plant tissues (e.g., in leaves, bracts, and/or trichomes) while still maintaining other desirable functional agronomic traits. Adding the trait of terpene, diterpene, and/or terpenoid production can be accomplished by back-crossing with selected desirable functional agronomic trait(s) and with plants that do not exhibit such traits and studying the pattern of inheritance in segregating generations. Those plants expressing the target trait(s) in a dominant fashion are preferably selected. Back-crossing is canned out by crossing the original fertile transgenic plants with a plant from an inbred line exhibiting desirable functional agronomic characteristics while not necessarily expressing the trait of terpene, diterpene, and/or terpenoid production in the plant. The resulting progeny can then be crossed back to the parent that expresses the terpenes, diterpenes, and/or terpenoids. The progeny from this cross will also segregate so that some of the progeny carry the trait and some do not. This back-crossing is repeated until the goal of acquiring an inbred line with the desirable functional agronomic traits, and with production of terpenes, diterpenes, and/or terpenoids within various tissues of the plant is achieved. The enzymes can be expressed in a dominant fashion.

Subsequent to back-crossing, the new transgenic plants can be evaluated for synthesis of terpenes, diterpenes, and/or terpenoids in selected plant lines. This can be done, for example, by gas chromatography, mass spectroscopy, or NMR analysis of whole plant cell walls (Kim, H., and Ralph, J. Solution-state 2D NMR of ball-milled plant cell wall gels in DMSO-$d_6$/pyridine-$d_5$. (2010) Org. Bio mol. Chem. 8(3), 576-591; Yelie, D. J., Ralph, J., and Frihart, C. R. Characterization of non-derivatized plant cell walls using high-resolution solution-state NMR spectroscopy. (2008) Magn. Reson. Chem. 46(6), 508-517; Kim, I-L, Ralph, J., and Akiyama, T. Solution-state 2D NMR of Ball-milled Plant Cell Wall Gels in DMSO-$d_6$. (2008) BioEnergy Research 1(1), 56-66; Lu, F., and Ralph, J. Non-degradative dissolution and acetylation of ball-milled plant cell walls; high-resolution solution-state NMR. (2003) Plant J. 35(4), 535-544). The new transgenic plants can also be evaluated for a battery of functional agronomic characteristics such as lodging, yield, resistance to disease, resistance to insect pests, drought resistance, and/or herbicide resistance.

Determination of Stably Transformed Plant Tissues: To confirm the presence of the nucleic acids encoding terpene synthesizing enzymes in the regenerating plants, or seeds or progeny derived from the regenerated plant, a variety of assays may be performed. Such assays include, for example, molecular biological assays, such as Southern and Northern blotting and PCR; biochemical assays, such as detecting the presence of enzyme products, for example, by enzyme assays, by immunological assays (ELISAs and Western blots). Various plant parts can be assayed, such as trichomes, leaves, bracts, seeds or roots. In some cases, the phenotype of the whole regenerated plant can be analyzed.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced nucleic acids. PCR can also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting may be used to detect the nucleic acid encoding the enzyme(s) in question, it may not provide information as to whether the preselected DNA segment is being expressed. Expression may be evaluated by specifically identifying the protein products of the introduced nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as, native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the enzyme such as evaluation by amino acid sequencing following purification. Other procedures may be additionally used.

The expression of a gene product can also be determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

Hosts

Terpenes, including diterpenes and terpenoids, can be made in a variety of host organisms either in vitro or in vivo. In some cases, the enzymes described herein can be made in host cells, and those enzymes can be extracted from the host cells for use in vitro. As used herein, a "host" means a cell, tissue or organism capable of replication. The host can have an expression cassette or expression vector that can include a nucleic acid segment encoding an enzyme that is involved in the biosynthesis of terpenes.

The term "host cell", as used herein, refers to any prokaryotic or eukaryotic cell that can be transformed with an expression cassettes or vector carrying the nucleic acid segment encoding an enzyme that is involved in the biosynthesis of one or more terpenes. The host cells can, for example, be a plant, bacterial, insect, or yeast cell. Expression cassettes encoding biosynthetic enzymes can be incorporated or transferred into a host ceil to facilitate manufacture of the enzymes described herein or the terpene, diterpene, or terpenoid products of those enzymes. The host cells can be present in an organism. For example, the host cells can be present in a host such as a plant.

For example, the enzymes, terpenes, diterpenes, and terpenoids can be made in a variety of plants or plant cells. Although some of the enzymes described herein are from species of the mint family, the enzymes, terpenes, diterpenes, and terpenoids can be made in species other than in mint plants or mint plant cells. The terpenes, diterpenes, and terpenoids can, for example, be made and extracted from, whole plants, plant parts, plant ceils, or a combination thereof. Enzymes can conveniently, for example, be produced in bacterial, insect, plant, or fungal (e.g., yeast) cells.

Examples of host cells, host tissues, host seeds and plants that may be used for producing terpenes and terpenoids (e.g., by incorporation of nucleic acids and expression systems described herein) include but are not limited to those useful for production of oils such as oilseeds, camelina, canola, castor bean, corn, flax, lupins, peanut, potatoes, safflower, soybean, sunflower, cottonseed, oil firewood trees, rapeseed, rutabaga, sorghum, walnut, and various nut species. Other types host cells, host tissues, host seeds and plants that can be used include fiber-containing plants, trees, flax, grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., poplar, pine, and eucalyptus), oil (oilseeds, camelina, canola, castor bean, lupins, potatoes, soybean, sunflower, cottonseed, oil firewood trees, rapeseed, rutabaga, sorghum), starch plants (wheat, potatoes, lupins, sunflower and cottonseed), and forage plants (alfalfa, clover and fescue). In some embodiments the plant is a gymnosperm. Examples of plants useful tor pulp and paper production include most pine species such as loblolly pine, Jack pine. Southern pine, Radiata pine, spruce, Douglas fir and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, pine, oak, maple, walnut, rubber tree, willow, and the like. Plants useful for generating forage include legumes such as alfalfa, as well as forage grasses such as bromegrass, and bluestem. In some cases, the plant is a Brassicaceae or other Solanaceae species. In some embodiments, the plant is not a species of *Arabidopsis*, for example, in some embodiments, the plant is not *Arabidopsis thaliana*.

Additional examples of hosts cells and host organisms include, without limitation, tobacco cells such as *Nicotiana benthamiana, Nicotiana tabacum, Nicotiana rustica, Nicotiana excelsior*, and *Nicotiana excelsiana* cells; cells of the genus *Escherichia* such as the species *Escherichia coif* cells of the genus *Clostridium* such as the species *Clostridium ljungdahlii, Clostridium autoethanogenum* or *Clostridium kluyveri*; cells of the genus *Corynebacterium* such as the species *Corynebacterium glutamicum*; cells of the genus *Cupriavidus* such as the species *Cupriavidus necator* or *Cupriavidus metallidurans*; cells of the genus *Pseudomonas* such as the species *Pseudomonas fluorescens, Pseudomonas putida* or *Pseudomonas oleavorans*; cells of the genus *Delftia* such as the species *Delftia acidovorans*; cells of the genus *Bacillus* such as the species *Bacillus subtilis*; cells of the genus *Lactobacillus* such as the species *Lactobacillus delbrueckii*; or cells of the genus *Lactococcus* such as the species *Lactococcus lactis*.

"Host cells" can further include, without limitation, those from yeast and other fungi, as well as, for example, insect ceils. Examples of suitable eukaryotic host cells include yeasts and fungi from the genus *Aspergillus* such as *Aspergillus niger*, from the genus *Saccharomyces* such as *Saccharomyces cerevisiae*; from the genus *Candida* such as *C. tropicalis, C. albicans, C. cloacae, C. guillermondii, C. intermedia, C. maltosa, C. parapsilosis*, and *C. zeylenoides*; from the genus *Pichia* (or *Komagataella*) such as *Pichia pastoris*; from the genus *Yarrowia* such as *Yarrowia lipolytica*: from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Khiyveromyces lactis* or from the genera *Exophiala, Mucor, Trichoderma, Cladosporium, Phanerochaete, Cladophialophora, Paecilomyces, Scedosporium*, and *Ophiostoma*.

In some cases, the host cells can have organelles that facilitate manufacture or storage of the terpenes, diterpenes, and terpenoids. Such organelles can include lipid droplets, smooth endoplasmic reticulum, plastids, trichomes, vacuoles, vesicles, plastids, and cellular membranes. During and after production of the terpenes, diterpenes, and terpenoids these organelles can be isolated as a semi-pure source of the of the terpenes, diterpenes, and terpenoids.

The Diterpene Skeletons of Lamiaceae and how to Make them

Enzymes responsible for all new skeletons were not specifically located, but considering the known skeletons and diTPS activities, the inventors have deduced how diverse skeletons arise and what strategies may be used for finding the enzymes responsible. All of the six diterpene skeletons with a known biosynthetic route in Lamiaceae contain a decalin core: Sk2, and Sk4 (FIG. 1B-1C) are skeletons of the direct products of TPS-c enzymes, while Sk1, Sk3, Sk6, and Sk14 fire skeletons of the products a TPS-e enzyme acting on a labdadiene diphosphate (Sk4) precursor.

Many diterpene skeletons with an intact decalin core can be made by as-yet undiscovered diTPSs from the TPS-c and TPS-e subfamilies, for example through methyl shifts during cyclization. Examples of diTPSs that catalyze methyl shifts are foe TPS-c enzymes SdKPS and ArTPS2 which produce the clerodane skeleton (Sk2), and the TPS-e enzyme OmTPS5 which has a product with the abietane skeleton (Sk3). The same mechanisms may form skeletons such as Sk8 and Sk12. Other decalin-containing skeletons, for example the nor-diterpenes (missing one or more methyl side chains, e.g. Sk7) are can be made by oxidative decarboxylation occurring after the TPS steps. Ring rearrangements catalyzed by TPS-e enzymes also have precedent, for example foe generation of ent-kaurene (with skeleton Sk1) or cur-atiserene (with skeleton Sk14) from ent-CPP (with skeleton Sk4), but always preserve the decaline core structure.

Diterpenoids lacking a decalin core are taxonomically restricted within Lamiaceae, with no single skeleton being reported in more than two clades (FIG. 1B). Many can be explained as modifications occurring after the TPS steps to decalin-containing skeletons. Cytochrome P450 driven ring contraction, akin to that in the gibberellin pathway, can play a role in the formation of skeletons such as Sk13. Ring opening and ring expansion may also occur, for example in pathways to compounds with the 6,7-seco-kaurane (Sk5), and icetaxane (Sk9) skeletons, respectively. Skeletons such as cembrane (Sk11), lacking any apparent biosynthetic connection to a decalin core can arise from diTPSs outside the TPS-c and TPS-e subfamilies. In Euphorbiaceae and Solanaceae, where cembranoid compounds are common, the relevant TPSs come from the TPS-a subfamily. Elucidation of pathways to the remaining diterpene skeletons in Lamiaceae will depend on broadening the search to new genera and species and new TPS subfamilies, eventually moving beyond TPSs to look at cytochromes P450 and other enzyme families.

Implications for Biotechnology

Arrays of compounds can be produced by combining class II diTPSs with different class I diTPSs. Particularly prolific enzymes for combinatorial biosynthesis have been Cyc2 from the bacterium *Streptomyces griseolosporeus* (Hamano et al. J Biol Chem 277(40):37098-37104 (2002); Dairi et 1. J Bacteriol 183(20):6085-6094 (2001)), which generates alkene moieties on prenyl-diphosphate substrates, and SsSS, which installs an alcohol at the 13 position and a double bond at the 14 position; both of these enzymes have demonstrated activity on 12 different class II enzyme products. The inventors have found that SsSS is also active on the products of PcTPS1 and ArTPS2. In addition, the inventors have found class 1 enzymes that provide routes to products that previously were biosynthetically inaccessible or poorly accessible. OmTPS3 is active on class II products with a labdane skeleton and normal absolute configuration, typically generating a trans-methyl-pentadiene moiety, as in 11, 34, and 24. An enzyme with similar activity, producing 24 and 34, was recently reported from the bacterium *Streptomyces cyslabdanicus* (Yamada et al. The Journal of Antibiotics 69(7):515-523 (2016); Ikeda et al. J Ind Microbiol Biotechnol 43(2-3):325-342 (2016)) but was not tested against additional substrates. LlTPS4 produces sandaracopimaradiene [27] from 31, with greater specificity than the earlier enzyme, *Euphorbia peplus* TPS8 (Andersen-Ranberg et al. Angew Chem Int Ed 55(6):2142-2146 (2016)). Finally, OmTPS5 enables efficient and specific production of palustradiene [29] from 31. The other known biosynthetic route to 29 is as a minor spontaneous degradation product of 13-hydroxy-8(14)-abietane from *Picea abies* levopimaradiene/abietadiene synthase and related enzymes.

ArTPS2 is of particular interest for applications in agricultural biotechnology. Neo-clerodane diterpenoids, particularly those with an epoxide moiety at the 4(18)-position, have garnered significant attention for their ability to deter insect herbivores. The 4(18)-desaturated product of ArTPS2 could be used in biosynthetic or semisynthetic routes to potent insect antifeedants.

Definitions

As used herein, the singular forms "a," "an," and "the" are intended to include the plural forms as well, unless the context clearly indicates otherwise. Also, as used herein, "and/or" refers to, and encompasses, any and all possible combinations of one or more of the associated listed items. Unless otherwise defined, all terms, including technical and scientific terms used in the description, have the same meaning as commonly understood by one of ordinary skill in the art to which this invention pertains.

The term "about", as used herein, can allow for a degree of variability in a value or range, for example, within 10%, within 5%, or within 1% of a stated value or of a stated limit of a range.

The term "enzyme" or "enzymes", as used herein, refers to a protein catalyst capable of catalyzing a reaction. Herein, the term does not mean only an isolated enzyme, but also includes a host cell expressing that enzyme. Accordingly, the conversion of A to B by enzyme C should also be construed to encompass the conversion of A to B by a host cell expressing enzyme C.

The term, "heterologous" when used in reference to a nucleic acid refers to a nucleic acid that has been manipulated in some way. For example, a heterologous nucleic acid includes a nucleic acid from one species introduced into another species. A heterologous nucleic acid also includes a nucleic acid native to an organism that has been altered in some way (e.g., mutated, added in multiple copies, linked to a non-native promoter or enhancer sequence, etc.). Heterologous nucleic acids can include cDNA forms of a nucleic acid; the cDNA may be expressed in either a sense (to produce mRNA) or anti-sense orientation (to produce an anti-sense RNA transcript that is complementary to the mRNA transcript). For example, heterologous nucleic acids can be distinguished from endogenous plant nucleic acids in that the heterologous nucleic acids are typically joined to nucleic acids comprising regulatory elements such as promoters that are not found naturally associated with the natural gene for the protein encoded by the heterologous gene. Heterologous nucleic acids can also be distinguished from endogenous plant nucleic acids in that the heterologous nucleic acids are in an unnatural chromosomal location or are associated with portions of the chromosome not found in nature (e.g., the heterologous nucleic acids are expressed in tissues where the gene is not normally expressed).

The terms "identical" or percent "identity", as used herein, in the context of two or more nucleic acids or polypeptide sequences, refer to two or more sequences or subsequences that are the same or have a specified percentage of amino acid residues or nucleotides that are the same (e.g., 75% identity, 80% identity, 85% identity, 90% identity, 95% identity, 97% identity, 98% identity, 99% identity, or 100% identity in pairwise comparison). Sequence identity can be determined by comparison and/or alignment of sequences for maximum correspondence over a comparison window, or over a designated region as measured using a sequence comparison algorithm, or by manual alignment and visual inspection. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. A "reference sequence" is a defined sequence used as a basis for a sequence comparison; a reference sequence may be a subset of a larger sequence.

As used herein, a "native" nucleic acid or polypeptide means a DNA, RNA or amino acid sequence or segment that has not been manipulated in vitro, i.e., has not been isolated, purified, amplified and/or modified.

As used herein, the term "plant" is used in its broadest sense. It includes, but is not limited to, any species of grass (fodder, ornamental or decorative), crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera.

The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, a leaf and a cell. Plant parts may comprise one or more of a tiller, plug, rhizome, sprig, stolen, meristem, crown, and the like. In some instances, the plant part can include vegetative tissues of the plant.

The terms "in operable combination," "in operable order," and "operably linked" refer to the linkage of nucleic acid sequences in such a manner that a nucleic acid molecule capable of directing the transcription of a coding region (e.g., gene) and/or the synthesis of a desired protein molecule is produced. The term also refers to the linkage of amino acid sequences in such a manner so that a functional protein is produced.

As used herein the term "terpene" includes any type of terpene or terpenoid, including for example any monoterpene, diterpene, sesquiterpene, sesterterpene, triterpene, tetraterpene, polyterpene, and any mixture thereof.

The term "transgenic" when used in reference to a plant or leaf or vegetative tissue or seed for example a "transgenic plant," transgenic leaf," "transgenic vegetative tissue," "transgenic seed," or a "transgenic host cell" refers to a plant or leaf or tissue or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

The following non-limiting Examples describe some procedures that can be performed to facilitate making and using the invention.

Example 1: Materials and Methods

This Example illustrates some of the materials and methods used in the development of the invention.
Data Mining A subset of the NAPRALERT database including all the occurrences of diterpenoids in mint species was obtained. NAPRALERT reports chemical mimes, but not structures. For Lamiaceae, the species reported in NAPRALERT largely overlap with those from the Dictionary of Natural Products (DNP), which does include structures. A simplifying assumption was therefore made that each unique name represents a unique compound, and structures for the 3080 Lamiaceae diterpenes in NAPRALERT were not all located due to the deficiencies of the NAPRALERT database.

For SISTEMAT, structure files were obtained by redrawing the structures from the publication by Alvarenga et al. (2001) into MarvinSketch (ChemAxon, Budapest, Hungary). The occurrence counts were obtained by transcribing the association table into a spreadsheet. A publicly available digital version of SISTEMAT, called SISTAMATX exists (see website at sistematx.ufpb.br/), but there is no option for bulk downloads, limiting assessment of its completeness or the ability to cross-reference it with other data. For the present work, the proprietary DNP therefore appeared to be one of the only viable option for many analyses.

Lamiaceae diterpene structures were obtained from the DNP by searching for them through the DNP web interface. Additional compounds were found by searching for individual species names for which transcriptome data was available. This additional search step was used because some species have been reclassified between families, or their family is not correctly annotated in the DNP. Records for all the Lamiaceae diterpenes were downloaded and converted into a spreadsheet using a Python script. Species names were extracted from the Biological Source field in a semi-automated method. The DNP contains structural information in the form of IUPAC International Chemical Identifier (InChI) strings (Heller et al. J Cheminform 7 (2015)). In most cases, the DNP InChIs do not include stereochemical information, so for consistency, all stereochemical information was ignored. Skeletons were extracted from, the structures using the RDKit (see website at rdkit.org) Python interface. Briefly, all bonds were converted into single bonds, bonds involving at least one non-carbon atom were broken, and the fragment with a carbon-count closest to 35 was retained as the skeleton. The resulting skeletons were then manually examined to correct those where the algorithm chose the wrong fragment, for example, a small number of diterpenoids are attached to acyl chains of more than 20 carbons, in which case the algorithm would incorrectly select the acyl chain as the skeleton; the diterpenoid was therefore selected instead. There are a few cases where sesquiterpenes or other terpenes seemed to have been misannotated in DNP as diterpenes, and those sesquiterpenes or other terpenes were left in the dataset, but their presence or absence does not significantly change any of the analyses.

For all three databases, genus and species names were cross-referenced to TaxIDs from the NCBI Taxonomy database (Federhen Nucleic Acids Res 40(D1): D136-D143 (2012)), first by automated text comparisons, then by manual inspection of un-matched names. Genus level TaxID assignments were possible for every entry in NAPRALERT and the DNP, but in some cases, species-level TaxID assignments were not possible, so species-level analyses were avoided.
Phylogenetic Trees Peptide sequences were aligned using Clustal Omega (v. 1.2.1) (Sievers et al., Molecular Systems Biology 7:539 (2011)) and maximum likelihood trees were generated using RAxML (v. 8.2.11) (Stamatakis Bioinformatics 30(9): 1312-1313 (2014)) using automatic model selection and 1000 bootstrap iterations. Tree visualizations were generated using ETE3 (Huerta-Cepas Mol Biol Evol 33(6):1635-1638 (2016)).
Plant Material, RNA Isolation and cDNA Synthesis The following types of plants were obtained from different commercial nurseries or botanical gardens: *Ajuga reptans* L., *Hyptis suaveolens* (L.) Poit., *Leonotis leonurus* (L.) R. Br., *Mentha spicata* L., *Nepeta mussinii* Spreng. ex Henckel, *Origanum majorana* L., *Perovskia atriplicifolia* Benth., *Plectranthus barbatus, Pogostemon cablin* (Blanco)

Benth., *Prunella vulgaris* L., and *Salvia officinalis* L. The plants were grown in a greenhouse under ambient photoperiod and 24° C. day/17° C. night temperatures. *Nicotiana benthamiana* were grown in a greenhouse under 16 h light (24° C.) and 8 h dark (17° C.) regime.

Total RNA from leaf tissues of *A. reptans, N. mussini, L. leonurus, P. atriplicifolia,* and *S. officinalis* was extracted using methods described by Hamberger et al. (*Plant Physiology* 157(4): 1677-1695 (2011)). Total RNA from leaves of *P. vulgaris, M. spicata, P. cablin, H. sauveolans, O. majorana* was extracted using the Spectrum Plant Total RNA Kit (Sigma-Aldrich, St. Louis, Mo., USA). RNA extraction was followed by DNase I digestion using DNA-Free™ DNA Removal Kit (Thermo Fisher Scientific, Waltham, Mass., USA). First-strand cDNAs were synthesized from 5 μg of total RNA, with oligo(dT) primer, using the RevertAid First Strand cDNA Synthesis Kit (Thermo Fisher Scientific, Waltham, Mass., USA). cDNA was diluted 5-fold and used as template for cloning of full length cDNAs. See Table 2 for primers and other oligonucleotides.

Characterization of diTPS Genes by Transient Expression in *N. benthamiana*

Full length coding sequences of diTPSs were cloned into pEAQ-HT vector (Sainsbury et al., 2009; kindly provided by Prof. G. Lomonossoff, John Innes Centre, UK) using In-Fusion® HD Cloning Plus (Takara Bio, California, USA). pEAQ-HT vector contains a copy of anti-post transcriptional gene silencing protein p19 that suppresses the silencing of transgenes (Voinnet et al. *The Plant Journal* 33(5):949-956). Expression vectors carrying full length coding sequence of candidate diTPS genes were transformed into the LBA4404 *A. tumefaciens* strain by electroporation. DXS and GGPPS are known to be the rate limiting enzymes in GGPP biosynthesis and have been shown to substantially increase the production of diterpenes in *N. benthamiana* system. Therefore, the *Plectranthus barbatus* 1-deoxy-D-xylulose 5-phosphate synthase (CfDXS) (genhank accession: KP889115) and geranylgeranyl diphosphate synthase (CfGGPPS) (genhank accession: KP889114) coding regions were cloned, and a chimeric polyprotein was created with a LP4-2A hybrid Sinker peptide between CfDXS and CfGGPPS. LP4/2A contains the first nine amino acids of LP4 (a linker peptide originating from a natural polyprotein occurring in seeds of *Impatiens balsamina*) and 20 amino acids of the self-processing FMDV 2A (2A is a peptide from the foot-and-mouth disease virus).

The transformed *A. tumefaciens* were subsequently transferred to 1 mL SOC media and grown for 1 hour at 28° C. 100 μL cultures were transferred to LB-agar solid media containing 50.0 μg/mL rifampicin and 50.0 μg/mL kanamycin and grown for 2 days. A single colony PCR positive clone was transferred to 10 mL LB media in a falcon tube containing 50.0 μg/mL rifampicin and 50.0 μg/mL kanamycin and grown at 28° C. over-night (at 225 rpm). About 1% of the primary culture was transferred to 25 mL of fresh LB media and grown overnight. Cells were pelleted by centrifugation at 4000×g for 15 min and resuspended in 10 mL water containing 200 μM acetosyringone. Cells were diluted with water-acetosyringone solution to a final $OD_{600}$ of 1.0 and incubated at 28° C. for 2-3 hours to increase the infectivity. Equal volumes of culture containing the plasmids with cDNA encoding different diTPS genes were mixed. Each combination of *A. tumefaciens* culture mixture was infiltrated into independent 4-5 weeks old *N. benthamiana* plants. Plants were grown for 5-7 days in the greenhouse before metabolite extraction. Leaf discs of 2 cm diameter (approximately 0.1 g fresh weight) were cut from the infiltrated leaves. Diterpenes were extracted in 1 mL n-hexane with 1 mg/L 1-eicosene as internal standard (IS) at room temperature overnight in an orbital shaker at 200 rpm. Plant material was collected by centrifugation and the organic phase transferred to GC vials for analysis.

In-Vitro Enzyme Activity Assays

To confirm the biosynthetic products obtained in *N. benthamiana*, diTPS combinations were tested in in vitro assays as described by Pateraki et al. (*Plant Physiol* 164(3): 1222-1236 (2014)). TargetP (Emanuelsson et al. *Journal of Molecular Biology* 300(4):1005-1016 (2000)) was used for prediction of the plastidial target sequence. Pseudo mature variants versions of HsTPS1, ArTPS2, PcTPS1, OmTPS3, OmTPS5, SsSS, CfTPS1, CfTPS2 and codon optimized GTPS3 (IDT, USA), lacking the predicted plastidial targeting sequences were cloned in pET-28b(+) (EMD Millipore, Burlington, Mass.), then expressed and purified from *E. coli*. The pET_diTPS constructs were transformed into chemically competent OverExpress™ C41(DE3) cells (Lucigen, Middleton, Wis., USA), the cells were inoculated in a starter culture with terrific broth medium and 50 μg mL$^{-1}$ kanamycin, then grown overnight. About 1% of the starter culture was used to inoculate 50 mL terrific broth medium having 50 μg mL$^{-1}$ kanamycin, and the culture was grown at 37° C. with mixing at 200 rpm until the $OD_{600}$ reached 0.4. Cultures were grown at 16° C. until an $OD_{600}$ of approximately 0.6-0.8 was achieved at which point cultures were induced by 0.2 mM IPTG. Expression was allowed to proceed overnight, and cells were harvested by centrifugation at 5000 g/4° C. for 15 minutes. Cell pellets were resuspended in lysis buffer containing 20 mM HEPES, pH 7.5, 0.5 M NaCl, 25 mM Imidazole, 5% [v/v] glycerol, using one protease inhibitor cocktail tablet per 100 mL (Sigma Aldrich, St. Louis, Mo., USA). Lysozyme (0.1 mg per liter) was added to the cell pellet, and the mixture was gently shaken for 30 min, then lysed by sonication. Cell lysate was centrifuged for 25 min at 14000 g, and the supernatant was subsequently used for purification of the recombinant proteins. Proteins were purified on 1-mL His SpinTrap columns (GE Healthcare Life Sciences, Piscataway, N.J., USA) using elution buffer (HEPES, pH 7.5, 0.5 M NaCl, 5% [v/v] glycerol, 350 mM Imidazole and 5 mM dithiothreitol [DTP]) and desalted on PD MiniTrap G-25 columns (GE Healthcare, Life Sciences, Piscataway, N.J., USA) with a desalting buffer (20 mM HEPES, pH 7.2, 350 mM NaCl, 5 mM DTT, 1 mM $MgCl_2$, 5% [v/v] glycerol). In-vitro diTPS assays were performed by adding 15 μM GGPP and 50-100 μg purified enzymes in 400 μL enzyme assay buffer (50 mM HEPES, pH 7.2, 7.5 mM $MgCl_2$, 5% [v/v] glycerol, 5 mM DTT). 500 mL n-hexane (Fluka GC-MS grade) containing 1 ng/ml 1-eicosene as internal standard was gently added as an overlay onto the reaction mix. Assays were incubated for 60-120 min at 30° C. with mixing at approximately 75 rpm, and the hexane overlay was subsequently removed by centrifugation at 1500×g for 15 min before proceeding for GC-MS analysis.

Metabolite Analysis of *O. majorana*

Fresh leaf, stem, root, and flowers (20 to 50 mg) of *O. majorana* were harvested. Flowers were further separated with forceps into two parts, the green part ("calyx"), and the rest of the flower ("corolla"). Tissues were extracted overnight in 500 μL of methyl tert-butyl ether. Extracts were concentrated to 100 μL and subjected to GC-MS analysis.

Compound Purification

For bulk production of diterpenes for structural determination, 15-30 *N. benthamiana* plants were vacuum infiltrated with diTPS combinations as well as CfGGPPS and CfDXS (46). After 5 days, 100-200 g (fresh weight) of leaves were subjected to two rounds of overnight extractions in 500 mL hexane, which was then concentrated using a rotary evaporator. Compounds were purified on silica gel columns using a mobile phase of hexane with 0-20% ethyl-acetate, in some cases, additional rounds of column purification, or preparative TLC using a hexane/ethyl-acetate or chloroform/methanol mobile phase, were necessary to obtain compounds of sufficient purity for structural determination by NMR.

GC-MS

All GC-MS analyses were performed on an Agilent 7890A GC with an Agilent VF-5 ms column (30 m×250 µm×0.25 µm, with 10 m EZ-Guard) and an Agilent 5975C detector. For N. benthamiana and in-vitro assays, the inlet was set to 250° C. splitless injection, using helium carrier gas with column flow of 1 mL/min. The oven program was 45° C. hold 1 min, 40° C./min to 230° C. 7° C./min to 320° C., hold 3 min. The detector was activated after a four-minute solvent delay. For analysis of O. majorana extracts, conditions were the same, except that the solvent cutoff was set to six minutes to allow monoterpenes to pass, and the oven program was a 45° C. hold for 1 min., 40° C./min to 200° C. 5° C./min to 260° C. 40° C./min to 320° C., with a hold for 3 min.

NMR and Optical Rotation

The NMR spectra for trans-biformene (Yamada et al. The Journal of Antibiotics 69(7):515-523 (2016)) were measured on a Bruker AVANCE 900 MHz spectrometer. Ail other spectra were measured on an Agilent DirectDrive2 500 MHz spectrometer. AH NMR was done in $CDCl_3$ solvent. The $CDCl_3$ peaks were referenced to 7.24 ppm and 77.23 ppm for $^1H$ and $^{13}C$ spectra, respectively. To aid in the interpretation of NMR spectra, the NAPROC-13 (Lopez-Perez et al. Bioinformatics 23(23):3256-3257 (2007)), and Spektraris (Fischedick et ah, Phytochemistry 113:87-95 (2015)) databases were used. Reconstruction of $^{13}C$ spectra from the literature was performed with MestReNova (Mestrelab Research, Santiago de Compostela, Spain). Optical rotation was measured in chloroform at ambient temperature using a Perkin Elmer Polarimeter 341 instrument.

TABLE 2

List of synthetic oligonucleotides

| Primer Name (gene) | Sequence |
|---|---|
| Amplification of full length genes from cDNA synthesized from plant tissues total RNA | |
| ZmAN2-F (ZmAN2) | ATGGTTCTTTCATCGTCTTGCACA (SEQ ID NO:61) |
| ZmAN2-R (ZmAN2) | TTATTTTGCGGCGGAAACAGGTTCA (SEQ ID NO: 62) |
| CfTPS2-F (CfTPS2) | AGATTGAGGATTCCATTGAGTACGTGAAGG (SEQ ID NO: 63) |
| CfTPS2-R (CfTPS2) | GAAGTTTAATATCCTTCATTCTTTATTACA (SEQ ID NO:64) |
| CfTPS3-F (CfTPS3) | AGCTCCATTCAACTAGAGTCATGTCGT (SEQ ID NO:65) |
| CfTPS3-R (CfTPS3) | TTCATCTGGCTTAACTAGTTGCTGACAC (SEQ ID NO:66) |
| CfTPS16-F (CfTPS16) | TTAAAGTACTCTCTCAAAGAGTACTTTGG (SEQ ID NO:67) |
| CfTPS16-R (CfTPS16) | GCGACCAACCATCATACGACT (SEQ ID NO:68) |
| LITPS1-F (LITPS1) | AATGGCCTCCACTGCATCCACTCTA (SEQ ID NO:69) |
| LITPS1-R (LITPS1) | CCATACTCATTCAACTGGTTCGAACA (SEQ ID NO:70) |
| LITPS4-F (LITPS4) | AGCCTGTGTACTCGAAATGTC (SEQ ID NO:71) |

TABLE 2-continued

List of synthetic oligonucleotides

| Primer Name (gene) | Sequence |
|---|---|
| LITPS4-R (LITPS4) | CAAGAGGATGATTCATGTACCAAC (SEQ ID NO:72) |
| SoTPS1-F (SoTPS1) | TCTCTTTCAAGAATATCCCCTCTC (SEQ ID NO:73) |
| SoTPS1-R (SoTPS1) | GGCATTCAATGATTTTGAGTCG (SEQ ID NO:74) |
| ArTPS1-F (ArTPS1) | AAATGGCCTCTTTGTCCACTCTC (SEQ ID NO:75) |
| ArTPS1-R (ArTPS1) | TTACGCAACTGGTTCGAAAAGCA (SEQ ID NO:76) |
| ArTPS2-F (ArTPS2) | TAATGTCATTTGCTTCCCAAGCCA (SEQ ID NO:77) |
| ArTPS2-R (ArTPS2) | GGCCTAGACTATACCTTCTCAAACAA (SEQ ID NO:78) |
| ArTPS3-F (ArTPS3) | AATGTCACTCTCGTTCACCATCAA (SEQ ID NO:79) |
| ArTPS3-R (ArTPS3) | ACTTCAAGAGGATGAAGTGTTTAGG (SEQ ID NO:80) |
| PaTPS1-F (PaTPS1) | CTCCAAAACTCGGGCCGGTAAAT (SEQ ID NO:81) |
| PaTPS1-R (PaTPSI) | TACGTATTTCCTCACAATCGAGCA (SEQ ID NO:82) |
| PaTPS3-F (PaTPS3) | CTAGAAATGTTACTTGCGTTCAAC (SEQ ID NO:83) |
| PaTPS3-R (PaTPS3) | GGGTAAGAGTTGAATTTAGATGTCT (SEQ ID NO:84) |
| NmTPS1-F (NmTPS1) | ATGACTTCAATATCCTCTCTAAATTTGAGC (SEQ ID N0:85) |
| NmTPS1-R (NmTPS1) | GAATATAGTAATCAGACGACCGGTCCA (SEQ ID N0:86) |
| NmTPS2-F (NmTPS2) | GCCATATCATGTCTCTTCCGCTCT (SEQ ID NO:87) |
| NmTPS2-R (NmTPS2) | TTATTCATGCACCTTAAAATCCTTGAGAG (SEQ ID NO:88) |
| OmTPS1-F (OmTPS1) | ATGACCGATGTATCCTCTCTTCGT (SEQ ID NO:89) |
| OmTPS1-R (OmTPS1) | AAACACTCACATAACCGGCCCAA (SEQ ID NO:90) |
| OmTPS3-F (OmTPS3) | GTCCTTGCTTTCGGAATACT (SEQ ID NO:91) |
| OmTPS3-R (OmTPS3) | GAAGTGATCTACAAGGATTCATAAA (SEQ ID NO:92) |
| OmTPS4-F (OmTPS4) | TCATTGATTTGCCCTGCATCCAC (SEQ ID N0:93) |
| OmTPS4-R (OmTPS4) | CAAAGCTAGTGCTGCTTCTGATT (SEQ ID N0:94) |
| OmTPS5-F (OmTPS5) | ATGGTATCTGCATGTCTAAAACTCAA (SEQ ID NO:95) |
| OmTPS5-R (OmTPS5) | CTTTCTCTCTCTTGTGCATCTTAGT (SEQ ID NO:96) |
| MsTPS1-F (MsTPS1) | ACGTTCATCTTCAATGAGTTCCA (SEQ ID N0:97) |
| MsTPS1-R (MsTPS1) | TACGTGTATGTCGATCTGTTCCAAT (SEQ ID NO:98) |
| PcTPS1-F (PcTPS1) | CATGTCATTTGCTTCTCAATCAC (SEQ ID NO:99) |
| PcTPS1-R (PcTPS1) | CCCATTATCTAAAAGTCTACATCACC (SEQ ID NO:100) |
| HsTPS1-F (HsTPS1) | TCCTCATAAAGCAATGGCGTATA (SEQ ID NO:101) |
| HsTPS1-R (HsTPS1) | CTAAGATTCAGACAATGGGCTCA (SEQ ID NO:102) |
| EpTPS8-F (EpTPS8) | GCAGACGCCAATCTTTCTTGGT (SEQ ID NO:103) |
| EpTPS8-R (EpTPS8) | TTATGAAGTTAAAAGGAGTGGTTCGTTGAC (SEQ ID N0:104) |
| PVTPS1-F (PVTPS1) | GGAACGAGAAATGTCACTCAC (SEQ ID NO:105) |
| PVTPS1-R (PVTPS1) | TTCTAGTTTCTCACAGAAGTCAA (SEQ ID NO:106) |
| LP4-2A Ver.1 sequence | TCAAATGCAGCAGACGAAGTTGCTACT CAACTTTTGAATTTTGACTTGCTGAAGTT GGCTGGTGATGTTGAGTCAAACCCTGGACCT (SEQ ID NO:107) |

TABLE 2-continued

List of synthetic oligonucleotides

| Primer Name (gene) | Sequence |
|---|---|
| *Cloning of full length diTPS genes into pEAQ-HT for transient expression in N. benthamiana* | |
| pEAQ_Infusion_CfTPS1-F (CfTPS1) | TTCTGCCCAAATTCGATGGGGTCTCTATCCACTATGA (SEQ ID NO:108) |
| pEAQ_Infustion_CfTPS1-R (CfTPS1) | AGTTAAAGGCCTCGATCAGGCGACTGGTTCGAAAAGTA (SEQ ID NO:109) |
| pEAQ_Infusion_SsSCS-F (SsSS) | TTCTGCCCAAATTCGATGTCGCTCGCCTTCAAC (SEQ ID NO:110) |
| pEAQ_Infusion_SsSCS-R (SsSS) | AGTTAAAGGCCTCGATCAAAAGACAAAGGATTCATA (SEQ ID NO:111) |
| pEAQ_Infusion_ZmAN2-F (ZmAN2) | TTCTGCCCAAATTCGATGGTTCTTTCATCGTCTTGCAC (SEQ ID No:112) |
| pEAQ_Infusion_ZmAN2-R (ZmAN2) | AGTTAAAGGCCTCGATTATTTTGCGGCGGAAACAGGT (SEQ ID NO:113) |
| pEAQ_Infusion_CfTPS2-F (CfTPS2) | TTCTGCCCAAATTCGATGAAAATGTTGATGATCAAAAGT (SEQ ID NO:114) |
| pEAQ_Infusion_CfTPS2-R (CfTPS2) | AGTTAAAGGCCTCGATCAGACCACTGGTTCAAATAGTA (SEQ ID NO:115) |
| pEAQ_Infusion_CfTPS3-F (CfTPS3) | TTCTGCCCAAATTCGATGTCGTCCCTCGCCGGCAACCT (SEQ ID NO:116) |
| pEAQ_Infusion_CfTPS3-R (CfTPS3) | AGTTAAAGGCCTCGACTAGTTGCTGACACAACTCATT (SEQ ID NO:117) |
| pEAQ_Infusion_CfTPS16-F (CfTPS16) | TTCTGCCCAAATTCGATGCAGGCTTCTATGTCATCT (SEQ ID NO:118) |
| pEAQ_infusion_CfTPS16-R (CfTPS16) | AGTTAAAGGCCTCGATCATACGACTGGTTCAAACATT (SEQ ID NO:119) |
| pEAQ_Infusion_LlTPS1-F (LlTPS1) | TTCTGCCCAAATTCGATGGCCTCCACTGCATCC (SEQ ID NO:120) |
| pEAQ_Infusion_LlTPS1-R (LlTPS1) | AGTTAAAGGCCTCGATCATTCAACTGGTTCGAACAA (SEQ ID NO:121) |
| pEAQ_Infusion_LlTPS2-F (LlTPS2) | TTCTGCCCAAATTCGATGATTCCTAATCCCGAAA (SEQ ID NO:122) |
| pEAQ_Infusion_LlTPS2-R (LlTPS2) | AGTTAAAGGCCTCGATTACATTGGCAATCCGATGAA (SEQ ID NO:123) |
| pEAQ_Infusion_LlTPS4-F (LlTPS4) | TTCTGCCCAAATTCGATGTCGGTGGCGTTCAACCT (SEQ ID NO:124) |
| pEAQ_Infusion_LlTPS4-R (LlTPS4) | AGTTAAAGGCCTCGATCAAGAGGATGATTCATGTACC (SEQ ID NO:125) |
| pEAQ_Infusion_SoTPS1-F (SoTPS1) | TTCTGCCCAAATTCGATGTCCCTCGCCTTCAACG (SEQ ID NO:126) |
| pEAQ_/Infusion_SoTPS1-R (SoTPS1) | AGTTAAAGGCCTCGATCATTTGCCACTCACATT (SEQ ID NO:127) |
| pEAQ_infusion_ArTPS1-F (ArTPS1) | TTCTGCCCAAATTCGATGGCCTCTTTGTCCACTTTCC (SEQ ID NO:128) |
| pEAQ_/Infusion_ArTPS1-R (ArTPS1) | AGTTAAAGGCCTCGATCACGCAACTGGTTCGAAAAGA (SEQ ID NO:129) |
| pEAQ_Infusion_ArTPS2-F (ArTPS2) | TTCTGCCCAAATTCGATGTCATTTGCTTCCCAGCCAC (SEQ ID NO:130) |
| pEAQ_Infusion_ArTPS2-R (ArTPS2) | AGTTAAAGGCCTCGACTAGACTACCTTCTCAAACA (SEQ ID NO:131) |
| pEAQ_Infusion_ArTPS3-F (ArTPS3) | TTCTGCCCAAATTCGATGTCACTCTCGTTCACCATCA (SEQ ID NO:132) |
| pEAQ_Infusion_ArTPS-R (ArTPS3) | AGTTAAAGGCCTCGATCAAGAGGATGAAGTGTTTAG (SEQ ID NO:133) |
| pEAQ_Infusion_PaTPS1-F (PaTPS1) | TTCTGCCCAAATTCGATGACCTCTATGTCCTCTCTAA (SEQ ID NO:134) |
| pEAQ_Infusion_PaTPS1-R (PaTPS1) | AGTTAAAGGCCTCGATCATACGACCGGTCCAAACAGT (SEQ ID NO:135) |
| pEAQ_Infusion_PaTPS3-F (PaTPS3) | TTCTGCCCAAATTCGATGTTACTTGCGTTCAACATAAGC (SEQ ID NO:136) |
| pEAQ_Infusion_PaTPS3-R (PaTPS3) | AGTTAAAGGCCTCGATTAATTAGGTAGGTAGAGGGGTT (SEQ ID NO:137) |
| pEAQ_Infusion__NmTPS1-F (NmTPS1) | ATATTCTGCCCAAATTCGATGACTTCAATATCCTCTCTAAATTTGAGCAATG (SEQ ID NO:138) |
| pEAQ_Infusion_NmTPS1-R (NmTPS1) | CAGAGTTAAAGGCCTCGATCAGACGACCGGTCCAA (SEQ ID NO:139) |
| pEAQ_Infusion_NmTPS2-F (NmTPS2) | TTCTGCCCAAATTCGATGTCTCTTCCGCTCTCCTCT (SEQ ID NO:140) |
| pEAQ_Infusion_NmTPS2-R (NmTPS2) | GATAAGTTAAAGGCCTCGATTATTCATGCACCTTAAAATCCTTGAGAGC (SEQ ID NO:141) |
| pEAQ_Infusion_OmTPS1-F (OmTPS1) | TTCTGCCCAAATTCGATGACCGATGTATCCTCTCTTC (SEQ ID NO:142) |
| pEAQ_Infusion_OmTPS1-R (OmTPS1) | AGTTAAAGGCCTCGATCACATAACCGGCCCAAACA (SEQ ID NO:143) |
| pEAQ_Infusion_OmTPS3-F (OmTPS3) | TTCTGCCCAAATTCGATGGCGTCGCTCGCGTTCAC (SEQ ID NO:144) |
| pEAQ_Infusion_OmTPS3-R (OmTPS3) | AGTTAAAGGCCTCGACTACAAGGATTCATAAATTAAGGA (SEQ ID NO:145) |
| pEAQ_Infusion_OmTPS4-F (OmTPS4) | TTCTGCCCAAATTCGCGAATGTCACTCGCCTTCAGC (SEQ ID NO:146) |
| pEAQ_Infusion_OmTPS4-R (OmTPS4) | AGTTAAAGGCCTCGAGCTAGGAGCTTAGGGTTTCAT (SEQ ID NO:147) |
| pEAQ_Infusion_OmTPS5-F (OmTPS5) | TTCTGCCCAAATTCGATGGTATCTGCATGTCTAAA (SEQ ID NO:148) |
| pEAQ_Infusion_OmTPS5-R (OmTPS5) | AGTTAAAGGCCTCGATCATGAAGGAATTGAAGGAA (SEQ ID NO:149) |
| pEAQ_Infusion | TTCTGCCCAAATTCGATGAGTTCCATTCGAAA |

TABLE 2-continued

List of synthetic oligonucleotides

| Primer Name (gene) | Sequence |
|---|---|
| _MsTPS1-F (MsTPS1) pEAQ_Infusion | TTT AAGT (SEQ ID NO:150) AGTTAAAGGCCTCGATCACTTGAGAGGCTCA AAC |
| _MsTPS1-R (MsTPS1) pEAQ_Infusion | ATCAT (SEQ ID NO:151) TTCTGCCCAAATTCGATGTCAT- TTGCTTCTCA |
| _PcTPS1-F (PCTPS1) pEAQ_Infusion | AT CAC (SEQ ID NO:152) AGTTAAAGGCCTCGACTACATCACCCTCT- CAA |
| _PcTPS1-R (PcTPS1) pEAQ_Infusion | ACA ATAC (SEQ ID NO:153) TTCTGCCCAAATTCGATGGCGTATATGA- TATC |
| _HsTPS1-F (HsTPS1) pEAQ_/Infusion | TAT TTCAAATCTC (SEQ ID NO:154) AGTTAAAGGCCTCGATCAGACAATGGGCTCA AAT |
| _HsTPS1-R (HsTPS1) pEAQ_Infusion | AGAAC (SEQ ID NO:155) TTCTGCCCAAATTC- GATGCAAGTCTCTCTCTC |
| _EpTPS8-F (EpTPS8) pEAQ_Infusion | C CTCA (SEQ ID NO:156) AGTTAAAGGCCTCGATTATGAAGTTAAAAGG AG |
| __EpTPS8-R (EpTPS8) pEAQ_Infusion | TGGTT (SEQ ID NO:157) TTCTGCCCAAATTCGCGAATGTCACT- CACTTT |
| _PVTPS1-F (PVTPS1) pEAQ_Infusion | CA ACG (SEQ ID NO:158) AGTTAAAGGCCTCGAGCTAGTTTCTCACAGA AG |
| _PVTPS1-R (PVTPS1) | TCAA (SEQ ID NO:159) |
| Cloning of diTPS genes into pET-28 b (+30) for E. coli expression | |
| pET28_CfTPS1-F (CfTPS1) | AGGAGATATACCATGGCCGAGATTCGAGTG CCAC (SEQ ID NO:160) |
| pET28_CfTPS1-R (CfTPS1) | GGTGGTGGTGCTCGAAGGCGACTGGTTCGAA AAG TAC (SEQ ID NO:161) |
| pET28__SsSS-F (SsSS) | AGGAGATATACCATGGATTTCATGGCGAAAA TGAA AGAGA (SEQ ID NO:162) |
| pET28__SsSS-R (SsSS) | GGTGGTGGTGCTCGAAAAAGACANAGGATTT CATAT (SEQ ID NO:163) |
| pET28__CfTPS2-F (cfTPS2) | AGGAGATATACCATGCAAATTCGTGGAAAGC AAAG ATCAC (SEQ ID NO:164) |
| pET28_CfTPS2-R (CfTPS2) | GGTGGTGGTGCTCGAAGACCACTGGTTCAAA TAG AACT (SEQ ID NO:165) |
| pET28_CfTPS3-F (CfTPS3) | AGGAGATATACCATGTCTAAATCATCTGCAG CTGT (SEQ ID NO:166) |
| pET28__CfTPS3-R (CfTPS3) | GGTGGTGGTGCTCGAAGTTGCTGACACAACT CATT (SEQ D NO:167) |
| pET28_OmTPS3-F (OmTPS3) | AGGAGATATACCATGACCGTCAAATGCTAC (SEQ ID NO:168) |
| pET28_OmTPS3-R (OmTPS3) | GGTGGTGGTGCTCGAACAAGGATTCATAAAT TAAG (SEQ ID NO:169) |
| pET28_OmTPS5-F (OmTPS5) | AGGAGATATACCATGACTGTCAAGTGCAGC (SEQ ID NO:170) |
| pET28_OmTPS5-R (OmTPS5) | GGTGGTGGTGCTCGAATGAAGGAATTGAAG (SEQ ID NO:171) |
| pET28_PcTPS1-F (pcTPS1) | AGGAGATATACCATGTTTATGCCCACTTC- CAT TAA ATGTA (SEQ ID NO:172) GGTGGTGGTGCTCGAACATCACCCTCTCAAA |
| pET28__PcTPS1-R (PcTPS1) | CAA TACTTTGG (SEQ ID NO:173) AGGAGATATACCATGGTAGCAAAAGTGATCG AGAG |
| pET28_HsTPS1-F (HsTPS1) | CCGAGTTA (SEQ ID NO:174) GGTGGTGGTGCTCGAAGACAATGGGCTCAAA TAGA |
| pET28_HsTPS1-R (HsTPS1) | ACTTTAAAT (SEQ. ID NO:175) |

Example 2: Diversity of Diterpenoids in Lamiaceae

To help determine the most promising species in which to find previously unknown hut useful diterpene synthase (diTPS) activities, a dataset of diterpene occurrences in Lamiaceae species and a dataset of functionally characterized diTPS genes from Lamiaceae were generated. Information about diterpene occurrence was collected from three sources, SISTEMAT, DNP, and NAPRALERT. SISTEMAT (Vestri et al. Phytochemistry 56(6):583-595 (2001)) contains Lamiaceae diterpenes reported up to 1997, including 91 unique carbon skeletons (the core alkanes, disregarding all desaturation, acyl-side chains, heteroatoms, and stereochemistry) from 295 species and 51 genera. An electronic copy of SISTEMAT was not available, so it was reconstructed based on the figures and tables in the paper.

The Dictionary of Natural Products (DNP; see website at dnp.chemnetbase.com, accessed Jan. 11, 2018) includes a wealth of information on diterpenes from Lamiaceae, including full structures and the species where those structures have been reported. NAPRALERT (Loub et al., J Chem Inf Comput Sci 25(2):99-103 (1985)) identifies compounds by their common name rather than their structure or skeleton, but it does associate the compounds to genus and species names, and gives various other information, such as the tissue where the compound was found.

To enable comparison among the databases, and cross-referencing with transcriptome and enzyme data, all genus and species manes were converted into TaxIDs from the NCBI Taxonomy database (Federhen Nucleic Acids Res 40(D1): D136-D143 (2012)). To put structure occurrences into clearer evolutionary context, each genus was annotated as a member of one of the 12 monophyletic clades that form the backbone of Lamiaceae, as delineated by Li and colleagues (Li et al. Scientific Reports 6:34343 (2016)).

In the context of diTPSs, examination of skeletons can be helpful because the skeleton often resembles the diterpene synthase product more obviously than a highly decorated downstream product would. Therefore, the skeletons were extracted from the DNP structures. An example of such skeleton extraction is shown below, where Table 3A provides an example of which class I diTPS generate which products when using a *N. benthamiana* transient expression. Bold numbers refer to assigned compound numbers; "np" indicates that the combination was tested but no product was detected; indicates that the combination was not tested. The following are newly identified enzymes: LITPS1, HsPS1, PcTPS1, ArTPS2, OmTPS1, ArTPS3, LITPS4, MsTPS1, NmTPS2, OmTPS3, OmTPS4, OmTPS5, PaTPS3, PvTPS1, and SoTPS1.

TABLE 3A

Index of Enzyme Types and Products Observed in Transient Expression Assays

| Enzyme | CfTPS1 [31] | CfTPS2 [10] | LlTPS1 [5] | ZmAN2 [16] | HsPS1 [21] | PcTPS1 [25] | ArTPS2 [38] | OmTPS1 [31] |
|---|---|---|---|---|---|---|---|---|
| ArTPS3 | 32 | 8 | 1, 2, 3 | np | — | — | np | — |
| LlTPS4 | 27 | 8 | 1, 2, 3 | np | — | — | — | — |
| MsTPS1 | 27 | 8 | 3 | np | — | — | np | — |
| NmTPS2 | np | np | np | 19 | — | — | np | — |
| OmTPS3 | 34 | 11 | 1, 2 | np | 24 | — | np | 34 |
| OmTPS4 | 33 | 8 | 1, 2, 3, 4 | 20 | — | — | — | 33 |
| OmTPS5 | 29 | 8 | 1, 2, 3 | np | — | — | np | 29 |
| PaTPS3 | 32 | 8 | 1, 2, 3 | np | — | — | — | — |
| PvTPS1 | 32 | 8 | 1, 2, 3 | np | — | — | — | — |
| SoTPS1 | 32 | 8 | 1, 2, 3 | np | — | — | — | — |
| CfTPS3 | 32 | 8 | 1, 2, 3 | np | 22 | np | np | 32 |
| SsSS | 33 | — | 4 | 20 | 23 | 26 | 37 | — |

Table 3B provides an example of an index of new class II diTPS enzymes and the products identified by functional assays of these enzymes using the *N. benthamiana* transient expression assay. The products were identified by GC-MS chromatography of hexane extracts from *N. benthamiana* transient expression assays that expressed new (+)-CPP synthases or new class II diTPSs along with reference combinations.

TABLE 3B

Products Identified for New Class II diTPS Enzymes

| Enzyme | Product |
|---|---|
| ArTPS1 | Copalyl-PP [31] |
| CfTPS16 | Copalyl-PP [31] |
| NmTPS1 | Copalyl-PP [31] |
| OmTPS1 | Copalyl-PP [31] |
| PaTPS1 | Copalyl-PP [31] |
| ArTPS2 | Neo-cleroda-4(18), 13E-dienyl-PP [38] |
| HsTPS1 | Labda-7,13E-dienyl-PP [21] |
| LlTPS1 | Peregrinol-PP [7] |
| PcTPS1 | Ent-labda-8,13E-dienyl-PP [25] |

Using data like that obtained in Tables 3A and 3B, a labdane skeleton was extracted from the forskolin structure shown below by deleting all heteroatoms, desaturations, and stereochemistry.

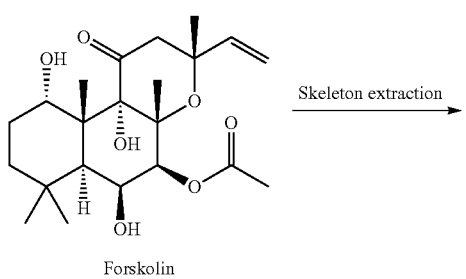

Forskolin

Skeleton extraction

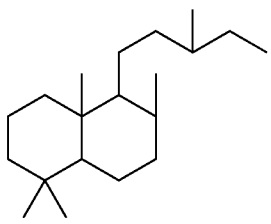

Labdane

A tabulation of the skeletons from SISTEMAT and DNP was therefore generated.

The three databases were relatively consistent in their estimations of the diversity and distribution of diterpenes and diterpene skeletons, as illustrated in Table 4 and FIG. 1B, 1D.

TABLE 4

Comparison of different sources for data about Lamiaceae diterpene chemotaxonomy

| | DNP | NAPRALERT | SISTEMAT |
|---|---|---|---|
| Genera | 67 | 60 | 44 |
| Species | 342 | 378 | — |
| Diterpene names | 3336 | 3080 | — |
| Diterpene structures | 3268 | — | — |
| Diterpene skeletons | 229 | — | 91 |

A total of 239 skeletons are represented, with five, the kaurane (Sk1), clerodane (Sk2), abietane (Sk3), labdane (Sk4), and pimarane (Sk6) being, by far, the most widely distributed and accounting for most of the total structures (Table 4, FIG. 1B-1C). The clerodane skeleton, for example, has the widest distribution, having been reported in 27 genera representing 9 of the 12 backbone clades, absent only in Tectona and two clades from which no diterpenes have yet been reported. The large number of less common, taxonomically restricted skeletons, including over 100 skeletons with only one associated compound (FIG. 1C), indicted to the inventors that searching across many species and genera would be a good strategy for finding diterpene synthases with new activities.

Example 3: Identifying Candidate Diterpene Synthase Genes

Through a comprehensive literature search, a reference set was built of known Lamiaceae diTPSs and their activities. Fifty-four functional diTPSs have been reported in this family, which correspond to thirty class II and 24 class I enzymes. Combinations of these diterpene synthases account for twenty-seven distinct products represented by six different skeletons, the five widely distributed skeletons, Sk1-4 and Sk6, as well as the less common atisane (Sk14) skeleton. This leaves 233 skeletons for which the biosynthetic route remains unknown. Further, a single skeleton can correspond to multiple distinct diTPS products, so there is also a possibility of finding new diTPS activities for skeletons already accounted for by known enzymes.

BLAST homology searches (Camacho et al. BMC Bioinformatics 10:421 (2009)) were performed to the list of Lamiaceae diTPSs to mine 48 leaf transcriptomes made available by the Mint Genome Project (Boachon et al. Molecular Plant. (2018)) for candidate diTPSs. The number of diTPS candidates was cross-referenced to the number of diterpenes and diterpene skeletons reported from each species and genus (Table 5). Table 5 shows species from which diTPSs were selected for cloning, the total number of diTPS candidate sequences, and the number of unique diterpene structures and skeletons for those species, based on DNP.

TABLE 5

Species from which diTPSs were Isolated

| Full name | Code | diTPS hits | Diterpenes | Skeletons |
|---|---|---|---|---|
| *Ajuga reptans* | Ar | 5 | 13 | 2 |
| *Hyptis suaveolens* | Hs | 7 | 4 | 1 |
| *Leonotis leonurus* | Ll | 5 | 14 | 2 |
| *Mentha spicata* | Ms | 5 | 0 | 0 |
| *Nepeta mussinii* | Nm | 3 | 0 | 0 |
| *Origanum majorana* | Om | 5 | 0 | 0 |
| *Perovskia atriplicifolia* | Pa | 5 | 2 | 2 |
| *Plectranthus barbatus* | Cf | 5 | 50 | 10 |
| *Pogostemon cablin* | Pc | 2 | 0 | 0 |
| *Prunella vulgaris* | Pv | 1 | 1 | 1 |
| *Salvia officinalis* | So | 5 | 13 | 5 |

A phylogenetic tree was generated from the peptide sequences from the reference set, alongside those from the new transcriptome data, including established substrates and products for each enzyme (FIG. 3A, 3B-1 to 3B-4). Candidate genes were selected from species such as *Mentha x spicata* and *Origanum majorana*, where the transcriptome data showed multiple candidate diTPSs likely existed but where few or no diterpene product structures have been reported. Genes were also selected that had relatively low homology to known enzymes. In this way, the inventors attempted to evenly cover the sequence homology space. A few candidates from *Plectranthus* and *Salvia* were also selected based on the great diversity of diterpenes that have been reported from these genera.

Example 4: Characterization of Class II diTPSs

Figure 3A:
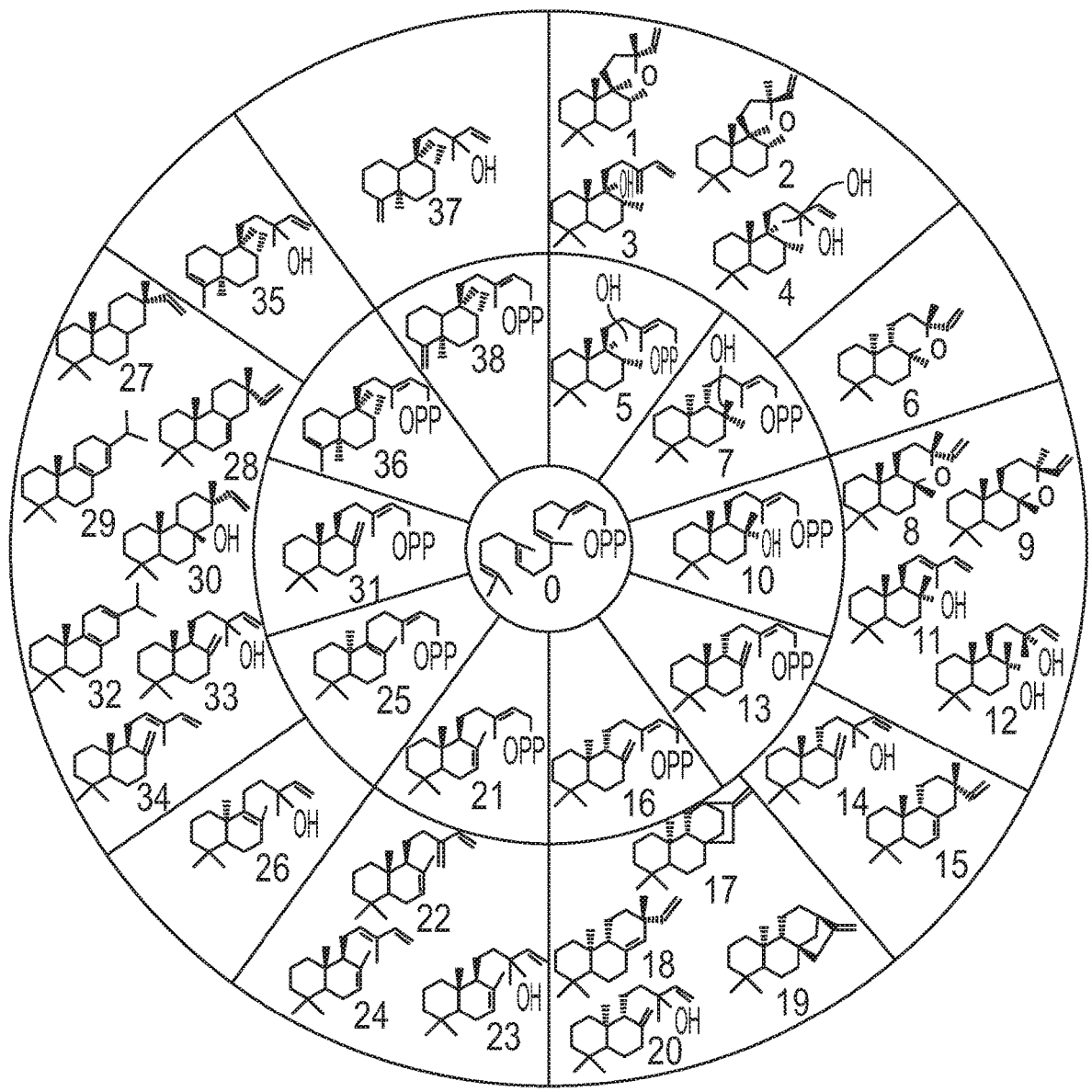
FIG. 3A-3B(A)-(H) show structures of products of diterpene synthases from Lamiaceae and a phylogenetic tree was generated from the peptide sequences.
Figure 3B:
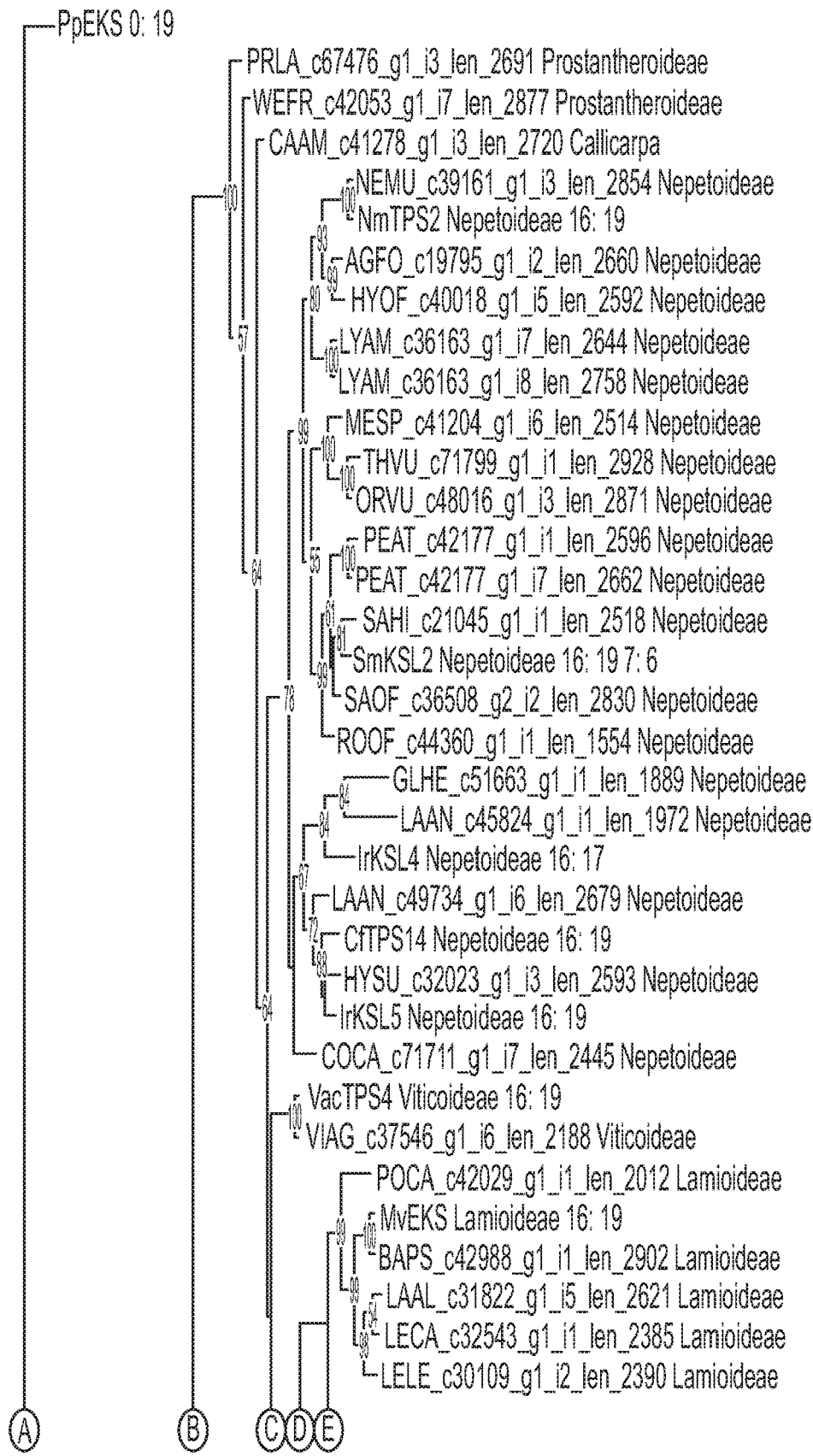
Figure 3B:
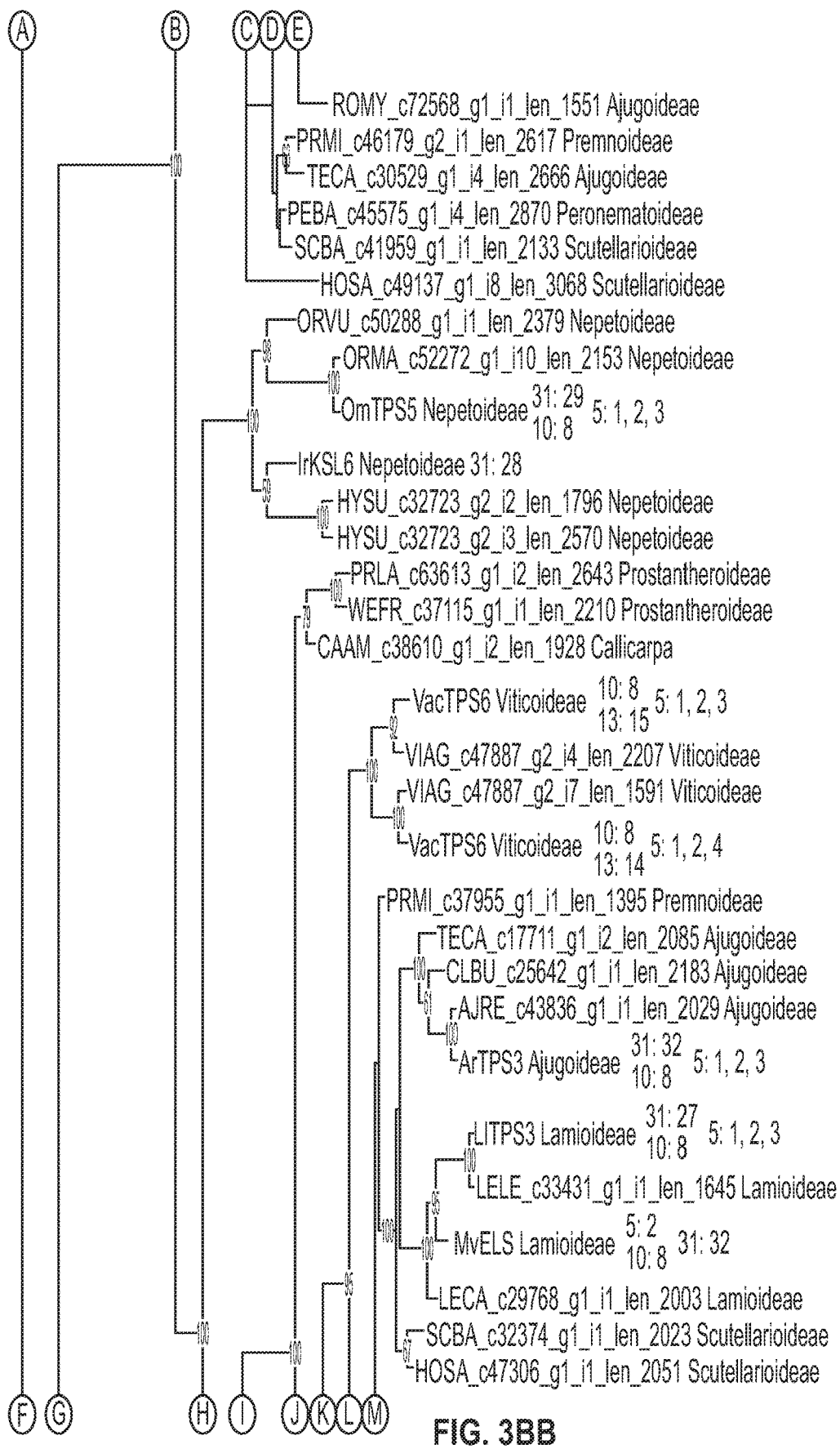
Figure 3B:
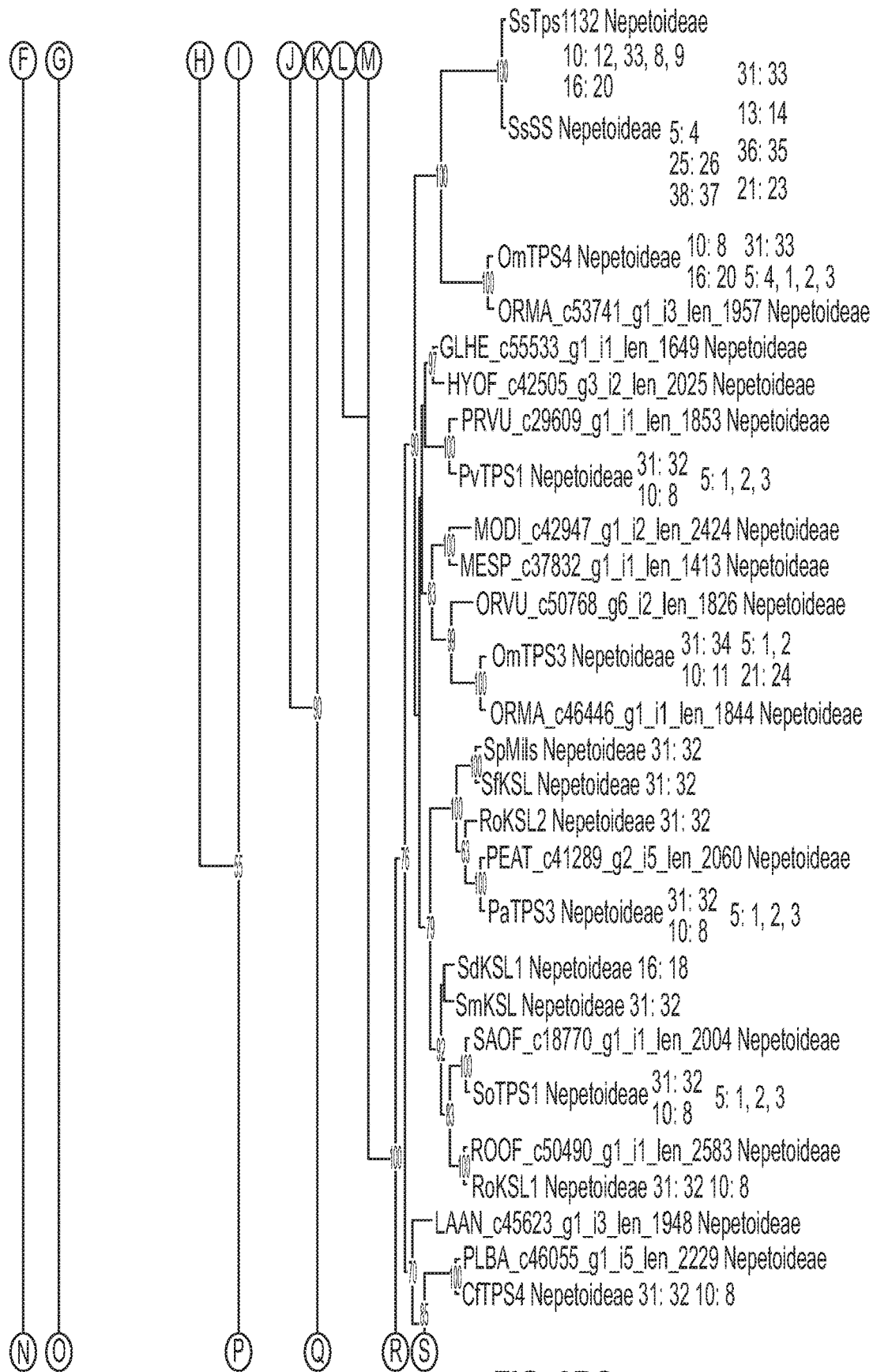
Figure 3B:
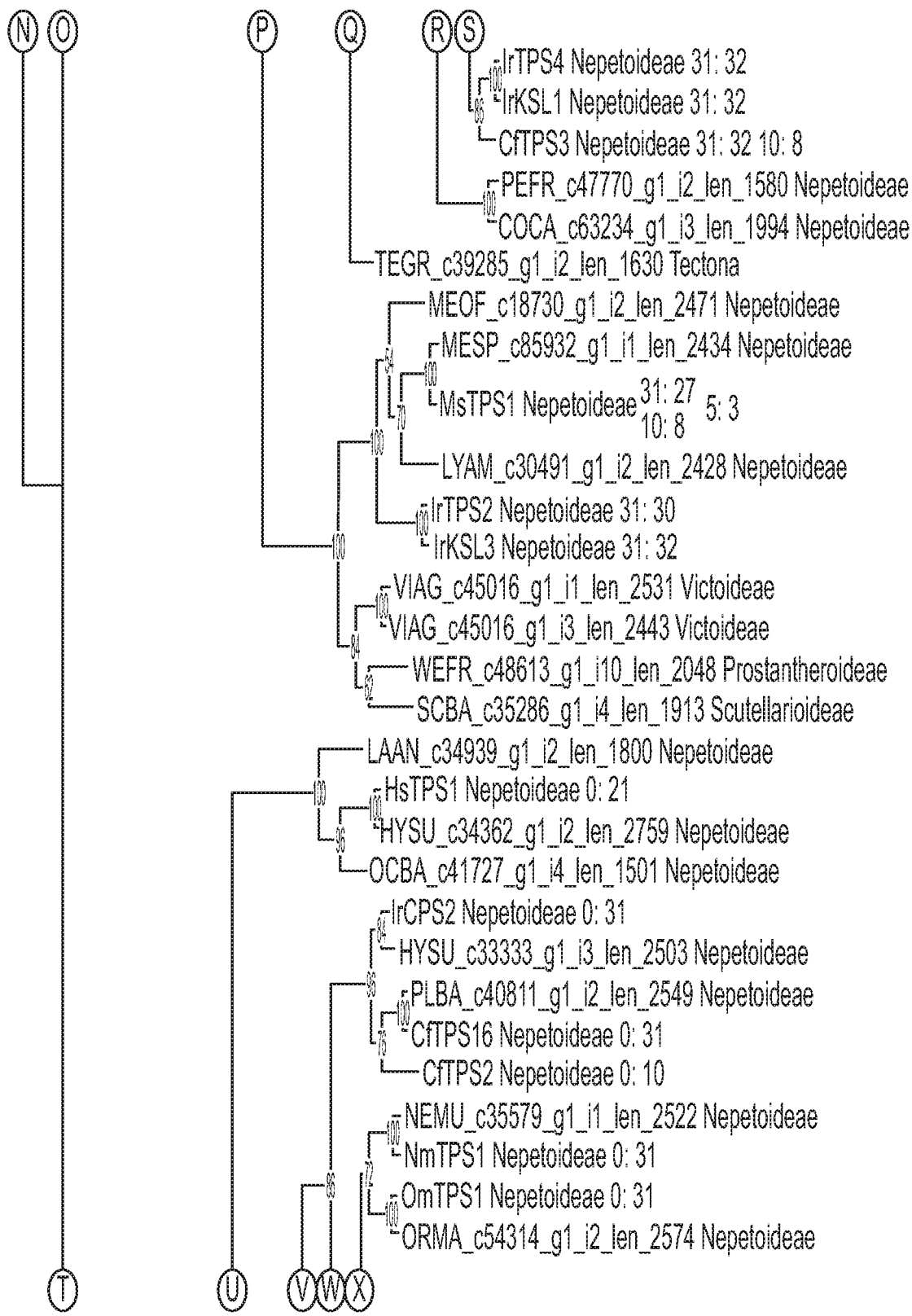
Figure 3B:
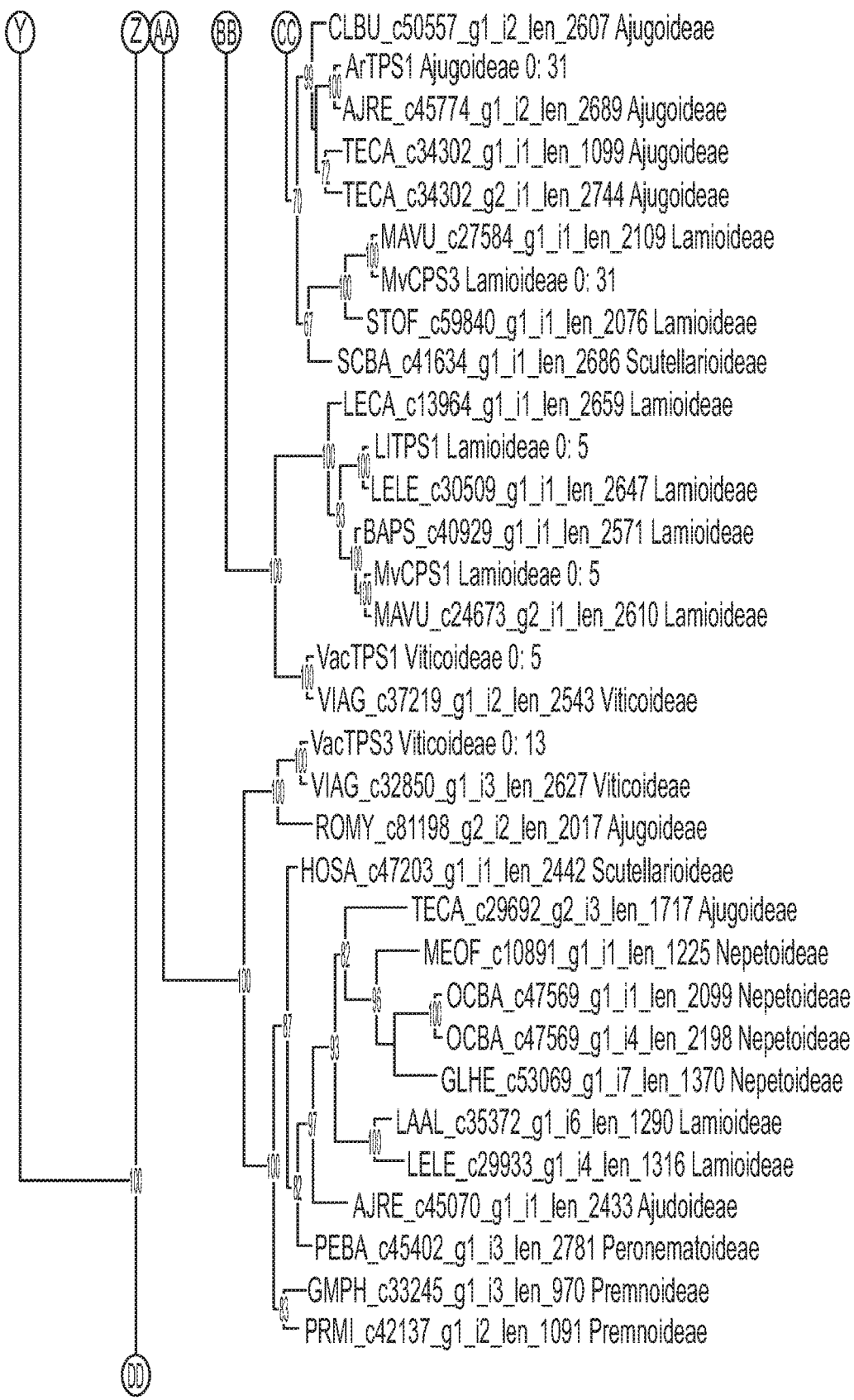
Figure 3B:
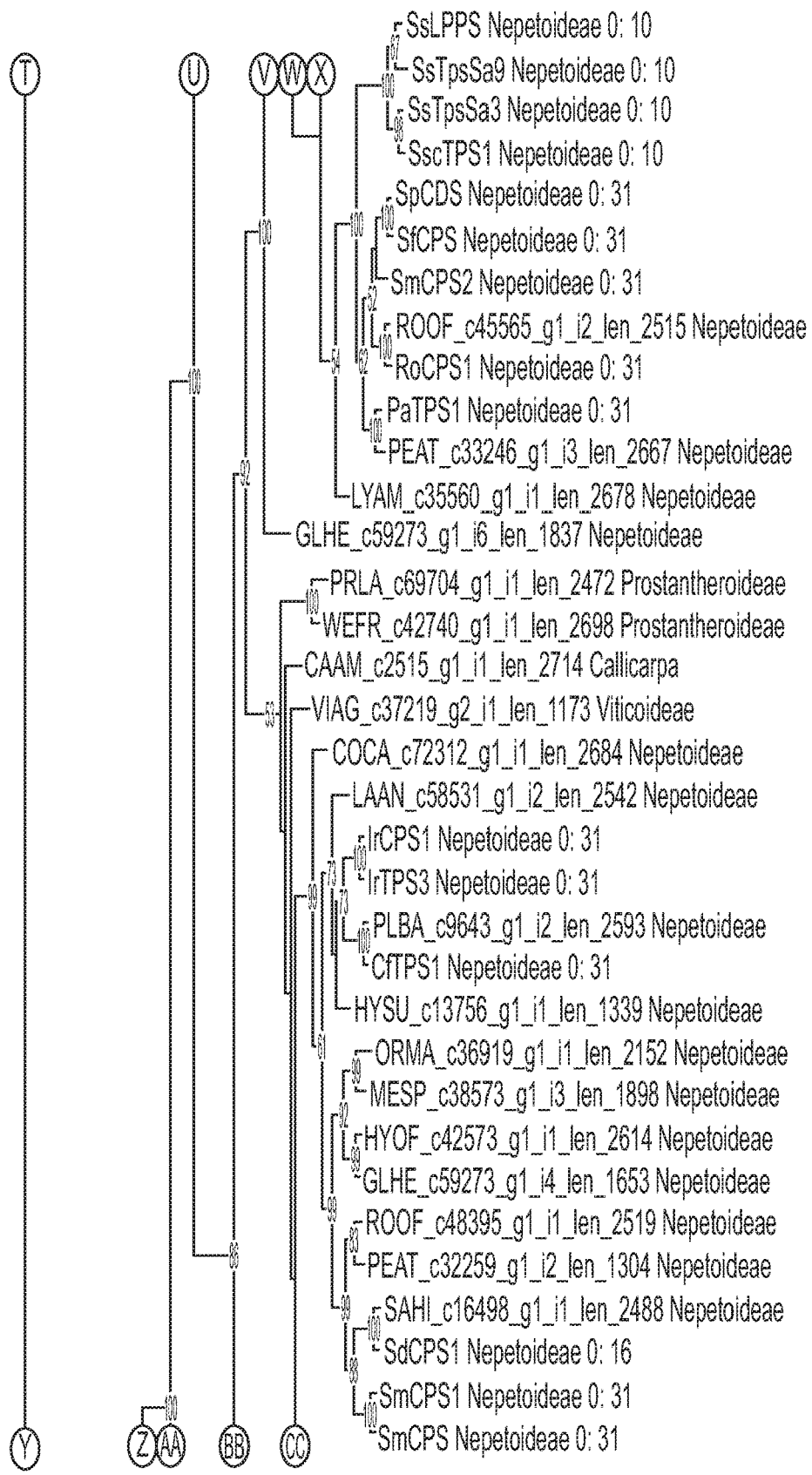
Figure 3B:
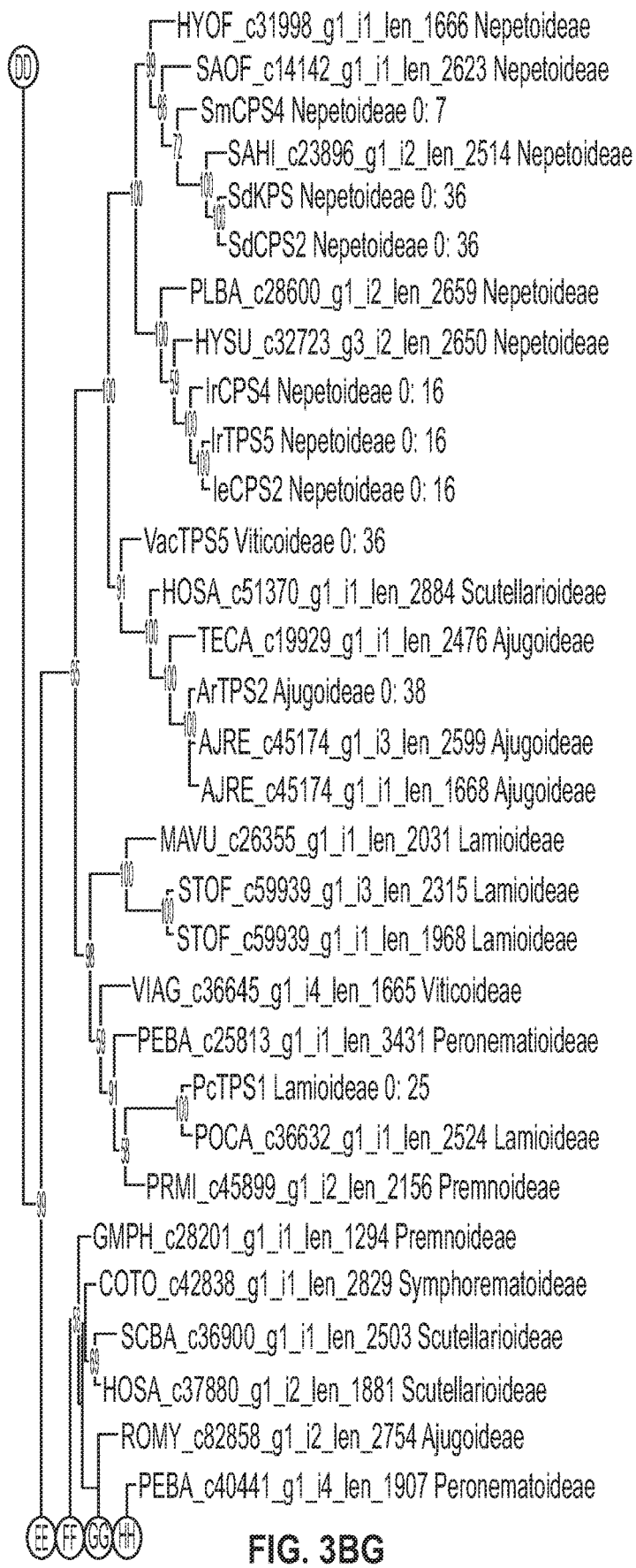
Figure 3B:
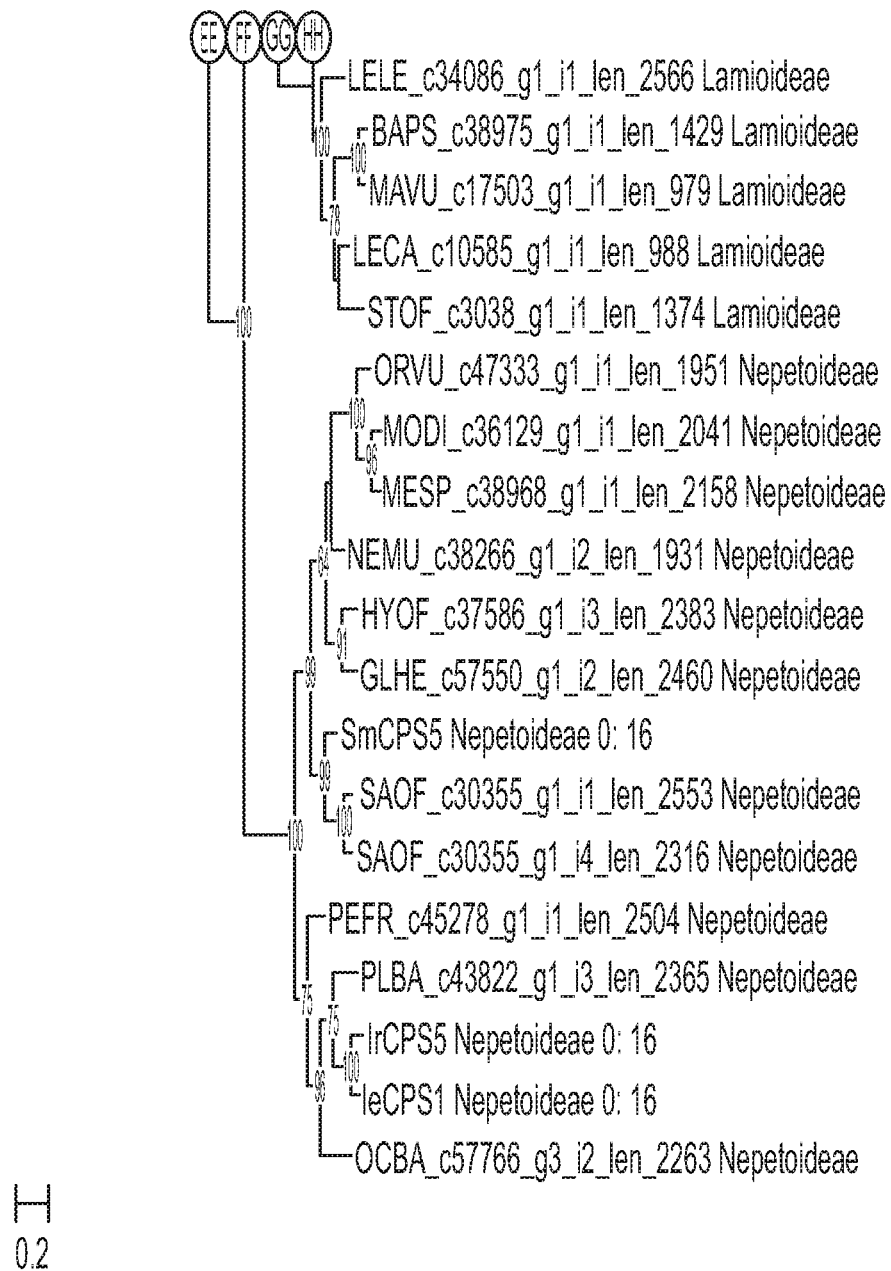

FIG. 3A presents a summary of Lamiaceae diTPS structures and activities reported from previous work, together with the newly characterized diTPS activities identified as described herein. Class II activities were established based on tire activities of extracts from *Nicotiana benthamiana* that transiently expressed the new genes, compared with the activities of known diTPS (or combinations) that were similarly expressed.

Class II diTPS products retained the diphosphate group from the GGPP substrate. When expressed in-vivo, whether in E. call or *N. benthamiana*, without a compatible class I diTPS, a diphosphate product degrades to the corresponding alcohol, presumably by the action of non-specific endogenous phosphatases. Due to difficulties in purifying and structurally characterizing diphosphate class II products it is customary in the field to instead characterize the alcohol derivatives (Heskes et al. Plant J 93(5):943-958 (2018); Pelot et al. Plant J 89(5):885-897 (2017)), which is the approach taken in this study. For clarity, the alcohol has been indicated by appending an "a" to the compound number, for example, 16a refers to ent-copalol.

ArTPS1, PaTPS1, NmTPS1, OmTPS1, and CfTPS1 were identified as (+)-copalyl diphosphate ((+)-CPP) [31] synthases by comparison to products of *Plectranthus barbatus* (synonym *Coleus forskohli*) CfTPS1, and the reference combination of CfTPS1 combined with CfTPS3, yielding miltiradiene (Pateraki et al. Plant Physiol 164(3):1222-1236 (2014)). LlTPS1 was identified as a peregrinol diphosphate (PgPP) [5] synthase based on a comparison of products with *Marrubium vulgare* MvCPS1 (Zerbe et al. Plant J 79(6): 914-927 (2014)), and MvCPS1 combined with *M. vulgare* 9,13-epoxylabdene synthase (MvELS), and *Salvia sclarea* sclareol synthase (SsSS) (Jia et al. Metabolic Engineering 37:24-34 (2016)).

Table 6 illustrates the distribution among selected Lamiaceae clades of diterpenes with various structural patterns. Blue enzyme names are placed according to the pattern they install and the clade of the species they were cloned from. A solid line indicates that only compounds with the bond-type shown at that position are counted. A dashed line indicates that all types of bonds and substituents are counted at that position. Based on data from the DNP.

TABLE 6:

Table 6A: Lamiaceae clades of diterpenes with various structural patterns.

Clerodane / Cleroda-4(18)-ene / 4(18)-epoxy-Clerodane

| | Clerodane | Cleroda-4(18)-ene | 4(18)-epoxy-Clerodane |
|---|---|---|---|
| Ajugoideae | 317 | (ArTPS2) 6 | 206 |
| Lamioideae | 32 | 3 | 1 |
| Nepetoideae | 132 | 1 | 1 |
| Scutellarioideae | 160 | 19 | 78 |
| Viticoideae | 1 | 0 | 0 |
| All clades | 668 | 31 | 289 |

Table 6B: Lamiaceae clades of diterpenes with various structural patterns.

| | Clerodane-3-ene | Labdane |
|---|---|---|
| Ajugoideae | 23 | 3 |
| Lamioideae | 25 | 201 |
| Nepetoideae | 84 | 60 |
| Seutellarioideae | 44 | 0 |
| Viticoideae | 0 | 37 |
| All clades | 189 | 300 |

Table 6C: Lamiaceae clades of diterpenes with various structural patterns.

| | Labda-8-ene | Labda-7-ene |
|---|---|---|
| Ajugoideae | 2 | 0 |
| Lamioideae | (PcTPS1)27 | 5 |
| Nepetoideae | 1 | (HsTPS1) 1 |
| Scutellarioideae | 0 | 0 |
| Viticoideae | 2 | 2 |
| AU clades | 33 | 9 |

HsTPS1 was identified as a (5S, 9S, 10S) labda-7,13E-dienyl diphosphate [21] synthase based on comparison to the product of an enzyme from *Grindelia robusta*, GrTPS2 (Zerbe et al. The Plant Journal 83(5):783-793 (2015)), and by NMR of the alcohol derivative [21a]. Normal absolute stereochemistry was assigned to the HsTPS1 product based on the optical rotation of 21a, $[\alpha]_D$+8.3° (c. 0.0007, CHCl$_3$) (c.f. lit. $[\alpha]_D$+5°, c. 1.0, CHCl$_3$ (Urones et al. Phytochemistry 35(3):713-719 (1994)); $[\alpha]_D^{25}$+12°, c. 0.69, CHCl$_3$ (Suzuki et al. Phytochemistry 22(5): 1294-1295 (1983)). When HsTPS1 was expressed in *N. benthamiana*, labda-7,13(16), 14-triene [22] was formed, which seemed to be enhanced by co-expression with CfTPS3. The combination of HsTPS1 with OmTPS3 produced labda-7,12E, 14-triene [24] (Roengsumran et al. Phytochemistry 50(3):449-453 (1999)), which has previously been accessible only by combinations of bacterial enzymes (Yamada et al. The Journal of Antibiotics 69(7):515-523 (2016)). Labdanes with a double bond at the 7-position have not been reported in *H. suaveolens*, and such labdanes do not seem to be common in Lamiaceae. Of nine compounds with the labdane skeleton and a double bond at position-7 (Table 6) only one was from the same clade as *H. suaveolens*. (13E)-ent-labda-7,13-dien-15-oic acid, from *Isodon scoparius* (Xiang et al. *Helvetica*

Chimica Acta 87(11):2860-2865 (2004)), has the opposite absolute stereochemistry to the HsTPS1 product, likely not deriving from a paralog of HsTPS1 because absolute stereochemistry of a skeleton is not known to change after the diTPS steps.

Figure 4A:
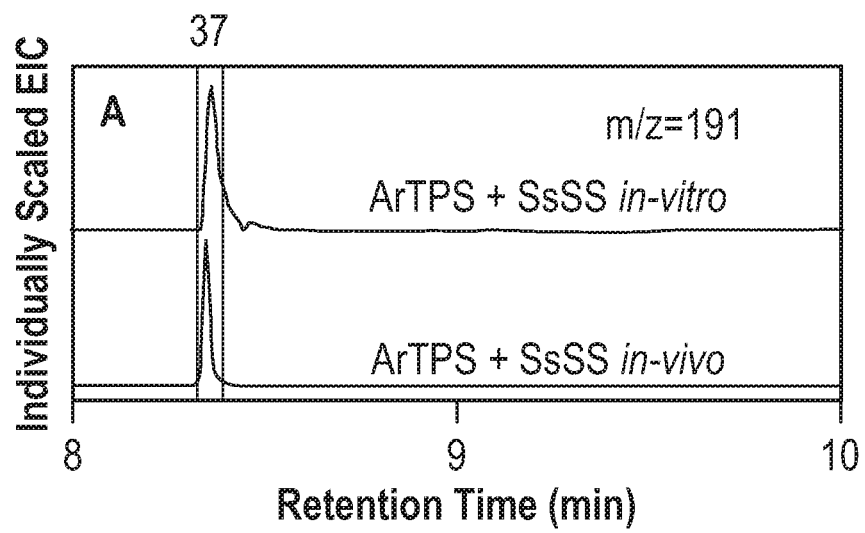
FIG. 4A-4C illustrate results of activity assays for several enzymes.
Figure 4B:
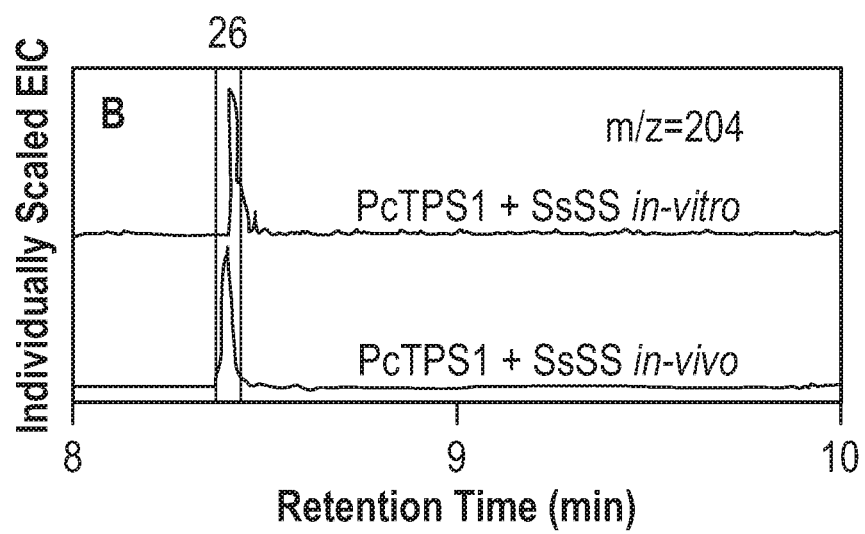
Figure 4C:
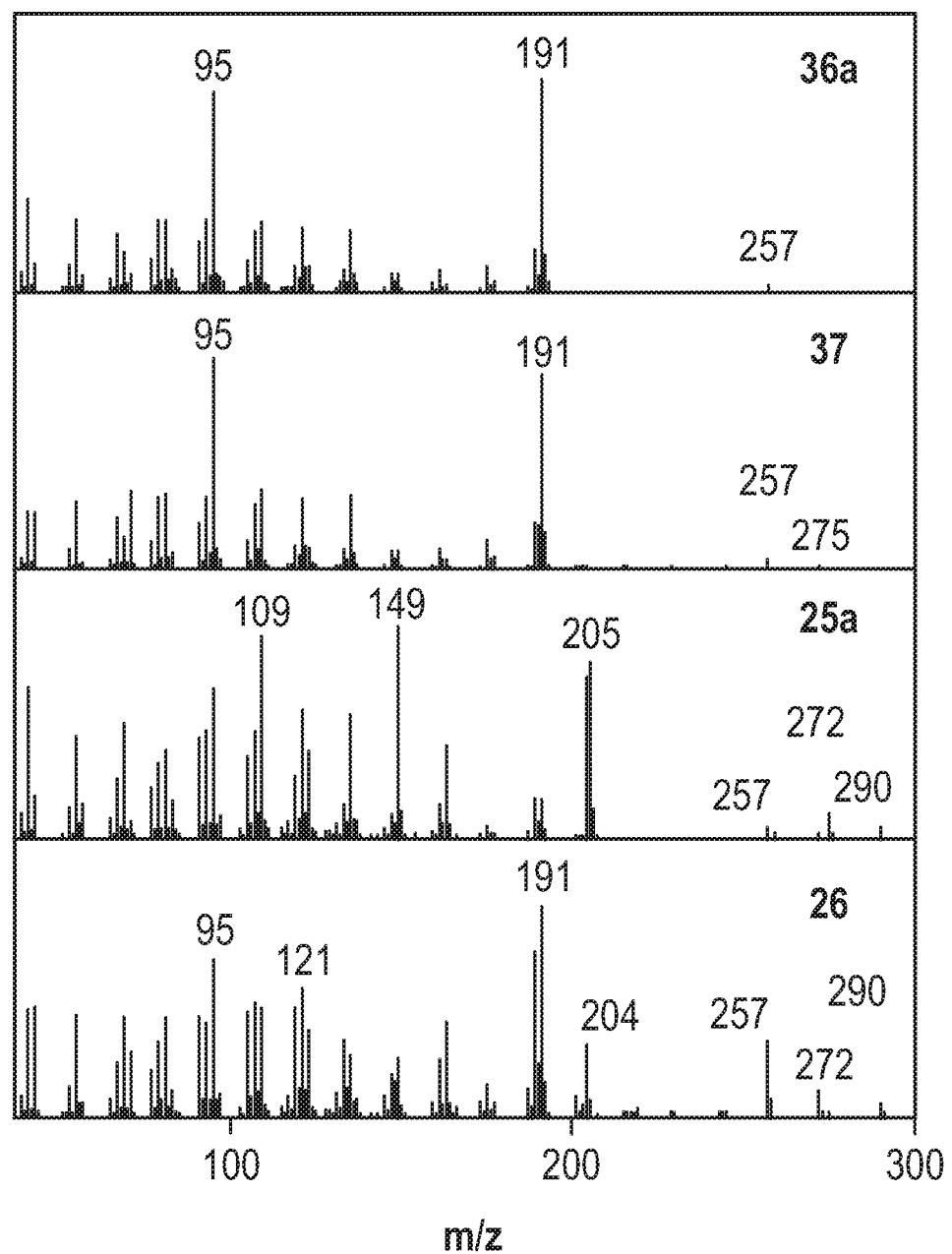

ArTPS2 was identified as a (5R,8R,9S,10R) neo-cleroda-4(18),13E-dienyl diphosphate [38] synthase. The combination of ArTPS2 and SsSS generated neo-cleroda-4(18),14-dien-13-ol [37] (FIG. 4A). The structures of compounds 37 and 38a were determined by NMR. The analysis included a comparison of compound 37 to chelodane (Rudi et al. J Nat Prod 55(10): 1408-1414 (1992)), which based on small differences in $^{13}C$ shifts, may be a stereoisomer of compound 37 at the 13 position, and a comparison of the NMR results for compound 38a with the NMR of its enantiomer (Ohaski et al. Bioorganic & Medicinal Chemistry Letters 4(24):2889-2892 (1994)). There were 20 to 19, and 20 to 17 NOE interactions in the NMR spectra of 37 and 38a, which closely resembled those reported for (−)-kolavelol [36a] (Pelot et al. Plant J 89(5):885-897 (2017)), indicating that the stereochemistry may be 5R,8R,9S,10R. The "neo" absolute configuration was established through optical rotation of 38a, $[\alpha]_D+30°$ (c. 0.0025, $CHCl_3$) (c.f. lit. $[\alpha]_D+20.9°$, c. 0.7, $CHCl_3$) (Monaco et al. Rendiconto della Academia delle scienze fisiche e matematiche 48:465-470 (1982)).

Previously reported clerodane diTPSs from Lamiaceae produce kolavenyl diphosphate [36] (Heskes et al. Plant J 93 (51:943-958 (2018); Chen et al. 1 Exp Bot 68(5):1109-1122 (2017); Pelot et al. Plant J 89(5):885-897 (2017)), and kolavenyl diphosphate [36] has a double bond at the 3-position. Clerodanes with desaturation at position-3 are spread throughout multiple clades but are most common in Nepetoideae (Table 6A-6C), which includes *Salvia divinorum*. Clerodanes with a double bond at the 4(18)-position are rare by comparison, but those with a 4(18)-epoxy moiety, make up nearly half of the clerodanes reported in Lamiaceae, including two-thirds of those reported from the Ajugoideae clade (Table 6A-6C), one of which is clerodin (Barton et al. *J Chem Soc:*5061-5073 (1961)) and from which the clerodane skeleton gets its name. Neo-cleroda-4(18),13E-dienyl diphosphate is a logical biosynthetic precursor for the 4(18)-epoxy clerodanes. It is unclear if any of the previously described diTPSs directly produce an epoxide moiety.

PcTPS1 was identified as a (10R)-labda-8,13E-dienyl diphosphate [25] synthase. The structure was established by comparison of $^{13}C$ NMR of compound 25a to previously reported spectra (Suzuki et al. Phytochemistry 22(5): 1294-1295 (1983)). The 10R (ent-) absolute stereochemistry was established by optical rotation of compound 25a $[\alpha]_D-64°$ (c. 0.0008, $CHCl_3$), (c.f. lit. $[\alpha]_D^{25}-71.2°$, c. 1.11, $CHCl_3$) (Arima et al. Tetrahedron: Asymmetry 18(14): 1701-1711 (2007)). The combination of PcTPS1 and SsSS, both in-vitro, and in *N. benthamiana* expression produced (10R)-labda-8,14-en-13-ol [26] (FIG. 4B), the structure of which was determined by comparison of $^{13}C$ NMR to a published spectrum (Wu & Lin Phytochemistry 44(1):101-105 (1997)). The double bond between positions 8 and 9 is present in 33 distinct compounds isolated from Lamiaceae (Table 6A-6C), most of which occur in the Lamioideae clade, which includes *Pogostemon cablin*, the source of PcTPS1. Absolute stereochemistries of the reported compounds are mixed, with some in the normal configuration (Boalino et al. J Nat Prod 67(4):714-717 (2004)), and others in the cut-configuration (Gray et al. Phytochemistry 63(4): 409-413 (2003)). As normal configuration 9-hydroxy labdanes tire also abundant in Lamioideae, it is possible that the normal configuration 8(9) desaturated labdanes arise from dehydratase activities downstream of a PgPP synthase (MvCPS1 and its paralogs), while those in the cur-configuration arise from paralogs of PcTPS1. Another possibility is that some of the 8(9) desaturated labdanes reported as having normal absolute stereochemistry are actually ent-labdanes that were mis-assigned, as has occurred in at least one documented case (Gray et al. Phytochemistry 63(4): 409-413 (2003)).

Example 5: Characterization of Class I diTPSs

Class I diTPS candidates were characterized by transient expression in *N. benthamiana* in combination with four class II enzymes:
  CfTPS1, a (+)-CPP [31] synthase;
  CfTPS2, a labda-13-en-8-ol diphosphate ((+)-8-LPP) [10] synthase (Paterakit et al. Plant Physiol 164(3): 1222-1236 (2014);
  LITPS1, a PgPP [5] synthase; or
  *Zea mays* ZmAN2, an ent-copalyl diphosphate (ent-CPP) [16] synthase (Harris et al. Plant Mol Biol 59(6):881-894 (2005)).

Figure 2B:
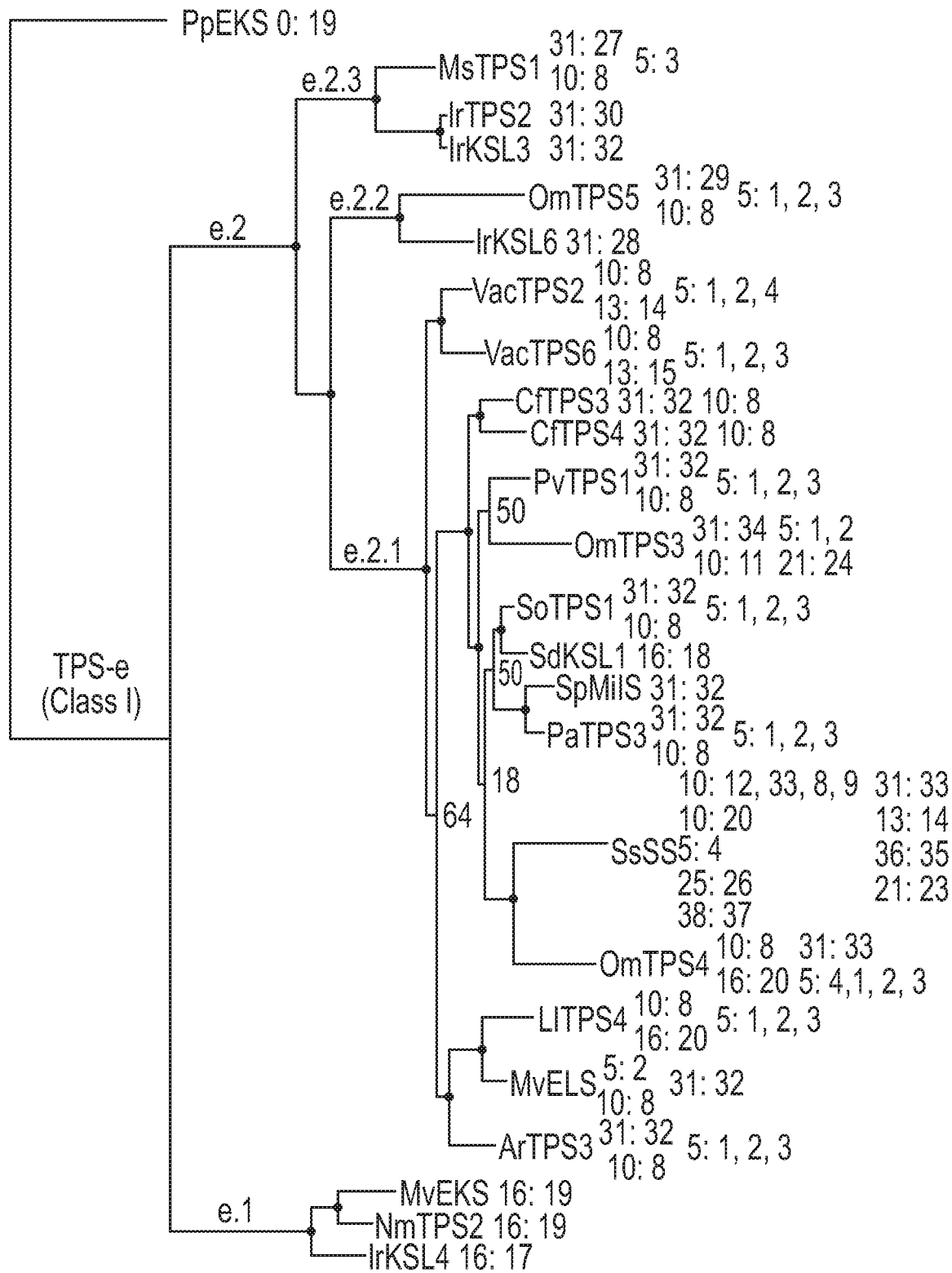
Figure 5A:
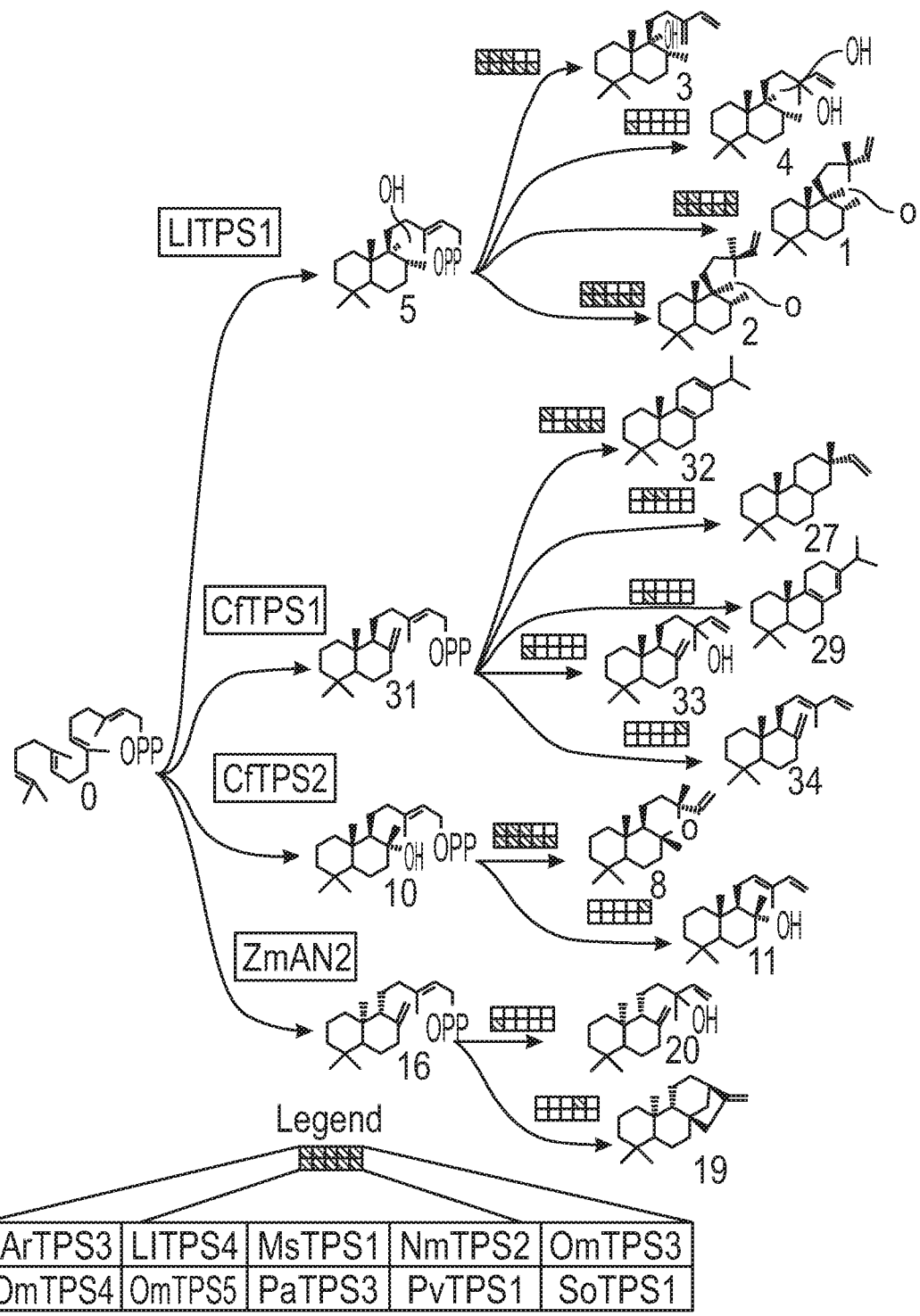
FIG. 5A-5B illustrates the structures that can be produced by the activities of new class I diTPSs.
Figure 5B:
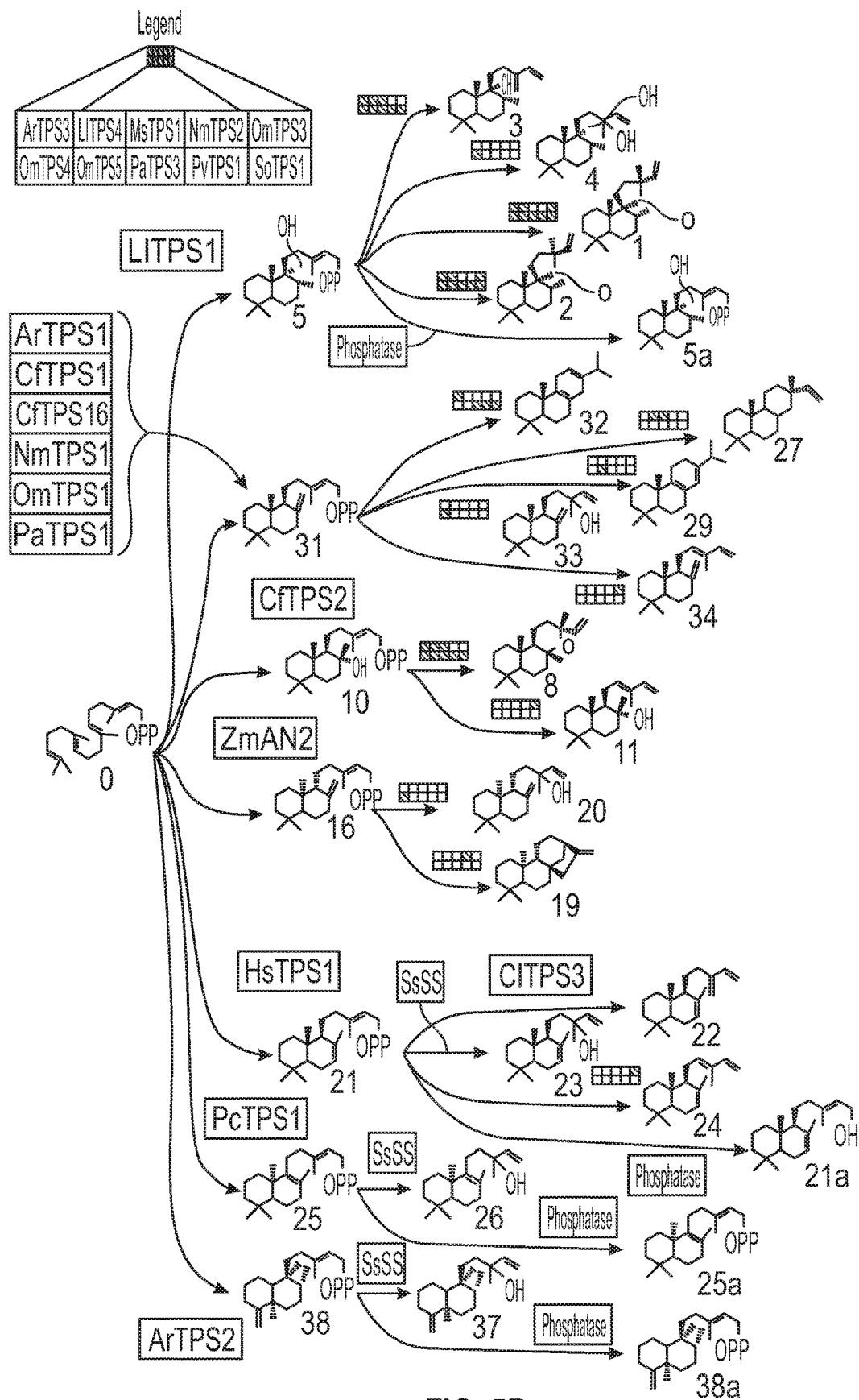

Substrates accepted by each enzyme and the products are indicated in FIG. 2B and FIG. 5. NmTPS2 was identified as an ent-kaurene [19] synthase, converting ent-CPP into ent-kaurene (identified using *Physcomitrella patens* extract as a standard (Zhan et al. Plant Physiology and Biochemistry 96:110-114 (2015))), but not showing activity with any other substrate. The only other enzyme to show activity with ent-CPP was OmTPS4, which produced ent-manool [20], just as SsSS produces from ent-CPP.

PaTPS3, PvTPS1, SoTPS1, ArTPS3, OmTPS4, LITPS4, OmTPS5, and MsTPS1 converted (+)-8-LPP to 13R-(+)-manoyl oxide [8], verified by comparison to the product of CfTPS2 and CfTPS3 (Paterakit et al. Plant Physiol 164(3): 1222-1236 (2014)). OmTPS3 produced trans-abienol [11]. The trans-abienol structure was determined by NMR, with the stereochemistry of the 12(13)-double bond supported by comparison of the NOESY spectrum to that of a commercial standard for cis-abienol (Toronto Research Chemicals, Toronto Canada). The trans-abienol showed clear NOE correlation between positions 16 and 11, while the cis-abienol standard showed correlations between 14 and 11.

PaTPS3, PvTPS1, SoTPS1, and ArTPS3, LITPS4, and OmTPS5 converted PgPP to a combination of 1, 2, and 3, with some variation in the ratios between the products. Because perigrinol [5a] spontaneously degrades into 1, 2, and 3 under GC conditions (Zerbe et al. Plant J 79(6):914-927 (2014)), it was difficult to distinguish whether these enzymes have low activity, but specific products, or moderate activity with a mix of products. Nevertheless, differences in relative amounts of the products observed between LITPS1 alone and in combination with these class 1 enzymes suggest that they do have some activity on PgPP. OmTPS4 produced 1, 2, 3, and 4. MsTPS1 produced only 3, and OmTPS3 produced only 1, and 2. PgPP products were established by comparison to MvCPS1, MvCPS1 with MvELS (Zerbe et al. Plant J 79(6):914-927 (2014)), and MvCPS1 with SsSS (Jia et al. Metabolic Engineering 37:24-34 (2016)).

PaTPS3, PvTPS1, SoTPS1, and ArTPS3 converted (+)-CPP to miltiradiene [32], similarly to CfTPS3. OmTPS4 produced manool [33], as compared to SsSS. LITPS4 and MsTPS1 produced sadaracopimaradiene [27], by comparison to a product from *Euphorbia peplus* EpTPS8 (Andersen-Ranberg et al. Angew Chem Int Ed 55(6):2142-2146 (2016)). OmTPS5 produced palustradiene [29], as compared to a minor product from *Abies grandis* abietadiene synthase (Vogel et al. J Biol Chem 271(38):23262-23268 (1996)). OmTPS3 produced trans-biformene [34], as established by comparison of $^{13}$C-NMR of compounds described by Bohlmann & Czerson, Phytochemistry 18(1): 115-118 (1979)), with a trans configuration further supported by clear NOE correlations between 16 and 11, and the absence of NOE correlations between 14 and 11.

Example 6: *Origanum majorana* Enzymes can Make Palustradiene and Other Diterpenoids The class I enzymes from *Origanum majorana*, OmTPS3, OmTPS4, and OmTPS5 all produced different products from (+)-CPP, which itself is the product of OmTPS1 from the same species. Despite the apparent richness of activities of enzymes from *O. majorana*, no reports of diterpenes were located from that species either in database searches, or in a subsequent literature search.

Figure 6A:
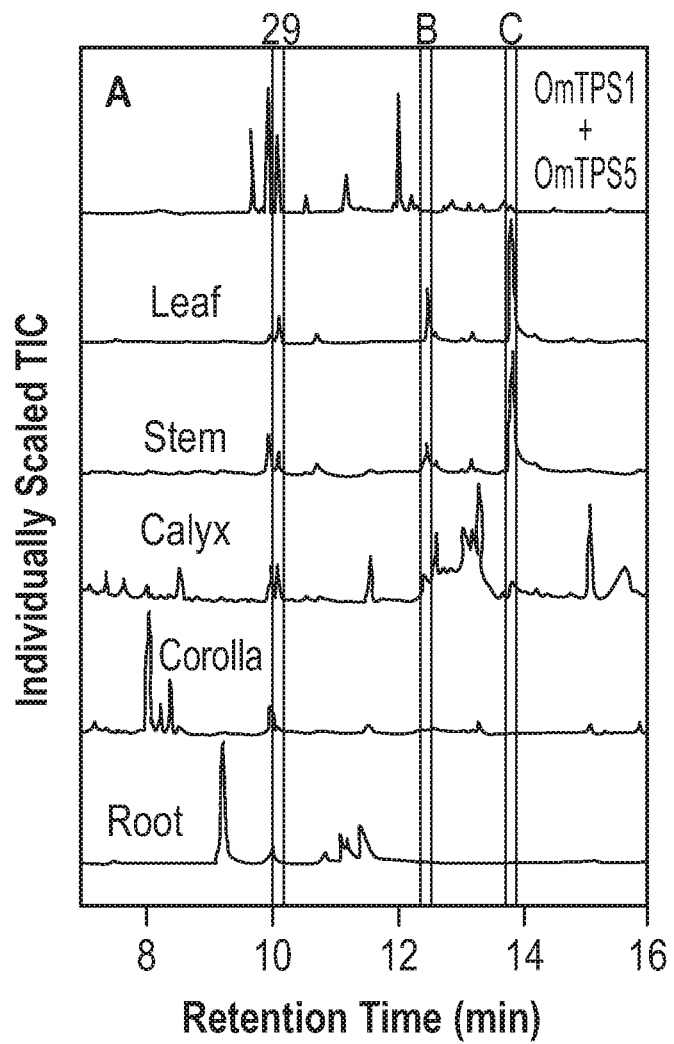
FIG. 6A-6C illustrate analysis of compounds from *O. majorana*.
Figure 6B:
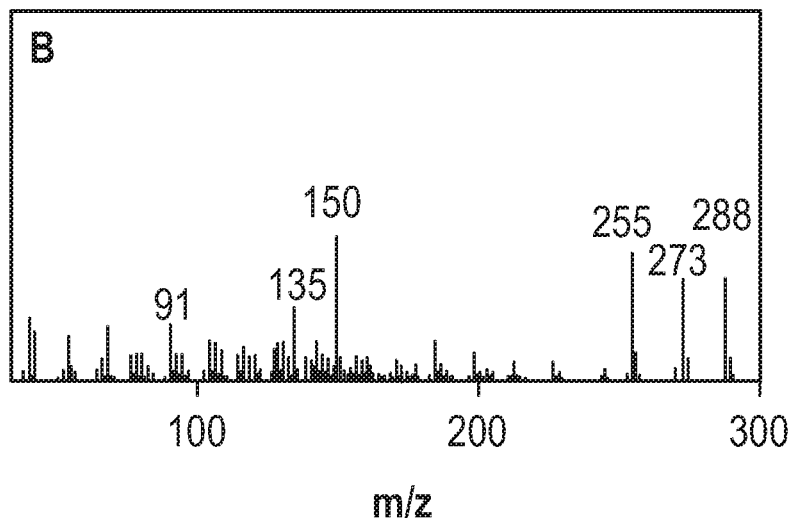
Figure 6C:
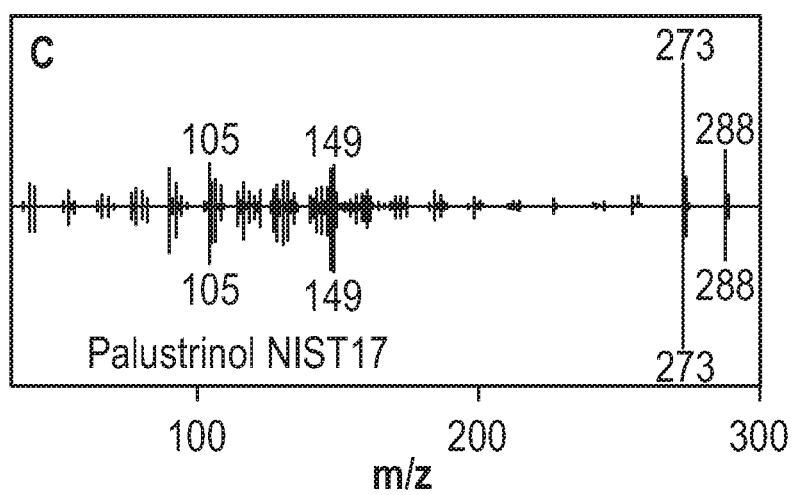
Figure 7A:
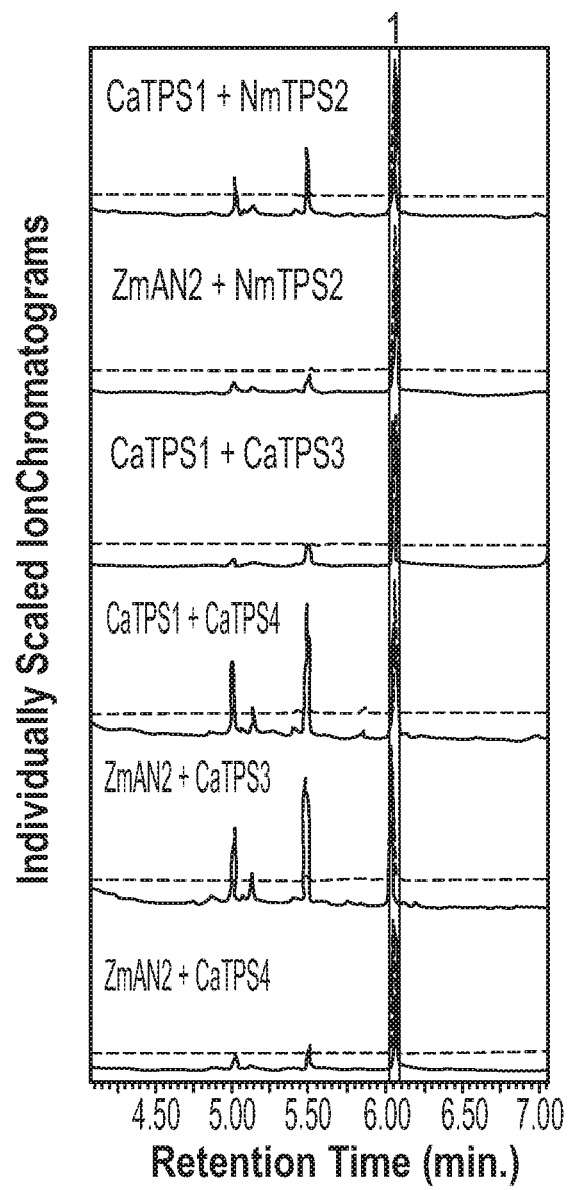
FIG. 7A-7C illustrate the activities of novel *Chiococca alba* terpene synthases CaTPS1-5.
Figure 7A:
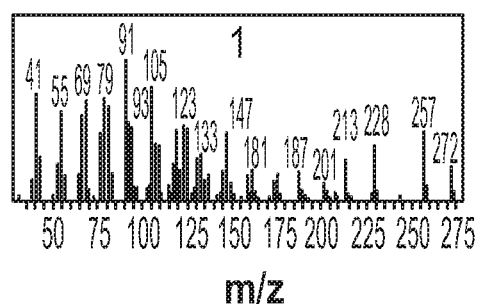
Figure 7B:
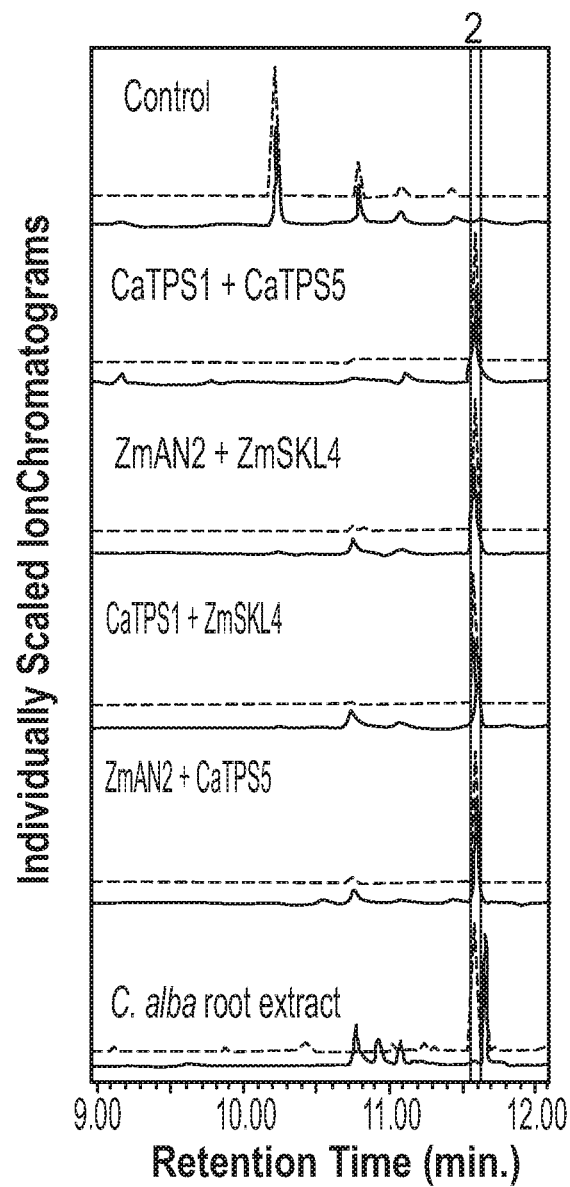
Figure 7B:
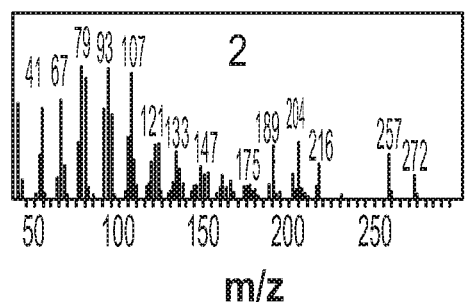
Figure 7C:
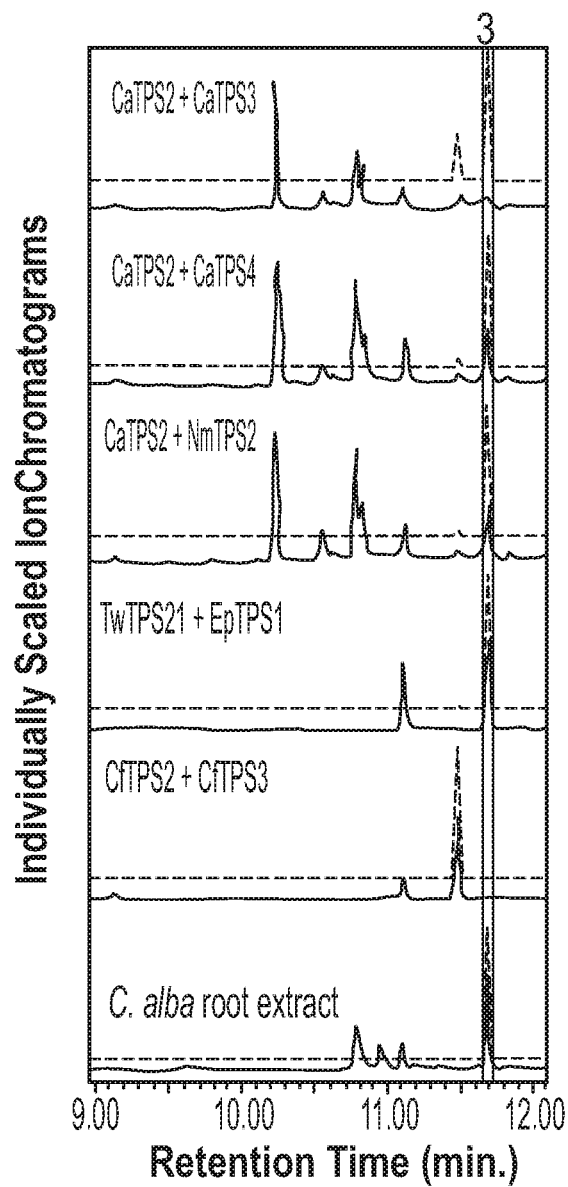
Figure 7C:
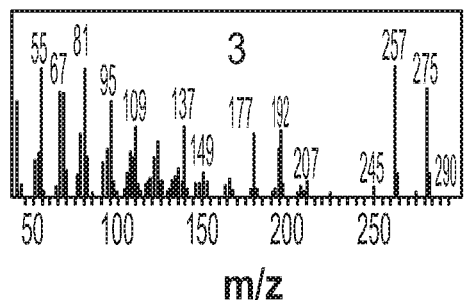

To determine whether diterpene synthases are active in *O. majorana*, the products of enzyme combinations with extracts from *O. majorana* leaf, stem, calyx, corolla, and root were evaluated. Palustradiene [29], the product of OmTPS1 and OmTPS5, was detected in all tissues except roots (FIG. 6). In addition, two diterpene alcohols were detected in the stem, leaf, and calyx. One diterpene alcohol, could not be identified, but the other was a close match to palustrinol, the 19-hydroxy derivative of palustradiene, in the NTST17 spectral library. The structures of the palustrinol, and the 19-hydroxy derivative of palustradiene are shown below.

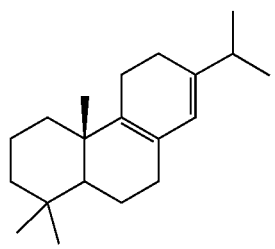

Palustradiene (29)

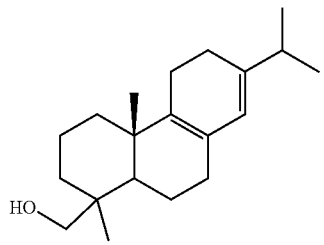

Palustrinol

Example 7: *Chiococca alba* Enzymes can Make 13(R)-Epi-Dolabradiene and Other Compounds This Example illustrates that enzymes from *Chiococca alba* can produce products such as ent-kaurene, ent-dolabradiene (13-epi-dolabradiene), and (13R)-ent-manoyl oxide.

Enzyme assays were prepared as described herein that separately or in combination contained the following enzymes and substrates:

class I terpene synthase enzyme from *Chiococca alba* (CaTPS1) with SoTPS2, SbTPS1, and SbTPS2 and the substrate ent-copalyl diphosphate.

class II terpene synthase enzyme from *Chiococca alba* (CaTPS2) with substrate ent-labda-13-en-8-ol diphosphate class III and class IV terpene synthase enzymes from *Chiococca alba* (CaTPS3 and CaTPS4) with substrate ent-kaurene class V terpene synthase enzyme from *Chiococca alba* (CaTPS5) with substrate ent-dolabradiene class I (−)-kolavenyl diphosphate synthase enzyme from *Salvia hispanica* (ShTPS1) with substrate (−)-kolavenyl diphosphate class I cleroda-4(18),13E-dienyl diphosphate synthase enzyme from *Teucrium canadense* (TcTPS1) with substrate clerodadienyl diphosphate class I sclareol synthase enzyme from *Salvia sclarea* (SsSCS) with substrate neo-clerodadienol.

FIG. 7 illustrates the activities of the newly obtained *Chiococca alba* terpene synthases CaTPS1-5. FIGS. 7A-7C show GC-MS-total ion and extracted ion chromatograms from in vivo assays within *N. benthamiana* that transiently expressed various combinations of enzymes. Mass spectra are shown below the chromatograms of FIG. 7A-7C for peaks (1) to (3) containing the following products of the enzymatic conversion: (1) ent-kaurene; (2) ent-dolabradiene (13-epi-dolabradiene); (3) (13R)-ent-manoyl oxide. The ent-dolabradiene was identified through extensive structural studies with NMR and the stereochemistry at C-13 was unequivocally corroborated by optical rotation. The ent-kaurene and (13R)-ent-manoyl oxide were identified through direct comparison with biosynthesized authentic standards with reference enzymes.

Compounds ent-dolabradiene (13-epi-dolabradiene) and (13R)-ent-manoyl oxide are plausible intermediates in the biosynthetic routes to the structurally unusual merilactone and ribenone, that have demonstrated activity against Leishmanina and potential anti-cancer activity (Piozzi, F., Bruno, M. Diterpenoids from Roots and Aerial Parts of the Genus Stachys Rec. Nat. Prod. 5, 1-11, (2011)).

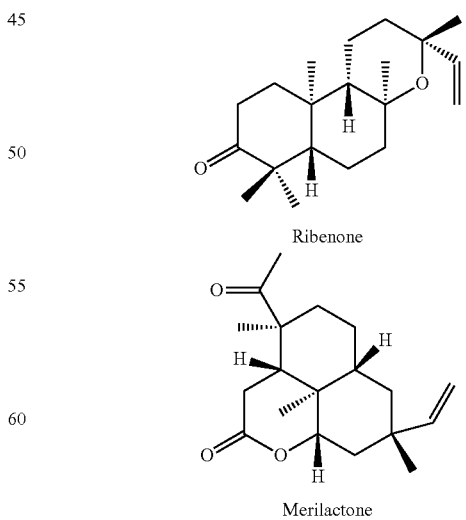

Ribenone

Merilactone

Both merilactone and ribenone are detected in the root extract of *C. alba*.

REFERENCES

1. Dictionary of Natural Products 26.2 Available at: http://dnp.cheninetbase.com [Accessed Jan. 11, 2018].
2. Peters R. T (2010) Two rings in them all: The labdane-related diterpenoids. *Natural product reports* 27(11):1521.
3. Chen F, Tholl D, Bohlmann J, Pichersky E (2011) The family of terpene synthases in plants: a mid-size family of genes for specialized metabolism that is highly diversified throughout the kingdom. *The Plant Journal* 66(1):212-229.
4. Zerbe P, Bohlmann J (2015) Plant diterpene synthases: exploring modularity and metabolic diversity for bioengineering. *Trends in Biotechnology* 33(7); 419-428.
5. Hamberger B, Bak S (2013) Plant P450s as versatile drivers for evolution of species-specific chemical diversity. *Philosophical Transactions of the Royal Society of London B: Biological Sciences* 368(1612):20120426.
6. Banerjee A, Hamberger B (2018) P450s controlling metabolic bifurcations in plant terpene specialized metabolism. *Phytochem Rev* 17(1): 81-111.
7. Pateraki I, et al. (2017) Total biosynthesis of the cyclic AMP booster forskolin from *Coleus forskohiii*. *eLife* 6:e23001.
8. Ondari M E, Walker K D (2008) The Taxol Pathway 10-O-Acetyltransferase Shows Regioselective Promiscuity with the Oxetane Hydroxyl of 4-Deacetyltaxanes. *J Am Chem Soc* 130(50):17187-17194.
9. Chau M, Walker K, Long R, Croteau R (2004) Regioselectivity of taxoid-O-acetyitransferases: heterologous expression and characterization of a new taxadien-5α-ol-O-acetyltransferase. *Archives of Biochemistry and Biophysics* 430(2):237-246.
10. Cui G, et al. (2015) Functional divergence of diterpene syntheses in the medicinal plant *Salvia miltiorrhiza* Bunge. *Plant Physiol* 169(3): 1607-1618.
11. Gao W, et al. (2009) A Functional Genomics Approach to Tanshinone Biosynthesis Provides Stereochemical Insights. *Org Lett* 11 (22):5170-5173.
12. Guo J, et al. (2013) CYP76AH1 catalyzes turnover of miltiradiene in tanshinones biosynthesis and enables heterologous production of ferruginol in yeasts. *PNAS* 110 (29):12108-12113.
13. Heskes A M, et al. (2018) Biosynthesis of bioactive diterpenoids in the medicinal plant Vitex agnus-castus. *Plant J* 93(5):943-958.
14. Zerbe P, et al. (2014) Diterpene synthases of the biosynthetic system of medicinally active diterpenoids in *Marrubium vulgare*. *Plant J* 79(6):914-927.
15. Chen X, Berim A, Dayan F E, Gang D R (2017) A (−)-kolavenyl diphosphate synthase catalyzes the first step of salvinorin A biosynthesis in *Salvia divinorum*. *J Exp Bot* 68(5):1109-1122.
16. Pelot K A, et al. (2017) Biosynthesis of the psychotropic plant diterpene salvinorin A: Discovery and characterization of the *Salvia divinorum* clerodienyl diphosphate synthase. *Plant J* 89(5):885-897.
17. Caniard A, et al. (2012) Discovery and functional characterization of two diterpene synthases for sciareol biosynthesis in *Salvia sclarea* (L.) and their relevance for perfume manufacture. *BMC Plant Biology* 12:119.
18. Günnewich N, et al. (2013) A diterpene synthase from the clary sage *Salvia sclarea* catalyzes the cyclization of geranylgeranyl diphosphate to (8R)-hydroxy-copalyl diphosphate. *Phytochemistry* 91:93-99.
19. Boachon B, et al. (2018) Phylogenomic Mining of the Mints Reveals Multiple Mechanisms Contributing to the Evolution of Chemical Diversity in Lamiaceae. *Molecular Plant*. doi:10.1016/j.molp.2018.06.002.
20. Coll J, Tandrón YA (2008) neo-Clerodane diterpenoids from *Ajuga*: structural elucidation and biological activity. *Phytochem Rev* 7(1):25.
21. Klein Gebbinck E A, Jansen B J M, de Groot A (2002) insect antifeedant activity of clerodane diterpenes and related model compounds. *Phytochemistry* 61(7):737-770.
22. Li R, Morris-Natschke S L, Lee K-H (2016) Clerodane diterpenes: sources, structures, and biological activities, *Nat Prod Rep* 33(10): 1166-1226.
23. Vestri Alvarenga S A, Pierre Gastmans J, do Vale Rodrigues G, Roberto H. Moreno P, de Paulo Emerenciano V (2001) A computer-assisted approach for chemotaxonomic studies—diterpenes in Lamiaceae. *Phytochemistry* 56(6):583-595.
24. Loub W D, Farnsworth N R, Soejarto D D, Quinn M L (1985) NAPRALERT: computer handling of natural product research data. *J Chem Inf Comput Sci* 25(2):99-103.
25. Federhen S (2012) The NCBI Taxonomy database. *Nucleic Acids Res* 40(D1):D136-D143.
26. Li B, et al. (2016) A large-scale chloroplast phylogeny of the Lamiaceae sheds new light on its subfamilial classification. *Scientific Reports* 6:34343.
27. Camacho C, et al. (2009) BLAST+: architecture and applications. *BMC Bioinformatics* 10:421.
28. Pateraki I, et al. (2014) Manoyl Oxide (13R), the Biosynthetic Precursor of Forskolin, Is Synthesized in Specialized Root Cork Cells in *Coleus forskohlii*. *Plant Physiol* 164(3):1222-1236.
29. Jia M, Potter K C, Peters R J (2016) Extreme promiscuity of a bacterial and a plant diterpene synthase enables combinatorial biosynthesis. *Metabolic Engineering* 37:24-34.
30. Zerbe P, et al. (2015) Exploring diterpene metabolism in non-model species: transcriptome-enabled discovery and functional characterization of labda-7,13 E-dienyl diphosphate synthase from *Grindelia rohusta*. *The Plant Journal* 83(5):783-793.
31. Urones J G, et al. (1994) Compounds with the labdane skeleton from *Halimium viscosum*. *Phytochemistry* 35 (31:713-719.
32. Suzuki H, Noma M, Kawashima N (1983) Two labdane diterpenoids from *Nicotiana setchellii*. *Phytochemistry* 2.2(5): 1294-1295.
33. Roengsumran S, Petsom A, Sommit D, Vilaivan T (1999) Labdane diterpenoids from Croton oblongifolius. *Phytochemistry* 50(3):449-453.
34. Yamada Y, Komatsu M, Ikeda H (2016) Chemical diversity of labdane-type bicyclic diterpene biosynthesis in Actinomycetales microorganisms. *The Journal of Antibiotics* 69(7):515-523.
35. Xiang W, Li R-T, Song Q-S, Na Z, Sun H-D ent-Clerodanoids from *Isodon scoparius*. *Helvetica Chimica Acta* 87(11):2860-2865.
36. Rudi A, Kashman Y (1992) Chelodane, Barekoxide, and Zaatirin—Three New Diterpenoids from the Marine Sponge Cbelonapiysilla erecta. *J Nat Prod* 55(10):1408-1414.
37. Ohsaki A, et al. (1994) The isolation and in vivo Potent Antitumor activity of clerodane diterpenoid from the oleoresin of the brazilian medicinal plant, copaifera langsdorfi desfon. *Bioorganic & Medicinal Chemistry Letters* 4(24):2889-2892.

38. Monaco P, Previtera L, Mangoni L (1982) Terpenes from the bled resin of Araucaria hunsteinii. *Rendiconto della Academia delle scienze fisiche e matematiche* 48:465-470.
39. Barton D H R, Cheung H T, Cross A D, Jackman L M, Martin-Smith M (1961) 1003. Diterpenoid bitter principles. Part III. The constitution of clerodin. *J Chem Soc:* 5061-5073.
40. Arima Y, Kinoshita M, Akita. H (2007) Natural product synthesis from (8aR)- and (8aS)-bicyclofamesols: synthesis of (+)-wiedendiol A, (+)-norsesterterpene diene ester and (−)-subersic acid. *Tetrahedron: Asymmetry* 18(14): 1701-1711.
41. Wu C-L, Hsiang-Ru Lin (1997) Labdanoids and bis (bibenzyls) from Jungermannia species. *Phytochemistry* 44(1): 101-105.
42. Boalino D M, McLean S, Reynolds W F, Tinto W F (2004) Labdane Diterpenes of Leonurus sibiricus. *J Nat Prod* 67(4):714-717.
43. Gray C A, Rivett D E A, Davies-Coleman M T (2003) The absolute stereochemistry of a diterpene from Ballota aucheri. *Phytochemistry* 63(4):409-413.
44. Harris L J, et al. (2005) The Maize An2 Gene is Induced by Fusarium Attack and Encodes an ent-Copalyl Diphosphate Synthase. *Plant Mol Biol* 59(6):881-894.
45. Zhan X, Bach S S, Hansen N L, Lunde C, Simonson H T (2015) Additional diterpenes from *Physcomitrella patens* synthesized by copalyl diphosphate/kaurene synthase (PpCPS/KS). *Plant Physiology and Biochemistry* 96:110-114.
46. Andersen-Ranberg J, et al. (2016) Expanding the Landscape of Diterpene Structural Diversity through Stereochemically Controlled Combinatorial Biosynthesis. *Angew Chem Int Ed* 55(6):2142-2146.
47. Vogel B S, Wildung M R, Vogel G, Croteau R (1996) Abietadiene synthase from grand fir (*Abies grandis*) cDNA isolation, characterization, and bacterial expression of a bifunctional diterpene cyclase involved in resin acid biosynthesis. *J Biol Chem* 271(38):23262-23268.
48. Bohlmann F, Czerson H (1979) Neue labdan-und pimaren-derivate aus *Palafoxia rosea*. *Phytochemistry* 18(1):115-118.
49. Li J-L, et al. (2012) IeCPS2 is potentially involved in the biosynthesis of pharmacologically active *Isodon diterpenoids* rather than gibberellin. *Phytochemistry* 76:32-39.
50. Jin B, et al. (2017) Functional diversification of kaurene synthase-like genes. *Plant Physiol* 174:973-955.
51. Hillwig M L, et al. (2011) Domain loss has independently occurred multiple times in plant terpene synthase evolution. *The Plant Journal* 68(6):1051-1060.
52. Pelot K A, Hagelthorn D M, Addison J B, Zerbe P (2017) Biosynthesis of the oxygenated diterpene nezukol in the medicinal plant *Isodon rubescens* is catalyzed by a pair of diterpene synthases. *PLOS ONE* 12(4):e0176507.
53. Helliwell C A, Chandler P M, Poole A, Dennis E S, Peacock W J (2001) The CYP88A cytochrome P450, ent-kaurenoic acid oxidase, catalyzes three steps of fee gibberellin biosynthesis pathway. *PNAS* 98(4):2065-2070.
54. Han Q-B, et al. (2006) Maoecrystal Z, a Cytotoxic Diterpene from *Isodon eriocalyx* with a Unique Skeleton. *Org Lett* 8(21):4727-4730.
55. Li X-N, et al. (2010) Structure and Cytotoxicity of Diterpenoids from *Isodon eriocalyx*. *J Nat Prod* 73(11): 1803-1809.
56. González A G, Andres L S, Luis J G, Brito I, Rodríguez M L (1991) Diterpenes from *Salvia mellifera*. *Phytochemistry* 30(12):4067-4070.
57. Chen Y-L, et al. (2008) Bioactive Cembrane Diterpenoids of Anisomeles indica. *J Nat Prod* 71 (7): 1207-1212.
58. Li L-M, et al. (2009) ent-Kaurane and Cembrane Diterpenoids from *Isodon sculponeatus* and Their Cytotoxicity. *J Nat Prod* 72(10):1851-1856.
59. Kirby J, et al. (2010) Cloning of casbene and neocembrene synthases from Eupborbiaceae plants and expression in *Saccharomyces cerevisiae*. *Phytochemistry* 71 (13): 1466-1473.
60. Ennajdaoui H, et al. (2010) Trichome specific expression of the tobacco (*Nicotiana sylvestris*) cembratrien-ol synthase genes is controlled by both activating and repressing cis-regions. *Plant Mol Biol* 73(6):673-685.
61. Hamano Y, et al. (2002) Functional Analysis of Eubacterial Diterpene Cyclases Responsible for Biosynthesis of a Diterpene Antibiotic, Terpentecin. *J Biol Chem* 277(40): 37098-37104.
62. Dairi T, et al. (2001) Eubacterial Diterpene Cyclase Genes Essential for Production of the Isoprenoid Antibiotic Terpentecin. *J Bacterial* 183(20):6085-6094.
63. Schalk M, et al. (2012) Toward a Biosynthetic Route to Sclareol and Amber Odorants. *J Am Chem Soc* 134(46): 18900-18903.
64. Ikeda H, Shin-ya K, Nagamitsu T, Tomoda H (2016) Biosynthesis of mercapturic acid derivative of the labdane-type diterpene, cyslabdan that potentiates imipenem activity against methicillin-resistant Staphylococcus aureus: cyslabdan is generated by mycothiol-mediated xenohiotic detoxification. *J Ind Microbiol Biotechnol* 43(2-3):325-342.
65. Keeling C I, Madilao L L, Zerbe P, Dullat H K, Bohlmann J (2011) The Primary Diterpene Synthase Products of *Picea abies* Levopimaradiene/Ahietadiene Synthase (PaLAS) Are Epimers of a Thermally Unstable Diterpenol. *J Biol Chem* 286(24):21145-21153.
66. Geuskens R B M, Luteijn J M, Schoonhoven L M (1983) Antifeedant activity of some ajugarin derivatives in three lepidopterous species. *Experientia* 39(4):403-404.
67. Belles X, Camps F, Coll J, Piulachs M D (1985) Insect antifeedant activity of clerodane diterpenoids against larvae of Spodoptera Littoralis (Boisd.) (Lepidoptera). *J Chem Ecol* 11(10):1439-1445.
68. Challis G L (2008) Genome Mining for Novel Natural Product Discovery. *J Med Chem* 51(9):2618-2628.
69. Xu H, et al. (2016) Analysis of the Genome Sequence of the Medicinal Plant *Salvia miltiorrhiza*. *Molecular Plant* 9(6):949-952.
70. King A J, Brown G D, Gild ay AD, Larson T R, Graham I A (2014) Production of Bioactive Diterpenoids in the Euphorbiaceae Depends on Evolutionarily Conserved Gene Clusters. *The Plant Cell Online* 26(8):3286-3298.
71. Huang A C, et al. (2017) Unearthing a sesterterpene biosynthetic repertoire in the Brassicaceae through genome mining reveals convergent evolution. *PNAS* 114 (29):E6005-E6014.
72. Busta L, Jetter R (2017) Moving beyond the ubiquitous: the diversity and biosynthesis of specialty compounds in plant cuticular waxes. *Phytodiem Rev.* 1-30.
73. Kodaraa Y, Shumway M, Leinonen R (2012) The sequence read archive: explosive growth of sequencing data. *Nucleic Acids Res* 40(D1):D54-D56.
74. Benson D A, et al. (2013) GenBank. *Nucleic Acids Res* 41(D1):D36-D42.
75. Kuhn S, Schlörer N E, Kolshorn H, Stoll R (2012) From chemical shift data through prediction to assignment and NMR LIMS—multiple functionalities of mnrshiftdb2. *Journal of Cheminformatics* 4(Suppl 1):P52.
76. Fischedick J T, Johnson S R, Ketchum R E B, Croteau R B, Lange B M (2015) NMR spectroscopic search module for Spektraris, an online resource for plant natural product identification—Taxane diterpenoids from Taxus x media cell suspension cultures as a case study. *Phytochemistry* 113:87-95.
77. Scotti M T, et al. (2018) SistematX, an Online Web-Based Cheminformatics Tool for Data Management of Secondary Metabolites. *Molecules* 23(1):103.
78. Heller S R, McNaught A, Pletnev I, Stein S, Tchekhovskoi D (2015) InChI, the IUPAC International Chemical Identifier. *J Cheminform* 7. doi: 10.1186/s13321-015-0068-4.
79. Sievers F, et al. (2011) Fast, scalable generation of high-quality protein multiple sequence alignments using Clustal Omega. *Molecular Systems Biology* 7:539.
80. Stamatakis A (2014) *RAxML version* 8: a tool for phylogenetic analysis and post-analysis of large phylogenies. *Bioinformatics* 30(9): 1312-1313.
81. Huerta-Cepas J, Serra F, Bork P (2016) ETE 3: Reconstruction, Analysis, and Visualization of Phylogenomic Data. *Mol Biol* Evol 33(6): 1635-1638.
82. Lopez-Perez J L, Theron R, del Olmo E, Diaz D (2007) NAPROC-13: a database tor the dereplication of natural product mixtures in bioassay-guided protocols. *Bioinformatics* 23(23):3256-3257.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various features of the invention according to the foregoing description provided in the specification and figures.

Statements:
1. An expression system comprising at least one expression cassette having a heterologous promoter operably linked to a nucleic acid segment encoding an enzyme with at least 90% sequence identity to SEQ ID NOT, 3, 5, 7, 9, 11, 13, 15, 17, 19, 21, 23, 25, 27, 29, 31, 33, 35, 37, 39, 41, 43, 45, 47, 49, 51, 53, 57, 59, or 176
2. The expression system of statement 1, wherein at least one expression cassette is within at least one expression vector.
3. The expression system of statement 1 or 2, wherein the expression system comprises two, or three, or four, or five expression cassettes or expression vectors, each expression cassette encoding a separate enzyme.
4. The expression system of statement 1, 2 or 3, wherein the expression system further comprises one or more expression cassettes having a promoter operably linked to a nucleic acid segment encoding an enzyme that can synthesize isopentenyl diphosphate (IPP), dimethylallyl diphosphate (DMAPP), or geranylgeranyl diphosphate (GGPP).
5. The expression system of statement 1-3 or 4, wherein the expression system has at least one expression cassette having a constitutive promoter.
6. The expression system of statement 1-3 or 4, wherein the expression system has at least one expression cassette having an inducible promoter.
7. The expression system of statement 1-5 or 6, wherein the expression system has at least one expression cassette having a CaMV 35S promoter, CaMV 19S promoter, nos promoter, AdhI promoter, sucrose synthase promoter, α-tubulin promoter, ubiquitin promoter, actin promoter, cab promoter, PEPCase promoter, R gene complex promoter, CYP71D16 trichome-specific promoter, CBTS (cembratrienol synthase) promotor, Z10 promoter from a 10 kD zein protein gene, Z27 promoter from a 27 kD zein protein gene, plastid rRNA-operon (rrn) promoter, tight inducible pea rbcS gene, RUBISCO-SSU light-inducible promoter (SSU) from tobacco, or rice actin promoter.
8. A host cell comprising the expression system of statement 1-6 or 7, which is heterologous to the host cell.
9. The host cell of statement 8, which is a plant cell, an algae cell, a fungal cell, a bacterial cell, or an insect cell.
10. The host cell of statement 8 or 9, which is a *Nicotiana benthamiana, Nicotiana tabacum, Nicotiana rustica, Nicotiana excelsior, Nicotiana excelsiana, Escherichia coli, Clostridium ljungdahlii, Clostridium autoethanogenum, Clostridium kluyveri, Corynebacterium glutamicum, Cupriavidus necator, Cupriavidus metallidurans; Pseudomonas fluorescens, Pseudomonas putida, Pseudomonas oleavorans; Delftia acidovorans, Bacillus subtilis, Lactobacillus delbrueckii, Lactococcus lactis, Aspergillus niger, Saccharomyces cerevisiae, Candida tropicalis, Candida albicans, Candida cloacae, Candida guillermondii, Candida Intermedia, Candida maltosa, Candida parapsilosis, Candida zeylenoides, Pichia pastoris, Yarrowia lipolytica, Issathenkia orientalis, Debaryomyces hansenii, Arxula adenoinivorans, Kluyveromyces lactis,* or *Exophiala, Mucor, Trichoderma, Cladosporium, Phanerochaete, Cladophialophora, Paecilomyces, Scedosporium,* or *Ophiostoma* cell.
11. The host cell of statement 8, 9 or 10, which is a *Nicotiana benthamiana*.
12. A method of synthesizing a terpene comprising incubating a host cell that has the expression system of any of statements 1-7.
13. A method for synthesizing a terpene comprising incubating a host cell comprising a heterologous expression system that includes at least one expression cassette having a heterologous promoter operably linked to a nucleic acid segment encoding an enzyme with at least 90% sequence identity to SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 57, 59, or 176.
14. A method for synthesizing a terpene comprising incubating a terpene precursor with an enzyme with at least 90% sequence identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 57, 59, or 176.
15. The method of statement 12, 13 or 14, wherein the terpene is a compound of formula I, II, or lit:

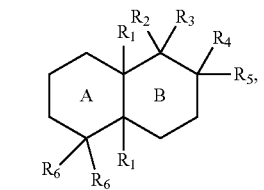
I

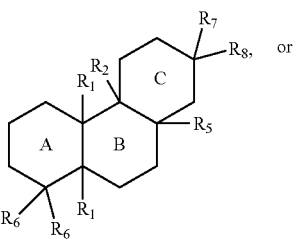
II    or

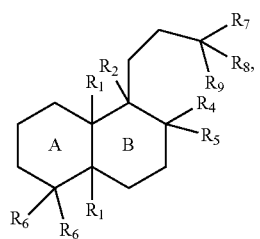
III wherein
- each $R_1$ can separately be hydrogen or lower alkyl;
- $R_2$ can be hydrogen, lower alkyl, hydroxy, a bond to an adjacent ring carbon, or form a $C_4$-$C_6$ cycloheteroalkyl with $R_3$;
- $R_3$ can be a branched $C_5$-$C_6$ alkyl with 0-2 double bonds, can form a $C_4$-$C_6$ cycloheteroalkyl with $R_2$; can form a cycloalkyl with $R_4$, or can form a cycloheteroalkyl ring with $R_4$, wherein the $C_5$-$C_6$ alkyl can optionally have one hydroxy, phosphate or diphosphate substituent, and wherein each cycloalkyl or cycloheteroalkyl ring can have 0-2 double bonds, and each cycloalkyl or cycloheteroalkyl ring can have 0-2 alkyl or 0-2 alkene substituents;
- $R_4$ can be hydrogen, lower alkyl, lower alkene, hydroxy, a carbon bonded to $R_9$, an oxygen bonded to $R_9$, form a cycloalkyl ring with $R_3$, or form a cycloheteroalkyl ring with $R_3$, wherein each cycloalkyl ring or cycloheteroalkyl ring can have 0-2 double bonds, and each cycloalkyl ring or cycloheteroalkyl ring can have 0-2 alkyl or 0-2 alkene substituents;
- $R_5$ can be hydrogen, hydroxy, lower alkyl, a lower alkene, a bond with an adjacent carbon, form a cycloalkyl ring with a ring atom of a ring formed by $R_3$ and $R_4$, wherein the cycloalkyl ring can have 0-2 double bonds, and the cycloalkyl ring can have 0-2 alkyl or 0-2 alkene substituents;
- each $R_6$ can separately be hydrogen, lower alkyl, lower alkene, or form a bond with an adjacent carbon;
- $R_7$ can be lower alkyl, lower alkene, or form a cycloalkyl ring with a $R_5$,
- $R_8$ can be lower alkyl, hydroxy, phosphate, diphosphate, or form a bond with an adjacent carbon; and
- $R_9$ can be hydrogen, lower alkyl, lower alkene, =$CH_2$, hydroxy, phosphate, diphosphate, form a bond with an adjacent carbon, form a cycloalkyl ring with $R_4$, or form a cycloheteroalkyl ring with $R_4$, wherein each cycloalkyl ring or cycloheteroalkyl ring can have 0-2 double bonds, and each cycloalkyl ring or cycloheteroalkyl ring can have 0-2 alkyl or 0-2 alkene substituents.

16. The method of statement 12-14 or 15 wherein the terpene is a compound with a skeleton selected from Sk1-Sk14:

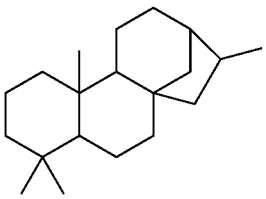
Sk1

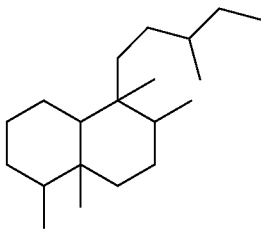
Sk2

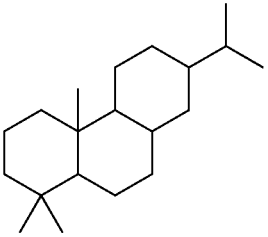
Sk3

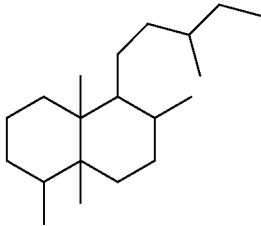
Sk4

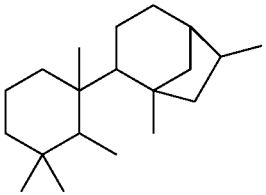
Sk5

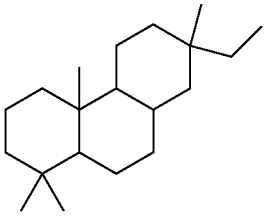
Sk6

123
-continued
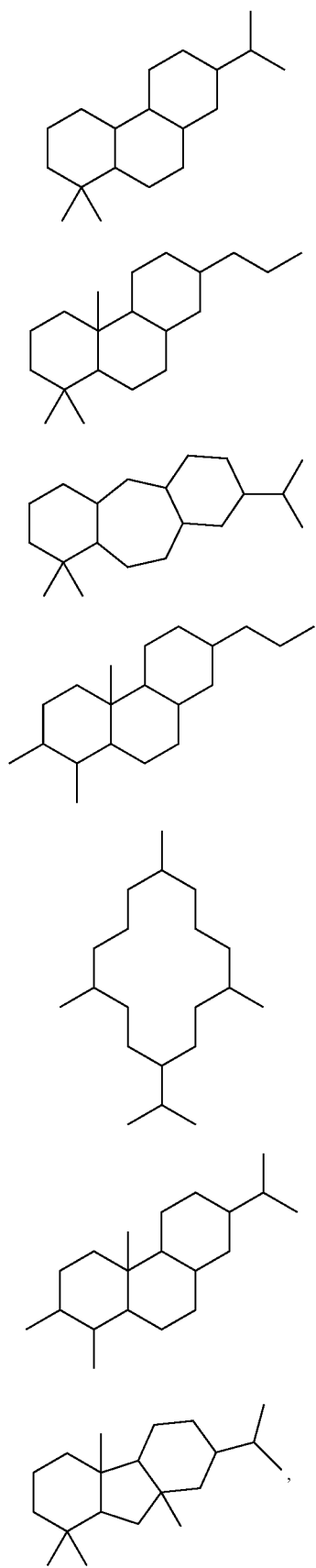
124
-continued
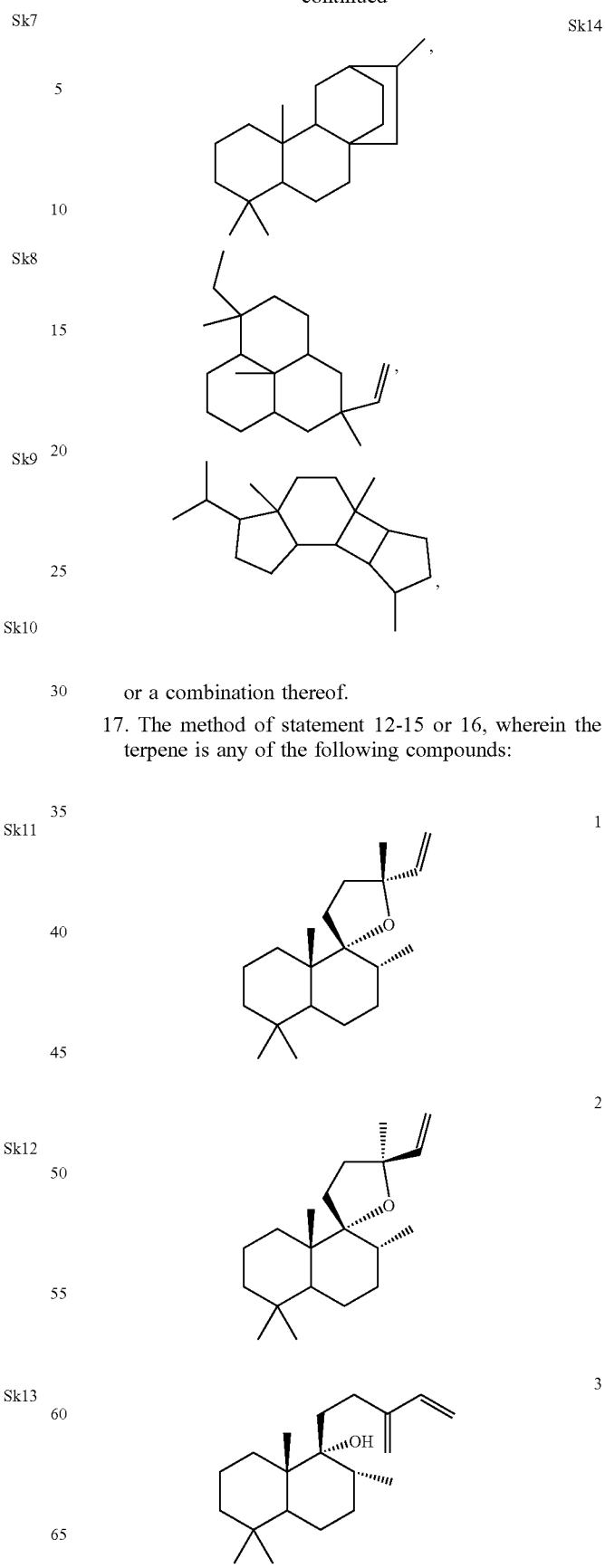
or a combination thereof.
17. The method of statement 12-15 or 16, wherein the terpene is any of the following compounds:

4
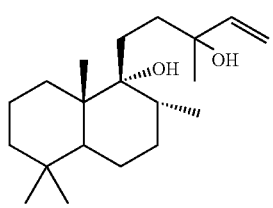
5
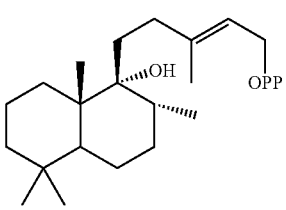
6
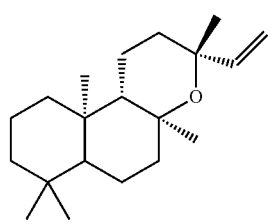
7
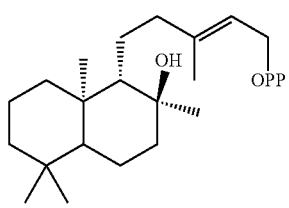
8
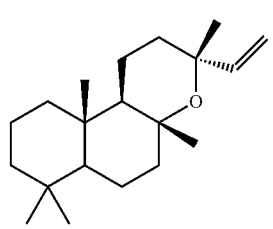
9
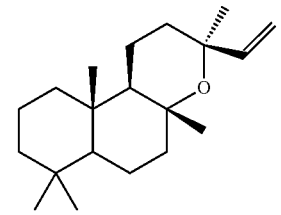
10
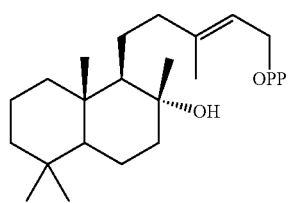
11
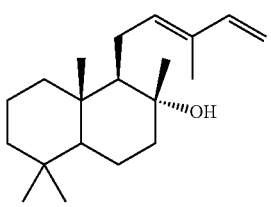
12
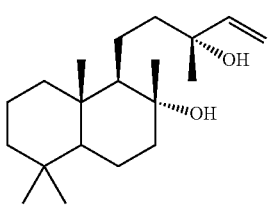
13
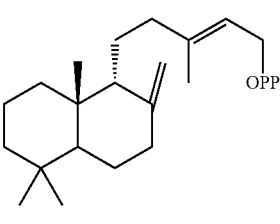
14
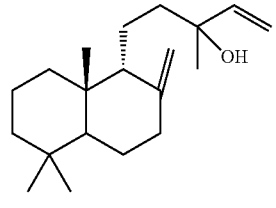
15
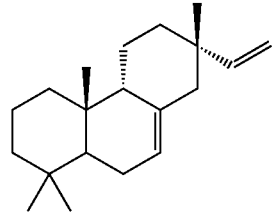
16
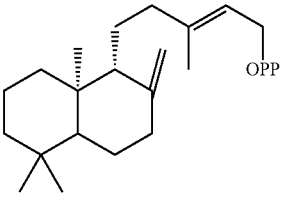
17
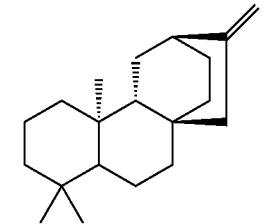

18
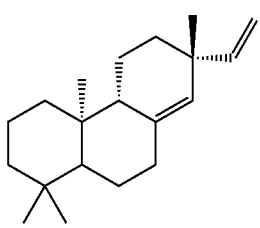
19
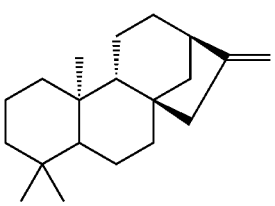
20
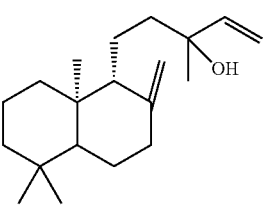
21
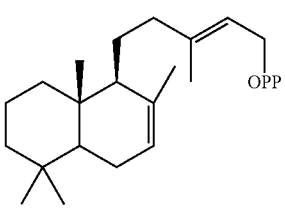
22
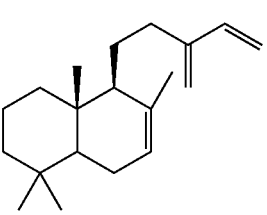
23
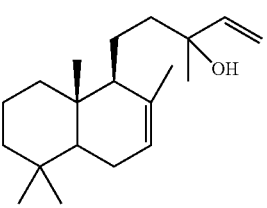
24
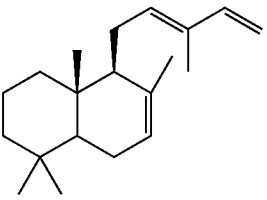
25
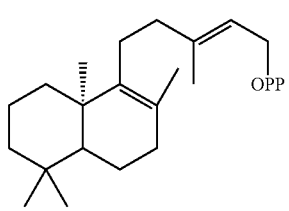
26
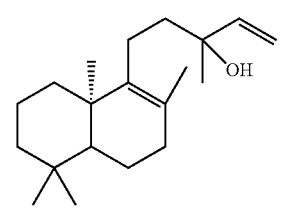
27
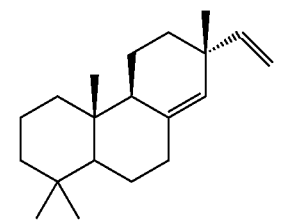
28
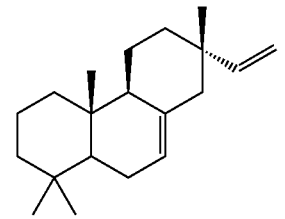
29
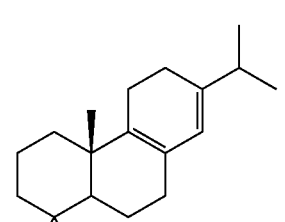
30
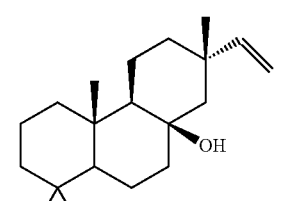
31
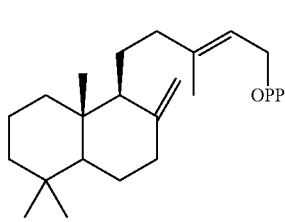

129
-continued
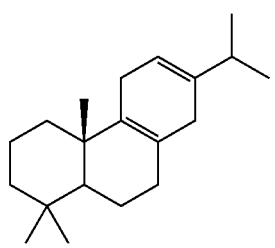
32
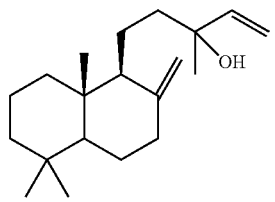
33
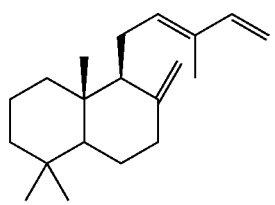
34
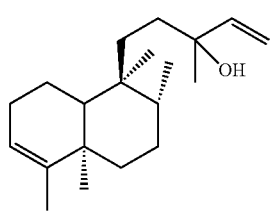
35
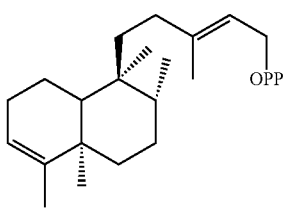
36
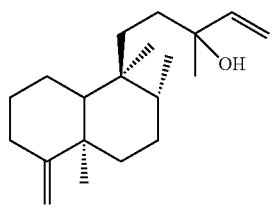
37
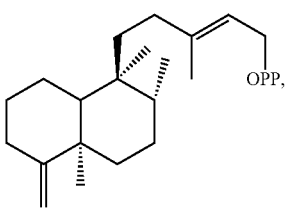
38
130
-continued
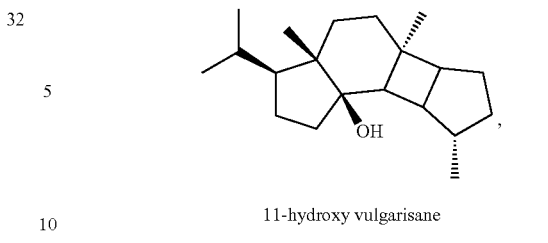
11-hydroxy vulgarisane
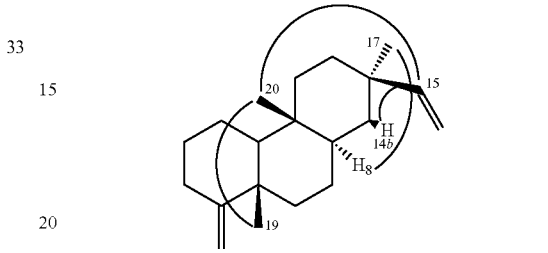
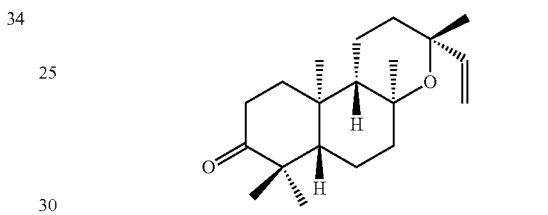
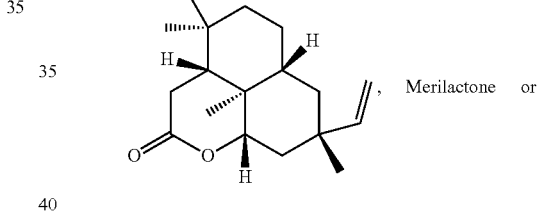
Merilactone or Ribenone
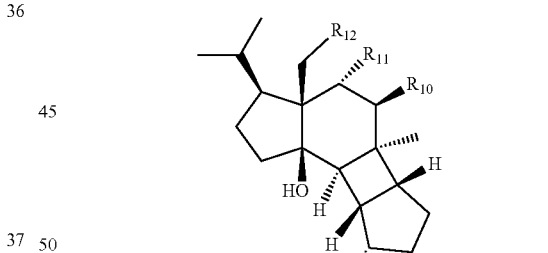
wherein:
Vulgarisin B (1)
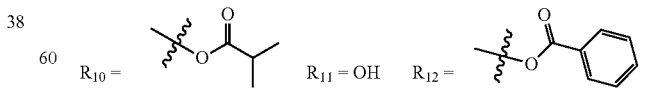
$R_{10}=$ , $R_{11}=OH$, $R_{12}=$
Vulgarisin C (2)
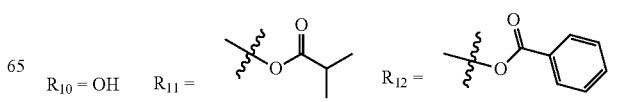
$R_{10}=OH$, $R_{11}=$ , $R_{12}=$ -continued Vulgarisin D (3)

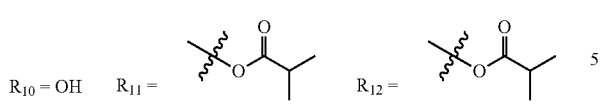

R₁₀ = OH  R₁₁ = [isobutyrate ester]  R₁₂ = [isobutyrate ester]

18. The method of statement 12-16 or 17, wherein the terpene is at least one of the following compounds:

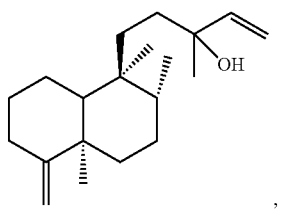

,

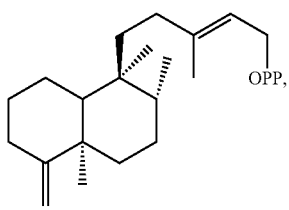

OPP,

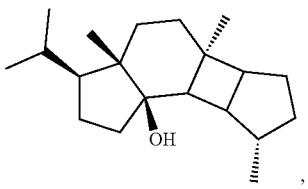

OH 11-hydroxy vulgarisane

,

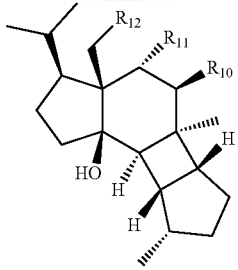

or
wherein:

Vulgarisin B (1)

R₁₀ = [isobutyrate]  R₁₁ = OH  R₁₂ = [benzoate]

Vulgarisin C (2)

R₁₀ = OH  R₁₁ = [isobutyrate]  R₁₂ = [benzoate]

Vulgarisin D (3)

R₁₀ = OH  R₁₁ = [isobutyrate]  R₁₂ = [isobutyrate]

19. The method of statement 12-17 or 18 wherein the terpene precursor is geranylgeranyl diphosphate (GGPP).

20. A compound selected from:

1

2

37

38

Ribenone, Merilactone ,

133
-continued
3
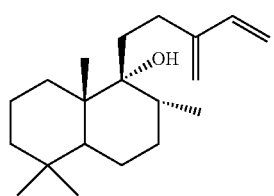
4
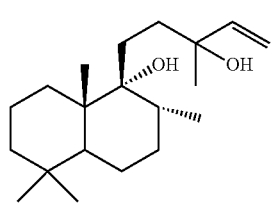
5
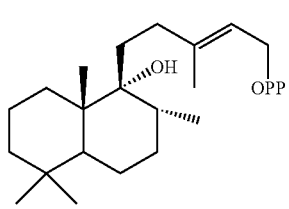
6
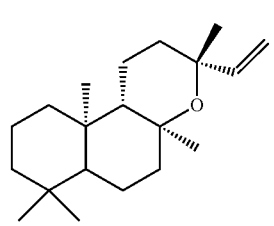
7
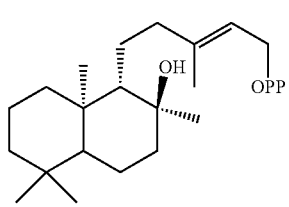
8
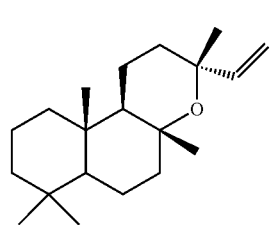
9
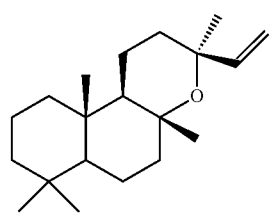
134
-continued
10
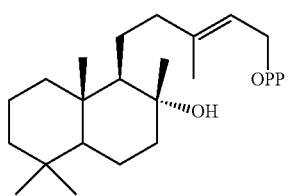
11
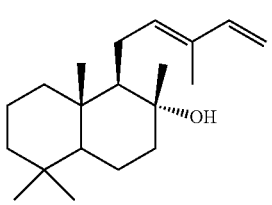
12
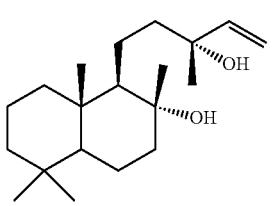
13
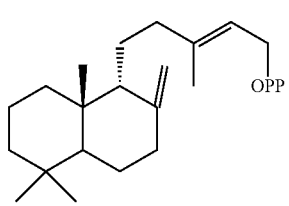
14
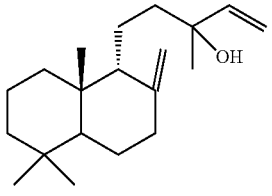
15
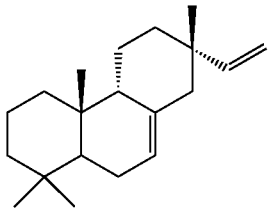
16
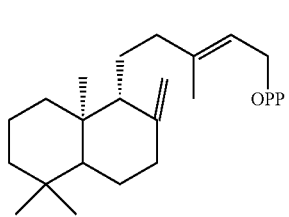

135
-continued
17
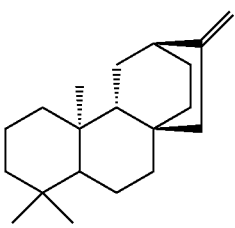
18
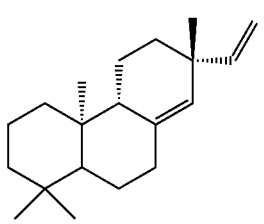
19
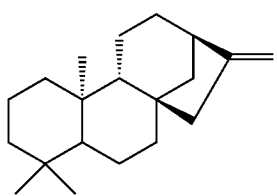
20
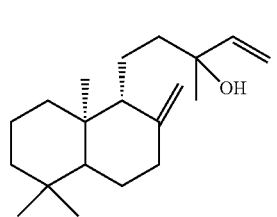
21
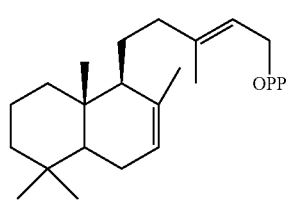
22
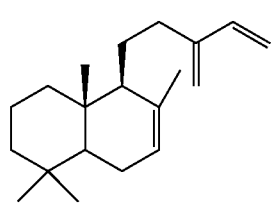
23
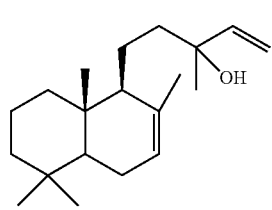
136
-continued
24
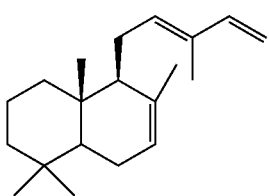
25
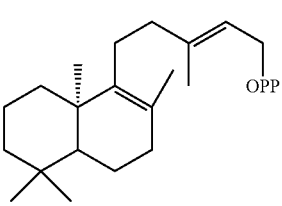
26
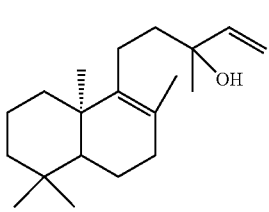
27
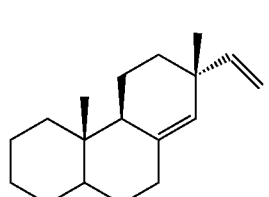
28
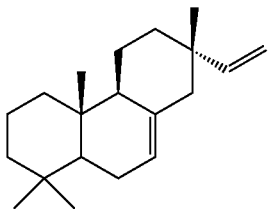
29
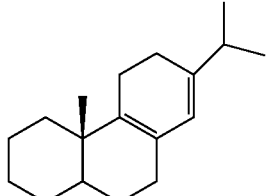
30
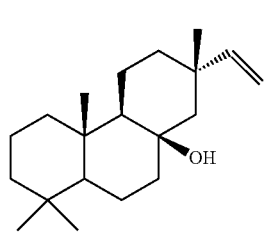

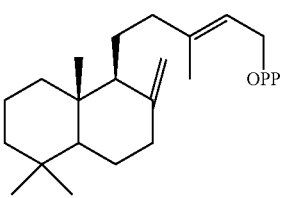
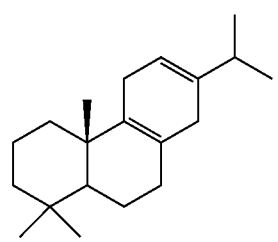
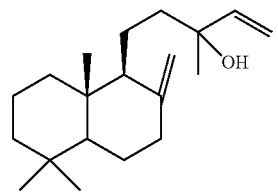
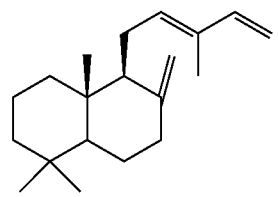
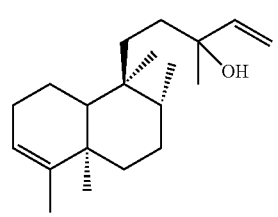
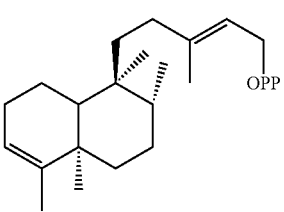
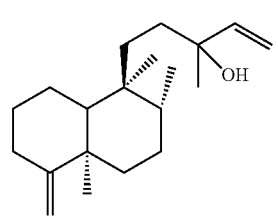
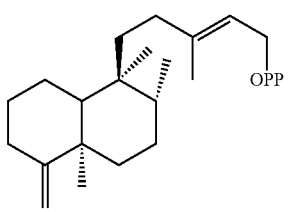
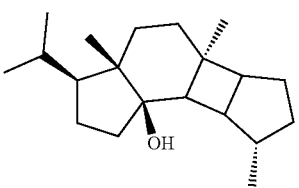
11-hydroxy vulgarisane
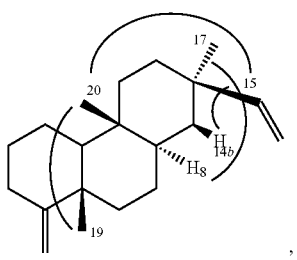
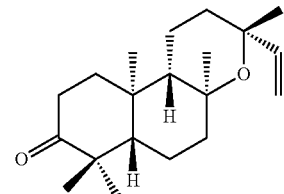
Ribenone
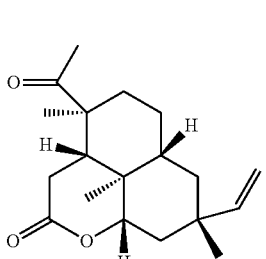
Merilactone
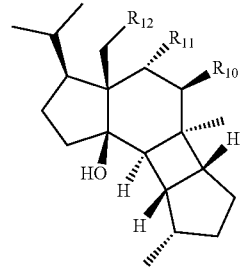
, or
wherein:
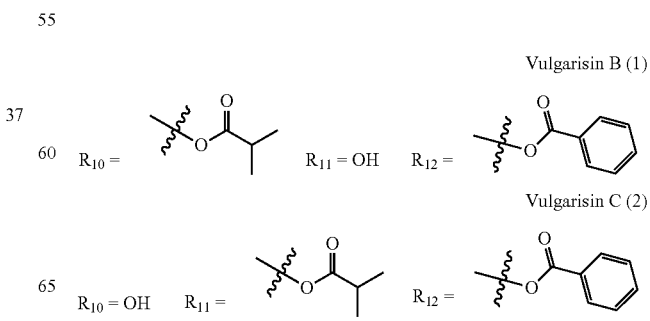
Vulgarisin B (1)
Vulgarisin C (2)

-continued
Vulgarisin D (3)
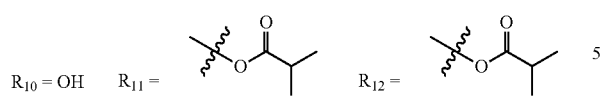
R10 = OH    R11 =    R12 =
21. A reaction mixture comprising one or more of the following:
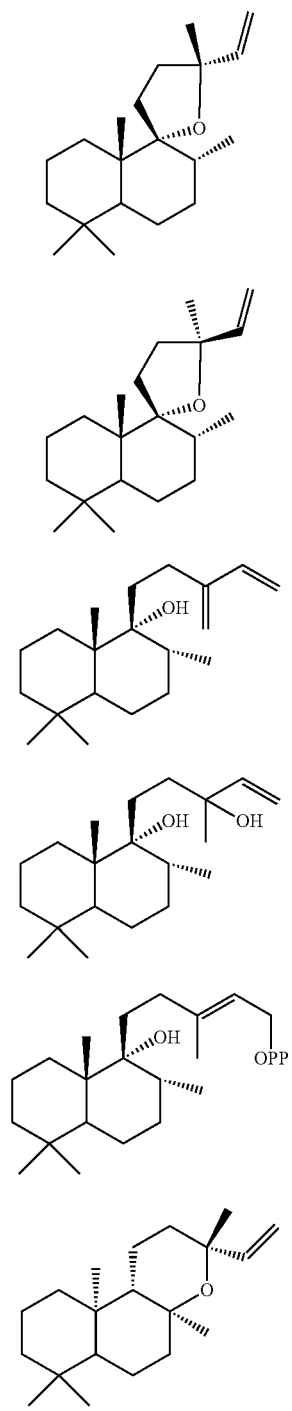
1
2
3
4
5
6
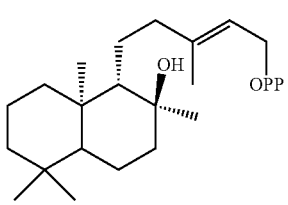
7
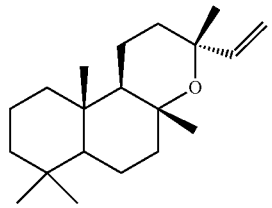
8
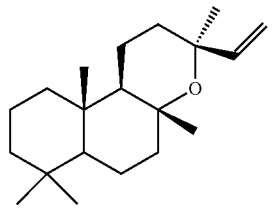
9
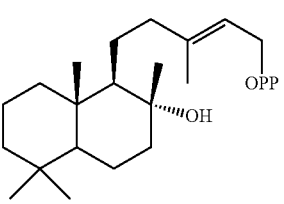
10
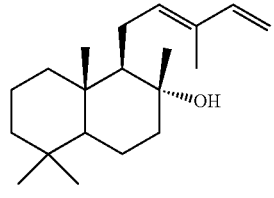
11
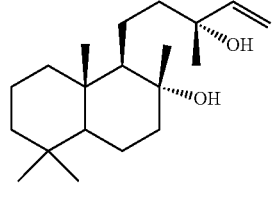
12
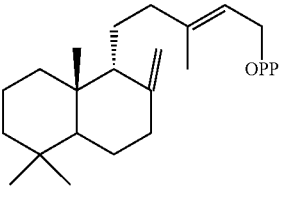
13
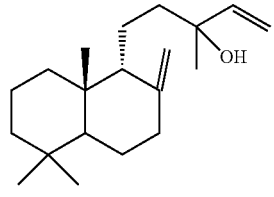
14

-continued
| | |
|---|---|
| 15 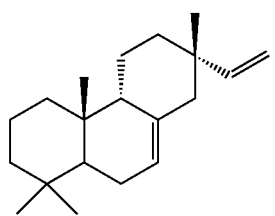 | 22 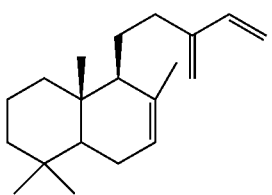 |
| 16 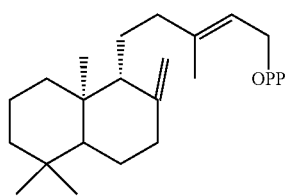 | 23 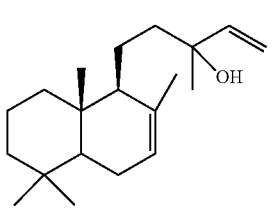 |
| 17 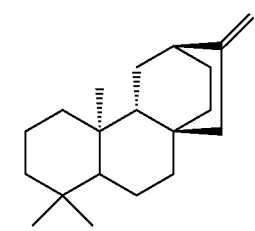 | 24 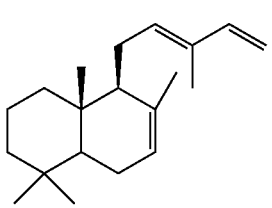 |
| 18 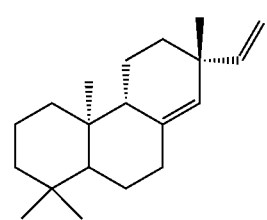 | 25 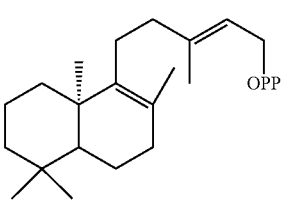 |
| 19 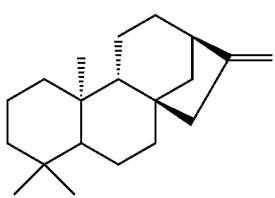 | 26 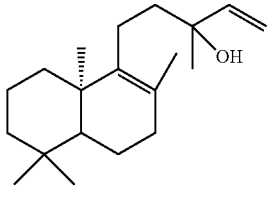 |
| 20 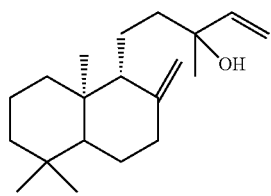 | 27 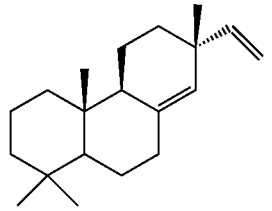 |
| 21 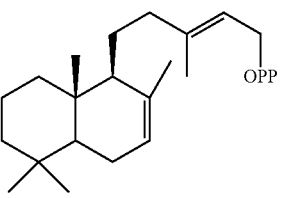 | 28 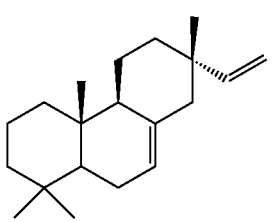 |

29
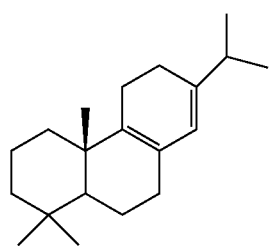
30
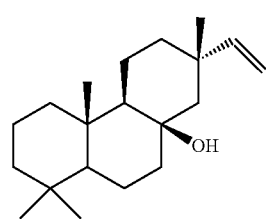
31
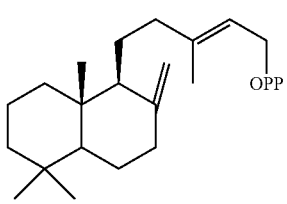
32
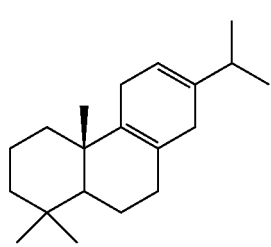
33
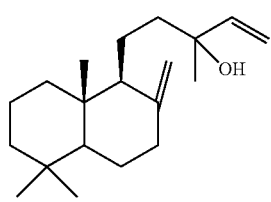
34
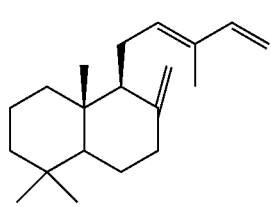
35
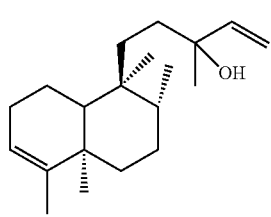
36
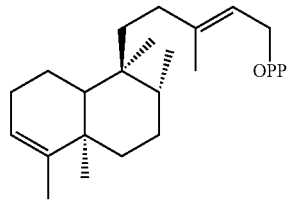
37
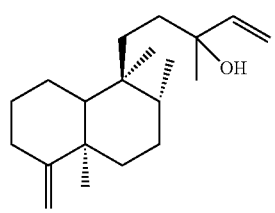
38
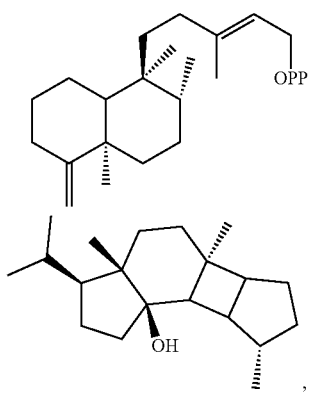
11-hydroxy vulgarisane
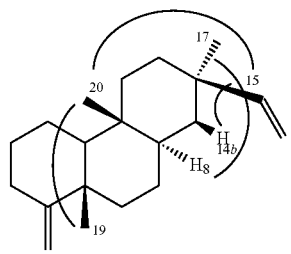
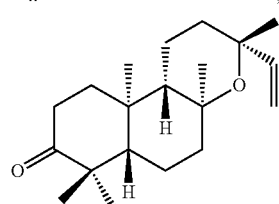
Ribenone
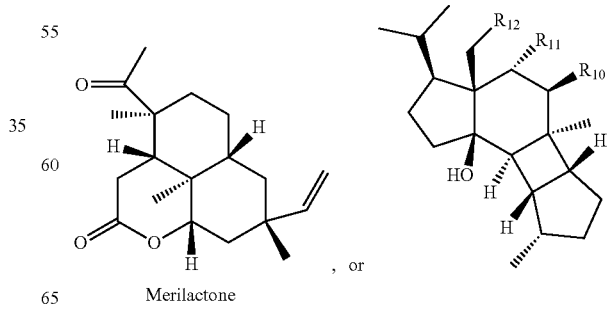
Merilactone , or wherein:

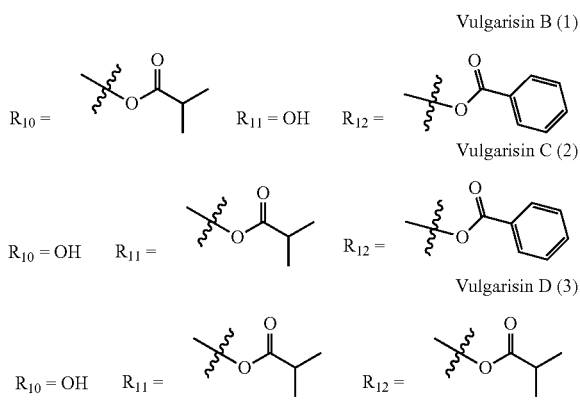

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and genetically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A method for synthesizing a terpene comprising incubating a terpene precursor with an enzyme with at least 95% sequence identity to the amino acid sequence of SEQ ID NO: 23.

2. The method of claim 1, wherein the precursor is isopentenyl diphosphate (IPP), dimethylallyl diphosphate (DMAPP), geranylgeranyl diphosphate (GGPP), or a combination thereof.

3. The method of claim 1, which comprises incubating a host cell that expresses a heterologous expression system comprising at least one expression cassette having a heterologous promoter operably linked to a nucleic acid segment encoding an enzyme with at least 95% sequence identity to the amino acid sequence of SEQ ID NO: 23.

4. The method of claim 1, wherein the terpene is a compound of formula I, II, or III:

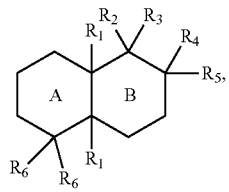

I

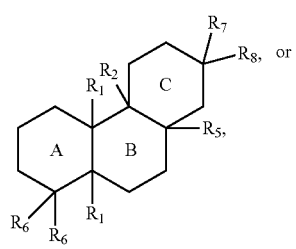

II

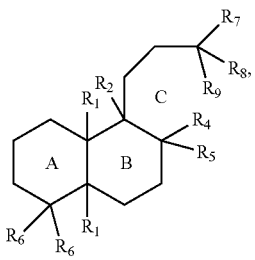

III wherein
each $R_1$ can separately be hydrogen or lower alkyl;
$R_2$ can be hydrogen, lower alkyl, hydroxy, a bond to an adjacent ring carbon, or form a $C_4$-$C_6$ cycloheteroalkyl with $R_3$;
$R_3$ can be a branched $C_5$-$C_6$ alkyl with 0-2 double bonds, can form a $C_4$-$C_6$ cycloheteroalkyl with $R_2$; can form a cycloalkyl with $R_4$, or can form a cycloheteroalkyl ring with $R_4$, wherein the $C_5$-$C_6$ alkyl can optionally have one hydroxy, phosphate or diphosphate substituent, and wherein each cycloalkyl or cycloheteroalkyl ring can have 0-2 double bonds, and each cycloalkyl or cycloheteroalkyl ring can have 0-2 alkyl or 0-2 alkene substituents;
$R_4$ can be hydrogen, lower alkyl, lower alkene, hydroxy, a carbon bonded to $R_9$, an oxygen bonded to $R_9$, form a cycloalkyl ring with $R_3$, or form a cycloheteroalkyl ring with $R_3$, wherein each cycloalkyl ring or cycloheteroalkyl ring can have 0-2 double bonds, and each cycloalkyl ring or cycloheteroalkyl ring can have 0-2 alkyl or 0-2 alkene substituents;
$R_5$ can be hydrogen, hydroxy, lower alkyl, a lower alkene, a bond with an adjacent carbon, form a cycloalkyl ring with a ring atom of a ring formed by $R_3$ and $R_4$, wherein the cycloalkyl ring can have 0-2 double bonds, and the cycloalkyl ring can have 0-2 alkyl or 0-2 alkene substituents;
each $R_6$ can separately be hydrogen, lower alkyl, lower alkene, or form a bond with an adjacent carbon;

R$_7$ can be lower alkyl, lower alkene, or form a cycloalkyl ring with a R$_5$,

R$_8$ can be lower alkyl, hydroxy, phosphate, diphosphate, or form a bond with an adjacent carbon; and R$_9$ can be hydrogen, lower alkyl, lower alkene, =CH$_2$, hydroxy, phosphate, diphosphate, form a bond with an adjacent carbon, form a cycloalkyl ring with R$_4$, or form a cycloheteroalkyl ring with R$_4$, wherein each cycloalkyl ring or cycloheteroalkyl ring can have 0-2 double bonds, and each cycloalkyl ring or cycloheteroalkyl ring can have 0-2 alkyl or 0-2 alkene substituents.

5. The method of claim 1, wherein the terpene is a compound with a skeleton selected from Sk1-Sk14:

Sk1
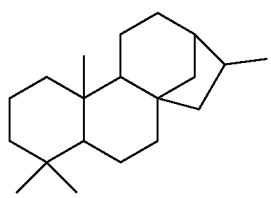

Sk2
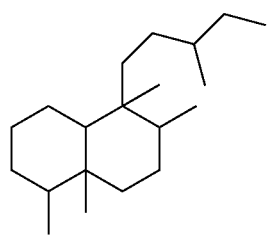

Sk3
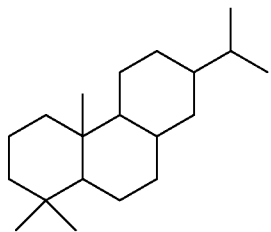

Sk4
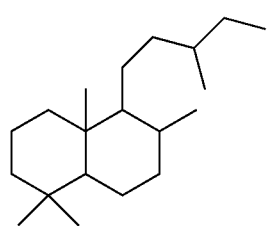

Sk5
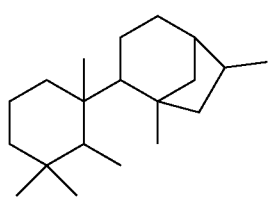

Sk6
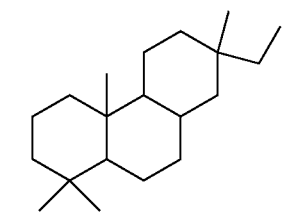

Sk7
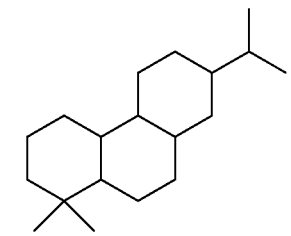

Sk8
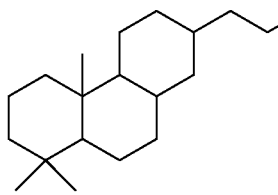

Sk9
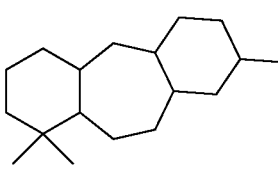

Sk10
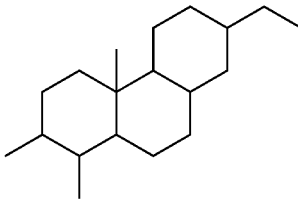

Sk11
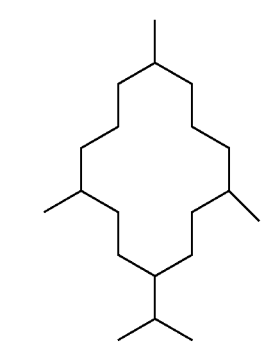

Sk12
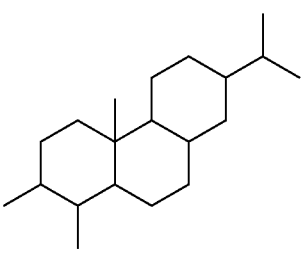

363
-continued
Sk13
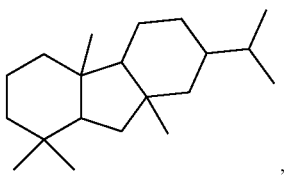
Sk14
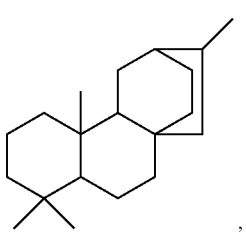
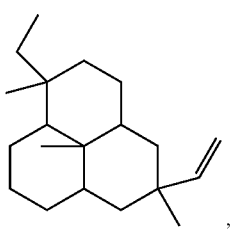
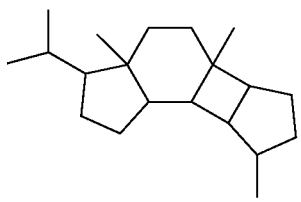
or combination thereof.
6. The method of claim 1, wherein the terpene is one or more of the following compounds:
1
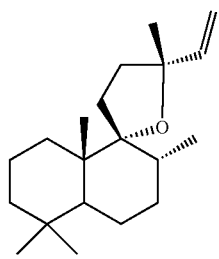
2
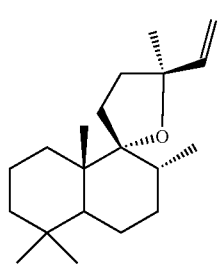
364
-continued
3
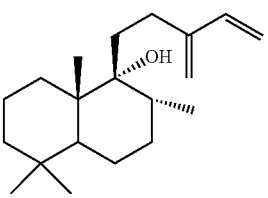
4
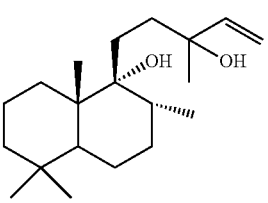
5
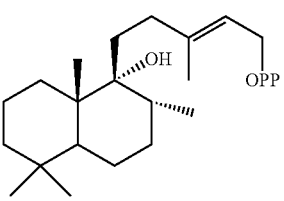
6
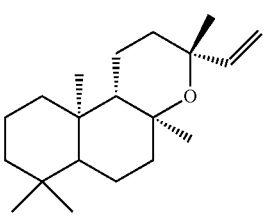
7
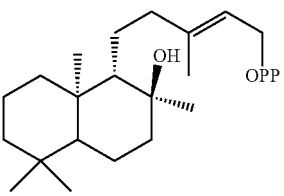
8
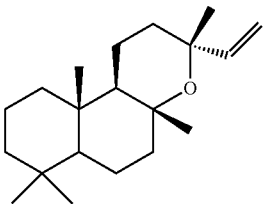
9
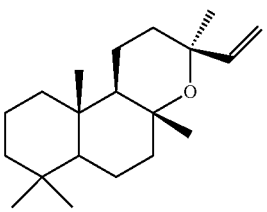

365
-continued
10
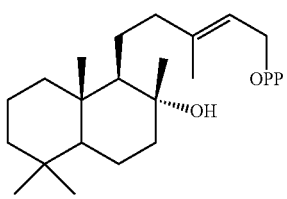
11
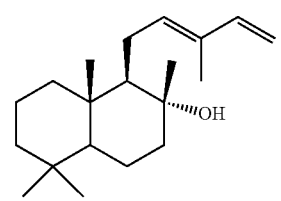
12
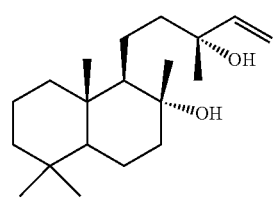
13
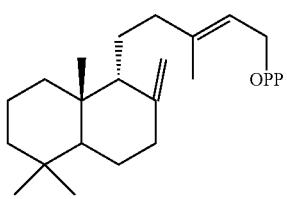
14
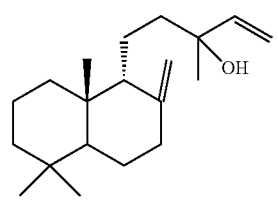
15
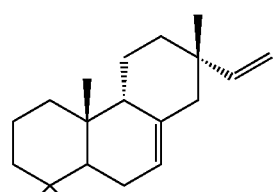
16
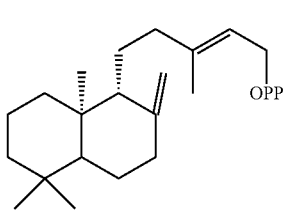
366
-continued
17
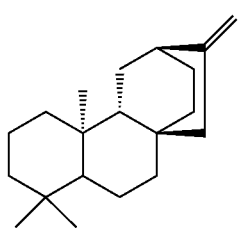
18
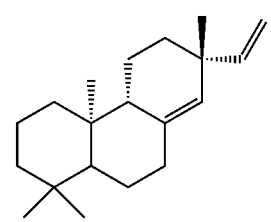
19
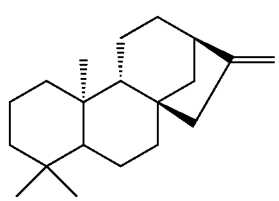
20
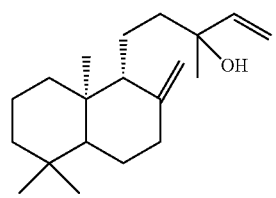
21
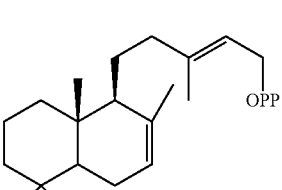
22
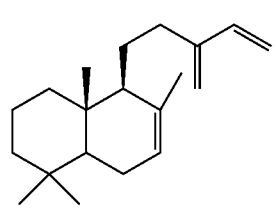
23
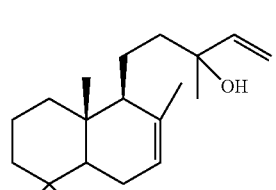

24
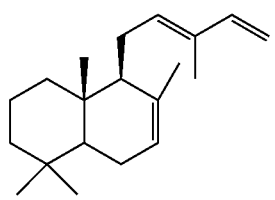
25
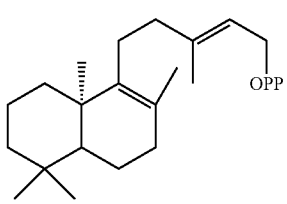
26
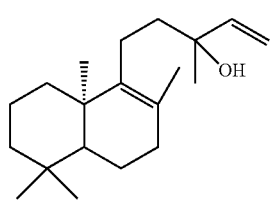
27
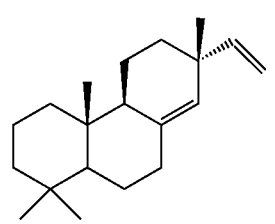
28
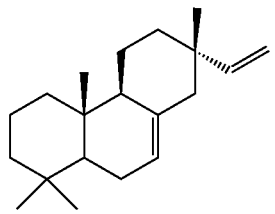
29
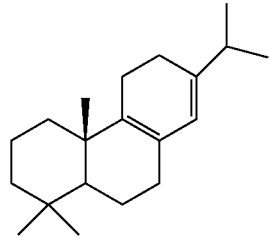
30
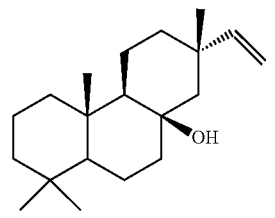
31
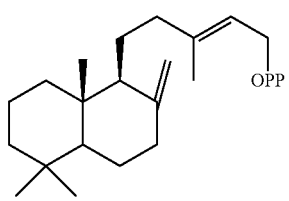
32
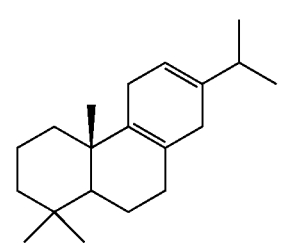
33
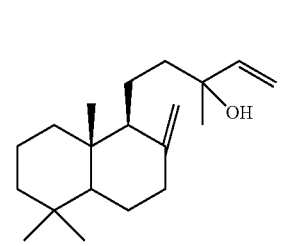
34
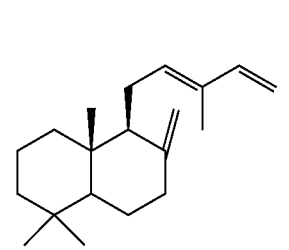
35
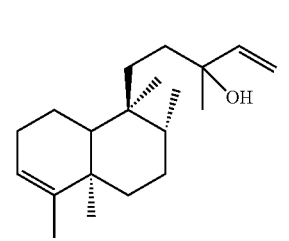
36
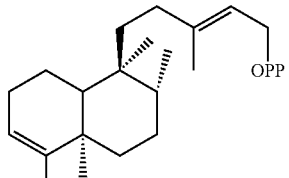
37
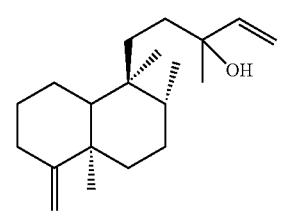

-continued

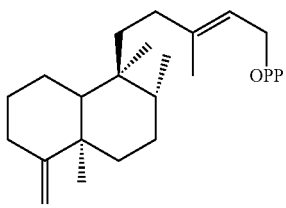

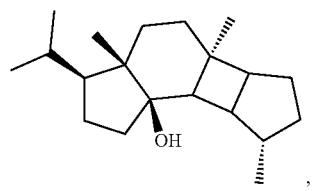
11-hydroxy vulgarisane

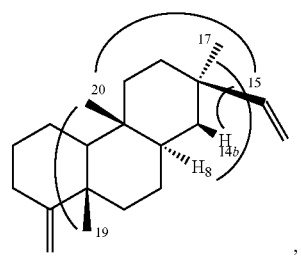
Ribenone

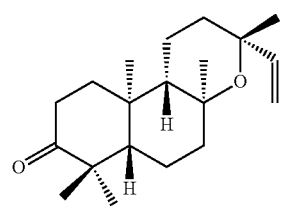
Merilactone , or

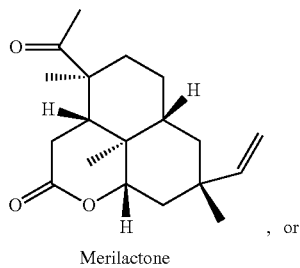

wherein:

Vulgarisin B (1)
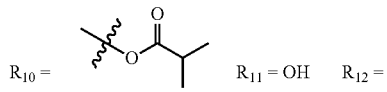

Vulgarisin C (2)
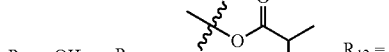
$R_{10}$ = OH    $R_{11}$ = 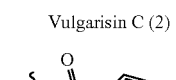    $R_{12}$ = 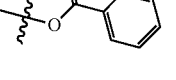

-continued

Vulgarisin D (3)
$R_{10}$ = OH    $R_{11}$ = 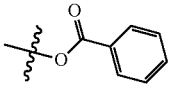    $R_{12}$ = 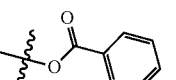.

7. A method for synthesizing a terpene comprising incubating a terpene precursor of a terpene of formula I, II, or III, with an enzyme with at least 95% sequence identity to SEQ ID NO: 23, wherein the terpene of formula I, II, or III is:

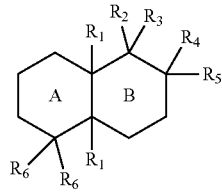

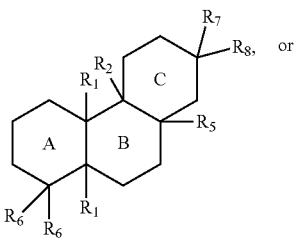

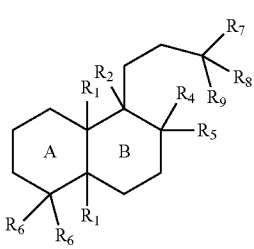

wherein
each $R_1$ can separately be hydrogen or lower alkyl;
$R_2$ can be hydrogen, lower alkyl, hydroxy, a bond to an adjacent ring carbon, or form a $C_4$-$C_6$ cycloheteroalkyl with $R_3$;
$R_3$ can be a branched $C_5$-$C_6$ alkyl with 0-2 double bonds, can form a $C_4$-$C_6$ cycloheteroalkyl with $R_2$; can form a cycloalkyl with $R_4$, or can form a cycloheteroalkyl ring with $R_4$, wherein the $C_5$-$C_6$ alkyl can optionally have one hydroxy, phosphate or diphosphate substituent, and wherein each cycloalkyl or cycloheteroalkyl ring can have 0-2 double bonds, and each cycloalkyl or cycloheteroalkyl ring can have 0-2 alkyl or 0-2 alkene substituents;
$R_4$ can be hydrogen, lower alkyl, lower alkene, hydroxy, a carbon bonded to $R_9$, an oxygen bonded to $R_9$, form a cycloalkyl ring with $R_3$, or form a cycloheteroalkyl ring with $R_3$, wherein each cycloalkyl ring or cycloheteroalkyl ring can have 0-2 double bonds, and each cycloalkyl ring or cycloheteroalkyl ring can have 0-2 alkyl or 0-2 alkene substituents;
$R_5$ can be hydrogen, hydroxy, lower alkyl, a lower alkene, a bond with an adjacent carbon, form a cycloalkyl ring with a ring atom of a ring formed by $R_3$ and $R_4$, wherein the cycloalkyl ring can have 0-2 double bonds, and the cycloalkyl ring can have 0-2 alkyl or 0-2 alkene substituents;

each $R_6$ can separately be hydrogen, lower alkyl, lower alkene, or form a bond with an adjacent carbon;

$R_7$ can be lower alkyl, lower alkene, or form a cycloalkyl ring with a $R_5$, $R_8$ can be lower alkyl, hydroxy, phosphate, diphosphate, or form a bond with an adjacent carbon; and $R_9$ can be hydrogen, lower alkyl, lower alkene, $=CH_2$, hydroxy, phosphate, diphosphate, form a bond with an adjacent carbon, form a cycloalkyl ring with $R_4$, or form a cycloheteroalkyl ring with $R_4$, wherein each cycloalkyl ring or cycloheteroalkyl ring can have 0-2 double bonds, and each cycloalkyl ring or cycloheteroalkyl ring can have 0-2 alkyl or 0-2 alkene substituents.

8. A method for synthesizing a terpene comprising incubating a terpene precursor with an enzyme with at least 95% sequence identity to SEQ ID NO: 23, wherein the terpene precursor comprises a diphosphate.

\* \* \* \* \*

SEQUENCE LISTING

```
<160> NUMBER OF SEQ ID NOS: 177

<210> SEQ ID NO 1
<211> LENGTH: 588
<212> TYPE: PRT
<213> ORGANISM: Ajuga reptans

<400> SEQUENCE: 1

Met Ser Leu Ser Phe Thr Ile Lys Val Thr Pro Phe Ser Gly Gln Arg
1               5                   10                  15

Val His Ser Ser Thr Glu Ser Phe Pro Ile Gln Gln Phe Pro Thr Ile
            20                  25                  30

Thr Thr Lys Ser Ala Met Ala Val Lys Cys Ser Ser Leu Ser Thr Ala
        35                  40                  45

Thr Val Ser Phe Gln Asp Phe Val Gly Lys Ile Arg Asp Thr Ile Asn
    50                  55                  60

Gly Lys Val Asp Asn Ser Pro Ala Ala Thr Thr Ile His Pro Ala Asp
65                  70                  75                  80

Ile Pro Ser Asn Leu Cys Val Val Asp Thr Leu Gln Arg Leu Gly Val
                85                  90                  95

Asp Arg Tyr Phe Gln Ser Glu Ile Asp Ser Val Leu Asn Asp Thr Tyr
            100                 105                 110

Arg Phe Trp Gln Gln Lys Gly Glu Asp Ile Phe Thr Asp Val Ala Cys
```

```
            115                 120                 125
Arg Ala Met Ala Phe Arg Leu Leu Arg Val Lys Gly Tyr Glu Val Ser
130                 135                 140

Ser Asp Glu Leu Ala Ser Tyr Ala Glu Gln Glu His Val Asn Leu Gln
145                 150                 155                 160

Pro Ser Asp Ile Thr Thr Val Ile Glu Leu Tyr Arg Ala Ser Gln Thr
                165                 170                 175

Arg Leu Tyr Glu Asp Glu Gly Asn Leu Glu Lys Leu His Thr Trp Thr
                180                 185                 190

Ser Asn Phe Leu Lys Gln Gln Leu Gln Ser Glu Thr Ile Ser Asp Glu
        195                 200                 205

Lys Leu His Lys Gln Val Glu Tyr Tyr Leu Lys Asn Tyr His Gly Ile
210                 215                 220

Leu Asp Arg Ala Gly Val Arg Gln Ser Leu Asp Leu Tyr Asp Ile Asn
225                 230                 235                 240

Gln Tyr Gln Asn Leu Lys Ser Thr Asp Arg Phe Pro Thr Leu Ser Asn
                245                 250                 255

Glu Asp Leu Leu Glu Phe Ala Lys Gln Asp Phe Asn Phe Cys Gln Ala
            260                 265                 270

Gln His Gln Lys Glu Leu Gln Gln Leu Gln Arg Trp Tyr Ala Asp Cys
        275                 280                 285

Lys Leu Asp Thr Leu Thr Tyr Gly Arg Asp Val Val Arg Val Ala Ser
290                 295                 300

Phe Leu Thr Ala Ala Ile Phe Gly Glu Pro Glu Phe Ser Asp Ala Arg
305                 310                 315                 320

Leu Ala Phe Ala Lys His Ile Ile Leu Val Thr Arg Ile Asp Asp Phe
                325                 330                 335

Phe Asp His Gly Gly Ser Ile Glu Glu Ser Tyr Lys Ile Leu Asp Leu
                340                 345                 350

Val Lys Glu Trp Glu Asp Lys Pro Ala Glu Glu Tyr Pro Ser Lys Glu
        355                 360                 365

Val Glu Ile Leu Phe Thr Ala Val Tyr Asn Thr Val Asn Asp Leu Ala
370                 375                 380

Glu Met Ala Tyr Ile Glu Gln Gly Arg Ser Ile Lys Pro Leu Leu Ile
385                 390                 395                 400

Lys Leu Trp Val Glu Ile Leu Thr Ser Phe Lys Lys Glu Leu Asp Ser
                405                 410                 415

Trp Thr Glu Asp Thr Glu Leu Thr Leu Glu Glu Tyr Leu Ala Ser Ser
                420                 425                 430

Trp Val Ser Ile Gly Cys Arg Ile Cys Ser Leu Asn Ser Leu Gln Phe
        435                 440                 445

Leu Gly Ile Thr Leu Ser Glu Met Leu Ser Ser Glu Glu Cys Met
            450                 455                 460

Glu Leu Cys Arg His Val Ser Ser Val Asp Arg Leu Leu Asn Asp Val
465                 470                 475                 480

Gln Thr Phe Glu Lys Glu Arg Leu Glu Asn Thr Ile Asn Ser Val Ser
                485                 490                 495

Leu Gln Leu Ala Glu Ala Gln Arg Glu Gly Arg Thr Ile Thr Glu Glu
            500                 505                 510

Glu Ala Met Ser Lys Ile Lys Asp Leu Ala Asp Tyr His Arg Arg Gln
        515                 520                 525

Leu Met Gln Met Val Tyr Lys Asp Gly Thr Ile Phe Pro Arg Gln Cys
530                 535                 540
```

```
Lys Asp Val Phe Leu Arg Val Cys Arg Ile Gly Tyr Tyr Leu Tyr Ala
545                 550                 555                 560

Ser Gly Asp Glu Phe Thr Thr Pro Gln Gln Met Met Gly Asp Met Lys
                565                 570                 575

Ser Leu Val Tyr Glu Pro Leu Asn Thr Ser Ser Ser
            580                 585

<210> SEQ ID NO 2
<211> LENGTH: 1767
<212> TYPE: DNA
<213> ORGANISM: Ajuga reptans

<400> SEQUENCE: 2
atgtcactct cgttcaccat caaagtcacc cccttttcgg gccagagagt tcacagcagc    60
acagaaagct ttccaatcca acaatttcca acgatcacca ccaaatccgc catggctgtc   120
aaatgcagca gcctcagtac cgcaacagta agcttccagg atttcgtcgg aaaaatcaga   180
gatacgatca acgggaaagt tgacaattct ccagcagcga ccactattca tcctgcagat   240
ataccctcca atctctgcgt ggtggatacc ctccaaagat tgggagttga ccgttacttc   300
caatctgaaa tcgacagcgt tcttaacgac acataccagg tctggcagca aaaggagaa    360 gatatcttca ctgatgttgc ttgtcgtgca atggcatttc gacttttgcg agttaaagga   420
tatgaagttt catcagatga actggcttcg tatgctgaac aagagcatgt taacctgcaa   480
ccaagtgaca taactacggt tatcgagctt acagagcat cacagacaag attatatgaa   540
gacgagggca atcttgagaa gttacatact tggactagca attttctgaa gcaacaattg   600
cagagtgaaa ctatttctga cgagaaattg cacaaacagg tggagtatta cttgaagaac   660
taccacggca tactagaccg tgctggagtt agacaaagtc tcgatttata tgacataaac   720
caataccaga atctaaaatc tacagataga ttccctactt taagtaacga agatttactt   780
gaattcgcga agcaagattt taacttttgc caagctcaac accagaaaga gcttcagcaa   840
ctgcaaaggt ggtatgcgga ttgtaaattg atacattga cttacggaag agatgtggta   900
cgtgttgcaa gtttcctgac agctgcaatt tttggtgagc tgaattctc tgatgctcgt   960 ctagccttcg ccaaacacat catcctcgtg acacgtattg atgatttctt cgatcatggt  1020
gggtctatag aagagtcata caagatcctg gatttagtaa agaatgggaa gataagcca   1080 gctgaggaat atccttccaa ggaagttgaa atcctcttta cagcagtata taatacagta  1140
aatgacttgg cagaaatggc ttatattgag caaggccgtt ccattaaacc tcttctaatt  1200
aaactgtggg ttgaaatact gacaagtttc aagaaagaac tggattcatg gacagaagac  1260
acagaactaa ccttggagga gtacttggct tcctcctggg tgtcgatcgg ttgcagaatc  1320
tgcagtctca attcgctgca gttccttggt ataacattat ccgaagaaat gctttcaagc  1380
gaagagtgca tggagttgtg taggcatgtt tcttcagtcg acaggctact caatgacgtg  1440
caaactttcg agaaggaacg cctagaaaat acgataaaca gtgtgagcct acagctagca  1500
gaagctcaga gagaaggaag aaccattaca gaagaggagg ctatgtcaaa gattaaagac  1560
ctggctgatt atcacaggag acaactgatg cagatggttt ataaggatgg gaccatattt  1620
ccgagacaat gcaaagatgt cttttgagg gtatgcagga ttggctacta cttatacgcg  1680
agcggcgatg aattcactac tccacaacaa atgatggggg atatgaaatc attggtttat  1740 gaaccctaa acacttcatc ctcttga                                       1767
```

```
<210> SEQ ID NO 3
<211> LENGTH: 567
<212> TYPE: PRT
<213> ORGANISM: Leonotis leonurus

<400> SEQUENCE: 3

Met Ser Val Ala Phe Asn Leu Ile Val Val Arg Phe Pro Gly His Gly
1               5                   10                  15

Ile Gln Ser Ser Arg Glu Thr Phe Pro Ala Lys Ile Ile Thr Arg Thr
            20                  25                  30

Lys Ser Ser Met Arg Phe Gln Ser Ser Leu Asn Thr Ser Thr Asp Phe
        35                  40                  45

Val Gly Lys Ile Arg Glu Met Ile Arg Gly Lys Thr Asp Asn Ser Ile
    50                  55                  60

Asn Pro Leu Asp Ile Pro Ser Thr Leu Cys Val Ile Asp Thr Leu His
65                  70                  75                  80

Ser Phe Gly Ile Asp Arg Tyr Phe Gln Ser Glu Ile Asn Ser Val Leu
                85                  90                  95

His His Thr Tyr Arg Leu Trp Asn Asp Arg Asn Asn Ile Ile Phe Lys
            100                 105                 110

Asp Val Ile Cys Cys Ala Ile Ala Phe Arg Leu Leu Arg Val Lys Gly
        115                 120                 125

Tyr Gln Val Ser Ser Asp Glu Leu Ala Pro Phe Ala Gln Gln Gln Val
    130                 135                 140

Thr Gly Leu Gln Thr Ser Asp Ile Ala Thr Ile Leu Glu Leu Tyr Arg
145                 150                 155                 160

Ala Ser Gln Glu Arg Leu His Glu Asp Asp Thr Leu Asp Lys Leu
                165                 170                 175

His Asp Trp Ser Ser Asn Leu Leu Lys Leu His Leu Leu Asn Glu Asn
            180                 185                 190

Ile Pro Asp His Lys Leu His Lys Arg Val Gly Tyr Phe Leu Lys Asn
        195                 200                 205

Tyr His Gly Met Leu Asp Arg Val Ala Val Arg Arg Asn Ile Asp Leu
    210                 215                 220

His Asn Ile Asn His Tyr Gln Ile Pro Glu Val Ala Asp Arg Phe Pro
225                 230                 235                 240

Thr Glu Ala Phe Leu Glu Phe Ser Arg Gln Asp Phe Asn Ile Cys Gln
                245                 250                 255

Ala Gln His Gln Lys Glu Leu Gln Gln Leu His Arg Trp Tyr Ala Asp
            260                 265                 270

Cys Arg Leu Asp Thr Leu Asn His Gly Thr Asp Val His Phe Ala
        275                 280                 285

Asn Phe Leu Thr Ser Ala Ile Phe Gly Glu Pro Glu Phe Ser Glu Ala
    290                 295                 300

Arg Leu Ala Phe Ala Lys Gln Val Ile Leu Ile Thr Arg Met Asp Asp
305                 310                 315                 320

Phe Phe Asp His Asp Gly Ser Arg Glu Glu Ser His Lys Ile Leu His
                325                 330                 335

Leu Val Gln Gln Trp Lys Glu Lys Pro Ala Glu Glu Tyr Gly Ser Lys
            340                 345                 350

Glu Val Glu Ile Leu Phe Thr Ala Val Tyr Thr Thr Val Asn Ser Leu
        355                 360                 365

Ala Glu Lys Ala Cys Met Glu Gln Gly Arg Ser Val Lys Gln Leu Leu
    370                 375                 380
```

```
Ile Lys Leu Trp Val Glu Leu Leu Thr Ser Phe Lys Lys Glu Leu Asp
385                 390                 395                 400

Ser Trp Thr Glu Lys Met Ala Leu Thr Leu Asp Glu Tyr Leu Ser Phe
            405                 410                 415

Ser Trp Val Ser Ile Gly Cys Arg Leu Cys Ile Leu Asn Ser Leu Gln
            420                 425                 430

Phe Leu Gly Ile Lys Leu Ser Glu Glu Met Leu Trp Ser Gln Glu Cys
            435                 440                 445

Leu Asp Leu Cys Arg His Val Ser Ser Val Val Arg Leu Leu Asn Asp
            450                 455                 460

Leu Gln Thr Phe Lys Lys Glu Arg Ile Glu Asn Thr Ile Asn Gly Val
465                 470                 475                 480

Asp Val Gln Leu Ala Ala Arg Lys Gly Glu Arg Ala Ile Thr Glu Glu
            485                 490                 495

Glu Ala Met Ser Lys Ile Lys Glu Met Ala Asp His His Arg Arg Lys
            500                 505                 510

Leu Met Gln Ile Val Tyr Lys Glu Gly Thr Ile Phe Pro Arg Glu Cys
            515                 520                 525

Lys Asp Val Phe Leu Arg Val Cys Arg Ile Gly Tyr Tyr Leu Tyr Ser
530                 535                 540

Gly Asp Glu Leu Thr Ser Pro Gln Gln Met Lys Glu Asp Met Lys Ala
545                 550                 555                 560

Leu Val His Glu Ser Ser Ser
            565

<210> SEQ ID NO 4
<211> LENGTH: 1704
<212> TYPE: DNA
<213> ORGANISM: Leonotis leonurus

<400> SEQUENCE: 4
atgtcggtgg cgttcaacct catagtcgtc cgttttccgg gccatggaat tcagagcagt      60
agagaaactt ttccagccaa aattattacc agaactaaat caagcatgag attccaaagc     120
agcctcaaca cttcaacaga tttcgtggga aaaataagag agatgatcag agggaaaact     180
gataattcta ttaatcccct ggatattccc tccactctat gcgtaatcga caccctacac     240
agcttcggaa ttgatcgcta cttccaatcc gaaatcaact ctgttcttca ccacacatac     300
agattatgga acgacagaaa taatatcatc ttcaaagatg tcatttgctg cgcaattgcc     360
tttagacttt tgcgagtgaa aggatatcaa gtctcatcag atgaactggc gccatttgcc     420
caacaacagg tgactggact acaaacaagc gacattgcca cgattctaga gctctacaga     480
gcatcacagg agagattaca cgaagacgac gacactcttg acaaactaca tgattggagc     540
agcaaccttc tgaagctgca tctgctgaat gagaacattc ctgatcataa actgcacaaa     600
cgggtggggt atttcttgaa gactaccat ggcatgctag atcgcgttgc ggttagacga     660
aacatcgacc ttcacaacat aaaccattac caaatcccag aagttgcaga taggttccct     720
actgaagctt ttcttgaatt ttcaaggcaa gatttttaata tttgccaagc tcaacaccag     780
aaagaacttc agcaactgca taggtggtat gcagattgta gattggacac actgaatcac     840
ggaacagacg tagtacatt tgctaatttt ctaacttcag caattttcgg agagcctgaa     900
ttctccgagg ctcgtctagc ctttgctaaa caggttatcc taataacacg tatggatgat     960
ttcttcgatc acgatgggtc tagagaagaa tcacacaaga tcctccatct agttcaacaa    1020
tggaaagaga agcccgccga agaatatggt tcaaaggaag ttgagatcct ctttacagca    1080
```

```
gtgtacacta cagtaaatag cttggcagaa aaggcttgta tggagcaagg ccgtagtgtc    1140
aaacaacttc taattaagct gtgggtcgag ctgctaacaa gtttcaagaa agaattggat    1200
tcatggacgg agaagatggc gctaaccttg gatgagtact tgtctttctc ctgggtgtca    1260
attggctgca gactctgcat tctcaattcc ctgcaatttc ttgggataaa attatctgaa    1320
gaaatgctgt ggagtcaaga gtgtctggat ttatgccggc atgtttcatc agtggttcgc    1380
ctgctcaacg atttacaaac tttcaagaag agcgcatag aaaatacgat aaacggtgtg    1440
gacgttcagc tagctgctcg taaaggcgaa agagccatta cagaagagga ggccatgtcc    1500
aagattaagg aaatggctga ccatcacagg agaaaactga tgcaaattgt gtataaagaa    1560
ggaaccattt ttccaagaga atgcaaagat gtgtttttga gagtgtgcag gattggctac    1620
tatctctact cgggcgatga gttaacttct ccacaacaaa tgaaggagga tatgaaagcg    1680
ttggtacatg aatcatcctc ttga                                           1704
```

<210> SEQ ID NO 5
<211> LENGTH: 751
<212> TYPE: PRT
<213> ORGANISM: Mentha spicata
<220> FEATURE:
<221> NAME/KEY: VARIANT
<222> LOCATION: (1)...(751)
<223> OTHER INFORMATION: Xaa = Any Amino Acid

<400> SEQUENCE: 5

```
Met Ser Ser Ile Arg Asn Leu Ser Leu His Ile Asp Leu Pro Lys Ala
1               5                   10                  15

Glu Lys Lys Leu Val Glu Lys Ile Arg Glu Arg Ile Arg Asn Gly Arg
                20                  25                  30

Val Glu Met Ser Pro Ser Ala Tyr Asp Thr Ala Trp Val Ala Met Val
            35                  40                  45

Pro Ser Arg Gly Tyr Ser Gly Arg Pro Gly Phe Pro Glu Cys Val Asp
        50                  55                  60

Trp Ile Ile Glu Asn Gln Asn Pro Asp Gly Ser Trp Gly Leu Asp Ser
65                  70                  75                  80

Asp Gln Pro Leu Leu Val Lys Asp Ser Leu Ser Ser Thr Leu Ala Cys
                85                  90                  95

Leu Leu Ala Leu Arg Lys Trp Lys Thr His Asn Gln Leu Val Gln Arg
            100                 105                 110

Gly Met Glu Phe Ile Asp Ser Arg Gly Trp Ala Ala Thr Asp Asp Asp
        115                 120                 125

Asn Gln Ile Ser Pro Ile Gly Phe Asn Ile Ala Phe Pro Ala Met Ile
    130                 135                 140

Asn Tyr Ala Lys Glu Leu Asn Leu Thr Leu Pro Leu His Pro Pro Ser
145                 150                 155                 160

Ile His Ser Leu Leu His Ile Arg Asp Ser Glu Ile Arg Lys Arg Asn
                165                 170                 175

Trp Glu Tyr Val Ala Glu Gly Val Val Asp Asp Thr Ser Asn Trp Lys
            180                 185                 190

Gln Ile Ile Gly Thr His Gln Arg Asn Asn Gly Ser Leu Phe Asn Ser
        195                 200                 205

Pro Ala Thr Thr Ala Ala Ala Val Ile His Ser His Asp Asp Lys Cys
    210                 215                 220

Phe Arg Tyr Leu Ile Ser Thr Leu Glu Asn Ser Asn Gly Gly Trp Val
225                 230                 235                 240
```

```
Pro Thr Ile Tyr Pro Tyr Asp Ile Tyr Ala Pro Leu Cys Met Ile Asp
                245                 250                 255

Thr Leu Glu Arg Leu Gly Ile His Thr Tyr Phe Glu Val Glu Leu Ser
            260                 265                 270

Gly Ile Phe Asp Asp Ile Tyr Arg Asn Trp Gln Glu Arg Glu Glu Glu
        275                 280                 285

Ile Phe Cys Asn Val Met Cys Arg Ala Leu Ala Phe Arg Leu Leu Arg
    290                 295                 300

Met Arg Gly Tyr His Val Ser Ser Asp Glu Leu Ala Glu Phe Val Asp
305                 310                 315                 320

Lys Glu Glu Phe Phe Asn Ser Val Ser Met Gln Glu Ser Gly Glu Gly
                325                 330                 335

Thr Val Leu Glu Leu Tyr Arg Ala Ser Leu Thr Lys Ile Asn Glu Glu
            340                 345                 350

Glu Arg Ile Leu Asp Lys Ile His Ala Trp Thr Lys Pro Phe Leu Lys
        355                 360                 365

His Gln Leu Leu Asn Arg Ser Ile Arg Asp Lys Arg Leu Glu Lys Gln
    370                 375                 380

Val Glu Tyr Asp Leu Lys Asn Phe Tyr Gly Ala Leu Val Arg Phe Gln
385                 390                 395                 400

Asn Arg Arg Thr Ile Asp Ser Tyr Asp Ala Lys Ser Ile Gln Ile Ser
                405                 410                 415

Lys Thr Ala Tyr Arg Cys Ser Thr Val Tyr Asn Glu Asp Phe Ile His
            420                 425                 430

Leu Ser Val Glu Asp Phe Lys Ile Ser Arg Ala Gln Tyr Leu Lys Glu
        435                 440                 445

Leu Glu Glu Met Asn Lys Trp Tyr Ser Asp Cys Arg Leu Asp Leu Leu
    450                 455                 460

Thr Lys Gly Arg Asn Ala Cys Arg Glu Ser Tyr Ile Leu Thr Ala Ala
465                 470                 475                 480

Ile Ile Val Asp Pro His Glu Ser Met Ala Arg Ile Ser Tyr Ala Gln
                485                 490                 495

Ser Ile Leu Leu Ile Thr Val Phe Asp Asp Phe Phe Asp His Tyr Gly
            500                 505                 510

Ser Lys Glu Glu Ala Leu Asn Ile Ile Asp Leu Val Lys Glu Trp Lys
        515                 520                 525

Pro Ala Gly Ser Tyr Cys Ser Lys Glu Val Glu Ile Leu Phe Thr Ala
    530                 535                 540

Leu His Asp Thr Ile Asn Glu Ile Ala Ala Lys Ala Asp Ala Glu Gln
545                 550                 555                 560

Gly Phe Ser Ser Lys Gln Gln Leu Ile Asn Met Trp Val Glu Leu Leu
                565                 570                 575

Glu Ser Ala Val Arg Glu Lys Asp Ser Leu Ser Xaa Asn Lys Val Ser
            580                 585                 590

Thr Leu Glu Glu Tyr Leu Ser Phe Ala Pro Ile Thr Ile Gly Cys Lys
        595                 600                 605

Leu Cys Val Leu Thr Ser Val His Phe Leu Gly Ile Lys Leu Ser Glu
    610                 615                 620

Glu Ile Trp Thr Ser Glu Glu Leu Ser Ser Leu Cys Arg His Gly Asn
625                 630                 635                 640

Val Val Cys Arg Leu Leu Asn Asp Leu Lys Thr Tyr Glu Arg Glu Arg
                645                 650                 655
```

```
Glu Glu Asn Thr Leu Asn Ser Val Ser Val Gln Thr Val Gly Gly
                660                 665                 670

Val Ser Glu Glu Glu Ala Val Thr Lys Val Glu Val Leu Glu Phe
            675                 680                 685

His Arg Arg Lys Val Met Gln Leu Ala Cys Arg Arg Gly Gly Ser Ser
        690                 695                 700

Val Pro Arg Glu Cys Lys Glu Leu Val Trp Lys Thr Cys Thr Ile Gly
705                 710                 715                 720

Tyr Cys Leu Tyr Gly His Asp Gly Gly Asp Glu Leu Ser Ser Pro Lys
                725                 730                 735

Asp Ile Leu Lys Asp Ile Asn Ala Met Met Phe Glu Pro Leu Lys
            740                 745                 750

<210> SEQ ID NO 6
<211> LENGTH: 2256
<212> TYPE: DNA
<213> ORGANISM: Mentha spicata
<220> FEATURE:
<221> NAME/KEY: misc_feature
<222> LOCATION: (1)...(2256)
<223> OTHER INFORMATION: n = A,T,C or G

<400> SEQUENCE: 6
atgagttcca ttcgaaattt aagtttgcat attgatctgc caaaggccga gaagaagttg      60
gttgagaaaa tcagagagag gataagaaat gggagggtgg agatgtcgcc gtcggcttac     120
gacaccgcgt gggtggccat ggtgccgtct cgaggatatt ccggcaggcc gggtttcccg     180
gagtgcgtgg attggataat cgagaaccag atccggacg  gtcgtgggg  tttggattcg     240 gatcaaccac ttctggtcaa agactccctc tcgtccacct tggcatgcct acttgccctg     300
cgtaaatgga aaacacacaa ccaactagtg caaaggggca tggagttcat cgactcccgt     360
ggttgggctg caactgatga tgacaatcag atttctccta ttggattcaa tattgccttt     420
cctgcaatga ttaattacgc caaagagctt aatttaactc tgcctctaca tccaccttcg     480
attcattcat tgttacacat tagagattca gaaataagaa agcgaaactg gaatacgta      540 gctgaaggag tagtcgacga tacaagcaat tggaagcaaa taatcggcac gcatcaaaga     600
aataatggat ccttgttcaa ctcacctgct accactgcag ctgctgttat tcactctcac     660
gacgataaat gttccgata  tttgatctcc actcttgaga attctaacgg tggatgggta     720
ccaactatct atccatacga tatatacgct cctctctgca tgatcgatac gctagaaaga     780
ttaggaatac acacatattt tgaagttgaa ctcagcggca tttttgatga catatacagg     840
aattggcaag agagagaaga agagatcttt tgtaatgtta tgtgtcgagc tctggcattt     900
cggcttctac gaatgagggg atatcatgtt tcatctgatg aactagcaga atttgtggac     960
aaggaggagt tttttaatag cgtgagcatg caagagagcg gcgaaggcac agtgcttgag    1020
ctttacagag cttcactcac aaaaatcaac gaagaagaaa ggattctcga caaaattcat    1080
gcatggacca aaccatttct caagcaccag cttctcaacc gcagcattcg cgacaaacga    1140
ttagagaagc aggtggaata cgacttgaag aacttctacg gcgcactagt ccgattccag    1200
aacagaagaa ccatcgactc atacgatgct aaatcaatcc aaatttcgaa acagcatat    1260 aggtgctcta cagtttacaa tgaagacttc atccatttat ccgttgagga cttcaaaatc    1320
tcccgagcac aatacctaaa agaacttgaa gaaatgaaca gtggtactc  tgattgtagg    1380 ttggacctct taactaaagg aagaaatgca tgtcgagaat cttacatttt aacagctgca    1440
atcattgtcg atcctcacga atccatggct cgaatctctt acgctcaatc tattcttctt    1500
```

-continued

```
ataactgttt tcgacgactt tttcgatcat tatgggtcta aagaagaggc tctcaatatt   1560
attgatctag tcaaggaatg aagccagct ggcagttact gctccaaaga agtggagatt    1620
ttgtttactg cattacacga cacgataaat gagattgcag ccaaggctga tgcagagcaa   1680
ggcttttctt ccaaacaaca gcttatcaac atgtgggtgg agctacttga gagcgccgtg   1740
agagaaaagg actcgctgag tggnaacaaa gtgtcgactc tagaagagta cttatctttc   1800
gcaccaatca ccatcggctg caaactttgc gtcctgacgt ctgtccattt cctcggaatc   1860
aaactgtccg aggaaatctg gacttccgag gagttgagca gtctgtgcag gcacggcaat   1920
gttgtctgca gactgctcaa cgacctcaag acttacgaga gagagcgcga agagaacacg   1980
ctcaacagcg tgagcgtgca gacagtggga ggaggcgttt cggaggaaga ggcggtgacg   2040
aaggtggagg aggtgttgga atttcataga agaaaagtga tgcagctcgc gtgtcgaaga   2100
ggaggaagca gtgttccgag agaatgtaag gagctggtgt ggaagacgtg cacgataggt   2160
tactgcttgt acggtcacga cggaggcgat gagttatcgt ctccgaagga tattctaaag   2220
gacattaatg caatgatgtt tgagcctctc aagtga                            2256
```

<210> SEQ ID NO 7
<211> LENGTH: 800
<212> TYPE: PRT
<213> ORGANISM: Nepeta mussinii

<400> SEQUENCE: 7

```
Met Ser Leu Pro Leu Ser Ser Cys Val Leu Phe Pro Pro Asn Asp Ser
1               5                   10                  15

Arg Phe Pro Val Ser Arg Phe Ser Arg Ala Ser Ala Ser Leu Glu Val
            20                  25                  30

Gly Leu Gln Gly Ala Thr Ser Ala Lys Val Ser Ser Gln Ser Ser Cys
        35                  40                  45

Phe Glu Glu Thr Lys Arg Arg Ile Thr Lys Leu Phe His Lys Asp Glu
    50                  55                  60

Leu Ser Val Ser Thr Tyr Asp Thr Ala Trp Val Ala Met Val Pro Ser
65                  70                  75                  80

Pro Thr Ser Ser Glu Glu Pro Cys Phe Pro Gly Cys Leu Thr Trp Leu
                85                  90                  95

Leu Glu Asn Gln Cys Arg Asp Gly Ser Trp Ala Arg Pro His His His
            100                 105                 110

Ser Leu Leu Lys Lys Asp Val Leu Ser Ser Thr Leu Ala Cys Ile Leu
        115                 120                 125

Ala Leu Lys Lys Trp Gly Val Gly Glu Glu Gln Ile Asn Lys Gly Leu
    130                 135                 140

His Phe Ile Glu Leu Asn Cys Ala Ser Ala Thr Glu Lys Cys Gln Ile
145                 150                 155                 160

Thr Pro Val Gly Phe Asp Ile Ile Phe Pro Ala Met Leu Asp Tyr Ala
                165                 170                 175

Arg Asp Phe Ser Leu Asn Leu Arg Leu Glu Pro Thr Thr Phe Asn Asp
            180                 185                 190

Leu Met Asp Lys Arg Asp Leu Glu Leu Lys Arg Cys Tyr Gln Asn Tyr
        195                 200                 205

Thr Pro Glu Arg Glu Ala Tyr Leu Ala Tyr Ile Val Glu Gly Met Gly
    210                 215                 220

Arg Leu Gln Asp Trp Glu Leu Val Met Lys Tyr Gln Arg Lys Asn Gly
225                 230                 235                 240
```

-continued

```
Ser Leu Phe Asn Cys Pro Ser Thr Thr Ala Ala Ala Phe Ile Ala Leu
                245                 250                 255

Arg Asp Ser Ala Cys Leu Asn Tyr Leu Asn Leu Ser Leu Lys Lys Phe
            260                 265                 270

Gly Asn Ala Val Pro Ala Val Tyr Pro Leu Asp Ile Tyr Ser Gln Leu
        275                 280                 285

Cys Thr Val Asp Asn Leu Glu Arg Leu Gly Ile Asn Gln Tyr Phe Ile
    290                 295                 300

Ala Glu Ile Gln Ser Val Leu Asp Glu Thr Tyr Arg Cys Trp Ile Gln
305                 310                 315                 320

Gly Asn Glu Asp Ile Phe Leu Asp Thr Ser Thr Cys Ala Leu Ala Phe
                325                 330                 335

Arg Ile Leu Arg Met Asn Gly Tyr Asp Val Thr Ser Asp Ser Leu Thr
            340                 345                 350

Lys Ile Leu Glu Glu Cys Phe Ser Ser Phe Arg Gly Asn Met Thr
        355                 360                 365

Asp Ile Asn Thr Thr Leu Asp Leu Tyr Arg Ala Ser Glu Leu Met Leu
    370                 375                 380

Tyr Pro Asp Glu Lys Asp Leu Glu Lys His Asn Leu Arg Leu Lys Leu
385                 390                 395                 400

Leu Leu Lys Gln Lys Leu Ser Thr Val Leu Ile Gln Ser Phe Gln Leu
                405                 410                 415

Gly Arg Asn Ile Asn Glu Glu Val Lys Gln Thr Leu Glu His Pro Phe
            420                 425                 430

Tyr Ala Ser Leu Asp Arg Ile Ala Lys Arg Lys Asn Ile Glu His Tyr
        435                 440                 445

Asn Phe Asp Asn Thr Arg Ile Leu Lys Thr Ser Tyr Cys Ser Pro Asn
    450                 455                 460

Phe Gly Asn Lys Asp Phe Phe Leu Ser Ile Glu Asp Phe Asn Trp
465                 470                 475                 480

Cys Gln Val Ile His Arg Gln Glu Leu Ala Glu Leu Glu Arg Trp Leu
                485                 490                 495

Ile Glu Asn Arg Leu Asp Glu Leu Lys Phe Ala Arg Ser Lys Ser Ala
            500                 505                 510

Tyr Cys Tyr Phe Ser Ala Ala Ala Thr Phe Phe Ala Pro Glu Leu Ser
        515                 520                 525

Asp Ala Arg Met Ser Trp Ala Lys Ser Gly Val Leu Thr Thr Val Val
    530                 535                 540

Asp Asp Phe Phe Asp Val Gly Gly Ser Met Glu Glu Leu Lys Asn Leu
545                 550                 555                 560

Ile Gln Leu Val Glu Leu Trp Asp Val Asp Ala Ser Thr Lys Cys Ser
                565                 570                 575

Ser His Asn Val His Ile Ile Phe Ser Ala Leu Arg Arg Thr Ile Tyr
            580                 585                 590

Glu Ile Gly Asn Lys Gly Phe Lys Leu Gln Gly Arg Asn Ile Thr Asn
        595                 600                 605

His Ile Ile Asp Ile Trp Leu Asp Leu Leu Asn Ser Met Met Lys Glu
    610                 615                 620

Thr Glu Trp Ala Arg Asp Asn Phe Val Pro Thr Ile Asp Glu Tyr Met
625                 630                 635                 640

Ser Asn Ala Tyr Thr Ser Phe Ala Leu Gly Pro Ile Val Leu Pro Thr
                645                 650                 655
```

```
Leu Tyr Leu Val Gly Pro Lys Leu Ser Glu Met Ile Asn His Ser
            660                 665                 670

Glu Tyr His Asn Leu Phe Lys Leu Met Ser Thr Cys Gly Arg Leu Leu
        675                 680                 685

Asn Asp Ile Arg Gly Tyr Glu Arg Glu Leu Lys Asp Gly Lys Leu Asn
    690                 695                 700

Ala Leu Ser Leu Tyr Ile Ile Asn Asn Gly Gly Lys Val Ser Lys Glu
705                 710                 715                 720

Ala Gly Ile Ser Glu Met Lys Ser Trp Ile Glu Ala Gln Arg Arg Glu
                725                 730                 735

Leu Leu Arg Leu Val Leu Glu Ser Asn Lys Ser Val Leu Pro Lys Ser
            740                 745                 750

Cys Lys Glu Leu Phe Trp His Met Cys Ser Val Val His Leu Phe Tyr
        755                 760                 765

Cys Lys Asp Asp Gly Phe Thr Ser Gln Asp Leu Ile Gln Val Val Asn
    770                 775                 780

Ala Val Ile His Glu Pro Ile Ala Leu Lys Asp Phe Lys Val His Glu
785                 790                 795                 800

<210> SEQ ID NO 8
<211> LENGTH: 2403
<212> TYPE: DNA
<213> ORGANISM: Nepeta mussinii

<400> SEQUENCE: 8
```

| | | | | |
|---|---|---|---|---|
| atgtctcttc | cgctctcctc | ttgtgtctta | tttcccccca | atgactcacg | ttttccggtc | 60 |
| tcccgctttt | ctcgcgcttc | agcttctttg | gaagtcgggc | ttcaaggagc | tacttcagca | 120 |
| aaagtctcct | cacaatcatc | gtgttttgag | gagacaaaga | gaaggataac | aaagttgttt | 180 |
| cataaggacg | aactttcggt | ttcgacatat | gacacagcat | gggttgctat | ggtcccttct | 240 |
| ccaacttctt | cagaggaacc | ttgcttccca | ggttgtttga | cttggttgct | tgaaaaccag | 300 |
| tgtcgagatg | gttcatgggc | tcgtccccac | catcactctt | tgttaaaaaa | agatgtcctt | 360 |
| tcttctacct | tggcatgcat | tctcgcactt | aaaaaatggg | gggttggtga | agaacaaatc | 420 |
| aacaagggtt | tgcattttat | agagctaaat | tgtgcttcag | ctaccgagaa | gtgtcaaatt | 480 |
| actcccgtgg | ggtttgacat | tatatttcct | gccatgcttg | attatgcaag | agacttctct | 540 |
| ttgaacttgc | gtttagagcc | aactacgttt | aatgatttga | tggataaaag | ggatttagag | 600 |
| ctcaaaaggt | gttaccaaaa | ttacacaccg | gagagggaag | catacttggc | atatatagtt | 660 |
| gaaggaatgg | gaagattgca | agattgggaa | ttggtgatga | aatatcaaag | aaagaatgga | 720 |
| tctcttttca | attgtccatc | tacaactgca | gcagctttta | ttgcccttcg | ggattctgcg | 780 |
| tgcctcaact | atctgaattt | gtctttgaaa | aagttcggga | atgcagttcc | tgcagtttat | 840 |
| cctctagata | tatattctca | actttgcacg | gttgataatc | ttgaaaggct | ggggatcaac | 900 |
| caatatttta | tagcagaaat | tcagtcgtgt | tggatgaaa | cgtacagatg | ttggatacag | 960 |
| ggaaacgaag | acatattttt | ggacacctca | acttgtgctt | tagcattccg | aatattgaga | 1020 |
| atgaatggct | atgatgtgac | ttcagattca | cttacaaaaa | tcctagaaga | gtgcttttca | 1080 |
| agttcctttc | gtgaaatat | gacagacatt | aacacaactc | ttgacttata | tagggcatca | 1140 |
| gaacttatgt | tatatccaga | tgaaaaggat | ctggagaaac | ataatttaag | gcttaaactc | 1200 |
| ttacttaagc | aaaaactatc | cactgtttta | atccaatcat | ttcaacttgg | aagaaatatc | 1260 |
| aatgaagagg | tgaaacagac | tctcgagcat | cccttttatg | caagtttgga | taggattgca | 1320 |

-continued

```
aagcggaaaa atatagagca ttacaacttt gataacacaa gaattcttaa aacttcatat    1380
tgttcgccaa attttggcaa caaggatttc ttttttcttt ccatagaaga cttcaattgg    1440
tgtcaagtca tacatcgaca agaactcgca gaacttgaaa gatggttaat tgaaaataga    1500
ttggatgagc tgaagtttgc aaggagtaag tctgcatact gttattttc tgcggcagca    1560 acttttttg ctccagaatt gtcggatgcc cgcatgtcat gggctaaaag tggtgttcta    1620
accacagtgg tagatgactt ttttgatgtt ggaggttcta tggaggaatt gaagaactta    1680
attcaattgg ttgaactatg ggatgtggat gctagcacaa aatgctcttc tcataatgtc    1740
catataatat tttcagcact taggcgcacc atctatgaga tagggaacaa aggatttaag    1800
ctacaaggac gtaacattac caatcatata attgacattt ggctagattt actaaactct    1860
atgatgaaag aaaccgaatg ggccagagac aactttgtcc caacaattga tgaatacatg    1920
agcaatgcat atacatcgtt tgctctgggg ccaattgtcc ttccaactct ctatcttgtc    1980
gggcccaagc tctcagaaga gatgattaac cactccgaat accataacct attcaaattg    2040
atgagtacgt gcggacgtct tctaaatgac atccgtggtt atgagagaga actgaaagat    2100
ggtaaattga acgcgttatc attgtacata attaataatg gtggtaaagt aagtaaagaa    2160
gctggcatct cggagatgaa aagttggatc gaggcacaac gaagagagtt actgagatta    2220
gttttggaga gcaacaaaag cgtccttccg aagtcgtgca aggaattgtt ttggcatatg    2280
tgctcagtgg tgcatctatt ctactgcaaa gatgatggat tcacctcgca ggatttgatt    2340
caagttgtaa atgcagttat tcatgaacct attgctctca aggattttaa ggtgcatgaa    2400
taa                                                                  2403
```

<210> SEQ ID NO 9
<211> LENGTH: 579
<212> TYPE: PRT
<213> ORGANISM: Origanum majorana

<400> SEQUENCE: 9

```
Met Ala Ser Leu Ala Phe Thr Pro Gly Ala Ala Thr Phe Ser Gly Asn
1               5                   10                  15

Val Val Arg Arg Arg Lys Asp Asn Phe Pro Val His Gly Phe Pro Thr
            20                  25                  30

Thr Ile Arg Ser Ser Val Ser Val Thr Val Lys Cys Tyr Val Ser Thr
        35                  40                  45

Thr Asn Leu Met Val Lys Ile Lys Glu Lys Phe Lys Gly Lys Asn Val
    50                  55                  60

Asn Ser Leu Thr Val Glu Ala Ala Asp Asp Met Pro Ser Asn Leu
65                  70                  75                  80

Cys Ile Ile Asp Thr Leu Gln Arg Leu Gly Ile Asp Arg Tyr Phe Gln
                85                  90                  95

Pro Gln Val Asp Ser Val Leu Asp His Ala Tyr Lys Leu Trp Gln Gly
            100                 105                 110

Lys Glu Lys Asp Thr Val Tyr Ser Asp Ile Ser Ile His Ala Met Ala
        115                 120                 125

Phe Arg Leu Leu Arg Val Lys Gly Tyr Gln Val Ser Ser Glu Glu Leu
    130                 135                 140

Asp Pro Tyr Ile Asp Val Glu Arg Met Lys Lys Leu Lys Thr Val Asp
145                 150                 155                 160

Val Pro Thr Val Ile Glu Leu Tyr Arg Ala Ala Gln Glu Arg Met Tyr
                165                 170                 175
```

-continued

```
Glu Glu Glu Gly Ser Leu Glu Arg Leu His Val Trp Ser Thr Asn Phe
            180                 185                 190

Leu Met His Gln Leu Gln Ala Asn Ser Ile Pro Asp Glu Lys Leu His
        195                 200                 205

Lys Leu Val Glu Tyr Tyr Leu Lys Asn Tyr His Gly Ile Leu Asp Arg
    210                 215                 220

Val Gly Val Arg Arg Asn Leu Asp Leu Phe Asp Ile Ser His Tyr Pro
225                 230                 235                 240

Thr Leu Arg Ala Arg Val Pro Asn Leu Cys Thr Glu Asp Phe Leu Ser
                245                 250                 255

Phe Ala Lys Glu Asp Phe Asn Thr Cys Gln Ala Gln His Gln Lys Glu
            260                 265                 270

His Glu Gln Leu Gln Arg Trp Phe Glu Asp Cys Arg Phe Asp Thr Leu
        275                 280                 285

Lys Phe Gly Arg Glu Thr Ala Val Gly Ala Ala His Phe Leu Ser Ser
    290                 295                 300

Ala Ile Leu Gly Glu Ser Glu Leu Cys Asn Val Arg Leu Ala Leu Ala
305                 310                 315                 320

Lys His Met Val Leu Val Val Phe Ile Asp Asp Phe Phe Asp His Tyr
                325                 330                 335

Gly Ser Arg Glu Asp Ser Phe Lys Ile Leu His Leu Leu Lys Glu Trp
            340                 345                 350

Lys Glu Lys Pro Ala Gly Glu Tyr Gly Ser Glu Val Glu Ile Leu
        355                 360                 365

Phe Thr Ala Val Tyr Asn Thr Val Asn Glu Leu Ala Glu Met Ala His
    370                 375                 380

Val Glu Gln Gly Arg Asn Ile Lys Gly Phe Leu Ile Glu Leu Trp Val
385                 390                 395                 400

Glu Ile Val Ser Ile Phe Lys Ile Glu Leu Asp Thr Trp Ser Asn Asp
                405                 410                 415

Thr Thr Leu Thr Leu Asp Glu Tyr Leu Ser Ser Ser Trp Val Ser Val
            420                 425                 430

Gly Cys Arg Ile Cys Ile Leu Val Ser Met Gln Leu Leu Gly Val Gln
        435                 440                 445

Leu Thr Asp Glu Met Leu Leu Ser Asp Glu Cys Ile Asn Leu Cys Lys
    450                 455                 460

His Val Ser Met Val Asp Arg Leu Leu Asn Asp Val Gly Thr Phe Glu
465                 470                 475                 480

Lys Glu Arg Lys Glu Asn Thr Gly Asn Ser Val Ser Leu Leu Leu Ala
                485                 490                 495

Ala Ala Val Lys Glu Gly Arg Pro Ile Thr Glu Glu Glu Ala Ile Ile
            500                 505                 510

Lys Ile Lys Lys Met Ala Glu Asn Glu Arg Arg Lys Leu Met Gln Ile
        515                 520                 525

Val Tyr Lys Arg Glu Ser Val Phe Pro Arg Lys Cys Lys Asp Met Phe
    530                 535                 540

Leu Lys Val Cys Arg Ile Gly Cys Tyr Leu Tyr Ala Ser Gly Asp Glu
545                 550                 555                 560

Phe Thr Ser Pro Gln Lys Met Lys Glu Asp Val Lys Ser Leu Ile Tyr
                565                 570                 575

Glu Ser Leu

<210> SEQ ID NO 10
```

<211> LENGTH: 1740
<212> TYPE: DNA
<213> ORGANISM: Origanum majorana

<400> SEQUENCE: 10

```
atggcgtcgc tcgcgttcac acccggagcc gccactttct ccggcaacgt agttcggagg     60
aggaaagata actttccggt ccacggattt ccgacgacga tcaggtcatc ggtctccgtc    120
accgtcaaat gctacgtcag tacaacgaat ttgatggtga aaatcaaaga gaagttcaag    180
ggtaaaaacg tcaattcgct gacagttgaa gctgctgatg acgatatgcc ctctaatctg    240
tgcataattg acaccctcca acgattggga atcgaccgtt acttccaacc ccaagtcgac    300
tctgttctcg accacgccta caactatgg caagggaaag agaagatac ggtgtattcg    360
gacattagta ttcatgcgat ggcatttaga cttttacgag tcaaaggcta tcaagtctct    420
tcggaggaac tggatccata catcgatgtg agcgaatga agaaactgaa acagttgat    480
gttccgacgg ttatcgaact gtacagagcg gcacaggaga gaatgtatga agaagaaggt    540
agccttgaga gactccatgt ttggagcacc aacttcctca tgcaccagct gcaggctaac    600
tcaattcctg atgaaaagct acacaaactg gtggaatact acttgaagaa ctaccatggc    660
atactggata gagttggagt tcgacgaaac ctcgacctat tcgacataag ccattatcca    720
acactcagag ctagggttcc gaacctatgt accgaagatt ttctatcgtt cgcgaaggaa    780
gatttcaata cttgccaagc ccaacaccag aagaacatg agcaactaca aaggtggttc    840
gaagattgta ggttcgatac gttgaagttc ggaagggaga cagccgtagg cgctgctcat    900
tttctatctt cagcaatact tggtgaatct gaactatgta atgttcgtct tgcccttgct    960
aagcatatgg tgcttgtggt attcatcgat gacttcttcg accattatgg ctctagagaa   1020
gactccttca agatcctcca cctcttaaaa gaatggaaag agaagccggc cggagaatac   1080
ggttccgagg aagtcgaaat cctcttcaca gccgtataca atacagtaaa cgagttggcg   1140
gagatggctc atgtcgaaca aggacgtaat atcaaaggat ttctaattga attgtgggtt   1200
gaaatagtgt caattttcaa gatagaactg gatacatgga gcaatgacac aacactaacc   1260
ttggatgagt acttgtcctc ctcatgggtg tcggtcggtt gcagaatctg catcctcgtc   1320
tcaatgcagc tcctcggtgt acaactaacc gacgaaatgc ttctgagcga cgagtgcata   1380
aacctgtgta agcatgtctc gatggtcgat cgcctcctca acgacgtcgg aacattcgag   1440
aaggaacgga aggagaatac aggaaacagt gtgagccttc tgctagcagc agctgtgaaa   1500
gaaggaaggc ctattaccga agaggaagct attattaaaa ttaaaaaaat ggcggaaaac   1560
gagaggagga aactaatgca gattgtgtat aaaagagaga gtgttttccc cagaaaatgc   1620
aaggatatgt tcttgaaggt gtgtagaatt gggtgctatc tatacgcgag cggcgacgaa   1680
tttacgtctc ctcagaaaat gaaggaagat gtgaaatcct taatttatga atccttgtag   1740
```

<210> SEQ ID NO 11
<211> LENGTH: 563
<212> TYPE: PRT
<213> ORGANISM: Origanum majorana

<400> SEQUENCE: 11

```
Met Ser Leu Ala Phe Ser His Val Ser Thr Phe Phe Ser Gly Gln Arg
1               5                   10                  15

Val Val Gly Ser Arg Arg Glu Ile Ile Pro Val Asn Gly Val Pro Thr
            20                  25                  30

Thr Ala Asn Lys Pro Ser Phe Ala Val Lys Cys Asn Leu Thr Thr Lys
```

-continued

```
                35                  40                  45
Asp Leu Met Val Lys Met Lys Glu Lys Leu Lys Gly Gln Asp Gly Asn
 50                  55                  60
Leu Thr Val Gly Val Ala Asp Met Pro Ser Ser Leu Cys Val Ile Asp
 65                  70                  75                  80
Thr Leu Glu Arg Leu Gly Val Asp Arg Tyr Phe Arg Ser Glu Ile His
                 85                  90                  95
Val Ile Leu His Asp Thr Tyr Arg Leu Trp Gln Gln Lys Asp Lys Asp
                100                 105                 110
Ile Cys Ser Asn Val Thr Thr His Ala Met Ala Phe Arg Leu Leu Arg
                115                 120                 125
Val Asn Gly Tyr Glu Val Ser Ser Glu Glu Leu Ala Pro Tyr Ala Asn
                130                 135                 140
Leu Glu His Phe Ser Gln Gln Lys Val Asp Thr Ala Met Ala Ile Glu
145                 150                 155                 160
Leu Tyr Arg Ala Ala Gln Glu Arg Ile His Glu Asp Glu Ser Gly Leu
                165                 170                 175
Asp Lys Ile Leu Ala Trp Thr Thr Thr Phe Leu Glu Gln Gln Leu Leu
                180                 185                 190
Thr Asn Ser Ile Leu Asp Asn Lys Leu His Lys Leu Val Glu Tyr Tyr
                195                 200                 205
Leu Asn Asn Tyr His Gly Gln Thr Asn Arg Val Gly Ala Arg Arg His
                210                 215                 220
Leu Asp Leu Tyr Glu Met Ser His Tyr Gln Asn Leu Lys Pro Ser His
225                 230                 235                 240
Ser Leu Cys Asn Glu Asp Leu Leu Ala Phe Ala Lys Gln Gly Phe Arg
                245                 250                 255
Asp Phe Gln Ile Gln Gln Lys Glu Phe Glu Gln Leu Gln Arg Trp
                260                 265                 270
Tyr Glu Asp Cys Arg Leu Asp Lys Leu Ser Tyr Gly Arg Asp Val Val
                275                 280                 285
Lys Ile Ser Ser Phe Met Ala Ser Ile Leu Met Asp Asp Pro Glu Leu
                290                 295                 300
Ala Asp Val Arg Leu Ser Ile Ala Lys Gln Met Val Leu Val Thr Arg
305                 310                 315                 320
Ile Asp Asp Phe Phe Asp His Gly Gly Ser Arg Glu Asp Ser Tyr Lys
                325                 330                 335
Ile Ile Glu Leu Val Lys Glu Trp Lys Glu Lys Ala Glu Tyr Asp Ser
                340                 345                 350
Glu Glu Val Lys Ile Leu Phe Thr Ala Val Tyr Thr Thr Val Asn Glu
                355                 360                 365
Leu Ala Glu Ala Cys Val Gln Gln Gly Arg Asn Ser Thr Thr Val Lys
                370                 375                 380
Glu Phe Leu Val Gln Leu Trp Ile Glu Ile Leu Ser Ala Phe Lys Val
385                 390                 395                 400
Glu Leu Asp Thr Trp Ser Asp Gly Thr Glu Val Ser Leu Asp Glu Tyr
                405                 410                 415
Leu Ser Trp Ser Trp Ile Ser Asn Gly Cys Arg Val Ser Ile Val Thr
                420                 425                 430
Thr Met His Leu Leu Pro Thr Lys Leu Cys Ser Asp Glu Met Leu Arg
                435                 440                 445
Ser Glu Glu Cys Lys Asp Leu Cys Arg His Val Ser Met Val Gly Arg
                450                 455                 460
```

```
Leu Leu Asn Asp Ile His Ser Phe Glu Lys Glu His Glu Glu Asn Thr
465                 470                 475                 480

Gly Asn Ser Val Ser Ile Leu Val Ala Gly Glu Asp Thr Glu Glu Glu
            485                 490                 495

Ala Ile Gly Lys Ile Lys Glu Ile Val Glu Tyr Glu Arg Arg Lys Leu
        500                 505                 510

Met Gln Ile Val Tyr Lys Arg Gly Thr Ile Leu Pro Arg Glu Cys Lys
        515                 520                 525

Asp Ile Phe Leu Lys Ala Cys Arg Ala Thr Phe Tyr Val Tyr Ser Ser
        530                 535                 540

Thr Asp Glu Phe Thr Ser Pro Arg Gln Val Met Glu Asp Met Lys Thr
545                 550                 555                 560

Leu Ser Ser

<210> SEQ ID NO 12
<211> LENGTH: 1692
<212> TYPE: DNA
<213> ORGANISM: Origanum majorana

<400> SEQUENCE: 12
```

| | | |
|---|---|---|
| atgtcactcg ccttcagcca tgttagtacc tttttctccg gccaaagagt cgtcggaagc | 60 |
| aggagagaga ttattccagt taacggagtt ccgacgacgg ccaataagcc gtcgttcgcc | 120 |
| gttaagtgca accttactac aaaggatttg atggtgaaaa tgaaggagaa gttgaagggg | 180 |
| caagacggta atttgactgt cggagtagcc gatatgccct ctagcctgtg cgtgatcgac | 240 |
| actcttgaaa ggttgggagt tgaccgatac ttccgatctg aaatccacgt tattctacac | 300 |
| gacacttacc ggttatggca acaaaaggac aaagatatat gttccaacgt tactactcat | 360 |
| gcaatggcgt ttagacttct gagagtgaat ggatacgagg tttcatcaga ggaactggct | 420 |
| ccatatgcta acctagagca ctttagccag caaaaagttg atactgcaat ggctatagag | 480 |
| ctctacagag cagcacagga gaaatacac gaagacgaga gcggtctcga caaaatactt | 540 |
| gcttggacca ccactttct cgagcaacag ctgctcacta actccattct tgacaataaa | 600 |
| ttgcataaac tggtggagta ctacttgaac aactaccacg ccaaacgaa tagggtcgga | 660 |
| gctagacgac acctcgacct atatgagatg agccattacc aaaatctaaa accttcacat | 720 |
| agtctatgca atgaagacct tctagcattt gcaaagcaag ttttcgaga tttcaaatc | 780 |
| cagcagcaga aagaattcga gcaactgcaa aggtggtatg aagattgcag gttggacaag | 840 |
| ttgagttatg ggagagatgt agtaaaaatt tctagtttca tggcttcaat attgatggat | 900 |
| gatccagaat tagccgatgt tcgtctctcc atcgccaaac agatggtgct cgtgacacgt | 960 |
| atcgatgatt tcttcgacca cggtggctct agagaagact cctacaagat cattgaacta | 1020 |
| gtaaaagaat ggaaggagaa ggcagaatac gattccgagg aagtaaaaat cctttttaca | 1080 |
| gcagtataca ccacagtaaa tgagctagca gaggcttgtg ttcaacaagg aaggaatagt | 1140 |
| actactgtca agaattcct agttcagttg tggattgaaa tactatcagc tttcaaggtc | 1200 |
| gagctagata cgtggagcga tggcacggaa gtaagcctgg acgagtactt gtcgtggtcg | 1260 |
| tggatttcga atggctgcag agtgtctata gtaacgacga tgcatttgct ccctacgaaa | 1320 |
| ttatgcagtg atgaaatgct taggagtgaa gagtgcaagg attttgtgtag catgttttct | 1380 |
| atggttggcc gcttgctcaa cgacatccac tcttttgaga aggagcatga ggagaatacg | 1440 |
| ggaaacagtg tgagcattct agtagcaggt gaggataccg aagaggaagc tattggaaag | 1500 |

```
atcaaagaga tagttgagta tgagaggaga aaattgatgc aaattgtgta caagagagga      1560
accattctcc caagagaatg caaagacata ttcttgaagg cgtgtagggc tacattttac      1620
gtgtactcga gcacggatga gtttacgtct cctcgacaag tgatggaaga tatgaaaacc      1680
ctaagctcct ag                                                          1692

<210> SEQ ID NO 13
<211> LENGTH: 604
<212> TYPE: PRT
<213> ORGANISM: Origanum majorana

<400> SEQUENCE: 13

Met Val Ser Ala Cys Leu Lys Leu Lys Asn Asn Pro Phe Leu Asp His
1               5                   10                  15

Arg Phe Arg Lys Ser Ser Asn Gly Phe Ser Val Asn Phe Pro Ala Thr
            20                  25                  30

Met Leu Thr Thr Val Lys Cys Ser Arg Asp Asn Ser Glu Asp Leu Ile
        35                  40                  45

Ala Lys Ile Lys Glu Arg Met Asn Glu Lys Phe Val Thr Val Pro Ala
    50                  55                  60

Arg Glu Tyr Ser Val Ile Glu His Arg Asn Pro Lys Pro Ala Trp Cys
65                  70                  75                  80

Gly Gly Leu Gln Ser Lys Thr Val Ile Glu Glu Val Cys Ser Arg
                85                  90                  95

Leu Phe Leu Val Glu His Leu Gln Asp Leu Gly Val Asp Arg Phe Phe
            100                 105                 110

Gln Ser Glu Ile Gln His Ile Leu His His Thr Phe Arg Leu Trp Gln
        115                 120                 125

Gln Lys Asp Glu Gln Val Phe Lys Asp Val Thr Cys Arg Ala Met Ala
    130                 135                 140

Phe Arg Leu Leu Arg Leu Glu Gly Tyr His Val Ser Ser Gly Glu Leu
145                 150                 155                 160

Gly Glu Tyr Val Asp Glu Glu Lys Phe Phe Arg Thr Val Arg Leu Glu
                165                 170                 175

Trp Arg Ser Thr Asp Thr Ile Leu Glu Leu Tyr Lys Ala Ser Gln Val
            180                 185                 190

Arg Leu Pro Glu Asp Asp Asn Asp Asn Ser Asn Ile Leu Lys Asn Leu
        195                 200                 205

His Glu Trp Thr Phe Ile Phe Leu Lys Glu Gln Leu Arg Arg Lys Thr
    210                 215                 220

Ile Leu Asp Lys Gly Leu Glu Arg Lys Val Glu Phe Tyr Leu Lys Asn
225                 230                 235                 240

Tyr His Gly Ile Leu Asp Ala Val Lys His Arg Arg Ser Leu Asp His
                245                 250                 255

Thr Arg Phe Trp Lys Thr Thr Ala Tyr Asn Pro Ala Val Tyr Asp Glu
            260                 265                 270

Asp Leu Phe Arg Leu Ser Ala Gln Asp Phe Met Ala Arg Gln Ala Gln
        275                 280                 285

Ser Gln Lys Glu Leu Glu Met Leu Leu Lys Trp Tyr Asp Glu Cys Arg
    290                 295                 300

Leu Asp Lys Met Glu Tyr Gly Arg Asn Val Ile His Val Ser His Phe
305                 310                 315                 320

Leu Asn Ala Asn Asn Phe Pro Asp Pro Arg Leu Ser Glu Thr Arg Leu
                325                 330                 335
```

```
Ser Phe Ala Lys Thr Met Thr Leu Val Thr Arg Leu Asp Asp Phe Phe
                340                 345                 350

Asp His His Gly Ser Arg Glu Asp Ser Val Leu Ile Ile Glu Leu Ile
            355                 360                 365

Arg Gln Trp Asn Glu Pro Ser Thr Ile Thr Thr Ile Phe Pro Ser Glu
        370                 375                 380

Glu Val Glu Ile Leu Tyr Ser Ala Leu His Ser Thr Val Thr Asp Ile
385                 390                 395                 400

Ala Glu Lys Ala Tyr Pro Ile Gln Gly Arg Cys Ile Lys Ser Leu Ile
                405                 410                 415

Ile His Leu Trp Val Glu Ile Leu Ser Ser Phe Met Ser Glu Met Asp
            420                 425                 430

Ser Cys Thr Ala Glu Thr Gln Pro Asp Phe His Glu Tyr Leu Gly Phe
        435                 440                 445

Ala Trp Ile Ser Ile Gly Cys Arg Ile Cys Ile Leu Ile Ala Ile His
        450                 455                 460

Phe Leu Gly Glu Lys Val Ser Gln Gln Met Val Met Gly Ala Glu Cys
465                 470                 475                 480

Thr Glu Leu Cys Arg His Val Ser Thr Ile Ala Arg Leu Leu Asn Asp
                485                 490                 495

Leu Gln Thr Phe Lys Lys Glu Arg Glu Arg Lys Val Asn Ser Val
            500                 505                 510

Ile Ile Gln Leu Lys Gly Asp Lys Ile Ser Glu Val Ala Val Ser
        515                 520                 525

Asn Ile Glu Arg Met Val Glu Tyr His Arg Lys Glu Leu Leu Lys Met
530                 535                 540

Val Val Arg Arg Glu Gly Ser Leu Val Pro Lys Arg Cys Lys Asp Val
545                 550                 555                 560

Phe Trp Lys Ser Cys Asn Ile Ala Tyr Tyr Leu Tyr Ala Phe Thr Asp
                565                 570                 575

Glu Phe Thr Ser Pro Gln Gln Met Lys Glu Asp Met Lys Leu Leu Phe
            580                 585                 590

Arg Asp Pro Ile Asn Cys Val Pro Ser Ile Pro Ser
        595                 600

<210> SEQ ID NO 14
<211> LENGTH: 1815
<212> TYPE: DNA
<213> ORGANISM: Origanum majorana

<400> SEQUENCE: 14
atggtatctg catgtctaaa actcaaaaat aatcctttct tggaccatcg attcaggaaa      60
agcagcaatg gattttcagt taattttccg gcgaccatgc tcaccactgt caagtgcagc     120
cgcgataatt cagaagactt gatagcaaag ataaagaaa  ggatgaatga aaaatttgtt     180
acggtgccgg cgagggaata ttccgtcatt gagcatcgga atccgaagcc ggcgtggtgc     240
ggtggtttgc aatccaaaac agtaatagaa gaagaagtgt gcagccgtct gtttctggtc     300
gaacaccttc aagatttagg agtagaccgc ttctttcaat cagaaatcca acatattcta     360
catcacacat tcagattatg gcagcaaaaa gatgaacaag ttttaaaga cgtgacatgt     420 cgcgccatgg cattcagact cctgcgtctc gaaggttatc atgtctcgtc aggagaattg     480
ggggagtatg ttgatgagga aaaattcttt agaacggtaa ggttagaatg agaagtacg     540 gatacaattc ttgagctgta caaagcatca caggtaagac tacctgaaga cgacaacgac     600
```

```
aattccaata tcctcaaaaa cttgcacgaa tggaccttca tattttttgaa ggagcagttg    660 cggcgtaaaa ctattcttga taaaggttta gagagaaagg tagaatttta cttgaagaat    720
taccacggca tattagacgc ggttaagcat agacgaagcc tcgatcacac acgattctgg    780
aaaactactg cgtataaccc tgcagtgtat gatgaggatc ttttccgatt gtcggcccaa    840
gatttcatgg ctcgccaagc tcagagccag aaggaacttg agatgttgct caagtggtac    900
gatgaatgta gactggacaa gatggagtat gggcgaaacg tgatacacgt ttcccatttc    960
ttaaacgcaa acaacttccc cgatcctcgc ctgtccgaaa ctcgtctatc ctttgcgaaa   1020
accatgactc tcgtcacgcg tttggatgat ttcttcgatc accatggctc tagagaagat   1080
tcggtcctca tcatcgaatt aataaggcag tggaatgagc cttcaactat tacaacaata   1140
ttcccctccg aagaagtgga gattctctac tctgcactcc actccaccgt aacagatata   1200
gcagagaagg cttatcccat ccagggtcgc tgcatcaaat cgctcataat tcatctgtgg   1260
gtcgagatac tgtcgagctt catgagcgaa atggactcgt gcaccgcgga aactcagccg   1320
gactttcacg agtacttagg gtttgcatgg atctcgatcg gctgcagaat ctgcattctc   1380
atagctatac atttcttggg ggagaaggta tctcaacaaa tggttatggg tgctgagtgc   1440
accgagttat gtaggcacgt ttctacgatc gcacgccttc tcaacgatct ccaaaccttt   1500
aagaaggaga gagaagagag gaaggtaaac agcgtgataa tccagctcaa agggggataag   1560 atatcggagg aggtggccgt gtcgaatata gagagaatgg ttgaatatca caggaaagag   1620
ctgctgaaga tggtggttcg gagagaagga agcttggttc ctaagaggtg taaggacgtg   1680
ttctggaaat cctgcaacat tgcttactat ctgtacgctt ttacagatga attcacttcg   1740
cctcaacaaa tgaaggaaga tatgaaacta ctctttcgtg atccaatcaa ctgcgttcct   1800
tcaattcctt catga                                                    1815
```

<210> SEQ ID NO 15
<211> LENGTH: 584
<212> TYPE: PRT
<213> ORGANISM: Perovskia atriplicifolia

<400> SEQUENCE: 15

```
Met Leu Leu Ala Phe Asn Ile Ser Asp Val Pro Leu Ser Gln His Arg
1               5                   10                  15

Val Ile Leu Ser Arg Arg Glu His Phe Pro Arg His Ala Phe Gln Glu
            20                  25                  30

Phe Pro Met Ile Ala Ala Thr Lys Ser Ser Val Asn Ala Ile Cys Ser
        35                  40                  45

Leu Ala Thr Pro Thr Asp Leu Met Gly Lys Ile Lys Glu Lys Phe Lys
    50                  55                  60

Ala Lys Asp Gly Asp Pro Leu Ala Ala Ala Ile Gln Leu Ala Ala
65                  70                  75                  80

Asp Ile Pro Ser Ser Leu Cys Ile Ile Asp Thr Leu Gln Arg Leu Gly
                85                  90                  95

Val Asp Arg Tyr Phe Gln Ser Glu Ile Asp Ser Ile Leu Glu Glu Thr
            100                 105                 110

His Lys Leu Trp Lys Val Lys Asp Arg Asp Ile Tyr Ser Glu Val Thr
        115                 120                 125

Thr His Ala Met Ala Phe Arg Leu Leu Arg Val Lys Gly Tyr Glu Val
    130                 135                 140

Ser Ser Glu Glu Leu Ala Pro Tyr Ala Glu Gln Glu Arg Phe Asp Leu
145                 150                 155                 160
```

```
Gln Thr Ile Asp Leu Ala Thr Val Ile Glu Leu Tyr Arg Ala Ala Gln
                165                 170                 175

Glu Arg Thr Cys Glu Glu Asn Asp Asn Ser Leu Glu Lys Leu Leu Ala
            180                 185                 190

Trp Thr Thr Thr Phe Leu Lys His Gln Leu Leu Thr Asn Ser Ile Pro
        195                 200                 205

Asp Thr Lys Leu His Lys Gln Val Glu Tyr Tyr Leu Lys Asn Tyr His
    210                 215                 220

Gly Ile Leu Asp Arg Met Gly Val Arg Arg Ser Leu Asp Leu Tyr Asp
225                 230                 235                 240

Ile Ser His Tyr Arg Pro Leu Arg Ala Arg Phe Pro Asn Leu Cys Asn
                245                 250                 255

Glu Asp Phe Leu Ser Phe Ala Arg Gln Asp Phe Ser Met Cys Gln Ala
            260                 265                 270

Gln His Gln Lys Glu Leu Glu Gln Leu Gln Arg Trp Tyr Ser Asp Cys
        275                 280                 285

Arg Leu Asp Ala Leu Leu Lys Phe Gly Arg Asn Val Val Arg Val Ser
    290                 295                 300

Ser Phe Leu Thr Ser Ala Ile Ile Gly Glu Pro Glu Leu Ser Glu Val
305                 310                 315                 320

Arg Leu Val Phe Ala Lys His Ile Ile Leu Val Thr Leu Ile Asp Asp
                325                 330                 335

Leu Phe Asp His Gly Gly Thr Arg Glu Glu Ser Tyr Lys Ile Leu Glu
            340                 345                 350

Leu Val Thr Glu Trp Lys Glu Lys Thr Ala Ala Glu Tyr Gly Ser Glu
        355                 360                 365

Glu Val Glu Ile Leu Phe Thr Ala Val Tyr Asn Thr Val Asn Glu Leu
    370                 375                 380

Val Glu Arg Ala His Val Glu Gln Gly Arg Ser Val Lys Glu Phe Leu
385                 390                 395                 400

Ile Lys Leu Trp Val Gln Ile Leu Ser Ile Phe Lys Ile Glu Leu Asp
                405                 410                 415

Thr Trp Ser Asp Glu Thr Ala Leu Thr Leu Asp Glu Tyr Leu Ser Ser
            420                 425                 430

Ser Trp Val Ser Ile Gly Cys Arg Ile Cys Ile Leu Met Ser Met Gln
        435                 440                 445

Phe Ile Gly Ile Lys Leu Thr Asp Glu Met Leu Leu Ser Glu Glu Cys
    450                 455                 460

Thr Asp Leu Cys Arg His Val Ser Met Val Asp Arg Leu Leu Asn Asp
465                 470                 475                 480

Val Gln Thr Phe Glu Lys Glu Arg Lys Glu Asn Thr Gly Asn Ser Val
                485                 490                 495

Ser Leu Leu Leu Ala Ala Asn Lys Asp Val Thr Glu Glu Glu Ala Ile
            500                 505                 510

Arg Arg Ala Lys Glu Met Ala Glu Cys Asn Arg Arg Gln Leu Met Gln
        515                 520                 525

Ile Val Tyr Lys Thr Gly Thr Ile Phe Pro Arg Lys Cys Lys Asp Met
    530                 535                 540

Phe Leu Lys Val Cys Arg Ile Gly Cys Tyr Leu Tyr Ala Ser Gly Asp
545                 550                 555                 560

Glu Phe Thr Ser Pro Gln Gln Met Met Glu Asp Met Lys Ser Leu Val
                565                 570                 575
```

Tyr Glu Pro Leu Tyr Leu Pro Asn
            580

<210> SEQ ID NO 16
<211> LENGTH: 1755
<212> TYPE: DNA
<213> ORGANISM: Perovskia atriplicifolia

<400> SEQUENCE: 16

| | | | | | |
|---|---|---|---|---|---:|
| atgttacttg | cgttcaacat | aagcgatgtc | cctctctcgc | agcatagagt | aattctgagc | 60 |
| aggagggaac | attttccacg | tcatgcattc | caggaatttc | cgatgatcgc | cgctactaag | 120 |
| tcatctgtta | atgccatttg | cagcctcgct | actccaactg | atttgatggg | aaaaataaaa | 180 |
| gagaagttca | aggccaagga | cggcgatcct | cttgccgccg | cggctattca | actcgcggcg | 240 |
| gatatacoct | cgagtctgtg | tataatcgac | accctccaga | ggtttgggagt | cgaccgatac | 300 |
| ttccaatccg | aaatcgactc | tattctagag | gaaacacaca | agttatggaa | agtgaaagat | 360 |
| agagatatat | actctgaggt | tactactcat | gcaatggcgt | ttagacttct | gcgagtgaag | 420 |
| ggatatgaag | tttcatcaga | ggaactagct | ccgtatgctg | agcaagagcg | ctttgacctg | 480 |
| caaacgattg | atctggcgac | ggttatcgag | ctttacagag | cagcacagga | gagaacatgc | 540 |
| gaagaaaacg | acaacagtct | tgagaaacta | cttgcttgga | ccaccaccct | tctcaagcac | 600 |
| caattgctca | ccaactccat | acctgacacc | aaattgcaca | acaggtgga | atactacttg | 660 |
| aagaactacc | acgggatatt | agatagaatg | ggagttagac | gaagcctcga | cctatacgac | 720 |
| ataagccatt | atcgacctct | gagagcaaga | ttccctaatc | tgtgtaatga | agatttccta | 780 |
| tcatttgcga | ggcaagattt | cagtatgtgc | caagcccaac | accagaagga | acttgagcaa | 840 |
| ctgcaaaggt | ggtattctga | ttgtaggttg | gacgcgttgt | tgaagtttgg | aagaaatgta | 900 |
| gtgcgcgttt | ctagctttct | gacttcagca | attattggtg | aacccgaatt | gtctgaagtt | 960 |
| cgactagtct | ttgccaaaca | tattattctc | gttacactta | ttgatgattt | attcgatcat | 1020 |
| ggtggaacta | gagaagagtc | atacaagatc | cttgaattag | taacagaatg | gaaagagaag | 1080 |
| accgcagcag | aatatggttc | cgaggaagtt | gaaatcctt | ttacagcggt | ctacaacaca | 1140 |
| gtaaatgagt | tggtagagag | ggctcatgtc | gaacaagggc | gcagtgtcaa | agaatttctt | 1200 |
| attaaactgt | gggttcaaat | actatcaatt | ttcaagatag | aattagatac | atggagcgat | 1260 |
| gagactgcgc | taaccttgga | tgaatacttg | tcttcgtcgt | gggtgtcaat | tggttgcaga | 1320 |
| atctgcattc | tcatgtcgat | gcaattcatc | ggtataaaat | taactgatga | aatgcttctg | 1380 |
| agtgaagagt | gcactgattt | tgtgtaggcat | gtttcgatgg | ttgaccggct | gctcaacgat | 1440 |
| gtgcaaacct | tcgagaagga | acgcaaagaa | aatacaggaa | acagtgtaag | ccttctgcta | 1500 |
| gcagctaaca | aagatgttac | tgaagaggaa | gcaattagaa | gagcaaaaga | aatggcggaa | 1560 |
| tgcaacagga | gacaactgat | gcagattgtg | tataaaacag | gaaccatttt | cccaagaaaa | 1620 |
| tgcaaagata | tgtttctcaa | ggtatgcagg | attggctgtt | atttgtatgc | aagcggcgac | 1680 |
| gaattcacat | ctccacaaca | aatgatggaa | gatatgaaat | ccttggttta | tgaacccctc | 1740 |
| tacctaccta | attaa | | | | | 1755 |

<210> SEQ ID NO 17
<211> LENGTH: 593
<212> TYPE: PRT
<213> ORGANISM: Perovskia atriplicifolia

<400> SEQUENCE: 17

```
Met Ser Leu Thr Phe Asn Ala Gly Val Val Arg Phe Ser Ser His Arg
 1               5                  10                  15

Val Arg Ser Thr Lys Asp Cys Phe Thr Val Tyr Gly Phe Pro Met Ile
            20                  25                  30

Ala Asn Lys Ala Ala Phe Ala Val Lys Cys Ser Leu Thr Pro Thr Asp
        35                  40                  45

Leu Met Gly Arg Val Glu Glu Lys Phe Lys Gly Lys Asn Gly Asn Ser
 50                  55                  60

Leu Ala Ala Ser Thr Thr Val Glu Ser Ala Asp Ile Pro Ser Asn Leu
 65                  70                  75                  80

Cys Ile Ile Asp Thr Leu Gln Arg Leu Gly Val Asp Arg Tyr Phe Gln
                85                  90                  95

Thr Glu Ile Asn Ala Ile Leu Glu Asp Thr Tyr Arg Leu Trp Glu Arg
               100                 105                 110

Lys Asp Lys Asp Ile Tyr Ser Asp Ala Thr Thr His Ala Met Ala Phe
            115                 120                 125

Arg Leu Leu Arg Val Lys Gly Tyr Glu Val Ser Ser Glu Glu Leu Ala
        130                 135                 140

Pro Tyr Ala Asp Gln Glu Cys Val Asn Val Gln Thr Ala Asp Val Ala
145                 150                 155                 160

Thr Val Ile Glu Leu Tyr Arg Ala Ala Gln Val Arg Ile Ser Glu Glu
                165                 170                 175

Glu Ser Ser Leu Lys Lys Leu His Ala Trp Thr Thr Thr Phe Leu Lys
            180                 185                 190

Tyr Gln Leu Gln Ser Asn Ser Ile Pro Glu Lys Lys Leu His Lys Leu
        195                 200                 205

Val Glu Tyr Tyr Leu Lys Asn Tyr His Gly Ile Leu Asp Arg Met Gly
210                 215                 220

Val Arg Met Asp Leu Asp Leu Phe Asp Ile Ser His Tyr Arg Thr Leu
225                 230                 235                 240

Gln Ala Ser Asp Arg Phe Ser Ser Leu Arg Asn Glu Asp Phe Leu Glu
                245                 250                 255

Phe Ala Arg Gln Asp Phe Asn Ile Cys Gln Ala Lys His Gln Lys Glu
            260                 265                 270

Leu Gln Gln Leu Gln Arg Trp Tyr Ala Asp Cys Arg Leu Asp Thr Leu
        275                 280                 285

Lys Phe Gly Arg Asp Val Val Arg Val Ala Asn Phe Leu Thr Ser Ala
290                 295                 300

Ile Phe Gly Glu Pro Glu Leu Ser Asp Ala Arg Leu Ile Phe Ala Lys
305                 310                 315                 320

His Ile Val Leu Val Thr Cys Ile Asp Glu Phe Phe Asp His Gly Gly
                325                 330                 335

Ser Lys Glu Glu Ser Tyr Lys Ile Leu Glu Leu Val Glu Glu Trp Lys
            340                 345                 350

Glu Lys Pro Thr Gly Glu Tyr Gly Cys Glu Glu Val Glu Ile Leu Phe
        355                 360                 365

Thr Ala Val Tyr Ser Thr Val Asn Glu Leu Ala Glu Met Ala His Val
370                 375                 380

Glu Gln Gly Arg Ser Val Lys Glu Phe Leu Val Lys Leu Trp Val Gln
385                 390                 395                 400

Ile Leu Ser Ile Phe Lys Ile Glu Leu Asp Thr Trp Ser Asp Asp Thr
                405                 410                 415

Glu Leu Thr Leu Asp Ser Tyr Leu Asn Asn Ser Trp Val Ser Ile Gly
```

|  | | | 420 | | | | | 425 | | | | 430 | |
|---|---|---|---|---|---|---|---|---|---|---|---|---|---|

Cys Arg Ile Cys Ile Leu Met Ser Met Gln Phe Ala Gly Val Lys Leu
    435       440       445

Ser Asp Glu Met Leu Leu Ser Glu Glu Cys Val Asp Leu Cys Arg His
 450        455       460

Val Ser Met Val Asp Arg Leu Leu Asn Asp Val Gln Thr Phe Glu Lys
465       470       475      480

Glu Arg Lys Glu Asn Thr Gly Asn Ser Val Ser Leu Leu Gln Ala Ala
    485       490       495

Ala Glu Arg Glu Gly Arg Ala Ile Thr Glu Glu Ala Ile Thr Gln
    500       505       510

Ile Lys Glu Leu Ala Glu Tyr His Arg Arg Lys Leu Met Gln Ile Val
    515       520       525

Tyr Lys Thr Asp Thr Ile Phe Pro Arg Lys Cys Lys Asp Met Phe Leu
    530       535       540

Lys Val Cys Arg Ile Gly Cys Tyr Leu Tyr Ala Ser Gly Asp Glu Phe
545       550       555      560

Thr Thr Pro Gln Gln Met Met Glu Asp Met Lys Ser Leu Val Tyr Gln
      565       570      575

Pro Leu Thr Val Asp Asp Met Ser Ala Lys Glu Leu Thr Ser Val Arg
    580       585       590

Asn

<210> SEQ ID NO 18
<211> LENGTH: 1782
<212> TYPE: DNA
<213> ORGANISM: Perovskia atriplicifolia

<400> SEQUENCE: 18

| | | | | | |
|---|---|---|---|---|---|
| atgtcactca | ctttcaacgc | tggagtcgtc | cgtttctcca | gccaccgcgt | tcggagcacg | 60 |
| aaagattgct | ttacagttta | cggatttccg | atgattgcaa | ataaggcagc | tttcgcagtt | 120 |
| aaatgcagcc | ttactccaac | cgatttgatg | gggagagtag | aggagaagtt | caagggcaaa | 180 |
| aatggtaatt | cactagcagc | ctcgacgacg | gttaatccg | cggatatacc | ctcgaacctg | 240 |
| tgtataatcg | acaccctcca | aagattggga | gtcgaccgat | actttcaaac | tgaaatcaat | 300 |
| gccattctag | aggacactta | cagattatgg | gaacgaaaag | acaaagacat | atattccgat | 360 |
| gccacaactc | acgcgatggc | gtttaggtta | ctacgagtga | aaggatacga | agtttcatca | 420 |
| gaggaactgg | ctccttacgc | tgatcaagag | tgcgtgaacg | tgcaaacggc | tgatgtggca | 480 |
| acagttatcg | agctttacag | agcagcgcag | gtgagaataa | gcgaagaaga | gagcagtctt | 540 |
| aagaagcttc | atgcttggac | caccaccttt | ctcaaatatc | agttgcagag | taactccata | 600 |
| cctgaaaaga | aactgcacaa | actggtggaa | tattacttga | agaactacca | tggcatattg | 660 |
| gatagaatgg | gagttcgaat | ggacctcgac | ttattcgaca | tcagccatta | tcgaactcta | 720 |
| caagcttccg | ataggttctc | tagtctgcgt | aacgaagatt | ttctagagtt | tgcaaggcaa | 780 |
| gatttcaata | tctgccaagc | caagcaccag | aaagaactcc | aacaactgca | aaggtggtat | 840 |
| gcagattgca | ggctcgacac | cttgaagttc | gggagagacg | tcgtacgcgt | tgctaatttt | 900 |
| ctgacttcag | caatctttgg | cgaacccgag | ctatccgatg | ctcgtctgat | ctttgccaag | 960 |
| catatcgtgc | tcgtaacatg | tatcgatgaa | ttcttcgatc | atggtgggtc | taaagaagag | 1020 |
| tcctacaaga | tccttgaatt | agtagaagaa | tggaaagaga | agccaactgg | agaatatggg | 1080 |
| tgtgaggagg | ttgagatcct | tttcacagca | gtgtacagta | cagtgaatga | gttggcagag | 1140 |

```
atggctcatg tcgaacaagg acgtagtgtg aaagagtttc tagttaaact gtgggtgcag   1200
atactgtcga ttttcaagat agaactggat acatggagtg atgacacgga actgacgttg   1260
gacagctact tgaacaactc gtgggtgtcg atcggatgca gaatctgcat tctcatgtcg   1320
atgcagttcg ccggtgtaaa actgtccgac gaaatgcttc tgagtgaaga gtgtgttgac   1380
ttgtgcaggc acgtctccat ggtcgatcgc ctcctgaacg atgtgcaaac tttcgagaag   1440
gaacgcaagg aaaatacagg aaacagtgtg agccttctgc aagcagcagc tgagagagaa   1500
ggaagagcca ttacagaaga ggaagctatt acacagatca agaattggc tgaataccac    1560 aggagaaaac tgatgcagat tgtgtacaaa acagacacca ttttcccaag aaaatgcaaa   1620
gatatgttct tgaaggtgtg caggattggg tgctatctgt acgcaagtgg agacgaattc   1680
acaactccac aacaaatgat ggaagacatg aaatcattgg tttatcaacc cctaacagtt   1740
gatgacatga gtgccaaaga attgacttct gtgagaaact ag                     1782
```

<210> SEQ ID NO 19
<211> LENGTH: 590
<212> TYPE: PRT
<213> ORGANISM: Salvia officinalis

<400> SEQUENCE: 19

```
Met Ser Leu Ala Phe Asn Ala Ala Val Ala Thr Phe Ser Gly His Arg
1               5                   10                  15

Ile Arg Ser Arg Arg Glu Ile Leu Pro Gly Gln Gly Phe Pro Met Ile
                20                  25                  30

Thr Asn Lys Ser Ser Phe Ala Val Lys Cys Asn Leu Thr Thr Thr Asp
            35                  40                  45

Leu Met Gly Lys Ile Thr Glu Lys Phe Lys Gly Arg Asp Ser Asn Phe
        50                  55                  60

Ser Ala Ala Thr Ala Val Gln Pro Ala Ala Asp Ile Pro Ser Asn Leu
65                  70                  75                  80

Cys Ile Ile Asp Thr Leu Gln Arg Leu Gly Val Asp Arg Tyr Phe Gln
                85                  90                  95

Ser Glu Ile Asp Thr Ile Leu Glu Asp Thr Tyr Arg Leu Trp Gln Arg
            100                 105                 110

Lys Glu Arg Glu Ile Phe Ser Asp Ile Thr Ile His Ala Met Ala Phe
        115                 120                 125

Arg Leu Leu Arg Val Lys Gly Tyr Val Val Ser Ser Glu Glu Leu Ala
130                 135                 140

Pro Tyr Ala Asp Gln Glu Arg Ile Asn Leu Gln Arg Ile Asp Val Ala
                145                 150                 155                 160

Thr Val Ile Glu Leu Tyr Arg Ala Ala Gln Glu Arg Ile Ser Glu Asp
            165                 170                 175

Glu Ser Ser Leu Glu Lys Leu His Ala Trp Thr Ala Thr Tyr Leu Lys
        180                 185                 190

Gln Gln Leu Leu Thr Asn Ser Ile Pro Asp Lys Lys Leu Asn Lys Leu
    195                 200                 205

Val Glu Cys Tyr Leu Lys Asn Tyr His Gly Ile Leu Asp Arg Met Gly
210                 215                 220

Val Arg Gln Asn Leu Asp Leu Tyr Asp Ile Ser His Tyr Gln Thr Leu
225                 230                 235                 240

Lys Ala Ala Asp Arg Phe Ser Asn Leu Arg Asn Glu Asp Phe Leu Ala
                245                 250                 255
```

```
Phe Ala Arg Gln Asp Phe Asn Ile Cys Gln Glu Gln His Gln Lys Glu
            260                 265                 270
Leu Gln Gln Leu Gln Arg Trp Tyr Ala Asp Cys Arg Leu Asp Thr Leu
        275                 280                 285
Lys Tyr Gly Arg Asp Val Val Arg Val Ala Asn Phe Leu Thr Ser Ala
    290                 295                 300
Ile Ile Gly Asp Pro Glu Leu Ser Glu Val Arg Leu Val Phe Ala Lys
305                 310                 315                 320
His Ile Val Leu Val Thr Arg Ile Asp Asp Phe Phe Asp His Gly Gly
                325                 330                 335
Ser Arg Glu Glu Ser Tyr Lys Ile Leu Glu Leu Leu Lys Glu Trp Lys
            340                 345                 350
Glu Lys Pro Ala Ala Glu Tyr Gly Ser Lys Glu Val Glu Ile Leu Phe
        355                 360                 365
Thr Ala Val Tyr Asn Thr Val Asn Glu Leu Ala Glu Met Ala His Ile
    370                 375                 380
Glu Gln Gly Arg Ser Val Lys Glu Phe Leu Ile Lys Leu Trp Val Gln
385                 390                 395                 400
Ile Ile Ser Ile Phe Lys Ile Glu Leu Asp Thr Trp Ser Asp Glu Thr
                405                 410                 415
Ala Leu Thr Leu Asp Glu Tyr Leu Ser Ser Ser Trp Val Ser Ile Gly
            420                 425                 430
Cys Arg Ile Cys Ile Leu Met Ser Met Gln Phe Ile Gly Ile Lys Leu
        435                 440                 445
Ser Asp Glu Met Leu Leu Ser Glu Glu Cys Ile Asp Leu Cys Arg His
    450                 455                 460
Val Ser Met Val Asp Arg Leu Leu Asn Asp Val Gln Thr Phe Glu Lys
465                 470                 475                 480
Glu Arg Lys Glu Asn Thr Gly Asn Ser Val Ser Leu Leu Leu Ala Ala
                485                 490                 495
Asn Lys Asp Asp Ser Ala Phe Thr Glu Glu Ala Ile Thr Lys Ala
            500                 505                 510
Lys Glu Met Ala Glu Cys Asn Arg Arg Gln Leu Met Lys Ile Val Tyr
        515                 520                 525
Lys Thr Gly Thr Ile Phe Pro Arg Lys Cys Lys Asp Met Phe Leu Lys
    530                 535                 540
Val Cys Arg Ile Gly Cys Tyr Leu Tyr Ala Ser Gly Asp Glu Phe Thr
545                 550                 555                 560
Ser Pro Gln Gln Met Met Glu Asp Met Lys Ser Leu Val Tyr Glu Pro
                565                 570                 575
Leu Thr Val Asp Pro Leu Glu Ala Lys Asn Val Ser Gly Lys
            580                 585                 590
```

<210> SEQ ID NO 20
<211> LENGTH: 1773
<212> TYPE: DNA
<213> ORGANISM: Salvia officinalis

<400> SEQUENCE: 20

```
atgtccctcg ccttcaacgc agcagttgcc actttctccg gccacagaat tcggagcagg     60
agagaaattc ttccggggca aggatttccg atgatcacca acaagtcgtc tttcgccgtg    120
aaatgtaacc ttactacaac agatttgatg ggcaagataa cagagaaatt caagggaaga    180
gacagtaatt tttcagcagc aacggctgtt caacctgcgg cggatatacc ctctaacctg    240
```

```
tgcataatcg acaccctcca aaggttggga gtcgaccgat acttccaatc tgaaatcgac    300
actattctag aggacacata caggttatgg caaaggaaag agagagagat attttcggat    360
ataactattc atgcaatggc atttagactt ttgcgagtta aaggatatgt agtttcatca    420
gaggaactgg ctccgtatgc tgaccaagag cgcattaacc tgcaaaggat tgatgtagcg    480
acagttatcg agctttacag agcagcacag gagagaataa gtgaagacga gagcagtctt    540
gagaaactac atgcttggac cgccacctat ctcaagcagc agctgctcac taactccatt    600
cctgacaaga aattgaacaa actggtggaa tgctacttga agaactatca cgggatatta    660
gatagaatgg gagttagaca aaacctcgac ctctacgaca taagccacta tcaaactcta    720
aaagctgcag ataggttctc taatctacgt aatgaagatt ttctagcatt tgcgaggcaa    780
gattttaata tttgccaaga acaacaccaa aaagaacttc agcaactgca aggtggtat     840 gcagattgta ggttggacac attgaagtat ggaagagatg tcgtgcgggt tgctaatttt    900
ctaacatcag caattattgg tgatcctgaa ttgtctgaag tccgtctagt cttcgccaaa    960
catattgtgc ttgtaacacg tattgatgat tttttcgatc atggtggatc tagagaagag   1020
tcctacaaga tccttgaatt actaaaagaa tggaaagaga agccagctgc agaatatggt   1080
tccaaagaag ttgaaattct tttcacagca gtatacaata cagtaaacga gttggcagag   1140
atggctcaca tcgaacaagg acgtagtgtt aaagaatttc taataaagct gtgggttcaa   1200
atcatatcga ttttcaagat agaattagat acatggagcg atgagacagc gctgaccttg   1260
gatgagtact tgtcttcgtc gtgggtgtca attgggtgca gaatctgcat tctcatgtcg   1320
atgcaattca ttggtataaa attatctgat gaaatgcttc tgagtgaaga gtgtattgat   1380
ttgtgtcggc atgtctccat ggttgaccgg ctgctcaacg acgtgcagac tttcgagaag   1440
gaacgcaagg aaaatacagg aaatagcgtg agccttctgc tagcagctaa caaagacgac   1500
agcgccttta ctgaagagga agctattaca aaagcaaaag aaatggcgga atgtaacagg   1560
agacaactga tgaagattgt gtataaaaca ggaaccattt tcccaagaaa atgcaaagat   1620
atgtttctga aggtatgcag gattggctgt tacttgtatg caagcggcga tgaattcaca   1680
tctccacaac aaatgatgga agatatgaaa tccttggtct atgaacccct aacagttgat   1740
cctctcgagg ccaaaaatgt gagtggcaaa tga                                1773
```

<210> SEQ ID NO 21
<211> LENGTH: 798
<212> TYPE: PRT
<213> ORGANISM: Ajuga reptans

<400> SEQUENCE: 21

```
Met Ala Ser Leu Ser Thr Phe His Leu Tyr Ser Ser Leu Leu His
1               5                   10                  15

Arg Lys Thr Leu Gln Ser Ser Pro Lys Leu Asn Leu Ser Ser Glu Cys
                20                  25                  30

Phe Ser Thr Arg Thr Trp Met Asn Ser Lys Asn Leu Ser Leu Asn
        35                  40                  45

Tyr Gln Val Asn Gln Lys Ile Gly Lys Leu Thr Gly Thr Arg Val Ala
    50                  55                  60

Thr Val Asp Ala Pro Gln Gln Leu Glu His Asp Ser Thr Ala Lys
65                  70                  75                  80

Gly His Asp Ile Val Asp Ile Glu Thr Gln Asp Pro Ile Glu Tyr Ile
                85                  90                  95

Arg Met Leu Leu Asn Thr Thr Gly Asp Gly Arg Ile Ser Val Ser Pro
```

```
                100             105             110
Tyr Asp Thr Ala Trp Ile Ala Leu Ile Lys Asp Val Glu Gly Arg Asp
            115             120             125
Phe Pro Gln Phe Pro Ser Ser Leu Glu Trp Ile Ala Asn His Gln Leu
        130             135             140
Ala Asp Gly Ser Trp Gly Asp Glu Gly Phe Phe Cys Val Tyr Asp Arg
145             150             155             160
Leu Val Asn Thr Ile Ala Cys Val Val Ala Leu Arg Ser Trp Asn Val
            165             170             175
His His Asp Lys Ser Gln Arg Gly Ile Gln Tyr Ile Lys Glu Asn Val
        180             185             190
His Gln Leu Lys Asp Gly Asn Ala Glu His Met Met Cys Gly Phe Glu
    195             200             205
Val Val Phe Pro Ala Leu Leu Gln Lys Ala Lys Asn Met Gly Ile Asp
210             215             220
Asp Leu Pro Tyr Glu Ala Pro Val Ile Gln Asp Ile Tyr His Thr Arg
225             230             235             240
Glu Gln Lys Leu Lys Arg Ile Pro Leu Glu Met Met His Lys Val Pro
            245             250             255
Thr Ser Leu Leu Phe Ser Leu Glu Gly Leu Glu Asn Leu Asp Trp Asp
        260             265             270
Lys Leu Leu Lys Leu Gln Ser Ala Asp Gly Ser Phe Leu Thr Ser Pro
    275             280             285
Ser Ser Thr Ala Phe Ala Phe Met Gln Thr Lys Asp Glu Lys Cys Phe
    290             295             300
Gln Phe Ile Lys Asn Thr Val Glu Thr Phe Asn Gly Gly Ala Pro His
305             310             315             320
Thr Tyr Pro Val Asp Val Phe Gly Arg Leu Trp Ala Val Asp Arg Leu
            325             330             335
Gln Arg Leu Gly Ile Ser Arg Phe Phe Glu Ala Glu Ile Ala Asp Cys
        340             345             350
Leu Ser His Ile His Arg Tyr Trp Asn Asp Lys Gly Leu Phe Ser Gly
    355             360             365
Arg Glu Ser Asp Phe Val Asp Ile Asp Asp Thr Ser Met Gly Phe Arg
    370             375             380
Leu Leu Arg Met Gln Gly Tyr Asp Val Ser Pro Asn Val Leu Arg Asn
385             390             395             400
Phe Lys Asn Gly Asp Lys Phe Ser Cys Tyr Gly Gly Gln Thr Ile Glu
            405             410             415
Ser Ser Thr Pro Ile Tyr Asn Leu Tyr Arg Ala Ser Gln Phe Arg Phe
        420             425             430
Pro Gly Glu Glu Ile Leu Glu Glu Ala Asp Lys Phe Ala His Glu Phe
    435             440             445
Leu Ser Glu Gln Leu Gly Asn Asn Gln Leu Leu Asp Lys Trp Val Ile
    450             455             460
Ser Asp Arg Leu Gln Glu Glu Ile Ser Ile Gly Leu Gly Met Pro Phe
465             470             475             480
Tyr Ala Thr Leu Pro Arg Val Glu Ala Ser Tyr Tyr Ile Gln His Tyr
            485             490             495
Ala Gly Ala Asp Asp Val Trp Ile Gly Lys Thr Leu Tyr Arg Met Pro
        500             505             510
Glu Ile Ser Asn Asp Thr Tyr Leu Glu Leu Ala Arg Asn Asp Phe Lys
    515             520             525
```

Arg Cys Gln Ala Gln His Gln Phe Glu Trp Ile Tyr Met Gln Glu Trp
            530                 535                 540

Tyr Glu Ser Cys Asn Ile Glu Glu Phe Gly Ile Ser Arg Lys Glu Leu
545                 550                 555                 560

Leu Arg Val Tyr Phe Leu Ala Cys Ser Ser Ile Phe Glu Val Glu Arg
                565                 570                 575

Thr Lys Glu Arg Met Ala Trp Ala Lys Ser Gln Ile Ile Ser Arg Met
            580                 585                 590

Ile Thr Ser Phe Phe Asn Lys Gln Thr Thr Ser Glu Glu Lys Glu
            595                 600                 605

Thr Leu Leu Thr Glu Phe Arg Asn Ile Asn Gly Leu His Lys Ser Asn
610                 615                 620

Asn Thr Arg Asp Gly Asp Met Asn Ile Val Leu Ala Thr Leu His Gln
625                 630                 635                 640

Phe Phe Ala Gly Phe Asp Arg Tyr Thr Ser His Gln Leu Lys Asn Ala
                645                 650                 655

Trp Gly Val Trp Leu Ser Lys Leu Gln Arg Gly Ala Val Asp Gly Gly
            660                 665                 670

Ala Asp Ala Glu Leu Ile Thr Thr Thr Ile Asn Val Cys Ala Gly His
            675                 680                 685

Ile Ala Leu Lys Glu Asp Ile Leu Ser His Asp Glu Tyr Lys Thr Leu
690                 695                 700

Thr Asp Leu Thr Ser Lys Ile Cys Gln Gln Leu Ser His Ile Gln Asn
705                 710                 715                 720

Glu Lys Val Val Glu Ile Asp Gly Gly Ile Thr Ala Lys Ser Arg Leu
                725                 730                 735

Lys Asn Glu Glu Leu Gln Arg Asp Met Gln Ser Leu Val Lys Leu Val
            740                 745                 750

Leu Glu Lys Ser Val Gly Leu Asn Arg Asn Ile Lys Gln Thr Phe Leu
            755                 760                 765

Thr Val Ala Lys Thr Tyr Tyr Tyr Arg Ala Tyr Asn Ala Glu Glu Thr
770                 775                 780

Met Asp Ala His Ile Phe Lys Val Leu Phe Glu Pro Val Ala
785                 790                 795

<210> SEQ ID NO 22
<211> LENGTH: 2397
<212> TYPE: DNA
<213> ORGANISM: Ajuga reptans

<400> SEQUENCE: 22
atggcctctt tgtccacttt ccacctctac tcttcctcac tccttcaccg caaaacactg      60
caatcttcac caaagcttaa cctgtcttca gaatgcttct ccaccagaac ttggatgaac     120
agcagcaaaa acttgtcgtt aaattaccaa gttaatcaga aaataggaaa gctgacaggg     180
actcgagttg ccactgtgga tgcgccacaa caacttgaac acgatgattc aactgctaaa     240
ggccatgata tagtcgatat tgaaactcag gatccaattg aatatattag aatgctgttg     300
aacacaacag gcgatggcag aatcagcgtt tcgccttacg acacagcatg gattgctctt     360
attaaggacg tggaaggacg tgattttcct caatttccat ccagccttga gtggatcgcg     420
aaccatcaac tcgctgatgg ttcatgggga gacgaaggat ttttctgtgt gtatgatcgg     480
ctcgtaaata ctatagcatg tgtcgtagca ttgagatcat ggaatgtcca tcacgacaag     540
agccaaagag gaatacaata tatcaaggaa aatgtgcatc aacttaagga tggaaatgct     600

```
gagcacatga tgtgtggttt cgaagtagtg tttcctgcac ttcttcaaaa agccaaaaat    660
atgggcattg atgatcttcc atatgaggct cctgtcatcc aggatattta ccatacaagg    720
gagcagaaat tgaaaaggat accattggag atgatgcaca agtgcctac ttctctgctg    780
tttagtttgg aaggactgga gaatttagat tgggataaac tccttaagtt gcagtcagct    840
gatggctctt tcctcacttc tccctcctct actgctttcg cattcatgca acaaaagac    900
gaaaatgct tccagttcat caagaacact gttgaaacct taatggagg agcaccacat    960
acttatccgg tcgatgtttt tggaagactt tgggcggttg ataggctgca gcgcctcgga    1020
atttctcgat tctttgaggc tgagattgct gattgcttaa gtcacattca tagatattgg    1080
aatgataagg ggcttttcag tggacgtgaa tcggactttg tcgatattga cgacacatcc    1140
atgggttca gacttctaag aatgcaaggc tatgatgtta gtccaaatgt actgaggaat    1200
ttcaagaatg gtgacaagtt tcatgttac ggaggtcaaa cgatcgagtc atcaactcca    1260
atatacaatc tgtacagagc ttctcaattc cggttttccag agaagaaat tcttgaagaa    1320
gccgacaagt tcgcccatga gttcttgtcc gaacagcttg gcaacaacca attgcttgat    1380
aaatgggtta tatccgaccg cttgcaggaa gagataagta ttggattggg gatgccattt    1440
tatgccaccc ttcccagagt tgaagcaagc tactatatac aacattacgc tggtgccgac    1500
gacgtgtgga tcggcaagac actctacagg atgccggaaa taagtaatga tacatacctg    1560
gagctagcaa gaaatgattt caagagatgc caagcacaac atcagttcga gtggatctac    1620
atgcaagaat ggtatgagag ttgcaacatt gaagaattcg ggataagccg aaaggagctc    1680
cttcgcgttt actttttggc ttgctctagc atctttgagg tcgagaggac taaagagaga    1740
atggcatggg caaaatctca aattatttct agaatgatca cttcttcttt taataaacaa    1800
actacttcat ctgaggaaaa agaaacactt ttaaccgaat tcagaaacat caacggtctg    1860
cacaaatcaa acaatacaag agatggagat atgaacattg tgcttgcaac cctccatcaa    1920
ttcttcgctg gatttgacag atatactagc catcaactga aaaatgcttg gggagtatgg    1980
ttgagcaagc tgcaacgagg agcagtagac ggtggagcag acgcagagct gataacaacc    2040
accataaacg tatgcgccgg tcatatagct cttaaggaag acatattgtc ccacgatgag    2100
tacaagactc tcaccgacct caccagcaag atttgtcagc agctttctca tattcaaaac    2160
gaaaaggttg tggaaattga cggtgggatt acagcaaaat ctaggttgaa gaatgaggaa    2220
ctgcaacgtg acatgcaatc attggtgaaa ttagtacttg agaaatcagt tgggctcaac    2280
cggaatataa agcaaacatt tctaacggtt gcaaaaacat actactacag agcctacaat    2340
gctgaggaaa ctatggatgc ccatatattc aaagttcttt tcgaaccagt tgcgtga       2397
```

<210> SEQ ID NO 23
<211> LENGTH: 798
<212> TYPE: PRT
<213> ORGANISM: Ajuga reptans

<400> SEQUENCE: 23

```
Met Ser Phe Ala Ser Gln Ala Thr Ser Leu Leu Ser Ser Pro Asn Arg
1               5                   10                  15

Leu Gly His Val Pro Thr Pro Ser Ser Pro Ala Arg Phe Ala Ala Gly
            20                  25                  30

Gly Ala Pro Phe Trp Lys Ile Leu Phe Thr Ala Arg Ser Asn Gly Gln
        35                  40                  45

Tyr Lys Ala Ile Ser Arg Ala Arg Asn Gln Gly Asn Val Glu Tyr Ile
```

-continued

```
                50                  55                  60
Asp Glu Ile Gln Lys Gly Pro Gln Val Val Leu Glu Ala Glu Asn Ser
 65                  70                  75                  80

Leu Glu Asp Asp Thr Gln Lys Asp Thr Asp Gln Ile Arg Glu Leu Val
                 85                  90                  95

Glu Asn Val Arg Val Lys Leu Gln Asn Ile Gly Gly Gly Ile Ser
                100                 105                 110

Ile Ser Ala Tyr Asp Thr Ala Trp Val Ala Leu Val Glu Asp Ile Asn
                115                 120                 125

Gly Ser Gly Gln Pro Gln Phe Pro Thr Ser Leu Asp Trp Ile Ser Asn
        130                 135                 140

His Gln Phe Pro Asp Gly Ser Trp Gly Ser Ser Lys Phe Leu Tyr Tyr
145                 150                 155                 160

Asp Arg Ile Leu Cys Thr Leu Ala Cys Ile Val Ala Leu Lys Thr Trp
                165                 170                 175

Asn Val His Pro Asp Lys Tyr His Lys Gly Leu Asp Phe Ile Arg Glu
                180                 185                 190

Asn Ile His Lys Leu Ala Asp Glu Glu Val His Met Pro Ile Gly
        195                 200                 205

Phe Glu Val Ala Phe Pro Ser Ile Ile Glu Thr Ala Lys Lys Val Gly
210                 215                 220

Ile Glu Ile Pro Glu Asp Phe Pro Gly Lys Lys Glu Ile Tyr Ala Lys
225                 230                 235                 240

Arg Asp Leu Lys Leu Lys Lys Ile Pro Met Asp Ile Leu His Lys Met
                245                 250                 255

Pro Thr Pro Leu Leu Phe Ser Ile Glu Gly Met Glu Gly Leu Asp Trp
                260                 265                 270

Gln Lys Leu Phe Lys Phe Arg Asp Asp Gly Ser Phe Leu Thr Ser Pro
        275                 280                 285

Ser Ser Thr Ala Tyr Ala Leu Gln Gln Thr Lys Asp Glu Leu Cys Leu
        290                 295                 300

Lys Tyr Leu Thr Asp Leu Val Lys Lys Asp Asn Gly Gly Val Pro Asn
305                 310                 315                 320

Ala Phe Pro Val Asp Leu Phe Asp Arg Asn Tyr Thr Val Asp Arg Leu
                325                 330                 335

Arg Arg Leu Gly Ile Ser Arg Tyr Phe Gln Pro Glu Ile Glu Glu Cys
                340                 345                 350

Met Lys Tyr Val Tyr Arg Phe Trp Asp Lys Arg Gly Ile Ser Trp Ala
                355                 360                 365

Arg Asn Thr Asn Val Gln Asp Leu Asp Asp Thr Ala Gln Gly Phe Arg
        370                 375                 380

Asn Leu Arg Met His Gly Tyr Glu Val Thr Leu Asp Val Phe Lys Gln
385                 390                 395                 400

Phe Glu Lys Cys Gly Glu Phe Phe Ser Phe His Gly Gln Ser Ser Asp
                405                 410                 415

Ala Val Leu Gly Met Phe Asn Leu Tyr Arg Ala Ser Gln Val Leu Phe
                420                 425                 430

Pro Gly Glu His Met Leu Ala Asp Ala Arg Lys Tyr Ala Ala Asn Tyr
        435                 440                 445

Leu His Lys Arg Arg Leu Asn Asn Arg Val Val Asp Lys Trp Ile Ile
        450                 455                 460

Asn Lys Asp Leu Glu Gly Glu Val Ala Tyr Gly Leu Asp Val Pro Phe
465                 470                 475                 480
```

```
Tyr Ala Ser Leu Pro Arg Leu Glu Ala Arg Phe Tyr Ile Glu Gln Tyr
            485                 490                 495

Gly Gly Ser Asp Asp Val Trp Ile Gly Lys Ala Leu Tyr Arg Met Val
        500                 505                 510

Asn Val Ser Cys Asp Thr Tyr Leu Glu Leu Ala Lys Leu Asp Tyr Asn
        515                 520                 525

Lys Cys Gln Ser Val His Gln Asn Glu Trp Lys Ser Phe Gln Lys Trp
    530                 535                 540

Tyr Lys Ser Cys Ser Leu Gly Glu Phe Gly Phe Ser Glu Gly Ser Leu
545                 550                 555                 560

Leu Gln Ala Tyr Tyr Ile Ala Ala Ser Thr Ile Phe Glu Pro Glu Lys
                565                 570                 575

Ser Gly Glu Arg Leu Ala Trp Ala Lys Thr Ala Ala Leu Met Glu Thr
            580                 585                 590

Ile Gln Gln Leu Ser Ser Gln Gln Lys Arg Glu Phe Val Asp Glu Phe
        595                 600                 605

Lys His Lys Asn Ile Leu Lys Asn Glu Asn Gly Glu Arg Tyr Arg Ser
    610                 615                 620

Ser Thr Ser Leu Val Glu Thr Leu Ile Ser Thr Val Asn Gln Leu Ser
625                 630                 635                 640

Ser Asp Ile Leu Leu Glu Gln Gly Arg Asp Val His Gln Glu Leu Cys
                645                 650                 655

His Val Trp Leu Lys Trp Leu Ser Thr Trp Glu Glu Arg Gly Asn Leu
            660                 665                 670

Val Glu Ala Glu Ala Glu Leu Leu Leu Arg Thr Leu His Leu Asn Ser
        675                 680                 685

Gly Leu Asp Glu Ser Ser Phe Ser His Pro Lys Tyr Gln Gln Leu Leu
    690                 695                 700

Glu Val Ser Thr Lys Val Cys His Leu Leu Arg Leu Phe Gln Lys Arg
705                 710                 715                 720

Lys Val Tyr Asp Pro Glu Gly Cys Thr Thr Asp Ile Ala Thr Gly Thr
                725                 730                 735

Thr Phe Gln Ile Glu Ala Cys Met Gln Glu Leu Val Lys Leu Val Phe
            740                 745                 750

Ser Arg Ser Ser Glu Asp Leu Asp Ser Leu Thr Lys Leu Arg Phe Leu
        755                 760                 765

Asp Val Ala Arg Ser Phe Tyr Tyr Thr Ala His Cys Asp Pro Gln Val
    770                 775                 780

Val Glu Ser His Ile Asp Lys Val Leu Phe Glu Lys Val Val
785                 790                 795
```

<210> SEQ ID NO 24
<211> LENGTH: 2397
<212> TYPE: DNA
<213> ORGANISM: Ajuga reptans

<400> SEQUENCE: 24

| | | |
|---|---|---|
| atgtcatttg cttcccaagc cacctccctc ctatcatccc ccaaccgtct cggccatgtt | | 60 |
| ccgacgccaa gctcgccggc tcgtttcgct gccggtggtg cccatttttg aagagatatta | | 120 |
| tttacagcta ggtctaatgg gcagtataaa gctatttcaa gagctcgtaa ccaaggaaat | | 180 |
| gtagagtaca ttgatgagat tcagaaaggc ccgcaagtcg tattggaggc agaaaacagc | | 240 |
| ttggaagatg acacacaaaa agatactgat cagataaggg aactagtgga aaatgtccga | | 300 |

```
gtaaagctgc agaatatcgg tggtggaggg ataagcatat cggcgtacga caccgcatgg    360
gtggcgctgg tggaggacat caacggcagt ggccagccac agtttccgac gagcctcgat    420
tggatatcga accatcagtt ccctgatggg tcatgggcca gcagcaagtt tttgtattat    480
gatcggattc tatgcacatt agcatgtata gttgcattga aaacctggaa tgtgcatcct    540
gataagtacc acaaagggtt ggatttcatc agagagaaca ttcacaagct tgcggacgaa    600
gaagaagtgc acatgccaat tgggttcgaa gtggcattcc catcaattat tgaaacagct    660
aaaaaagtag gaatcgaaat ccctgaggat tttcctggca agaaagaaat ttatgcaaaa    720
agagatttaa agctaaaaaa aataccaatg gatatactgc ataaaatgcc acaccattg    780 ctcttcagca tagaaggaat ggaaggcctt gactggcaaa agctattcaa attccgcgat    840
gatggctcgt ttcttacgtc tccgtcctca acagcctatg cactccagca aacaaaggat    900
gagctatgcc tcaagtatct aacagatctt gtcaagaaag acaacggagg agttccgaat    960
gcatttccag tagacctgtt tgatcgtaac tatacagtag accgcttgcg aaggctagga    1020
atttcacggt actttcaacc tgaaattgaa gaatgcatga aatatgttta cagattttgg    1080
gataaaagag gaattagctg ggcaagaaat accaatgttc aggaccttga tgacactgca    1140
cagggattca ggaatttaag gatgcatggt tatgaagtca ctctagatgt tttcaaacaa    1200
tttgagaaat gtggagagtt tttcagtttt catgggcaat ccagcgatgc tgttttagga    1260
atgttcaact tgtaccgggc ttctcaggtt ttatttccgg gagaacacat gcttgcagat    1320
gcgaggaagt atgcagccaa ctatttgcat aaacgaagac ttaataatag ggtggtcgac    1380
aaatggatta tcaacaaaga ccttgaaggc gaggtggcat atgggctaga tgttccgttc    1440
tacgccagcc tacctcgact cgaagcaagg ttctacatag aacaatatgg gggtagtgat    1500
gatgtgtgga ttggaaaagc tttatacaga atggtaaatg taagctgcga cacttacctt    1560
gagctagcaa aattagacta caacaaatgc caatccgtgc atcagaatga gtggaaaagc    1620
tttcaaaaat ggtacaaaag ttgcagtctt ggggagtttg ggttcagtga aggaagccta    1680
ctccaagctt actacatagc agcctcaact atattcgagc cagagaaatc aggagaacgc    1740
ctagcttggg ctaaaacagc agctctaatg gagacaattc aacaactttc cagccagcaa    1800
aaacgtgaat tgttgatga attcaaacat aaaaacatac tgaagaatga aaatggagaa    1860
aggtatagat caagtaccag tttggtagag actctgataa gcactgtaaa tcagctctca    1920
tcagacatac tattggagca aggcagagac gttcatcaag aattatgtca cgtgtggcta    1980
aaatggctga gtacatggga ggaaagagga aacctggtgg aagcggaagc cgagcttctt    2040
ctgcgaacct acatctcaa cagcggattg gatgaatcat cattttccca ccctaaatat    2100
caacagctct tggaggtgtc taccaaagtt tgccacctcc ttcgcctatt tcagaaacga    2160
aaggtgtatg atcccgaagg tgtacaacc gacatagcaa caggaacaac gttccagata    2220
gaagcatgca tgcaagaact agtgaaatta gtgttcagca gatcctcaga agatttagat    2280
tctcttacta agttgagatt tttggatgtt gctagaagtt tctattacac tgcccattgt    2340
gatccacagg tggtcgagtc ccacatcgat aaagtattgt ttgagaaggt agtctag    2397
```

<210> SEQ ID NO 25
<211> LENGTH: 800
<212> TYPE: PRT
<213> ORGANISM: Plectranthus barbatus
<220> FEATURE:
<221> NAME/KEY: VARIANT
<222> LOCATION: (1)...(800)
<223> OTHER INFORMATION: Xaa = Any Amino Acid

<400> SEQUENCE: 25

```
Met Gln Ala Ser Met Ser Ser Leu Asn Leu Asn Asn Ala Pro Ala Val
1               5                   10                  15

Cys Ser Ser Arg Ser Gln Leu Ser Ala Lys Leu His Pro Pro Glu Tyr
            20                  25                  30

Ser Thr Val Gly Ala Trp Leu Asn Arg Gly Asn Lys Asn Gln Arg Leu
        35                  40                  45

Gly Tyr Arg Ile Arg Pro Lys Gln Leu Ser Lys Leu Thr Glu Cys Arg
    50                  55                  60

Val Ala Ser Ala Asp Val Ser Gln Glu Ile Gly Lys Val Gly Gln Ser
65                  70                  75                  80

Val Arg Thr Pro Glu Glu Val Asn Lys Lys Ile Glu Glu Ser Ile Lys
                85                  90                  95

Tyr Val Lys Glu Leu Leu Met Thr Ser Gly Asp Gly Arg Ile Ser Val
            100                 105                 110

Ala Pro Tyr Asp Thr Ala Ile Val Ala Leu Ile Lys Asp Leu Glu Gly
        115                 120                 125

Arg Asp Ala Pro Glu Phe Pro Ser Cys Leu Glu Trp Ile Ala Asn Asn
130                 135                 140

Gln Lys Asp Asp Gly Ser Trp Gly Asp Asp Phe Phe Cys Ile Tyr Asp
145                 150                 155                 160

Arg Ile Val Asn Thr Ile Ala Ser Val Val Ala Leu Lys Ser Trp Asn
                165                 170                 175

Val His Pro Asp Lys Ile Glu Arg Gly Val Ser Tyr Ile Lys Glu Asn
            180                 185                 190

Ala His Lys Leu Lys Gly Gly Asn Leu Glu His Met Thr Ser Gly Phe
        195                 200                 205

Glu Phe Val Val Pro Gly Cys Phe Asp Arg Ala Lys Ala Leu Gly Ile
210                 215                 220

Glu Gly Leu Pro Tyr Asp Asp Pro Ile Ile Lys Glu Ile Tyr Ala Thr
225                 230                 235                 240

Lys Glu Arg Arg Leu Ser Lys Val Pro Lys Asp Met Ile Tyr Lys Val
                245                 250                 255

Pro Thr Thr Leu Leu Phe Ser Leu Glu Gly Leu Gly Met Glu Asp Leu
            260                 265                 270

Asp Trp Gln Lys Ile Leu Lys Leu Gln Ser Gly Asp Gly Ser Phe Leu
        275                 280                 285

Thr Ser Pro Ser Ser Thr Ala Tyr Ala Phe Met Gln Thr Gly Asp Glu
    290                 295                 300

Lys Cys Tyr Lys Phe Leu Gln Asn Ala Val Arg Asn Cys Asn Gly Gly
305                 310                 315                 320

Ala Pro His Thr Tyr Pro Val Asp Val Phe Ala Arg Leu Trp Ala Val
                325                 330                 335

Asp Arg Leu Gln Arg Leu Gly Ile Ser Arg Phe Phe Gln Pro Glu Ile
            340                 345                 350

Lys Phe Cys Leu Asp His Ile Lys Asn Val Trp Thr Lys Asn Gly Val
        355                 360                 365

Phe Ser Gly Arg Asp Ser Glu Phe Val Asp Ile Asp Asp Thr Ser Met
    370                 375                 380

Gly Ile Arg Leu Leu Lys Met His Gly Tyr Asp Val Asp Pro Asn Ala
385                 390                 395                 400

Leu Lys His Phe Lys Gln Glu Asp Gly Arg Phe Ser Cys Tyr Gly Gly
```

```
            405                 410                 415
Gln Met Ile Glu Ser Ala Ser Pro Ile Tyr Asn Leu Tyr Arg Ala Ala
        420                 425                 430

Gln Leu Arg Phe Pro Gly Glu Ile Leu Glu Ala Thr Lys Phe
    435                 440                 445

Ala Tyr Asn Phe Leu Gln Gln Lys Leu Ala Asn Asn Gln Ile Gln Glu
    450                 455                 460

Lys Trp Val Ile Ser Glu His Leu Ile Asp Glu Ile Lys Met Gly Leu
465                 470                 475                 480

Lys Met Pro Trp Tyr Ala Thr Leu Pro Arg Val Glu Ala Ser Tyr Tyr
                485                 490                 495

Leu Gln Tyr Tyr Ala Ala Ser Gly Asp Val Trp Ile Gly Lys Thr Phe
            500                 505                 510

Tyr Arg Met Pro Glu Ile Ser Asn Asp Thr Tyr Lys Glu Leu Ala Leu
                515                 520                 525

Leu Asp Phe Asn Arg Cys Gln Ala Gln His Gln Phe Glu Trp Ile Tyr
        530                 535                 540

Met Gln Glu Trp Tyr Gln Ser Asn Asn Ile Lys Glu Phe Gly Ile Ser
545                 550                 555                 560

Lys Lys Glu Leu Leu Leu Ala Tyr Phe Leu Ala Ala Thr Ile Phe
                565                 570                 575

Glu Pro Glu Arg Ser Gln Glu Arg Ile Val Trp Ala Lys Thr Gln Val
                580                 585                 590

Val Ser Lys Met Ile Thr Ser Phe Leu Ser Gln Glu Asn Ala Leu Ser
            595                 600                 605

Ser Xaa Gln Lys Thr Ala Leu Phe Ile Asp Phe Gly His Ser Ile Asn
        610                 615                 620

Gly Leu Asn Gln Ile Thr Ser Val Glu Lys Glu Asn Gly Leu Ala Gln
625                 630                 635                 640

Thr Val Leu Ala Thr Phe Gly Gln Leu Leu Glu Glu Phe Asp Arg Tyr
                645                 650                 655

Thr Arg His Gln Leu Lys Asn Ala Trp Ser Gln Trp Phe Met Lys Leu
            660                 665                 670

Gln Gln Gly Asp Asp Asn Gly Gly Ala Asp Ala Glu Leu Leu Ala Asn
        675                 680                 685

Thr Leu Asn Ile Cys Ala Gly His Ile Ala Phe Asn Glu Asp Ile Leu
    690                 695                 700

Ser His Asn Glu Tyr Thr Ser Leu Ser Ser Leu Thr Asn Lys Ile Cys
705                 710                 715                 720

Gln Arg Leu Ser Gln Ile Arg Asp Asn Lys Ile Leu Glu Ile Glu Asp
                725                 730                 735

Gly Ser Ile Lys Asp Lys Glu Leu Gln Glu Met Gln Ala Leu Val
            740                 745                 750

Lys Leu Val Leu Glu Glu Thr Gly Gly Ile Asp Arg Asn Ile Lys Gln
            755                 760                 765

Thr Phe Leu Ser Val Phe Lys Met Phe Tyr Tyr Arg Ala Tyr His Asp
    770                 775                 780

Ala Glu Ala Ile Asp Xaa His Ile Phe Lys Val Met Phe Glu Pro Val
785                 790                 795                 800

<210> SEQ ID NO 26
<211> LENGTH: 2406
<212> TYPE: DNA
<213> ORGANISM: Plectranthus barbatus
```

<220> FEATURE:
<221> NAME/KEY: misc_feature
<222> LOCATION: (1)...(2406)
<223> OTHER INFORMATION: n = A,T,C or G

<400> SEQUENCE: 26

| | | | | |
|---|---|---|---|---|
| atgcaggctt | ctatgtcatc | tctgaacttg | aacaatgcac | cggccgtctg | cagcagcagg | 60 |
| tcacagctat | ccgctaaact | tcacccgccg | gaatattcca | ccgtgggtgc | atggctgaat | 120 |
| cgtggcaaca | aaaccagcg | gttgggctac | cggattcgtc | caaagcaact | atcaaaacta | 180 |
| actgagtgtc | gagtagcaag | tgcagatgtg | tcacaagaga | ttggaaaagt | cggccaatct | 240 |
| gttcggactc | ctgaagaggt | aaataaaaag | atagaggaat | ccatcaagta | cgtgaaggag | 300 |
| ctgctgatga | cgtcgggcga | cgggcgaatc | agtgtggcgc | cctacgacac | ggccatagtt | 360 |
| gcccttatca | aggacttgga | agggcgcgat | gccccggagt | ttccatcttg | cttggagtgg | 420 |
| attgcaaaca | atcaaaaaga | cgatggttct | tgggggatg | acttcttctg | catctatgat | 480 |
| cggatcgtta | ataccatagc | atccgtcgtc | gccttaaaat | catggaatgt | gcacccagac | 540 |
| aagattgaga | gaggagtatc | ctacatcaag | gaaaacgcgc | ataaactaaa | aggtgggaat | 600 |
| ctcgaacaca | tgcatcagg | gttcgagttc | gtggttcccg | gctgttttga | cagagccaaa | 660 |
| gccttgggga | tcgaaggcct | tccctatgat | gatcccatca | tcaaggagat | ttatgctaca | 720 |
| aaagaaagga | gattgagcaa | ggtaccgaag | gacatgatct | acaaagttcc | gacaactcta | 780 |
| ttgtttagtt | tagagggact | gggcatggag | gatttggact | ggcaaaagat | actgaaactg | 840 |
| cagtcgggcg | acggctcatt | cctcacctct | ccgtcgtcca | ccgcctacgc | attcatgcag | 900 |
| accggagacg | aaaaatgcta | caaattcctc | cagaacgccg | tcagaaattg | caacggcgga | 960 |
| gcgccgcaca | cttatccagt | cgacgtcttt | gcacggctct | gggcggtcga | ccgacttcag | 1020 |
| cgactcggaa | tttctcgctt | ctttcagccc | gagatcaagt | tttgcctaga | ccacatcaaa | 1080 |
| aatgtgtgga | ctaagaacgg | agttttcagt | ggacgggatt | cagagtttgt | ggatatcgac | 1140 |
| gacacatcca | tgggcatcag | gcttctgaaa | atgcacggat | acgatgtcga | cccaaatgca | 1200 |
| ctgaaacatt | tcaagcagga | ggatgggagg | ttttcatgct | acggtggtca | aatgatcgag | 1260 |
| tctgcatctc | cgatttacaa | tctctacagg | gctgctcagc | ttcgttttcc | aggagaagaa | 1320 |
| attcttgaag | aagccactaa | atttgcctac | aacttcctgc | aacagaagct | ggccaacaat | 1380 |
| caaattcaag | aaaagtgggt | catatccgag | cacctaattg | atgagataaa | aatgggattg | 1440 |
| aagatgccat | ggtacgccac | cctacctaga | gttgaggctt | catactatct | ccaatattat | 1500 |
| gcagcttctg | gcgacgtatg | gattggcaag | actttttaca | ggatgccaga | aataagtaat | 1560 |
| gacacgtaca | agagcttgc | actattggat | ttcaaccgat | gccaagcaca | acatcagttc | 1620 |
| gaatggattt | acatgcaaga | gtggtatcaa | agcaacaaca | ttaaagaatt | tgggataagc | 1680 |
| aagaaagagc | ttcttcttgc | ttacttcttg | gctgctgcaa | ccattttga | acccgaacga | 1740 |
| tcgcaagagc | ggatcgtgtg | ggctaaaacc | caagttgttt | ctaagatgat | cacatcgttt | 1800 |
| ctgtctcaag | aaaacgcttt | gtcatcggan | caaaagactg | cacttttcat | cgattttggg | 1860 |
| catagtatca | atggcctcaa | tcaaataact | agtgttgaga | agagaatgg | gcttgctcag | 1920 |
| actgtgctgg | caaccttcgg | acaactactc | gaggaattcg | acagatacac | aaggcatcaa | 1980 |
| ctgaaaaatg | cttggagcca | atggttcatg | aaactgcagc | aaggagatga | caatggcggg | 2040 |
| gcagacgcag | agctcctagc | aaacacattg | aacatctgcg | ctggtcatat | tgctttttaac | 2100 |
| gaagacatat | tatctcacaa | cgaatacacc | tctctctcct | ccctcacaaa | caaaatctgt | 2160 |

-continued

```
cagcggctaa gtcaaattcg agataataag atactggaaa ttgaggatgg gagcataaaa    2220
gataaggaac tagaacagga aatgcaggcg ctggtgaagt tagtcctgga agaaaccggt    2280
ggcatcgaca ggaacatcaa gcaaacattt ttgtcagttt tcaaaatgtt ttactacaga    2340
gcctaccacg atgctgaggc tatcgatgnc catattttca agtaatgtt tgaaccagtc     2400 gtatga                                                               2406
```

<210> SEQ ID NO 27
<211> LENGTH: 776
<212> TYPE: PRT
<213> ORGANISM: Hyptis suaveolens

<400> SEQUENCE: 27

```
Met Ala Tyr Met Ile Ser Ile Ser Asn Leu Asn Cys Ser Ser Leu Leu
1               5                   10                  15

Asn Thr Asn Leu Ser Ala Lys Ile Gln Leu His Gln Gly Leu Lys Gly
            20                  25                  30

Thr Trp Leu Lys Thr Ser Lys Arg Met Cys Met Asp Gln Gln Val His
        35                  40                  45

Gly Lys Gln Ile Ala Lys Val Ile Glu Ser Arg Val Thr Asp Lys Asp
    50                  55                  60

Val Ser Thr Ala Gln Asp Phe Glu Val Leu Lys Val Asn Arg Val Glu
65                  70                  75                  80

Asp Leu Ile Ser Ser Ile Lys Ser Ser Leu Lys Thr Met Glu Asp Gly
                85                  90                  95

Arg Ile Ser Val Ser Pro Tyr Ser Thr Ser Trp Ile Ala Leu Ile Pro
            100                 105                 110

Ser Ile Asp Gly Arg Gln Thr Pro Gln Phe Pro Ser Ser Leu Glu Trp
        115                 120                 125

Ile Val Lys His Gln Leu Ser Asp Gly Ser Trp Gly Asp Ala Leu Phe
    130                 135                 140

Phe Cys Val Tyr Asp Arg Leu Val Asn Thr Ile Ala Cys Ile Ile Ala
145                 150                 155                 160

Leu His Thr Trp Lys Val His Ala Asp Lys Val Lys Lys Gly Val Ser
                165                 170                 175

Phe Val Lys Glu Asn Ile Trp Lys Leu Glu Asp Ala Asn Glu Val His
            180                 185                 190

Met Thr Ser Gly Phe Glu Val Ile Phe Pro Ile Leu Leu Arg Arg Ala
        195                 200                 205

Arg Asp Met Gly Ile Asp Gly Leu Pro Ser Asp Thr Pro Val Val
    210                 215                 220

Arg Met Ile Ser Ala Ala Arg Asp His Lys Leu Lys Lys Ile Pro Arg
225                 230                 235                 240

Glu Val Met His Gln Val Thr Thr Thr Leu Leu Tyr Ser Leu Glu Gly
                245                 250                 255

Leu Glu Asp Leu Asp Trp Ser Arg Leu Phe Lys Leu Gln Ser Ala Asp
            260                 265                 270

Gly Ser Phe Leu Thr Ser Pro Ser Ser Thr Ala Phe Ala Phe Met Gln
        275                 280                 285

Thr Asn Asn His Asn Cys Leu Arg Phe Ile Thr Ser Val Val Gln Thr
    290                 295                 300

Phe Asn Gly Gly Ala Pro Asp Asn Tyr Pro Ile Asp Ile Phe Ala Arg
305                 310                 315                 320

Leu Trp Ala Val Asp Arg Leu Gln Arg Leu Gly Ile Ser Arg Phe Phe
```

```
                325                 330                 335
Glu Gln Glu Ile Asn Asp Cys Leu Ser Tyr Val Tyr Arg Phe Trp Asn
            340                 345                 350
Ala Asn Gly Val Phe Ser Ala Gly Ala Thr Asn Phe Cys Asp Leu Asp
        355                 360                 365
Asp Thr Ser Met Ala Phe Arg Leu Leu Arg Leu His Gly Tyr Asp Val
    370                 375                 380
Asp Pro Asn Val Leu Arg Lys Phe Lys Glu Gly Asp Arg Phe Cys Cys
385                 390                 395                 400
His Ser Gly Glu Val Ala Met Ser Thr Ser Pro Thr Tyr Ala Leu Tyr
                405                 410                 415
Arg Ala Ser Gln Ile Gln Phe Pro Gly Glu Ile Leu Asp Glu Ala
            420                 425                 430
Phe Ser Phe Thr Arg Asp Tyr Leu Gln Asp Trp Leu Ala Arg Asp Gln
        435                 440                 445
Val Leu Asp Lys Trp Ile Val Ser Lys Asp Leu Pro Asp Glu Ile Lys
    450                 455                 460
Val Gly Leu Glu Val Pro Trp Tyr Ala Ser Leu Pro Arg Val Glu Ala
465                 470                 475                 480
Ala Tyr Tyr Met Gln Arg His Tyr Gly Gly Ser Thr Asp Ala Trp Val
                485                 490                 495
Ala Lys Thr Cys Tyr Arg Met Pro Asp Val Ser Asn Asp Tyr Leu
            500                 505                 510
Glu Leu Ala Arg Leu Asp Phe Lys Arg Cys Gln Ala Gln His Gln Ser
        515                 520                 525
Glu Leu Ser Tyr Met Gln Arg Trp Tyr Asp Ser Cys Asn Val Glu Glu
    530                 535                 540
Phe Gly Ile Ser Arg Lys Glu Leu Leu Val Ala Tyr Phe Val Ala Ala
545                 550                 555                 560
Ala Thr Ile Phe Glu Pro Glu Arg Ala Thr Glu Arg Ile Val Trp Ala
                565                 570                 575
Lys Thr Glu Ile Val Ser Lys Met Ile Lys Ala Phe Phe Gly Glu Asp
            580                 585                 590
Ser Leu Asp Gln Lys Thr Met Leu Leu Lys Glu Phe Arg Asn Ser Ile
        595                 600                 605
Asn Asn Gly Ser His Arg Phe Met Lys Ser Glu His Arg Ile Val Asn
    610                 615                 620
Ile Leu Leu Gln Ala Leu Gln Glu Leu Leu His Gly Ser Asp Asp Cys
625                 630                 635                 640
Arg Ile Gly Gln Leu Lys Asn Ala Trp Tyr Glu Trp Leu Met Lys Phe
                645                 650                 655
Glu Gly Gly Asp Glu Ala Ser Leu Trp Gly Gly Glu Leu Leu Val
            660                 665                 670
Thr Thr Leu Asn Ile Cys Thr Ala His Phe Leu Gln His His Asp Leu
        675                 680                 685
Leu Leu Asn His Asp Tyr Ile Thr Leu Ser Glu Leu Thr Asn Lys Ile
    690                 695                 700
Cys Leu Lys Leu Ser Gln Ile Gln Val Gly Glu Met Asn Glu Met Arg
705                 710                 715                 720
Glu Asp Met Gln Ala Leu Thr Lys Leu Val Ile Gly Glu Ser Cys Ile
                725                 730                 735
Val Asn Lys Asn Ile Lys Gln Thr Phe Leu Ala Val Ala Lys Thr Phe
            740                 745                 750
```

Tyr Tyr Arg Ala Tyr Phe Asp Ala Asp Thr Val Asp Leu His Ile Phe
        755                 760                 765

Lys Val Leu Phe Glu Pro Ile Val
    770                 775

<210> SEQ ID NO 28
<211> LENGTH: 2331
<212> TYPE: DNA
<213> ORGANISM: Hyptis suaveolens

<400> SEQUENCE: 28

| | | | | | |
|---|---|---|---|---|---|
| atggcgtata | tgatatctat | ttcaaatctc | aactgttcct | cgctactaaa | caccaatctt | 60 |
| tcagcaaaga | ttcagctgca | ccaaggtctc | aaaggaacat | ggctaaaaac | cagcaaacgc | 120 |
| atgtgcatgg | atcaacaggt | tcatggcaag | cagatagcaa | aagtgatcga | gagccgagtt | 180 |
| actgataagg | atgtttccac | tgctcaggac | tttgaagtgt | taaaggtcaa | tagagtggag | 240 |
| gatctgatat | caagcattaa | gagttcattg | aagacaatgg | aagatggaag | aataagcgtg | 300 |
| tcgccctaca | gcacatcatg | gatcgcactc | attccaagta | ttgatgggcg | ccagacgccc | 360 |
| cagtttccat | cttcactgga | gtggatcgtg | aagcatcagc | tatcagatgg | ttcatggggt | 420 |
| gatgcccttt | ttttctgcgt | ttatgatcgt | ctcgtaaata | cgattgcatg | catcattgcc | 480 |
| ctgcacacct | ggaaggttca | tgcagacaag | gttaaaaaag | gagtaagttt | tgtgaaggaa | 540 |
| aatatatgga | acttgaaga | cgccaacgag | gtccacatga | ctagtggttt | cgaagttata | 600 |
| tttcccatcc | ttcttcgaag | agcacgagac | atgggaattg | atggtcttcc | ttctgatgat | 660 |
| actccagttg | ttaggatgat | ttctgctgct | agggatcaca | aattgaaaaa | gattccgagg | 720 |
| gaggtgatgc | accaagtgac | aacaactcta | ttatatagtt | tggaagggtt | ggaagattta | 780 |
| gactggtcaa | ggcttttcaa | acttcagtca | gctgatggtt | cattcttaac | ttctccatct | 840 |
| tcaactgcct | tcgcattcat | gcaaactaat | aaccacaatt | gcttgagatt | catcactagc | 900 |
| gttgtccaaa | cattcaatgg | aggagctcca | gataactatc | caatcgacat | cttttgcgaga | 960 |
| ctgtgggcag | ttgacaggtt | acagcggtta | gggatttctc | gtttcttcga | gcaggagata | 1020 |
| aatgattgcc | taagctatgt | atatagattt | tggaatgcaa | atggagtttt | cagtgcagga | 1080 |
| gccactaatt | tttgtgatct | tgacgacaca | tccatggctt | tccggctact | acgtttgcat | 1140 |
| ggatatgatg | tcgacccaaa | tgttctgagg | aaattcaaag | agggagacag | attctgttgc | 1200 |
| cacagtggtg | aagtggcgat | gtcgacatcg | ccaacgtacg | ctctctacag | agcttcccaa | 1260 |
| attcagtttc | caggagaaga | aattctggat | gaagccttca | gcttcactcg | cgactatcta | 1320 |
| caggactggt | tagcaagaga | tcaagttctt | gataagtgga | ttgtatccaa | ggaccttcca | 1380 |
| gatgagatta | aggtaggact | agaggtgcca | tggtatgcca | gctgccacg | ggtagaggct | 1440 |
| gcttattaca | tgcaacgaca | ttacggcggg | tctactgatg | cgtgggtggc | caagacttgt | 1500 |
| tacaggatgc | ctgatgtgag | caacgatgat | tacctggagc | ttgcaagatt | ggatttcaag | 1560 |
| agatgtcaag | cccaacatca | gagtgaattg | agttacatgc | aacgatggta | tgacagttgc | 1620 |
| aatgtcgaag | aattcggaat | aagcagaaaa | gagttgcttg | tagcttatt | tgtggctgct | 1680 |
| gcaactattt | ttgaacctga | gagagcaact | gagagaattg | tgtgggcaaa | aactgaaata | 1740 |
| gtttctaaga | tgatcaaagc | attttttggt | gaagactcat | tagaccaaaa | aactatgttg | 1800 |
| ttaaaagaat | tcagaaacag | catcaataat | ggctccccaca | gattcatgaa | gagtgagcat | 1860 |
| agaatcgtca | acattctact | acaagccttg | caggagctat | tacatggatc | tgatgattgt | 1920 |

```
cgtattggtc aactcaaaaa tgcttggtat gagtggctga tgaaattcga gggaggagat    1980
gaagcaagtt tgtggggaga aggagagctt cttgtcacca ccttaaacat ttgcacagct    2040
catttccttc aacaccatga tttactgttg aatcatgact acataactct ttctgagctc    2100
acaaacaaga tctgcctcaa gctttctcag attcaggtag gagaaatgaa tgaaatgaga    2160
gaagatatgc aggcgttgac gaaattagtg attggggaat catgcatcgt caacaaaaac    2220
attaagcaaa catttcttgc agttgcaaag actttctatt acagagccta cttcgatgcc    2280
gacaccgttg atctccatat atttaaagtt ctatttgagc ccattgtctg a             2331
```

<210> SEQ ID NO 29
<211> LENGTH: 787
<212> TYPE: PRT
<213> ORGANISM: Leonotis leonurus

<400> SEQUENCE: 29

```
Met Ala Ser Thr Ala Ser Thr Leu Asn Leu Thr Ile Asn Ser Thr Pro
1               5                   10                  15

Phe Val Ser Thr Lys Thr Gln Ala Lys Val Ser Leu Pro Ala Cys Leu
            20                  25                  30

Trp Met Gln Asp Arg Ser Ser Arg His Val Ser Leu Lys His Lys
        35                  40                  45

Phe Cys Arg Asn Gln Gln Leu Lys Cys Arg Ala Ser Leu Asp Val Gln
    50                  55                  60

Gln Val Arg Asp Glu Val Phe Ser Thr Ala Gln Ser Pro Glu Ser Val
65                  70                  75                  80

Asp Lys Lys Ile Glu Glu Arg Lys Lys Trp Val Lys Asn Leu Leu Ser
                85                  90                  95

Thr Met Asp Asp Gly Arg Ile Asn Trp Ser Ala Tyr Asp Thr Ala Trp
            100                 105                 110

Ile Ser Leu Ile Lys Glu Phe Glu Gly Arg Asp Ala Pro Gln Phe Pro
        115                 120                 125

Ser Thr Leu Met Arg Ile Ala Glu Asn Gln Leu Ala Asp Gly Ser Trp
    130                 135                 140

Gly Asp Pro Asp Tyr Asp Cys Ser Tyr Asp Arg Ile Ile Asn Thr Leu
145                 150                 155                 160

Ala Cys Val Val Ala Leu Thr Thr Trp Asn Ala His Pro Glu His Asn
                165                 170                 175

Lys Lys Gly Ile Lys Tyr Ile Lys Glu Asn Met Tyr Lys Leu Glu Glu
            180                 185                 190

Thr Pro Val Val Leu Met Thr Ser Ala Phe Glu Val Phe Pro Ala
        195                 200                 205

Leu Leu Asn Arg Ala Lys Asn Leu Gly Ile Gln Asp Leu Pro Tyr Asp
    210                 215                 220

Met Pro Ile Val Lys Glu Ile Cys Lys Ile Gly Asp Glu Lys Leu Ala
225                 230                 235                 240

Arg Ile Pro Lys Lys Met Met Glu Lys Glu Pro Thr Ser Leu Met Tyr
                245                 250                 255

Ala Ala Glu Gly Val Glu Asn Leu Asp Trp Glu Lys Leu Leu Lys Gln
            260                 265                 270

Arg Thr Pro Glu Asn Gly Ser Phe Leu Ser Ser Pro Ala Ala Thr Ala
        275                 280                 285

Val Ala Phe Met His Thr Lys Asp Glu Asn Cys Leu Arg Tyr Ile Met
    290                 295                 300
```

```
Tyr Leu Leu Asp Lys Phe Asn Gly Gly Ala Pro Asn Val Tyr Pro Ile
305                 310                 315                 320

Asp Leu Trp Ser Arg Leu Trp Ala Thr Asp Arg Ile Gln Arg Leu Gly
            325                 330                 335

Ile Ser Arg Phe Phe Lys Glu Glu Ile Lys Glu Ile Leu Ser Tyr Val
            340                 345                 350

Tyr Ser Tyr Trp Thr Asp Ile Gly Val Tyr Cys Thr Arg Asp Ser Lys
        355                 360                 365

Tyr Ala Asp Ile Asp Asp Thr Ser Met Gly Phe Arg Leu Leu Arg Met
370                 375                 380

His Gly Phe Lys Met Asp Pro Asn Val Phe Lys Tyr Phe Gln Lys Asp
385                 390                 395                 400

Asp Arg Phe Val Cys Leu Gly Gly Gln Met Asn Asp Ser Pro Thr Ala
                405                 410                 415

Thr Tyr Asn Leu Tyr Arg Ala Ala Gln Tyr Gln Phe Pro Gly Glu Lys
            420                 425                 430

Ile Leu Glu Asp Ala Arg Lys Phe Ser Gln Glu Phe Leu Gln His Cys
            435                 440                 445

Ile Asp Thr Asn Asn Leu Leu Asp Lys Trp Val Ile Ser Pro Arg Phe
450                 455                 460

Pro Glu Glu Leu Lys Phe Gly Met Glu Met Thr Trp Tyr Ser Cys Leu
465                 470                 475                 480

Pro Arg Ile Glu Ala Arg Tyr Tyr Val Gln His Tyr Gly Ala Thr Glu
                485                 490                 495

Asp Val Trp Leu Gly Lys Thr Phe Phe Arg Met Glu Glu Ile Ser Asn
            500                 505                 510

Glu Asn Tyr Lys Glu Leu Ala Lys Leu Asp Phe Ser Lys Cys Gln Ala
            515                 520                 525

Gln His Gln Thr Glu Trp Ile His Met Gln Glu Trp Tyr Glu Ser Ser
        530                 535                 540

Asn Ala Lys Glu Phe Gly Ile Ser Arg Lys Asp Leu Leu Phe Ala Tyr
545                 550                 555                 560

Phe Leu Ala Ala Ala Ser Ile Phe Glu Thr Glu Arg Ala Lys Glu Arg
                565                 570                 575

Ile Leu Trp Ala Lys Ser Gln Ile Ile Cys Lys Met Val Lys Ser Tyr
            580                 585                 590

Leu Glu Asn Gln Thr Ala Ser Leu Glu His Lys Ile Ala Phe Leu Thr
            595                 600                 605

Gly Phe Gly Asp Asn Asn Gly Leu His Thr Ile Asn Lys Gly Ser
610                 615                 620

Gly Pro Val Asn Asn Val Met Arg Thr Leu Gln Gln Leu Leu Gly Glu
625                 630                 635                 640

Phe Asp Gly Tyr Ile Ser Ser Gln Leu Glu Asn Ala Trp Ala Ala Trp
                645                 650                 655

Leu Thr Lys Leu Glu Gln Gly Glu Ala Asn Asp Gly Glu Leu Leu Ala
            660                 665                 670

Thr Thr Leu Asn Ile Cys Ser Gly Arg Ile Val Tyr Asn Glu Asp Thr
            675                 680                 685

Leu Ser Asn Lys Glu Tyr Lys Ala Phe Ala Asp Leu Thr Asn Lys Ile
            690                 695                 700

Cys Gln Asn Leu Ala Gln Ile Gln Asn Lys Gly Asp Glu Ile Lys
705                 710                 715                 720

Asp Pro Asn Glu Gly Glu Lys Asp Lys Glu Val Glu Gln Gly Met Gln
```

```
                              725                 730                 735
        Ala Leu Ala Lys Leu Val Phe Glu Glu Ser Gly Leu Glu Arg Ser Ile
                          740                 745                 750

Lys Glu Thr Phe Leu Ala Val Val Arg Thr Tyr His Tyr Gly Ala Tyr
                      755                 760                 765

Val Ala Asp Glu Lys Ile Asp Val His Met Phe Lys Val Leu Phe Glu
                  770                 775                 780

Pro Val Glu
        785

<210> SEQ ID NO 30
<211> LENGTH: 2364
<212> TYPE: DNA
<213> ORGANISM: Leonotis leonurus

<400> SEQUENCE: 30
atggcctcca ctgcatccac tctaaatttg accatcaata gtacaccatt tgtaagcacc      60
aaaacgcaag caaaggtttc cttgcccgca tgtttatgga tgcaggatag aagcagcagt     120
agacacgtgt cgttaaaaca caaattctgt cgaaatcaac aacttaagtg tcgagcaagt     180
ctggatgttc agcaagtacg tgatgaagtt ttttccactg ctcaatcccc tgaatcggtg     240
gataaaaaaa tagaggaacg taaaaaatgg gtgaagaatt tgttgagtac aatggacgat     300
ggacgaataa attggtcagc ctatgacacg gcatggattt cacttattaa agaatttgaa     360
ggacgagatg ctccccagtt tccgtcgact ctcatgcgca tcgcggagaa ccaattggcc     420
gacgggtcat ggggcgatcc agattacgac tgctcctatg atcggataat aaacacacta     480
gcgtgtgttg tagccttgac aacatggaat gctcatcctg aacacaataa aaaaggaata     540
aaatacatca aggaaaatat gtataaacta gaagagacgc ctgttgtact catgactagt     600
gcatttgaag ttgtgtttcc ggcgcttctt aacagagcta aaaacttggg cattcaagat     660
cttccctatg atatgcccat cgtgaaggag atttgtaaaa tagggatgaa gaagttggca     720
aggataccaa agaaaatgat ggagaaagag ccaacatcgc tgatgtatgc cgcggaagga     780
gtcgaaaact tggactggga aaagcttctg aaacagcgga cacccgagaa tggctcgttc     840
ctctcttccc cggccgcaac tgccgttgca tttatgcaca caaaagatga aaattgctta     900
agatacatca tgtacctttt ggacaaattt aatggaggag caccaaatgt ttatccgatc     960
gacctctggt caagactttg ggcaacggac aggatacaac gtctgggaat tccccgcttc    1020
tttaaggaag agattaagga aatcttaagt tatgtctata gctattggac agacattgga    1080
gtctattgta cacgagattc caaatatgct gacattgacg acacatccat gggattcagg    1140
cttctgagga tgcacggatt taaaatggac ccaaatgtat ttaaatactt ccagaaagac    1200
gacagatttg tttgtctagg tggtcaaatg aatgattctc caactgcaac atacaatctt    1260
tacagggctg ctcaatacca atttccaggt gaaaaaattc tagaagatgc tagaaagttc    1320
tctcaagagt ttctacaaca ttgtatagac accaataacc ttctagataa atgggtgata    1380
tccccgcgct ttccggaaga gttgaaattt ggaatggaga tgacatggta ttcctgccta    1440
ccacgaattg aggctagata ctacgtacaa cattatggtg ctacagagga cgtctggctt    1500
ggaaagactt ttttcaggat ggaagaaatc agtaatgaga actataagga gcttgcaaaa    1560
cttgatttca gtaaatgcca agcacaacat cagacagagt ggattcatat gcaagagtgg    1620
tatgaaagta gcaatgctaa ggaatttggg ataagcagaa aagacctact ttttgcttac    1680
tttttggctg cagcttccat atttgaaacc gaaagggcaa aagagagaat tctgtgggca    1740
```

```
aaatctcaaa ttatttgcaa gatggttaag tcatatctgg aaaaccaaac ggcgtcgttg    1800
gagcacaaaa tcgccttttt aactggattc ggagataaca acaatggcct gcacacaatt    1860 aataagggt ctggacctgt taacaatgtc atgagaaccc tccaacagct ccttggagaa     1920
ttcgacggat atattagtag tcaattggaa aatgcttggg cagcatggtt gacgaaactc    1980
gagcaaggcg aggccaacga tgcgagctc ctcgcaacca cactaaacat tgttctggg     2040 cgtattgtgt ataacgagga tacattatcg aacaaggagt acaaggcttt cgcagacctc    2100
acaaataaaa tttgtcaaaa tcttgctcaa atccaaaata aaagggtga cgaaattaag    2160 gatccgaatg aaggcgaaaa ggacaaggaa gtcgagcaag gcatgcaggc attggctaag    2220
ttagtttttg aggaatctgg gcttgagagg agtatcaaag aaacattctt agcagtggtg    2280
agaacttatc actatggggc ctatgttgct gatgagaaga ttgatgtcca catgttcaag    2340
gttttgttcg aaccagttga atga                                          2364
```

<210> SEQ ID NO 31
<211> LENGTH: 799
<212> TYPE: PRT
<213> ORGANISM: Nepeta mussinii

<400> SEQUENCE: 31

```
Met Thr Ser Ile Ser Ser Leu Asn Leu Ser Asn Ala Ala Ala Ala Arg
1               5                   10                  15

Arg Arg Leu Gln Leu Pro Ala Asn Val His Leu Pro Glu Phe His Ser
            20                  25                  30

Val Cys Ala Trp Leu Asn Ser Ser Lys His Asp Pro Phe Ser Cys
        35                  40                  45

Arg Ile His Arg Lys Gln Lys Ser Lys Val Thr Glu Cys Arg Val Ala
    50                  55                  60

Ser Val Asp Ala Ser Pro Val Ser Asp His Lys Met Ser Ser Pro Val
65                  70                  75                  80

Gln Thr Gln Glu Glu Ala Asn Lys Asn Met Glu Glu Ser Ile Glu Tyr
                85                  90                  95

Ile Lys Asn Leu Leu Met Thr Ser Gly Asp Gly Arg Ile Ser Val Ser
            100                 105                 110

Ala Tyr Asp Thr Ser Ile Val Ala Leu Ile Lys Asp Ile Glu Gly Arg
        115                 120                 125

Asp Ala Pro Gln Phe Pro Ser Cys Leu Glu Trp Ile Gly Gln Asn Gln
    130                 135                 140

Lys Ala Asp Gly Ser Trp Gly Asp Asp Phe Phe Cys Ile Tyr Asp Arg
145                 150                 155                 160

Phe Val Asn Thr Leu Ala Cys Ile Val Ala Leu Lys Ser Trp Asn Leu
                165                 170                 175

His Pro His Lys Ile Gln Lys Gly Val Thr Tyr Ile Lys Lys Asn Val
            180                 185                 190

His Lys Leu Lys Asp Gly Arg Pro Glu Leu Met Thr Ser Gly Phe Glu
        195                 200                 205

Ile Cys Val Pro Ala Ile Leu Gln Arg Ala Lys Asp Leu Gly Ile Gln
    210                 215                 220

Asp Leu Pro Tyr Asp Asp Pro Met Ile Lys Gln Ile Thr Asp Thr Lys
225                 230                 235                 240

Glu Arg Arg Leu Lys Lys Ile Pro Lys Asp Phe Ile Tyr Gln Leu Pro
                245                 250                 255
```

-continued

```
Thr Thr Leu Leu Phe Ser Leu Glu Gly Gln Glu Asn Leu Asp Trp Glu
            260                 265                 270

Lys Ile Leu Lys Leu Gln Ser Ala Asp Gly Ser Phe Leu Thr Ser Pro
        275                 280                 285

Ser Ser Thr Ala Ala Val Phe Met His Thr Lys Asp Glu Lys Cys Leu
    290                 295                 300

Lys Phe Ile Glu Asn Ala Val Lys Asn Cys Asp Gly Gly Val Pro His
305                 310                 315                 320

Thr Tyr Pro Val Asp Val Phe Ala Arg Leu Trp Ala Val Asp Arg Leu
                325                 330                 335

Gln Arg Leu Gly Ile Ser Arg Phe Phe Gln Pro Glu Ile Lys Tyr Phe
            340                 345                 350

Leu Asp His Ile Gln Ser Val Trp Thr Glu Asn Gly Val Phe Ser Gly
        355                 360                 365

Arg Asp Ser Gln Phe Cys Asp Ile Asp Asp Thr Ser Met Gly Ile Arg
    370                 375                 380

Leu Leu Lys Met His Gly Tyr Lys Ile Asp Pro Asn Ala Leu Glu His
385                 390                 395                 400

Phe Lys Gln Glu Asp Gly Lys Phe Ser Cys Tyr Gly Gly Gln Met Ile
                405                 410                 415

Glu Ser Ala Ser Pro Ile Tyr Asn Leu Tyr Arg Ala Ala Gln Leu Arg
            420                 425                 430

Phe Pro Gly Glu Glu Ile Leu Glu Glu Ala Ile Lys Phe Ser Tyr Asn
        435                 440                 445

Phe Leu Gln Glu Lys Leu Ala Lys Asp Glu Ile Gln Glu Lys Trp Val
    450                 455                 460

Ile Ser Glu His Leu Ile Asp Glu Ile Lys Ile Gly Leu Lys Met Pro
465                 470                 475                 480

Trp Tyr Ala Thr Leu Pro Arg Val Glu Ala Ala Tyr Tyr Leu Asp Tyr
                485                 490                 495

Tyr Ala Gly Ser Gly Asp Val Trp Ile Gly Lys Thr Phe Tyr Arg Met
            500                 505                 510

Pro Glu Ile Ser Asn Asp Thr Tyr Lys Glu Met Ala Ile Leu Asp Phe
        515                 520                 525

Asn Arg Cys Gln Ala Gln His Gln Phe Glu Trp Ile Tyr Met Gln Glu
    530                 535                 540

Trp Tyr Glu Ser Ser Asn Val Lys Glu Phe Gly Ile Ser Lys Lys Glu
545                 550                 555                 560

Leu Leu Val Ala Tyr Phe Leu Ala Ala Ser Thr Ile Phe Glu Pro Glu
                565                 570                 575

Arg Ala Gln Glu Arg Ile Met Trp Ala Lys Thr Lys Ile Val Ser Lys
            580                 585                 590

Met Ile Ala Ser Ser Leu Asn Lys Gln Thr Thr Leu Ser Leu Asp Gln
        595                 600                 605

Lys Thr Ala Leu Phe Thr Gln Leu Glu His Ser Leu Asn Gly Leu Asp
    610                 615                 620

Ser Asp Glu Lys Asp Asn Gly Val Ala Glu Thr Lys Asn Leu Val Ala
625                 630                 635                 640

Thr Phe Gln Gln Leu Leu Asp Gly Phe Asp Lys Tyr Thr Arg His Gln
                645                 650                 655

Leu Lys Asn Ala Trp Ser Gln Trp Leu Lys Gln Val Gln Gln Gly Glu
            660                 665                 670

Ala Thr Gly Gly Ala Asp Ala Glu Leu Glu Ala Asn Thr Leu Asn Ile
```

|  | 675 | 680 | 685 |
|---|---|---|---|

Cys Ala Gly His Ile Ala Phe Asn Glu Gln Val Leu Ser His Asn Glu
690                     695                     700

Tyr Thr Thr Leu Ser Thr Leu Thr Asn Lys Ile Cys His Arg Leu Thr
705                     710                     715                     720

Gln Ile Gln Asp Lys Lys Thr Leu Glu Ile Ile Asp Gly Gly Ile Arg
                    725                     730                     735

Tyr Lys Glu Leu Glu Gln Glu Met Gln Ala Leu Val Lys Leu Val Val
                740                     745                     750

Glu Glu Asn Asp Gly Gly Ile Asp Arg Asn Ile Lys Gln Thr Phe
                    755                     760                     765

Leu Ser Val Phe Lys Asn Tyr Tyr Tyr Ser Ala Tyr His Asp Ala His
770                     775                     780

Thr Thr Asp Val His Ile Phe Lys Val Leu Phe Gly Pro Val Val
785                     790                     795

<210> SEQ ID NO 32
<211> LENGTH: 2400
<212> TYPE: DNA
<213> ORGANISM: Nepeta mussinii

<400> SEQUENCE: 32

```
atgacttcaa tatcctctct aaatttgagc aatgcagcag ctgctcgccg caggttacaa      60
ctaccagcaa acgttcacct gccggaattt cactccgtct gtgcatggct gaatagcagc     120
agcaaacacg atcccttag ttgccgaatt catcgaaagc aaaaatcgaa agtaaccgag      180
tgtcgagtag caagcgtgga tgcatcacca gtgagtgatc ataaaatgag ttctcctgtt     240
caaactcaag aagaggcaaa taaaaatatg gaggagtcaa tcgagtacat aaagaatttg     300
ttgatgacat ctggagacgg gcgaataagc gtgtcggcat acgacacgtc aatagtcgcc     360
ctaattaagg acatagaagg acgggacgcc ccgcaatttc catcatgcct ggagtggatc     420
gggcaaaacc aaaaggccga tggctcgtgg ggggacgact tcttctgtat ttacgaccgc     480
ttcgtaaata cactagcatg tatcgtggcc ttgaaatcat ggaaccttca ccctcacaag     540
attcaaaaag gagtgacata catcaagaaa aacgtgcata gcttaaaga tgggaggcct      600
gagctgatga cgtcagggtt cgaaatttgt gttcccgcca ttcttcaaag agccaaagac     660
ttgggcatcc aagatcttcc ctatgatgat cccatgatta acagatcac tgatacgaaa     720
gagcgacgac tcaaaaagat accgaaggat tttatatacc aattgccgac gactttactc     780
ttcagtttgg aagggcagga gaatttggac tgggaaaaga tactcaaact gcagtcagct     840
gacggctcct tccttacttc gccgtcctcc accgccgccg tcttcatgca taccaaagat     900
gaaaaatgct tgaagttcat agagaacgcc gtcaaaaatt gcgacggcgg agtgcccat      960
acctacccag tagacgtgtt tgcaagactt tgggcagttg acagactaca acgcctaggg    1020
atttctcgct tttttcagcc tgagattaaa tatttcttag atcacataca aagcgtttgg    1080
actgagaacg gagttttcag tggacgagat tcacaatttt gcgacattga tgatacgtcc    1140
atggggataa ggcttctgaa aatgcatgga tacaaaatcg acccaaatgc acttgagcat    1200
ttcaagcagg aggatggtaa attttcgtgc tacggtggtc aaatgatcga gtctgcatca    1260
ccgatataca atctgtaccg agctgctcaa ctccgatttc aggagaaga aattcttgaa     1320
gaggccatta aattttccta taactttttg caagaaaagc tagccaagga tgaaattcaa    1380
gaaaaatggg tcatatcgga gcacttaatt gatgagatta agatcgggct aaagatgcca    1440
```

-continued

```
tggtacgcca ctctaccccg agttgaagct gcatattacc tggactatta tgcaggatcc    1500
ggcgatgtgt ggattggcaa gactttctac aggatgccag aaatcagtaa tgatacatac    1560
aaagaaatgg ccattttgga tttcaaccga tgccaagcac aacatcagtt tgaatggatt    1620
tacatgcaag agtggtatga agtagcaac gtaaaggaat ttgggataag caaaaaagag     1680
ctacttgttg cttatttctt ggctgcatca accatatttg aaccggaaag agcacaagag    1740
aggattatgt gggcaaaaac aaaaattgtt tccaaaatga tcgcatcatc tcttaacaaa    1800
caaaccactc tatcgttaga ccaaaagact gcactttta cccaactcga acatagtctc     1860
aatggcctcg acagtgatga aaagataat ggagtagctg agacgaaaaa tctagtggca     1920
accttccagc agctgctaga tggattcgac aaatacactc gccatcaatt gaaaaatgct    1980
tggagccagt ggttgaagca agtgcagcaa ggagaggcga ccgggggcgc agacgcggag    2040
ctggaagcaa acacgttgaa catctgtgcc ggtcatatcg cattcaacga acaagtatta    2100
tcgcacaacg aatacacaac tctctccaca ctcacaaaca agatctgcca ccggcttacc    2160
caaattcaag acaaaaagac gcttgagata atcgacggcg cataagata taaggagctg     2220
gagcaggaga tgcaggcgtt ggtgaaatta gttgttgaag aaacgacgg cggcggcata     2280
gacaggaata ttaaacaaac attttttatca gttttcaaga attattacta cagtgcctac    2340
cacgatgctc acacaaccga tgttcatatt ttcaaagtat tatttggacc ggtcgtctga    2400
```

<210> SEQ ID NO 33
<211> LENGTH: 796
<212> TYPE: PRT
<213> ORGANISM: Origanum majorana

<400> SEQUENCE: 33

```
Met Thr Asp Val Ser Ser Leu Arg Leu Ser Asn Ala Pro Ala Ala Gly
1               5                   10                  15

Gly Arg Leu Pro Leu Pro Gly Lys Val His Leu Pro Glu Phe Arg Thr
            20                  25                  30

Val Cys Ala Trp Leu Asn Asn Gly Cys Lys Tyr Glu Pro Leu Thr Cys
        35                  40                  45

Arg Ile Ser Arg Arg Lys Ile Ser Glu Cys Arg Val Ala Ser Leu Asn
    50                  55                  60

Ser Ser Gln Leu Ile Glu Lys Val Gly Ser Pro Ala Gln Ser Leu Glu
65                  70                  75                  80

Glu Ala Asn Lys Lys Ile Glu Asp Ser Ile Glu Tyr Ile Lys Asn Leu
                85                  90                  95

Leu Met Thr Ser Gly Asp Gly Arg Ile Ser Val Ser Ala Tyr Asp Thr
            100                 105                 110

Ser Leu Val Ala Leu Ile Lys Asp Val Lys Gly Arg Asp Ala Pro Gln
        115                 120                 125

Phe Pro Ser Cys Leu Glu Trp Ile Ala Gln Asn Gln Met Ala Asp Gly
    130                 135                 140

Ser Trp Gly Asp Glu Phe Phe Cys Ile Tyr Asp Arg Ile Val Asn Thr
145                 150                 155                 160

Leu Ala Cys Leu Val Ala Leu Lys Ser Trp Asn Leu His Pro Asp Lys
                165                 170                 175

Ile Glu Lys Gly Val Thr Tyr Ile Asn Glu Asn Val His Lys Leu Lys
            180                 185                 190

Asp Gly Ser Thr Glu His Met Thr Ser Gly Phe Glu Ile Val Val Pro
        195                 200                 205
```

-continued

```
Ala Thr Leu Glu Arg Ala Lys Val Leu Gly Ile Gln Gly Leu Pro Tyr
    210                 215                 220

Asp His Pro Phe Ile Lys Glu Ile Ile Asn Thr Lys Glu Arg Arg Leu
225                 230                 235                 240

Ser Lys Ile Pro Lys Asp Leu Ile Tyr Lys Leu Pro Thr Thr Leu Leu
                245                 250                 255

Phe Ser Leu Glu Gly Gln Gly Glu Leu Asp Trp Glu Lys Ile Leu Lys
            260                 265                 270

Leu Gln Ser Ser Asp Gly Ser Phe Leu Thr Ser Pro Ser Ser Thr Ala
        275                 280                 285

Ser Val Phe Met Arg Thr Lys Asp Glu Lys Cys Leu Lys Phe Ile Glu
    290                 295                 300

Asn Ala Val Lys Asn Cys Gly Gly Ala Pro His Thr Tyr Pro Val
305                 310                 315                 320

Asp Val Phe Ala Arg Leu Trp Ala Val Asp Arg Leu Gln Arg Leu Gly
                325                 330                 335

Ile Ser Arg Phe Phe Gln His Glu Ile Lys Tyr Phe Leu Asp His Ile
            340                 345                 350

Asn Ser Val Trp Thr Glu Asn Gly Val Phe Ser Gly Arg Asp Ser Gln
        355                 360                 365

Phe Cys Asp Ile Asp Asp Thr Ser Met Gly Val Arg Leu Leu Lys Met
    370                 375                 380

His Gly Tyr Asn Val Asp Pro Asn Ala Leu Lys His Phe Lys Gln Glu
385                 390                 395                 400

Asp Gly Lys Phe Ser Cys Tyr Pro Gly Gln Met Ile Glu Ser Ala Ser
                405                 410                 415

Pro Ile Tyr Asn Leu Tyr Arg Ala Ala Gln Leu Arg Phe Pro Gly Glu
            420                 425                 430

Glu Ile Leu Glu Glu Ala Ser Arg Phe Ala Phe Asn Phe Leu Gln Glu
        435                 440                 445

Lys Ile Ala Asn His Glu Ile Gln Glu Lys Trp Val Ile Ser Glu His
    450                 455                 460

Leu Ile Asp Glu Ile Lys Leu Gly Leu Lys Met Pro Trp Tyr Ala Thr
465                 470                 475                 480

Leu Pro Arg Val Glu Ala Ala Tyr Tyr Leu Glu Tyr Tyr Ala Gly Ser
                485                 490                 495

Gly Asp Val Trp Ile Gly Lys Thr Phe Tyr Arg Met Pro Glu Ile Ser
            500                 505                 510

Asn Asp Thr Tyr Lys Glu Val Ala Ile Leu Asp Phe Asn Thr Cys Gln
        515                 520                 525

Ala Gln His Gln Phe Glu Trp Ile Tyr Met Gln Glu Trp Tyr Glu Ser
    530                 535                 540

Ser Lys Val Lys Asp Phe Gly Ile Ser Lys Lys Asp Leu Leu Val Ala
545                 550                 555                 560

Tyr Phe Leu Ala Ala Ser Thr Ile Phe Glu Pro Glu Arg Thr Gln Glu
                565                 570                 575

Arg Ile Ile Trp Ala Lys Thr Leu Ile Leu Ser Arg Met Ile Thr Ser
            580                 585                 590

Phe Leu Asn Lys Gln Ala Thr Leu Ser Ser Gln Lys Asn Ala Ile
        595                 600                 605

Leu Thr Gln Leu Gly Glu Ser Val Asp Gly Leu Asp Lys Ile Tyr Ser
    610                 615                 620

Gly Glu Lys Asp Ser Gly Leu Ala Glu Thr Leu Leu Ala Thr Phe Gln
```

Gln Leu Leu Asp Gly Phe Asp Arg Tyr Thr Arg His Gln Leu Arg Asn
625                 630                 635                 640

Ala Trp Gly Gln Trp Leu Met Lys Val Gln Gln Gly Glu Ala Asn Gly
            645                 650                 655

Gly Ala Asp Ala Glu Leu Ile Ala Asn Thr Leu Asn Ile Cys Ala Gly
        660                 665                 670

Leu Ile Ala Phe Asn Glu Asp Val Leu Leu His Ser Glu Tyr Thr Thr
    675                 680                 685

690                 695                 700

Leu Ser Ser Leu Thr Asn Lys Ile Cys Gln Arg Leu Ser Gln Ile Glu
705                 710                 715                 720

Asp Glu Lys Thr Leu Glu Val Ile Gly Gly Ile Lys Asp Lys Glu
                725                 730                 735

Leu Glu Glu Asp Ile Gln Ala Leu Val Lys Leu Ala Leu Glu Glu Asn
            740                 745                 750

Gly Gly Cys Gly Val Asp Arg Arg Ile Lys Gln Ser Phe Leu Ser Val
        755                 760                 765

Phe Lys Thr Phe Tyr Tyr Arg Ala Tyr His Asp Ala Glu Thr Thr Asp
    770                 775                 780

Leu His Ile Phe Lys Val Leu Phe Gly Pro Val Met
785                 790                 795

<210> SEQ ID NO 34
<211> LENGTH: 2391
<212> TYPE: DNA
<213> ORGANISM: Origanum majorana

<400> SEQUENCE: 34
atgaccgatg tatcctctct tcgtttgagc aatgcaccag ctgccggcgg caggttgccg     60
ctgccgggaa aggttcacct gcctgaattt cgcaccgttt gtgcatggtt gaacaatggc    120
tgcaaatacg agcccttgac ttgtcgaatt agtcgacgga agatatctga atgtcgagta    180
gcaagtctga attcgtcgca actaattgaa aaggtcggtt ctcctgctca atctctagaa    240
gaggcaaaca aaaagatcga ggactccatc gagtacatta agaatctatt gatgacatct    300
ggcgacgggc ggataagtgt gtcggcttac gacacgtcgc tagtcgccct aataaaggac    360
gtgaaaggac gagatgcccc tcagttcccg tcgtgcctgg agtggatagc gcaaaaccaa    420
atggccgacg ggtcgtgggg ggatgagttc ttctgtattt acgaccggat cgtgaataca    480
ttagcatgcc tcgttgcctt gaaatcatgg aaccttcacc ccgacaagat cgaaaaagga    540
gtgacgtaca tcaacgaaaa tgtgcacaaa ctgaaagacg ggagcaccga gcacatgacg    600
tcagggttcg aaatcgtggt ccccgccact ctagaaagag ccaaagtctt gggcatccaa    660
ggcctcccct tgatgatcc cttcattaag gagattatta atactaagga gcgaagatta    720
agcaaaatac ccaaggattt gatatacaaa ctgccaacga cgctgctgtt cagtttagaa    780
gggcagggag aattagattg ggaaaagata ctgaaactgc agtcaagcga tggctccttc    840
cttacttcgc cctcgtcgac cgcctccgtc ttcatgcgga cgaaagacga gaaatgcctc    900
aagttcattg agaacgccgt taagaattgc ggcggggag cgccgcatac ttacccagtg    960
gatgtgtttg caagactttg gcagttgac agactacagc gattagggat ttctcgattc   1020
ttccaacacg agattaaata cttcttagat cacattaaca gtgtatggac cgagaatgga   1080
gttttcagtg gacgagattc acaatttgt gatatcgacg acacttctat gggagttagg   1140
cttctaaaaa tgcatggata caatgttgat ccaaatgcgc tcaagcattt caagcaggag   1200

-continued

```
gatggcaaat tctcttgcta ccctggccaa atgatcgagt ctgcatctcc gatatacaat    1260
ctctaccgag ccgctcaact ccggttcccc ggagaagaaa ttctcgaaga agcaagtcga    1320
ttcgccttca actttctgca ggaaaagata gccaaccatg aaattcaaga aaatgggtc     1380 atatctgagc acttaattga tgagataaag ttgggactga agatgccatg gtacgcgact    1440
ctgccccgag ttgaggccgc ttattatcta gagtattatg ctggctcagg cgacgtatgg    1500
attggaaaga cttctaccg gatgccggaa atcagtaacg atacgtataa agaggtggcc     1560
attttggatt tcaacacatg ccaagctcaa caccagtttg aatggattta catgcaagag    1620
tggtacgaaa gtagcaaggt taaagatttc gggataagca aaaaggacct acttgttgct    1680
tactttctgg cggcatcgac tatatttgaa cccgaaagaa cacaagagag gattatttgg    1740
gcaaaaaccc taattctttc taggatgatc acatcatttc tcaacaaaca agctacactt    1800
tcatcccaac aaaagaatgc catcttaaca caacttggag agagtgtcga tggcctcgat    1860
aaaatatata gtggtgagaa agattctggg ctggctgaga ctctgctggc taccttccag    1920
caactgctcg acggattcga tagatacact cgccatcaac tgagaaatgc ttgggggcaa    1980
tggttgatga agtgcagca aggagaggcc aacggtggcg ccgacgctga gctcatagca     2040
aacacactca atatctgcgc cggccttatc gccttcaacg aagacgtatt gttgcacagc    2100
gaatacacga ctctctcctc cctcaccaac aaaatatgcc agcgccttag ccagattgaa    2160
gatgaaaaga cgcttgaagt gattgaaggg ggcataaaag ataaggaact ggaggaggat    2220
attcaggcgt tggtgaagct agccctcgaa gaaacggcg gctgcggcgt cgacagaaga     2280
atcaagcagt cattcttatc agtattcaag acttttttact acagagccta ccatgatgct    2340
gagaccaccg atcttcatat tttcaaagta ctgtttgggc cggttatgtg a             2391
```

<210> SEQ ID NO 35
<211> LENGTH: 798
<212> TYPE: PRT
<213> ORGANISM: Perovskia atriplicifolia

<400> SEQUENCE: 35

```
Met Thr Ser Met Ser Ser Leu Asn Leu Ser Arg Ala Pro Ala Thr Thr
  1               5                  10                  15

His Arg Leu Gln Leu Gln Ala Lys Val His Val Pro Glu Phe Tyr Ala
                 20                  25                  30

Val Cys Ala Trp Leu Asn Ser Ser Lys Gln Ala Pro Leu Ser Cys
             35                  40                  45

Gln Ile Arg Cys Lys Gln Leu Ser Arg Val Thr Glu Cys Arg Val Ala
     50                  55                  60

Ser Leu Asp Ala Ser Gln Val Ser Glu Lys Asp Thr Ser His Val Gln
 65                  70                  75                  80

Thr Pro Asp Glu Val Asn Lys Lys Ile Glu Asp Tyr Ile Glu Tyr Val
                 85                  90                  95

Lys Asn Leu Leu Met Thr Ser Gly Asp Gly Arg Ile Ser Val Ser Pro
                100                 105                 110

Tyr Asp Thr Ser Ile Val Ala Leu Ile Lys Asp Ser Lys Gly Arg Asn
            115                 120                 125

Ile Pro Gln Phe Pro Ser Cys Leu Glu Trp Ile Ala Gln His Gln Met
    130                 135                 140

Ala Asp Gly Ser Trp Gly Asp Gln Phe Phe Cys Ile Tyr Asp Arg Ile
145                 150                 155                 160
```

-continued

```
Leu Asn Thr Leu Ala Cys Val Val Ala Leu Lys Ser Trp Asn Val His
                165                 170                 175
Gly Asp Met Ile Glu Lys Gly Val Thr Tyr Val Lys Glu Asn Val His
            180                 185                 190
Lys Leu Lys Asp Gly Asn Ile Glu His Met Thr Ser Gly Phe Glu Ile
        195                 200                 205
Val Val Pro Ala Leu Val Gln Arg Ala Lys Asp Leu Gly Ile Gln Gly
    210                 215                 220
Leu Pro Tyr Asp Asp Pro Leu Ile Lys Glu Ile Ala Asp Thr Lys Glu
225                 230                 235                 240
Arg Arg Leu Lys Lys Ile Pro Lys Asp Met Ile Tyr Gln Thr Pro Thr
                245                 250                 255
Thr Leu Leu Phe Ser Leu Glu Gly Gln Gly Asp Leu Glu Trp Glu Lys
            260                 265                 270
Ile Leu Lys Leu Gln Ser Gly Asp Gly Ser Phe Leu Thr Ser Pro Ser
        275                 280                 285
Ser Thr Ala His Val Phe Val Gln Thr Lys Asp Glu Lys Cys Leu Lys
    290                 295                 300
Phe Ile Glu Asn Ala Val Lys Asn Cys Ser Gly Gly Ala Pro His Thr
305                 310                 315                 320
Tyr Pro Val Asp Val Phe Ala Arg Leu Trp Ala Ile Asp Arg Leu Gln
                325                 330                 335
Arg Leu Gly Ile Ser Arg Phe Phe Gln Pro Glu Ile Lys Tyr Phe Ile
            340                 345                 350
Asp His Ile Asn Ser Val Trp Thr Glu Asn Gly Val Phe Ser Gly Arg
        355                 360                 365
Asp Ser Glu Phe Cys Asp Ile Asp Asp Thr Ser Met Gly Ile Arg Leu
    370                 375                 380
Leu Lys Met His Gly Tyr Lys Val Asp Pro Asn Ala Leu Asn His Phe
385                 390                 395                 400
Lys Gln Gln Asp Gly Lys Phe Ser Cys Tyr Gly Gly Gln Met Ile Glu
                405                 410                 415
Ser Ala Ser Pro Ile Tyr Asn Leu Tyr Arg Ala Ala Gln Leu Arg Phe
            420                 425                 430
Pro Gly Glu Glu Ile Leu Glu Glu Ala Ser Lys Phe Ala Phe Asn Phe
        435                 440                 445
Leu Gln Glu Lys Ile Ala Asn Asp Gln Phe Gln Glu Lys Trp Val Ile
    450                 455                 460
Ser Asp His Leu Ile Asp Glu Val Lys Leu Gly Leu Lys Met Pro Trp
465                 470                 475                 480
Tyr Ala Thr Leu Pro Arg Val Glu Ala Ala Tyr Tyr Leu Gln Tyr Tyr
                485                 490                 495
Ala Gly Ser Gly Asp Val Trp Ile Gly Lys Val Phe Tyr Arg Met Pro
            500                 505                 510
Glu Ile Ser Asn Asp Thr Tyr Lys Glu Leu Ala Ile Leu Asp Phe Asn
        515                 520                 525
Arg Cys Gln Ala Gln His Gln Phe Glu Trp Ile Tyr Met Gln Glu Trp
    530                 535                 540
Tyr His Arg Ser Ser Val Ser Glu Phe Gly Ile Ser Lys Lys Glu Leu
545                 550                 555                 560
Leu Arg Thr Tyr Phe Leu Ala Ala Ala Thr Ile Phe Glu Pro Glu Arg
                565                 570                 575
Thr Gln Glu Arg Leu Val Trp Ala Lys Thr Gln Ile Val Ser Arg Met
```

|   |   |   | 580 |   |   |   | 585 |   |   |   | 590 |   |
|---|---|---|---|---|---|---|---|---|---|---|---|---|
Ile Thr Ser Phe Val Asn Asn Gly Thr Thr Leu Ser Leu Asp Gln Met
                595                 600                 605

Thr Ala Leu Ala Thr Gln Ile Gly His Asn Phe Asp Gly Leu Asp Gln
        610                 615                 620

Ile Ile Ser Ala Met Lys Asp His Gly Leu Ala Gly Thr Leu Leu Thr
625                 630                 635                 640

Thr Phe Gln Gln Leu Leu Asp Gly Phe Asp Arg Tyr Thr Arg His Gln
                645                 650                 655

Leu Lys Asn Ala Trp Ser Gln Trp Phe Met Lys Leu Gln Gln Gly Glu
            660                 665                 670

Ala Asn Gly Gly Glu Asp Ala Glu Leu Leu Ala Asn Thr Leu Asn Ile
        675                 680                 685

Cys Ala Gly Phe Ile Ala Phe Asn Glu Asp Val Leu Ser His Asp Glu
        690                 695                 700

Tyr Thr Thr Leu Ser Thr Leu Thr Asn Lys Ile Cys Lys Arg Leu Ser
705                 710                 715                 720

Gln Ile Gln Asp Lys Lys Ala Leu Glu Val Val Asp Gly Ser Ile Lys
                725                 730                 735

Asp Lys Glu Leu Glu Gln Asp Met Gln Ala Leu Val Lys Leu Val Leu
            740                 745                 750

Glu Glu Asn Gly Gly Gly Val Asp Arg Asn Ile Lys Gln Thr Phe Leu
        755                 760                 765

Ser Val Phe Lys Thr Phe Tyr Tyr Thr Ala Tyr His Asp Asp Glu Thr
    770                 775                 780

Thr Asp Val His Ile Phe Lys Val Leu Phe Gly Pro Val Val
785                 790                 795

<210> SEQ ID NO 36
<211> LENGTH: 2397
<212> TYPE: DNA
<213> ORGANISM: Perovskia atriplicifolia

<400> SEQUENCE: 36

| | | |
|---|---|---|
| atgacctcta tgtcctctct aaatttgagc agagcaccag ctaccaccca ccggttacag | 60 |
| ctacaggcaa aggttcacgt gccggaattt tatgccgtgt gtgcatggct gaatagcagc | 120 |
| agcaaacagg cacccttgag ttgccaaatt cgctgcaagc aactatcaag agtaactgaa | 180 |
| tgtcgggtag caagtctgga tgcgtcgcaa gtgagtgaaa agacacttc tcatgtccaa | 240 |
| actcccgatg aggtgaacaa aaagatcgag gactatatcg agtacgtcaa gaatctgttg | 300 |
| atgacgtcgg gcgacgggcg aataagcgtg tcgccctacg acacgtcaat agtcgccctt | 360 |
| attaaggact cgaaagggcg caacatcccg cagtttccgt cgtgcctcga gtggatagcg | 420 |
| cagcaccaaa tggcggatgg ctcatggggg gatcaattct tctgcattta cgaccggatt | 480 |
| ctaaatacat tagcatgtgt cgtagctttg aaatcctgga acgttcacgg tgacatgatc | 540 |
| gaaaaggag tgacgtacgt caaggaaaat gtgcataagc ttaaagatgg aatattgag | 600 |
| cacatgacgt cggggttcga aattgtggtt cccgcccttg ttcaaagagc caaagacttg | 660 |
| ggcatccaag gcctgcccta tgatgatccc ctcatcaagg agattgctga tacaaaagaa | 720 |
| agaagattga aaaagatacc caaggatatg atttaccaaa cgccaacgac attactattc | 780 |
| agtttagaag gcagggagaa tttggagtgg gaaaagatac tgaaactgca gtcaggcgat | 840 |
| ggctccttcc tcacttcgcc gtcatccacc gcccacgtgt tcgtgcagac caaagatgaa | 900 |

| | | |
|---|---|---|
| aaatgcttga aattcatcga gaacgccgtc aagaattgca gtggaggagc gccgcatact | 960 | |
| tatccagtcg atgtcttcgc aagactttgg gcaattgaca gactacaacg cctaggaatt | 1020 | |
| tctcgtttct tccagccgga aattaagtat tcatagacc acatcaacag cgtttggaca | 1080 | |
| gagaacggag ttttcagtgg gcgagattcg gaattttgcg atattgatga cacgtccatg | 1140 | |
| ggcatcaggc ttctcaaaat gcacggatac aaagtcgacc caaatgcact caatcatttc | 1200 | |
| aagcagcaag atggtaaatt ttcttgctac ggtggtcaaa tgatcgagtc tgcatctcca | 1260 | |
| atatacaatc tctacagggc tgctcagcta cgatttccag gagaagaaat tcttgaagaa | 1320 | |
| gccagtaaat ttgcctttaa cttttttgcaa gaaaaaatag ccaacgatca atttcaagaa | 1380 | |
| aaatgggtga tatccgacca cttaatcgat gaggtgaagc tcgggctgaa gatgccatgg | 1440 | |
| tacgccactc taccccgggt tgaggctgca tattatctac aatactatgc tggttctggc | 1500 | |
| gacgtatgga ttggcaaggt tttctacagg atgccggaaa tcagcaatga tacatacaaa | 1560 | |
| gagctggcca tattggattt caacagatgc caagcacagc atcagttcga atggatttat | 1620 | |
| atgcaagagt ggtatcacag aagcagcgtt agtgaattcg ggataagcaa aaaagagctg | 1680 | |
| cttcgtactt actttctggc tgcagcaacc atattcgaac ccgagagaac acaagagagg | 1740 | |
| cttgtgtggg caaaaaccca aattgtctct aggatgatca catcatttgt taacaatgga | 1800 | |
| actacactat ctttggacca aatgactgca cttgcaacac aaatcggcca taatttcgat | 1860 | |
| ggcctcgatc aaataattag tgctatgaaa gatcatggac tggctgggac tctgctgaca | 1920 | |
| accttccagc aacttctaga tggattcgac agatacactc gccatcaact caaaaatgct | 1980 | |
| tggagccaat ggttcatgaa actccagcaa ggggaggcga acggcgggga agacgcggag | 2040 | |
| ctcctagcaa acacgctcaa catctgcgcg ggtttcattg ctttcaacga agacgtattg | 2100 | |
| tcgcacgatg aatacacgac tctctccacc cttacaaaca aatctgcaa gcgccttagc | 2160 | |
| caaattcaag ataaaaaggc gctggaagtt gtcgacggga gcataaagga taaggagctc | 2220 | |
| gaacaggata tgcaggcgtt ggtgaagttg gtccttgaag aaaatggcgg cggcgtcgac | 2280 | |
| aggaacatca aacagacatt tttgtccgtt ttcaagactt tttactacac cgcctaccac | 2340 | |
| gatgatgaga ccactgatgt tcatattttc aaagtactgt ttggaccggt cgtatga | 2397 | |

<210> SEQ ID NO 37
<211> LENGTH: 783
<212> TYPE: PRT
<213> ORGANISM: Pogostemon cablin

<400> SEQUENCE: 37

Met Ser Phe Ala Ser Gln Ser His Val Ala Phe Val Leu Arg Arg Pro
1               5                   10                  15

Ser Ala Val Ala Pro Pro Pro Thr Arg Ile Pro Thr Thr Ala Ala
            20                  25                  30

Leu Ser Pro Leu Lys Pro Gly Asp Phe Ser His Gly Arg Ser Ser Phe
        35                  40                  45

Met Pro Thr Ser Ile Lys Cys Asn Ala Ile Ser Thr Ser Arg Val Glu
    50                  55                  60

Glu Tyr Lys Tyr Thr Asp Asp His Asn Gln Ser Gly Leu Leu Glu His
65                  70                  75                  80

Asp Gly Leu Ile Ser Asp Lys Ile Asn Glu Leu Val Thr Lys Ile Gln
                85                  90                  95

Leu Met Leu Gln Asn Met Asp Asp Gly Glu Ile Ser Ile Ser Pro Tyr
            100                 105                 110

-continued

```
Asp Thr Ala Trp Val Ser Leu Val Glu Asp Val Gly Asn Asp Arg
        115                 120                 125
Pro Gln Phe Pro Thr Ser Leu Glu Trp Ile Ser Asn Asn Gln Leu Pro
130                 135                 140
Asp Gly Ser Trp Gly Asp Pro Asn Ala Phe Leu Val His Asp Arg Ile
145                 150                 155                 160
Leu Asn Thr Leu Ala Cys Val Val Ala Leu Lys Ser Trp Lys Met His
                165                 170                 175
Pro His Lys Cys Asn Arg Gly Val Ser Phe Val Arg Glu Asn Ile Tyr
            180                 185                 190
Arg Met Asp Asp Glu Lys Glu Glu His Met Pro Asn Gly Phe Glu Val
        195                 200                 205
Val Phe Pro Ala Leu Leu Gln Lys Ala Lys Thr Leu Asn Ile Asp Ile
    210                 215                 220
Pro Tyr Glu Phe Pro Gly Ile Gln Lys Phe Tyr Ala Lys Arg Asp Leu
225                 230                 235                 240
Lys Phe Ala Arg Ile Pro Met Asp Ile Leu His Ser Val Pro Thr Thr
                245                 250                 255
Leu Leu Phe Ser Leu Glu Gly Val Arg Cys Gly Leu Asp Leu Asp Trp
            260                 265                 270
Gly Lys Leu Leu Glu Leu Gln Ala Ala Asp Gly Ser Phe Leu Tyr Ser
        275                 280                 285
Pro Ser Ser Thr Ala Phe Ala Leu Glu Gln Thr Lys Asp Gln Asn Cys
    290                 295                 300
Leu Lys Tyr Leu Ser Lys Leu Val Arg Lys Phe Asp Gly Gly Val Pro
305                 310                 315                 320
Asn Val Tyr Pro Val Asp Leu Phe Glu His Asn Trp Ala Val Asp Arg
                325                 330                 335
Leu Gln Arg Leu Gly Ile Ser Arg Tyr Phe Thr Pro Glu Ile Asn Gln
            340                 345                 350
Cys Leu Asp Tyr Ser Tyr Arg Tyr Trp Ser Asn Ser Lys Gly Met Tyr
        355                 360                 365
Ser Ala Ser Asn Ser Gln Ile Gln Asp Val Asp Asp Thr Ala Met Gly
    370                 375                 380
Phe Arg Leu Leu Arg Leu Asn Gly Tyr Asp Val Ser Thr Gln Gly Phe
385                 390                 395                 400
Arg Gln Phe Glu Ala Gly Gly Asp Phe Phe Cys Phe Ala Gly Gln Ser
                405                 410                 415
Ser Gln Ala Val Thr Gly Met Tyr Asn Leu Tyr Arg Ala Ser Gln Val
            420                 425                 430
Met Phe Pro Gly Glu Lys Leu Leu Glu Asp Ala Lys Lys Phe Ser Thr
        435                 440                 445
Asn Phe Leu Gln Gln Lys Arg Ala Asn Asn Gln Leu Thr Asp Lys Trp
    450                 455                 460
Val Ile Ala Lys Asp Val Pro Ala Glu Val Gly Tyr Ala Leu Asp Ile
465                 470                 475                 480
Pro Trp Tyr Ala Ser Leu Pro Arg Leu Glu Ala Arg Phe Phe Ile Gln
                485                 490                 495
Gln Tyr Gly Gly Asp Asp Asp Val Trp Ile Gly Lys Thr Leu Tyr Arg
            500                 505                 510
Met Gly Tyr Val Asn Asn Asn Thr Tyr Leu Glu Leu Ala Lys Leu Asp
        515                 520                 525
Tyr Asn Thr Cys Gln Arg Leu His Gln His Glu Trp Ile Thr Ile Gln
```

```
                 530              535              540
Arg Trp Tyr Glu Ile Asn Leu Lys Ile Thr Ser Val Gly Leu Ser Lys
545                 550              555              560

Arg Gly Val Leu Leu Ser Tyr Leu Ala Ala Ala Asn Leu Phe Glu
                565              570              575

Pro Gln Asn Ser Thr His Arg Ile Ala Trp Ala Lys Thr Ser Ile Leu
                580              585              590

Val Ser Ala Ile Gln Leu Ser Pro Leu Gln Lys Arg Asp Phe Ile Asn
                595              600              605

Gln Phe His Arg Ser Thr Ala Asn Asn Gly Tyr Glu Thr Ser Asn Val
        610              615              620

Leu Val Lys Ser Val Ile Lys Gly Val His Glu Leu Ser Met Asp Ala
625              630              635              640

Met Leu Thr His Asn Lys Asp Ile His Arg Gln Leu Phe Asn Ala Trp
                    645              650              655

Arg Lys Trp Met Ser Val Trp Glu Glu Gly Gly Asp Gly Glu Ala Glu
                660              665              670

Leu Leu Leu Ser Thr Leu Asn Thr Cys Asp Gly Val Asp Glu Ser Thr
                675              680              685

Phe Ser Asp Pro Lys Tyr Glu His Leu Leu Glu Ile Thr Val Arg Val
690              695              700

Thr His Gln Leu His Leu Ile Gln Asn Ala Glu Thr Lys Arg Val Gly
705              710              715              720

Asp Arg Glu Glu Ile Asp Leu Ser Met Gln Gln Leu Val Lys Leu Val
                    725              730              735

Phe Thr Lys Ser Ser Ser Asp Leu Asp Ser Cys Ile Lys Gln Arg Phe
                740              745              750

Phe Ala Ile Ala Arg Ser Phe Tyr Tyr Val Ala His Cys Asp Pro Glu
                755              760              765

Met Val Asp Ser His Ile Ala Lys Val Leu Phe Glu Arg Val Met
                770              775              780

<210> SEQ ID NO 38
<211> LENGTH: 2352
<212> TYPE: DNA
<213> ORGANISM: Pogostemon cablin

<400> SEQUENCE: 38
atgtcatttg cttctcaatc acatgtcgcc tttgtactcc gacggccatc tgccgttgct      60
ccgccaccac cgactagaat tccgacaaca gccgctcttt ctcctctcaa accaggtgat     120
ttttcccatg gcagatcatc atttatgccc acttccatta aatgtaatgc aatttccaca     180
tctcgcgtcg aagaatacaa gtacacggat gatcataatc agagtggttt attggagcat     240
gatggtttga tatcagacaa gataaatgaa ttggtgacca agatacaatt gatgctacaa     300
aacatggatg acggagagat aagcatctcc ccatatgaca ccgcatgggt gtcgttggtg     360
gaggatgtgg gcggcaacga ccgcccacag tttcctacga gcctggagtg gatatcgaat     420
aaccagctcc ccgacggctc gtggggcgac ccgaatgcct ttttggtgca cgaccgtatc     480
ctcaacacat tggcatgcgt cgttgcactc aaatcctgga aatgcaccc ccacaaatgc      540 aatagaggag ttagtttcgt gagagaaaat atatacagaa tggatgatga aaagaggaa      600 cacatgccaa atggattcga agtggtattt ccagcactcc ttcaaaaagc gaaaacccta     660
aacattgata tcccgtacga gtttccagga atacaaaaat tttatgccaa agagattta      720
```

-continued

```
aaattcgcca ggattccaat ggatatattg catagcgttc cgacaacatt actgttcagc     780
ttagaaggtg taagatgtgg tcttgatctg gattggggga agcttctaga attgcaagct     840
gctgatggct catttctcta ctctccatcc tctactgcct ttgcactaga acaaaccaag     900
gatcaaaact gcctcaaata tctatctaaa cttgttcgaa aattcgatgg cggagtaccc     960
aacgtgtacc cggtggactt gttcgaacat aattgggcag ttgatcgtct ccaaaggctc    1020
ggaatttctc gttattttac gcctgaaatc aaccaatgtc ttgattattc ttacagatat    1080
tggtcaaata gtaaagggat gtactcggca agcaattccc agattcagga cgttgatgac    1140
accgccatgg gattcaggct tttgagactc aacggctacg atgtctctac acaagggttt    1200
aggcaattcg aggcaggggg ggacttcttc tgcttcgcgg ggcagtcgag ccaagctgta    1260
accggaatgt acaacctcta cagagcttcc caagtgatgt tccctggaga gaagctactg    1320
gaagatgcca agaaattctc caccaacttc ttgcaacaaa aacgagccaa taccagctc     1380 actgacaagt gggttattgc caaagatgtt ccagctgagg tgggatatgc cttggatatt    1440
ccctggtatg ccagtctgcc ccgactggaa gcaagatttt tcatacaaca atacggtgga    1500
gacgacgacg tttggatcgg caaaaccttg tatagaatgg gatatgtgaa caacaacact    1560
tatctggaac tcgcaaagct agactacaac acctgccaaa ggttgcatca gcatgagtgg    1620
ataaccattc aacgatggta cgaaattaat ttaaaaatta ctagtgttgg gttgagcaaa    1680 agagggtcc tgttgagtta ttacttagcc gcagccaatc tgtttgagcc tcaaaactca    1740
acacaccgca tcgcttgggc caaaacttcg attttagtaa gcgctattca actttctccc    1800
ctccaaaagc gcgactttat taaccaattc caccgctcca ccgcaaataa tgggtatgaa    1860
acaagtaatg tgttggtgaa gagtgtaatc aagggtgtgc atgagctctc catggacgct    1920
atgttgacgc acaataaaga catacatcgc caacttttta atgcttggcg aaagtggatg    1980
tcagtgtggg aagagggagg tgatggagaa gcggagctgt tattgtcgac gcttaacacg    2040
tgcgacggag tagatgaatc cacattcagc gatcccaaat acgagcacct cttagagatc    2100
accgtcagag tcacccacca gcttcatctc attcagaatg cagagacgaa gcgtgtgggt    2160
gaccgtgagg aaatagattt gagcatgcaa caacttgtta agttggtgtt cactaaatca    2220
tcatcggatc tggattcttg tatcaagcaa agatttttg cgattgccag aagtttctat     2280
tacgtggctc attgtgatcc ggagatggtg gactcccaca tagccaaagt attgtttgag    2340
agggtgatgt ag                                                        2352
```

<210> SEQ ID NO 39
<211> LENGTH: 599
<212> TYPE: PRT
<213> ORGANISM: Prunella vulgaris

<400> SEQUENCE: 39

```
Met Ser Ser Leu Ser Ile Pro Phe Ser Ser Ala Ile Cys Thr Ser Ser
1               5                   10                  15

Ile Pro Lys Ile Ser Thr Gly His His Arg Arg Thr Ala Arg Met Pro
            20                  25                  30

Ala His Asp Thr Ser Arg Leu Val Phe Arg Pro Ser Ala Val Met Val
        35                  40                  45

Glu Gly Ser Pro Met Thr Thr Ser Ser Asn Gly Lys Glu Val Gln Arg
    50                  55                  60

Leu Ile Thr Thr Phe Lys Pro Ser Met Trp Lys Asp Ile Phe Ser Thr
65                  70                  75                  80
```

```
Phe Ser Phe Asp Asn Gln Val Gln Glu Lys Tyr Leu Lys Glu Ile Glu
                 85                  90                  95

Glu Leu Lys Lys Glu Val Arg Ser Thr Leu Met Ser Ala Thr His Arg
            100                 105                 110

Lys Leu Phe Asp Leu Ile Asp Asn Leu Glu Arg Met Gly Ile Ala Tyr
            115                 120                 125

His Phe Glu Thr Glu Ile Glu Asp Lys Leu Lys Gln Ala His Ala Ser
130                 135                 140

Leu Glu Glu Glu Asp Asp Tyr Asp Leu Phe Thr Thr Ala Leu Arg Phe
145                 150                 155                 160

Arg Leu Leu Arg Gln His Arg Tyr His Val Ser Cys Asp Pro Phe Ala
                165                 170                 175

Lys Phe Val Asp Gln Asp Asn Lys Leu Lys Glu Ser Leu Ser Ser Asp
            180                 185                 190

Val Glu Gly Leu Leu Ser Leu Phe Glu Ala Ser His Leu Arg Ile His
            195                 200                 205

Asn Glu Asp Val Leu Asp Glu Ala Ile Val Phe Thr Thr His His Leu
210                 215                 220

Asn Arg Met Met Pro Gln Leu Glu Ser Pro Leu Lys Glu Val Lys
225                 230                 235                 240

His Ala Leu Arg Tyr Pro Leu His Lys Cys Leu Gly Ile Leu Ser Leu
                245                 250                 255

Arg Phe His Ile Asp Arg Tyr Glu Asn Asp Lys Ser Arg Asp Glu Val
                260                 265                 270

Val Leu Arg Leu Gly Gln Val Asn Phe Asn Tyr Met Gln Asn Ile Tyr
            275                 280                 285

Met Asn Glu Leu Tyr Glu Ile Thr Thr Trp Asn Lys Leu Gln Met
290                 295                 300

Thr Ser Lys Val Pro Tyr Phe Arg Asp Arg Leu Val Glu Cys Tyr Met
305                 310                 315                 320

Trp Gly Leu Ala Tyr His Phe Glu Pro Glu Tyr Ala Pro Val Arg Val
                325                 330                 335

Leu Ile Thr Lys Tyr Tyr Met Thr Ala Thr Thr Val Asp Asp Thr Tyr
            340                 345                 350

Asp Asn Tyr Ala Thr Leu Glu Glu Ile Glu Leu Phe Thr Gln Ala Ile
            355                 360                 365

Asp Arg Trp Ser Glu Asp Glu Ile Asp Gln Leu Pro Asp Glu Tyr Leu
            370                 375                 380

Lys Ile Val Tyr Lys Gly Leu Met Asn Phe Thr Glu Glu Phe Arg Arg
385                 390                 395                 400

Asp Ala Glu Glu Arg Gly Lys Gly Tyr Val Ile Pro Tyr Phe Ile Glu
                405                 410                 415

Glu Thr Lys Arg Ala Thr Gln Gly Tyr Ala Asn Glu Gln Arg Trp Ile
            420                 425                 430

Met Lys Arg Glu Met Pro Ser Phe Glu Glu Tyr Met Val Asn Ser Arg
            435                 440                 445

Val Thr Ser Leu Met Tyr Val Thr Tyr Val Ala Val Ala Val Ile
            450                 455                 460

Glu Ser Ala Thr Lys Glu Thr Val Asp Trp Ala Leu Ser Asp Ser Asp
465                 470                 475                 480

Ile Phe Val Tyr Thr Asn Asp Ile Gly Arg Leu Ile Asp Asp Leu Ala
                485                 490                 495

Thr His Arg Arg Glu Arg Lys Asp Gly Thr Met Leu Thr Ser Met Asp
```

```
              500              505              510
Tyr Tyr Met Lys Glu Tyr Gly Gly Thr Met Glu Glu Gly Glu Ala Ala
            515              520              525

Phe Arg Lys Leu Met Glu Glu Lys Trp Lys Leu Leu Asn Ala Ala Trp
            530              535              540

Val Asp Thr Ile Asn Gly Lys Glu Ser Lys Glu Ile Val Val Gln Val
545              550              555              560

Leu Asp Leu Ala Arg Ile Cys Gly Thr Leu Tyr Gly Asp Glu Glu Asp
                565              570              575

Gly Phe Thr Tyr Pro Glu Lys Asn Phe Ala Pro Leu Val Ala Ala Leu
                580              585              590

Leu Met Asn Pro Ile His Ile
            595

<210> SEQ ID NO 40
<211> LENGTH: 1800
<212> TYPE: DNA
<213> ORGANISM: Prunella vulgaris

<400> SEQUENCE: 40
```

| | | |
|---|---|---|
| atgagctctc tctcaattcc cttttcttcc gccatttgca cttcatcaat cccaaagatc | 60 |
| agtactgggc atcatcgccg caccgcgagg atgcccgcgc acgacacatc gcgtctcgtc | 120 |
| tttcgccctt cagctgtgat ggtggaagga agtccgatga ctacttcaag caacgggaag | 180 |
| gaagtccaac gacttataac cactttcaag cctagcatgt ggaaagatat tttttctacc | 240 |
| ttctctttcg ataatcaggt gcaagaaaag tatttgaaag aaattgagga attgaagaaa | 300 |
| gaagtaagaa gcacactaat gagtgctacg cataggaaat tgtttgactt gatcgacaat | 360 |
| ctcgagcgta tgggaatcgc ctatcatttc gagacagaaa tcgaagacaa gctcaaacaa | 420 |
| gctcatgctt ctctagagga ggaagatgac tacgacttgt tcactactgc acttcgcttt | 480 |
| cgtctgctca gacaacatcg ctatcatgtt tcttgcgatc cctttgcgaa atttgttgac | 540 |
| caagacaaca aattgaaaga gagtcttagt agcgacgtcg aggggctatt aagcttgttc | 600 |
| gaggcatccc atcttcggat ccacaacgag gatgttctag atgaagctat agtgttcaca | 660 |
| acccatcact tgaatcgaat gatgccacaa ttggaatcgc cccttaaaga agaagtgaag | 720 |
| catgctcttc gatacccct tcacaagtgt cttggaatcc ttagccttcg ttttcatatc | 780 |
| gacagatatg agaatgataa gtcgagggat gaagttgttc tcagactagg ccaagttaat | 840 |
| ttcaattaca tgcagaacat ttacatgaac gagctctatg aaatcaccac gtggtggaac | 900 |
| aagttgcaga tgacttcaaa agtaccttac tttagagata gattggtaga gtgctatatg | 960 |
| tggggtttgg catatcattt cgaaccagaa tacgctcccg ttcgagtcct cattaccaag | 1020 |
| tactatatga ccgccacaac tgtcgacgat acctatgata ttatgctac actcgaagaa | 1080 |
| atcgaactct tcactcaggc cattgacagg tggagcgagg atgagattga tcagctacct | 1140 |
| gatgaatacc taaaaatagt gtacaaaggt ctaatgaact tcactgaaga gtttagacgt | 1200 |
| gacgcagaag agcgagggaa aggctatgtg attccttact ttattgaaga aacgaagaga | 1260 |
| gcaacacagg gttatgcaaa cgagcagagg tggataatga agagaaat gccgagtttt | 1320 |
| gaagagtata tggtgaactc aagggtaaca tcacttatgt atgtgaccta cgttgctgtt | 1380 |
| gtggcagtca tagaatcagc taccaaagaa accgtagatt gggcgctaag tgactccgat | 1440 |
| atctttgtct acactaacga tatcggccga cttatcgacg accttgccac tcatcgacgc | 1500 |
| gagaggaaag acgggacaat gcttacatcg atggattatt acatgaagga atatggcggt | 1560 |

```
acgatggaag aggggggaagc tgcatttagg aaattgatgg aggagaaatg gaaactttg      1620 aatgcagcat gggtagatac tattaatgga aaagagtcga aggaaatagt tgtgcaagtt      1680
ctcgacctcg ccaggatatg cggaacgctc tatggggacg aagaagatgg cttcacctac      1740
ccagagaaga attttgcacc actcgttgct gctctattga tgaatcctat acatatttga      1800
```

```
<210> SEQ ID NO 41
<211> LENGTH: 821
<212> TYPE: PRT
<213> ORGANISM: Chiococca alba

<400> SEQUENCE: 41

Met Ser Ser Ser Thr Ser Ala Ala Thr Leu Leu Gly Leu Ser Pro
1               5                   10                  15

Ala Ser Arg Arg Phe Val Ser Phe Pro Pro Ala Asn Gly Pro Ile Glu
            20                  25                  30

Thr Ile Thr Gly Ile Trp Ser Pro Gly Lys Ala Leu His His Phe Asn
        35                  40                  45

Phe Arg Leu Arg Cys Ser Thr Val Ser Ser Pro Arg Thr Gln Glu Leu
    50                  55                  60

Gly Gln Val Ser Gln Asn Gly Met Ser Gly Ile Lys Trp His Asp Ile
65                  70                  75                  80

Val Glu Glu Gly Val Thr Glu Lys Gly Thr Leu Glu Ala Asn Thr Ser
                85                  90                  95

Ser Trp Ile Lys Glu Ser Ile Glu Ala Ile Arg Trp Met Leu Arg Thr
            100                 105                 110

Met Asp Asp Gly Asp Ile Ser Ile Ser Ala Tyr Asp Thr Ala Trp Val
        115                 120                 125

Ala Leu Val Glu Asp Ile Asn Gly Ser Gly Gly Pro Gln Phe Pro Ser
    130                 135                 140

Ser Leu Glu Trp Ile Ala Asn Asn Gln Leu Pro Asp Gly Ser Trp Gly
145                 150                 155                 160

Asp Ser Asp Ile Phe Ser Ala His Asp Arg Ile Leu Asn Thr Leu Gly
                165                 170                 175

Cys Val Val Ala Leu Lys Ser Trp Asn Met His Pro Glu Lys Ser Glu
            180                 185                 190

Lys Gly Leu Leu Tyr Leu Arg Asp Asn Ile His Lys Leu Glu Asp Glu
        195                 200                 205

Asn Val Glu His Met Pro Ile Gly Phe Glu Val Ala Phe Pro Ser Leu
    210                 215                 220

Ile Glu Ile Ala Lys Lys Leu Ser Ile Asp Ile Pro Asp Asp Ser Ala
225                 230                 235                 240

Ile Leu Gln Glu Ile Tyr Ala Arg Arg Asn Leu Lys Leu Thr Arg Ile
                245                 250                 255

Pro Lys Asp Ile Met His Thr Val Pro Thr Thr Leu Leu His Ser Leu
            260                 265                 270

Glu Gly Met Pro Glu Leu Asp Trp Lys Arg Leu Ile Ser Leu Lys Cys
        275                 280                 285

Glu Asp Gly Ser Phe Leu Phe Ser Pro Ser Ser Thr Ala Phe Ala Leu
    290                 295                 300

Thr Gln Thr Lys Asp Ala Asp Cys Leu Arg Tyr Leu Thr Lys Thr Val
305                 310                 315                 320

Gln Lys Phe Asn Gly Gly Val Pro Asn Val Tyr Pro Val Asp Leu Phe
                325                 330                 335
```

-continued

Glu His Ile Trp Ala Val Asp Arg Leu Gln Arg Leu Gly Ile Ser Arg
                340                 345                 350

Tyr Phe Gln Ser Glu Ile Arg Glu Cys Ile Asp Tyr Val His Arg Tyr
            355                 360                 365

Trp Thr Asp Lys Gly Ile Cys Trp Ala Arg Asn Thr His Val Tyr Asp
370                 375                 380

Ile Asp Asp Thr Ala Met Gly Phe Arg Leu Leu Arg Leu His Gly Tyr
385                 390                 395                 400

Asp Val Ser Ala Asp Val Phe Arg Tyr Tyr Glu Lys Asp Gly Glu Phe
                405                 410                 415

Val Cys Phe Ala Gly Gln Ser Asn Gln Ala Val Thr Gly Met Tyr Asn
            420                 425                 430

Leu Tyr Arg Ala Ser Gln Val Met Phe Pro Gly Glu Asn Ile Leu Ser
        435                 440                 445

Asp Ala Arg Lys Phe Ser Ser Glu Phe Leu His Asp Lys Arg Ala Asn
    450                 455                 460

Asn Glu Leu Leu Asp Lys Trp Ile Ile Thr Lys Asp Leu Pro Gly Glu
465                 470                 475                 480

Val Ala Tyr Ala Leu Asp Val Pro Trp Tyr Ala Ser Leu Pro Arg Leu
                485                 490                 495

Glu Thr Arg Leu Tyr Leu Glu Gln Tyr Gly Gly Glu Asp Asp Val Trp
            500                 505                 510

Ile Gly Lys Thr Leu Tyr Arg Met Gln Lys Val Asn Asn Ile Tyr
        515                 520                 525

Leu Glu Leu Gly Lys Leu Asp Tyr Asn Asn Cys Gln Ala Leu His Gln
    530                 535                 540

Leu Glu Trp Arg Ser Ile Gln Lys Trp Tyr Asn Glu Cys Gly Leu Gly
545                 550                 555                 560

Glu Tyr Gly Leu Ser Glu Arg Ser Leu Leu Ser Tyr Tyr Leu Ala
                565                 570                 575

Ala Ala Ser Ile Phe Glu Pro Glu Arg Ser Lys Glu Arg Leu Ala Trp
            580                 585                 590

Ala Lys Thr Thr Met Leu Ile Arg Thr Ile Glu Ser Tyr Leu Ser Ser
        595                 600                 605

Glu Gln Met Val Glu Asp His Asn Gly Ala Phe Val Ser Glu Phe Gln
    610                 615                 620

Tyr Tyr Cys Ser Asn Leu Asp Tyr Val Asn Gly Gly Arg His Lys Pro
625                 630                 635                 640

Thr Gln Arg Leu Val Arg Thr Leu Leu Gly Thr Leu Asn Gln Ile Ser
                645                 650                 655

Leu Asp Ala Val Leu Val His Gly Arg Asp Ile His Gln Tyr Leu Arg
            660                 665                 670

Gln Ala Trp Glu Lys Trp Leu Ile Ala Leu Gln Glu Gly Asp Asp Ser
        675                 680                 685

Asp Met Gly Gln Glu Glu Ala Glu Leu Leu Val Arg Thr Leu Asn Leu
    690                 695                 700

Cys Ala Gly Arg Tyr Ala Ser Glu Glu Leu Leu Leu Ser His Pro Lys
705                 710                 715                 720

Tyr Gln Gln Leu Leu His Ile Thr Thr Arg Val Cys Asn Gln Ile Arg
                725                 730                 735

His Phe Gln His Lys Lys Val Gln Asp Gly Glu Asn Gly Arg Ala Asn
            740                 745                 750

| | | | | | | | | | | | | |
|---|---|---|---|---|---|---|---|---|---|---|---|---|
| Met | Gly | Asp | Gly | Ile | Thr | Ser | Ile | Ser | Ser | Ile | Glu | Ser | Asp | Met | Gln |
| | | | 755 | | | | 760 | | | | 765 | |

| Glu | Leu | Thr | Lys | Leu | Val | Val | Gly | Asn | Thr | Gln | Asn | Asp | Leu | Asp | Ala |
|---|---|---|---|---|---|---|---|---|---|---|---|---|---|---|---|
| | 770 | | | | 775 | | | | 780 | | | | | |

| Asp | Thr | Lys | Gln | Thr | Phe | Leu | Thr | Val | Ala | Lys | Ser | Phe | Tyr | Tyr | Thr |
|---|---|---|---|---|---|---|---|---|---|---|---|---|---|---|---|
| 785 | | | | 790 | | | | 795 | | | | | 800 |

| Ala | His | Cys | Asn | Pro | Gly | Thr | Ile | Asn | Cys | His | Ile | Ala | Lys | Val | Leu |
|---|---|---|---|---|---|---|---|---|---|---|---|---|---|---|---|
| | | | 805 | | | | 810 | | | | 815 | |

Phe Glu Arg Val Leu
      820

<210> SEQ ID NO 42
<211> LENGTH: 2466
<212> TYPE: DNA
<213> ORGANISM: Chiococca alba

<400> SEQUENCE: 42

```
atgtcttctt ctacctcagc agcagcaacc cttctcggat tatcgccggc aagccgccgg      60
tttgtatcat ttcctccggc aaatggacct atagaaacta ttaccggtat ttggtcgccc     120
ggcaaagctc ttcatcactt taatttccgt ctgcgttgta gcacggtgtc cagtcctcgc     180
acccaagaat tgggccaggt gtcacaaaat ggcatgtctg gtataaagtg gcatgacata     240
gtggaagaag gagtcacaga aaaggaact  cttgaggcga acacatcaag ctggataaaa     300
gaaagcatag aagccattcg ttggatgctg cgtaccatgg atgacgggga tatcagcata     360
tctgcttatg atactgcatg ggttgccctt gtggaagata tcaacggaag tggcggtcct     420
caatttcctt caagcctcga gtggattgcc aacaatcagc ttcctgatgg ttcatggggc     480
gacagcgaca tcttttcagc tcacgatcgg attctcaaca ctttgggatg cgttgttgca     540
ttaaaatctt ggaacatgca ccctgaaaag agtgaaaaag gattattata tttaagggat     600
aacattcaca gcttgagga  tgaaaatgtc gagcacatgc ctatcggttt tgaagtggca     660
tttccttcac taattgagat agccaaaaag ttgagcattg atattccgga tgattctgca     720
atcttgcagg agatatatgc cagaagaaat ctaaagctaa caaggatacc gaaggacatt     780
atgcacacag tgcccacaac attgctccac agcttggaag gcatgccaga actagactgg     840
aaaaggctaa tatctctaaa gtgtgaggat ggttcctttc tgttttctcc atcctccact     900
gcttttgccc tcacgcaaac taagatgct  gattgcctca gatatttaac taaaaccgta     960
caaaaattca atggaggagt tcccaatgtt taccccgtgg acttattcga acacatctgg    1020
gctgttgatc gacttcaaag actaggaatt tctcgatact tccagtcaga atccgcgag    1080
tgcatcgatt atgttcaccg atattggacg gataaaggta tctgttgggc tagaaatacc    1140
cacgtttatg acattgatga tacagctatg ggttttagac ttctaaggtt gcatggctac    1200
gatgtttctg cagatgtttt cagatactat gagaaggatg gcgaattcgt ttgctttgcc    1260
ggacagtcaa accaggcggt gaccggaatg tataacctgt atagagcttc tcaagtgatg    1320
tttccagggg agaatatact ttcggatgct aggaaattct cgtccgaatt cttgcatgat    1380
aagcgagcca acaatgagct cctagataaa tggatcataa ccaaagattt gcctggggag    1440
gtagcatatg ctttagatgt tccatggtat gccagtttac ctcgtttaga aaccagattg    1500
tatttggaac aatatggcgg cgaagatgat gtctggattg caagacattg tacaggatg     1560
caaaaagtta acaacaacat ctatcttgaa cttggcaaat tagattacaa caactgtcag    1620
gcattgcatc agcttgagtg gagaagcatc caaaaatggt acaatgaatg cggtcttgga    1680
```

-continued

```
gagtacggat taagcgagag aagcctcctt ctttcgtatt atttggccgc agccagtata    1740
tttgaaccgg agaggtcaaa ggaacggctt gcctgggcca aaactactat gctaatccgc    1800
acaattgaat cttatttgag tagtgaacaa atggttgagg atcacaatgg agcctttgtt    1860
agcgagttcc aatactattg cagtaaccct gactacgtaa atggtggaag cataagccaa    1920
acacaaaggc tagtgaggac tctactcgga actttaaatc agatttcttt ggacgcagtg    1980
ttagtccacg gcagagatat ccatcaatat ttgcgtcaag cctgggaaaa gtggttgata    2040
gctttgcaag agggagatga tagtgacatg ggtcaagagg aagcagaact tttagtgcgc    2100
acactaaacc tatgcgccgg tcgctacgca tcggaggagc tattgttgtc ccatcccaag    2160
tatcaacaac ttttgcacat cactactaga gtctgtaacc aaattcgtca tttccaacac    2220
aaaaaggtgc aagatgggga aaatggaaga gcaaacatgg gtgatggcat cacaagcatc    2280
agctcaatag agtcggacat gcaagaacta acgaaattag ttgtcggcaa tacccaaaac    2340
gatctagatg ctgatacgaa gcaaacattt ctcacggtgg caaaaagctt ctactacacc    2400
gcccactgca atcccggaac aatcaattgc catattgcta agtattatt tgagagagta    2460 ctttga                                                                2466
```

<210> SEQ ID NO 43
<211> LENGTH: 747
<212> TYPE: PRT
<213> ORGANISM: Chiococca alba

<400> SEQUENCE: 43

```
Met Pro Val Ile Lys Ser His Glu Phe Ile Glu Glu Val Gly Pro Glu
  1               5                  10                  15

Lys Gly Thr Leu Lys Leu Ser Arg Ser Ser Arg Ile Asn Glu Leu Val
             20                  25                  30

Glu Ser Ile Gln Thr Met Leu Gln Ser Met Asp Asp Gly Glu Ile Ser
         35                  40                  45

Met Ser Ala Tyr Asp Thr Ala Trp Val Ala Leu Val Glu Asp Ile Asn
     50                  55                  60

Gly Ser Ser Tyr Pro Gln Phe Pro Met Ser Leu Glu Trp Ile Ala Asn
 65                  70                  75                  80

Asn Gln Leu Pro Asp Gly Ser Trp Gly Asp Gly Ser Ile Phe Ser Val
                 85                  90                  95

His Asp Arg Ile Ile Ser Thr Leu Gly Cys Val Leu Ala Leu Lys Ser
            100                 105                 110

Trp Asn Met His Pro Asp Lys Ser Glu Lys Gly Leu Leu Phe Ile Arg
        115                 120                 125

Asp Asn Ile His Lys Val Gly Asp Glu Ser Ala Glu His Met Pro Ile
    130                 135                 140

Gly Phe Glu Val Val Phe Pro Ser Leu Ile Glu Arg Ala Lys Asn Leu
145                 150                 155                 160

Asp Ile Asp Ile Pro Asp Ile Ser Ala Ile Leu Gln Glu Ile Tyr Ala
                165                 170                 175

Arg Arg Asn Leu Lys Leu Ala Arg Ile Pro Lys Asp Ile Leu Tyr Thr
            180                 185                 190

Val Pro Thr Thr Leu Leu His Ser Leu Glu Gly Met Pro Glu Leu Asp
        195                 200                 205

Trp Gln Lys Leu Leu Pro Leu Lys Cys Glu Asp Gly Ser Phe Leu Phe
    210                 215                 220

Ser Pro Ser Cys Thr Ala Phe Ala Leu Met Gln Thr Lys Asp Gly Asp
```

```
            225                 230                 235                 240
    Cys Leu Arg Tyr Leu Thr Asn Thr Ile Glu Lys Phe Asn Gly Gly Val
                    245                 250                 255
    Pro Gly Val Tyr Pro Val Asp Leu Phe Glu His Ile Trp Ala Val Asp
                    260                 265                 270
    Arg Leu Gln Arg Leu Gly Ile Ser Arg Tyr Phe Gln Thr Glu Ile Glu
                    275                 280                 285
    Glu Cys Met Ser Tyr Val Tyr Arg Tyr Trp Thr Asp Lys Gly Ile Cys
                290                 295                 300
    Trp Ala Arg Asn Ser Lys Val Glu Asp Ile Asp Asp Thr Ala Met Gly
    305                 310                 315                 320
    Phe Arg Leu Leu Arg Leu His Gly Tyr Met Val Ser Ala Asp Val Phe
                    325                 330                 335
    Ala Gln Phe Glu Lys Gly Gly Glu Phe Val Cys Phe Ala Gly Gln Ser
                    340                 345                 350
    Asn Gln Ala Leu Thr Gly Met Phe Asn Leu Tyr Arg Ala Ser Gln Val
                    355                 360                 365
    Met Phe Pro Gly Glu Lys Ile Leu Ala Asp Ala Lys Lys Phe Ser Ser
            370                 375                 380
    Asn Phe Leu His Glu Lys Arg Ala Asn Asn Glu Leu Leu Asp Lys Trp
    385                 390                 395                 400
    Ile Ile Thr Lys Asp Leu Pro Gly Glu Val Thr Tyr Ala Leu Asp Val
                    405                 410                 415
    Pro Trp Tyr Ala Ser Leu Pro Arg Val Glu Thr Arg Leu Tyr Leu Glu
                    420                 425                 430
    Gln Tyr Gly Gly Glu Asp Asp Val Trp Ile Ala Lys Thr Leu Tyr Arg
                    435                 440                 445
    Met Arg Lys Val Asn Asn Lys Ile Tyr Leu Glu Leu Gly Ile Leu Asp
            450                 455                 460
    Tyr Asn Asn Cys Gln Ala Leu His Gln Leu Glu Trp Arg Ser Ile Gln
    465                 470                 475                 480
    Lys Trp Tyr Lys Asp Ser Gly Leu Glu Glu Tyr Gly Leu Ser Glu Arg
                    485                 490                 495
    Asn Leu Leu Leu Ala Tyr Tyr Leu Ala Thr Ala Cys Ile Phe Glu Pro
                    500                 505                 510
    Glu Arg Leu Val Glu Arg Leu Ser Trp Ala Lys Thr Thr Ala Leu Ile
            515                 520                 525
    Tyr Thr Thr Lys Ser Tyr Phe Arg Thr Glu Cys Asn Ser Gly Glu Gln
            530                 535                 540
    Arg Lys Ala Phe Leu His Glu Phe Gln Gln Tyr Cys Asn Asp Leu Asp
    545                 550                 555                 560
    Tyr Val Ser Gly Ala Arg His Lys Pro Thr Ile Arg Leu Ile Glu Ala
                    565                 570                 575
    Leu Leu Gly Thr Leu Glu Gln Val Ser Leu Asp Ala Ile Leu Asp His
                    580                 585                 590
    Gly Arg Tyr Ile His Gln Asp Leu Arg Asn Ala Trp Glu Lys Trp Leu
                    595                 600                 605
    Ile Ala Leu Gln Glu Gly Val Asp Met Asp Gln Glu Ala Glu Leu
            610                 615                 620
    Thr Val Leu Thr Leu His Leu Cys Ala Gly Ser Tyr Thr Ser Glu Glu
    625                 630                 635                 640
    Leu Leu Leu Ser His Pro Lys Tyr Gln Gln Leu Leu Asn Ile Thr Ser
                    645                 650                 655
```

```
Arg Val Cys His Gln Ile Arg Gln Phe Gln Arg Glu Lys Ala Gln Asp
            660                 665                 670

Thr Asp Asn Gly Arg Glu Asn Leu Val Ala Ile Thr Ser Ile Lys Ala
        675                 680                 685

Ile Glu Ser Asp Met Gln Glu Leu Ala Lys Leu Val Leu Thr Lys Ser
    690                 695                 700

Thr Gly Asp Leu Ala Ala Lys Ile Lys Gln Thr Phe Leu Ile Val Ala
705                 710                 715                 720

Lys Ser Phe Tyr Tyr Thr Ala His Cys Leu Pro Gly Ile Ile Ser Thr
                725                 730                 735

His Ile Ala Lys Val Leu Phe Glu Lys Val Phe
            740                 745
```

<210> SEQ ID NO 44
<211> LENGTH: 2244
<212> TYPE: DNA
<213> ORGANISM: Chiococca alba

<400> SEQUENCE: 44

```
atgccagtaa taaagtcgca tgagtttatt gaagaggtcg gcccggaaaa aggaactctg      60
aagctgagca gatcaagtag gataaacgaa cttgtagaat caattcaaac gatgcttcaa     120
tcgatggatg atggggaaat aagcatgtct gcttatgaca ccgcgtgggt tgcccttgtg     180
gaagatatta atggaagcag ctaccctcaa ttccctatga gcctcgagtg gattgccaac     240
aatcagcttc ctgatggttc atggggtgac ggcagtatct tttcggttca tgatcggata     300
atcagcacat taggatgtgt tcttgcatta aaatcatgga acatgcaccc ggacaaaagc     360
gaaaaaggac tgttatttat aagggacaat attcacaagg ttggagatga gagcgctgag     420
cacatgccta ttggttttga ggtggtattt ccttcgctta ttgagagagc caaaaacttg     480
gacattgata ttccagatat ttctgctatc ttgcaagaga tttatgcacg aagaaatcta     540
aagctcgcaa ggattccaaa ggatatactg tataccgtgc ccacgacatt acttcatagc     600
ttagaaggaa tgccagaact ggactggcaa aagctactgc cattaaaatg tgaggatggt     660
tcatttctat tttctccatc gtgcactgct tttgccctca tgcagactaa ggatggtgat     720
tgcctcagat atctaactaa taccatagaa aaattcaatg ggggagttcc cggtgtatac     780
cctgtggact tgttcgaaca catttgggct gttgatcgct tgcaaagact aggaatttcc     840
cggtattttc agacagaaat tgaagaatgt atgagttatg tttaccgata ttggacggat     900
aaaggtatct gttgggctag aaactccaaa gttgaagaca tcgatgacac agccatgggt     960
tttagacttc taaggttgca tggttacatg gtttctgcag atgtgtttgc acagtttgag    1020
aaaggggggtg aattcgtttg ctttgctgga cagtcgaacc aggcgctgac tggaatgttt    1080
aacctgtata gagcttctca gtaatgtttt ccaggggaga agatacttgc tgatgccaag    1140
aaattctcat cgaacttctt acatgaaaag cgtgcaaaca acgagcttct agataaatgg    1200
atcataacta agatttgcc tggagaggtg acgtatgcgc tagatgttcc atggtacgcc    1260
agtttacctc gtgtagaaac gagattatat ctggaacaat atggaggaga ggatgatgtc    1320
tggattgcca agacattgta caggatgaga aaagttaaca caaaaattta ccttgaactt    1380
ggcatattag attacaataa ctgtcaagca ttgcatcagc tggagtggag aagcatccaa    1440
aaatggtata aggattctgg ccttgaagag tacgggttga gcgagaggaa ccttctcctg    1500
gcatattatc tggccacagc ttgtatattt gaacccgaaa ggttggtgga gcgcctttcc    1560
```

-continued

```
tgggcgaaaa caaccgcctt aatctacaca acaaaatctt atttcagaac tgaatgcaac   1620
tctggggaac agagaaaagc ttttcttcat gagttccaac agtactgcaa tgacctggac   1680
tacgttagtg gcgcaaggca caagccaaca ataagattga tcgaagctct acttggaacc   1740
ctagagcagg tctcttttga tgcaatatta gatcatggcc gatatatcca tcaagatttg   1800
cgtaatgctt gggagaaatg gttgatagct ttgcaagagg gagttgacat ggaccaagaa   1860
gaagcagaac ttacagtgct cacactacac ctgtgtgccg gcagctacac atcggaggag   1920
ttactgttat ctcatcccaa gtatcaacaa ctttttaaata tcactagtag agtctgccac   1980
caaattcgtc aattccagcg cgaaaaggca caggatacgg ataatggaag agaaaacttg   2040
gttgccatca caagcatcaa ggcgatagaa tcagacatgc aagaacttgc gaaattagtt   2100
ctgaccaaat ccactggcga tttagctgct aaaatcaagc aaacatttct tatagtggca   2160
aagagcttct actacaccgc acattgcctt cctggaatta tcagtaccca cattgccaaa   2220
gtactatttg agaaagtttt ctga                                         2244
```

<210> SEQ ID NO 45
<211> LENGTH: 822
<212> TYPE: PRT
<213> ORGANISM: Chiococca alba

<400> SEQUENCE: 45

```
Met Met Met Met Met Val Val Met Asn Thr Ala Pro Ala His Ser Tyr
1               5                   10                  15

His Pro Phe Pro Phe Ala Gly Pro Lys Ser Ser Ala Thr Leu Phe Ser
            20                  25                  30

Asn Tyr Tyr Cys Ser Ser Arg Lys Lys Ser Ser Pro Arg Ile Ser
        35                  40                  45

Ala Ser Val Ser Leu Leu Thr Gly Val Glu Ser Thr Thr Ala Ile Asn
    50                  55                  60

Ser Ser Asp Pro Glu Ile Lys Glu Arg Ile Arg Lys Leu Phe His Asp
65                  70                  75                  80

Val Asp Ile Ser Leu Ser Ser Tyr Asp Thr Ala Trp Val Ala Met Val
                85                  90                  95

Pro Ala Pro His Ser Ser Gln Ser Pro Leu Phe Pro Gln Cys Ile Asn
            100                 105                 110

Trp Leu Leu Asp Asn Gln Leu Pro Asp Gly Ser Trp Ser Leu Pro Pro
        115                 120                 125

Pro His His His Pro Leu Leu Leu Lys Asp Ala Leu Ser Ser Thr Leu
    130                 135                 140

Ala Cys Val Leu Ala Leu Arg Arg Trp Gly Ile Gly Gln Glu Gln Val
145                 150                 155                 160

Asp Lys Gly Ile Arg Phe Val Glu Leu Asn Phe Ala Ser Ala Ser Asp
                165                 170                 175

Gln Asn Gln His Leu Pro Val Gly Phe Asp Ile Phe Pro Gly Met
            180                 185                 190

Leu Glu Tyr Ala Arg Asp Leu Asn Leu Asn Leu Gln Leu Glu Ser Ala
        195                 200                 205

Thr Val Asn Ala Leu Leu Leu Lys Arg Asp Gln Glu Leu Thr Arg Phe
    210                 215                 220

Phe Lys Ser Tyr Ser Asp Glu Ser Lys Ala Tyr Leu Ala Tyr Val Ser
225                 230                 235                 240

Glu Gly Ile Val Lys Leu Gln Asn Trp Asp Thr Val Met Lys Phe Gln
                245                 250                 255
```

-continued

Arg Lys Asn Gly Ser Leu Phe Asn Ser Pro Ser Ala Thr Ala Ala Ala
            260                 265                 270

Val Met His Val His Asn Pro Gly Cys Leu Asp Tyr Leu His Ser Val
            275                 280                 285

Leu Glu Lys His Gly Asn Ala Val Pro Thr Val Tyr Pro Leu Asp Ile
            290                 295                 300

Tyr Pro Arg Leu Cys Leu Val Asp Asn Leu Glu Arg Leu Gly Ile Cys
305                 310                 315                 320

Gly His Phe Arg Lys Glu Ile Leu Ser Val Leu Asp Asp Thr Tyr Arg
                325                 330                 335

Cys Trp Met Gln Gly Asp Glu Glu Ile Phe Ala Glu Lys Ser Thr Cys
                340                 345                 350

Ala Ile Ala Phe Thr Leu Leu Arg Lys His Gly Tyr Asn Ile Ser Ala
                355                 360                 365

Asp Pro Leu Thr Pro Phe Leu Lys Glu Glu Cys Phe Ser Asn Ser Leu
            370                 375                 380

Gly Gly Cys Leu Lys Asp Thr Ser Ala Val Leu Glu Leu Tyr Arg Ala
385                 390                 395                 400

Leu Glu Met Ile Ile Ser Gln Asn Glu Ser Ala Leu Val Lys Lys Ser
                405                 410                 415

Leu Trp Ser Arg Ser Phe Leu Lys Glu His Ile Ser Gly Gly Cys Asp
            420                 425                 430

Leu Lys Gly Phe Ser Asn Gln Ile Ser Ile Leu Val Asp Asp Ile Leu
            435                 440                 445

Asn Phe Pro Ser His Ala Thr Leu Gln Arg Val Ala Asn Arg Arg Ser
            450                 455                 460

Ile Glu Gln Tyr Asn Leu Asp Ser Thr Lys Ile Leu Lys Thr Ser Tyr
465                 470                 475                 480

Cys Ser Ser Asn Phe Ser Asn Lys Asp Leu Leu Ile Leu Ala Val Lys
                485                 490                 495

Asp Phe Asn His Cys Gln Leu Ile His Arg Glu Glu Leu Lys Glu Leu
            500                 505                 510

Glu Arg Trp Val Thr Asp Asn Arg Leu Asp Lys Leu Lys Phe Ala Arg
            515                 520                 525

Gln Lys Ser Ala Tyr Cys Tyr Phe Ser Ala Ala Thr Ile Phe Ser
            530                 535                 540

Pro Glu Leu Ser Asp Ala Arg Met Ser Trp Ala Lys Asn Gly Val Leu
545                 550                 555                 560

Ala Thr Leu Val Asp Asp Phe Phe Asp Val Gly Gly Ser Leu Glu Glu
                565                 570                 575

Leu Lys Lys Leu Ile Glu Leu Val Glu Lys Trp Asp Ile Asn Val Ser
            580                 585                 590

Asp Gly Cys Cys Ser Glu Pro Val Gln Ile Leu Phe Ser Ala Leu His
            595                 600                 605

Ser Thr Ile Gln Glu Ile Gly Asp Lys Ala Phe Lys Trp Gln Ala Arg
            610                 615                 620

Ser Val Thr Asn His Ile Phe Lys Ile Trp Leu Asp Leu Leu Asn Ser
625                 630                 635                 640

Met Leu Arg Glu Ala Glu Trp Ala Arg Asn Ala Thr Val Pro Thr Val
                645                 650                 655

Glu Glu Tyr Met Thr Asn Gly Tyr Val Ser Phe Ala Leu Gly Pro Ile
                660                 665                 670

```
Ile Leu Pro Ala Leu Tyr Leu Val Gly Pro Lys Leu Ser Glu Glu Val
            675                 680                 685

Val Lys Asp Ser Glu Phe His Ser Leu Phe Lys Leu Val Ser Thr Cys
    690                 695                 700

Gly Arg Leu Leu Asn Asp Val His Ser Phe Glu Arg Glu Ser Lys Ser
705                 710                 715                 720

Gly Gln Leu Asn Ala Leu Ser Leu Arg Leu Ile His Gly Val Gly
                725                 730                 735

Ile Thr Glu Ala Ala Val Ala Glu Met Lys Ser Ser Ile Glu Asn
            740                 745                 750

Leu Arg Arg Glu Leu Leu Arg Leu Val Leu Arg Lys Glu Gly Ser Val
            755                 760                 765

Val Pro Arg Ala Cys Lys Asp Leu Phe Trp Asn Met Ser Lys Val Leu
    770                 775                 780

His Gln Phe Tyr Asn Lys Asp Asp Gly Phe Thr Ser Glu Glu Met Ile
785                 790                 795                 800

Gln Leu Val Lys Ser Ile Ile Tyr Glu Pro Ile Ala Val Asn Glu Phe
                805                 810                 815

Leu Asn Ser Cys His Thr
                820

<210> SEQ ID NO 46
<211> LENGTH: 2469
<212> TYPE: DNA
<213> ORGANISM: Chiococca alba

<400> SEQUENCE: 46
atgatgatga tgatggtggt gatgaacaca gctcccgccc actcttacca tcctttcccc      60
tttgccggcc caaaatcctc agccacactt tttccaatt attattgttc cagtaggaag      120
aaatcatcgc cacctcgcat ctctgcctca gtttctttgc taactggagt tgaaagcaca     180
actgcaatta attcttcaga cccggagatc aaagaaagaa taggaaaact atttcatgat     240
gttgatatct cgctttcttc atatgacact gcatgggtgg caatggtccc tgctccacat     300
tcttcccagt ctccccttttt tccccagtgc attaattggt tattggacaa tcagcttcct     360
gatggctcat ggagtcttcc tcctcctcat catcatcctc tattacttaa agatgcatta     420
tcctctaccc ttgcatgtgt tcttgcgctc aggagatggg gaattggtca agaacaagtt     480
gacaagggta ttcgttttgt tgagttaaat tttgcttcag catctgacca gaaccagcat     540
ttgccagttg gatttgacat tatattccct ggcatgctcg aatatgctag agatttaaat     600
ttaaatcttc aactagaatc tgcaacagta aatgccttac ttcttaaaag agatcaggag     660
cttacaagat tctttaaaag ctactcagac gagagtaaag cataccttgc atatgtatca     720
gaaggtatag taaagttaca gaactgggat acagttatga agttccaaag aaagaacggg     780
tcactattca attcaccttc agctacagca gctgctgtta tgcatgtcca caatcctggt     840
tgcctcgatt accttcactc agtgttggag aagcatggaa atgctgttcc aacagtttac     900
cctttggata tatccacg cctctgcttg gttgacaacc ttgagagact gggtatttgt     960
ggtcatttta ggaaggaaat tctgagtgta ttggatgata catacagatg ctggatgcag     1020
ggggatgaag agatatttgc agaaaaatca acttgtgcca tagcatttac attattgcga     1080
aagcatgggt acaacatctc tgcagatcca ttgaccccat tcttaaagga gagtgttttt     1140
tccaattctt tgggtggatg tttgaaagat actagtgctg tacttgaatt ataccgggca     1200
ttagagatga ttattagcca gaatgaatca gctctggtga aaaaaagctt gtggtccaga     1260
```

-continued

```
agcttcctga aagagcatat ttctggtggt tgtgatttaa agggattcag caatcaaatt    1320
tccatactgg tggatgatat cctcaacttt ccatcgcatg ctactttgca acgggttgct    1380
aacaggagaa gcatagagca atacaactta gacagtacaa aaattttaaa aacttcatat    1440
tgctcgtcga attttagcaa caaagattta ttgatcctgg cagtcaaaga ttttaatcat    1500
tgccaactca tacaccgtga agaactgaaa gaactagaaa ggtgggtcac agacaataga    1560
ttggacaagt taaagtttgc taggcagaag tctgcatact gttacttttc tgctgcagca    1620
accatattct cacctgaact ttctgatgcc cgcatgtcat gggccaagaa tggtgtactt    1680
gctactttgg ttgatgactt ctttgacgtg ggaggttctc tagaggaatt aaagaaactg    1740
attgagttgg ttgaaaagtg ggatataaat gtcagtgatg gttgttgctc tgaaccagtg    1800
caaatcctct tctcagcact acatagtaca atccaggaga ttggagataa agcattcaaa    1860
tggcaagcac gcagtgtaac aaaccacata tttaagatat ggttagattt gcttaattct    1920
atgttgaggg aagctgagtg ggctagaaat gcaacagtgc ctacagttga agaatatatg    1980
acaaatggtt atgtatcatt tgctttgggg ccaattatcc tccctgctct ttatcttgtt    2040
ggacctaagc tgtcagagga agtagttaag gattctgaat tccactccct tttttaagcta   2100
gtgagtacct gtgggcggct tctgaatgat gtccacagct tcgagaggga atcaaagtcc    2160
ggccaactaa atgctctgtc tctgcgcctg attcatggtg gtgttggcat tactgaagca    2220
gctgctgttg cagagatgaa gagttcaatt gagaatctaa ggagagaact gctgagacta    2280
gtcttgcgca aagagggtag tgtagttcca agagcttgca aggatttgtt ttggaatatg    2340
agtaaagtgc tacatcaatt ttacaacaaa gatgatggat ttacttcaga ggagatgatt    2400
cagcttgtga agtcgatcat ttatgagcca attgcggtca atgaattttt gaatagttgc    2460
catacatga                                                            2469
```

<210> SEQ ID NO 47
<211> LENGTH: 817
<212> TYPE: PRT
<213> ORGANISM: Chiococca alba

<400> SEQUENCE: 47

```
Met Met Ile Met Val Met Asn Thr Ala Pro Val His Ala Tyr His Ala
1               5                   10                  15

Leu Pro Ile Pro Thr Gln Lys Ser Ser Thr Thr Leu Phe Pro Asn Tyr
                20                  25                  30

Asn Cys Ser Ser Arg Lys Lys Ser Pro Pro Arg Ile Ser Ala Ala
            35                  40                  45

Ser Val Ser Leu Gln Thr Gly Val Glu Arg Thr Thr Ala Ile His Ser
        50                  55                  60

Ser Asp Leu Glu Ile Lys Glu Arg Ile Arg Lys Leu Phe His Asp Val
65                  70                  75                  80

Asp Ile Ser Leu Ser Ser Tyr Asp Thr Ala Trp Val Ala Met Val Pro
                85                  90                  95

Ala Pro His Ser Ser Gln Ser Pro Leu Phe Pro Gln Cys Ile Asn Trp
            100                 105                 110

Leu Leu Asp Asn Gln Leu Pro Asp Gly Ser Trp Ser Leu Pro Pro His
        115                 120                 125

His His His His Pro Leu Leu Leu Lys Asp Ala Leu Ser Ser Thr
    130                 135                 140

Leu Ala Cys Val Leu Ala Leu Arg Arg Trp Gly Ile Gly Gln Glu Gln
```

```
            145                 150                 155                 160
        Val Asp Lys Gly Ile Arg Phe Val Glu Leu Asn Phe Ala Ser Ala Ser
                        165                 170                 175
        Asp Gln Asn Gln His Leu Pro Val Gly Phe Asp Ile Ile Phe Pro Gly
                        180                 185                 190
        Met Leu Glu Tyr Ala Arg Asp Leu Asn Leu Asn Leu Gln Leu Glu Ser
                        195                 200                 205
        Ala Thr Val Asp Ala Leu Leu Leu Lys Arg Asp Gln Glu Leu Ile Arg
                        210                 215                 220
        Phe Phe Lys Ser Tyr Ser Asp Glu Ser Lys Ala Tyr Leu Ala Tyr Val
        225                 230                 235                 240
        Ser Glu Gly Ile Ile Lys Leu Gln Asn Trp Asp Thr Val Met Lys Phe
                        245                 250                 255
        Gln Arg Lys Asn Gly Ser Leu Phe Asn Ser Pro Ser Ala Thr Ala Ala
                        260                 265                 270
        Ala Val Met His Val His Asn Pro Gly Cys Leu Asp Tyr Leu His Ser
                        275                 280                 285
        Val Leu Glu Lys His Gly Asn Ala Val Pro Thr Val Tyr Pro Leu Asp
                        290                 295                 300
        Ile Tyr Pro Arg Leu Cys Leu Val Asp Asn Leu Glu Arg Leu Gly Ile
        305                 310                 315                 320
        Cys Gly His Phe Arg Lys Glu Ile Leu Ser Val Leu Asp Asp Thr Tyr
                        325                 330                 335
        Arg Cys Trp Met Gln Gly Asp Glu Glu Ile Phe Ala Glu Lys Ser Thr
                        340                 345                 350
        Cys Ala Ile Ala Phe Thr Leu Leu Arg Lys His Gly Tyr Asn Ile Ser
                        355                 360                 365
        Ala Asp Pro Leu Thr Pro Phe Leu Lys Glu Glu Cys Phe Ser Asn Ser
                        370                 375                 380
        Leu Gly Gly Cys Leu Lys Asp Thr Ser Ala Val Leu Glu Leu Tyr Arg
        385                 390                 395                 400
        Ala Leu Glu Met Ile Ile Ser Gln Asn Glu Ser Ala Leu Val Lys Lys
                        405                 410                 415
        Ser Leu Trp Ser Arg Ser Phe Leu Lys Glu His Ile Ser Gly Gly Cys
                        420                 425                 430
        Asp Leu Lys Gly Phe Ser Asn Gln Ile Ser Lys Gln Val Asp Asp Ile
                        435                 440                 445
        Leu Asn Phe Pro Ser His Ala Thr Leu Gln Arg Val Ala Asn Arg Arg
                        450                 455                 460
        Ser Ile Glu Gln Tyr Asn Leu Asp Ser Thr Lys Ile Leu Lys Thr Ser
        465                 470                 475                 480
        Tyr Cys Ser Ser Asn Phe Ser Asn Lys Asp Leu Leu Ile Leu Ala Val
                        485                 490                 495
        Lys Asp Phe Asn His Cys Gln Leu Ile His Arg Glu Leu Lys Glu
                        500                 505                 510
        Leu Glu Arg Trp Val Ala Asp Asn Arg Leu Asp Lys Leu Lys Phe Ala
                        515                 520                 525
        Arg Gln Lys Ser Ala Tyr Cys Tyr Phe Ser Ala Ala Thr Ile Phe
                        530                 535                 540
        Ser Pro Glu Leu Ser Asp Ala Arg Ile Ser Trp Ala Lys Asn Gly Val
        545                 550                 555                 560
        Leu Thr Thr Leu Val Asp Asp Phe Phe Asp Val Gly Gly Ser Leu Glu
                        565                 570                 575
```

```
Glu Leu Lys Lys Leu Ile Glu Leu Val Glu Lys Trp Asp Ile Asn Val
            580                 585                 590

Ser Asp Gly Cys Cys Ser Glu Pro Val Gln Ile Leu Phe Ser Ala Leu
        595                 600                 605

His Ser Thr Ile Gln Glu Ile Gly Asp Lys Ala Phe Lys Trp Gln Ala
610                 615                 620

Arg Ser Val Thr Asn His Ile Ile Lys Ile Trp Leu Asp Leu Leu Asn
625                 630                 635                 640

Ser Met Leu Arg Glu Ala Glu Trp Ala Arg Asn Ala Thr Val Pro Thr
            645                 650                 655

Val Glu Glu Tyr Met Thr Asn Gly Tyr Val Ser Phe Ala Leu Gly Pro
            660                 665                 670

Ile Ile Leu Pro Ala Leu Tyr Leu Val Gly Pro Lys Leu Ser Glu Glu
        675                 680                 685

Leu Val Lys Asp Ser Glu Phe His Ser Leu Phe Lys Leu Val Ser Thr
690                 695                 700

Cys Gly Arg Leu Leu Asn Asp Val His Ser Phe Glu Arg Glu Ser Lys
705                 710                 715                 720

Ala Gly Gln Leu Asn Ala Leu Ser Leu Arg Leu Ile His Gly Gly Val
            725                 730                 735

Gly Ile Thr Glu Ala Ala Ala Val Ala Glu Met Lys Ser Ser Ile Glu
            740                 745                 750

Lys Gln Arg Arg Glu Leu Leu Arg Leu Val Leu Arg Lys Glu Gly Ser
        755                 760                 765

Val Val Pro Arg Ala Cys Lys Asp Leu Phe Trp Asn Met Ser Arg Val
770                 775                 780

Leu His Gln Phe Tyr Val Lys Asp Asp Gly Phe Thr Ser Glu Glu Met
785                 790                 795                 800

Ile Glu Leu Val Lys Ser Ile Ile Tyr Glu Pro Ile Ala Val Asn Glu
            805                 810                 815

Phe

<210> SEQ ID NO 48
<211> LENGTH: 2454
<212> TYPE: DNA
<213> ORGANISM: Chiococca alba

<400> SEQUENCE: 48
atgatgataa tggtgatgaa cacagctccc gtccacgctt accacgcttt acccattccc      60
acccaaaaat cctcaaccac acttttccc aattataact gttccagtag aagaaatca       120 tcgccacctc gcatctctgc cgcctcagtt tctttgcaaa ctggagttga agaacgacg      180 gcaattcatt cttcagacct agagatcaaa gaaagaataa ggaaactatt tcatgatgtt      240
gatatctcgc tttcttcata tgacactgca tgggtggcaa tggtccctgc tccacattct      300
tcccagtctc ccctttttcc ccagtgcatt aattggttat tggacaatca gcttcctgat      360
ggctcatgga gtcttcctcc tcatcatcat catcatcatc cctattacta taagatgca       420 ttatcctcta cgcttgcatg tgttcttgcg ctcaggagat ggggaattgg tcaagaacaa      480
gttgacaagg gtattcgttt tgttgagtta aattttgctt ctgcatctga ccagaaccag      540
catttgccag ttggatttga cattatattc cctggcatgc tcgaatatgc tagagattta      600
aatttaaatc ttcaactaga atccgcaact gtagatgcct tacttctcaa agagatcag       660 gagcttataa gattctttaa aagctactca gacgagagta aagcatacct tgcatatgta      720
```

```
tcagaaggta tcataaagtt acagaactgg gatacagtta tgaagttcca aagaaagaac    780
gggtcactgt tcaattcacc ttcagctaca gcagctgctg ttatgcatgt ccacaatcct    840
ggctgcctcg attaccttca ctcagtgttg agaagcatg gcaatgctgt tccaacagtt     900
tacccttt gg atatatatcc acgcctctgc ttggttgaca accttgagag actgggtatt   960
tgtggtcatt ttaggaagga aattctgagt gtattggatg atacatacag atgctggatg   1020
cagggggatg aagagatatt tgcagaaaaa tcaacttgtg ccatagcatt tacattattg   1080
cgaaagcatg ggtacaacat ctctgcagat ccattgaccc cattcttaaa ggaagagtgt   1140
ttttccaatt ctttgggtgg atgtttgaaa gatactagtg ctgtacttga attataccgg   1200
gcattagaga tgattattag ccagaatgaa tcagctctgg tgaaaaaaag cttgtggtcc   1260
agaagcttcc tgaaagagca tatttctggt ggttgtgatt taagggatt cagcaatcaa   1320
atttccaaac aggtggatga tatcctcaac tttccatcgc atgctacttt gcaacgggtt   1380
gctaacagga gaagcataga gcaatacaac ttagacagta caaaaatttt aaaaacttca   1440
tattgctcgt cgaattttag taacaaagat ttattgatcc tggcagtcaa agattttaat   1500
cattgccaac tcatacaccg tgaagaactg aaagaactag aaaggtgggt cgcagacaat   1560
agattggaca agttaaagtt tgctaggcag aagtctgcat actgttactt ttctgctgca   1620
gcaaccatat tctcacctga actttctgat gcccgcatct catgggccaa aaatggtgta   1680
cttactactt tggttgatga cttctttgac gtgggaggtt ctctagagga attaaagaaa   1740
ctgattgagt tggttgaaaa gtgggatata aatgtcagtg atggttgttg ctctgaacca   1800
gtgcaaatcc tcttctcagc actacatagt acaatccagg agattggaga taaagcattc   1860
aaatggcaag cacgcagtgt aacaaaccac ataattaaga tatggttaga tttgcttaat   1920
tctatgttga gggaagctga gtgggctaga aatgcaacag tgcctacagt tgaagaatat   1980
atgacaaatg gttatgtatc atttgccttg gggccaatta tcctccctgc tctttatctt   2040
gttggaccta agctgtcaga ggaattagtt aaggattctg aattccactc ccttttttaag  2100
ctagtgagta cctgtgggcg gcttctgaat gatgtccaca gcttcgagag gaatcaaag   2160
gccggccaac taaatgctct ttctctgcgc ctgattcatg tggagttgg cattactgaa   2220
gcagctgctg ttgcagagat gaagagttca attgagaagc aaaggagaga actgctgaga   2280
ctagtcttgc gcaaagaggg tagtgtagtt ccaagagctt gcaaggattt gttttggaat   2340
atgagtaggg tgctacatca atttttacgtc aaagatgatg gatttacttc agaggagatg   2400
attgagcttg tgaagtcgat catttatgag ccaattgcgg tcaatgaatt ttga         2454
```

<210> SEQ ID NO 49  
<211> LENGTH: 796  
<212> TYPE: PRT  
<213> ORGANISM: Chiococca alba
<400> SEQUENCE: 49

```
Met Ile His Thr Leu Pro His Gly Gly Gln Ala His Phe Ile Ser His
  1               5                  10                  15

Lys Thr Gln Pro Tyr Tyr Ser Ser Arg Pro Arg Phe Ser Ser Ala Ala
             20                  25                  30

Ser Leu Asp Thr Arg Val Arg Arg Thr Ser Pro Ser Asn Ser Ser Val
         35                  40                  45

Leu Asp Phe Asn Glu Thr Lys Glu Arg Ile Thr Lys Leu Phe His Asn
     50                  55                  60
```

```
Val Asp Tyr Ser Ile Ser Ser Tyr Asp Thr Ala Trp Val Ala Met Val
 65                  70                  75                  80

Pro Asp Pro His Ser Ser Gln Ala Pro Leu Phe Pro Glu Cys Ile Asn
                 85                  90                  95

Trp Leu Leu Asp Asn Gln Phe His Asp Gly Ser Trp Ser Leu Pro His
            100                 105                 110

His Asn Ser Leu Leu Leu Lys Asp Val Leu Ser Ser Thr Leu Ala Cys
        115                 120                 125

Val Leu Ala Leu Lys Arg Trp Gly Ile Gly Gly Arg Gln Ile Asp Lys
    130                 135                 140

Gly Val Arg Phe Ile Glu Met Asn Phe Gly Ser Ala Ser Asp Asn Cys
145                 150                 155                 160

Gln His Thr Pro Ile Gly Phe Asp Ile Ile Phe Pro Gly Met Leu Glu
                165                 170                 175

Asn Ala Arg Asp Leu Asp Leu Asn Leu Arg Leu Glu Pro Arg Ile Val
            180                 185                 190

Thr Asp Met Gln Arg Lys Arg Asp Met Gln Leu Thr Arg Leu His Glu
        195                 200                 205

Ser Asp Leu Lys Gly Asp Gln Ala Tyr Leu Ala Tyr Val Ser Glu Gly
    210                 215                 220

Met Gln Lys Leu Gln Asn Trp Asp Leu Ala Met Lys Phe Gln Arg Lys
225                 230                 235                 240

Asn Gly Ser Leu Phe Asn Ser Pro Ser Ala Thr Ala Ala Val Met
                245                 250                 255

His Val Gln Asn Pro Ala Ser Leu Asn Tyr Leu His Ser Val Val Asp
            260                 265                 270

Lys Phe Gly His Ala Val Pro Ala Val Tyr Pro Leu Asp Leu Tyr Ala
        275                 280                 285

Arg Leu Cys Leu Val Asp Asn Leu Glu Arg Leu Gly Ile Cys Arg His
    290                 295                 300

Phe Thr Asn Glu Ile Glu Ile Val Met Glu Asp Thr Tyr Arg Cys Trp
305                 310                 315                 320

Leu Gln Asp Asp Glu Asp Ile Phe Ala Glu Ile Ser Thr Cys Ala Leu
                325                 330                 335

Ala Phe Arg Leu Leu Arg Lys His Gly Tyr Val Val Ser Pro Asp Pro
            340                 345                 350

Leu Thr Lys Ile Ile Glu Glu Glu Asp Val Ser Asn Ser Ser Gly Asn
        355                 360                 365

Gly Tyr Trp Asn Asp Ile His Ala Val Met Glu Val His Arg Ala Ser
    370                 375                 380

Glu Val Val Ile His Glu Asn Glu Ser Asp Leu Lys Asn Gln Asn Thr
385                 390                 395                 400

Ile Ser Lys His Leu Leu Arg His His Leu Phe Asn Gly Ser Asp Val
                405                 410                 415

Lys Pro Phe Pro Asn Pro Ile Tyr Lys Gln Val Asp Tyr Ala Leu Lys
            420                 425                 430

Phe Pro Thr Pro Leu Ile Leu Gln Arg Val Glu Asn Lys Thr Leu Ile
        435                 440                 445

Gln Asn Tyr Asp Val Asp Ser Thr Arg Leu Leu Lys Thr Ser Tyr Arg
    450                 455                 460

Ser Ser Asn Phe Cys Asn Glu Asp Leu Leu Arg Leu Ala Val Lys Asp
465                 470                 475                 480

Phe Asn Asp Cys Gln Leu Leu His Arg Lys Glu Leu Lys Glu Leu Glu
```

```
                485                 490                 495
Arg Trp Ser Ala Asp Asn Arg Leu His Glu Leu Lys Phe Ala Arg Gln
            500                 505                 510
Lys Ala Ile Tyr Cys Ser Phe Ser Ala Ala Thr Ile Phe Ile Pro
            515                 520                 525
Glu Trp Tyr Glu Ala Arg Met Ser Leu Ala Lys Asn Ser Val Leu Ala
            530                 535                 540
Thr Val Val Asp Asp Phe Phe Asp Val Gly Gly Ser Met Glu Glu Leu
545                 550                 555                 560
Lys Lys Leu Ile Glu Phe Val Glu Lys Trp Asp Ile Asp Ile Thr Lys
                565                 570                 575
Glu Ser Cys Ser Glu Pro Leu Lys Ile Ile Phe Ser Ala Leu His Ser
            580                 585                 590
Thr Ile Ser Glu Ile Gly Glu Gln Ala Val Lys Trp Gln Gly Arg Asn
            595                 600                 605
Val Thr Ser His Ile Ile Glu Ile Trp Leu Asp Leu Leu Asn Ser Met
610                 615                 620
Leu Arg Glu Ser Glu Trp Thr Thr Asp Val His Met Pro Thr Leu Asp
625                 630                 635                 640
Glu Tyr Met Glu Ala Ala Tyr Val Ser Phe Ala Met Gly Pro Ile Ile
                645                 650                 655
Ile Pro Ala Leu Tyr Phe Val Gly Pro Lys Leu Ser Asp Glu Ile Val
            660                 665                 670
Arg Asp Pro Glu Ile Arg Ser Leu His Lys Leu Val Ser Ile Cys Gly
            675                 680                 685
Arg Leu Leu Asn Asp Met Gln Gly Phe Glu Arg Glu Lys Lys Ala Gly
            690                 695                 700
Lys Pro Asn Ala Val Ser Ile Arg Ile Ser Gln Asn Gly Asp Gly Ile
705                 710                 715                 720
Thr Glu Ser Ala Ala Phe Glu Glu Val Lys Met Glu Leu Glu Asp Ala
                725                 730                 735
Arg Arg Glu Leu Leu Arg Leu Val Val Gln Lys Asp Gly Ser Val Val
            740                 745                 750
Pro Arg Ala Cys Lys Asp Ala Phe Trp Ser Val Ser Arg Met Leu His
            755                 760                 765
His Phe Tyr Phe Asn Asn Asp Gly Tyr Thr Ser Glu Val Glu Met Val
            770                 775                 780
Glu Leu Val Asn Ser Ile Ile His Glu Pro Leu Lys
785                 790                 795

<210> SEQ ID NO 50
<211> LENGTH: 2391
<212> TYPE: DNA
<213> ORGANISM: Chiococca alba

<400> SEQUENCE: 50
atgattcata ctctccctca tggcggccag gctcacttca tttcccacaa aacacagcct      60
tattattcca gtagacctcg cttttcttca gcagcttctt tggacacacg agtccggaga     120
acatcgccct ctaattcctc tgtcctagac ttcaacgaga ccaaagaaag aatcacaaaa     180
ttatttcata tgttgatta ttcaatttct tcatatgata cagcatgggt tgctatggtc      240
ccggacccac attcttctca ggctcccctt ttcccagagt gcataaattg gttgctagat     300
aatcaatttc atgatggctc ctggagtctt cctcatcaca attctctatt gcttaaggat     360
```

```
gttttatcct ctacgcttgc gtgtgttctt gctcttaaga gatggggaat aggaggaagg    420
cagattgaca aaggtgttcg ctttattgag atgaattttg gctcagcatc tgacaattgc    480
cagcatactc caataggatt tgacataata tttccaggaa tgcttgaaaa tgccagagat    540
ttggatctaa atcttagact agaacccaga attgtaactg acatgcaacg taaaagagac    600
atgcagctta caagactcca tgaaagcgat ctaaaggggg accaagcata cttggcatat    660
gtatccgaag ggatgcaaaa gttacagaat tgggatttgg cgatgaagtt tcaaaggaag    720
aatggatcgc tcttcaactc accatcagct acagcagccg ctgttatgca tgtccaaaat    780
cctgcttccc tcaattatct tcattcagtc gtcgacaaat tcggccatgc agttccggct    840
gtttacccct tggatctcta tgcgcgcctt tgcttggttg acaatcttga gaggctgggt    900
atctgtcgac attttactaa tgaaattgaa attgtaatgg aggacacgta caggtgctgg    960
ctgcaggatg atgaagatat atttgccgaa atatcaactt gtgccttagc ttttcggtta   1020
ttgagaaaac atggctatgt tgtctcccca gatccactga caaaaatcat agaagaagaa   1080
gatgtttcca attcttctgg taatggatat tggaatgata tacatgctgt aatggaagtg   1140
catcgggcat cagaggtggt tatacatgaa aatgaatcag atttaaagaa tcaaaatacc   1200
atatcaaaac accttctcag acaccatctt ttcaatggtt ctgatgtgaa gccctttcct   1260
aatccaatat acaagcaggt ggactatgct ctcaagtttc caacccccctt aattctacaa   1320 cgtgttgaaa acaagaccct catacagaac tacgacgtag acagtacaag acttcttaaa   1380
acttcatatc gatcatcaaa tttctgcaat gaagatttac tgaggttagc agtgaaagat   1440
tttaatgact gtcaactcct gcaccggaaa gaactaaaag aactagaaag atggtccgca   1500
gataacagac tgcacgaact aaaaatttgct cggcagaaag ctatatactg ctccttttct   1560
gctgcagcaa cgattttcat acctgaatgg tacgaagccc gcatgtcatt ggccaaaaat   1620
agtgtacttg ctactgtggt tgatgacttc tttgatgtgg gtggtcgat ggaggaatta   1680 aagaagctaa ttgaatttgt tgaaaagtgg gatattgaca tcaccaagga atcctgctct   1740
gagccactca aaatcatatt ttcagcactg cacagtacaa tctctgagat tggagagcaa   1800
gcagttaaat ggcaaggacg caatgtaaca agccacataa ttgagatctg gttggatttg   1860
ctcaattcga tgttgaggga gtctgaatgg actacagatg tgcacatgcc aacattggat   1920
gaatatatgg aagctgctta tgtatcattc gccatgggc caattatcat ccctgctctg   1980
tattttgttg ggcctaagct atctgatgaa attgttcggg atcctgaaat acgatccctc   2040
cataagcttg tgagcatttg tgggcggctt ctaaatgata tgcaagggt cgagagggaa   2100 aagaaggctg gtaaaccaaa tgccgtgtct atacgcatta gtcaaaatgg tgatggcatt   2160
accgaatcag cagcttttcga agaagtgaag atggaattag aggatgcaag agagaattg    2220 ctaagattag ttgtgcaaaa agatggtagt gtagttccaa gagcttgcaa ggatgcgttt   2280
tggagcgtaa gcagaatgtt gcatcatttc tacttcaata atgatggata cacgtcagag   2340
gtggagatgg ttgagctcgt gaattcaatt attcatgaac cactaaaata a            2391
```

<210> SEQ ID NO 51
<211> LENGTH: 792
<212> TYPE: PRT
<213> ORGANISM: Salvia hispanica

<400> SEQUENCE: 51

Met Ser Ile Gln Ala Asn Met Ser Phe Ala Thr Ser Leu His Arg Ser
1               5                   10                  15

```
Thr Thr Pro Gly Val Gly Leu Pro Leu Lys Pro Cys Ile Ser Pro Ser
            20                  25                  30

Pro Ser Leu Ser Phe Ser Pro Asn Phe Gly Thr Phe Asn Asn Thr Ser
        35                  40                  45

Leu Arg Leu Lys Pro Glu Ala Gly Ser Lys Ser Tyr Glu Gly Ile Arg
    50                  55                  60

Arg Ser His Gln Leu Ala Ala Ser Thr Ile Leu Glu Gly Gln Thr Pro
65                  70                  75                  80

Ile Thr Pro Glu Val Glu Ser Glu Lys Thr Arg Leu Ile Glu Arg Ile
                85                  90                  95

Arg Ser Met Leu Gln Asp Met Asp Asn Asp Gly Gln Ile Ser Val Ser
            100                 105                 110

Pro Tyr Asp Thr Ala Trp Val Ala Leu Val Glu Asp Ile Gly Gly Ser
        115                 120                 125

Gly Gly Pro Gln Phe Pro Thr Ser Leu Glu Trp Ile Ser Asn His Gln
130                 135                 140

Tyr Asp Asp Gly Ser Trp Gly Asp Arg Lys Phe Val Leu Tyr Asp Arg
145                 150                 155                 160

Ile Leu Asn Thr Leu Ala Cys Val Val Ala Leu Thr Asn Trp Lys Met
                165                 170                 175

His Pro Asn Lys Cys Glu Lys Gly Leu Arg Phe Ile His Glu Asn Ile
            180                 185                 190

Lys Lys Leu Ala Asp Glu Asp Glu Glu Leu Met Pro Val Gly Phe Glu
        195                 200                 205

Ile Ala Leu Pro Ser Val Ile Asp Leu Ala Lys Arg Leu Gly Ile Glu
210                 215                 220

Ile Pro Glu Asn Ser Ala Ser Ile Lys Arg Ile Tyr Glu Leu Arg Asp
225                 230                 235                 240

Ser Lys Leu Lys Lys Ile Pro Met Asp Leu Val His Lys Arg Pro Thr
                245                 250                 255

Ser Leu Leu Phe Ser Leu Glu Gly Met Glu Gly Leu Asn Trp Asp Lys
            260                 265                 270

Leu Met Asn Phe Leu Ala Glu Gly Ser Phe Leu Ser Ser Pro Ser Ser
        275                 280                 285

Thr Ala Tyr Ala Leu Gln His Thr Lys Asn Glu Leu Cys Leu Glu Tyr
290                 295                 300

Leu Leu Lys Ala Val Lys Arg Phe Asn Gly Gly Val Pro Asn Ala Tyr
305                 310                 315                 320

Pro Val Asp Met Phe Glu His Leu Trp Ser Val Asp Arg Leu Gln Arg
                325                 330                 335

Leu Gly Ile Ser Arg Tyr Phe Gln Ala Glu Ile Glu Glu Asn Met Ala
            340                 345                 350

Tyr Ala Tyr Arg Tyr Trp Thr Asn Lys Gly Ile Thr Trp Ala Arg Asn
        355                 360                 365

Met Val Val Gln Asp Ser Asp Ser Ala Gly Phe Arg Leu Leu
370                 375                 380

Arg Leu Tyr Gly Tyr Asp Ile Pro Ile Asp Val Phe Lys His Phe Glu
385                 390                 395                 400

Gln Gly Gly Gln Phe Cys Ser Ile Pro Gly Gln Met Thr His Ala Ile
                405                 410                 415

Thr Gly Met Tyr Asn Leu Tyr Arg Ala Ser Glu Leu Leu Phe Pro Gly
            420                 425                 430

Glu His Ile Leu Ser Asp Ala Arg Lys Tyr Thr Gly Asn Phe Leu His
```

|   |   |   | 435 |   |   |   | 440 |   |   |   | 445 |   |   |
|---|---|---|---|---|---|---|---|---|---|---|---|---|---|

Gln Arg Arg Ile Thr Asn Thr Val Val Asp Lys Trp Ile Ile Thr Lys
450                     455                     460

Asp Leu His Gly Glu Val Ala Tyr Ala Leu Asp Val Pro Phe Tyr Ala
465                     470                     475                     480

Ser Leu Pro Arg Leu Glu Ala Arg Phe Phe Ile Glu Gln Tyr Gly Gly
                485                     490                     495

Asp Glu Asp Val Trp Ile Gly Lys Thr Leu Tyr Arg Met Phe Lys Val
                500                     505                     510

Asn Ser Asp Thr Tyr Leu Glu Met Ala Lys Leu Asp Tyr Lys Gln Cys
                515                     520                     525

Gln Ser Val His Gln Leu Glu Trp Asn Ser Met Gln Arg Leu Tyr Arg
530                     535                     540

Asp Cys Asn Leu Gly Glu Phe Gly Leu Ser Glu Arg Ser Leu Leu Leu
545                     550                     555                     560

Ala Tyr Tyr Ile Ala Ala Ser Thr Thr Phe Glu Pro Glu Lys Ser Ser
                565                     570                     575

Glu Arg Leu Ala Trp Ala Ile Thr Thr Ile Leu Val Glu Ile Ile Ala
                580                     585                     590

Ser Gln Lys Leu Ser Asp Glu Gln Lys Arg Glu Phe Val Asp Glu Phe
                595                     600                     605

Val Lys Gly Ser Ile Val Asn Asn Gln Asn Gly Gly Arg His Lys Pro
610                     615                     620

Gly Asn Arg Leu Val Glu Val Leu Ile Asn Asn Ile Thr Leu Met Ala
625                     630                     635                     640

Glu Gly Arg Gly Thr Tyr Gln Gln Leu Ser Asn Ala Trp Lys Lys Trp
                645                     650                     655

Leu Lys Thr Trp Glu Glu Gly Gly Asp Leu Gly Glu Ala Glu Ala Arg
                660                     665                     670

Leu Leu Leu His Thr Ile His Leu Ser Ser Gly Leu Asp Asp Ser Ser
                675                     680                     685

Phe Ser His Pro Lys Tyr Gln Gln Leu Leu Glu Ala Thr Ser Lys Val
690                     695                     700

Cys His Gln Leu Arg Val Phe Gln Ser Val Lys Val Tyr Asp Asp Gln
705                     710                     715                     720

Glu Ser Thr Ser Gln Leu Val Thr Arg Thr Thr Phe Gln Ile Glu Ala
                725                     730                     735

Gly Met Gln Glu Leu Val Lys Leu Val Phe Thr Lys Thr Leu Glu Asp
                740                     745                     750

Leu Pro Ser Thr Thr Lys Gln Ser Phe Phe Ser Val Ala Arg Ser Phe
                755                     760                     765

Tyr Tyr Thr Ala Cys Ile His Ala Asp Thr Ile Asp Ser His Ile Asn
770                     775                     780

Lys Val Leu Phe Glu Lys Ile Val
785                     790

<210> SEQ ID NO 52
<211> LENGTH: 2379
<212> TYPE: DNA
<213> ORGANISM: Salvia hispanica

<400> SEQUENCE: 52
atgagtattc aagcaaacat gtcatttgcc acctccctcc accgatcaac caccccggga      60
gttggccttc cgctaaaacc atgtatctct ccctctccct ctctttcctt ttccccaaac     120

```
tttggcactt ttaacaacac aagtttgaga ctcaaaccag aggctgggag caaaagttat    180
gaggggattc gaagaagtca tcaattagca gcatcaacaa ttttggaggg tcaaactccg    240
attactccgg aggttgaatc ggagaaaaca cgcctgattg aaaggattcg ttcgatgtta    300
caagacatgg acaacgatgg ccagataagt gtgtcaccat acgacacagc atgggtggcg    360
ctcgtggaag atattggtgg cagcggaggg ccacagtttc caacgagcct agagtggatt    420
tctaaccacc agtacgacga tggatcgtgg gggatcgca aatttgttct ctatgaccgg    480
atactcaata cattagcatg tgttgtcgca ctcacgaatt ggaaaatgca tcctaacaaa    540
tgcgaaaaag ggttgaggtt tattcatgag aatattaaga aactcgcgga tgaagatgaa    600
gagctcatgc ccgtaggatt cgaaatcgca ctgccatcag tcattgattt agctaaaaga    660
ctgggtatag aaatcccaga aaattctgca agcataaaaa gaatttatga attgagagat    720
tcaaaactta aaaaaatacc aatggattta gtgcacaaaa ggcccacatc actactcttc    780
agcttggaag gcatggaagg ccttaactgg gacaaactaa tgaattttct agccgagggt    840
tcgtttcttt catcgccatc gtccactgcc tacgctctcc aacacaccaa gaatgagtta    900
tgcctagagt atttactcaa ggcagtcaag agattcaatg gtggagttcc aaatgcatac    960
cctgtcgaca tgtttgagca tctgtggtcc gtggatcgct acagagatt aggaatttct    1020 cggtattttc aagctgaaat tgaagaaaac atggcctatg cttacagata ctggacaaat    1080
aaaggaatca cctgggcaag aaatatggtt gtccaagaca gtgacgacag cgcacaggga    1140
ttcaggctct taaggttgta cggatacgat attcctatag atgttttcaa acatttcgag    1200
caaggtggac aattctgcag cataccagga cagatgacac acgctattac aggaatgtac    1260
aacttgtata gagcttctga acttctgttc cctggagaac acatacttc tgatgctaga    1320 aaatacacag gtaacttctt gcatcaaaga agaattacta acacggtagt agacaagtgg    1380
atcattacca aagaccttca cggcgaggtg gcttatgcat tggatgtgcc attctacgcc    1440
agtctgccac gactggaagc acgattcttc atagaacaat atgggggtga tgaagatgtt    1500
tggattggga aaacattgta caggatgttt aaagtaaact ccgacacata ccttgagatg    1560
gcaaaattag attacaaaca atgccagtct gtgcatcagt tagagtggaa tagcatgcaa    1620
agattgtata gagattgcaa tctaggagag tttgggttga gcgaaagaag ccttctccta    1680
gcttactaca tagcagcctc aactacattt gagccgaaaa aatcaagtga aagactggct    1740
tgggctataa caacaatttt agtcgaaata atcgcatccc aaaaactctc tgatgagcaa    1800
aagagagagt ttgttgatga atttgtaaaa ggaagcatcg tcaataacca aaatggagga    1860
agacataaac cgggaaacag attggttgaa gttttgatca acaatataac actgatggca    1920
gaaggcagag gcacatatca gcagttgtct aatgcgtgga aaaatggct aaagacatgg    1980 gaagagggag gtgacctggg ggaagcagaa gcacggcttc tcctgcacac gatacatttg    2040
agctccggat tggatgattc atcatttcc catccaaaat atcagcagct cttggaggca    2100
accagcaaag tctgccacca acttcgcgta ttccagagtg taaggtgta tgatgaccaa    2160 gagtctacaa gccaactggt aactaggaca actttccaaa tagaagcagg catgcaagaa    2220
ctagtgaaat tagttttcac aaaaaccttg gaagatttgc cttctactac caagcaaagc    2280
ttttttagtg ttgctagaag tttctattac actgcctgta ttcatgcaga cactatagac    2340
tcccacataa acaaagtatt gtttgaaaaa attgtctag                           2379
```

<210> SEQ ID NO 53

```
<211> LENGTH: 790
<212> TYPE: PRT
<213> ORGANISM: Teucrium canadense

<400> SEQUENCE: 53

Met Ser Phe Ala Ser Gln Ala Thr Ser Leu Leu Leu Ser Ser His Asn
1               5                   10                  15

Ala Thr Ala Leu Pro Pro Leu Ser Ala Arg Leu Pro Pro Leu Thr
            20                  25                  30

Ala Gly Ala Ala Pro Phe Gly Arg Ile Ser Phe Thr Thr Ser Leu
        35                  40                  45

Arg Gln Tyr Lys Leu Val Ser Arg Ala Gln Ser Gln Glu Val Asp Glu
    50                  55                  60

Ile Glu Lys Val Thr Gln Val Leu Glu Ala Glu Lys Asp Ile Asp
65                  70                  75                  80

Gln Glu Ala Lys Val Arg Glu Leu Val Glu Asn Val Arg Val Lys Leu
                85                  90                  95

Gln Asn Ile Gly Glu Gly Gly Ile Ser Ile Ser Pro Tyr Asp Thr Ala
            100                 105                 110

Trp Val Ala Leu Val Glu Asp Val Gly Gly Ser Gly Arg Pro Gln Phe
        115                 120                 125

Pro Glu Ser Leu Asp Trp Ile Ser Asn His Gln Phe Pro Asp Gly Ser
    130                 135                 140

Trp Gly Ser His Lys Phe Leu Tyr Tyr Asp Arg Val Leu Cys Thr Leu
145                 150                 155                 160

Ala Cys Ile Val Ala Leu Lys Thr Trp Asn Leu His Pro His Lys Phe
                165                 170                 175

Asp Lys Gly Leu Lys Phe Val Arg Glu Asn Ile Gly Lys Leu Ala Asp
            180                 185                 190

Glu Glu Asp Val His Met Pro Ile Gly Phe Glu Val Ala Phe Pro Ser
        195                 200                 205

Leu Ile Glu Thr Ala Lys Arg Lys Gly Ile Asp Ile Pro Glu Asp Phe
    210                 215                 220

Pro Gly Lys Lys Glu Ile Tyr Ala Lys Arg Asp Leu Lys Leu Lys Lys
225                 230                 235                 240

Ile Pro Met Asp Ile Leu His Lys Ile Pro Thr Pro Leu Leu Phe Ser
                245                 250                 255

Ile Glu Gly Ile Glu Gly Leu Asp Trp Gln Lys Leu Phe Lys Phe Arg
            260                 265                 270

Asp His Gly Ser Phe Leu Thr Ser Pro Ser Ser Thr Ala His Ala Leu
        275                 280                 285

Gln Gln Thr Lys Asp Glu Leu Cys Leu Lys Tyr Leu Thr Asn Leu Val
    290                 295                 300

Lys Lys Asn Asn Gly Gly Val Pro Asn Ala Phe Pro Val Asp Leu Phe
305                 310                 315                 320

Asp Arg Asn Tyr Thr Val Asp Arg Leu Arg Arg Leu Gly Ile Leu Arg
                325                 330                 335

Tyr Phe Gln Pro Glu Ile Glu Glu Cys Met Lys Tyr Val Tyr Arg Phe
            340                 345                 350

Trp Asp Lys Arg Gly Ile Ser Trp Ala Arg Asn Thr His Val Gln Asp
        355                 360                 365

Leu Asp Asp Thr Val Gln Gly Phe Arg Asn Leu Arg Met His Gly Tyr
    370                 375                 380

Asp Val Thr Leu Asp Val Phe Lys Gln Phe Glu Arg Cys Gly Glu Phe
```

```
            385                 390                 395                 400
        Phe Ser Phe His Gly Gln Ser Ser Asp Ala Val Leu Gly Met Phe Asn
                        405                 410                 415
        Leu Tyr Arg Ala Ser Gln Val Leu Phe Pro Gly Glu Asp Met Leu Ala
                        420                 425                 430
        Asp Ala Arg Lys Tyr Ala Ala Asn Tyr Leu His Lys Arg Arg Val Ser
                        435                 440                 445
        Asn Arg Val Val Asp Lys Trp Ile Ile Asn Lys Asp Leu Pro Gly Glu
                        450                 455                 460
        Val Ala Tyr Gly Leu Asp Val Pro Phe Tyr Ala Ser Leu Pro Arg Leu
        465                 470                 475                 480
        Glu Ala Arg Phe Tyr Val Glu Gln Tyr Gly Asn Asp Val Trp
                        485                 490                 495
        Ile Gly Lys Ala Leu Tyr Arg Met Leu Asn Val Ser Cys Asp Thr Tyr
                        500                 505                 510
        Leu Glu Leu Ala Lys Leu Asp Tyr Asn Ile Cys Gln Ala Val His Gln
                        515                 520                 525
        Lys Glu Trp Lys Ser Phe Gln Lys Trp His Arg Asp Gly Glu Phe Gly
                        530                 535                 540
        Leu Asp Glu Lys Ser Leu Leu Ala Tyr Tyr Ile Ala Ala Ser Thr
        545                 550                 555                 560
        Val Phe Glu Pro Glu Lys Ser Leu Glu Arg Leu Ala Trp Ala Lys Thr
                        565                 570                 575
        Ala Val Leu Met Glu Ala Ile Leu Ser Gln Gln Leu Pro Ser Thr Lys
                        580                 585                 590
        Lys His Glu Leu Val Asp Glu Phe Lys His Ala Ser Ile Leu Asn Asn
                        595                 600                 605
        Gln Asn Gly Gly Ser Tyr Lys Thr Arg Thr Pro Leu Val Glu Thr Leu
                        610                 615                 620
        Val Asn Ala Ile Ser Glu Leu Ser Thr Thr Ile Leu Leu Glu Gln Asp
        625                 630                 635                 640
        Arg Asp Ile His Leu Gln Leu Ser Asn Ala Trp Leu Lys Trp Leu Ser
                        645                 650                 655
        Arg Trp Glu Ala Arg Gly Asn Leu Val Glu Ala Glu Ala Glu Leu Leu
                        660                 665                 670
        Leu Gln Thr Leu His Leu Ser Asn Gly Leu Glu Glu Ser Ser Phe Ser
                        675                 680                 685
        His Pro Lys Tyr Gln Gln Leu Leu Gln Val Thr Ser Lys Val Cys His
                        690                 695                 700
        Leu Leu Arg Leu Phe Gln Lys Arg Lys Val His Asp Pro Glu Gly Cys
        705                 710                 715                 720
        Thr Thr Asp Ile Ala Thr Gly Thr Thr Phe Gln Ile Glu Ala Cys Met
                        725                 730                 735
        Gln Gln Val Val Lys Leu Val Phe Thr Lys Ser Ser His Asp Leu Asp
                        740                 745                 750
        Ser Val Val Lys Gln Arg Phe Leu Asp Val Ala Arg Ser Phe Tyr Tyr
                        755                 760                 765
        Thr Ala His Cys Asp Pro Gln Val Ile Gln Ser His Ile Asn Lys Val
                        770                 775                 780
        Leu Phe Glu Lys Val Val
        785                 790

<210> SEQ ID NO 54
```

<211> LENGTH: 2373
<212> TYPE: DNA
<213> ORGANISM: Teucrium canadense

<400> SEQUENCE: 54

```
atgtcatttg cttcccaagc cacctccctc ctcctttctt cccacaacgc caccgctctt      60
ccgcctctct ctgccgcccg ccttccgcct ctcactgccg gtgctgctcc attcggaaga     120
atatcattta ctactacctc tcttcggcag tataaactgg tgtcaagagc tcaaagccaa     180
gaggtggatg agattgaaaa agtgacacaa gtggtattgg aggcagaaaa agacatcgat     240
caagaggcga aggtaaggga gctggtggaa aatgtccgag tgaagctgca aaatatcggg     300
gaaggaggga taagcatatc gccgtacgac accgcatggg tggcgctggt ggaggatgtc     360
ggcggcagcg gcagaccgca gttcccggag agcctggatt ggatatcaaa ccaccagttc     420
ccggacgggt cgtggggcag ccacaaattc ttgtactatg accgggtttt gtgcacgtta     480
gcatgtatag ttgcattgaa acttggaat ctgcatcctc acaaattcga caaagggttg     540
aaattcgtca gagagaacat tggaaagctc gcggatgaag aagacgtgca catgccgatt     600
gggttcgaag tggcattccc atcacttata gagactgcaa agagaaaagg aattgacatc     660
ccggaagatt tccctggcaa gaaagaaatc tatgcaaaaa gagacctaaa gctgaaaaag     720
atacctatgg atatactgca caaaatcccc acaccattac tgttcagcat agaagggata     780
gaaggccttg attggcagaa gctattcaaa ttccgcgatc acggctcctt cctcacgtcc     840
ccgtcctcaa cggcccacgc tctccagcaa acaaggacg agttatgcct caaatatctg     900
accaatcttg tcaaaagaa caatggggga gttccaaatg catttccggt ggacctattt     960
gatcgtaact atacagtaga tcgcctgagg aggctgggaa ttttgcgcta ttttcaacct    1020
gaaatcgagg aatgcatgaa atatgtatac agattctggg ataaaagagg aatcagctgg    1080
gcaagaaata cccatgttca ggaccttgat gataccgtac agggattcag gaacttaagg    1140
atgcatggtt atgatgtcac cttagatgtt ttcaaacagt tcgagagatg tggagaattc    1200
tttagcttcc acgggcaatc aagtgatgct gtcttaggaa tgttcaactt gtaccgagct    1260
tctcaggttc tgtttccagg agaagacatg cttgcagatg caaggaagta cgcggccaac    1320
tatttgcata aagaagagt tagtaatagg gtcgtggaca aatggattat taacaaagat    1380
cttccaggcg aggtggcgta tgggctagat gttccgttct acgccagtct acctcgactg    1440
gaagcaagat tctacgtcga acaatatggg ggtaacgatg atgtctggat ggaaaagct    1500
ttatatagaa tgttgaatgt gagctgtgat acttaccttg agctagcaaa attagactac    1560
aatatttgcc aggctgtgca tcagaaagag tggaaaagct ttcaaaaatg gcacagggat    1620
ggggagtttg gattggatga aaaaagctta cttttagctt actacatagc agcctcgact    1680
gttttcgagc ctgaaaaatc tctagagcga ctggcttggg ctaaaaccgc agttctaatg    1740
gaggcaattt tgtcccaaca acttcctagc acaaaaaaac atgagcttgt tgacgaattt    1800
aaacatgcaa gcatcctcaa caaccaaaat ggaggaagct ataaaacaag aactcctttg    1860
gtagagactc tagtaaacgc cataagtgag ctctcaacta ccatactatt ggagcaagac    1920
agagacattc atctgcaatt atctaatgcg tggctgaagt ggctaagtag atgggaggca    1980
agaggcaacc tagtggaagc agaagcagag cttcttctgc aaaccttaca tctgagcaat    2040
ggattagaag aatcatcatt ttctcatcca aaatatcaac aactcttaca ggttaccagc    2100
aaagtctgtc acctacttcg gctattccag aaacgaaagg tgcatgatcc ggaagggtgt    2160
acaacagaca ttgcaacagg gacaacttc caaatagaag catgcatgca acaagtagtg    2220
```

```
aaattagtgt tcaccaaatc ctcacatgat ttagattctg ttgttaagca gagattttg    2280 gatgttgcca gaagttttcta ttacacagcc cactgtgatc cacaagtgat ccagtcccac   2340
attaataaag tgttgtttga aaaagtagtc tag                                2373
```

<210> SEQ ID NO 55
<211> LENGTH: 785
<212> TYPE: PRT
<213> ORGANISM: Salvia officinalis

<400> SEQUENCE: 55

```
Met Ser Phe Ala Ser Thr Thr Ser Leu Leu Arg Pro Ser Val Thr Gly
1               5                   10                  15

Phe Gly Val Ser Pro Arg Val Thr Ser Thr Ser Ile Leu Ser Arg Ser
            20                  25                  30

Tyr Gly Gln Ile Leu Lys Gly Lys Thr Lys Tyr Ile Thr Asp Asn Arg
        35                  40                  45

Arg Asn Arg Gln Leu Ala Val Lys Phe Glu Gly Gln Ile Ala Leu Asp
    50                  55                  60

Leu Glu Asp Gly Val Ala Lys Gln Thr Asn Gln Glu Ala Glu Ser Glu
65                  70                  75                  80

Lys Ile Arg Gln Leu Lys Gly Lys Ile Arg Trp Ile Leu Gln Asn Met
                85                  90                  95

Glu Asp Gly Glu Met Ser Val Ser Pro Tyr Asp Thr Ala Trp Val Ala
            100                 105                 110

Leu Val Glu Asp Ile Ser Gly Gly Gly Pro Gln Phe Pro Thr Ser
        115                 120                 125

Leu Glu Trp Ile Ser Lys Asn Gln Leu Ala Asp Gly Ser Trp Gly Asp
    130                 135                 140

Pro Asn Tyr Phe Leu Leu Tyr Asp Arg Ile Leu Asn Thr Leu Ala Cys
145                 150                 155                 160

Val Val Ala Leu Thr Thr Trp Asn Met His Pro His Lys Cys Asp Gln
                165                 170                 175

Gly Leu Arg Phe Ile Arg Asp Asn Ile Glu Lys Leu Glu Asp Glu Asp
            180                 185                 190

Glu Glu Leu Ile Leu Val Gly Phe Glu Ile Ala Leu Pro Ser Leu Ile
        195                 200                 205

Asp Tyr Ala Gln Asn Leu Gly Ile Gln Ile Gln Tyr Asp Ser Pro Phe
    210                 215                 220

Ile Lys Lys Ile Cys Ala Lys Arg Asp Leu Lys Leu Arg Lys Ile Pro
225                 230                 235                 240

Met Asp Leu Met His Arg Lys Pro Thr Ser Leu Leu Tyr Ser Leu Glu
                245                 250                 255

Gly Met Glu Gly Leu Glu Trp Glu Lys Leu Met Asn Leu Arg Ser Glu
            260                 265                 270

Gly Ser Phe Leu Ser Ser Pro Ser Ser Thr Ala Tyr Ala Leu Gln His
        275                 280                 285

Thr Lys Asp Glu Leu Cys Leu Asp Tyr Leu Val Lys Ala Val Asn Lys
    290                 295                 300

Phe Asn Gly Gly Val Pro Asn Val Tyr Pro Val Asp Met Tyr Glu His
305                 310                 315                 320

Leu Trp Cys Val Asp Arg Leu Gln Arg Leu Gly Ile Ser Arg Tyr Phe
                325                 330                 335

Gln Leu Glu Ile Gln Gln Cys Leu Asp Tyr Val Tyr Arg Tyr Trp Thr
```

```
            340                 345                 350
Asn Glu Gly Ile Ser Trp Ala Arg Tyr Thr Asn Ile Arg Asp Ser Asp
        355                 360                 365
Asp Thr Ala Met Gly Phe Arg Leu Leu Arg Leu Tyr Gly Tyr Asp Val
370                 375                 380
Ser Ile Asp Ala Phe Lys Pro Phe Glu Glu Ser Gly Glu Phe Tyr Ser
385                 390                 395                 400
Met Ala Gly Gln Met Asn His Ala Val Thr Gly Met Tyr Asn Leu Tyr
                405                 410                 415
Arg Ala Ser Gln Leu Met Phe Pro Gln Glu His Ile Leu Ser Asp Ala
            420                 425                 430
Arg Asn Phe Ser Ala Lys Phe Leu His Gln Lys Arg Thr Asn Ala
            435                 440                 445
Leu Val Asp Lys Trp Ile Ile Thr Lys Asp Leu Pro Gly Glu Val Gly
450                 455                 460
Tyr Ala Leu Asp Val Pro Phe Tyr Ala Ser Leu Pro Arg Leu Glu Ala
465                 470                 475                 480
Arg Phe Phe Leu Glu Gln Tyr Gly Gly Asp Asp Val Trp Ile Gly
                485                 490                 495
Lys Thr Leu Tyr Arg Met Pro Tyr Val Asn Ser Asn Thr Tyr Leu Glu
                500                 505                 510
Leu Ala Lys Val Asp Tyr Lys Asn Cys Gln Ser Val His Gln Leu Glu
            515                 520                 525
Trp Lys Ser Met Gln Lys Trp Tyr Arg Glu Cys Asn Ile Gly Glu Phe
            530                 535                 540
Gly Leu Ser Glu Arg Ser Leu Leu Ala Tyr Tyr Ile Ala Ala Ser
545                 550                 555                 560
Thr Thr Phe Glu Pro Glu Lys Ser Gly Glu Arg Leu Ala Trp Ala Thr
                565                 570                 575
Thr Ala Ile Leu Ile Glu Thr Ile Ala Ser Gln Gln Leu Ser Asp Glu
                580                 585                 590
Gln Lys Arg Glu Phe Val Asp Glu Phe Glu Asn Ser Ile Ile Ile Lys
            595                 600                 605
Asn Gln Asn Gly Gly Arg Tyr Lys Ala Arg Asn Arg Leu Val Lys Val
            610                 615                 620
Leu Ile Asn Thr Val Thr Leu Val Ala Glu Gly Arg Gly Ile Asn Gln
625                 630                 635                 640
Gln Leu Phe Asn Ala Trp Gln Lys Trp Leu Lys Thr Trp Glu Glu Gly
                645                 650                 655
Gly Asp Met Gly Glu Ala Glu Ala Gln Leu Leu Leu Arg Thr Leu His
                660                 665                 670
Leu Ser Ser Gly Phe Asp Gln Ser Ser Phe Ser His Pro Lys Tyr Glu
            675                 680                 685
Gln Leu Leu Glu Ala Thr Ser Lys Val Cys His Gln Leu Arg Leu Phe
            690                 695                 700
Gln Asn Arg Lys Val Asp Asp Gly Gln Gly Cys Ile Ser Arg Leu Val
705                 710                 715                 720
Ile Gly Thr Thr Ser Gln Ile Glu Ala Gly Met Gln Glu Val Val Lys
                725                 730                 735
Leu Val Phe Thr Lys Thr Ser Gln Asp Leu Thr Ser Ala Thr Lys Gln
                740                 745                 750
Ser Phe Phe Asn Ile Ala Arg Ser Phe Tyr Tyr Thr Ala Tyr Phe His
            755                 760                 765
```

Ala Asp Thr Ile Asp Ser His Ile Tyr Lys Val Leu Phe Gln Thr Ile
     770                 775                 780

Val
785

<210> SEQ ID NO 56
<211> LENGTH: 2358
<212> TYPE: DNA
<213> ORGANISM: Salvia officinalis

<400> SEQUENCE: 56

| | | | | |
|---|---|---|---|---|
| atgtcatttg | cttccaccac | ctccctcctc | cgaccaagcg | tcactgggtt | cggtgtttct | 60 |
| ccaagggtta | cttccacctc | cattcttagc | cgaagttatg | gtcaaatatt | aaaaggaaaa | 120 |
| acaaaataca | taactgataa | ccgtagaaat | cgacaattgg | cggtaaaatt | tgagggccaa | 180 |
| attgctttgg | atttggagga | tggcgtagca | agcagacga | atcaagaggc | ggaatctgag | 240 |
| aagataaggc | aactgaaggg | aaagatccga | tggattctgc | aaaacatgga | ggacggcgag | 300 |
| atgagcgtgt | cgccgtacga | caccgcatgg | gtggcgctgg | tggaagatat | cagcggcggc | 360 |
| ggcgggccgc | agttcccgac | gagcctcgag | tggatttcca | agaatcagtt | ggcggatggg | 420 |
| tcatgggggg | atcctaatta | tttccttctc | tacgacagaa | tactcaatac | tttagcatgt | 480 |
| gtagtcgcac | tcacgacttg | gaatatgcat | cctcacaaat | gcgatcaagg | gttgaggttt | 540 |
| ataagagaca | acattgagaa | acttgaggat | gaagatgagg | agctaattct | cgtaggattc | 600 |
| gagatcgcac | tgccttcact | cattgattat | gctcaaaacc | ttgggataca | aatccaatat | 660 |
| gattctccat | tcattaaaaa | aatttgtgca | agagagatc | taaaactcag | aaaaatacca | 720 |
| atggatttaa | tgcacagaaa | gccaacatca | ttgctctaca | gcttggaagg | catggaaggc | 780 |
| cttgagtggg | aaaagctaat | gaatttgcga | tcggagggtt | cgtttctgtc | atcgccgtcg | 840 |
| tccacggcct | acgctctcca | acacaccaag | gatgagttat | gccttgacta | tctggtcaag | 900 |
| gcggtcaaca | aattcaatgg | tggagttccc | aacgtgtacc | ctgtcgacat | gtatgagcat | 960 |
| ctatggtgcg | tagaccgctt | gcagaggttg | ggaatttctc | gctatttca | acttgaaatt | 1020 |
| caacaatgcc | tcgactatgt | ttacagatac | tggacaaatg | aaggaatttc | gtgggcaaga | 1080 |
| tatactaata | tccgggatag | tgacgacacc | gcaatgggat | tcaggcttct | aaggttgtac | 1140 |
| ggctatgatg | tctctataga | tgcttttaaa | ccattcgagg | aaagcggaga | attctatagc | 1200 |
| atggcagggc | agatgaacca | cgctgttaca | ggaatgtaca | acttgtacag | agcttctcaa | 1260 |
| cttatgttcc | ctcaagaaca | catactttcc | gatgccagaa | acttctctgc | caaattcttg | 1320 |
| catcaaaaga | ggcgtactaa | tgcactagta | gacaagtgga | tcattaccaa | agaccttccc | 1380 |
| ggcgaggttg | gatatgcatt | ggatgtgccg | ttctacgcca | gtctgcctcg | actggaagca | 1440 |
| cgattcttct | tagaacaata | tgggggtgat | gatgatgttt | ggattggaaa | aactttgtac | 1500 |
| aggatgccat | atgtgaactc | caacacatac | cttgagcttg | caaaagtaga | ctacaaaaac | 1560 |
| tgccagtccg | tgcatcagtt | ggagtggaag | agcatgcaaa | aatggtacag | agaatgcaat | 1620 |
| ataggtgagt | ttgggttgag | cgaaagaagc | cttctcctag | cttactacat | agcagcctca | 1680 |
| actacattcg | agccagaaaa | atcaggtgag | cggctcgctt | gggctacaac | agcaatttta | 1740 |
| atcgagacaa | tcgcgtccca | acaactctcc | gatgaacaaa | agagagagtt | cgttgatgaa | 1800 |
| tttgaaaaca | gcatcattat | caagaatcaa | aatggaggga | gatataaagc | aagaaacaga | 1860 |
| ttggtcaagg | ttttgatcaa | cactgtaaca | ctggtagcag | aaggcagagg | cataaatcag | 1920 |

```
cagttgttta atgcgtggca aaaatggcta agacatggg aagaaggagg tgacatgggg    1980
gaagcagaag cccagcttct tctgcgcacg ctacatttga gctccggatt cgatcaatca    2040
tcattttccc atccaaaata tgagcagctc ttggaggcga ccagcaaagt ttgccaccaa    2100
cttcgcctat tccagaatcg aaaggtggat gatggccaag ggtgtataag tcgattggta    2160
attgggacaa cttcccaaat agaagcaggc atgcaagaag tagtgaaatt agttttcacc    2220
aaaacctcac aagacttgac ttctgctacc aagcaaagct ttttcaatat tgctagaagt    2280
ttctattata ctgcctactt tcatgcagac actatagact cccacatata caaagtattg    2340
tttcaaacaa tagtatag                                                  2358
```

<210> SEQ ID NO 57
<211> LENGTH: 808
<212> TYPE: PRT
<213> ORGANISM: Scutellaria baicalensis

<400> SEQUENCE: 57

```
Met Pro Phe Leu Leu Pro Ser Ser Ala Thr Ser Ser Pro Ala Phe Tyr
1               5                   10                  15

Thr Pro Ala Ala Pro Leu Ala Gly His His Val Phe Pro Ser Phe Lys
            20                  25                  30

Pro Leu Ile Ile Ser Arg Ser Ser Leu Gln Cys Asn Ala Ile Ser Arg
        35                  40                  45

Pro Arg Thr Gln Glu Tyr Ile Asp Val Ile Gln Asn Gly Leu Pro Val
    50                  55                  60

Ile Lys Trp His Glu Ala Val Glu Glu Asp Glu Thr Asp Lys Asp Ser
65                  70                  75                  80

Leu Asn Lys Glu Ala Thr Ser Asp Lys Ile Arg Glu Leu Val Asn Leu
                85                  90                  95

Ile Arg Ser Met Leu Gln Ser Met Gly Asp Gly Glu Ile Ser Ser Ser
            100                 105                 110

Pro Tyr Asp Ala Ala Trp Val Ala Leu Val Pro Asp Val Gly Gly Ser
        115                 120                 125

Gly Gly Pro Gln Phe Pro Ser Ser Leu Glu Trp Ile Ser Lys Asn Gln
    130                 135                 140

Leu Pro Asp Gly Ser Trp Gly Asp Thr Cys Thr Phe Ser Ile Tyr Asp
145                 150                 155                 160

Arg Ile Ile Asn Thr Leu Ala Cys Val Val Ala Leu Lys Ser Trp Asn
                165                 170                 175

Ile His Pro His Lys Thr Tyr Gln Gly Ile Ser Phe Ile Lys Ala Asn
            180                 185                 190

Met Asp Lys Leu Glu Asp Glu Asn Glu Glu His Met Pro Ile Gly Phe
        195                 200                 205

Glu Val Ala Leu Pro Ser Leu Ile Glu Ile Ala Lys Arg Leu Asp Ile
    210                 215                 220

Asp Ile Ser Ser Asp Ser Arg Gly Leu Gln Glu Ile Tyr Thr Arg Arg
225                 230                 235                 240

Glu Val Lys Leu Lys Arg Ile Pro Lys Glu Ile Met His Gln Val Pro
                245                 250                 255

Thr Thr Leu Leu His Ser Leu Glu Gly Met Ala Glu Leu Thr Trp His
            260                 265                 270

Lys Leu Leu Lys Leu Gln Cys Gln Asp Gly Ser Phe Leu Phe Ser Pro
        275                 280                 285

Ser Ser Thr Ala Phe Ala Leu His Gln Thr Lys Asp His Asn Cys Leu
```

```
            290                 295                 300
His Tyr Leu Thr Lys Tyr Val His Lys Phe His Gly Val Pro Asn
305                 310                 315                 320

Val Tyr Pro Val Asp Leu Phe Glu His Leu Trp Ala Val Asp Arg Ile
                    325                 330                 335

Gln Arg Leu Gly Ile Ser Arg His Phe Lys Pro Gln Val Asp Glu Cys
                340                 345                 350

Ile Ala Tyr Val Tyr Arg Tyr Trp Thr Asp Lys Gly Ile Cys Trp Ala
            355                 360                 365

Arg Asn Ser Val Val Gln Asp Leu Asp Thr Ala Met Gly Phe Arg
370                 375                 380

Leu Leu Arg Leu His Gly Tyr Asp Val Ser Ala Asp Val Phe Lys His
385                 390                 395                 400

Phe Glu Asn Gly Gly Glu Phe Phe Cys Phe Lys Gly Gln Ser Thr Gln
                405                 410                 415

Ala Val Thr Gly Met Tyr Asn Leu Tyr Arg Ala Ser Gln Leu Met Phe
                420                 425                 430

Pro Gly Glu Ser Ile Leu Glu Asp Ala Lys Thr Phe Ser Ser Lys Phe
            435                 440                 445

Leu Gln Arg Lys Arg Ala Asn Asn Glu Leu Leu Asp Lys Trp Ile Ile
    450                 455                 460

Thr Lys Asp Leu Pro Gly Glu Val Gly Tyr Ala Leu Asp Val Pro Trp
465                 470                 475                 480

Tyr Ala Ser Leu Pro Arg Val Glu Thr Arg Phe Tyr Leu Glu Gln Tyr
                485                 490                 495

Gly Gly Glu Asp Asp Val Trp Ile Gly Lys Thr Leu Tyr Arg Met Pro
            500                 505                 510

Tyr Val Asn Asn Asn Lys Tyr Leu Glu Leu Ala Lys Leu Asp Tyr Ser
        515                 520                 525

Asn Cys Gln Ser Leu His Gln Gln Glu Trp Lys Asn Ile Gln Lys Trp
530                 535                 540

Tyr Glu Ser Cys Asn Leu Gly Glu Phe Gly Leu Ser Glu Arg Arg Val
545                 550                 555                 560

Leu Leu Ala Tyr Tyr Val Ala Ala Ala Cys Ile Tyr Glu Pro Glu Lys
                565                 570                 575

Ser Asn Gln Arg Leu Ala Trp Ala Lys Thr Val Ile Leu Met Glu Thr
            580                 585                 590

Ile Thr Ser Tyr Phe Glu His Gln Gln Leu Ser Ala Glu Gln Arg Arg
        595                 600                 605

Ala Phe Val Asn Glu Phe Glu His Gly Ser Ile Leu Lys Tyr Ala Asn
610                 615                 620

Gly Gly Arg Tyr Lys Arg Arg Ser Val Leu Gly Thr Leu Leu Lys Thr
625                 630                 635                 640

Leu Asn Gln Leu Ser Leu Asp Ile Leu Leu Thr His Gly Arg Asn Val
                645                 650                 655

His Gln Pro Phe Lys Asn Ala Trp His Lys Trp Leu Lys Thr Trp Glu
            660                 665                 670

Glu Gly Gly Asp Ile Glu Glu Gly Glu Ala Glu Val Leu Val Arg Thr
        675                 680                 685

Leu Asn Leu Ser Gly Glu Gly Arg His Asp Ser Tyr Val Leu Glu Gln
690                 695                 700

Ser Leu Leu Ser Gln Pro Ile Tyr Glu Gln Leu Leu Lys Ala Thr Met
705                 710                 715                 720
```

```
Ser Val Cys Lys Lys Leu Arg Leu Phe Gln His Arg Lys Asp Glu Asn
            725                 730                 735

Gly Cys Met Thr Lys Met Arg Gly Ile Thr Thr Leu Glu Ile Glu Ser
            740                 745                 750

Glu Met Gln Glu Leu Val Lys Leu Val Phe Thr Lys Ser Ser Asp Asp
            755                 760                 765

Leu Asp Cys Glu Ile Lys Gln Asn Phe Phe Thr Ile Ala Arg Ser Phe
            770                 775                 780

Tyr Tyr Val Ala Tyr Cys Asn Gln Gly Thr Ile Asn Phe His Ile Ala
785                 790                 795                 800

Lys Val Leu Phe Glu Arg Val Leu
            805

<210> SEQ ID NO 58
<211> LENGTH: 2427
<212> TYPE: DNA
<213> ORGANISM: Scutellaria baicalensis

<400> SEQUENCE: 58
```

| | | | | | |
|---|---|---|---|---|---|
| atgcctttcc | tcctcccttc | ctccgccacc | agctcccccg | cgttctatac | tccggccgcg | 60 |
| cctctcgccg | gtcatcatgt | ttttccatct | ttcaagccac | tcattatttc | ccgttcttca | 120 |
| ctccaatgca | atgcaatctc | tcgacctcgt | acccaagaat | acatagatgt | gattcagaat | 180 |
| ggattgccag | taataaagtg | gcacgaagct | gtggaagaag | atgagacaga | taaagattct | 240 |
| cttaataagg | aggccacgtc | agacaagata | agagagttgg | taaatctgat | ccgttcgatg | 300 |
| ctccaatcaa | tgggcgacgg | agagataagc | tcgtcgccgt | acgacgccgc | atgggtggcg | 360 |
| ctggtgccgg | acgtcggcgg | ctccggcggg | ccccagttcc | cctccagcct | cgaatggata | 420 |
| tccaaaaacc | aactccccga | cggctcctgg | ggcgacacgt | gtacctttc | catttatgat | 480 |
| cgaatcatca | acacactggc | ttgcgttgtt | gctttgaaat | cttggaacat | acatccccac | 540 |
| aaaacttatc | aagggatttc | attcataaag | gcaaatatgg | acaaacttga | agacgagaac | 600 |
| gaggagcaca | tgccgatcgg | atttgaagtg | gcactcccgt | cgctaatcga | gatagcgaaa | 660 |
| aggctcgata | tcgatatttc | cagcgattcg | agagggctgc | aagagatata | cacgaggagg | 720 |
| gaggtaaagc | tgaaaaggat | accgaaagag | ataatgcacc | aagtgcccac | aacactgctt | 780 |
| catagcttgg | agggtatggc | cgagctgacg | tggcacaagc | ttttgaaatt | acagtgccaa | 840 |
| gatggctcct | ttcttttctc | tccatcttca | actgcctttg | ctcttcacca | aactaaggac | 900 |
| cataattgtc | tccattattt | gaccaaatat | gttcacaaat | tcatggtgg | agtgccaaat | 960 |
| gtgtatccgg | tggacttgtt | cgagcatcta | tgggcagttg | atcggatcca | acggctgggg | 1020 |
| atttcccggc | atttcaagcc | ccaagttgat | gaatgtattg | cctatgttta | tagatattgg | 1080 |
| acagataaag | gaatatgctg | ggcaagaaat | tcagtagttc | aagatcttga | tgacacagcc | 1140 |
| atgggattca | ggcttcttag | gttgcatggc | tacgatgttt | cagcagatgt | tttcaaacat | 1200 |
| tttgaaaatg | gtggagagtt | cttctgcttc | aaagggcaaa | gcacgcaggc | agtgactgga | 1260 |
| atgtacaatc | tgtacagagc | ttctcagttg | atgtttcctg | gagaaagcat | actggaagat | 1320 |
| gctaagacct | tctcatctaa | gtttttgcaa | cgaaaacgag | ccaataacga | gttgttagat | 1380 |
| aagtggatta | ttaccaagga | tcttcctgga | gaggtgggat | atgctctaga | tgtaccatgg | 1440 |
| tatgctagct | tacctagagt | tgaaactaga | ttctacttgg | aacaaatatgg | tggtgaagat | 1500 |
| gatgtttgga | ttggcaaaac | tttatacagg | atgccatatg | ttaacaataa | taaatatcta | 1560 |

-continued

```
gaactggcaa aattagacta tagtaactgc cagtcattac atcaacaaga gtggaaaaac    1620
attcaaaaat ggtatgagag ttgcaatctg ggagaatttg gtttgagtga aagaagggtt    1680
ctactagcct actacgtagc tgctgcgtgt atatatgagc ccgaaaagtc aaaccagcgc    1740
ttggcttggg ccaaaaccgt aattttaatg gagactatta cttcctattt tgagcaccaa    1800
caactctccg cagaacagag acgcgccttt gttaatgaat ttgaacatgg gagtatcctc    1860
aaatatgcaa atggaggaag atacaaaagg aggagtgttt tggggacttt gctcaaaaca    1920
ctaaatcagc tttcattgga tatattattg acacacggtc gaaacgtcca tcagcctttc    1980
aaaaatgcgt ggcacaagtg gctaaaaacg tgggaagaag gaggtgacat tgaagaaggc    2040
gaagcagagg tattggtccg aaccctaaac ctaagcggcg aagggaggca cgactcctat    2100
gtattggagc aatcattatt gtcacaacct atatatgaac aacttttgaa agccaccatg    2160
agtgtttgca agaagcttcg attgttccaa catcgaaagg atgagaatgg atgtatgacg    2220
aagatgagag gcattacaac gttagagata gaatcggaga tgcaagaatt agtgaaatta    2280
gtatttacta atcctcaga tgatttagat tgtgaaatta aacaaaactt ttttacaatt    2340
gctaggagtt tctattatgt ggcttattgt aaccaaggaa ctatcaactt tcacattgct    2400
aaggtgctct tgaaagagt tctttag                                         2427
```

<210> SEQ ID NO 59
<211> LENGTH: 802
<212> TYPE: PRT
<213> ORGANISM: Scutellaria baicalensis

<400> SEQUENCE: 59

```
Met Ala Ser Leu Ser Thr Leu Ser Leu Asn Phe Ser Pro Ala Ile His
1               5                   10                  15

Arg Lys Ile Gln Gln Ser Ser Ala Lys Leu Gln Phe Gln Gly His Cys
            20                  25                  30

Phe Thr Ile Ser Ser Cys Met Asn Asn Ser Lys Arg Leu Ser Leu Asn
        35                  40                  45

His Gln Ser Asn His Lys Arg Thr Ser Asn Val Ser Glu Leu Gln Val
    50                  55                  60

Ala Thr Leu Asp Ala Pro Gln Ile Arg Glu Lys Glu Asp Tyr Ser Thr
65                  70                  75                  80

Ala Gln Gly Tyr Glu Lys Val Asp Glu Val Asp Pro Ile Glu Tyr
                85                  90                  95

Ile Arg Met Leu Leu Asn Thr Thr Gly Asp Gly Arg Ile Ser Val Ser
            100                 105                 110

Pro Tyr Asp Thr Ala Trp Ile Ala Leu Ile Lys Asp Val Glu Gly Arg
        115                 120                 125

Asp Ala Pro Gln Phe Pro Ser Ser Leu Glu Trp Ile Ala Asn Asn Gln
    130                 135                 140

Leu Ser Asp Gly Ser Trp Gly Asp Glu Lys Phe Phe Cys Val Tyr Asp
145                 150                 155                 160

Arg Leu Val Asn Thr Leu Ala Cys Val Val Ala Leu Arg Ser Trp Asn
                165                 170                 175

Ile Asp Ala Glu Lys Ser Glu Lys Gly Ile Arg Tyr Ile Lys Glu Asn
            180                 185                 190

Val Asp Lys Leu Lys Asp Gly Asn Pro Glu His Met Thr Cys Gly Phe
        195                 200                 205

Glu Val Val Phe Pro Ser Leu Leu Gln Arg Ala Gln Ser Met Gly Ile
    210                 215                 220
```

-continued

His Asp Leu Pro Tyr Asp Ala Pro Val Ile Gln Asp Ile Tyr Asn Thr
225                 230                 235                 240

Arg Glu Ser Lys Leu Lys Arg Ile Pro Met Glu Val Met His Lys Val
            245                 250                 255

Pro Thr Ser Leu Leu Phe Ser Leu Glu Gly Leu Glu Asn Leu Glu Trp
        260                 265                 270

Asp Lys Leu Leu Lys Leu Gln Ser Ser Asp Gly Ser Phe Leu Thr Ser
    275                 280                 285

Pro Ser Ser Thr Ala Tyr Ala Phe Met His Thr Lys Asp Pro Lys Cys
290                 295                 300

Phe Glu Phe Ile Lys Asn Thr Val Glu Thr Phe Asn Gly Gly Ala Pro
305                 310                 315                 320

His Thr Tyr Pro Val Asp Val Phe Gly Arg Leu Trp Ala Ile Asp Arg
                325                 330                 335

Leu Gln Arg Leu Gly Ile Ser Arg Phe Phe Glu Ser Glu Ile Ala Asp
            340                 345                 350

Cys Leu Asp His Ile Tyr Lys Tyr Trp Thr Asp Lys Gly Val Phe Ser
        355                 360                 365

Gly Arg Glu Ser Asp Phe Val Asp Val Asp Asp Thr Ser Met Gly Val
370                 375                 380

Arg Leu Leu Arg Met His Gly Tyr Gln Val Asp Pro Asn Val Leu Arg
385                 390                 395                 400

Asn Phe Lys Gln Gly Asp Lys Phe Ser Cys Tyr Gly Gly Gln Met Ile
                405                 410                 415

Glu Ser Ser Ser Pro Ile Tyr Asn Leu Tyr Arg Ala Ser Gln Leu Arg
            420                 425                 430

Phe Pro Gly Glu Asp Ile Leu Glu Asp Ala Asn Lys Phe Ala Tyr Glu
        435                 440                 445

Phe Leu Gln Glu Gln Leu Ser Asn Asn Gln Leu Leu Asp Lys Trp Val
450                 455                 460

Ile Ser Lys His Leu Pro Asp Glu Ile Lys Leu Gly Leu Gln Met Pro
465                 470                 475                 480

Trp Tyr Ala Thr Leu Pro Arg Val Glu Ala Lys Tyr Tyr Leu Gln Tyr
                485                 490                 495

Tyr Ala Gly Ala Asp Asp Val Trp Ile Gly Lys Thr Leu Tyr Arg Met
            500                 505                 510

Pro Glu Ile Ser Asn Asp Thr Tyr Leu Glu Leu Ala Arg Met Asp Phe
        515                 520                 525

Lys Arg Cys Gln Ala Gln His Gln Phe Glu Trp Ile Ser Met Gln Glu
530                 535                 540

Trp Tyr Glu Ser Cys Asn Ile Glu Glu Phe Gly Ile Ser Arg Lys Glu
545                 550                 555                 560

Leu Leu Gln Ala Tyr Phe Leu Ala Cys Ser Ser Val Phe Glu Leu Glu
                565                 570                 575

Arg Thr Thr Glu Arg Ile Gly Trp Ala Lys Ser Gln Ile Ile Ser Arg
            580                 585                 590

Met Ile Ala Ser Phe Phe Asn Asn Glu Thr Thr Thr Ala Asp Glu Lys
        595                 600                 605

Asp Ala Leu Leu Thr Arg Phe Arg Asn Ile Asn Gly Pro Asn Lys Thr
610                 615                 620

Lys Ser Gly Gln Arg Glu Ser Glu Ala Val Asn Met Leu Val Ala Thr
625                 630                 635                 640

```
Leu Gln Gln Tyr Leu Ala Gly Phe Asp Arg Tyr Thr Arg His Gln Leu
                645                 650                 655
Lys Asp Ala Trp Ser Val Trp Phe Arg Lys Val Gln Glu Glu Glu Ala
660                 665                 670
Ile Tyr Gly Ala Glu Ala Glu Leu Leu Thr Thr Thr Leu Asn Ile Cys
    675                 680                 685
Ala Gly His Ile Ala Phe Asp Glu Asn Ile Met Ala Asn Lys Asp Tyr
690                 695                 700
Thr Thr Leu Ser Ser Leu Thr Ser Lys Ile Cys Gln Lys Leu Ser Glu
705                 710                 715                 720
Ile Arg Asn Glu Lys Val Glu Glu Met Glu Ser Gly Ile Lys Ala Lys
                725                 730                 735
Ser Ser Ile Lys Asp Lys Glu Val Glu His Asp Met Gln Ser Leu Val
                740                 745                 750
Lys Leu Val Leu Glu Arg Cys Glu Gly Ile Asn Asn Arg Lys Leu Lys
            755                 760                 765
Gln Thr Phe Leu Ser Val Ala Lys Thr Tyr Tyr Arg Ala Tyr Asn
770                 775                 780
Ala Asp Glu Thr Met Asp Ile His Met Phe Lys Val Leu Phe Glu Pro
785                 790                 795                 800
Val Met
```

```
<210> SEQ ID NO 60
<211> LENGTH: 2409
<212> TYPE: DNA
<213> ORGANISM: Scutellaria baicalensis

<400> SEQUENCE: 60
atggcctctc tatcaactct gagcctcaac ttttccccag caattcaccg caaaatacag      60
caatcatctg caaaacttca gttccaggga cattgtttca ccataagttc atgcatgaac     120
aacagtaaaa gactgtcttt gaaccaccaa tctaatcaca aagaacgtc aaacgtatct     180 gagctgcaag ttgccacttt ggatgcgccc caaatacgtg aaaaagaaga ctactccact     240
gctcaaggct atgagaaggt ggatgaagta gaggatccta tcgaatatat tagaatgctg     300
ttgaacacaa caggtgatgg gcgaataagt gtgtcgccat acgacacagc ctggatcgct     360
cttattaaag acgtggaagg acgtgatgct ccccagttcc catctagtct cgaatggatt     420
gccaataatc aactgagtga tgggtcgtgg ggcgatgaga agtttttctg tgtgtatgat     480
cgccttgtta atacacttgc atgtgtcgtg gcattgagat catggaatat tgatgctgaa     540
aagagcgaga aggaataag atacataaaa gaaaacgtgg ataaactgaa agatgggaat     600
ccagagcaca tgacctgtgg ttttgaggtg gtgtttcctt cccttcttca gagagcccaa     660
agtatgggaa ttcatgatct tccctatgat gctcctgtca tccaagacat ttacaatacc     720
agggagagta aattgaaaag gattccaatg gaggttatgc acaaggtgcc aacatctcta     780
ttgttcagct tggaaggatt ggagaatttg gagtgggata agctcctcaa acttcagtct     840
tctgatggtt cattcctcac ttctccatcc tcaactgcct atgctttcat gcacactaag     900
gaccctaaat gcttcgaatt catcaaaaac accgtcgaaa catttaatgg aggagcacct     960
catacttatc cggtggatgt ttttggaaga ctgtgggcca ttgacaggct gcagcgcctc    1020
ggaatctctc gcttctttga gtccgagatt gctgattgct agatcacat ctataaatat    1080 tggacagaca aggagtgtt cagtggaaga gaatcagatt tgtggatgt ggatgacaca     1140 tccatgggtg ttaggcttct aaggatgcac ggatatcaag ttgatccaaa tgtattgagg    1200
```

```
aacttcaagc agggtgacaa attttcatgc tatggtggtc aaatgataga gtcatcatct    1260
ccgatataca atctctatag ggcttctcaa ctccgatttc caggagaaga cattcttgaa    1320
gatgccaaca aattcgcata cgagttcttg caagaacagc tatccaacaa tcaacttttg    1380
gacaaatggg ttatatccaa gcacttgcct gatgagataa agcttggatt gcagatgcca    1440
tggtatgcca ccctaccccg agtggaggct aaatactacc tacagtatta tgctggtgct    1500
gatgatgtct ggatcggcaa gactctctac agaatgccag aaatcagtaa tgatacatat    1560
ctggagttag caagaatgga tttcaagaga tgccaagcac agcatcaatt tgagtggatt    1620
tccatgcaag aatggtatga agttgcaac attgaagaat ttgggataag cagaaaagag     1680
cttcttcagg cttactttt ggcctgctca agtgtatttg aactcgagag acaacagag      1740 agaataggat gggccaaatc ccaaattatt caaggatga tagcttcttt cttcaacaat     1800
gaaactacaa cagccgatga aaagatgca cttttaacca gattcagaaa catcaatggc     1860
ccaaacaaaa caaaaagtgg tcagagagag agtgaagctg tgaacatgtt ggtagcaacg    1920
ctccaacaat acctggcagg atttgataga tataccagac atcaattgaa agatgcttgg    1980
agtgtgtggt tcagaaaagt gcaagaagaa gaggccatct acggggcaga agcggagctt    2040
ctaacaacca ccttaaacat ctgtgctggt catattgctt tcgacgaaaa cataatggcc    2100
aacaaagatt acaccactct ttccagcctt acaagcaaaa tttgccagaa gctttctgaa    2160
attcgaaatg aaaaggttga ggaatggag agtggaatta aagcaaaatc aagcatcaaa    2220
gacaaggaag tggaacatga tatgcagtca ctggtgaaat tagtcctgga gagatgtgaa    2280
ggcataaaca acagaaaact gaagcaaaca tttctatcgg ttgcaaaaac atattactac    2340
agagcctata atgctgatga aaccatggac atccatatgt tcaaagtact tttcgaacca    2400
gtcatgtga                                                             2409

<210> SEQ ID NO 61
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 61
atggttcttt catcgtcttg caca                                             24

<210> SEQ ID NO 62
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 62
ttattttgcg gcggaaacag gttca                                            25

<210> SEQ ID NO 63
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 63
agattgagga ttccattgag tacgtgaagg                                       30
```

<210> SEQ ID NO 64
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 64
gaagtttaat atccttcatt ctttattaca                                30

<210> SEQ ID NO 65
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 65
agctccattc aactagagtc atgtcgt                                   27

<210> SEQ ID NO 66
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 66
ttcatctggc ttaactagtt gctgacac                                  28

<210> SEQ ID NO 67
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 67
ttaaagtact ctctcaaaga gtactttgg                                 29

<210> SEQ ID NO 68
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 68
gcgaccaacc atcatacgac t                                         21

<210> SEQ ID NO 69
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 69
aatggcctcc actgcatcca ctcta                                     25

<210> SEQ ID NO 70
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 70
ccatactcat tcaactggtt cgaaca					26

<210> SEQ ID NO 71
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 71
agcctgtgta ctcgaaatgt c						21

<210> SEQ ID NO 72
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 72
caagaggatg attcatgtac caac					24

<210> SEQ ID NO 73
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 73
tctctttcaa gaatatcccc tctc					24

<210> SEQ ID NO 74
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 74
ggcattcaat gattttgagt cg					22

<210> SEQ ID NO 75
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 75
aaatggcctc tttgtccact ctc					23

<210> SEQ ID NO 76
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 76
ttacgcaact ggttcgaaaa gca					23

<210> SEQ ID NO 77

```
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 77
taatgtcatt tgcttcccaa gcca                                          24

<210> SEQ ID NO 78
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 78
ggcctagact accttctcaa acaa                                          24

<210> SEQ ID NO 79
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 79
aatgtcactc tcgttcacca tcaa                                          24

<210> SEQ ID NO 80
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 80
acttcaagag gatgaagtgt ttagg                                         25

<210> SEQ ID NO 81
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 81
ctccaaaact cgggccggta aat                                           23

<210> SEQ ID NO 82
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 82
tacgtatttc ctcacaatcg agca                                          24

<210> SEQ ID NO 83
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 83
```
ctagaaatgt tacttgcgtt caac                                          24

<210> SEQ ID NO 84
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 84
gggtaagagt tgaatttaga tgtct                                         25

<210> SEQ ID NO 85
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 85
atgacttcaa tatcctctct aaatttgagc                                    30

<210> SEQ ID NO 86
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 86
gaatatagta atcagacgac cggtcca                                       27

<210> SEQ ID NO 87
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 87
gccatatcat gtctcttccg ctct                                          24

<210> SEQ ID NO 88
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 88
ttattcatgc accttaaaat ccttgagag                                     29

<210> SEQ ID NO 89
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 89
atgaccgatg tatcctctct tcgt                                          24

<210> SEQ ID NO 90
<211> LENGTH: 23
<212> TYPE: DNA

```
<213> ORGANISM: Artificial Sequence
<220> FEATURE:
<223> OTHER INFORMATION: A synthetic oligonucleotide

<400> SEQUENCE: 90
aaacactcac ataaccggcc caa                                           23

<210> SEQ ID NO 91
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 91
gtccttgctt tcggaatact                                               20

<210> SEQ ID NO 92
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 92
gaagtgatct acaaggattc ataaa                                         25

<210> SEQ ID NO 93
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 93
tcattgattt gccctgcatc cac                                           23

<210> SEQ ID NO 94
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 94
caaagctagt gctgcttctg att                                           23

<210> SEQ ID NO 95
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 95
atggtatctg catgtctaaa actcaa                                        26

<210> SEQ ID NO 96
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 96
ctttctctct cttgtgcatc ttagt                                         25
```

<210> SEQ ID NO 97
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 97
acgttcatct tcaatgagtt cca                                    23

<210> SEQ ID NO 98
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 98
tacgtgtatg tcgatctgtt ccaat                                  25

<210> SEQ ID NO 99
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 99
catgtcattt gcttctcaat cac                                    23

<210> SEQ ID NO 100
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 100
cccattatct aaaagtctac atcacc                                 26

<210> SEQ ID NO 101
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 101
tcctcataaa gcaatggcgt ata                                    23

<210> SEQ ID NO 102
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 102
ctaagattca gacaatgggc tca                                    23

<210> SEQ ID NO 103
<211> LENGTH: 22
<212> TYPE: DNA
<213> ORGANISM: Artificial Sequence
<220> FEATURE:

<223> OTHER INFORMATION: A synthetic oligonucleotide

<400> SEQUENCE: 103
gcagacgcca atctttcttg gt                                        22

<210> SEQ ID NO 104
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 104
ttatgaagtt aaaaggagtg gttcgttgac                                30

<210> SEQ ID NO 105
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 105
ggaacgagaa atgtcactca c                                         21

<210> SEQ ID NO 106
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 106
ttctagtttc tcacagaagt caa                                       23

<210> SEQ ID NO 107
<211> LENGTH: 87
<212> TYPE: DNA
<213> ORGANISM: Artificial Sequence
<220> FEATURE:
<223> OTHER INFORMATION: A synthetic oligonucleotide

<400> SEQUENCE: 107
tcaaatgcag cagacgaagt tgctactcaa cttttgaatt ttgacttgct gaagttggct    60
ggtgatgttg agtcaaaccc tggacct                                       87

<210> SEQ ID NO 108
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 108
ttctgcccaa attcgatggg gtctctatcc actatga                        37

<210> SEQ ID NO 109
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 109
agttaaaggc ctcgatcagg cgactggttc gaaaagta                       38

<210> SEQ ID NO 110
<211> LENGTH: 33
<212> TYPE: DNA
<213> ORGANISM: Artificial Sequence
<220> FEATURE:
<223> OTHER INFORMATION: A synthetic oligonucleotide

<400> SEQUENCE: 110
ttctgcccaa attcgatgtc gctcgccttc aac                              33

<210> SEQ ID NO 111
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 111
agttaaaggc ctcgatcaaa agacaaagga tttcata                          37

<210> SEQ ID NO 112
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 112
ttctgcccaa attcgatggt tctttcatcg tcttgcac                         38

<210> SEQ ID NO 113
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 113
agttaaaggc ctcgattatt ttgcggcgga aacaggt                          37

<210> SEQ ID NO 114
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 114
ttctgcccaa attcgatgaa aatgttgatg atcaaaagt                        39

<210> SEQ ID NO 115
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 115
agttaaaggc ctcgatcaga ccactggttc aaatagta                         38

<210> SEQ ID NO 116
<211> LENGTH: 38
<212> TYPE: DNA
<213> ORGANISM: Artificial Sequence
<220> FEATURE:

<223> OTHER INFORMATION: A synthetic oligonucleotide

<400> SEQUENCE: 116
ttctgcccaa attcgatgtc gtccctcgcc ggcaacct                     38

<210> SEQ ID NO 117
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 117
agttaaaggc ctcgactagt tgctgacaca actcatt                     37

<210> SEQ ID NO 118
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 118
ttctgcccaa attcgatgca ggcttctatg tcatct                      36

<210> SEQ ID NO 119
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 119
agttaaaggc ctcgatcata cgactggttc aaacatt                     37

<210> SEQ ID NO 120
<211> LENGTH: 33
<212> TYPE: DNA
<213> ORGANISM: Artificial Sequence
<220> FEATURE:
<223> OTHER INFORMATION: A synthetic oligonucleotide

<400> SEQUENCE: 120
ttctgcccaa attcgatggc ctccactgca tcc                         33

<210> SEQ ID NO 121
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 121
agttaaaggc ctcgatcatt caactggttc gaacaa                      36

<210> SEQ ID NO 122
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 122
ttctgcccaa attcgatgat tcctaatccc gaaa                        34

```
<210> SEQ ID NO 123
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 123
agttaaaggc ctcgattaca ttggcaatcc gatgaa                                    36

<210> SEQ ID NO 124
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 124
ttctgcccaa attcgatgtc ggtggcgttc aacct                                     35

<210> SEQ ID NO 125
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 125
agttaaaggc ctcgatcaag aggatgattc atgtacc                                   37

<210> SEQ ID NO 126
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 126
ttctgcccaa attcgatgtc cctcgccttc aacg                                      34

<210> SEQ ID NO 127
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 127
agttaaaggc ctcgatcatt tgccactcac attt                                      34

<210> SEQ ID NO 128
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 128
ttctgcccaa attcgatggc ctctttgtcc actttcc                                   37

<210> SEQ ID NO 129
<211> LENGTH: 37
<212> TYPE: DNA
<213> ORGANISM: Artificial Sequence
<220> FEATURE:
<223> OTHER INFORMATION: A synthetic oligonucleotide
```

```
<400> SEQUENCE: 129
agttaaaggc ctcgatcacg caactggttc gaaaaga                              37

<210> SEQ ID NO 130
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 130
ttctgcccaa attcgatgtc atttgcttcc caagccac                             38

<210> SEQ ID NO 131
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 131
agttaaaggc ctcgactaga ctaccttctc aaacaatac                            39

<210> SEQ ID NO 132
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 132
ttctgcccaa attcgatgtc actctcgttc accatca                              37

<210> SEQ ID NO 133
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 133
agttaaaggc ctcgatcaag aggatgaagt gtttag                               36

<210> SEQ ID NO 134
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 134
ttctgcccaa attcgatgac ctctatgtcc tctctaa                              37

<210> SEQ ID NO 135
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 135
agttaaaggc ctcgatcata cgaccggtcc aaacagt                              37

<210> SEQ ID NO 136
<211> LENGTH: 39
```

```
<212> TYPE: DNA
<213> ORGANISM: Artificial Sequence
<220> FEATURE:
<223> OTHER INFORMATION: A synthetic oligonucleotide

<400> SEQUENCE: 136
ttctgcccaa attcgatgtt acttgcgttc aacataagc                    39

<210> SEQ ID NO 137
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 137
agttaaaggc ctcgattaat taggtaggta gaggggtt                     38

<210> SEQ ID NO 138
<211> LENGTH: 52
<212> TYPE: DNA
<213> ORGANISM: Artificial Sequence
<220> FEATURE:
<223> OTHER INFORMATION: A synthetic oligonucleotide

<400> SEQUENCE: 138
atattctgcc caaattcgat gacttcaata tcctctctaa atttgagcaa tg      52

<210> SEQ ID NO 139
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 139
cagagttaaa ggcctcgatc agacgaccgg tccaa                         35

<210> SEQ ID NO 140
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 140
ttctgcccaa attcgatgtc tcttccgctc tcctct                        36

<210> SEQ ID NO 141
<211> LENGTH: 49
<212> TYPE: DNA
<213> ORGANISM: Artificial Sequence
<220> FEATURE:
<223> OTHER INFORMATION: A synthetic oligonucleotide

<400> SEQUENCE: 141
gataagttaa aggcctcgat tattcatgca ccttaaaatc cttgagagc          49

<210> SEQ ID NO 142
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 142
```

```
ttctgcccaa attcgatgac cgatgtatcc tctcttc                              37

<210> SEQ ID NO 143
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 143
agttaaaggc ctcgatcaca taaccggccc aaaca                                35

<210> SEQ ID NO 144
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 144
ttctgcccaa attcgatggc gtcgctcgcg ttcac                                35

<210> SEQ ID NO 145
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 145
agttaaaggc ctcgactaca aggattcata aattaagga                            39

<210> SEQ ID NO 146
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 146
ttctgcccaa attcgcgaat gtcactcgcc ttcagc                               36

<210> SEQ ID NO 147
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 147
agttaaaggc ctcgagctag gagcttaggg tttcat                               37

<210> SEQ ID NO 148
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 148
ttctgcccaa attcgatggt atctgcatgt ctaaa                                35

<210> SEQ ID NO 149
<211> LENGTH: 35
<212> TYPE: DNA
<213> ORGANISM: Artificial Sequence
```

<220> FEATURE:
<223> OTHER INFORMATION: A synthetic oligonucleotide

<400> SEQUENCE: 149
agttaaaggc ctcgatcatg aaggaattga aggaa     35

<210> SEQ ID NO 150
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 150
ttctgcccaa attcgatgag ttccattcga aatttaagt     39

<210> SEQ ID NO 151
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 151
agttaaaggc ctcgatcact tgagaggctc aaacatcat     39

<210> SEQ ID NO 152
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 152
ttctgcccaa attcgatgtc atttgcttct caatcac     37

<210> SEQ ID NO 153
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 153
agttaaaggc ctcgactaca tcaccctctc aaacaatac     39

<210> SEQ ID NO 154
<211> LENGTH: 45
<212> TYPE: DNA
<213> ORGANISM: Artificial Sequence
<220> FEATURE:
<223> OTHER INFORMATION: A synthetic oligonucleotide

<400> SEQUENCE: 154
ttctgcccaa attcgatggc gtatatgata tctatttcaa atctc     45

<210> SEQ ID NO 155
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 155
agttaaaggc ctcgatcaga caatgggctc aaatagaac     39

<210> SEQ ID NO 156
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 156
ttctgcccaa attcgatgca agtctctctc tccctca                              37

<210> SEQ ID NO 157
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 157
agttaaaggc ctcgattatg aagttaaaag gagtggtt                             38

<210> SEQ ID NO 158
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 158
ttctgcccaa attcgcgaat gtcactcact ttcaacg                              37

<210> SEQ ID NO 159
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 159
agttaaaggc ctcgagctag tttctcacag aagtcaa                              37

<210> SEQ ID NO 160
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 160
aggagatata ccatggccga gattcgagtt gccac                                35

<210> SEQ ID NO 161
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 161
ggtggtggtg ctcgaaggcg actggttcga aaagtac                              37

<210> SEQ ID NO 162
<211> LENGTH: 40
<212> TYPE: DNA
<213> ORGANISM: Artificial Sequence
<220> FEATURE:
<223> OTHER INFORMATION: A synthetic oligonucleotide

```
<400> SEQUENCE: 162
aggagatata ccatggattt catggcgaaa atgaaagaga                    40

<210> SEQ ID NO 163
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 163
ggtggtggtg ctcgaaaaag acaaaggatt tcatat                        36

<210> SEQ ID NO 164
<211> LENGTH: 40
<212> TYPE: DNA
<213> ORGANISM: Artificial Sequence
<220> FEATURE:
<223> OTHER INFORMATION: A synthetic oligonucleotide

<400> SEQUENCE: 164
aggagatata ccatgcaaat tcgtggaaag caaagatcac                    40

<210> SEQ ID NO 165
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 165
ggtggtggtg ctcgaagacc actggttcaa atagaact                      38

<210> SEQ ID NO 166
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 166
aggagatata ccatgtctaa atcatctgca gctgt                         35

<210> SEQ ID NO 167
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 167
ggtggtggtg ctcgaagttg ctgacacaac tcatt                         35

<210> SEQ ID NO 168
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 168
aggagatata ccatgaccgt caaatgctac                               30

<210> SEQ ID NO 169
```

```
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 169
ggtggtggtg ctcgaacaag gattcataaa ttaag                          35

<210> SEQ ID NO 170
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 170
aggagatata ccatgactgt caagtgcagc                                30

<210> SEQ ID NO 171
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 171
ggtggtggtg ctcgaatgaa ggaattgaag                                30

<210> SEQ ID NO 172
<211> LENGTH: 40
<212> TYPE: DNA
<213> ORGANISM: Artificial Sequence
<220> FEATURE:
<223> OTHER INFORMATION: A synthetic oligonucleotide

<400> SEQUENCE: 172
aggagatata ccatgtttat gcccacttcc attaaatgta                     40

<210> SEQ ID NO 173
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 173
ggtggtggtg ctcgaacatc accctctcaa acaatacttt gg                  42

<210> SEQ ID NO 174
<211> LENGTH: 43
<212> TYPE: DNA
<213> ORGANISM: Artificial Sequence
<220> FEATURE:
<223> OTHER INFORMATION: A synthetic oligonucleotide

<400> SEQUENCE: 174
aggagatata ccatggtagc aaaagtgatc gagagccgag tta                 43

<210> SEQ ID NO 175
<211> LENGTH: 44
<212> TYPE: DNA
<213> ORGANISM: Artificial Sequence
<220> FEATURE:
<223> OTHER INFORMATION: A synthetic oligonucleotide

<400> SEQUENCE: 175
```

```
ggtggtggtg ctcgaagaca atgggctcaa atagaacttt aaat                    44
```

<210> SEQ ID NO 176
<211> LENGTH: 575
<212> TYPE: PRT
<213> ORGANISM: Salvia sclarea

<400> SEQUENCE: 176

```
Met Ser Leu Ala Phe Asn Val Gly Val Thr Pro Phe Ser Gly Gln Arg
1               5                   10                  15

Val Gly Ser Arg Lys Glu Lys Phe Pro Val Gln Gly Phe Pro Val Thr
            20                  25                  30

Thr Pro Asn Arg Ser Arg Leu Ile Val Asn Cys Ser Leu Thr Thr Ile
        35                  40                  45

Asp Phe Met Ala Lys Met Lys Glu Asn Phe Lys Arg Glu Asp Asp Lys
    50                  55                  60

Phe Pro Thr Thr Thr Thr Leu Arg Ser Glu Asp Ile Pro Ser Asn Leu
65                  70                  75                  80

Cys Ile Ile Asp Thr Leu Gln Arg Leu Gly Val Asp Gln Phe Phe Gln
                85                  90                  95

Tyr Glu Ile Asn Thr Ile Leu Asp Asn Thr Phe Arg Leu Trp Gln Glu
            100                 105                 110

Lys His Lys Val Ile Tyr Gly Asn Val Thr Thr His Ala Met Ala Phe
        115                 120                 125

Arg Leu Leu Arg Val Lys Gly Tyr Glu Val Ser Ser Glu Glu Leu Ala
    130                 135                 140

Pro Tyr Gly Asn Gln Glu Ala Val Ser Gln Gln Thr Asn Asp Leu Pro
145                 150                 155                 160

Met Ile Ile Glu Leu Tyr Arg Ala Ala Asn Glu Arg Ile Tyr Glu Glu
                165                 170                 175

Glu Arg Ser Leu Glu Lys Ile Leu Ala Trp Thr Thr Ile Phe Leu Asn
            180                 185                 190

Lys Gln Val Gln Asp Asn Ser Ile Pro Asp Lys Lys Leu His Lys Leu
        195                 200                 205

Val Glu Phe Tyr Leu Arg Asn Tyr Lys Gly Ile Thr Ile Arg Leu Gly
    210                 215                 220

Ala Arg Arg Asn Leu Glu Leu Tyr Asp Met Thr Tyr Tyr Gln Ala Leu
225                 230                 235                 240

Lys Ser Thr Asn Arg Phe Ser Asn Leu Cys Asn Glu Asp Phe Leu Val
                245                 250                 255

Phe Ala Lys Gln Asp Phe Asp Ile His Glu Ala Gln Asn Gln Lys Gly
            260                 265                 270

Leu Gln Gln Leu Gln Arg Trp Tyr Ala Asp Cys Arg Leu Asp Thr Leu
        275                 280                 285

Asn Phe Gly Arg Asp Val Val Ile Ile Ala Asn Tyr Leu Ala Ser Leu
    290                 295                 300

Ile Ile Gly Asp His Ala Phe Asp Tyr Val Arg Leu Ala Phe Ala Lys
305                 310                 315                 320

Thr Ser Val Leu Val Thr Ile Met Asp Asp Phe Phe Asp Cys His Gly
                325                 330                 335

Ser Ser Gln Glu Cys Asp Lys Ile Ile Glu Leu Val Lys Glu Trp Lys
            340                 345                 350

Glu Asn Pro Asp Ala Glu Tyr Gly Ser Glu Glu Leu Glu Ile Leu Phe
        355                 360                 365
```

```
Met Ala Leu Tyr Asn Thr Val Asn Glu Leu Ala Glu Arg Ala Arg Val
    370                 375                 380

Glu Gln Gly Arg Ser Val Lys Glu Phe Leu Val Lys Leu Trp Val Glu
385                 390                 395                 400

Ile Leu Ser Ala Phe Lys Ile Glu Leu Asp Thr Trp Ser Asn Gly Thr
                405                 410                 415

Gln Gln Ser Phe Asp Glu Tyr Ile Ser Ser Ser Trp Leu Ser Asn Gly
            420                 425                 430

Ser Arg Leu Thr Gly Leu Leu Thr Met Gln Phe Val Gly Val Lys Leu
        435                 440                 445

Ser Asp Glu Met Leu Met Ser Glu Glu Cys Thr Asp Leu Ala Arg His
    450                 455                 460

Val Cys Met Val Gly Arg Leu Leu Asn Asp Val Cys Ser Ser Glu Arg
465                 470                 475                 480

Glu Arg Glu Glu Asn Ile Ala Gly Lys Ser Tyr Ser Ile Leu Leu Ala
                485                 490                 495

Thr Glu Lys Asp Gly Arg Lys Val Ser Glu Asp Glu Ala Ile Ala Glu
                500                 505                 510

Ile Asn Glu Met Val Glu Tyr His Trp Arg Lys Val Leu Gln Ile Val
            515                 520                 525

Tyr Lys Lys Glu Ser Ile Leu Pro Arg Arg Cys Lys Asp Val Phe Leu
    530                 535                 540

Glu Met Ala Lys Gly Thr Phe Tyr Ala Tyr Gly Ile Asn Asp Glu Leu
545                 550                 555                 560

Thr Ser Pro Gln Gln Ser Lys Glu Asp Met Lys Ser Phe Val Phe
                565                 570                 575

<210> SEQ ID NO 177
<211> LENGTH: 1728
<212> TYPE: DNA
<213> ORGANISM: Salvia sclarea

<400> SEQUENCE: 177
atgtcgctcg ccttcaacgt cggagttacg cctttctccg gccaaagagt tgggagcagg      60
aaagaaaaat ttccagtcca aggatttcct gtgaccaccc ccaataggtc acgtctcatc     120
gttaactgca gccttactac aatagatttc atggcgaaaa tgaaagagaa tttcaagagg     180
gaagacgata aatttccaac gacaacgact cttcgatccg aagatatacc ctctaatttg     240
tgtataatcg acacccttca aggttggggg tcgatcaat tcttccaata tgaaatcaac     300
actattctag ataacacatt caggttgtgg caagaaaaac acaaagttat atatggcaat     360
gttactactc atgcaatggc atttaggctt ttgcgagtga aggatacga agtttcatca     420 gaggagttgg ctccatatgg taaccaagag gctgttagcc agcaaacaaa tgacctgccg     480
atgattattg agctttatag agcagcaaat gagagaatat atgaagaaga gaggagtctt     540
gaaaaaattc ttgcttggac taccatcttt ctcaataagc aagtgcaaga aactcaatt      600 cccgacaaaa aactgcacaa actggtggaa ttctacttga ggaattacaa aggcataacc     660
ataagattgg gagctagacg aaacctcgag ctatatgaca tgacctacta tcaagctctg     720
aaatctacaa acaggttctc taatttatgc aacgaagatt ttctagtttt cgcaaagcaa     780
gatttcgata tacatgaagc ccagaaccag aaaggactt c aacaactgca aggtggtat      840 gcagattgta ggttgacac cttaaacttt ggaagagatg tagttattat tgctaattat     900
ttggcttcat taattattgg tgatcatgcg tttgactatg ttcgtctcgc atttgccaaa     960
```

```
acatctgtgc ttgtaacaat tatggatgat tttttcgact gtcatggctc tagtcaagag    1020
tgtgacaaga tcattgaatt agtaaaagaa tggaaggaga atccggatgc agagtacgga    1080
tctgaggagc ttgagatcct ttttatggcg ttgtacaata cagtaaatga gttggcggag    1140
agggctcgtg ttgaacaggg gcgtagtgtc aaagagtttc tagtcaaact gtgggttgaa    1200
atactctcag ctttcaagat agaattagat acatggagca atggcacgca gcaaagcttc    1260
gatgaataca tttcttcgtc gtggttgtcg aacggttccc ggctgacagg tctcctgacg    1320
atgcaattcg tcggagtaaa attgtccgat gaaatgctta tgagtgaaga gtgcactgat    1380
ttggctaggc atgtctgtat ggtcggccgg ctgctcaacg acgtgtgcag ttctgagagg    1440
gagcgcgagg aaaatattgc aggaaaaagt tatagcattc tactagcaac tgagaaagat    1500
ggaagaaaag ttagtgaaga tgaagccatt gcagagatca atgaaatggt tgaatatcac    1560
tggagaaaag tgttgcagat tgtgtataaa aaagaaagca ttttgccaag aagatgcaaa    1620
gatgtatttt tggagatggc taagggtacg ttttatgctt atgggatcaa cgatgaattg    1680
acttctcctc agcaatccaa ggaagatatg aaatcctttg tcttttga                1728
```